United States Patent
Lee et al.

(10) Patent No.: US 11,678,576 B2
(45) Date of Patent: Jun. 13, 2023

(54) HETEROCYCLIC COMPOUND AND ORGANIC LIGHT EMITTING ELEMENT COMPRISING SAME

(71) Applicant: LT MATERIALS CO., LTD., Yongin (KR)

(72) Inventors: Yun-Ji Lee, Osan-si (KR); Han-Kook Oh, Osan-si (KR); Hye-Su Ji, Osan-si (KR); Won-Jang Jeong, Hwaseong-si (KR); Jin-Seok Choi, Suwon-si (KR); Dae-Hyuk Choi, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 305 days.

(21) Appl. No.: 16/649,290

(22) PCT Filed: Sep. 28, 2018

(86) PCT No.: PCT/KR2018/011606
§ 371 (c)(1),
(2) Date: Mar. 20, 2020

(87) PCT Pub. No.: WO2020/067594
PCT Pub. Date: Apr. 2, 2020

(65) Prior Publication Data
US 2021/0202863 A1    Jul. 1, 2021

(51) Int. Cl.
*H01L 51/00* (2006.01)
*C07D 471/04* (2006.01)
(Continued)

(52) U.S. Cl.
CPC ........ *H01L 51/0072* (2013.01); *C07D 471/04* (2013.01); *C09K 11/06* (2013.01);
(Continued)

(58) Field of Classification Search
CPC ............. H01L 51/0054; H01L 51/0056; H01L 51/0058; H01L 51/0067; H01L 51/0073;
(Continued)

(56) References Cited

U.S. PATENT DOCUMENTS 4,356,429 A    10/1982   Tang
2006/0251918 A1  11/2006  Iwakuma
(Continued)

FOREIGN PATENT DOCUMENTS

JP       2005-317314 A      11/2005
KR   10-2010-0108924 A      10/2010
(Continued)

OTHER PUBLICATIONS

Kuwabara et al., "Thermally Stable Multilayered Organic Electroluminescent Devices Using Novel Starburst Molecules, 4,4',4"-Tri(N-carbazolyl) triphenylamine (TCTA) and 4,4' ,4"-Tris(3-methviphenyphenylamino)triphenlamine (m-MTDATA), as Hole-Transport Materials", Adv. Mater. 1994, vol. 6, No. 9, pp. 677-679.
Extended European Search Report for European Application No. 18932973.3, dated Mar. 18, 2022.

*Primary Examiner* — Sheng-Bai Zhu
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

11 Claims, 3 Drawing Sheets

(51) Int. Cl.
*C09K 11/06* (2006.01)
*H01L 51/50* (2006.01)
*H01L 51/52* (2006.01)

(52) U.S. Cl.
CPC ...... *H01L 51/0052* (2013.01); *H01L 51/0054* (2013.01); *H01L 51/0056* (2013.01); *H01L 51/0058* (2013.01); *H01L 51/0067* (2013.01); *H01L 51/0073* (2013.01); *H01L 51/0074* (2013.01); *C09K 2211/1018* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5278* (2013.01)

(58) Field of Classification Search
CPC ............. H01L 51/0074; H01L 51/0072; H01L 51/0052; C07D 471/04; C09K 11/06
USPC ......................................................... 257/40
See application file for complete search history.

(56) References Cited

U.S. PATENT DOCUMENTS

| | | | |
|---|---|---|---|
| 2011/0175079 A1* | 7/2011 | Yokoyama | H01L 51/0072 546/85 |
| 2014/0284556 A1* | 9/2014 | Cheng | H01L 51/0072 546/61 |
| 2015/0325799 A1 | 11/2015 | Hwang et al. | |
| 2016/0285010 A1* | 9/2016 | Yoon | C09K 11/06 |
| 2017/0213984 A1* | 7/2017 | Kim | H01L 51/50 |

FOREIGN PATENT DOCUMENTS

| | | |
|---|---|---|
| KR | 10-1036780 B1 | 5/2011 |
| KR | 10-2011-0076892 A | 7/2011 |
| KR | 10-2011-0105268 A | 9/2011 |
| KR | 10-2014-0079306 A | 6/2014 |
| KR | 10-2018-0072245 A | 6/2018 |
| WO | WO 2011/010842 A2 | 1/2011 |

* cited by examiner

[FIG. 1]
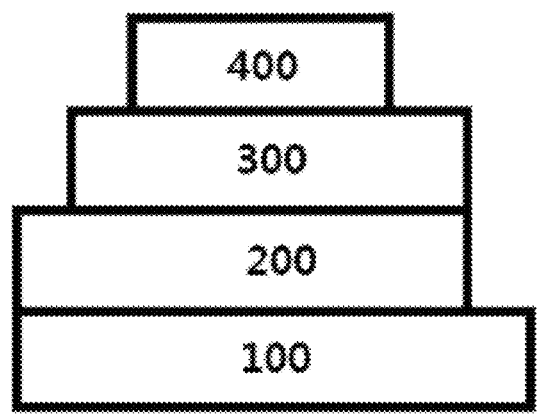
[FIG. 2]
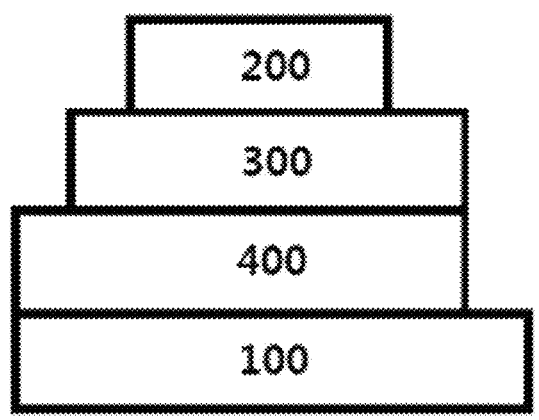

[FIG. 3]
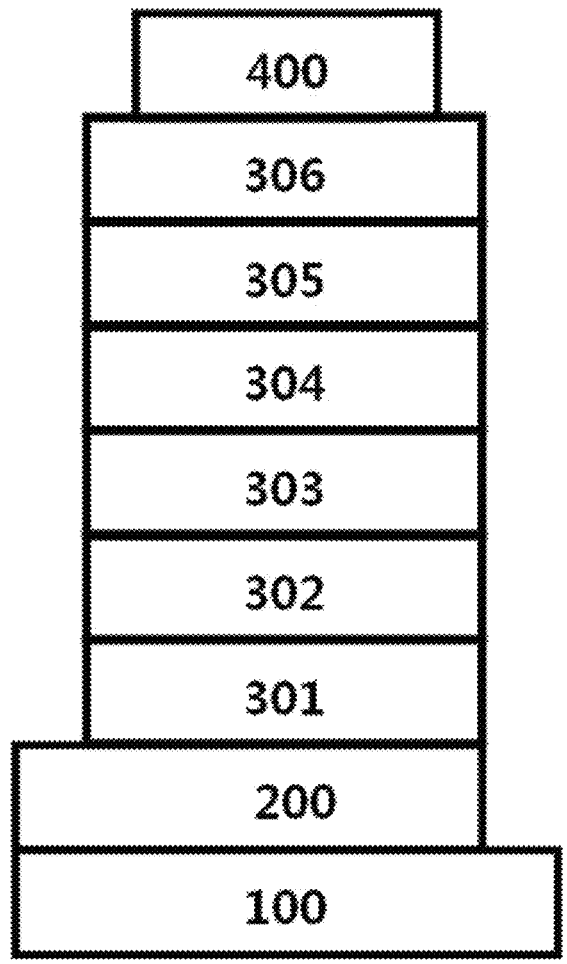

[FIG. 4]

| CATHODE |
| --- |
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT EMITTING ELEMENT COMPRISING SAME

TECHNICAL FIELD

The present specification relates to a heterocyclic compound and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present disclosure is directed to providing a novel heterocyclic compound and an organic light emitting device comprising the same.

Technical Solution

One embodiment of the present application provides a heterocyclic compound represented by the following Chemical Formula 1.

[Chemical Formula 1]

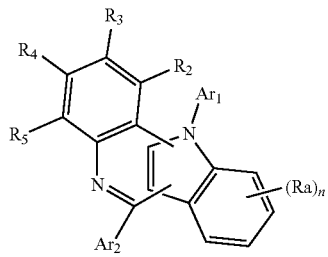

In Chemical Formula 1, $R_2$ to $R_5$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring, Ra is hydrogen; a substituted or unsubstituted alkyl group; a substituted or unsubstituted aryl group; or a substituted or unsubstituted heteroaryl group, $Ar_1$ is represented by -(L1)p-(Z1)q, $Ar_2$ is represented by -(L2)r-(Z2)s, L1 and L2 are the same as or different from each other, and each independently a substituted or unsubstituted arylene group; or a substituted or unsubstituted heteroarylene group, Z1 and Z2 are the same as or different from each other, and each independently selected form the group consisting of deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, R, R' and R" are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, p and r are an integer of 1 to 4, q and s are an integer of 1 to 3, and n is an integer of 0 to 4.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to one embodiment of the present application.

Advantageous Effects

The compound described in the present specification can be used as an organic material layer material of an organic light emitting device. The compound is capable of performing a role of a hole injection material, a hole transfer material, a light emitting material, an electron transfer material, an electron injection material and the like in the organic light emitting device. Particularly, the compound can be used as an electron transfer layer material, a hole blocking layer material or a charge generation layer material of the organic light emitting device.

Specifically, when using the compound represented by Chemical Formula 1 in the organic material layer, a driving voltage is lowered and light efficiency is enhanced in the device, and device lifetime properties can be enhanced by thermal stability of the compound.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent comprising Si, having the Si atom directly linked as a radical, and is represented by $-SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

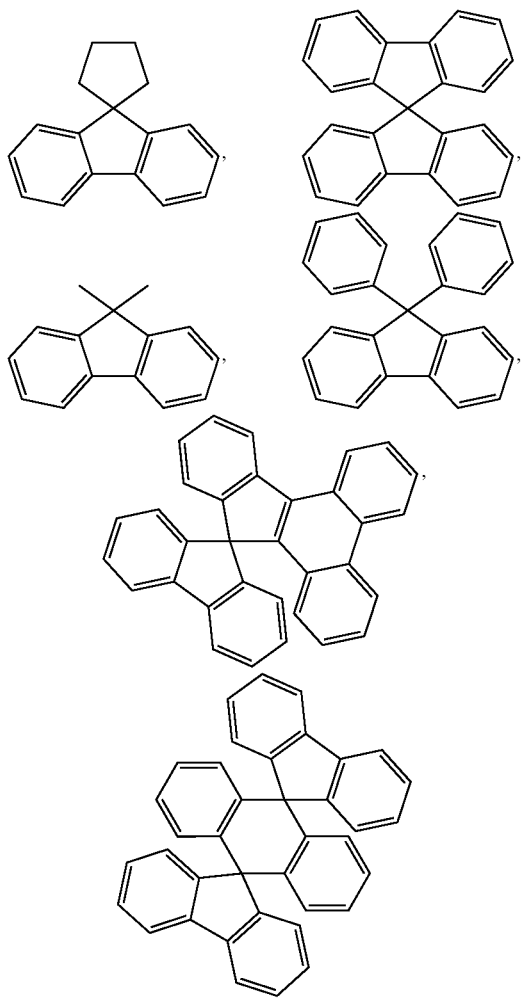

and the like may be included. However, the structure is not limited thereto.

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; $-NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

In the present specification, specific examples of the phosphine oxide group may comprise a diphenylphosphine oxide group, a dinaphthylphosphine oxide and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a compound represented by Chemical Formula 1.

Chemical Formula 1 has a structure of a quinoline group being fused to an indole group, and when having an indole group, Chemical Formula 1 has a sp3 unshared electron pair instead of a sp2 unshared electron pair in the structure. Accordingly, hole transfer properties are particularly superior compared to when having benzothiophene or benzofuran with a sp2 noncovalent bond. This affects exciton formation in a light emitting layer when used as an organic material layer of an organic light emitting device afterword resulting in an increase in the device efficiency and lifetime.

In one embodiment of the present application, $R_2$ to $R_5$ of Chemical Formula 1 are the same as or different from each other, and may be each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aliphatic or aromatic hydrocarbon ring.

In another embodiment, $R_2$ to $R_5$ of Chemical Formula 1 are the same as or different from each other, and may be each independently selected from the group consisting of hydrogen; a substituted or unsubstituted C1 to C60 aryl group; and a substituted or unsubstituted C2 to C60 heteroaryl group, or two or more groups adjacent to each other may bond to each other to form a substituted or unsubstituted aromatic hydrocarbon ring.

In another embodiment, $R_2$ to $R_5$ of Chemical Formula 1 are the same as or different from each other, and may be each independently hydrogen, or two or more groups adjacent to each other may bond to each other to form a substituted or unsubstituted C2 to C60 aromatic hydrocarbon ring.

In another embodiment, $R_2$ to $R_5$ of Chemical Formula 1 are the same as or different from each other, and may be each independently hydrogen, or two or more groups adjacent to each other may bond to each other to form a C2 to C40 aromatic hydrocarbon ring.

In another embodiment, $R_2$ to $R_5$ of Chemical Formula 1 are the same as or different from each other, and may be each independently hydrogen, or two or more groups adjacent to each other may bond to each other to form a benzene ring.

In one embodiment of the present application, $R_2$ and $R_3$ among $R_2$ to $R_5$ of Chemical Formula 1 bond to each other to form a benzene ring, and the rest may be hydrogen.

In one embodiment of the present application, $R_3$ and $R_4$ among $R_2$ to $R_5$ of Chemical Formula 1 bond to each other to form a benzene ring, and the rest may be hydrogen.

In one embodiment of the present application, $R_4$ and $R_5$ among $R_2$ to $R_5$ of Chemical Formula 1 bond to each other to form a benzene ring, and the rest may be hydrogen.

In one embodiment of the present application, Ra of Chemical Formula 1 may be hydrogen; a substituted or unsubstituted alkyl group; a substituted or unsubstituted aryl group; or a substituted or unsubstituted heteroaryl group.

In another embodiment, Ra of Chemical Formula 1 may be hydrogen; a substituted or unsubstituted C6 to C60 aryl group; or a substituted or unsubstituted C2 to C60 heteroaryl group.

In another embodiment, Ra of Chemical Formula 1 may be hydrogen; a C6 to C40 aryl group; or a C2 to C40 heteroaryl group.

In another embodiment, Ra of Chemical Formula 1 may be hydrogen.

In one embodiment of the present application, $Ar_1$ may be represented by -(L1)p-(Z1)q, and $Ar_2$ may be represented by -(L2)r-(Z2)s.

By $Ar_1$ and $Ar_2$ of Chemical Formula 1 of the present application being substituted with each substituent, thermal stability is superior compared to when single substituted, and structurally, indole-structured substituents controlling hole transfer properties may be introduced more diversely compared to when single substituted, and controlling structural properties may be superior.

In one embodiment of the present application, L1 and L2 are the same as or different from each other, and may be each independently a substituted or unsubstituted arylene group; or a substituted or unsubstituted heteroarylene group.

In another embodiment, L1 and L2 are the same as or different from each other, and may be each independently a substituted or unsubstituted C6 to C60 arylene group; or a substituted or unsubstituted C2 to C60 heteroarylene group.

In another embodiment, L1 and L2 are the same as or different from each other, and may be each independently a C6 to C40 arylene group; or a C2 to C40 heteroarylene group.

In another embodiment, L1 and L2 are the same as or different from each other, and may be each independently a C6 to C40 arylene group; or a C2 to C40 heteroarylene group.

In another embodiment, L1 and L2 are the same as or different from each other, and may be each independently a phenylene group; a biphenylene group; a naphthalene group; a phenanthrenylene group; a triphenylenylene group; a fluoranthenylene group; a pyrenylene group; a divalent pyridine group; a divalent pyrimidine group; or a divalent triazine group.

In one embodiment of the present application, L1 may be a substituted or unsubstituted C6 to C60 arylene group; or a substituted or unsubstituted C2 to C60 heteroarylene group.

In another embodiment, L1 may be a substituted or unsubstituted C6 to C40 arylene group; or a substituted or unsubstituted C2 to C40 heteroarylene group.

In another embodiment, L1 may be a C6 to C40 arylene group; or a C2 to C40 heteroarylene group.

In another embodiment, L1 may be a phenylene group; a biphenylene group; a naphthalene group; a phenanthrenylene group; a divalent pyridine group; a divalent pyrimidine group; or a divalent triazine group.

In one embodiment of the present application, L2 may be a substituted or unsubstituted C6 to C60 arylene group; or a substituted or unsubstituted C2 to C60 heteroarylene group.

In another embodiment, L2 may be a substituted or unsubstituted C6 to C40 arylene group; or a substituted or unsubstituted C2 to C40 heteroarylene group.

In another embodiment, L2 may be a C6 to C40 arylene group; or a C2 to C40 heteroarylene group.

In another embodiment, L2 may be a phenylene group; a biphenylene group; a naphthalene group; a phenanthrenylene group; a triphenylenylene group; a fluoranthenylene group; a pyrenylene group; a divalent pyridine group; a divalent pyrimidine group; or a divalent triazine group.

In one embodiment of the present application, Z1 and Z2 are the same as or different from each other, and may be each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group.

In another embodiment, Z1 and Z2 are the same as or different from each other, and may be each independently hydrogen; a substituted or unsubstituted aryl group; a substituted or unsubstituted heteroaryl group; or P(=O)RR'.

In another embodiment, Z1 and Z2 are the same as or different from each other, and may be each independently hydrogen; a substituted or unsubstituted C6 to C60 aryl group; a substituted or unsubstituted C2 to C60 heteroaryl group; or P(=O)RR'.

In another embodiment, Z1 and Z2 are the same as or different from each other, and may be each independently hydrogen; a substituted or unsubstituted C6 to C40 aryl group; a substituted or unsubstituted C2 to C40 heteroaryl group; or P(=O)RR'.

In another embodiment, Z1 and Z2 are the same as or different from each other, and may be each independently hydrogen; a C6 to C40 aryl group unsubstituted or substituted with one or more substituents selected from the group consisting of a C6 to C40 aryl group, a C2 to C40 heteroaryl group, a C1 to C40 alkyl group and —CN; a C2 to C40 heteroaryl group unsubstituted or substituted with a C6 to C40 aryl group; or P(=O)RR', and the substituent may be unsubstituted or substituted again with a C1 to C40 alkyl group; or a C6 to C40 aryl group.

In another embodiment, Z1 and Z2 are the same as or different from each other, and may be each independently hydrogen; P(=O)RR'; a phenyl group unsubstituted or substituted with one or more substituents selected from the group consisting of a 9,9'-dimethylfluorene group, —CN, a triphenylene group, a phenanthrene group, a phenyl group, a dibenzofuran group and a dibenzothiophene group; a phenyl group unsubstituted or substituted with a carbazole group unsubstituted or substituted with a phenyl group; a biphenyl group; a triphenylene group; a fluorene group unsubstituted or substituted with a methyl group; a phenanthrene group; a spirofluorene group; a pyridine group; a carbazole group; a dibenzofuran group; a dibenzothiophene group; or a phenanthroline group unsubstituted or substituted with a phenyl group.

In one embodiment of the present application, Z1 may be hydrogen; P(=O)RR'; a phenyl group unsubstituted or substituted with one or more substituents selected from the group consisting of a carbazole group unsubstituted or substituted with a phenyl group, a dibenzofuran group and a dibenzothiophene group; a biphenyl group; a spirobifluorene group; a fluorene group unsubstituted or substituted with a methyl group; a pyridine group; a dibenzofuran group; a dibenzothiophene group; or a phenanthroline group unsubstituted or substituted with a phenyl group.

In one embodiment of the present application, Z2 may be hydrogen; P(=O)RR'; a phenyl group unsubstituted or substituted with one or more substituents selected from the group consisting of a phenyl group, a phenanthrene group, a triphenylene group, —CN, a 9,9'-dimethylfluorene group, a carbazole group and a dibenzofuran group; a biphenyl group; a triphenylene group; a fluorene group unsubstituted or substituted with a methyl group; a phenanthrene group; a pyridine group; a carbazole group; or a dibenzofuran group.

In one embodiment of the present application, R, R' and R" are the same as or different from each other, and may be each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group.

In another embodiment, R, R' and R" are the same as or different from each other, and may be each independently a substituted or unsubstituted aryl group.

In another embodiment, R, R' and R" are the same as or different from each other, and may be each independently a substituted or unsubstituted C6 to C60 aryl group.

In another embodiment, R, R' and R" are the same as or different from each other, and may be each independently a substituted or unsubstituted C6 to C40 aryl group.

In another embodiment, R, R' and R" are the same as or different from each other, and may be each independently a C6 to C40 aryl group.

In another embodiment, R, R' and R" are the same as or different from each other, and may be each independently a phenyl group.

In the heterocyclic compound provided in one embodiment of the present application, Chemical Formula 1 may be represented by any one of the following Chemical Formulae 2 to 9.

[Chemical Formula 2]

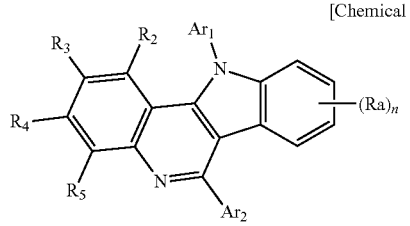

[Chemical Formula 3]

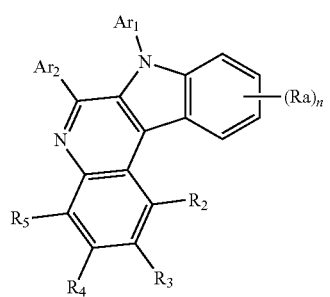

[Chemical Formula 4]

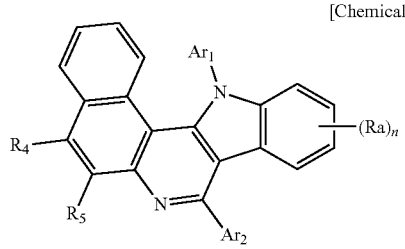

[Chemical Formula 5]

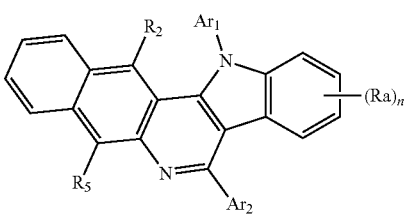

[Chemical Formula 6]

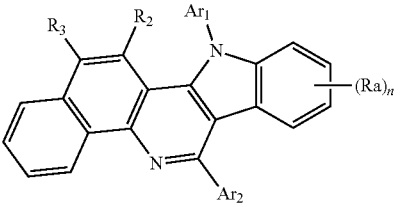

[Chemical Formula 7]

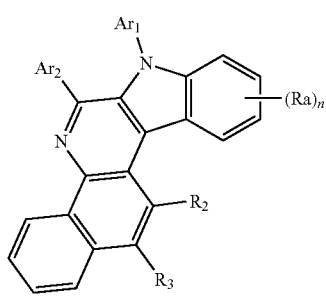

[Chemical Formula 8]

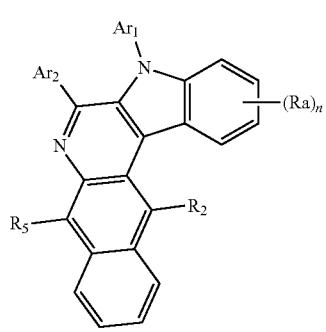

[Chemical Formula 9]

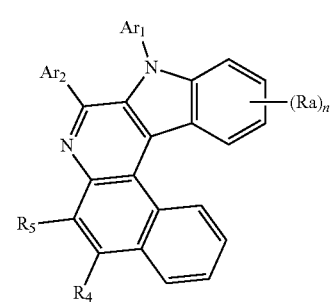

In Chemical Formulae 2 to 9,

Ra, $Ar_1$, $Ar_2$, $R_2$ to $R_5$ and n have the same definitions as in Chemical Formula 1.

In the heterocyclic compound provided in one embodiment of the present application, Chemical Formula 1 is represented by any one of the following compounds.

1
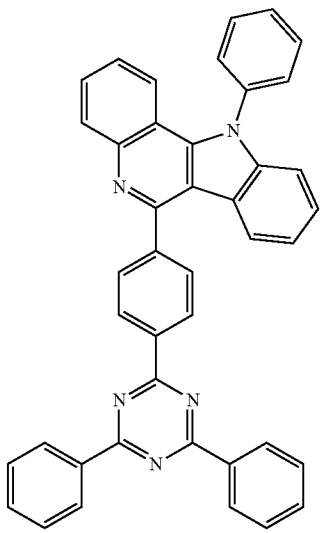 [SMILES: c1ccc(-c2cc(-c3ccc(-c4nc5ccccc5c5c4c4ccccc4n5-c4ccccc4)cc3)nc(-c3ccccc3)n2)cc1]
2
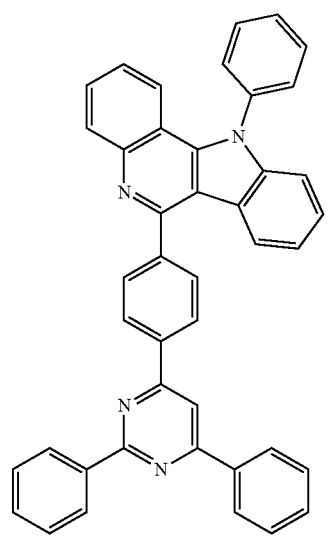
4
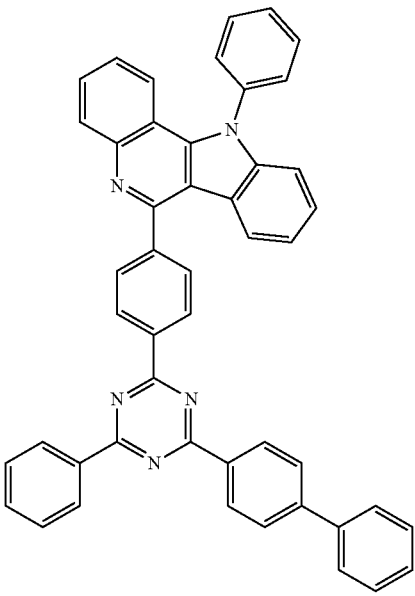 [SMILES: c1ccc(-c2ccc(-c3nc(-c4ccccc4)nc(-c4ccc(-c5nc6ccccc6c6c5c5ccccc5n6-c5ccccc5)cc4)n3)cc2)cc1]
5
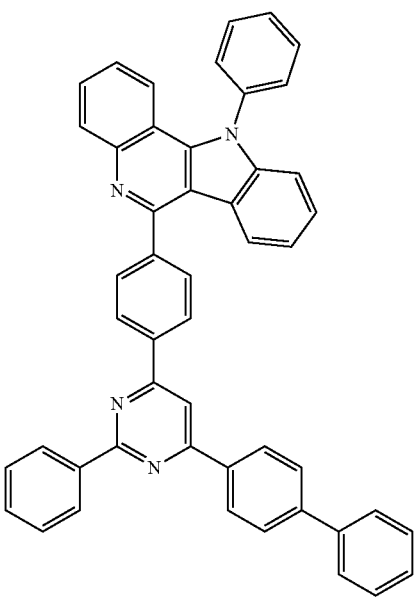

6
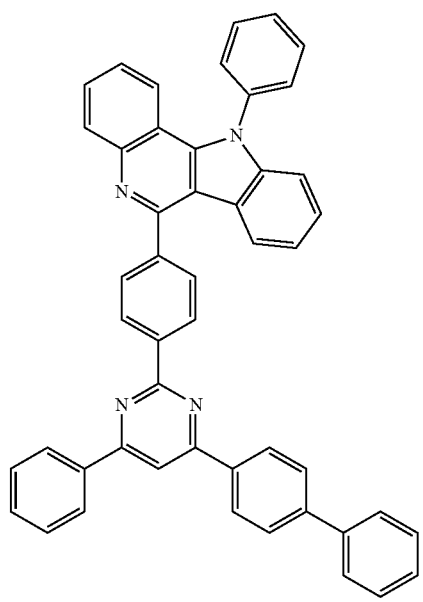 [SMILES: c1ccc(-c2ccc(-c3cc(-c4ccccc4)nc(-c4ccc(-c5nc6ccccc6c6c5c5ccccc5n6-c5ccccc5)cc4)n3)cc2)cc1]
8
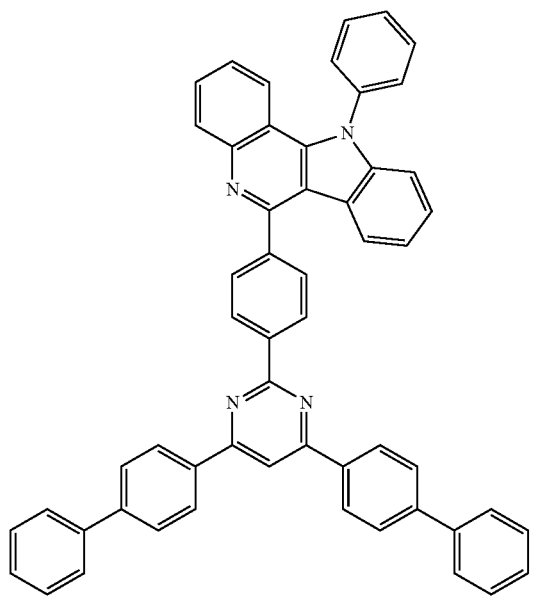
7
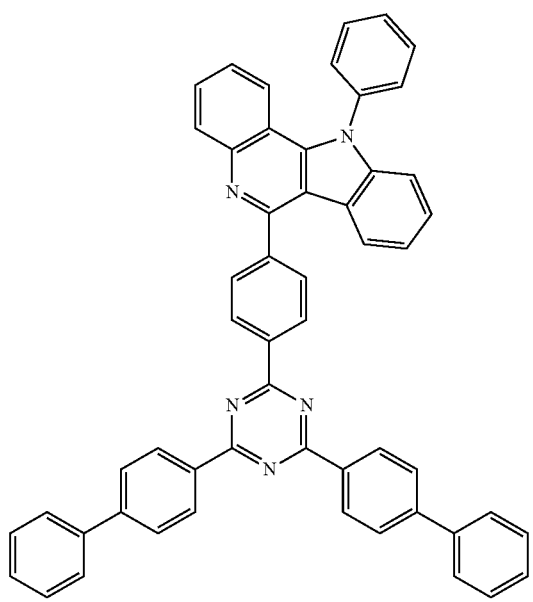 [SMILES: c1ccc(-c2ccc(-c3nc(-c4ccc(-c5ccccc5)cc4)nc(-c4ccc(-c5nc6ccccc6c6c5c5ccccc5n6-c5ccccc5)cc4)n3)cc2)cc1]
9
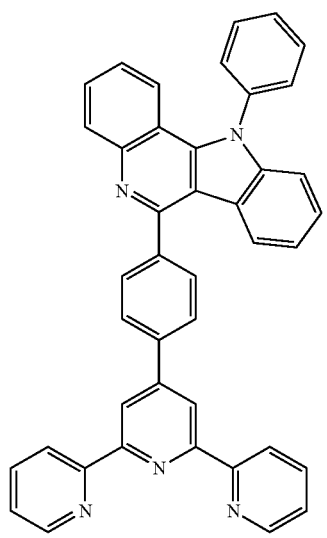

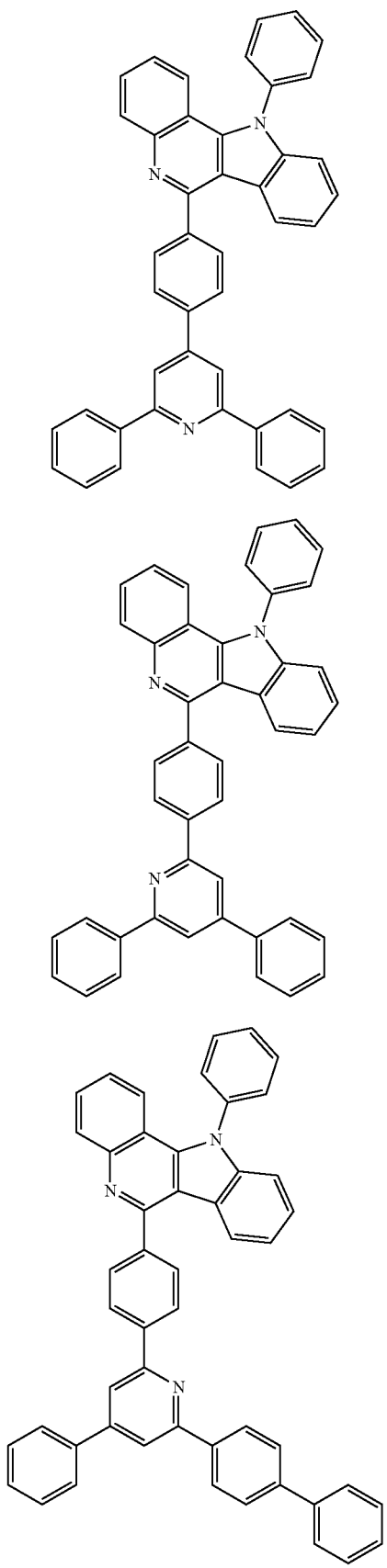
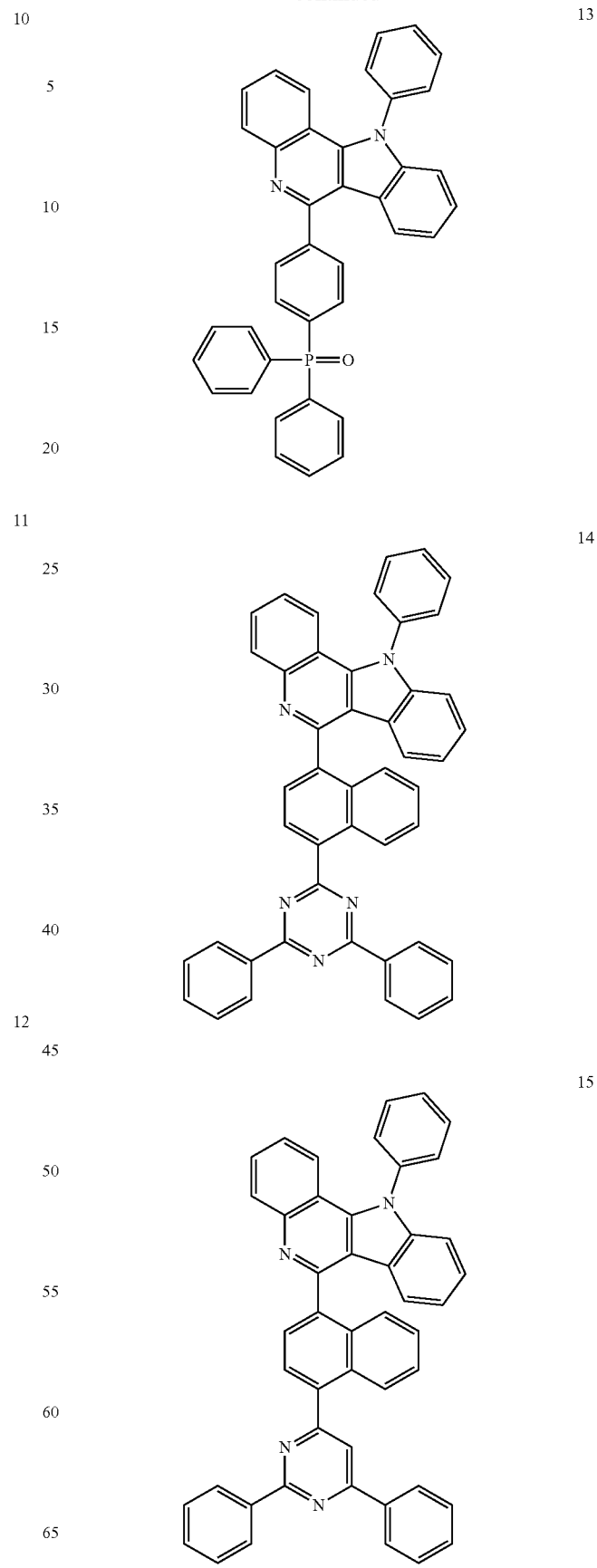

16
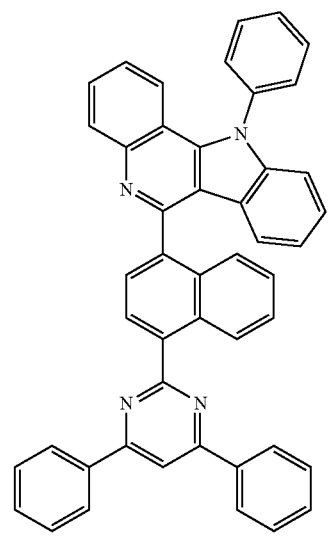
17
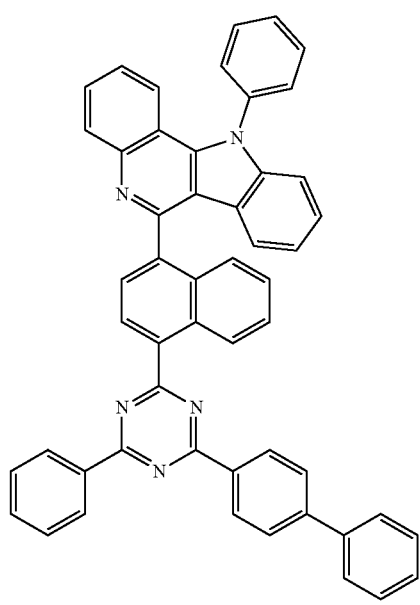
18
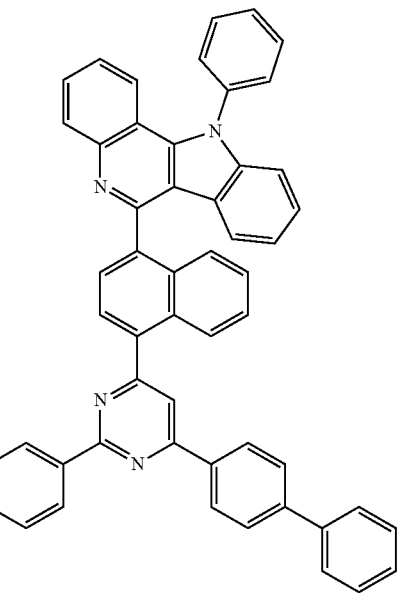
19
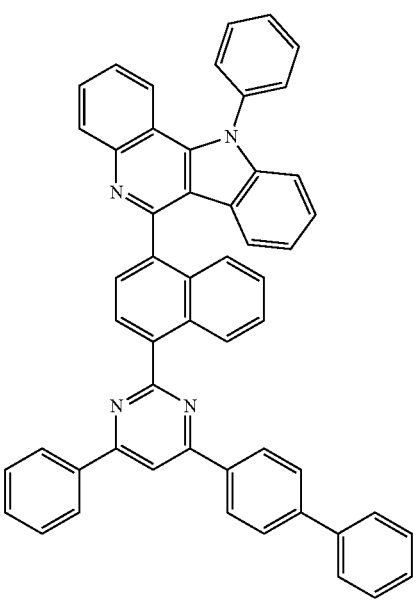

20
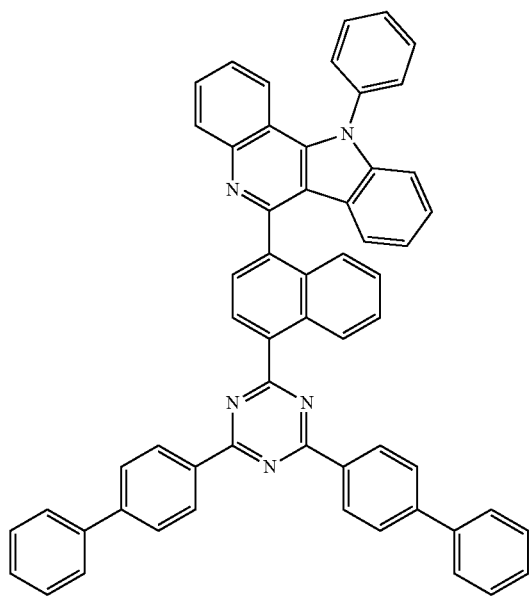
22
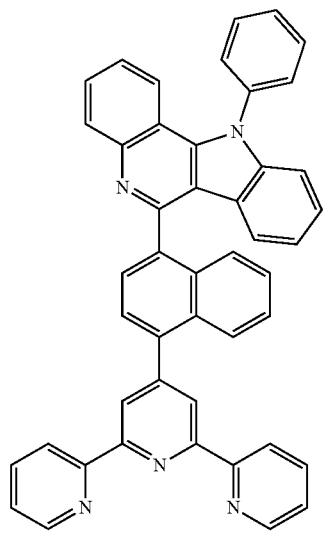
23
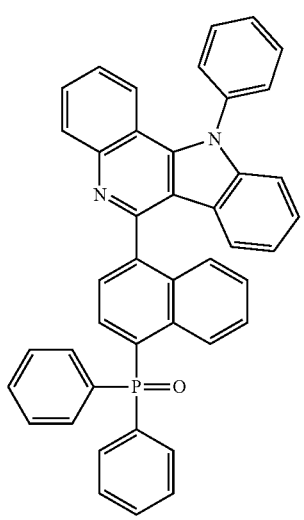

24
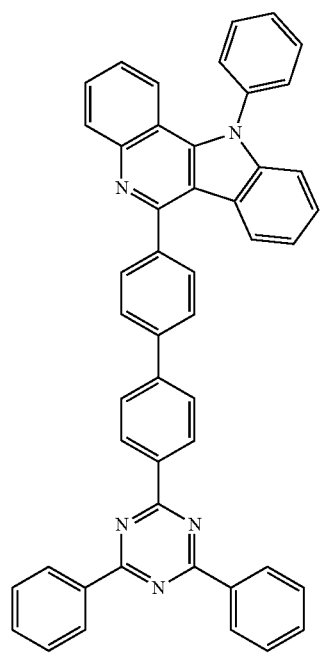
26
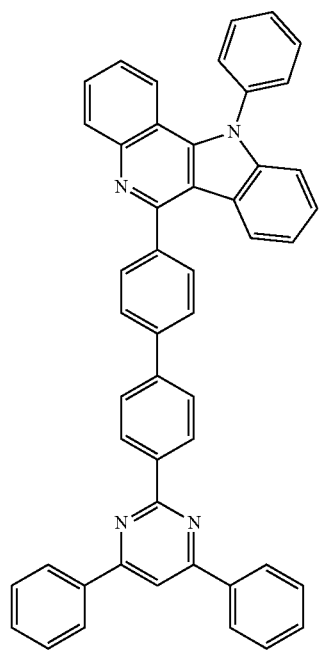 [SMILES: c1ccc(-c2cc(-c3ccccc3)nc(-c3ccc(-c4ccc(-c5nc6ccccc6c6c5c5ccccc5n6-c5ccccc5)cc4)cc3)n2)cc1]
25
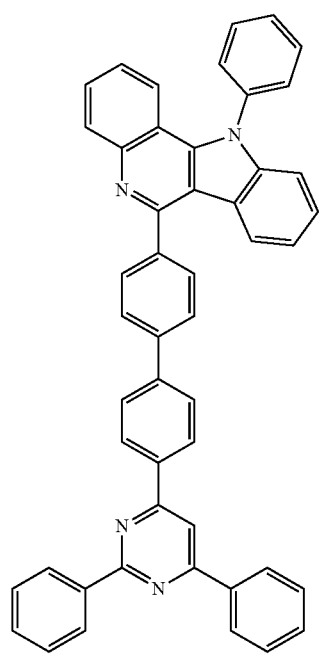
27
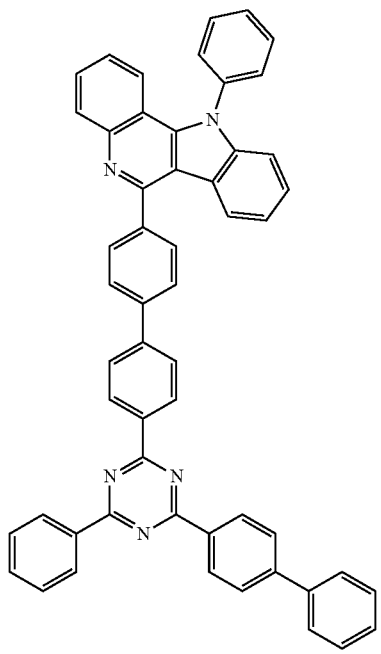

28
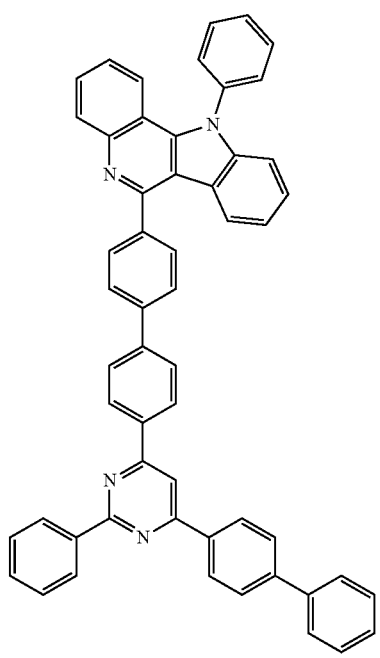
29
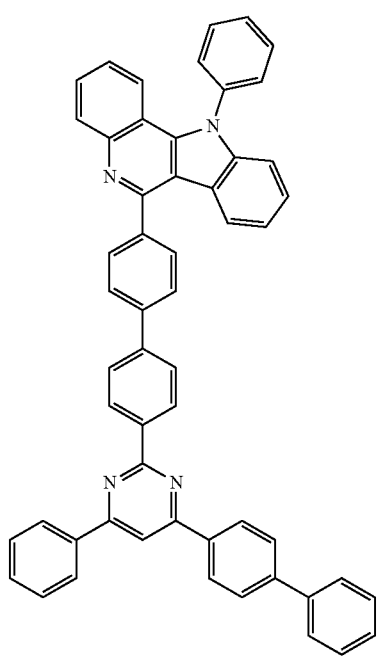 [SMILES: c1ccc(-c2ccc(-c3cc(-c4ccc(-c5ccc(-c6nc7ccccc7c7c6c6ccccc6n7-c6ccccc6)cc5)cc4)nc(-c4ccccc4)n3)cc2)cc1]
30
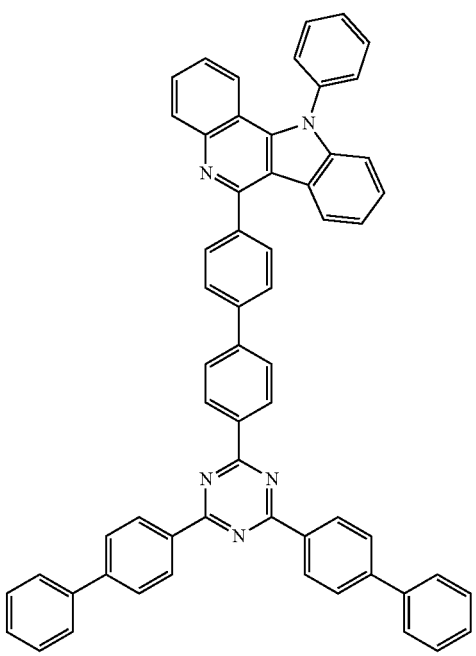
31
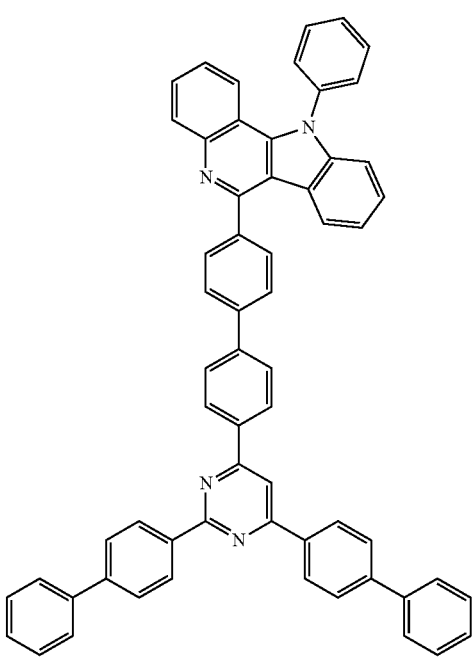 [SMILES: c1ccc(-c2ccc(-c3cc(-c4ccc(-c5ccc(-c6nc7ccccc7c7c6c6ccccc6n7-c6ccccc6)cc5)cc4)nc(-c4ccc(-c5ccccc5)cc4)n3)cc2)cc1]

32
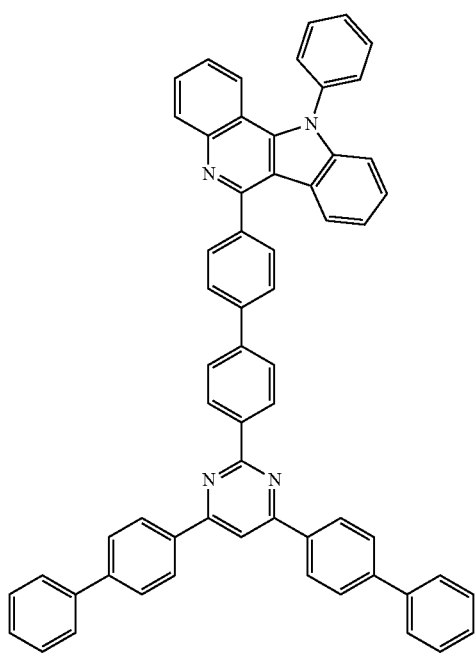
33
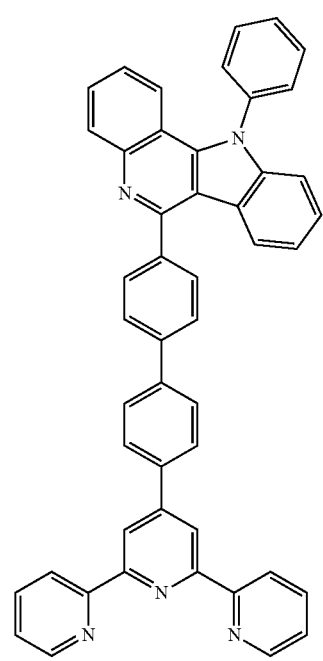 [SMILES: c1ccc(-n2c3ccccc3c3c(-c4ccc(-c5ccc(-c6cc(-c7ccccn7)nc(-c7ccccn7)c6)cc5)cc4)nc4ccccc4c32)cc1]
34
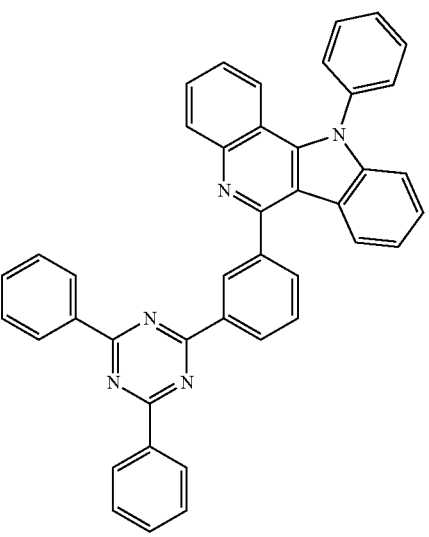
35

36
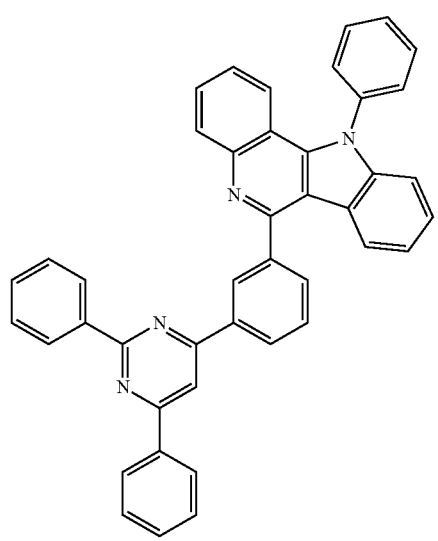
37
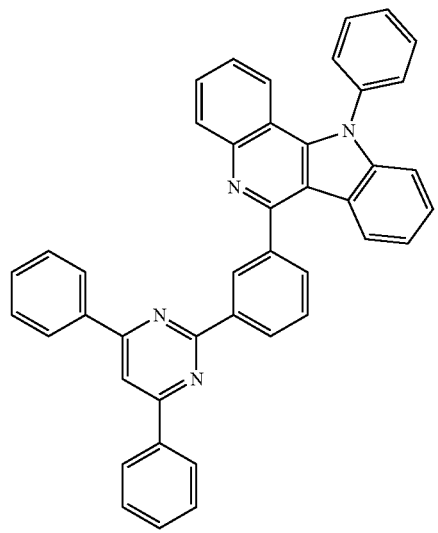
38
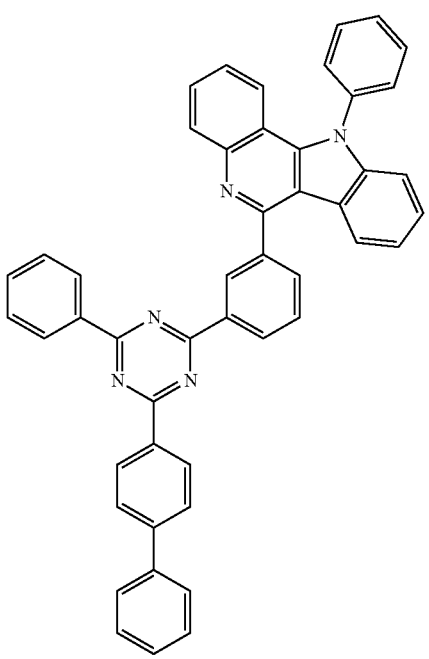
39
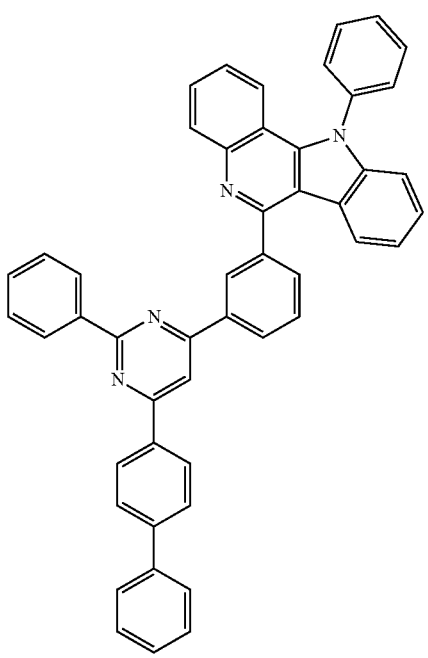

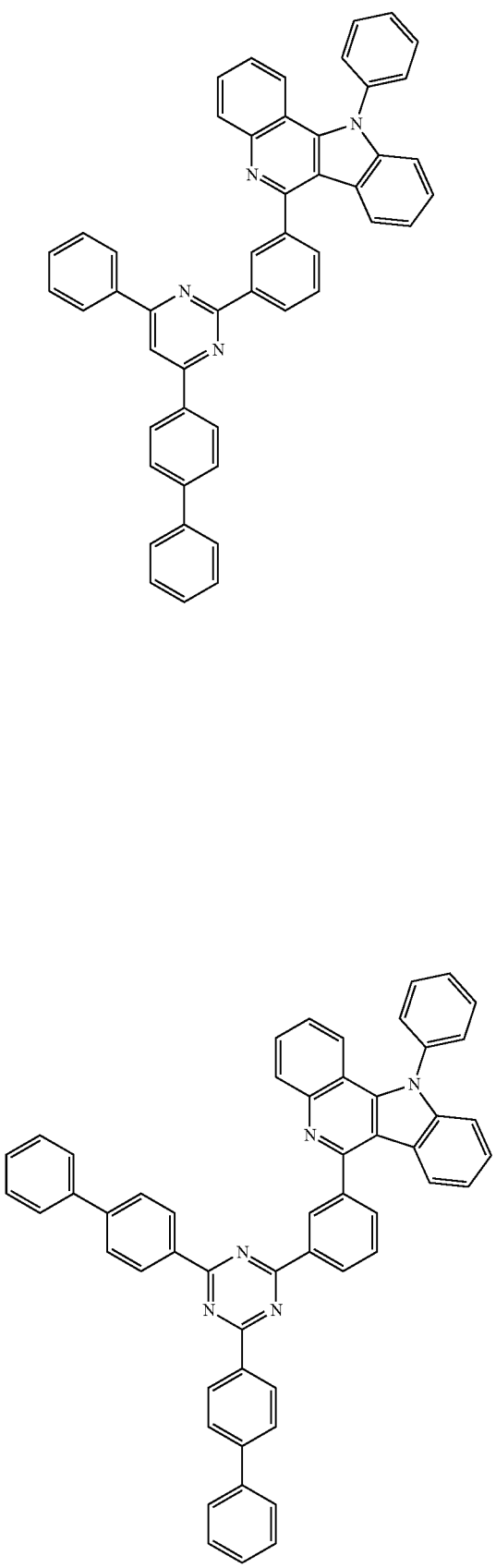
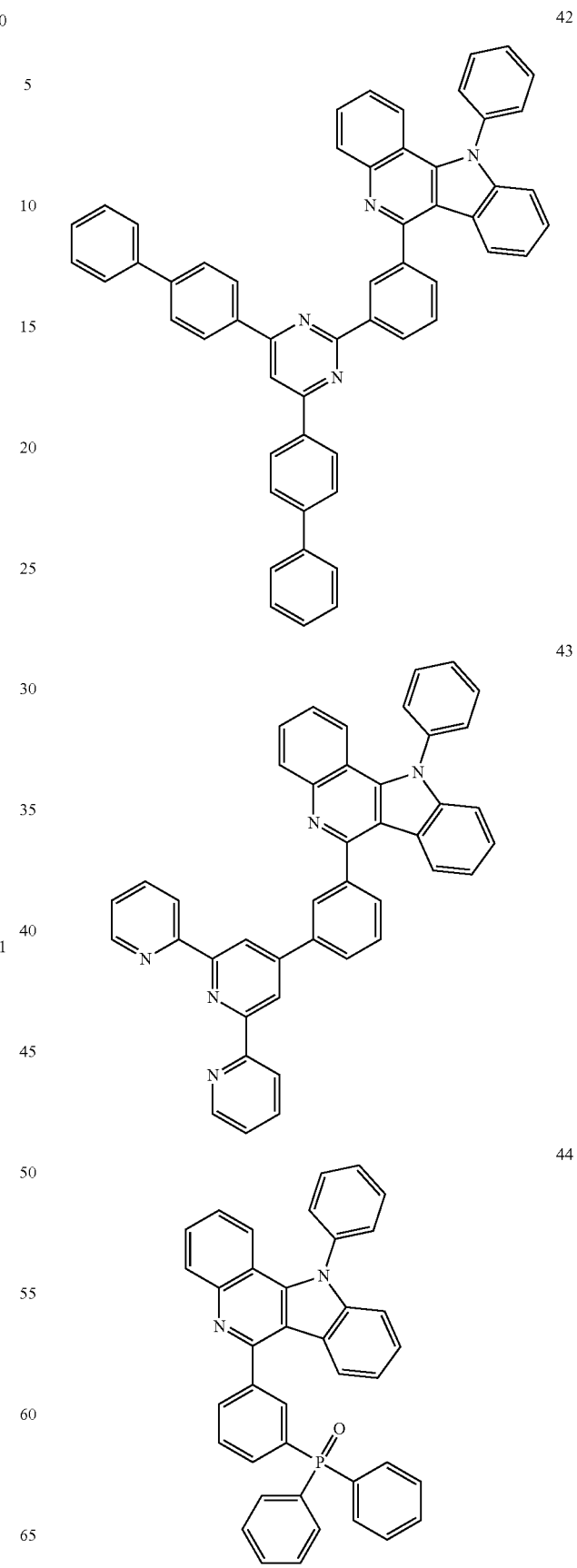

45
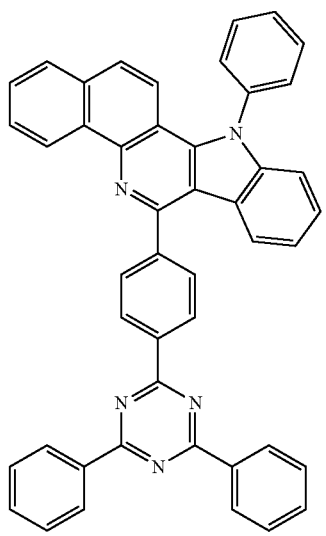
46
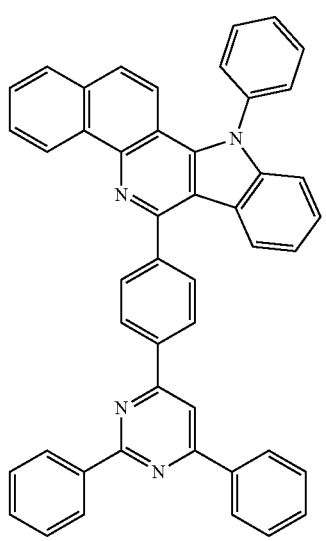
47
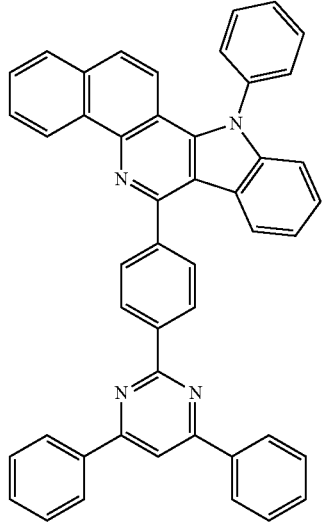
48
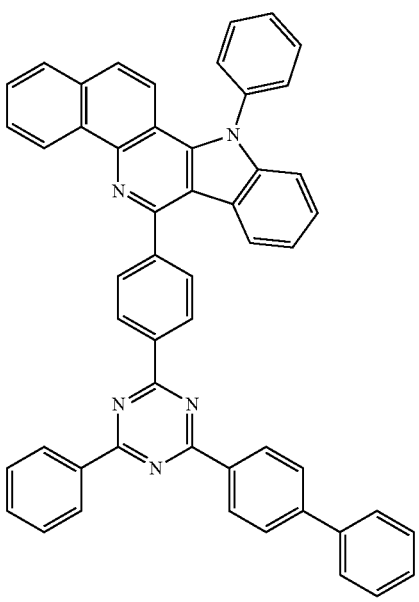
49
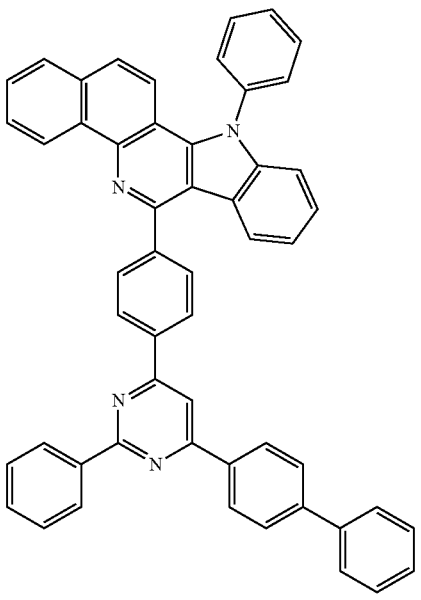

50
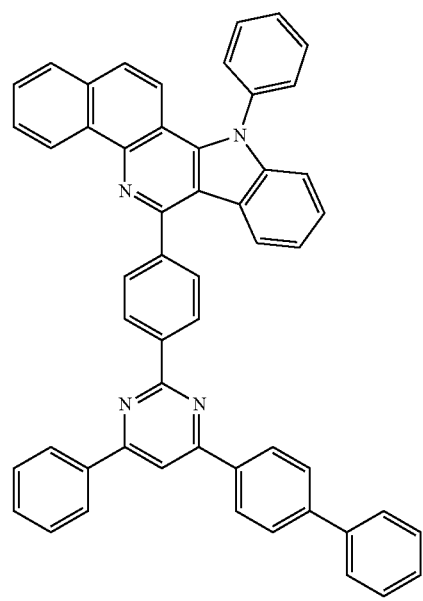
52
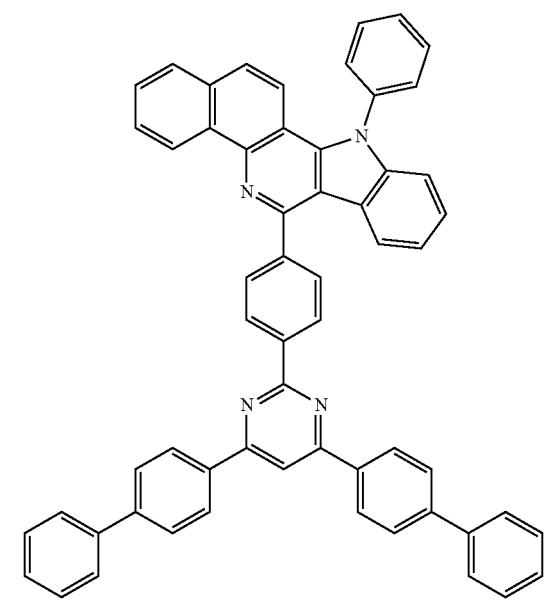
51
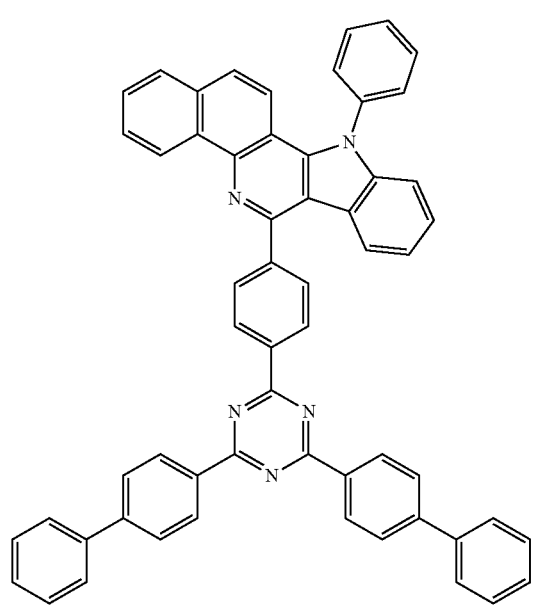
53
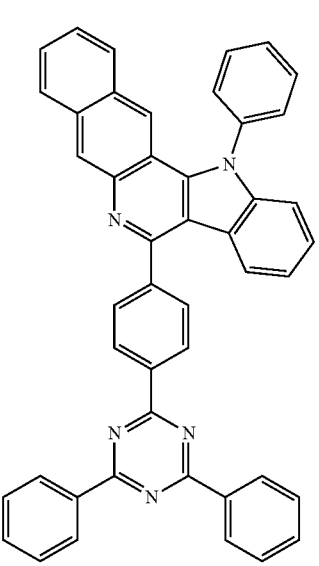

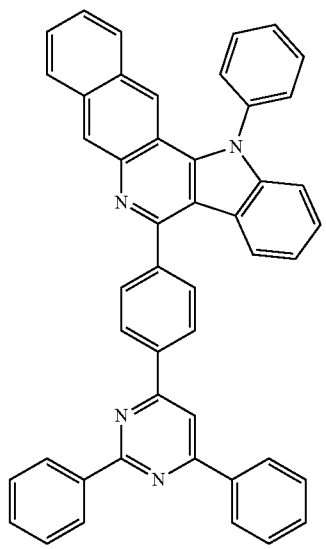
54
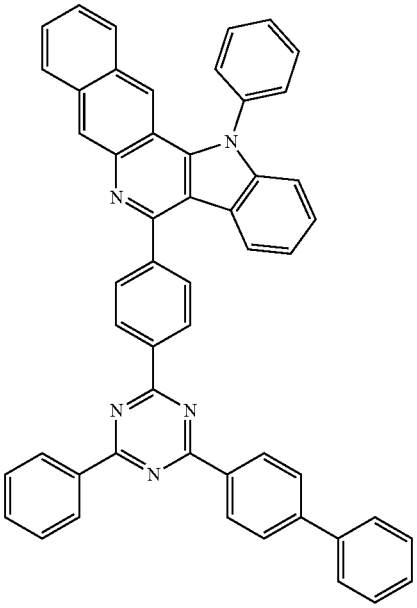
56
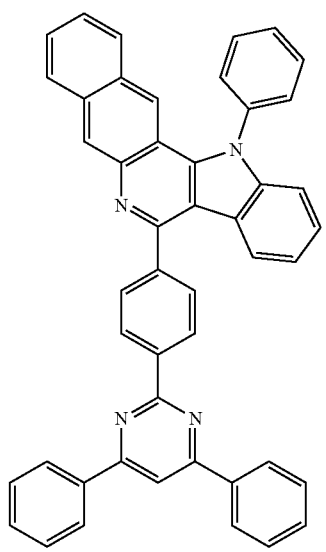
55
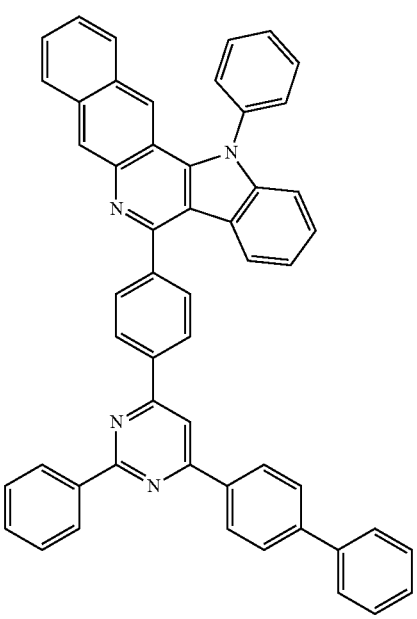
57

58
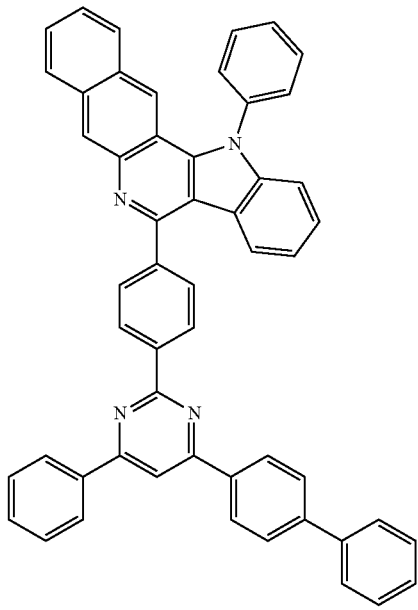
59
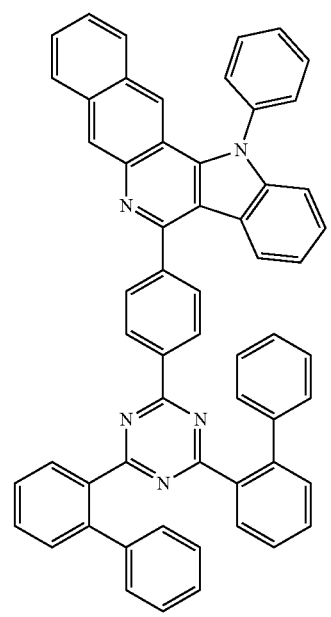
60
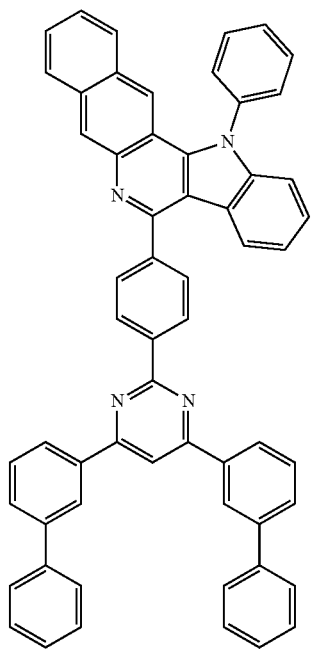
61
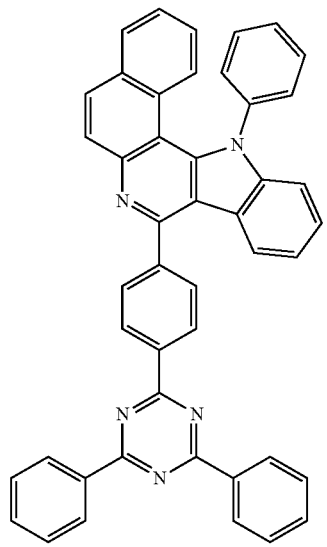

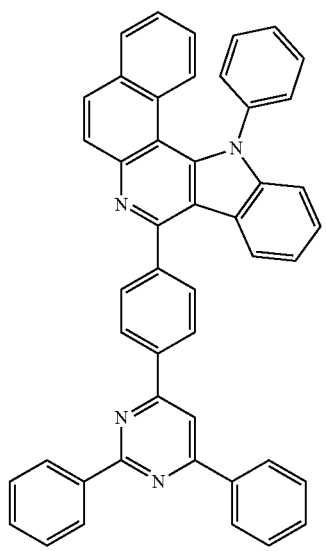
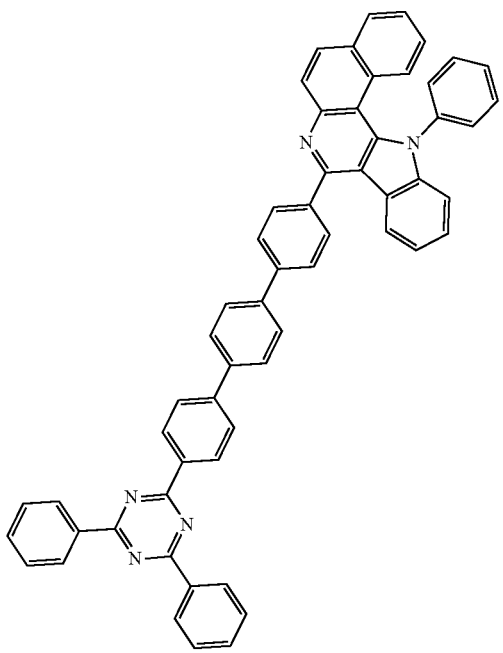
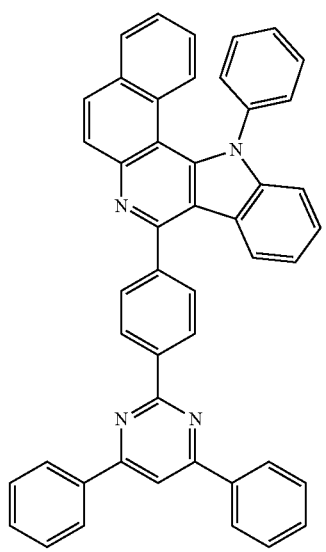
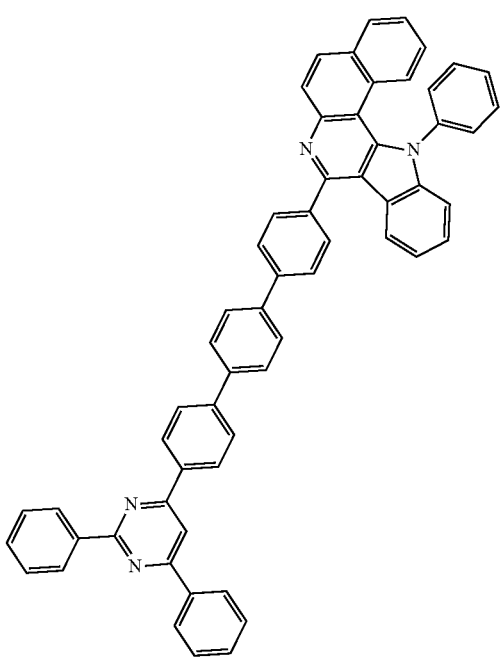

66
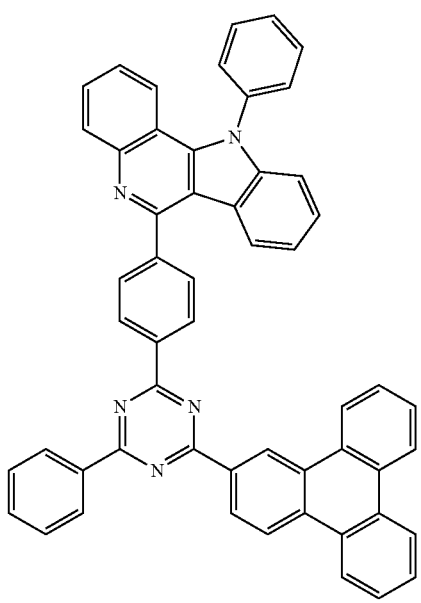 [SMILES: c1ccc(-c2nc(-c3ccc(-c4nc5ccccc5c5c4c4ccccc4n5-c4ccccc4)cc3)nc(-c3ccc4c5ccccc5c5ccccc5c4c3)n2)cc1]
68
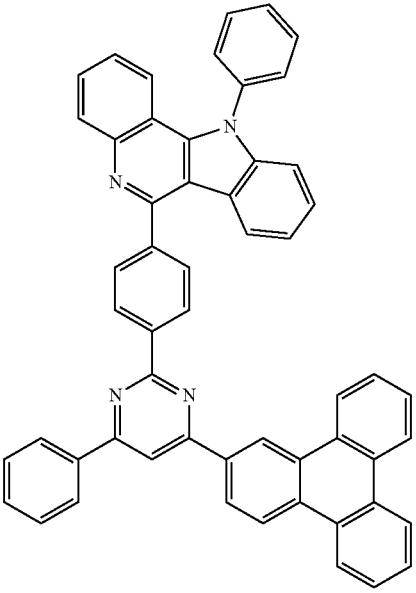 [SMILES: c1ccc(-c2cc(-c3ccc4c5ccccc5c5ccccc5c4c3)nc(-c3ccc(-c4nc5ccccc5c5c4c4ccccc4n5-c4ccccc4)cc3)n2)cc1]
67
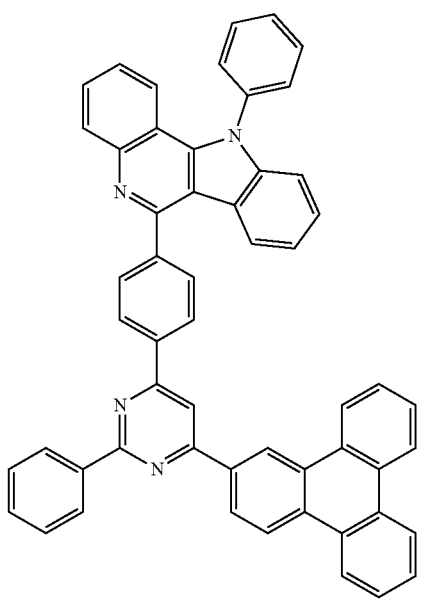
69
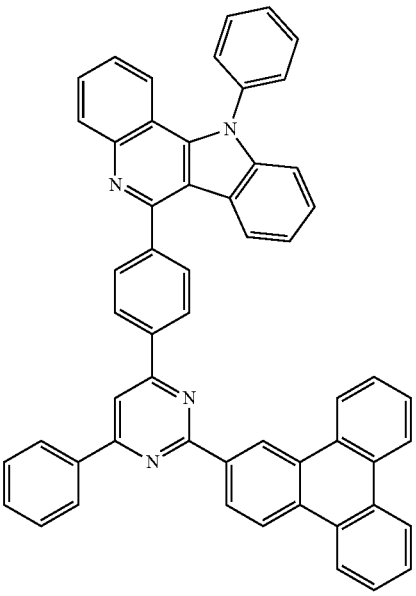

70
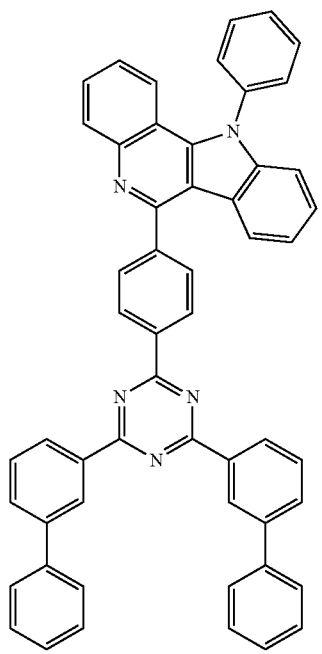
72
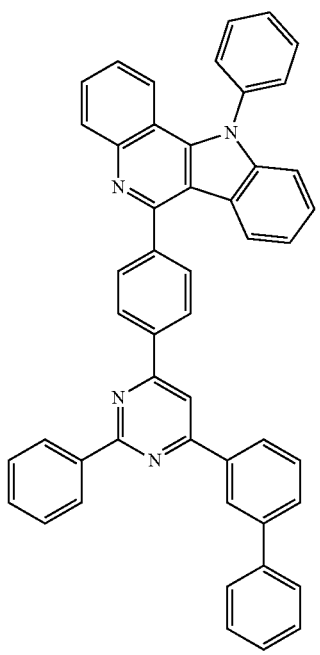
71
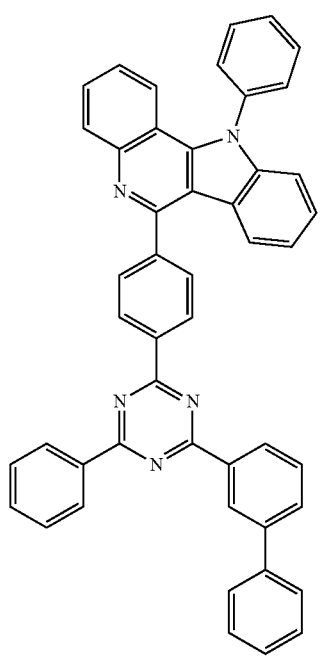
73
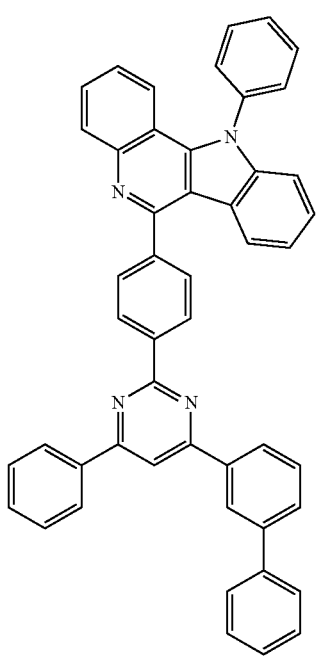 [SMILES: c1ccc(-c2cccc(-c3cc(-c4ccccc4)nc(-c4ccc(-c5nc6ccccc6c6c5c5ccccc5n6-c5ccccc5)cc4)n3)c2)cc1]

74
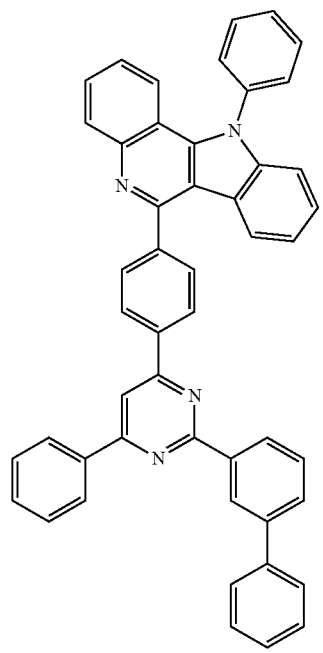
75
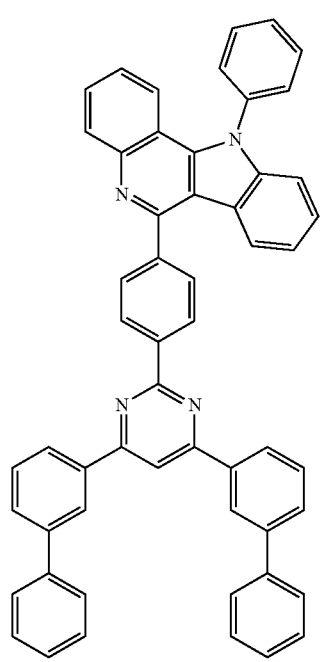
76
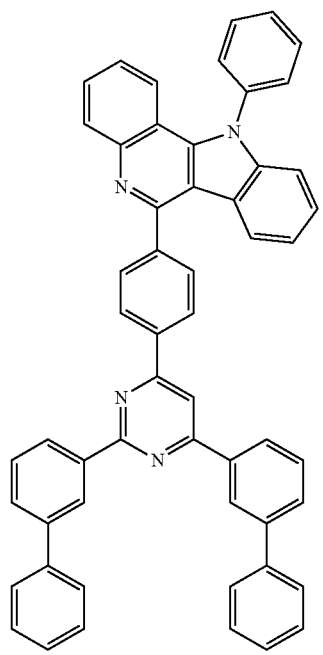
77
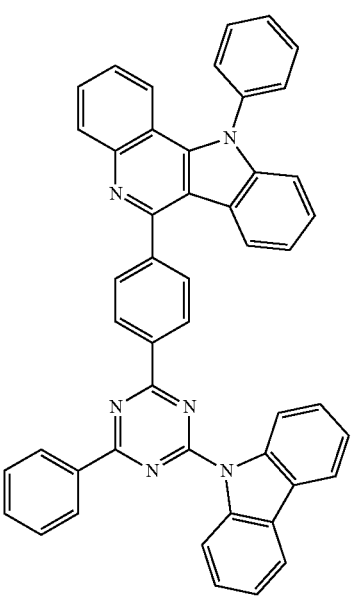 [SMILES: c1ccc(-c2nc(-c3ccc(-c4nc5ccccc5c5c4c4ccccc4n5-c4ccccc4)cc3)nc(-n3c4ccccc4c4ccccc43)n2)cc1]

78
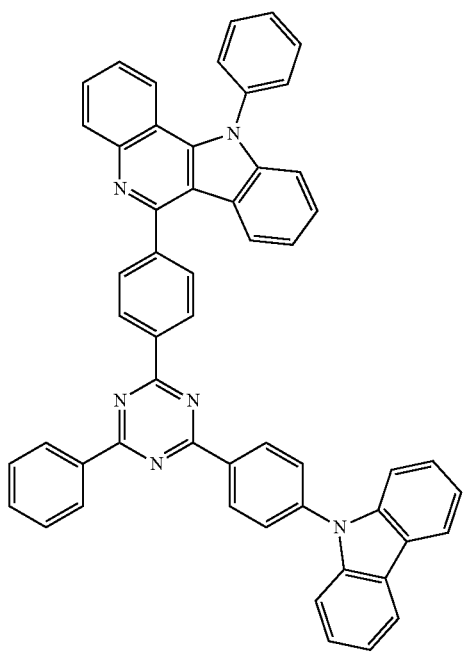
79
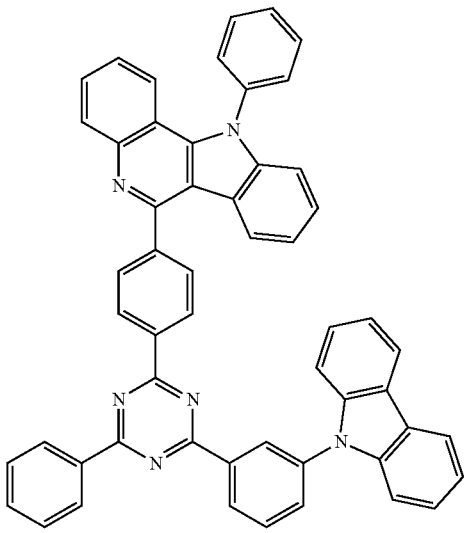
80
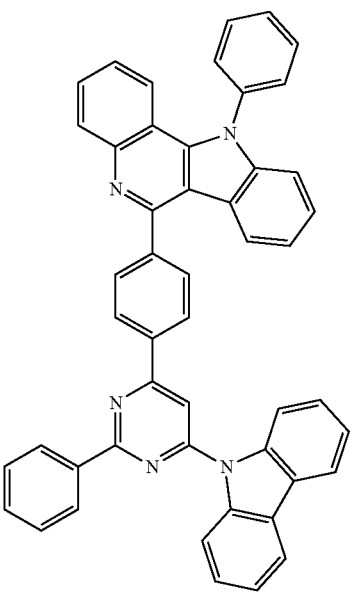
81
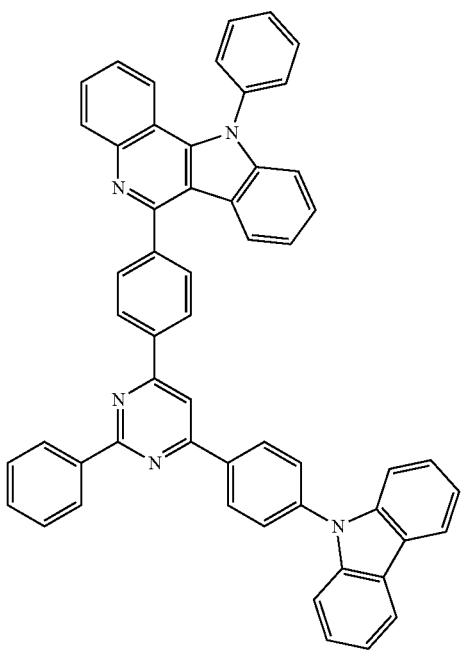

82
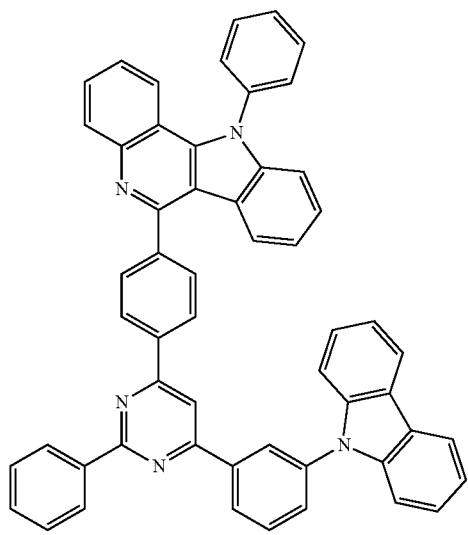
83
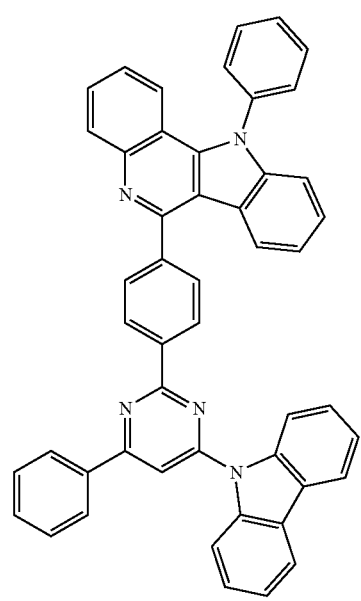
84
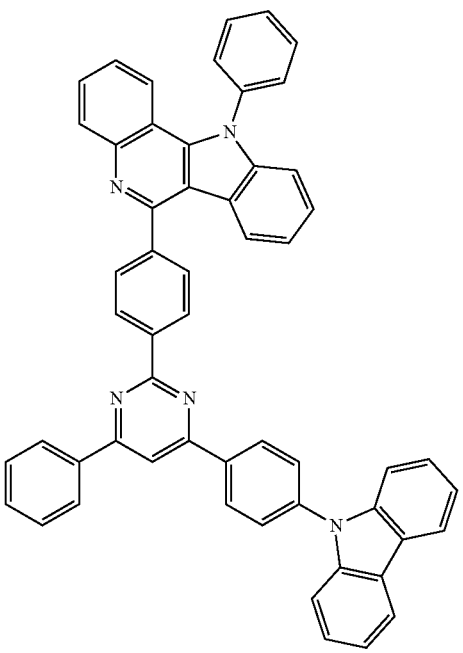 [SMILES: c1ccc(-c2nc(-c3ccc(-c4nc5ccccc5c5c4c4ccccc4n5-c4ccccc4)cc3)nc(-c3ccc(-n4c5ccccc5c5ccccc54)cc3)n2)cc1]
85
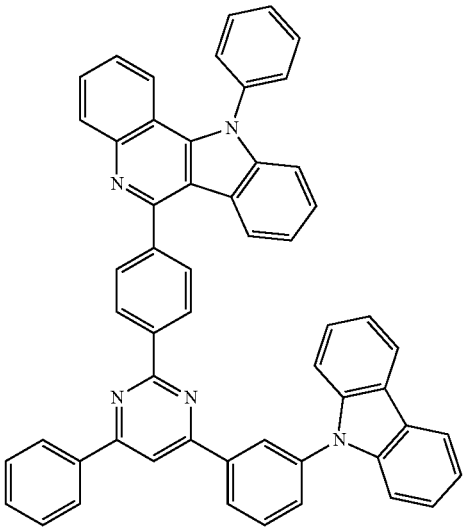

86
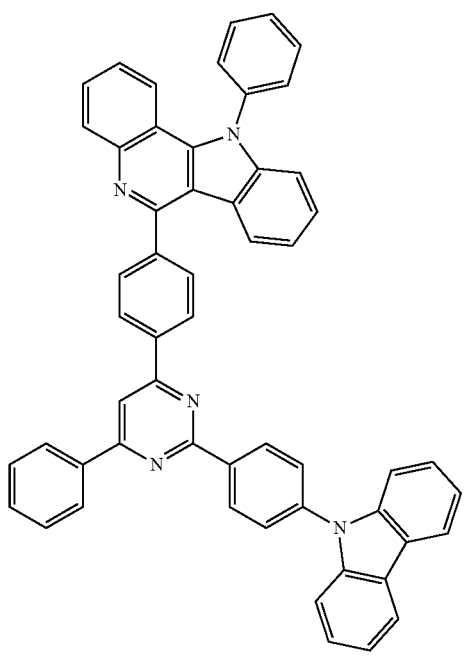
87
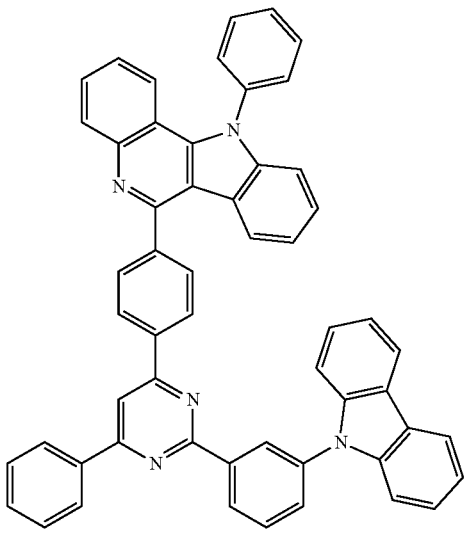
88
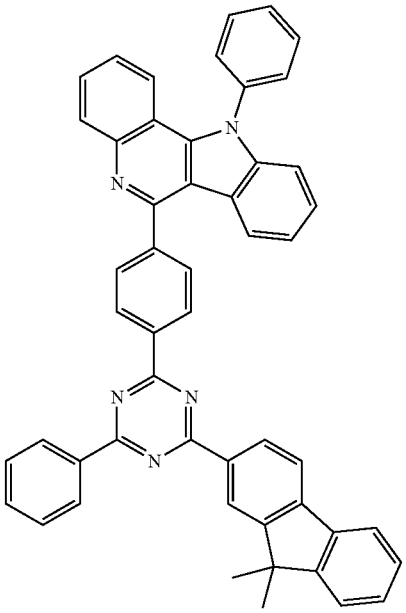 [SMILES: CC1(C)c2ccccc2-c2ccc(-c3nc(-c4ccccc4)nc(-c4ccc(-c5nc6ccccc6c6c5c5ccccc5n6-c5ccccc5)cc4)n3)cc21]
89
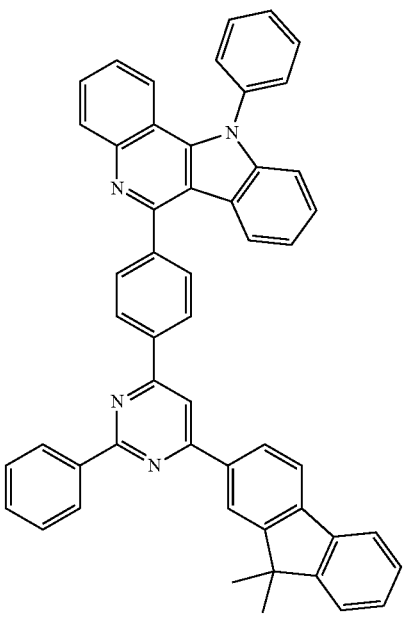

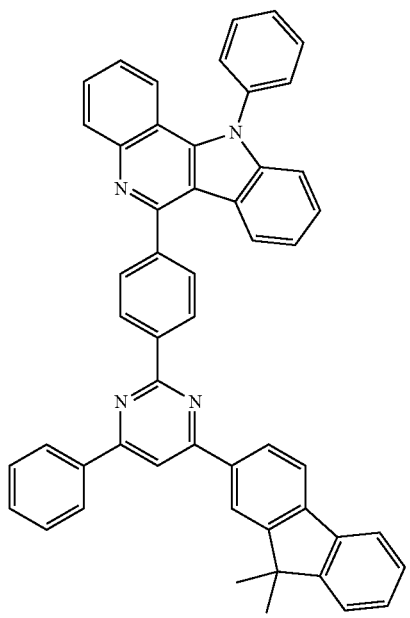
90
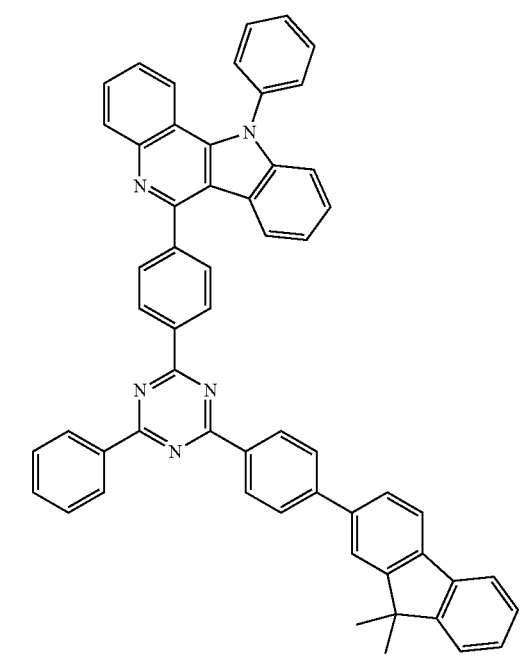
92
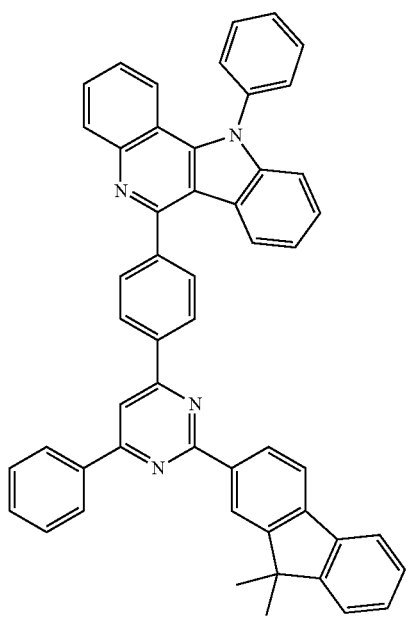
91
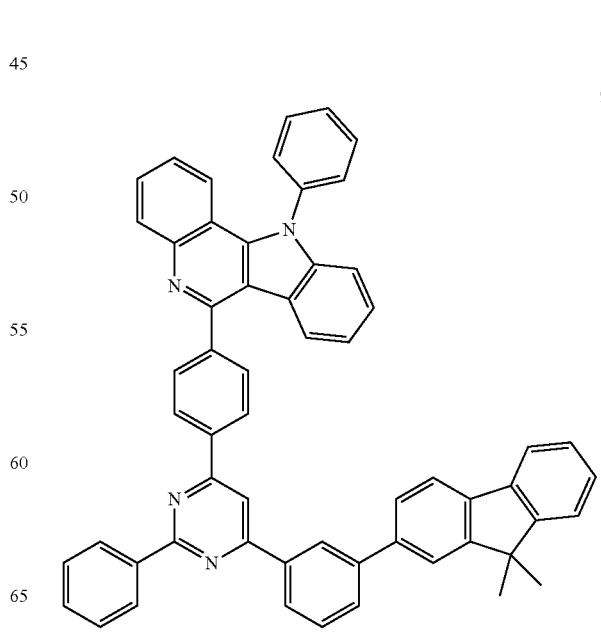
93

94
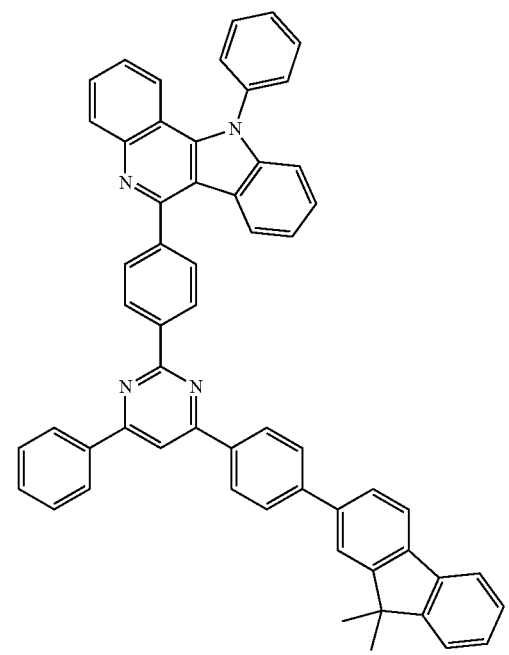
95
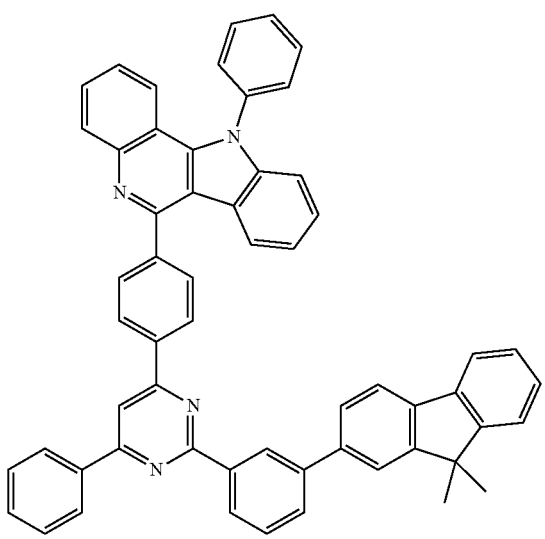 [SMILES: CC1(C)c2ccccc2-c2ccc(-c3cccc(-c4cc(-c5ccc(-c6nc7ccccc7c7c6c6ccccc6n7-c6ccccc6)cc5)nc(-c5ccccc5)n4)c3)cc21]
96
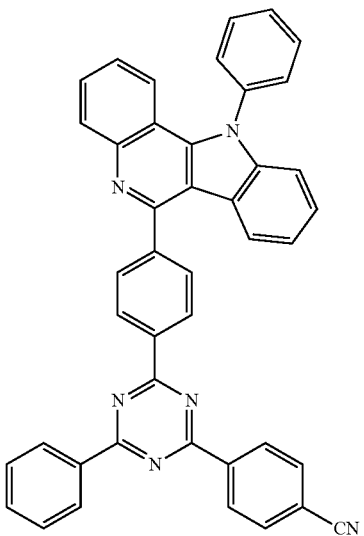 [SMILES: N#Cc1ccc(-c2nc(-c3ccccc3)nc(-c3ccc(-c4nc5ccccc5c5c4c4ccccc4n5-c4ccccc4)cc3)n2)cc1]
97
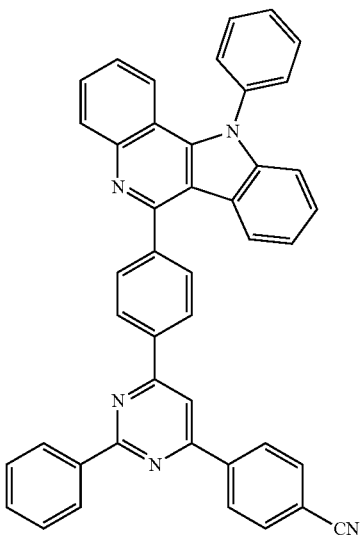
98

99
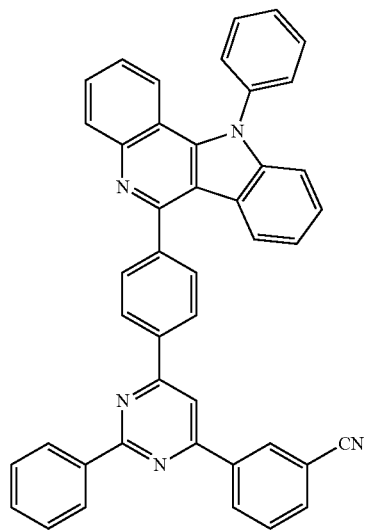
100
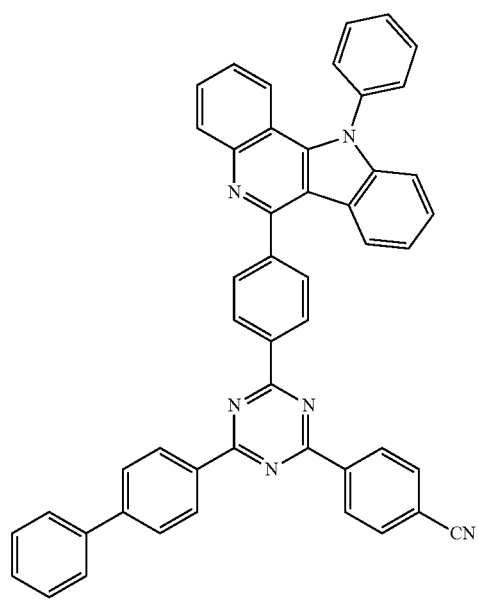 [SMILES: N#Cc1ccc(-c2nc(-c3ccc(-c4ccccc4)cc3)nc(-c3ccc(-c4nc5ccccc5c5c4c4ccccc4n5-c4ccccc4)cc3)n2)cc1]
101
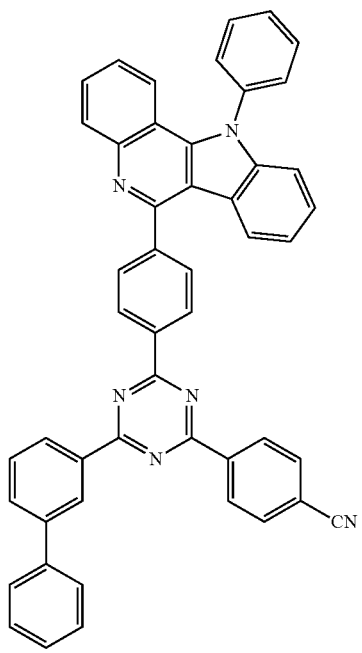 [SMILES: N#Cc1ccc(-c2nc(-c3ccc(-c4nc5ccccc5c5c4c4ccccc4n5-c4ccccc4)cc3)nc(-c3cccc(-c4ccccc4)c3)n2)cc1]
102
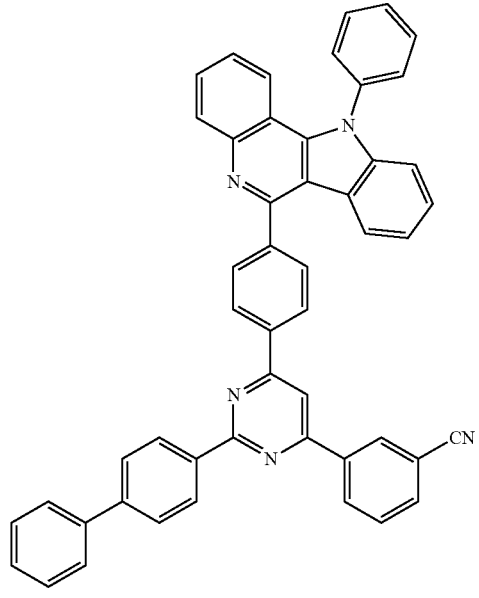

103
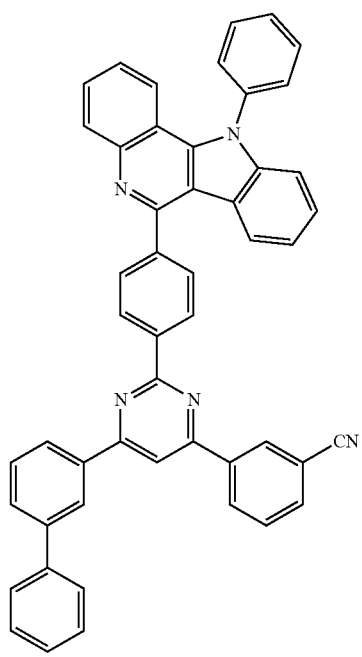
104
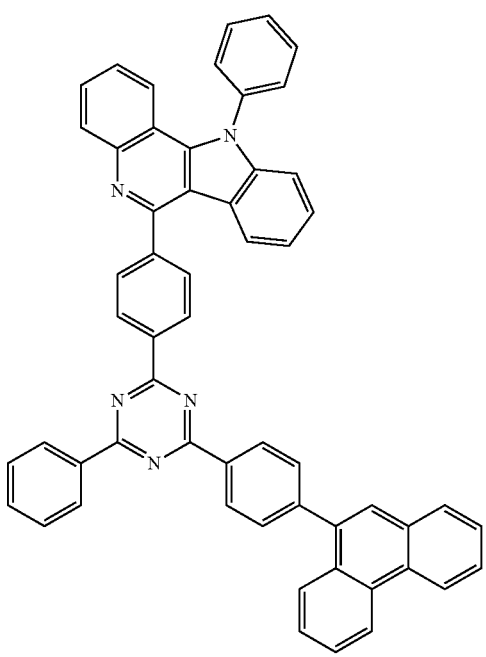 [SMILES: c1ccc(-c2nc(-c3ccc(-c4cc5ccccc5c5ccccc45)cc3)nc(-c3ccc(-c4nc5ccccc5c5c4c4ccccc4n5-c4ccccc4)cc3)n2)cc1]
105
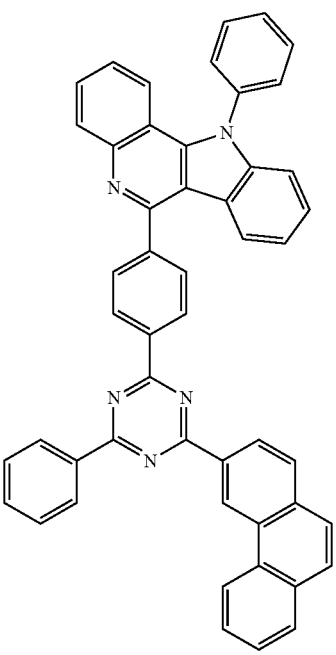 [SMILES: c1ccc(-c2nc(-c3ccc(-c4nc5ccccc5c5c4c4ccccc4n5-c4ccccc4)cc3)nc(-c3ccc4ccc5ccccc5c4c3)n2)cc1]
106
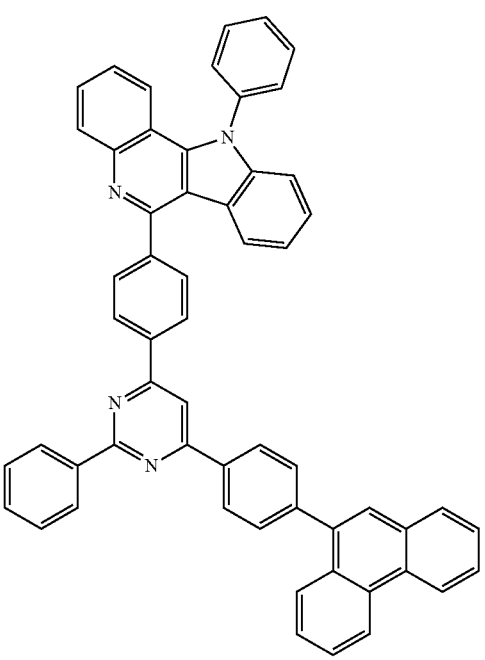

107
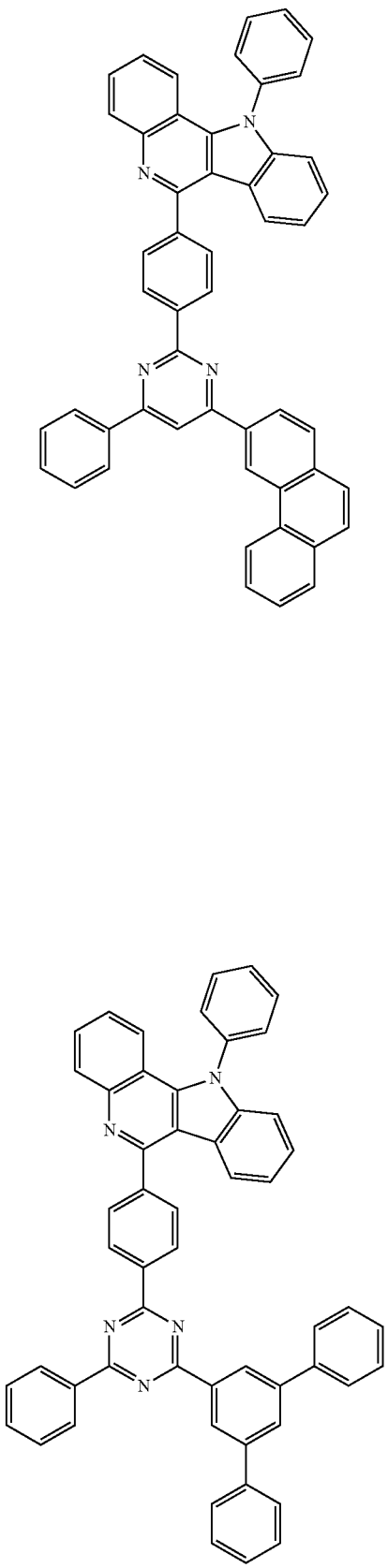
108
109
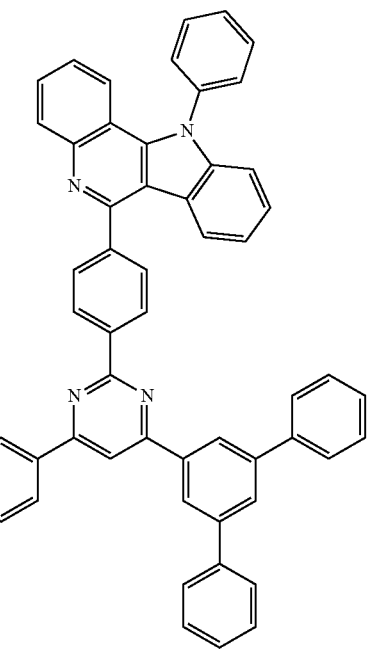
110
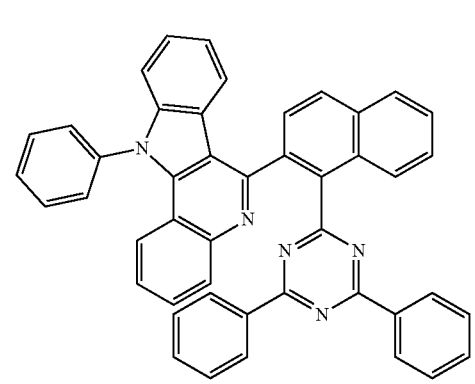
111
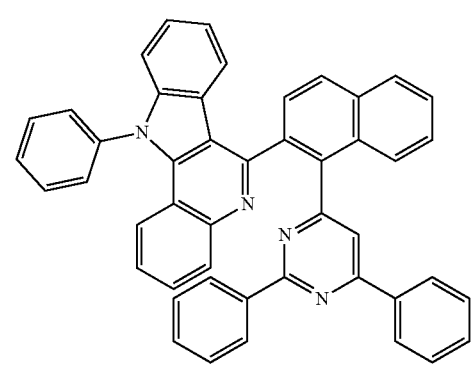

112
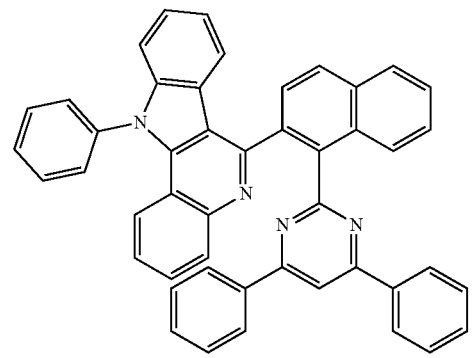
113
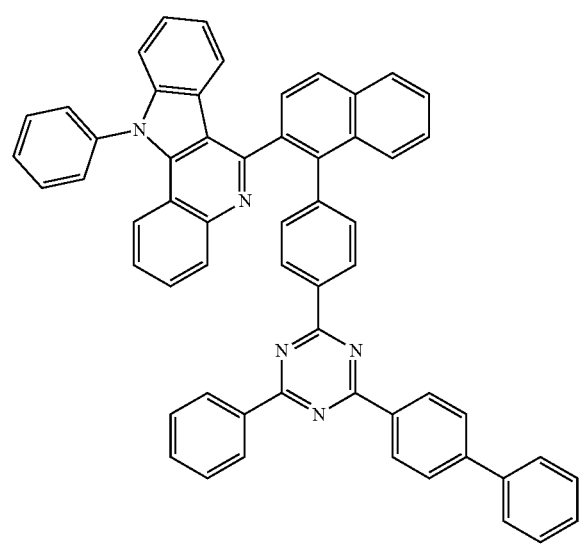
114
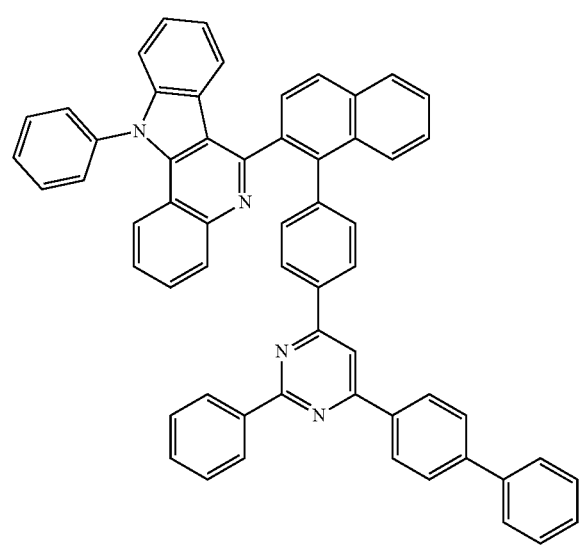
115
116
117
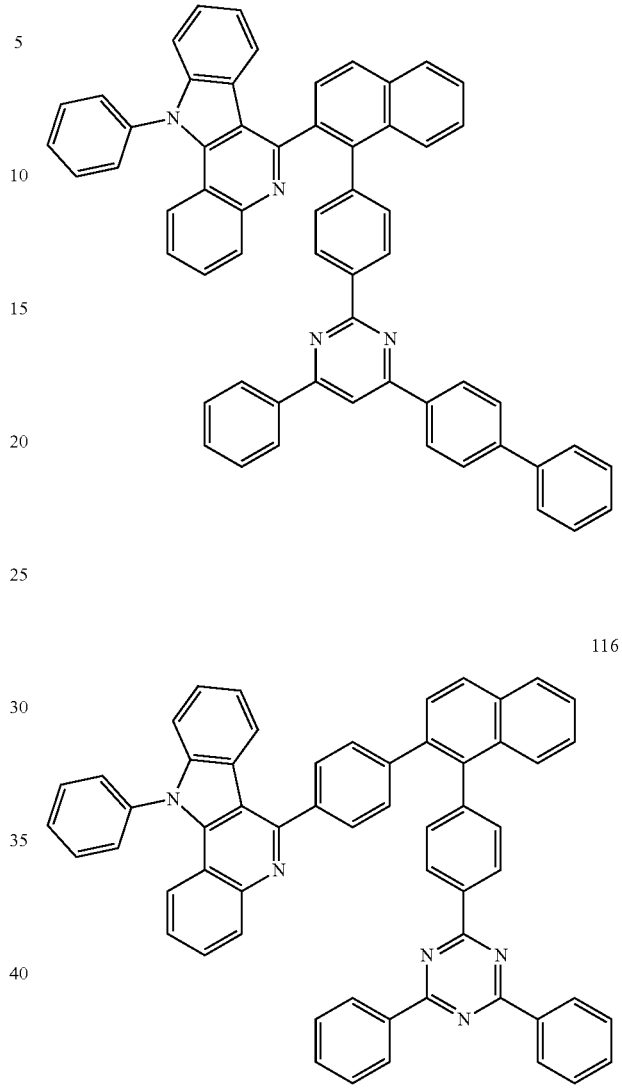

118
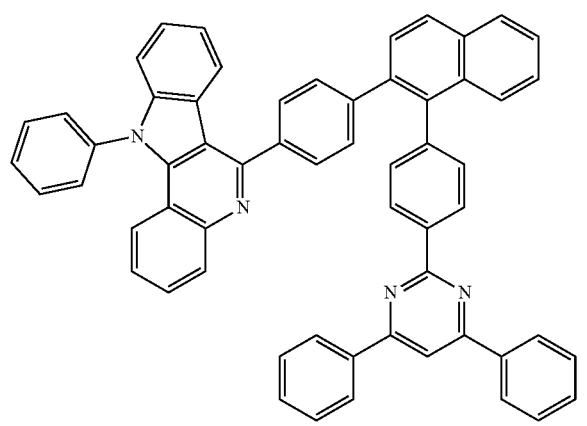
119
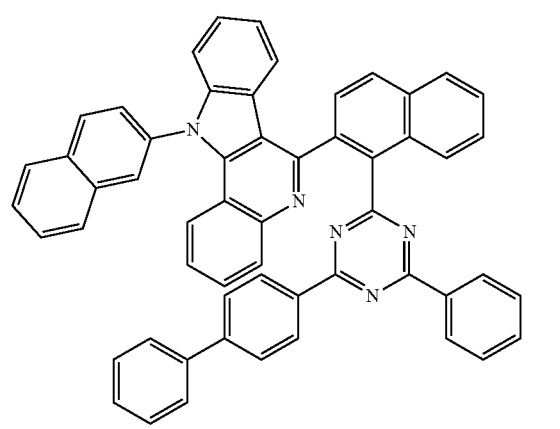
120
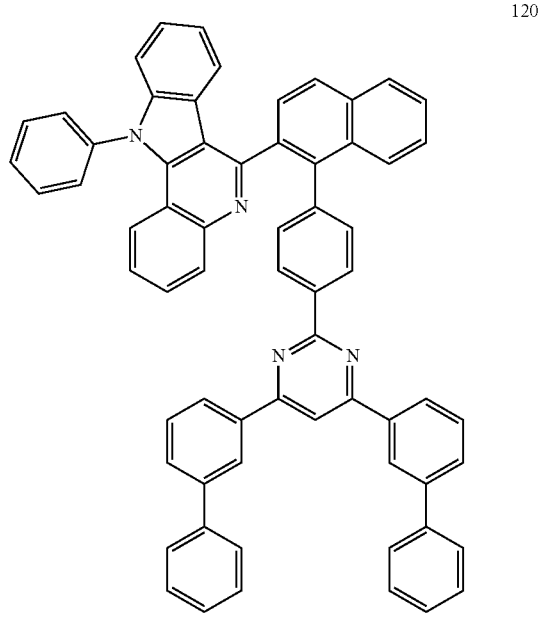
121
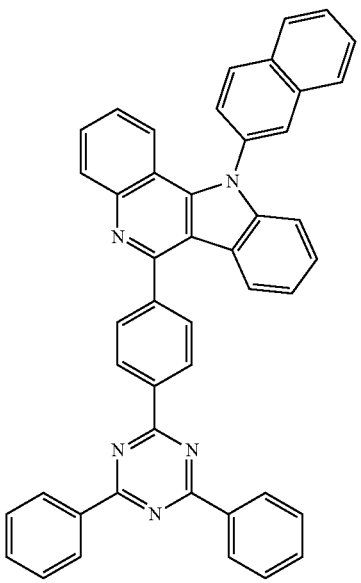
122
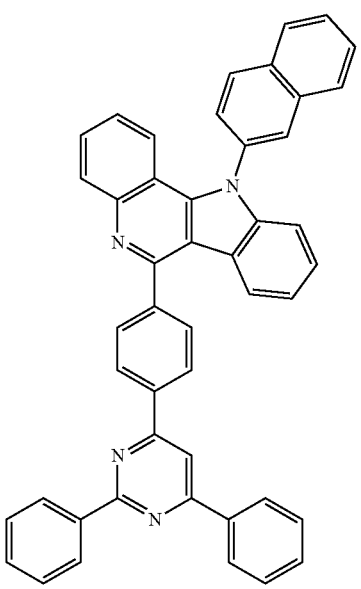

123
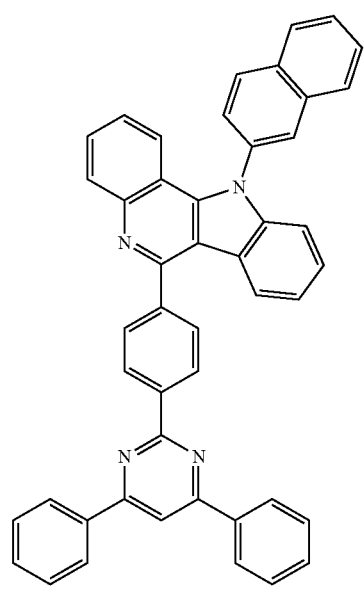
125
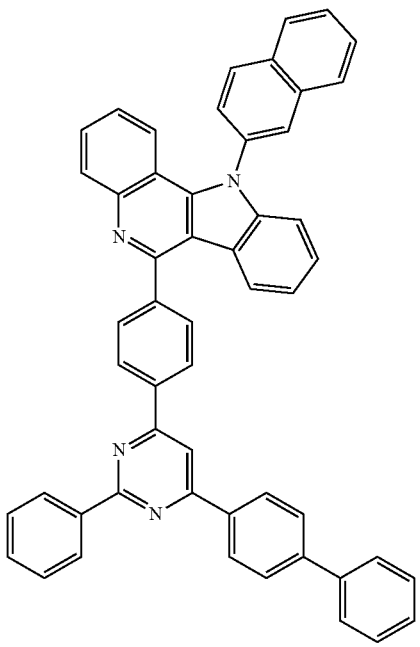
124
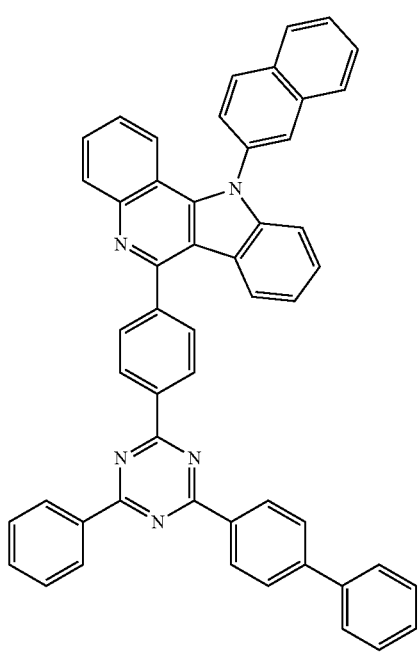
126
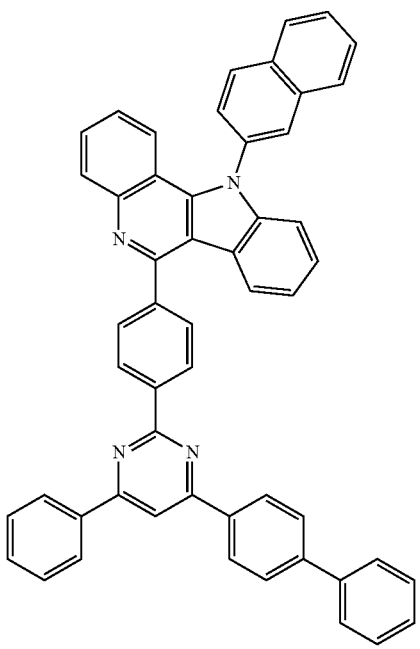

127
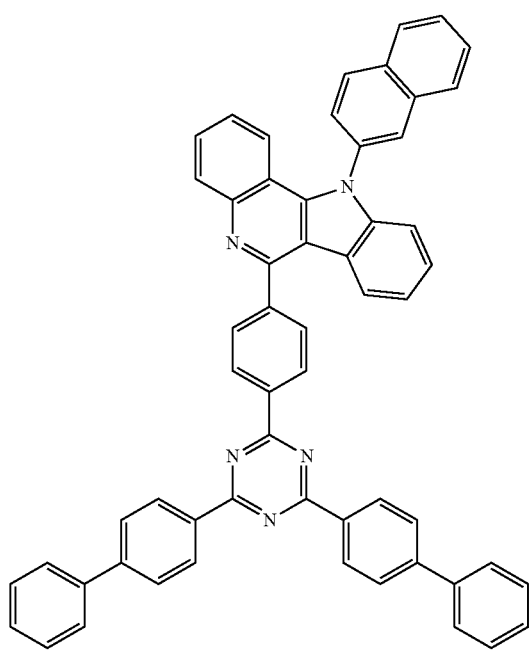
128
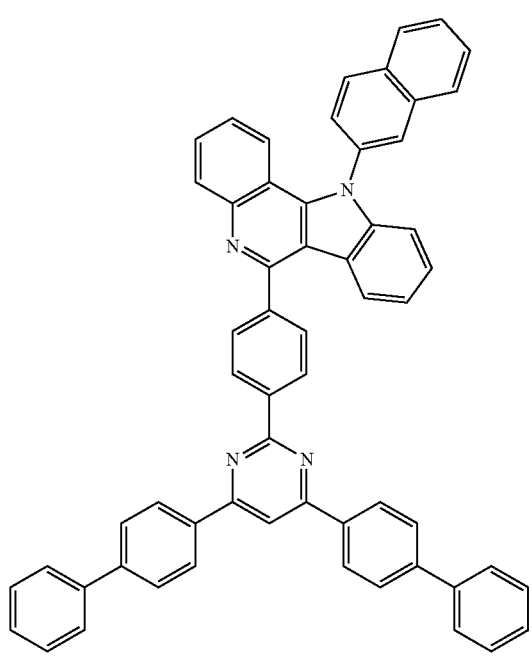
129
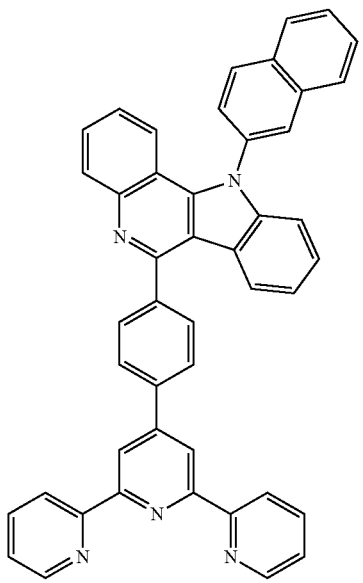
130
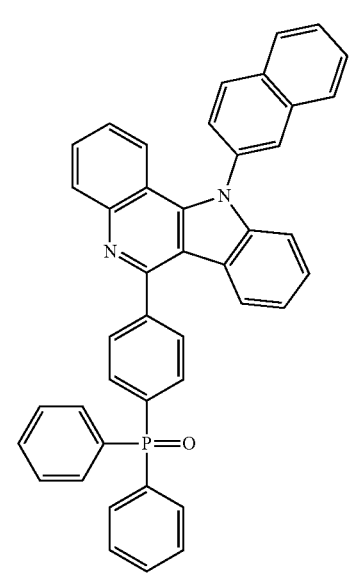

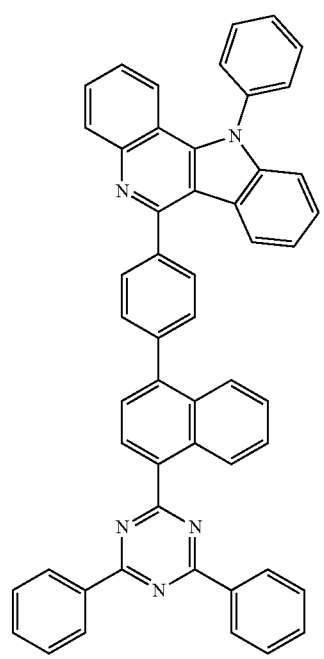
131
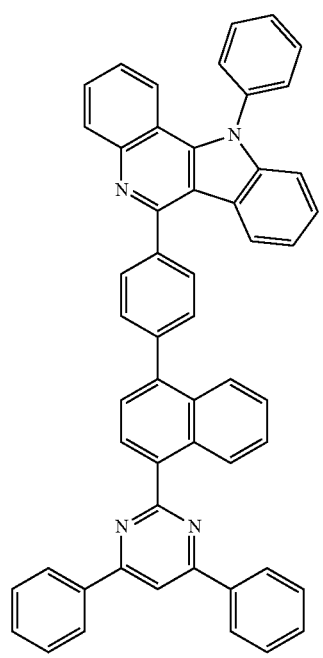 [SMILES: c1ccc(-c2nc(-c3ccccc3)nc(-c3ccc(-c4ccc(-c5nc6ccccc6c6c5c5ccccc5n6-c5ccccc5)cc4)c4ccccc34)n2)cc1]
133
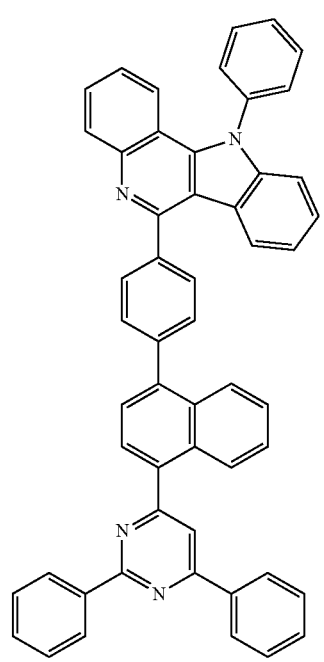
132
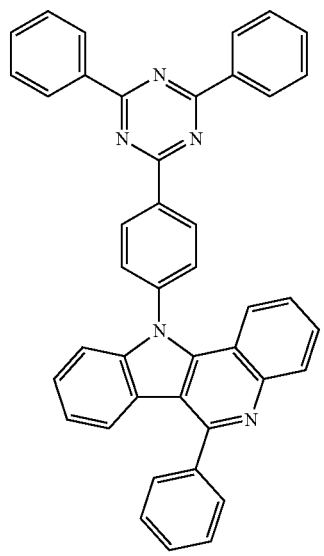 [SMILES: c1ccc(-c2nc(-c3ccccc3)nc(-c3ccc(-n4c5ccccc5c5c(-c6ccccc6)nc6ccccc6c54)cc3)n2)cc1]
134

135
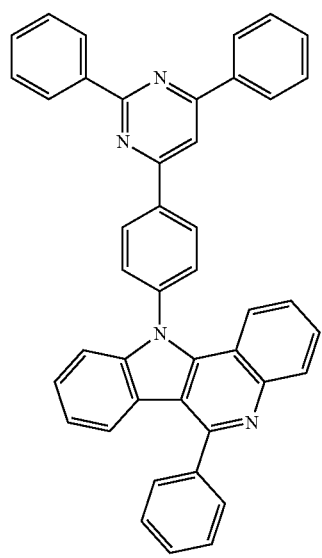
136
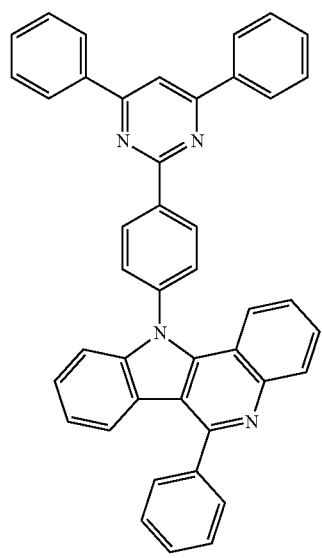
137
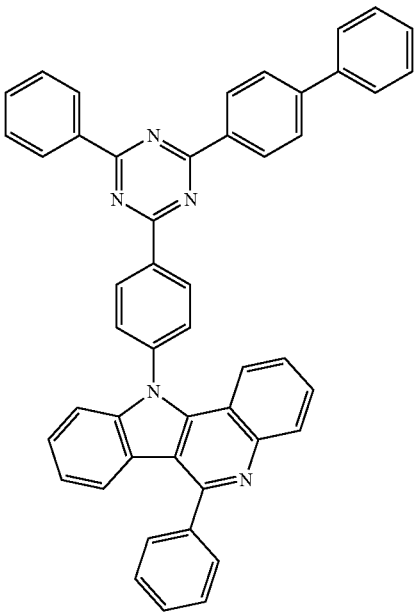 [SMILES: c1ccc(-c2ccc(-c3nc(-c4ccccc4)nc(-c4ccc(-n5c6ccccc6c6c(-c7ccccc7)nc7ccccc7c65)cc4)n3)cc2)cc1]
138
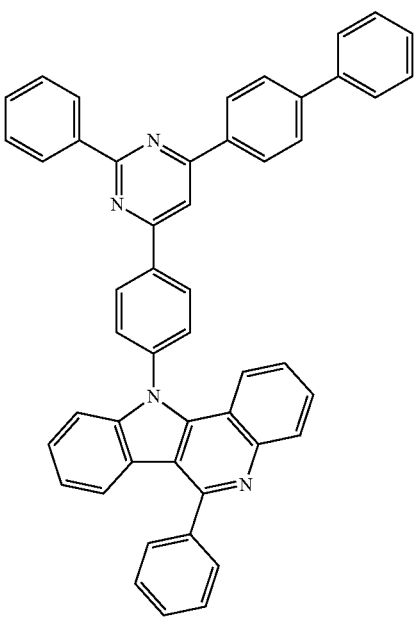

77
-continued
139
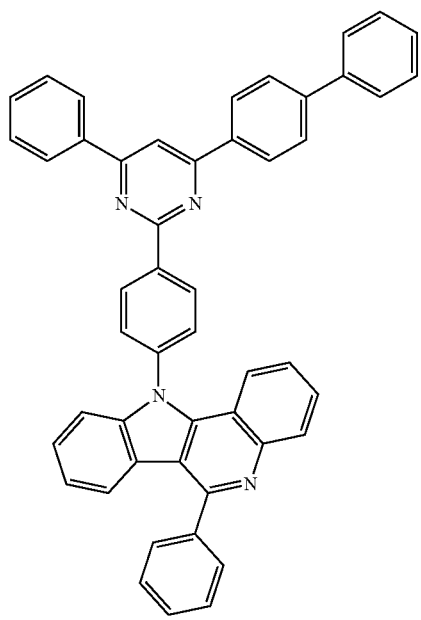 [SMILES: c1ccc(-c2ccc(-c3cc(-c4ccccc4)nc(-c4ccc(-n5c6ccccc6c6c(-c7ccccc7)nc7ccccc7c65)cc4)n3)cc2)cc1]
140
78
-continued
141
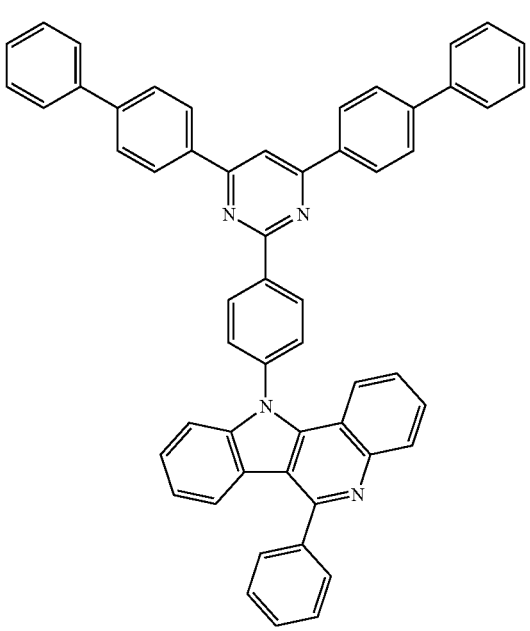 [SMILES: c1ccc(-c2ccc(-c3cc(-c4ccc(-c5ccccc5)cc4)nc(-c4ccc(-n5c6ccccc6c6c(-c7ccccc7)nc7ccccc7c65)cc4)n3)cc2)cc1]
142
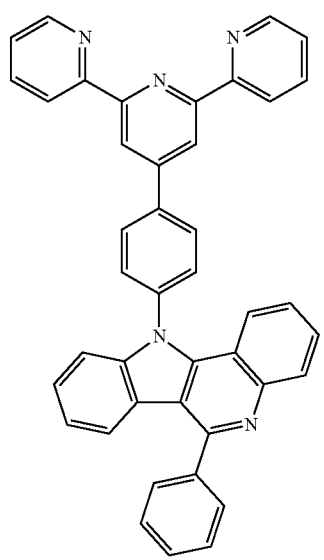

143
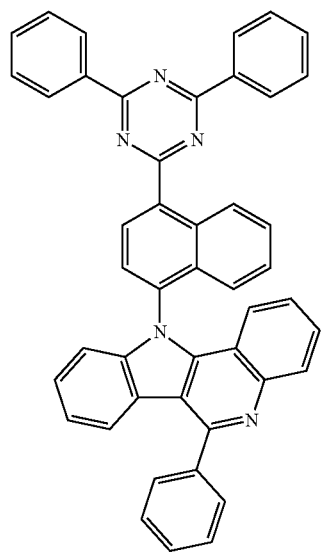 [SMILES: c1ccc(-c2nc(-c3ccccc3)nc(-c3ccc(-n4c5ccccc5c5c(-c6ccccc6)nc6ccccc6c54)c4ccccc34)n2)cc1]
144
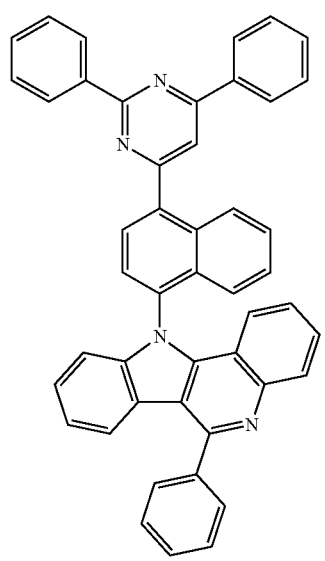
145
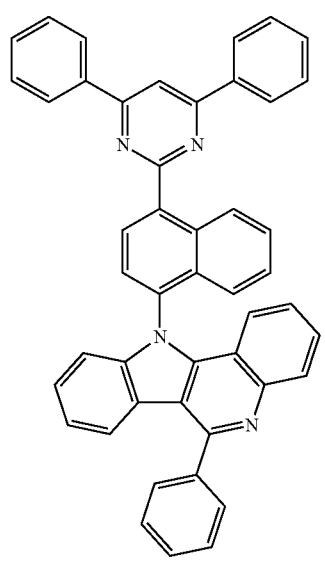
146
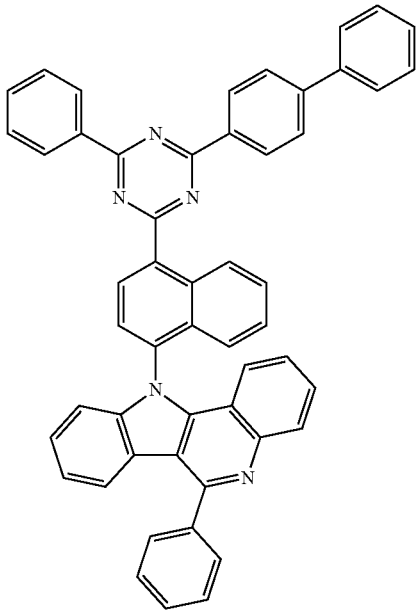 [SMILES: c1ccc(-c2ccc(-c3nc(-c4ccccc4)nc(-c4ccc(-n5c6ccccc6c6c(-c7ccccc7)nc7ccccc7c65)c5ccccc45)n3)cc2)cc1]
147
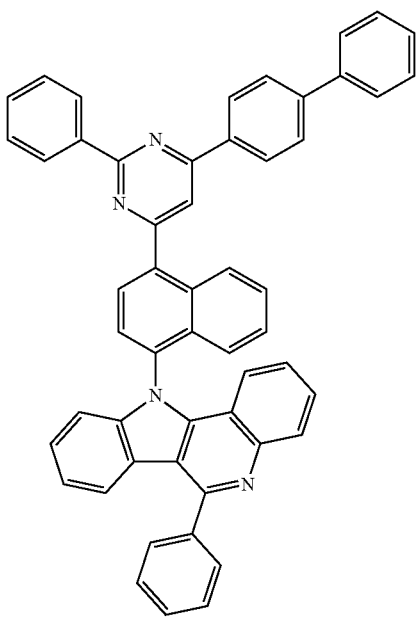

148
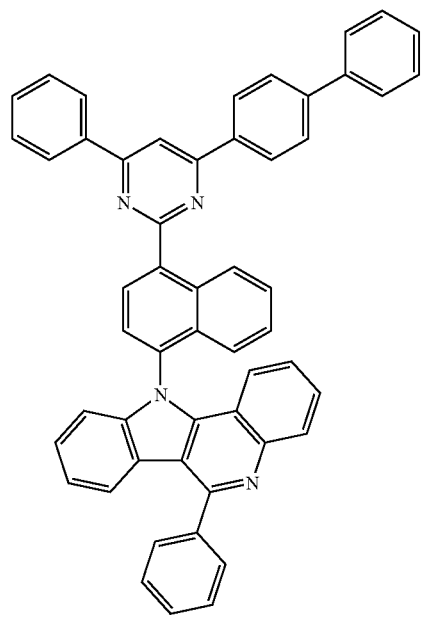
149
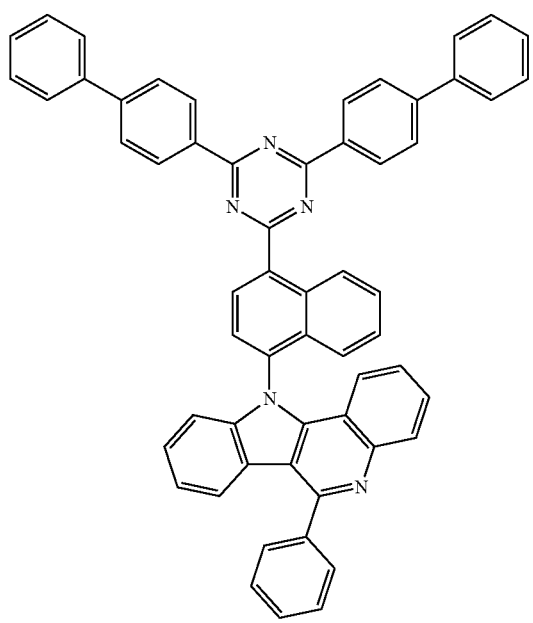 [SMILES: c1ccc(-c2ccc(-c3nc(-c4ccc(-c5ccccc5)cc4)nc(-c4ccc(-n5c6ccccc6c6c(-c7ccccc7)nc7ccccc7c65)c5ccccc45)n3)cc2)cc1]
150
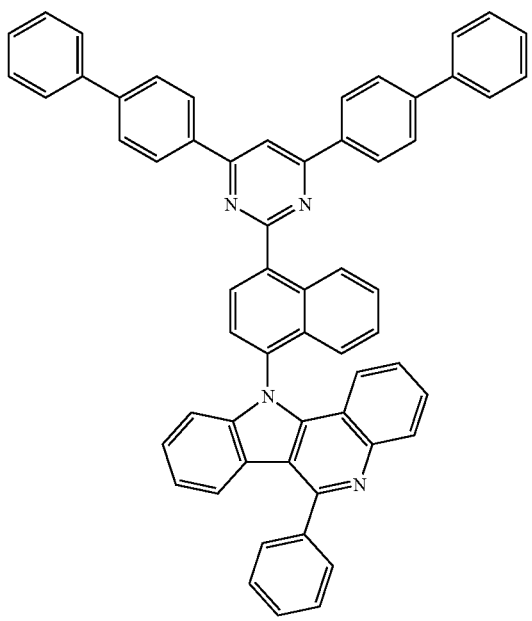
151
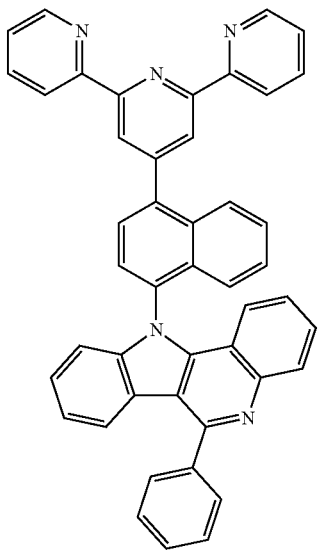

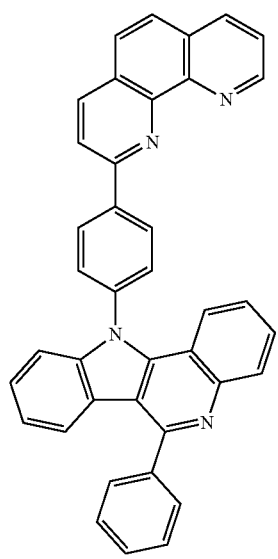
152
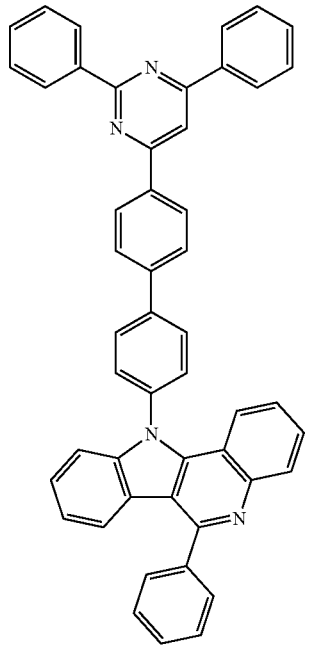
154
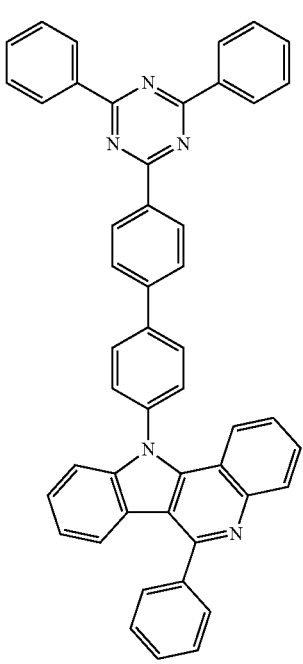
153
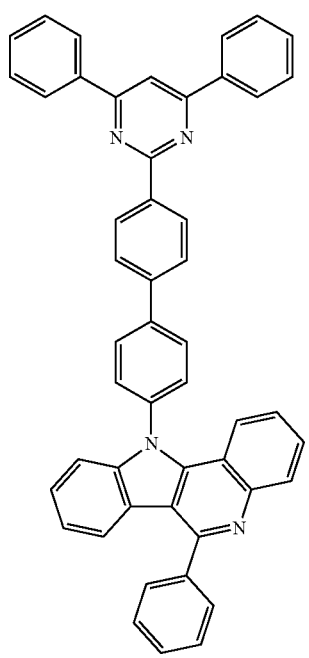
155

156
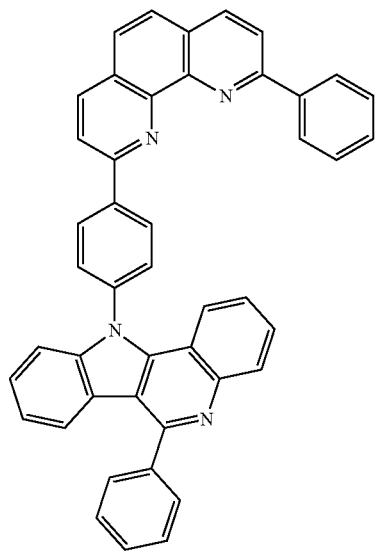
157
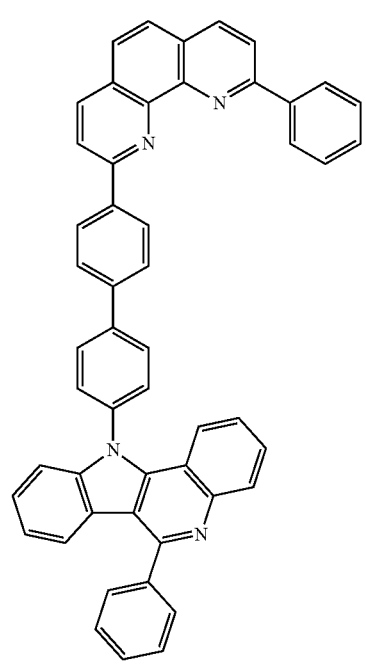
158
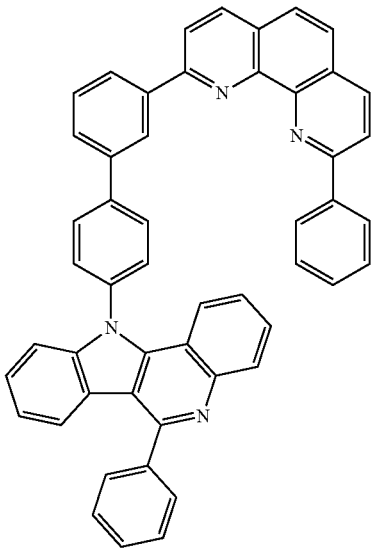
159
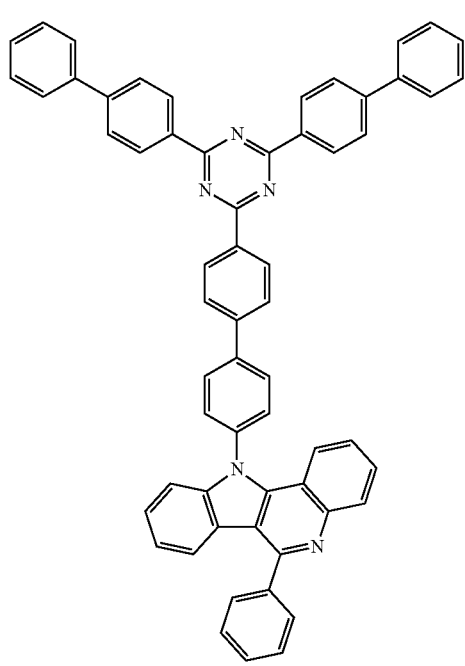

87
-continued
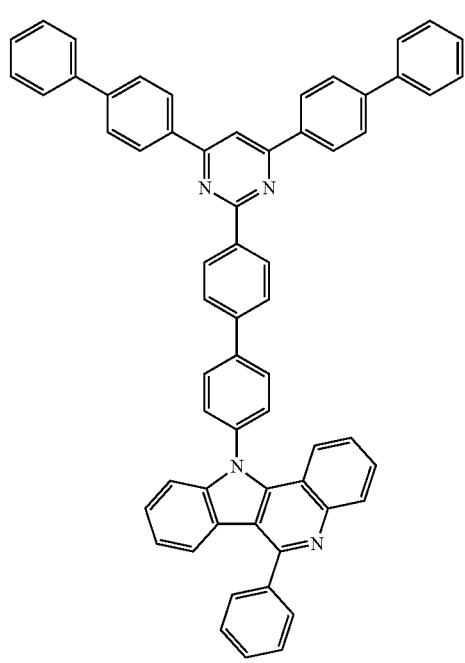
160
88
-continued
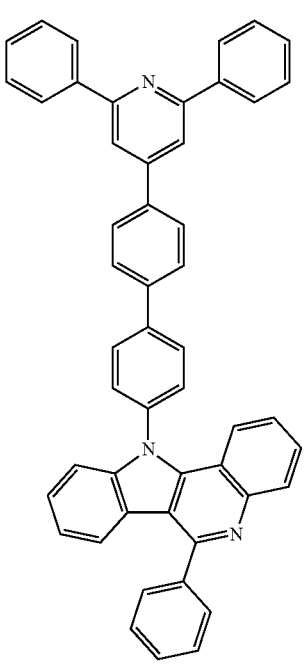
162
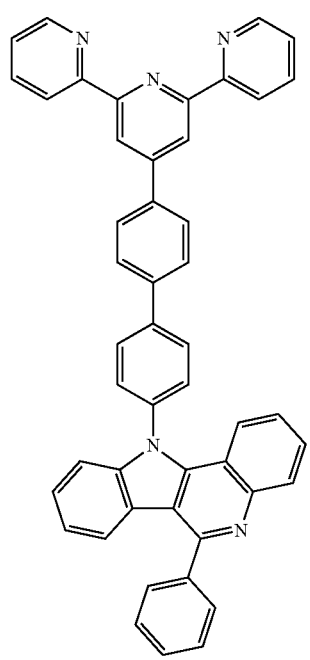
161
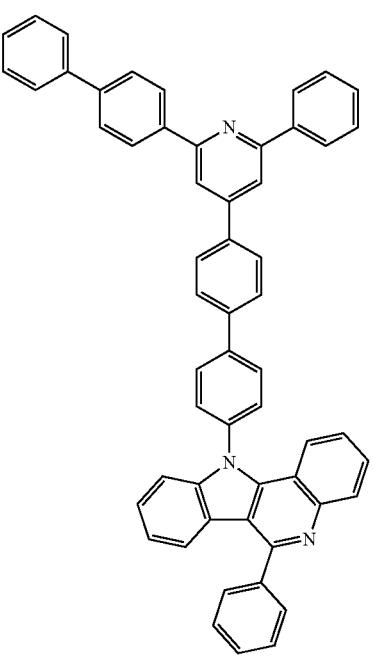
163

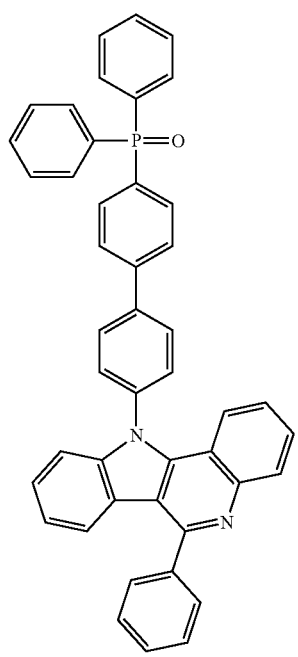
164
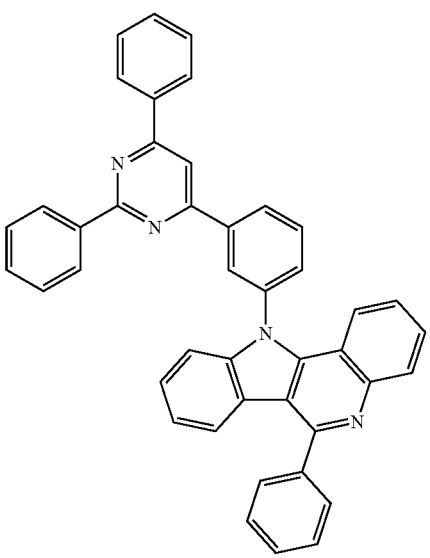
166
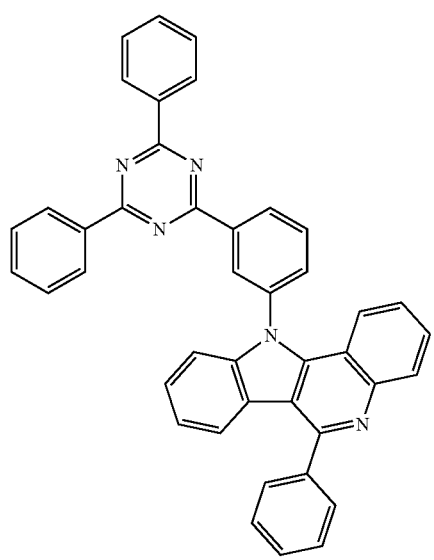
165

168
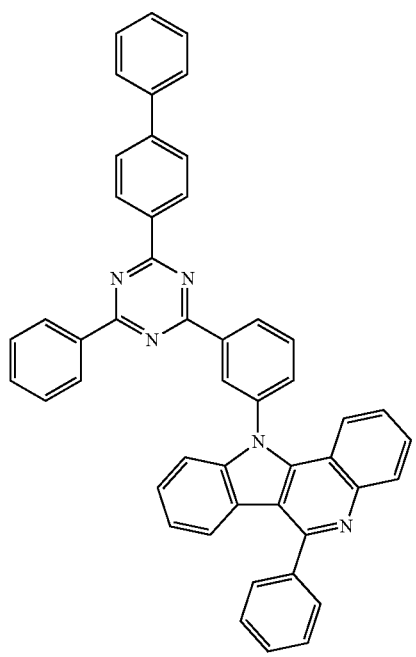
169
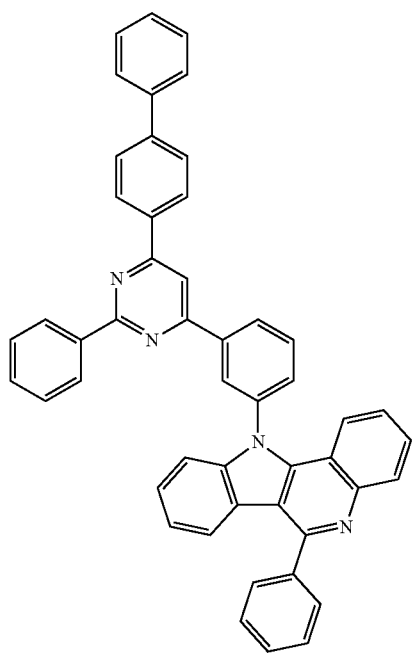
170
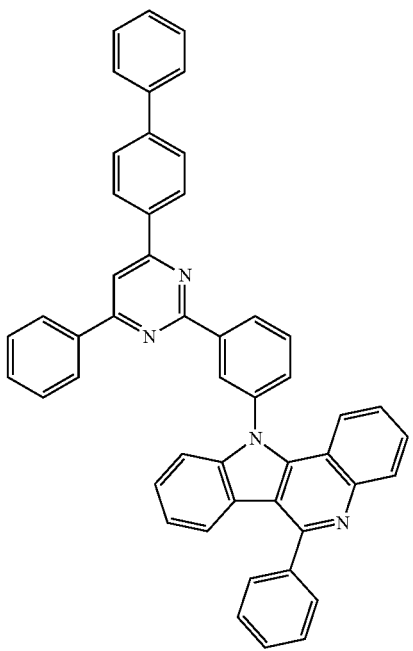
171
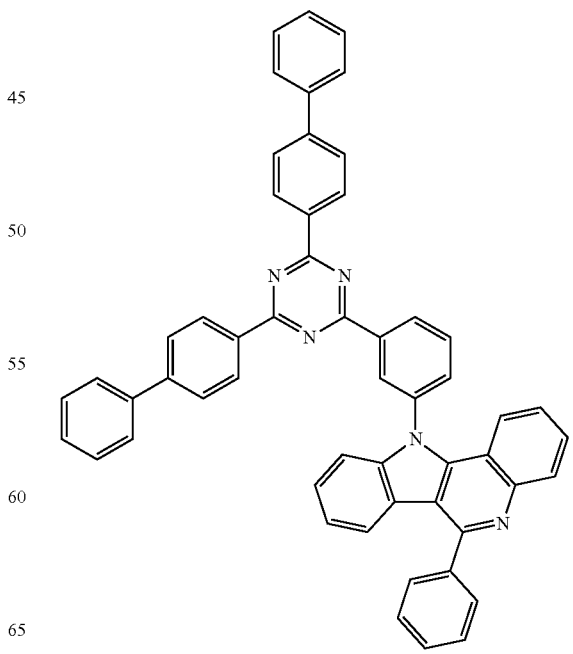

172
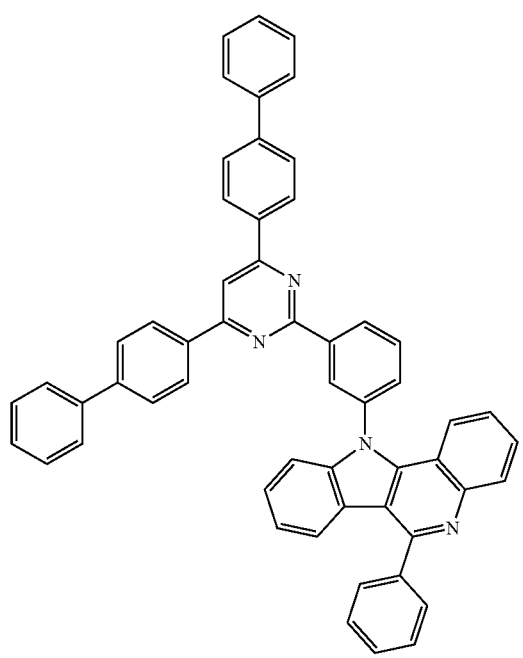
174
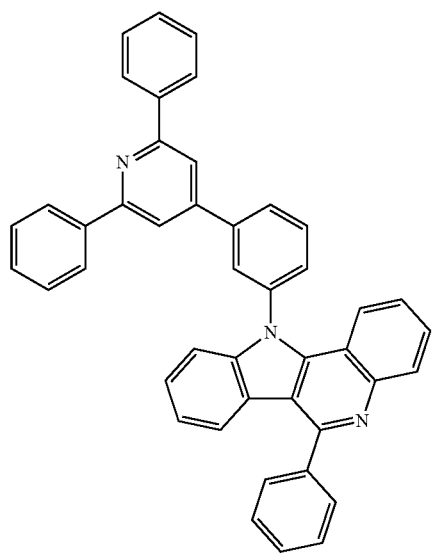
173
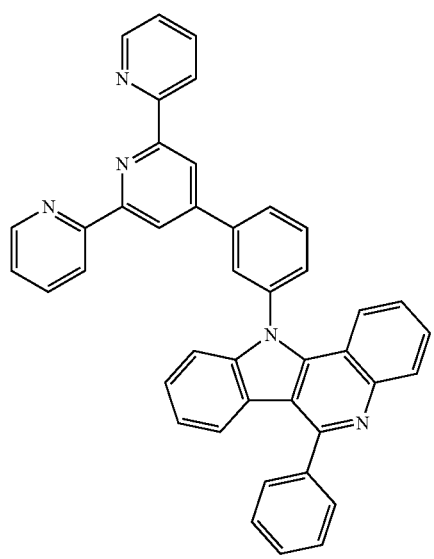
175
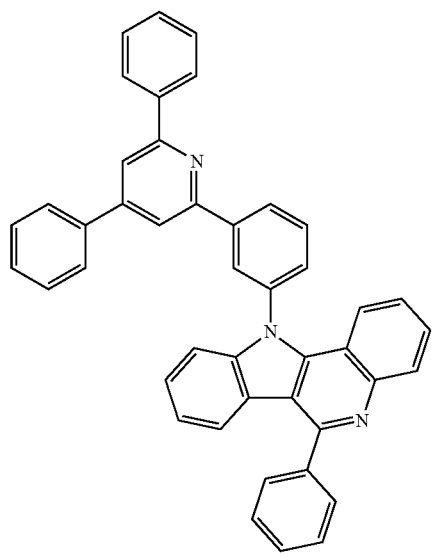

-continued
176
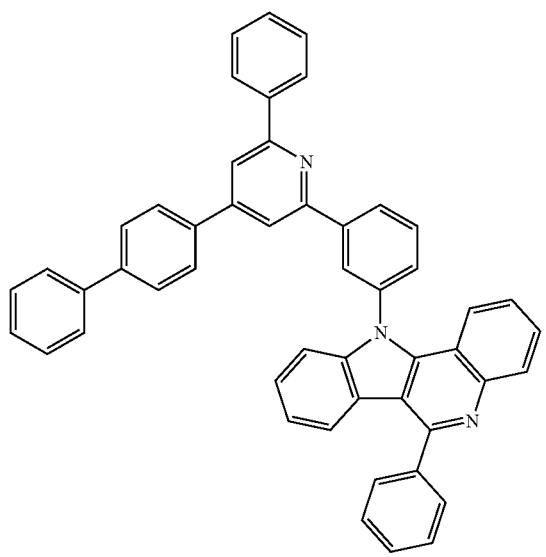
177
178
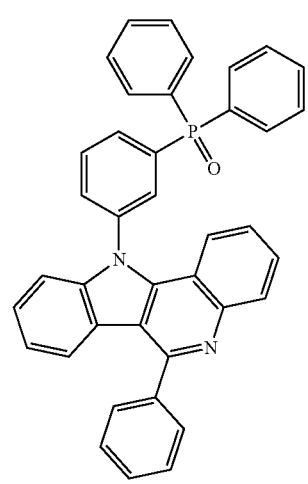
-continued
179
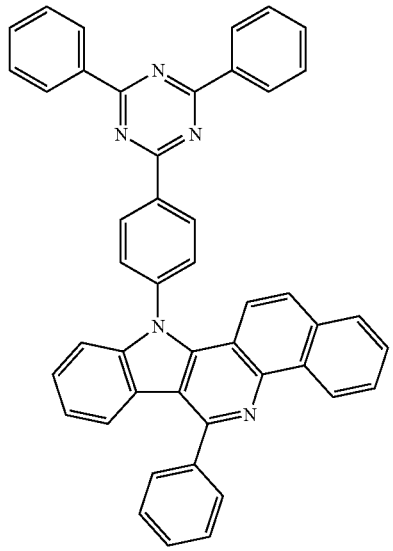
180
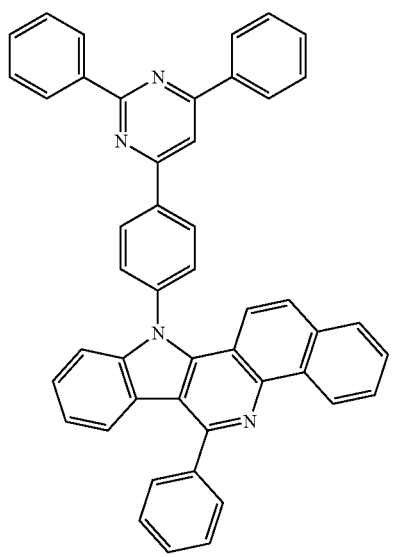
181

182
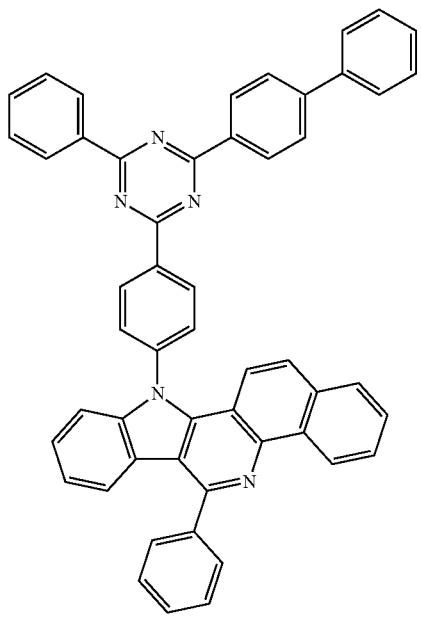
184
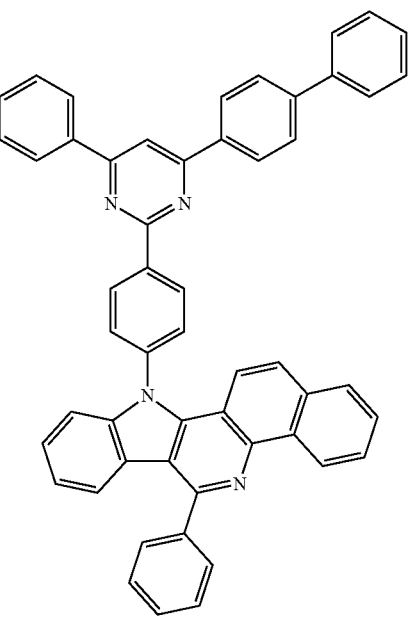
183
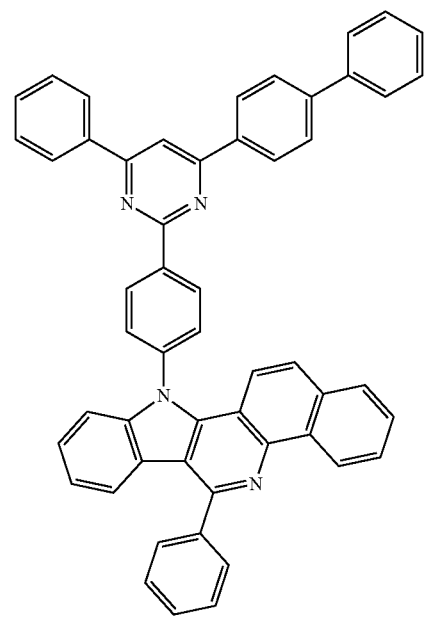
185
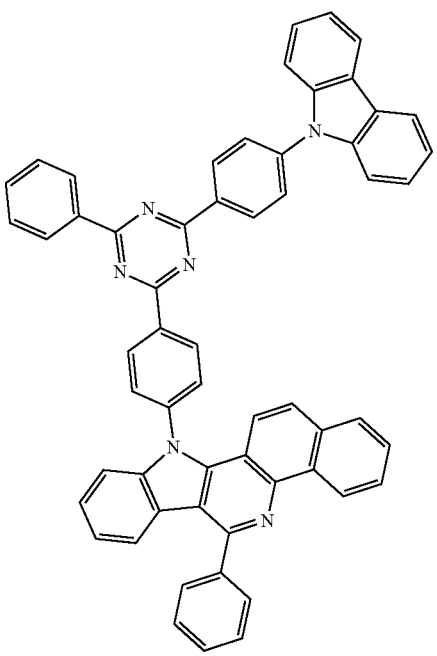

186
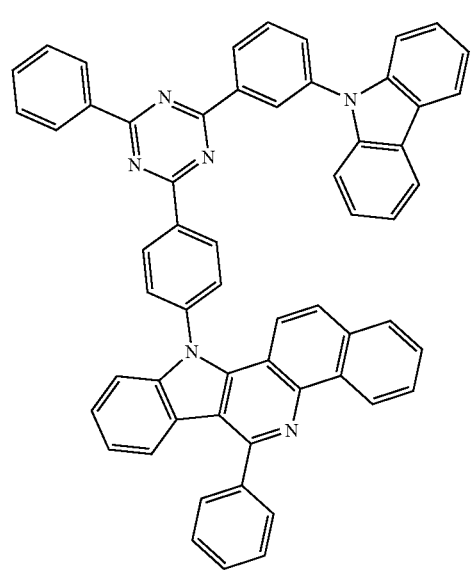
187
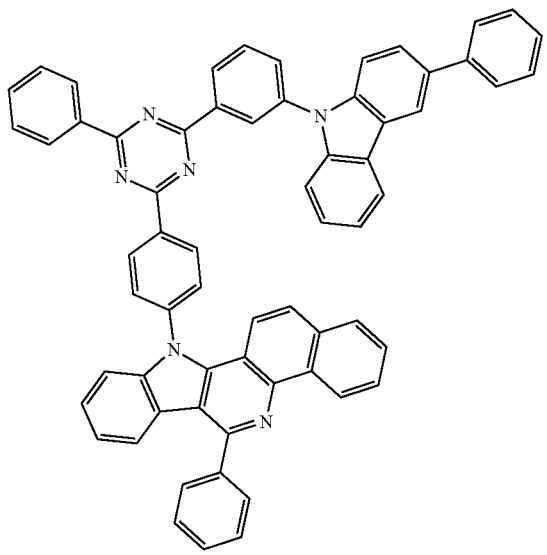
188
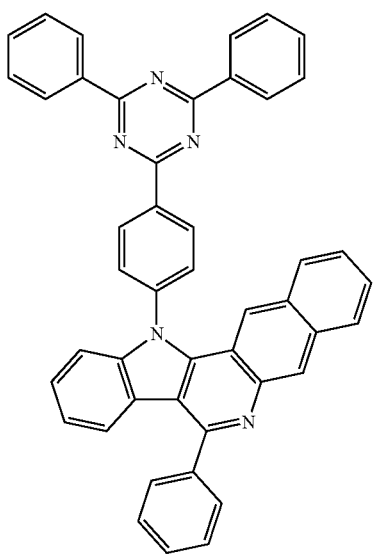
189
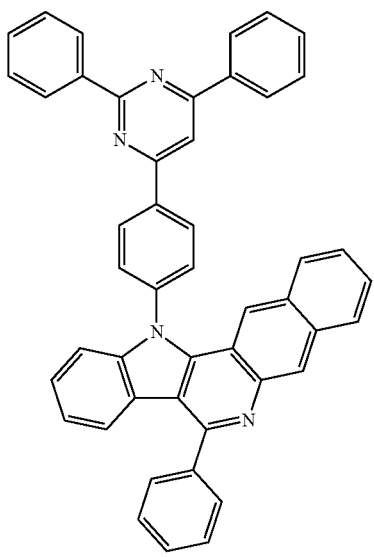
190
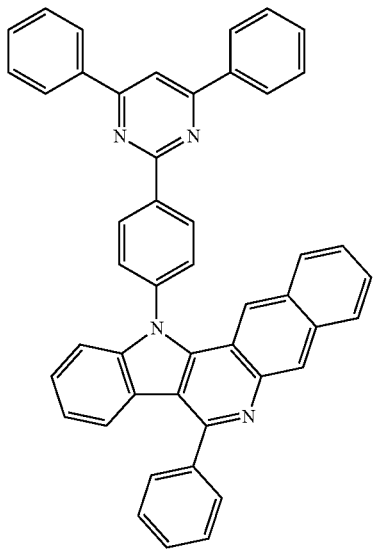

191
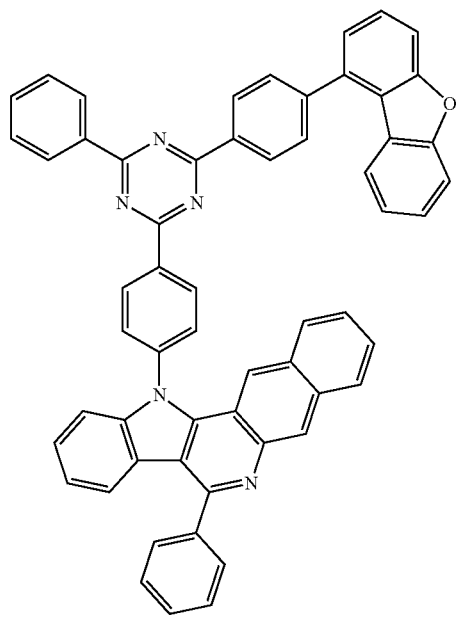
192
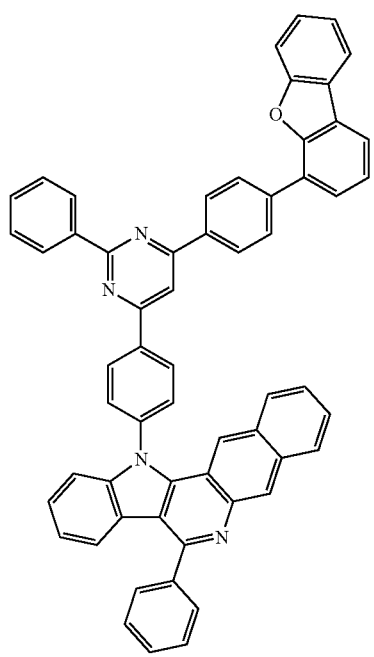
193
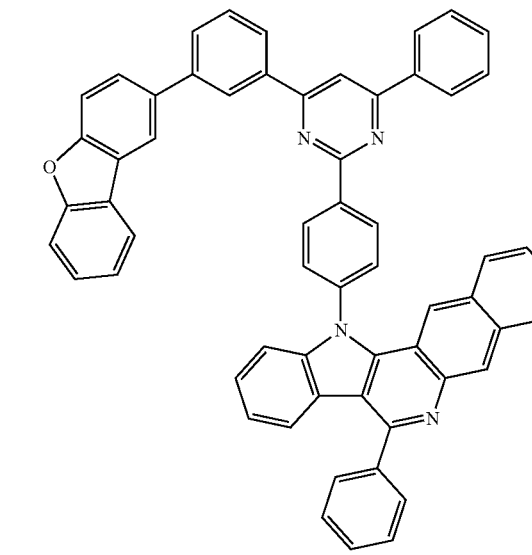
194
195
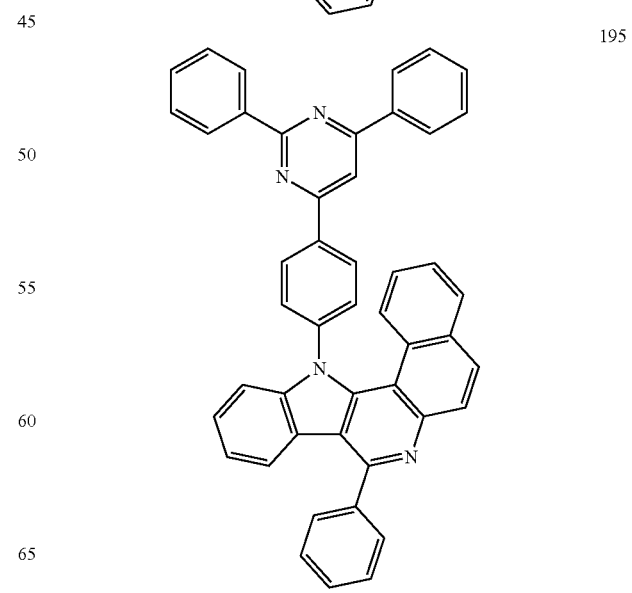

196
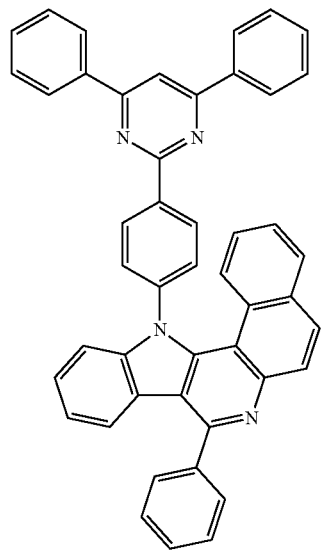
197
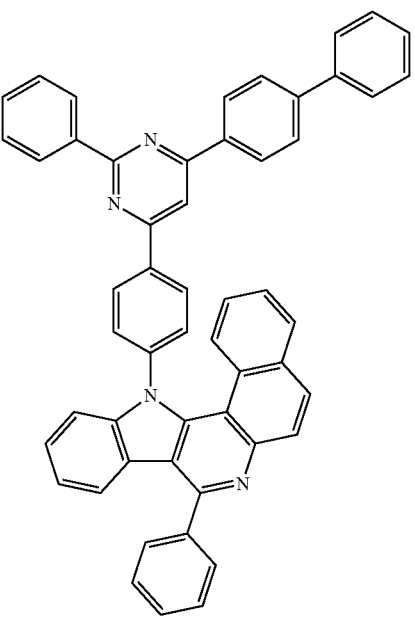
198
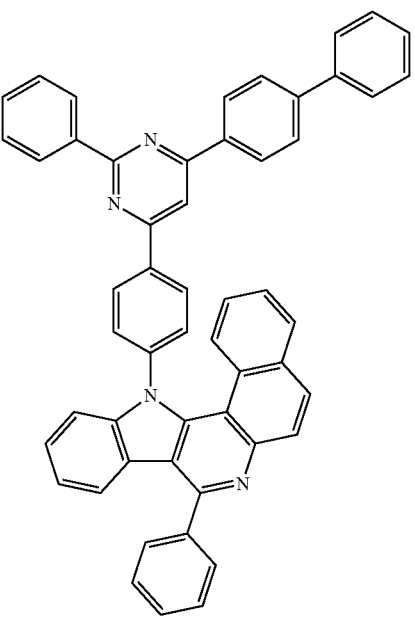
199
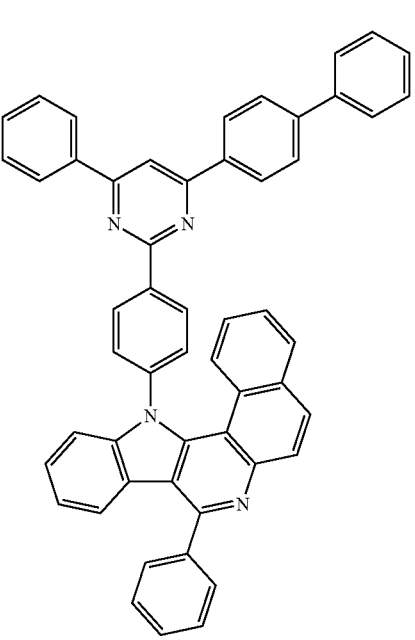

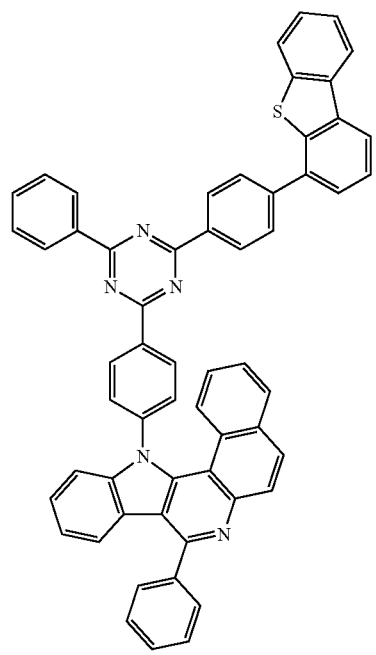
200
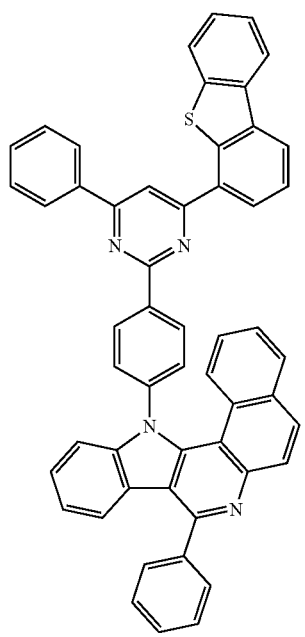
202
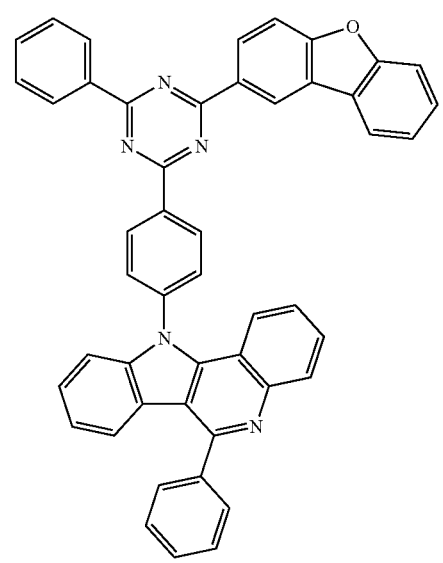
203

107
-continued
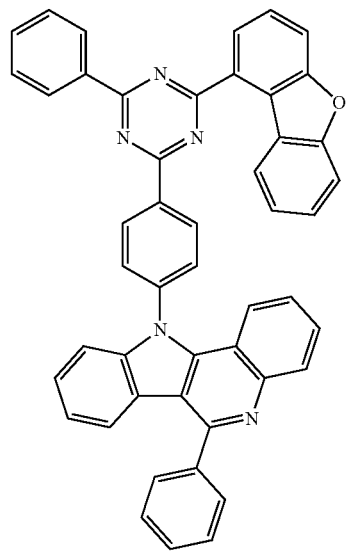
204
108
-continued
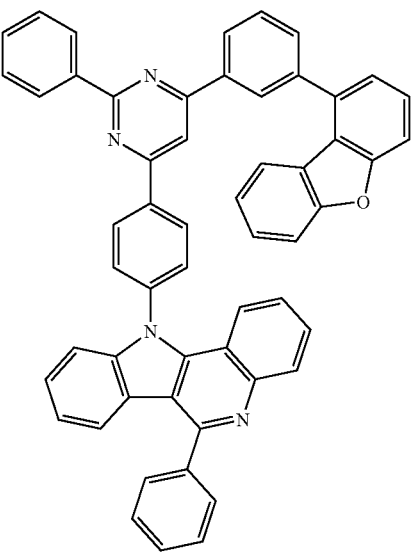
206
205
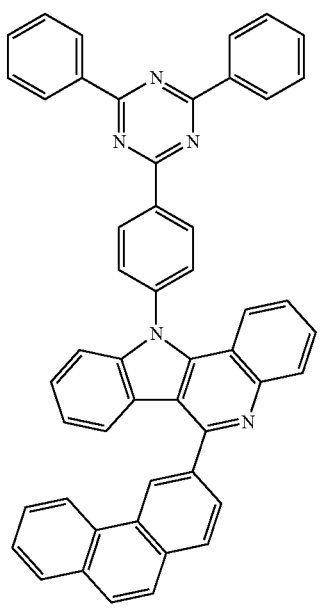
207

208
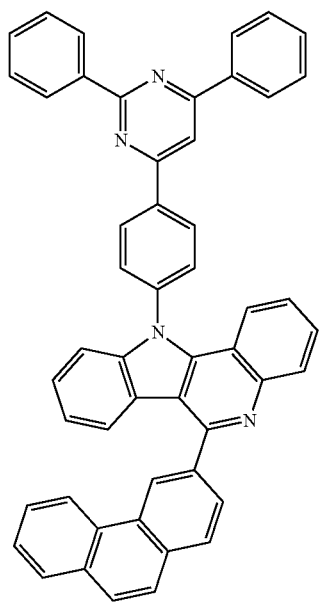
209
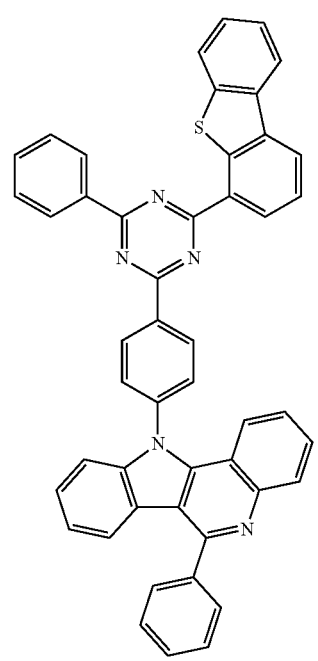
210
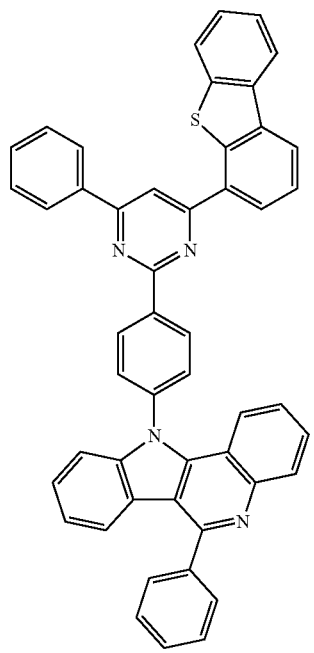
211
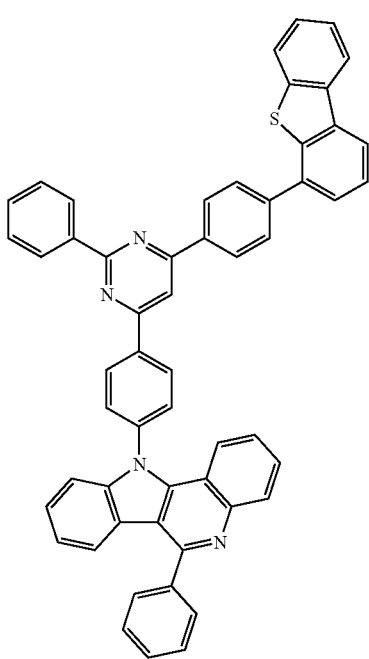

111
-continued
212
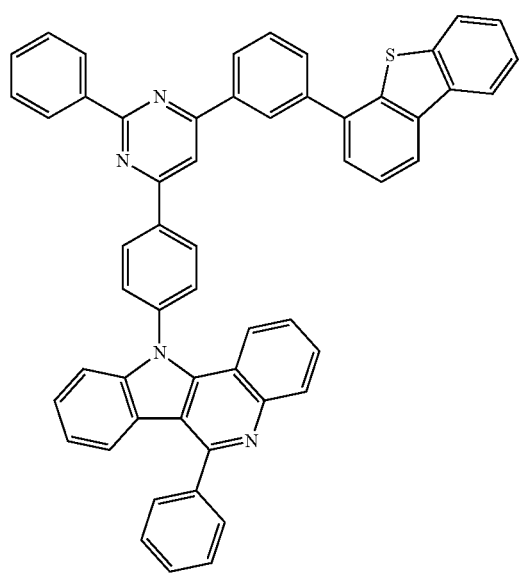
213
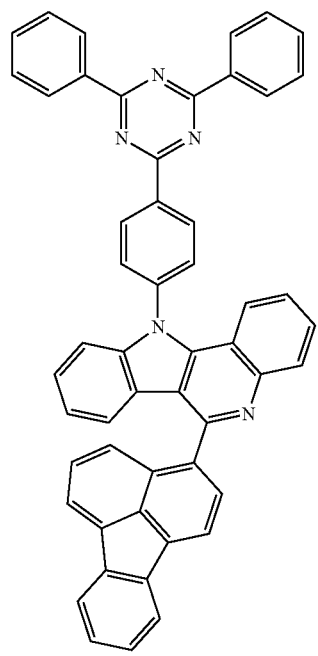
112
-continued
214
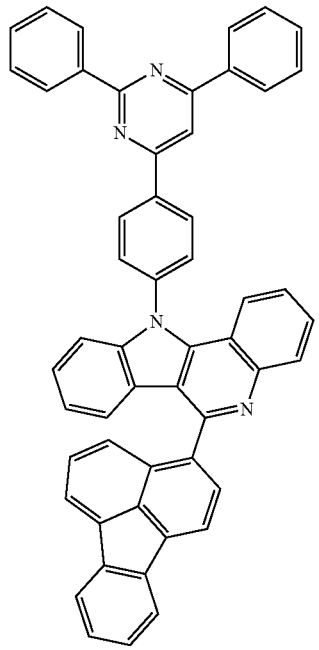
215
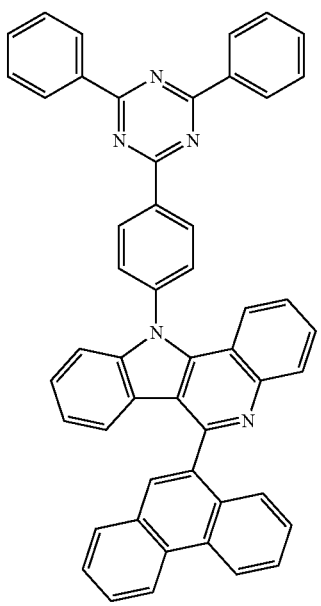

216
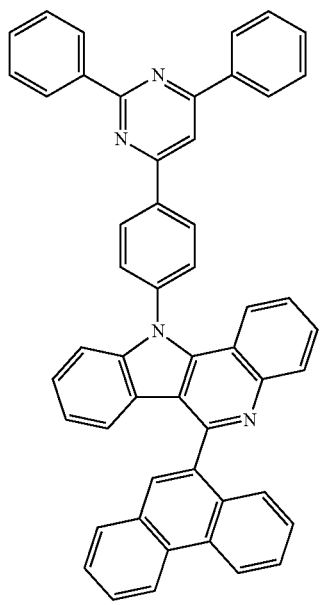
217
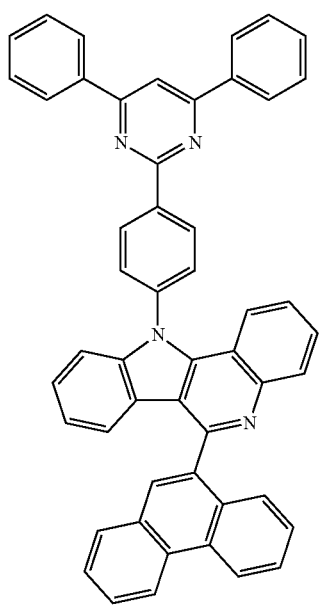
218
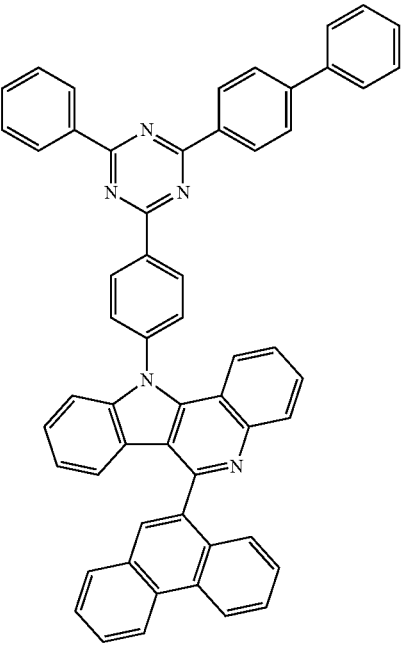
219
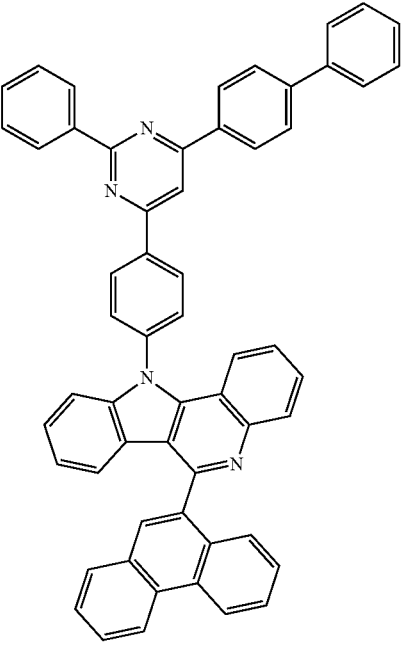

220
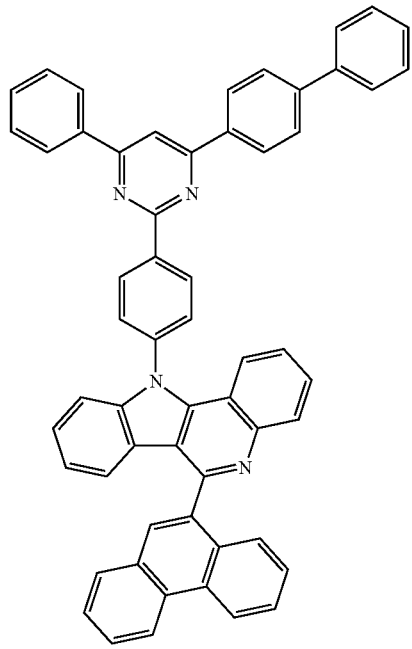
222
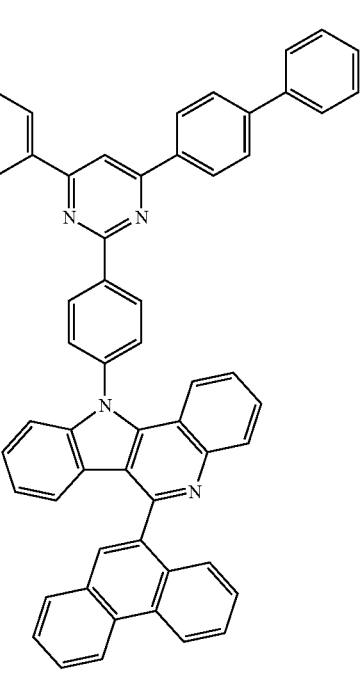
221
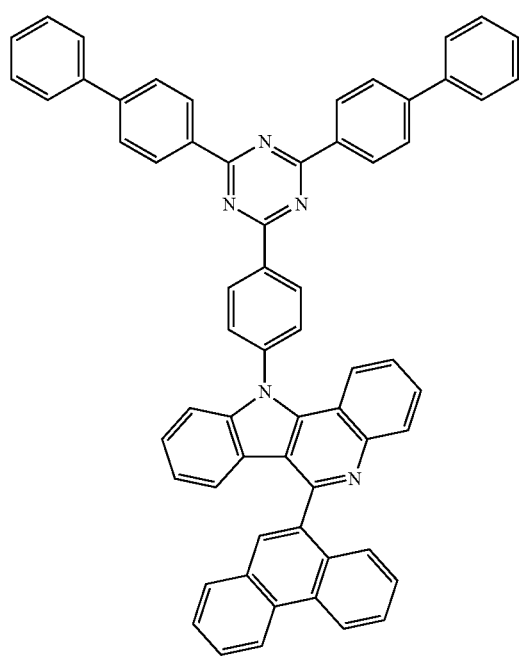
223
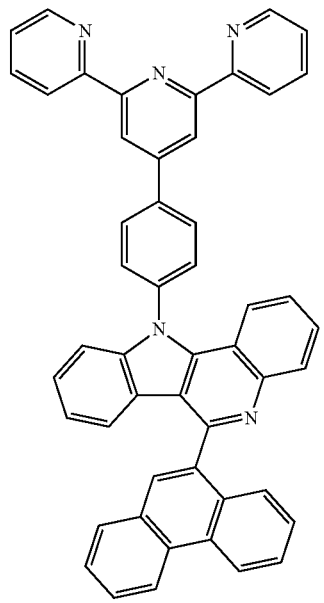

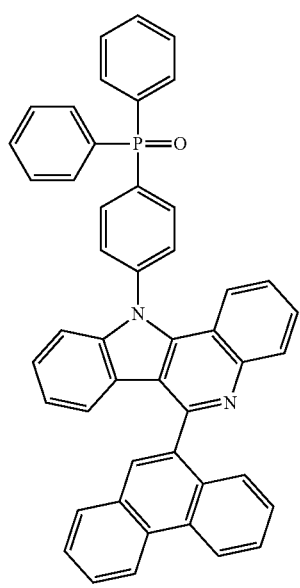
224
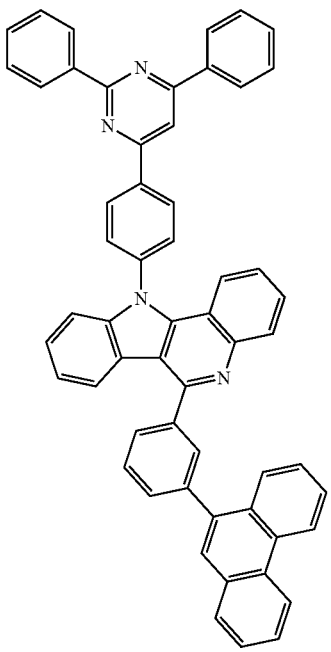
226
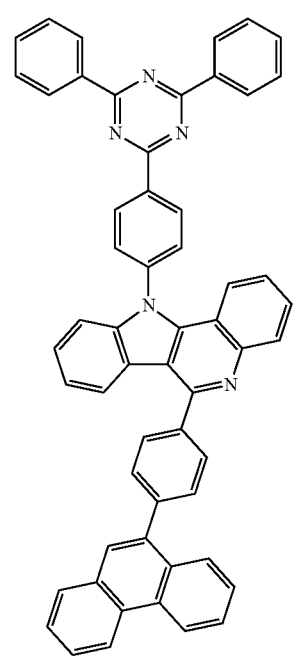
225
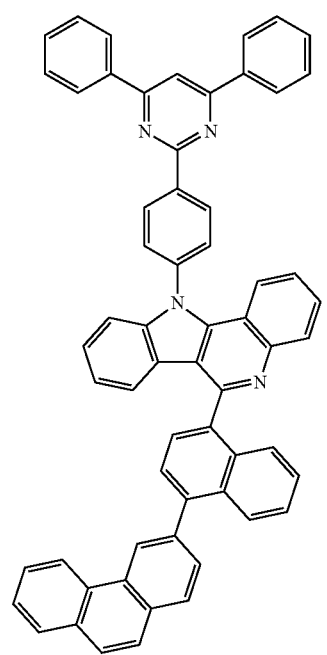
227

-continued
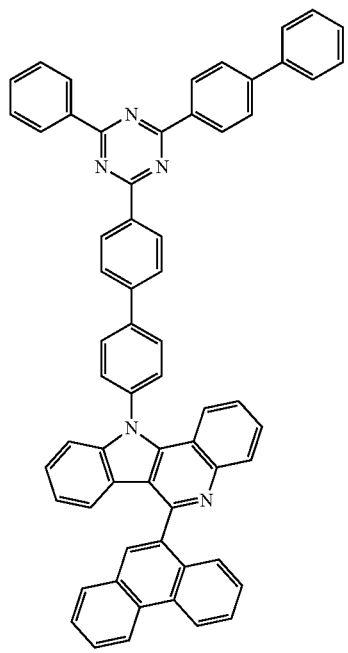
228
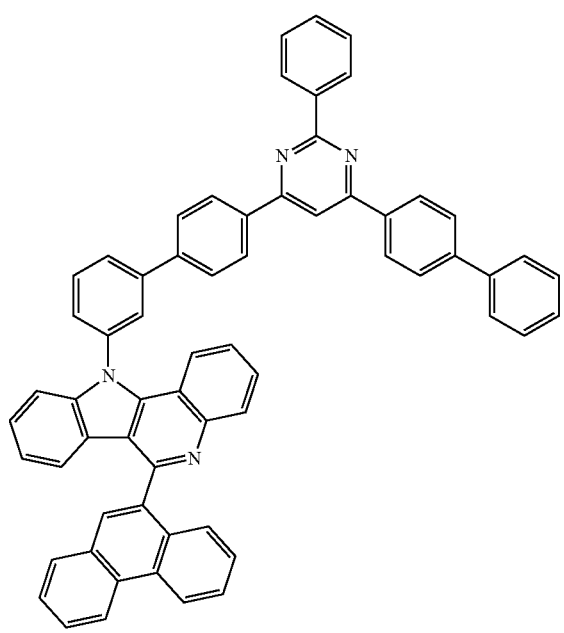
229
-continued
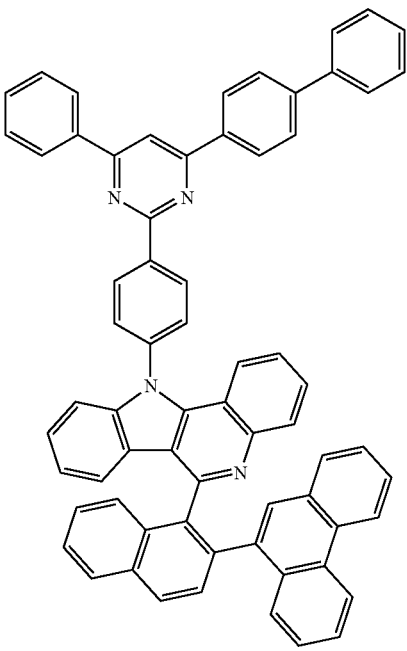
230
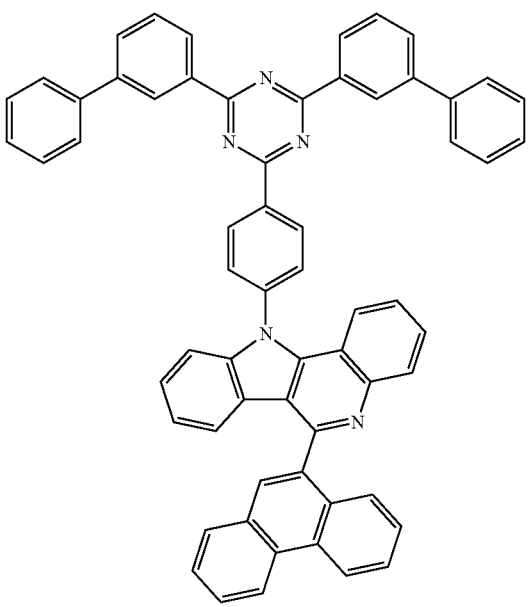
231

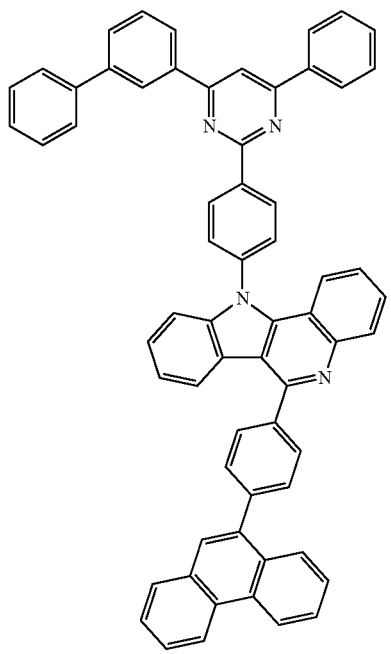
232
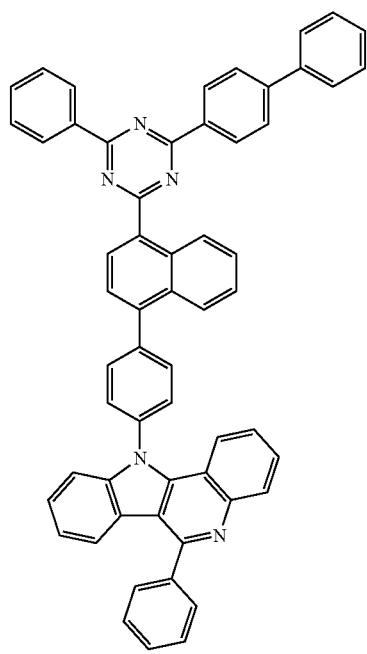
234
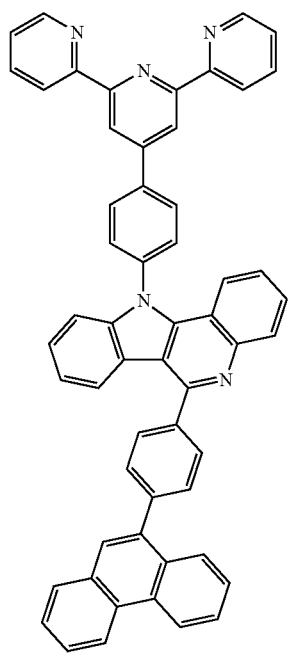
233
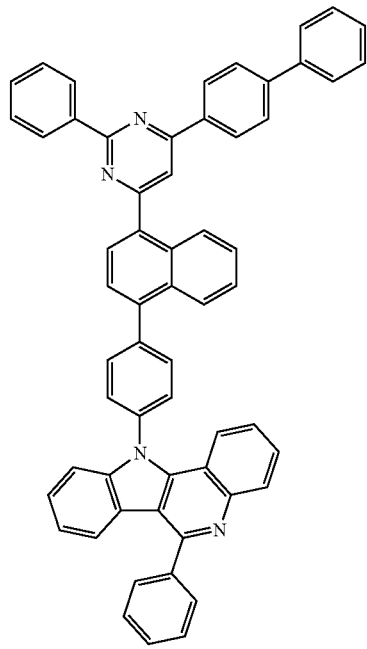
235

236
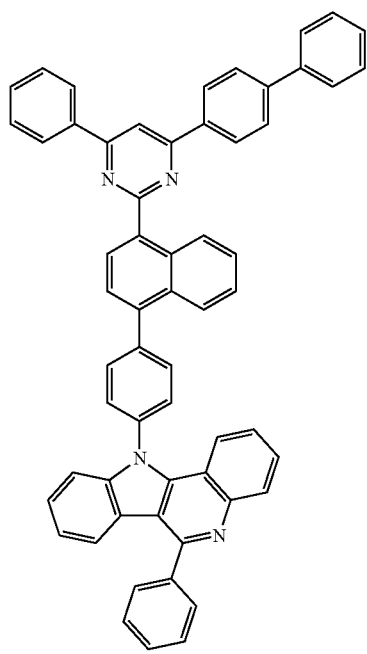
237
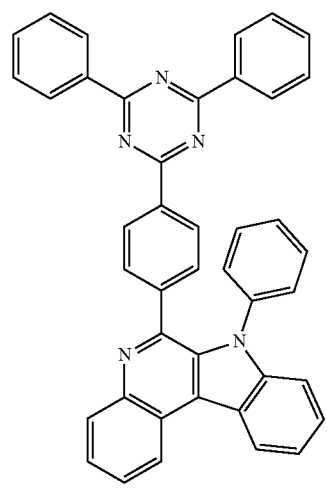
238
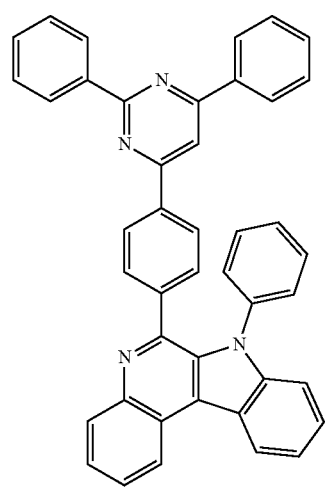
239
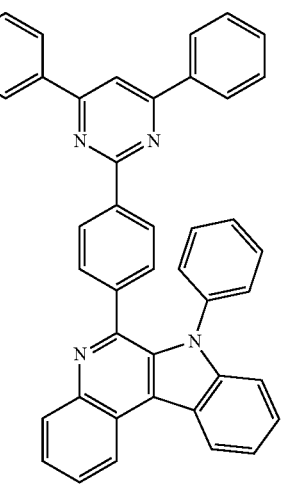
240
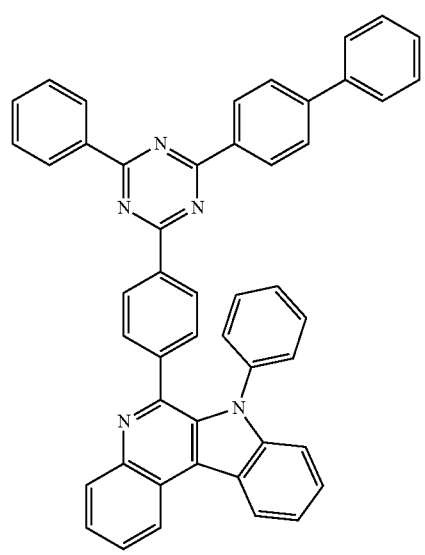
241
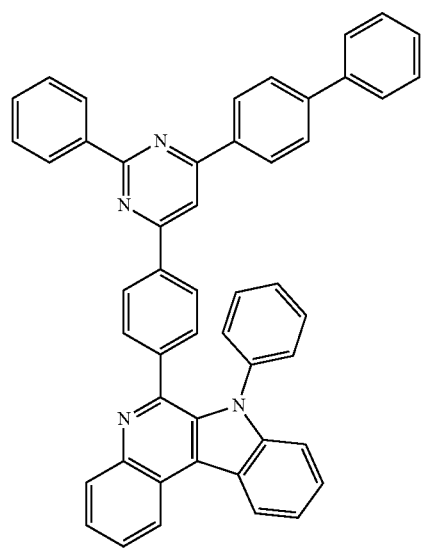

242
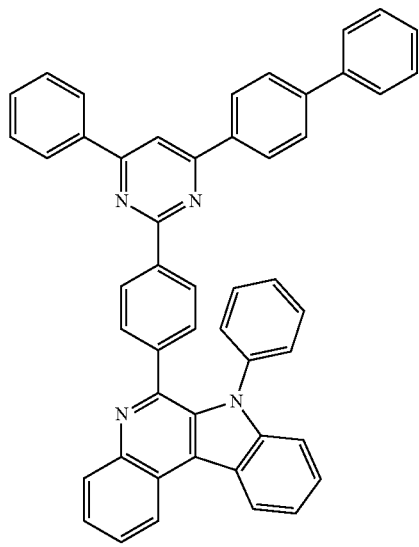
243
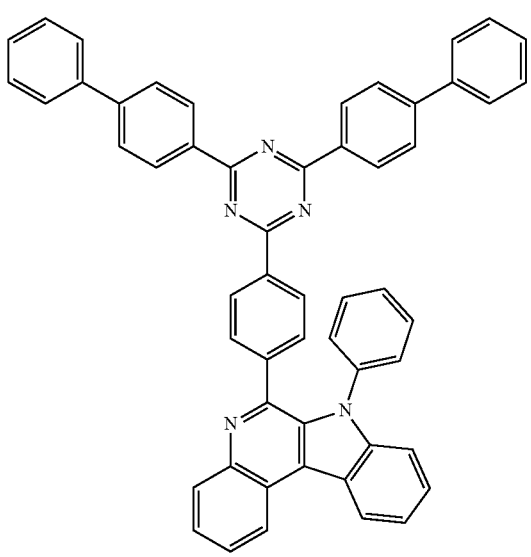
244
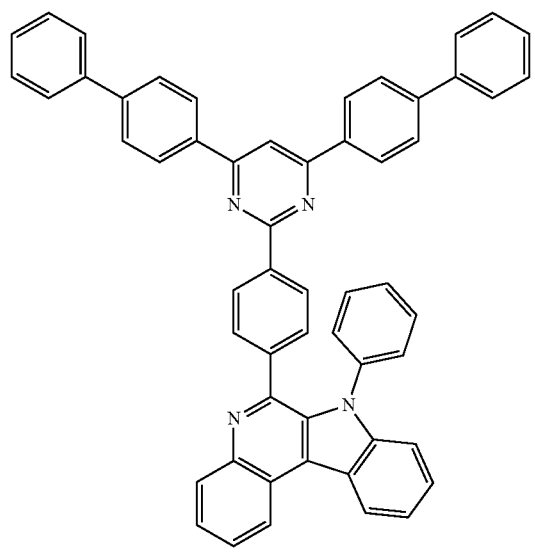
245
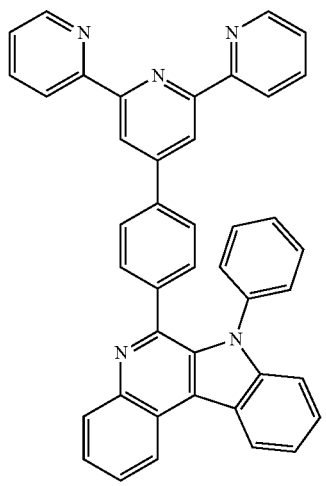
246
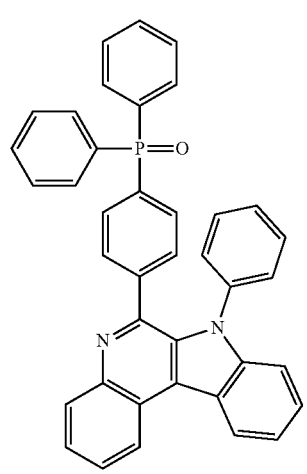

247
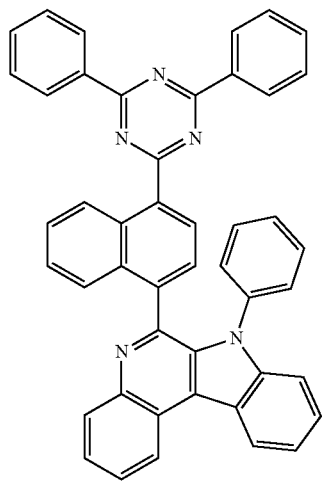
248
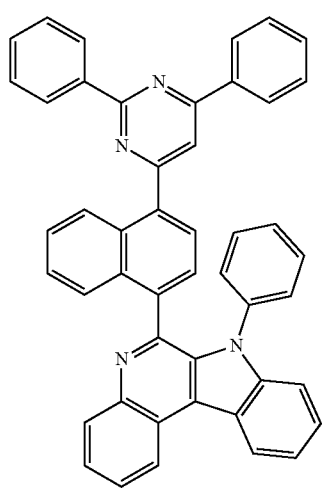
249
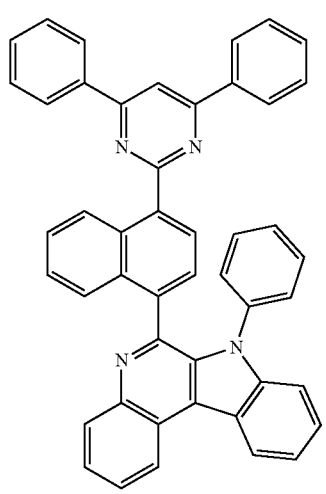
250
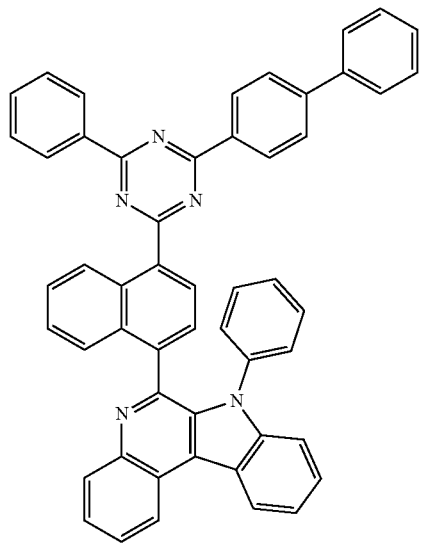
251
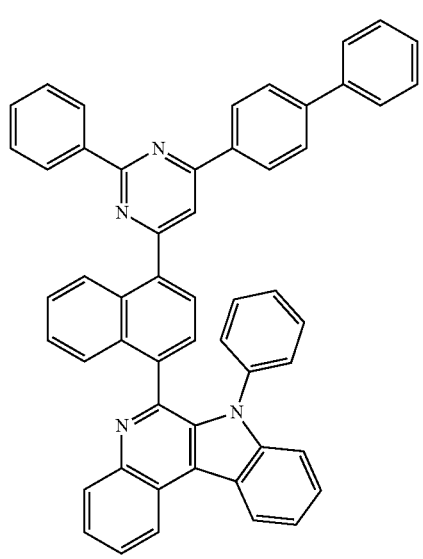
252
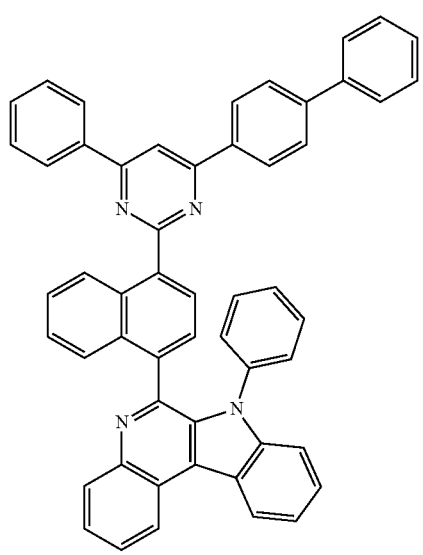

129
-continued
253
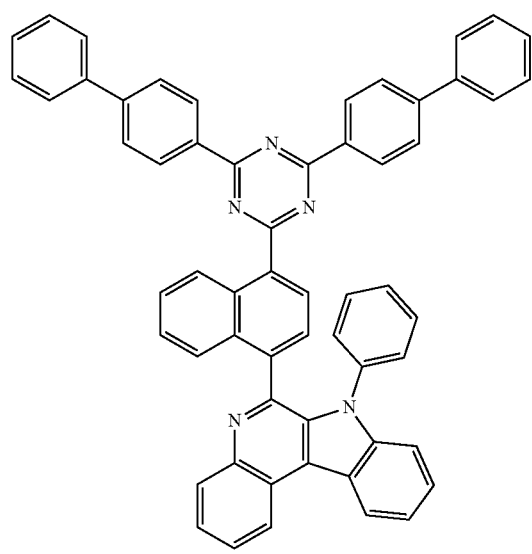
254
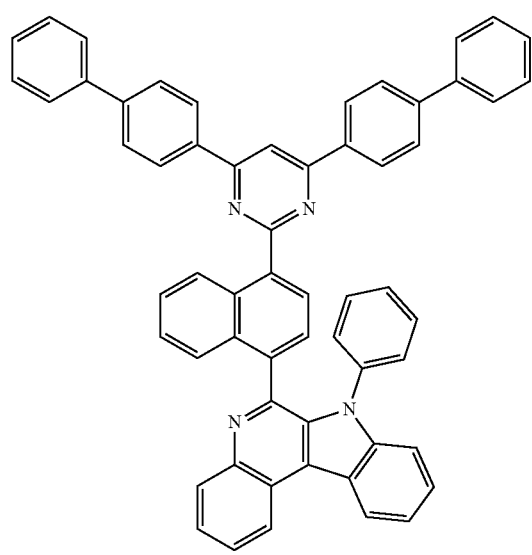
255
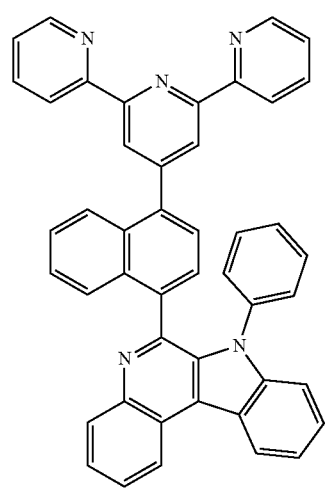
130
-continued
256
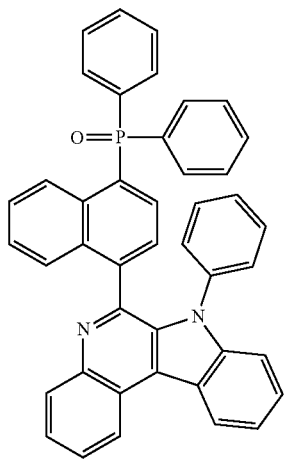
257
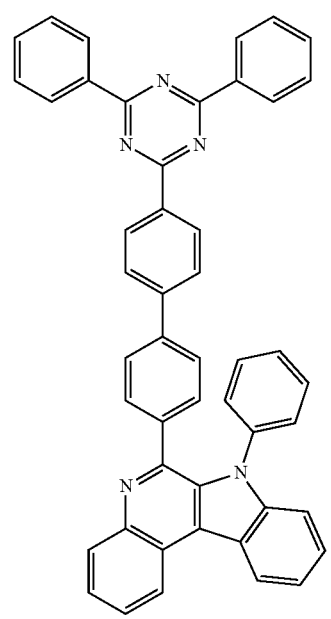

131
-continued
258
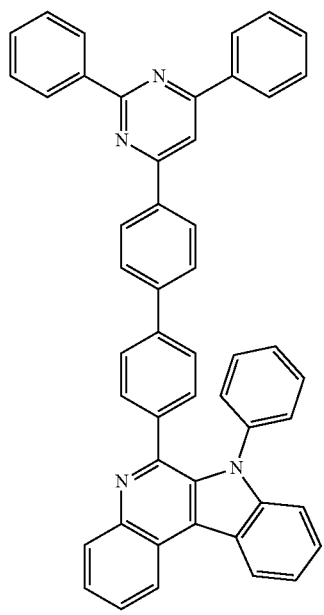
259
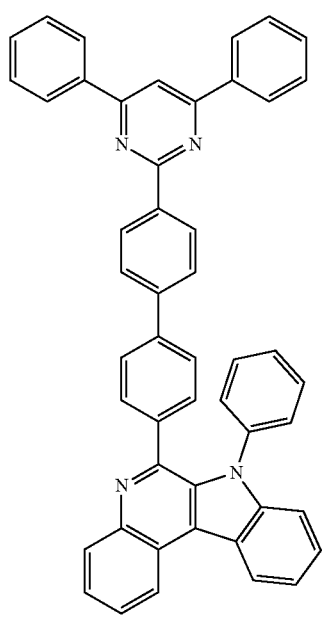
132
-continued
260
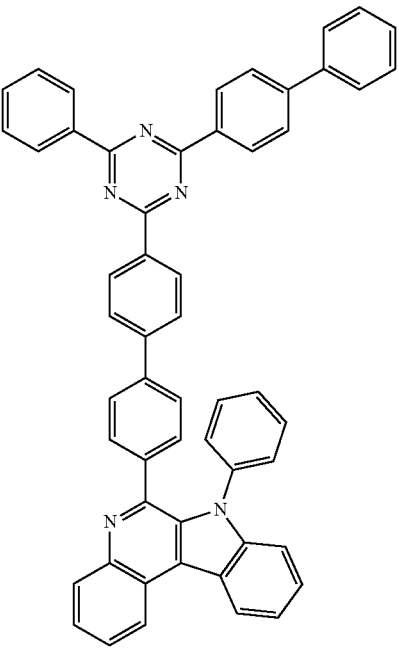
261
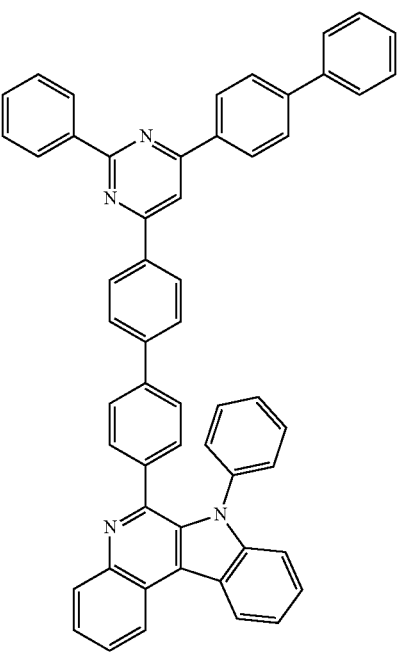

133
-continued
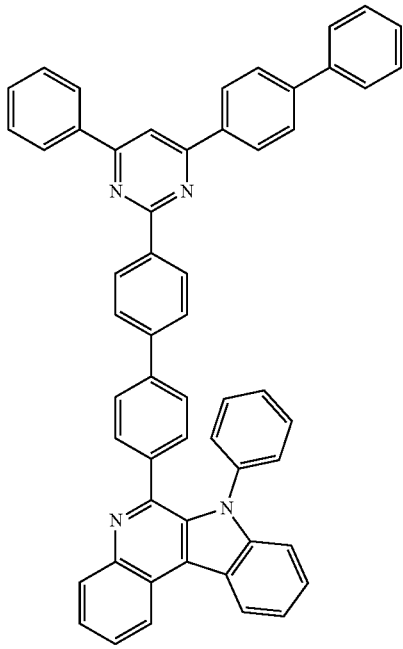
262
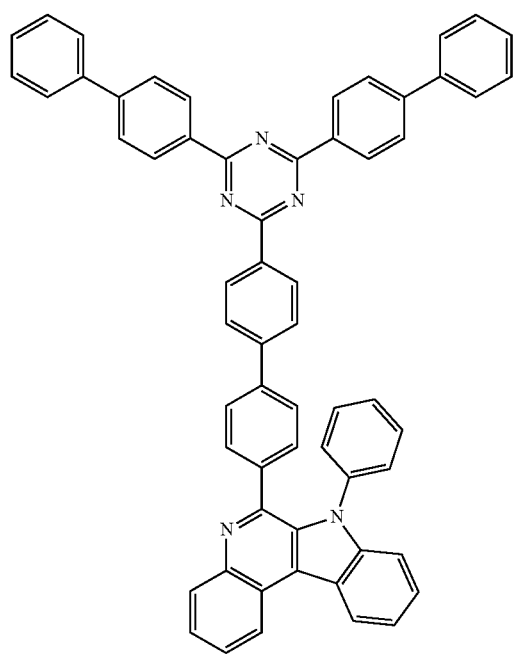
263
134
-continued
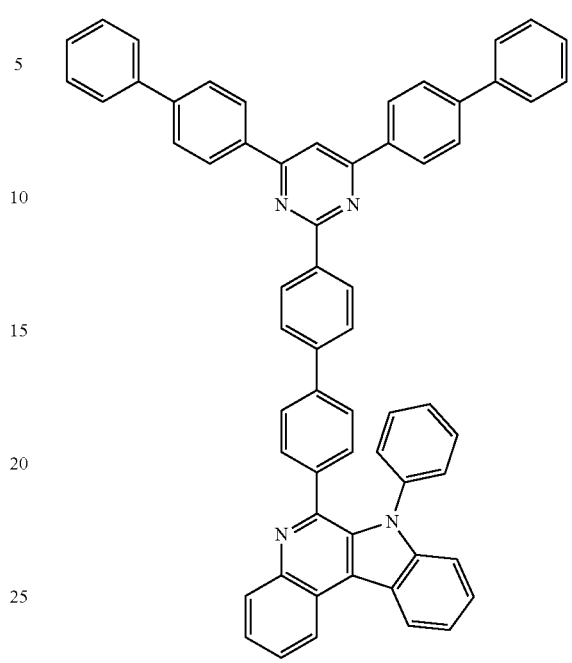
264
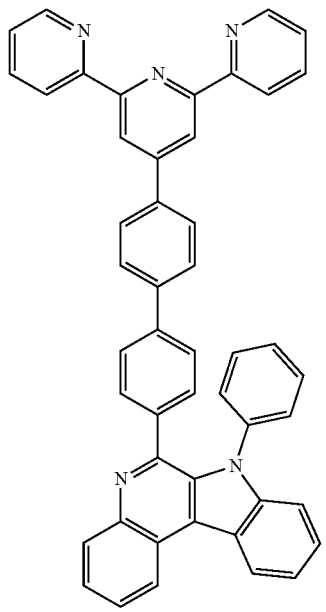
265

266
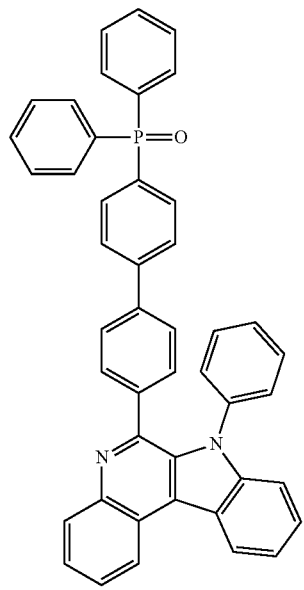
267
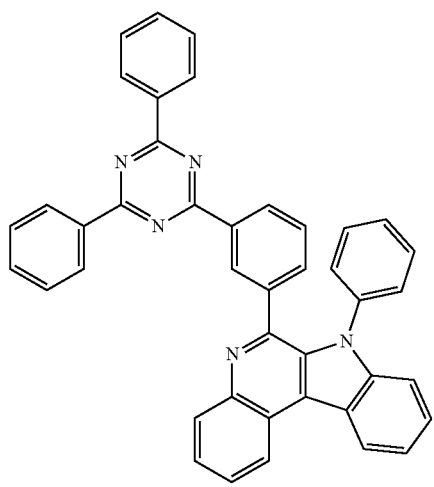
268
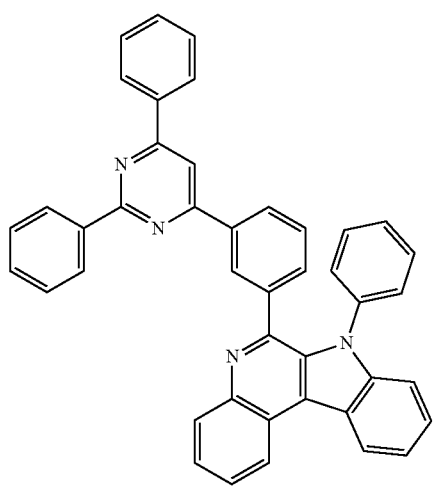
269
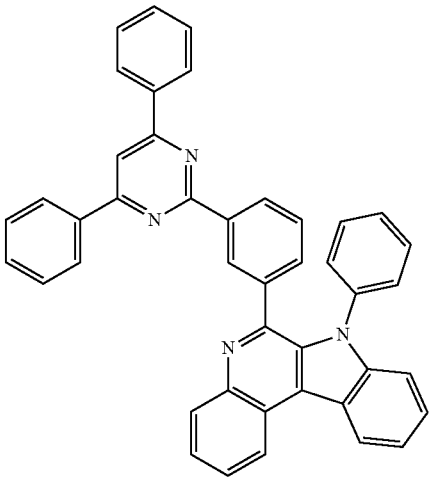
270
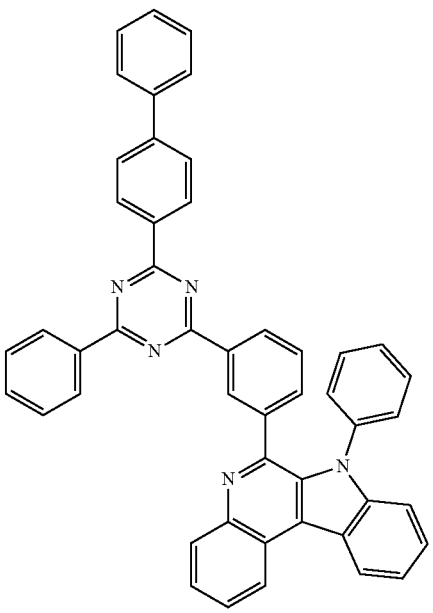

271
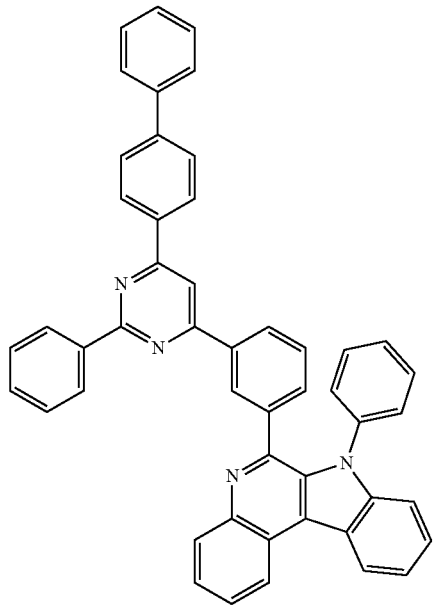
272
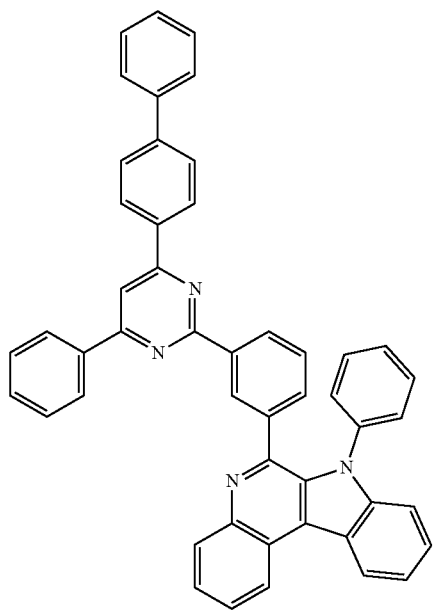
273
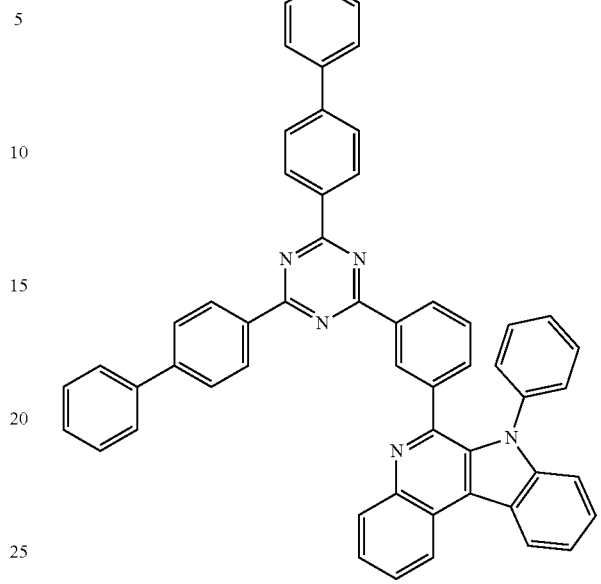
274
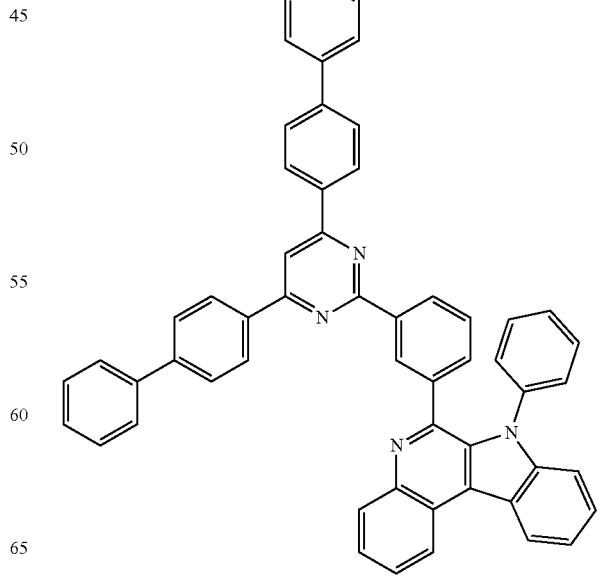

275
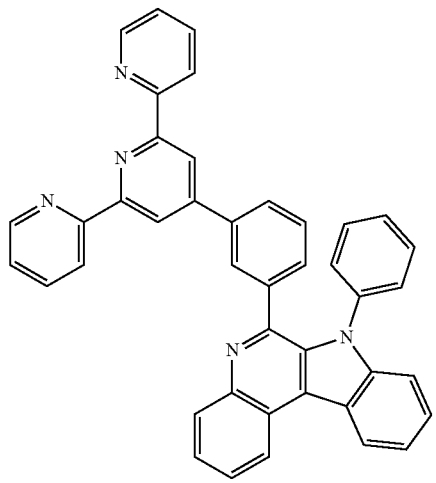
276
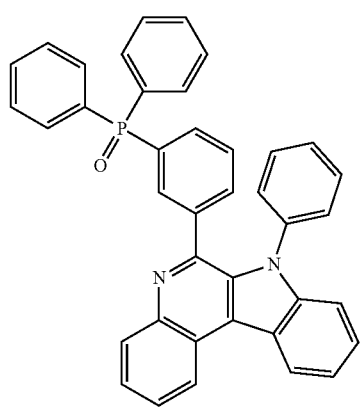
278
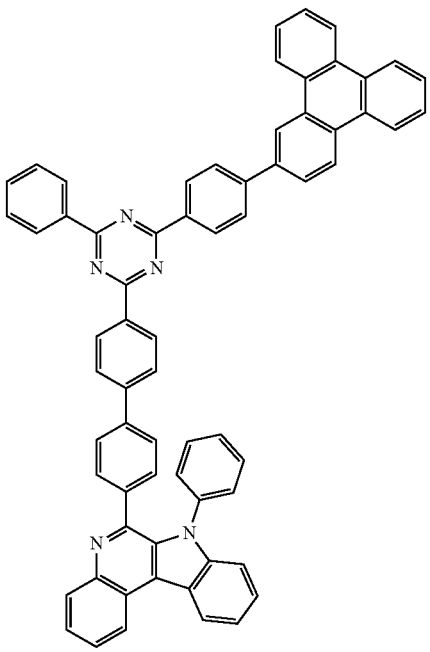
277
279
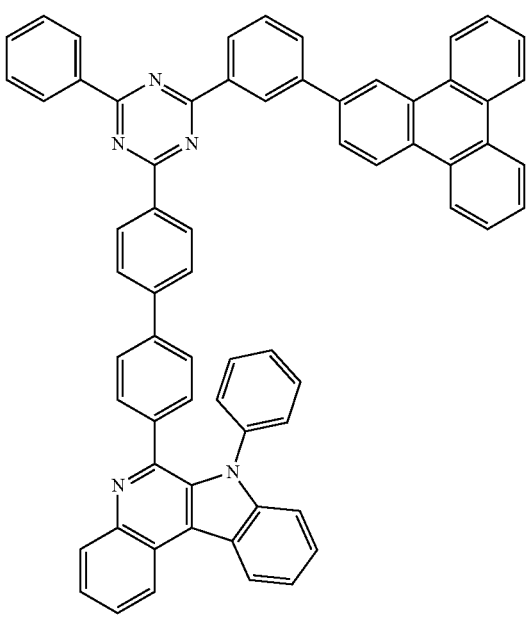

141
-continued
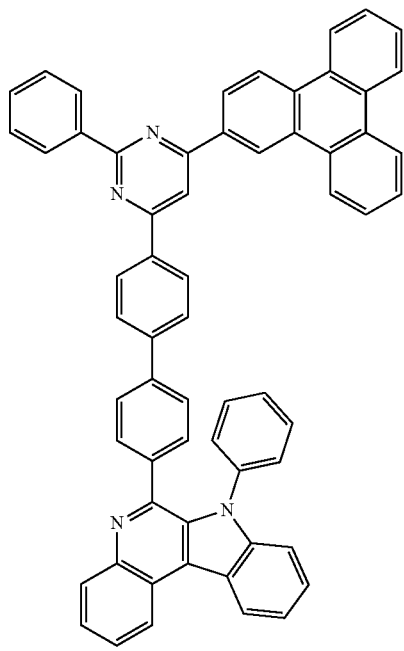
280
281
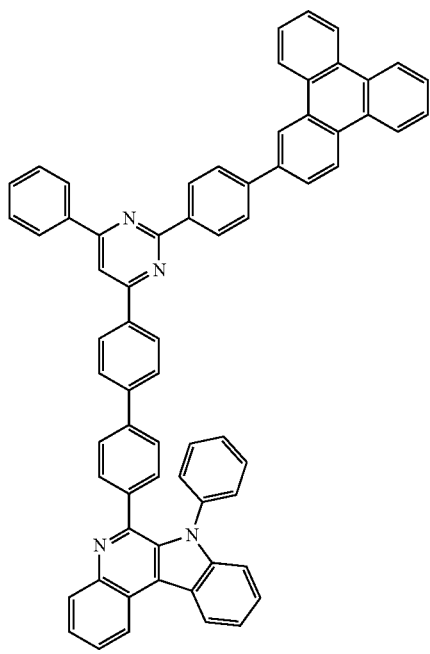
142
-continued
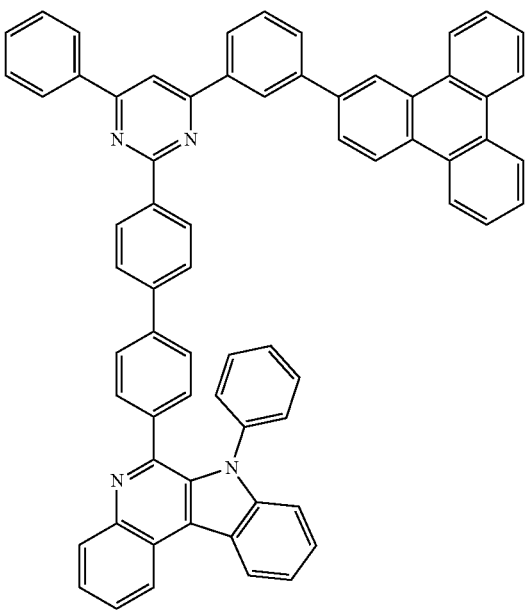
282
283
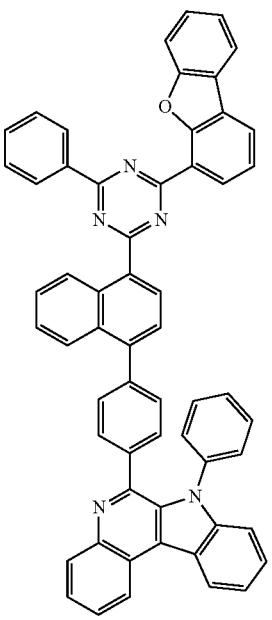

284
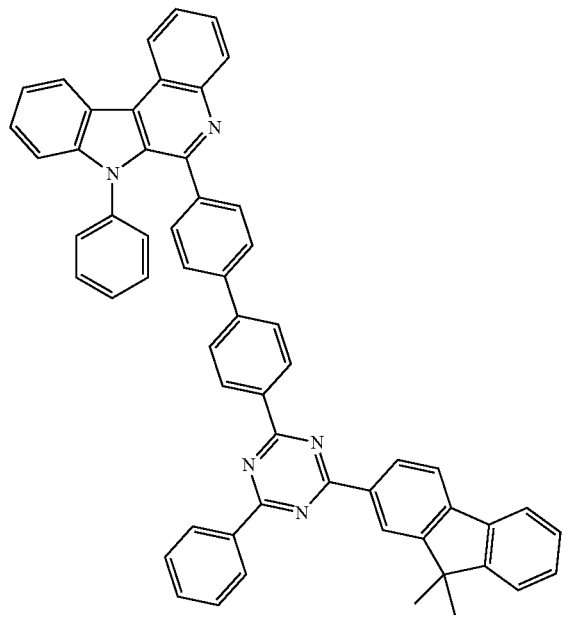
285
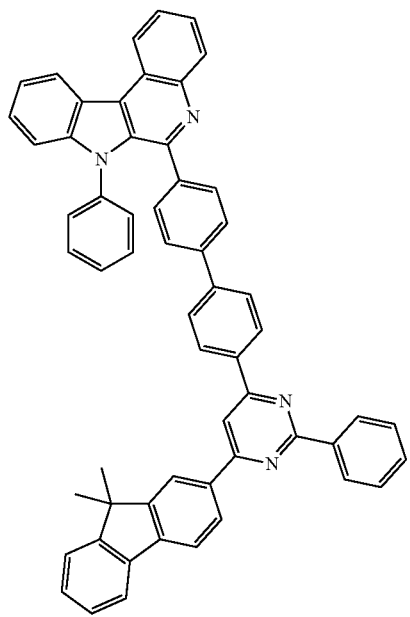
286
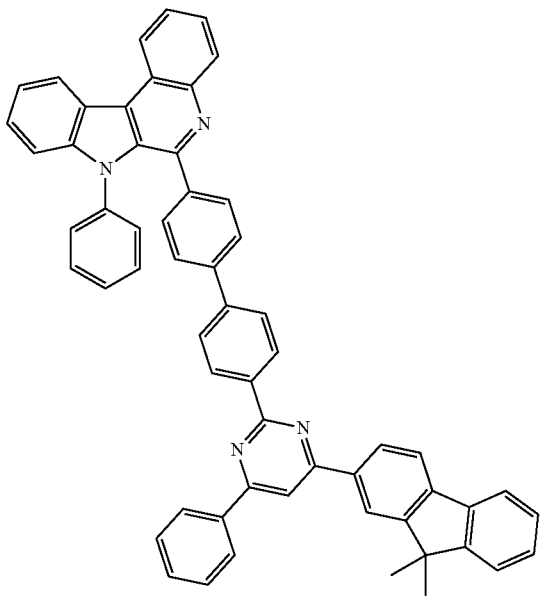
287
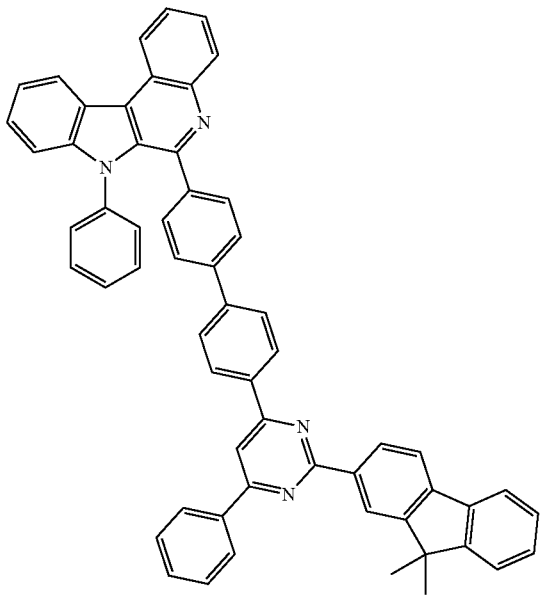

288
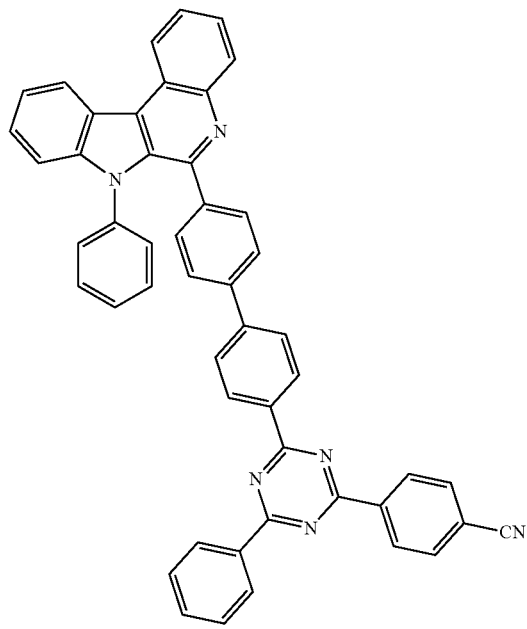
290
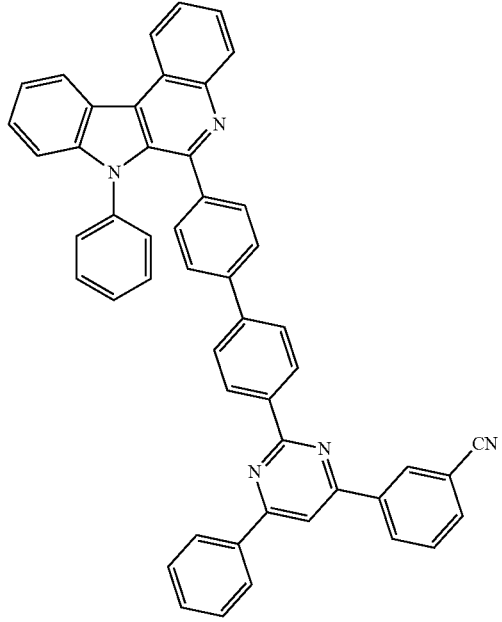
289
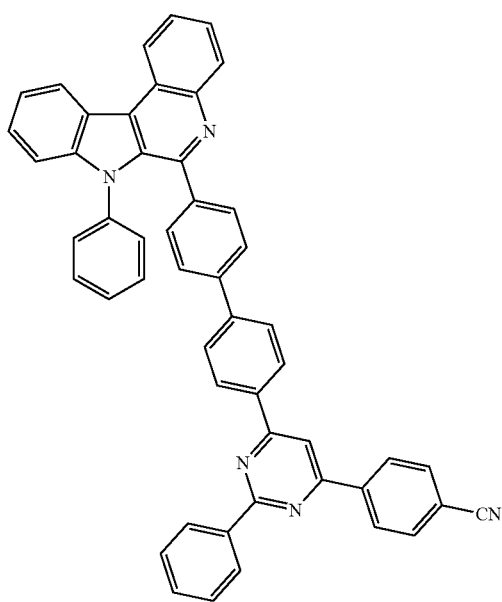
291
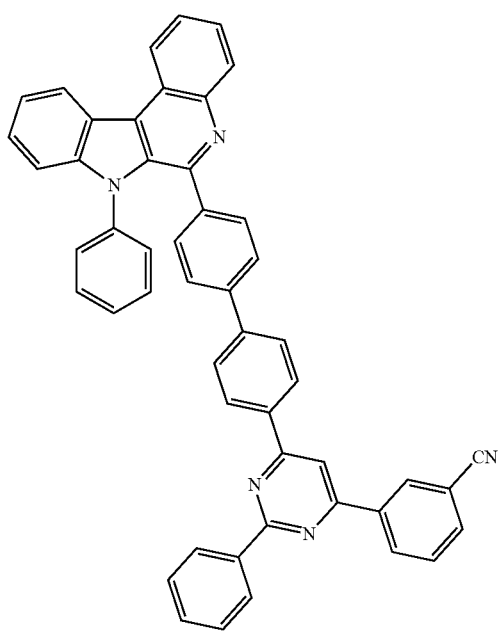

292
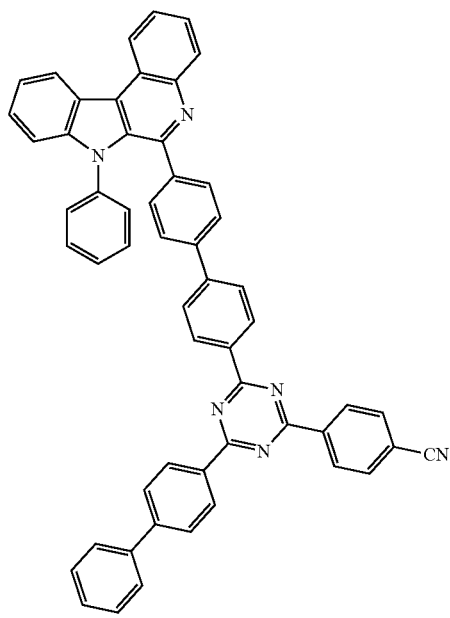
293
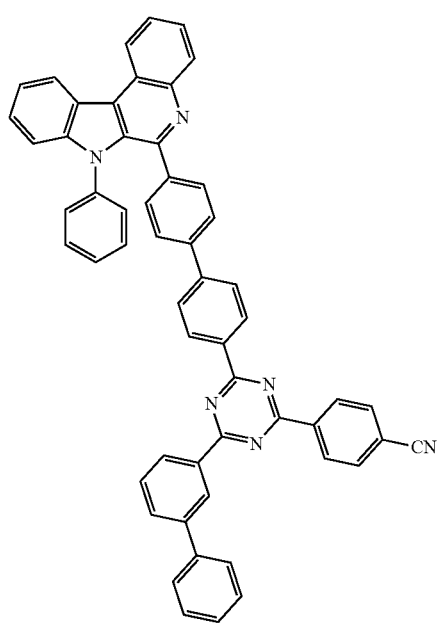
294
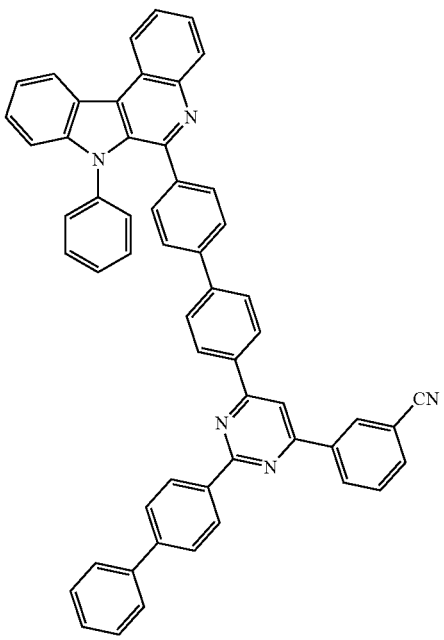
295
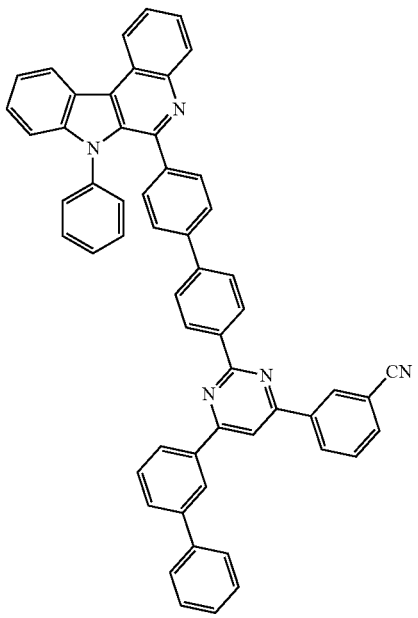

296
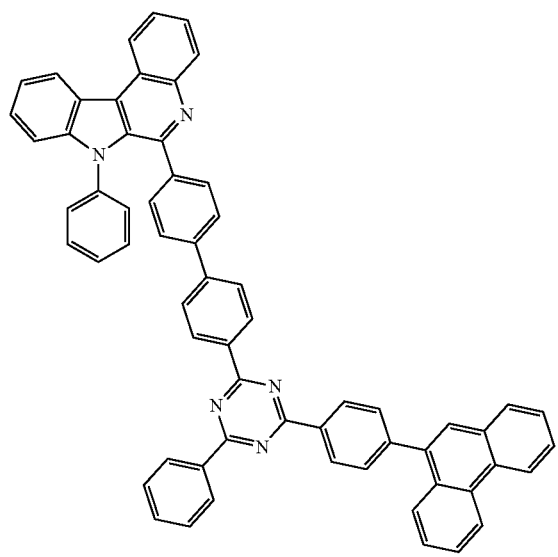
298
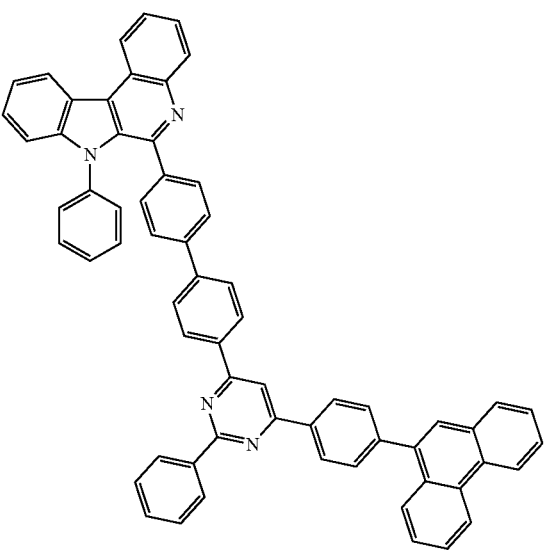
297
299
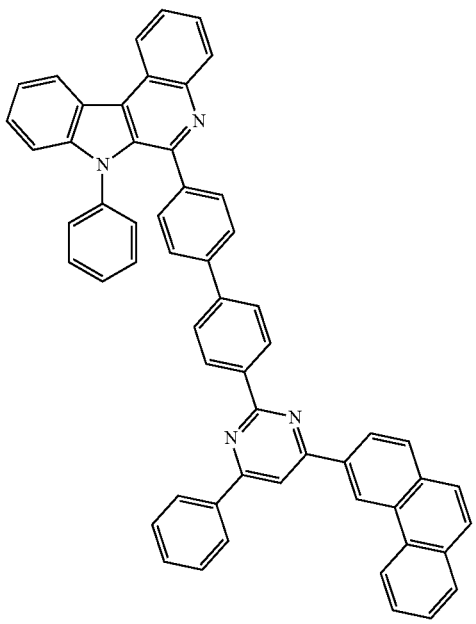

151
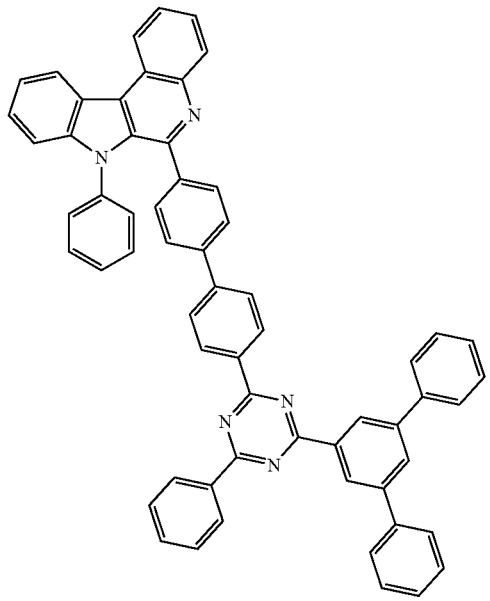
300
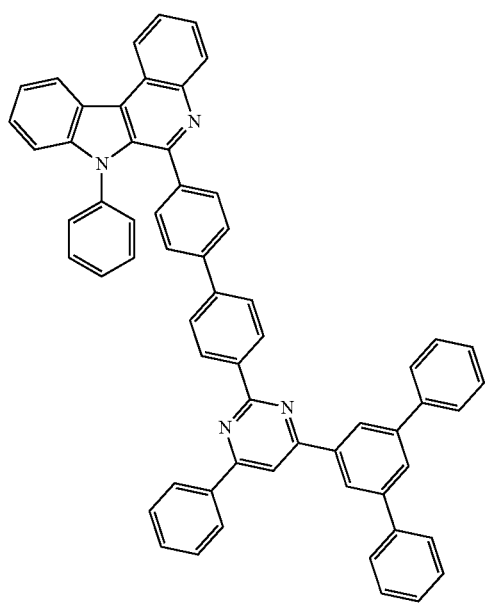
301
152
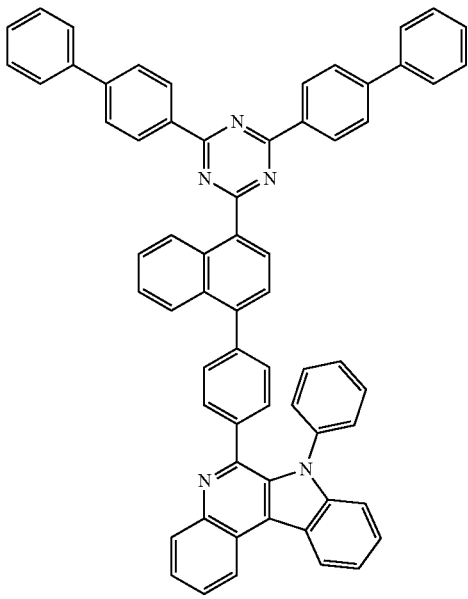
302
303

153
-continued
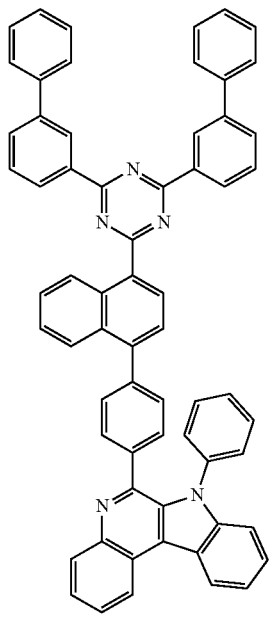
304
154
-continued
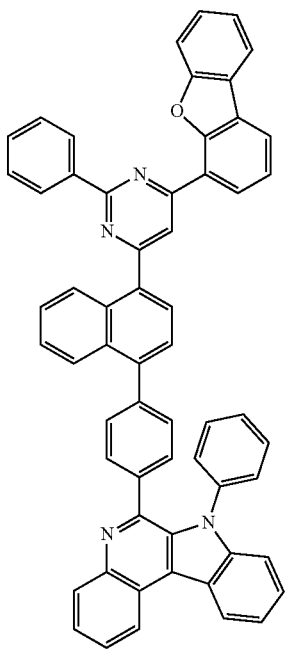
306
307
305
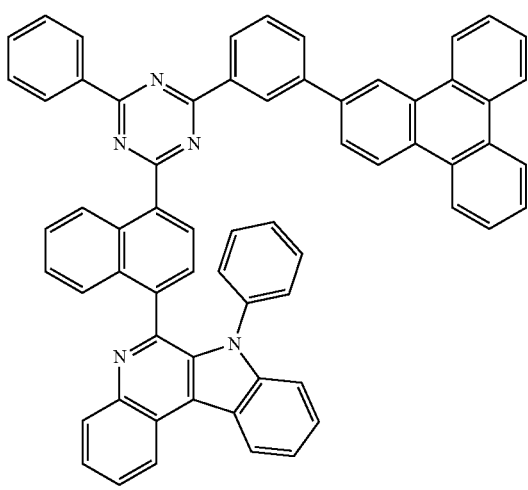
308
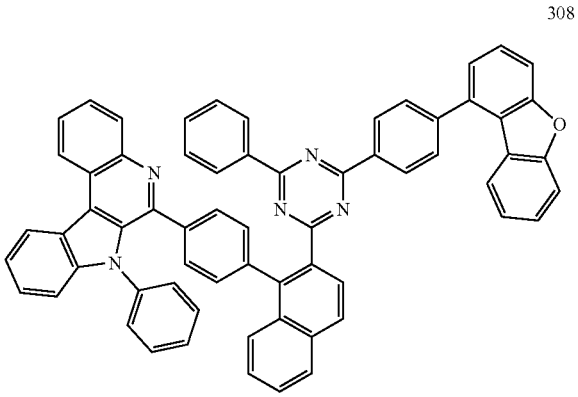

309
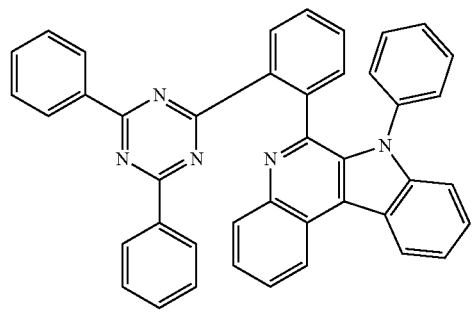
310
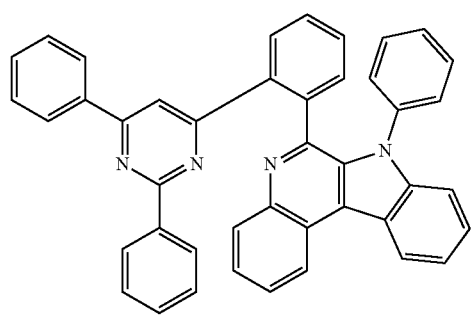
311
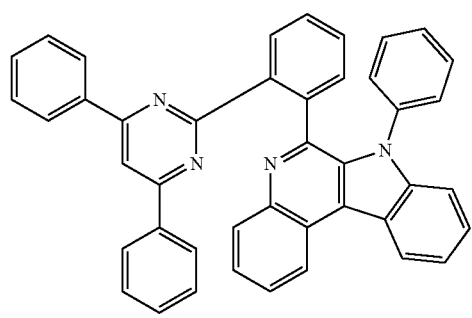
312
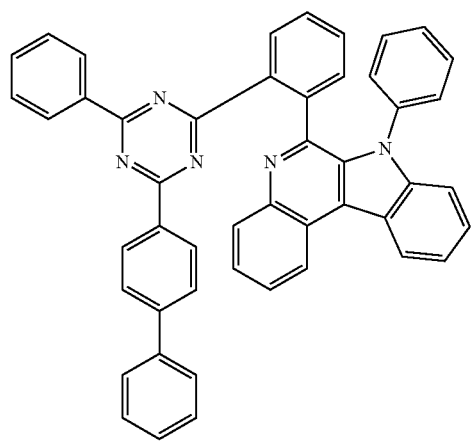
313
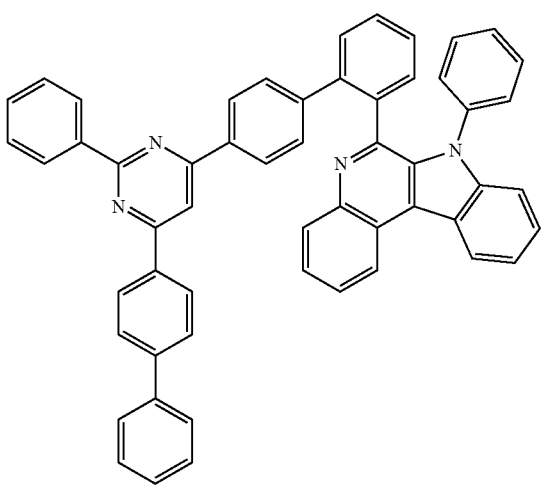
314
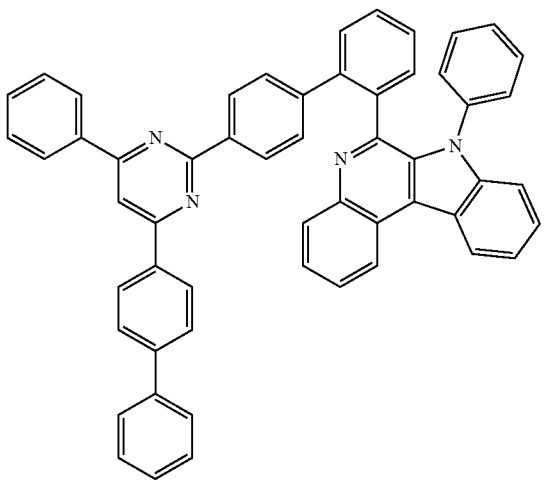
315
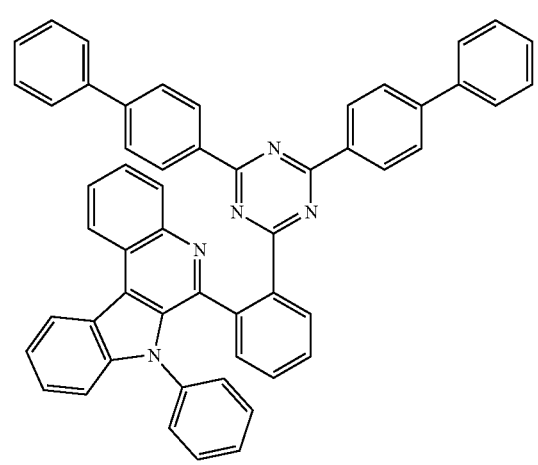

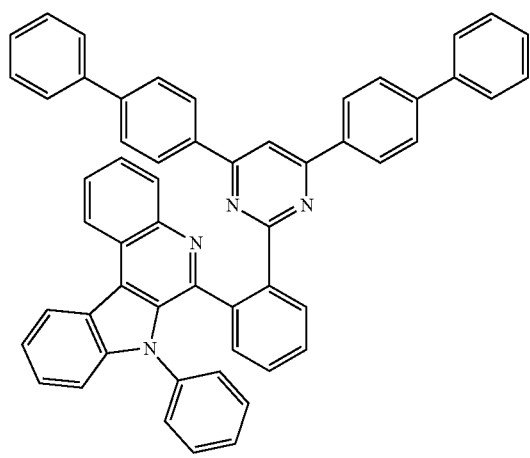
316
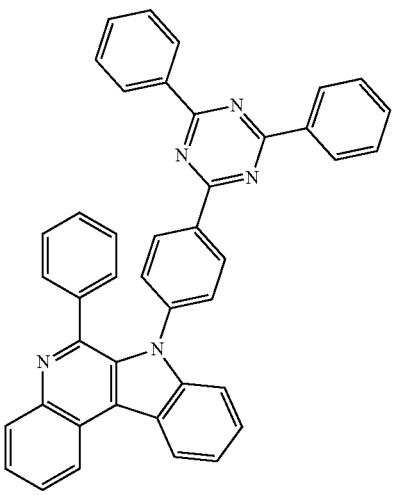
319
317
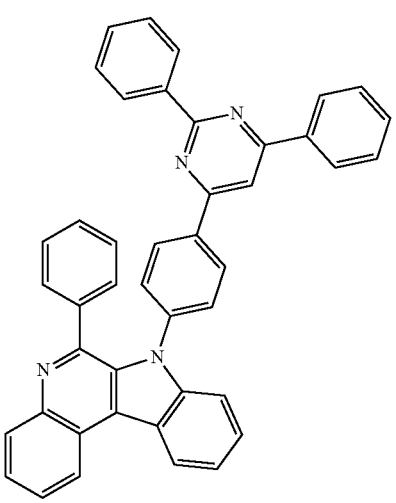
320
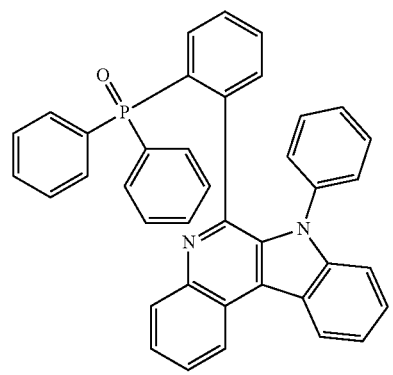
318
321

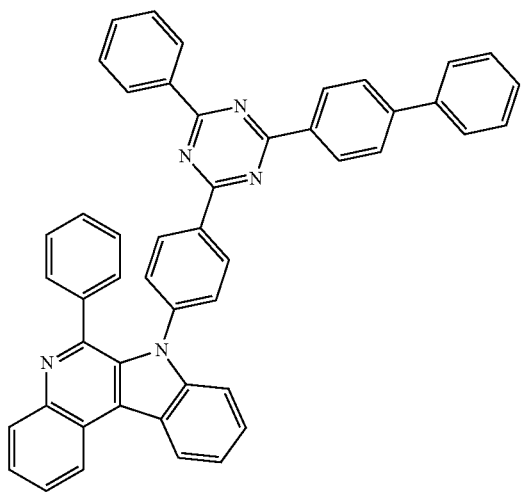
322
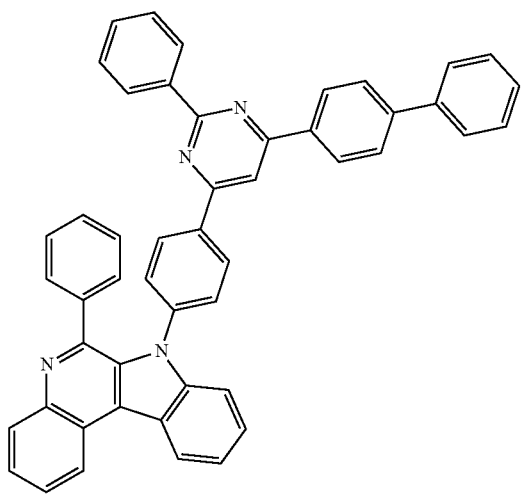
323
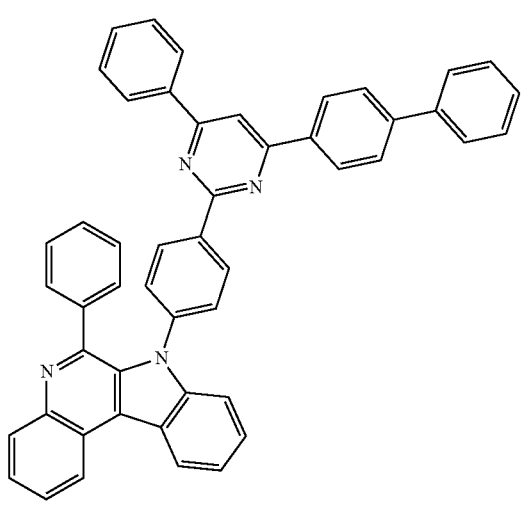
324
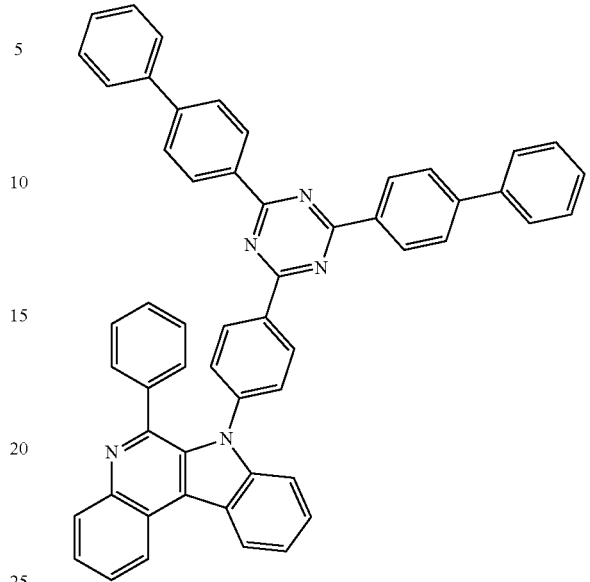
325
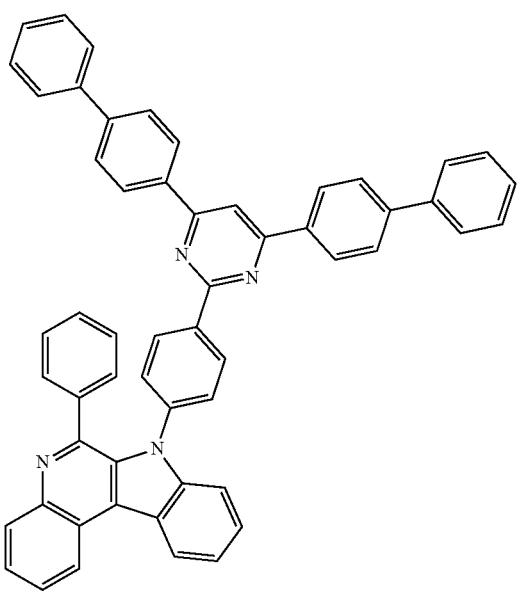
326

161
-continued
327
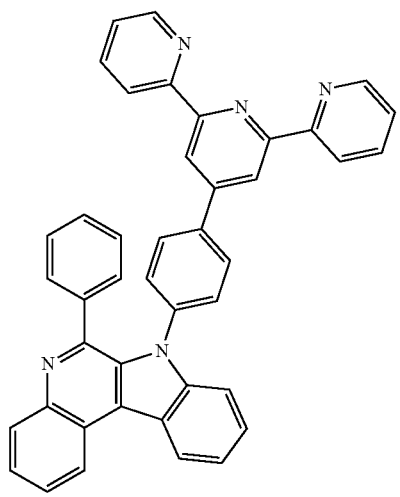
328
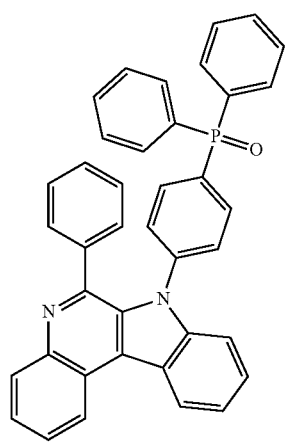
329
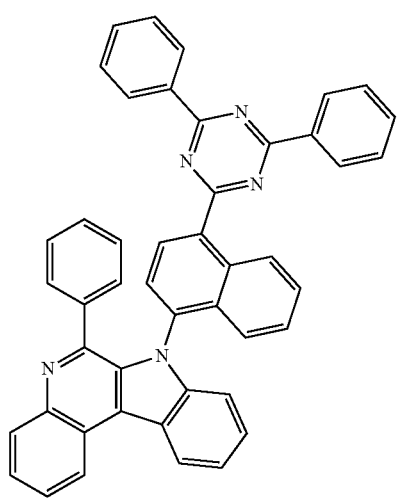
162
-continued
330
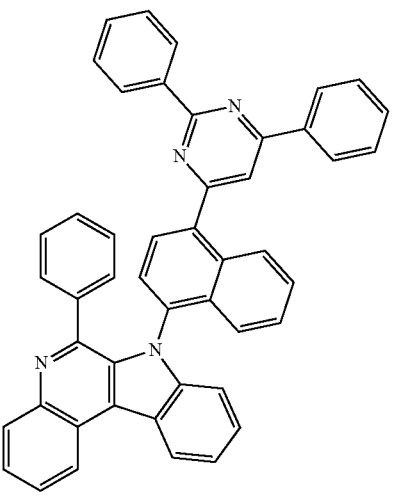
331
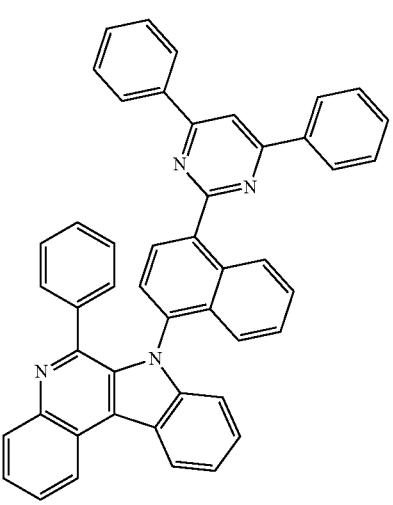
332
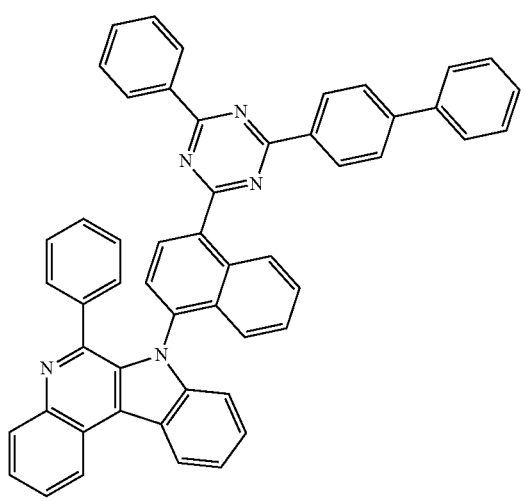

-continued
333
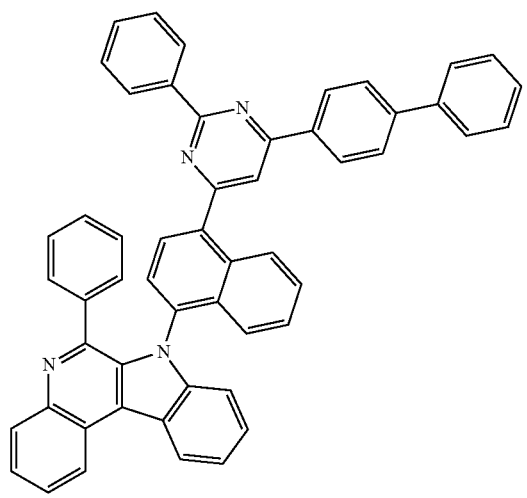
334
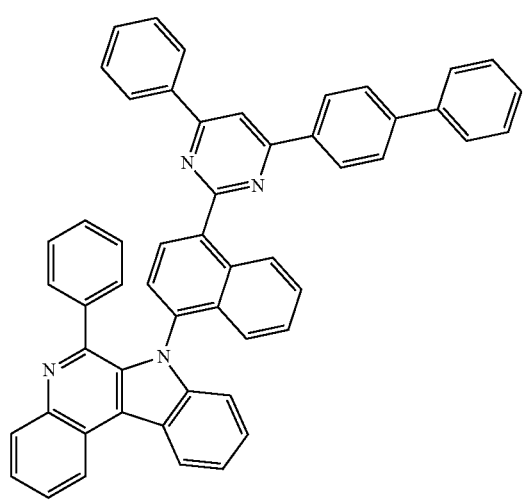
335
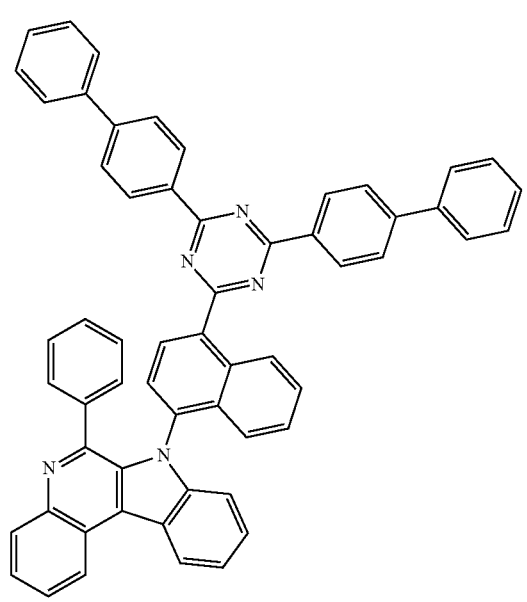
-continued
336
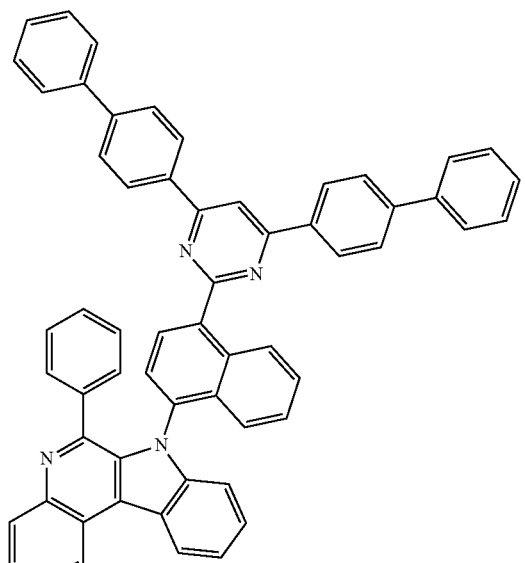
337
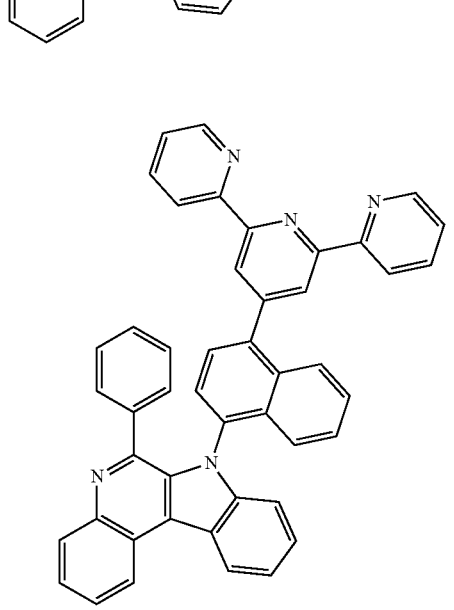
338
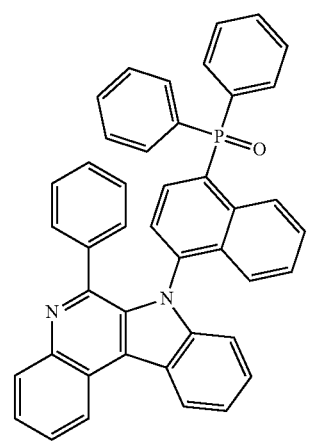

-continued
339
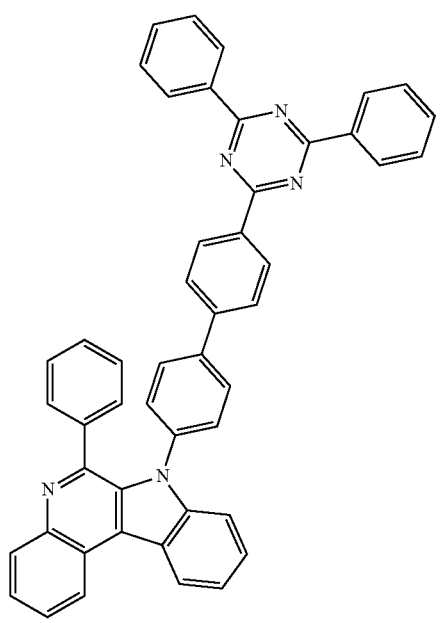
340
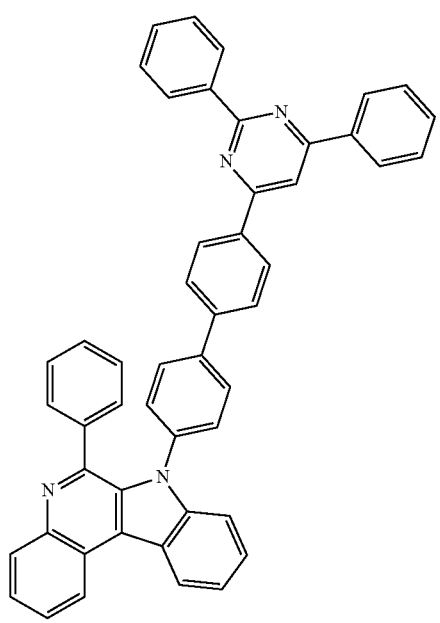
-continued
341
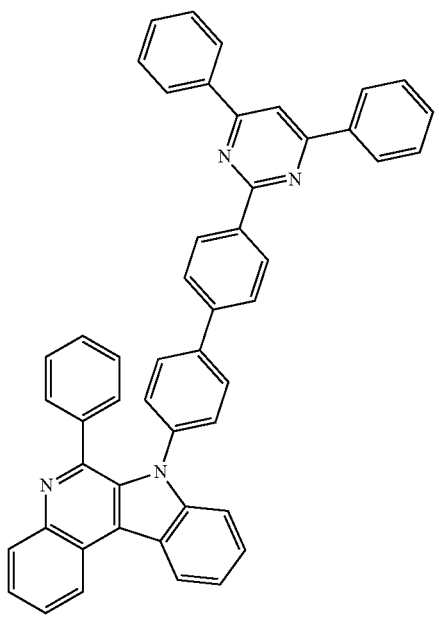
342
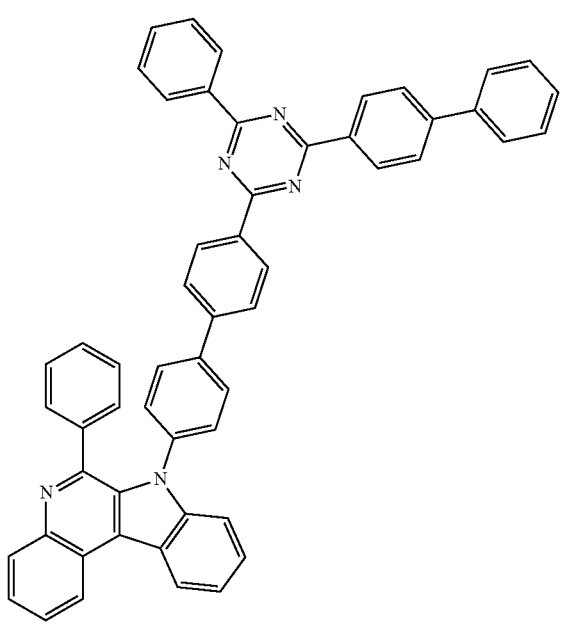

343
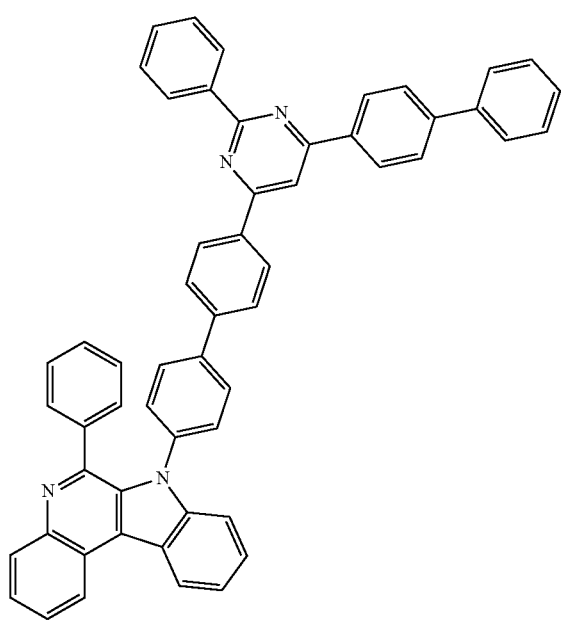
344
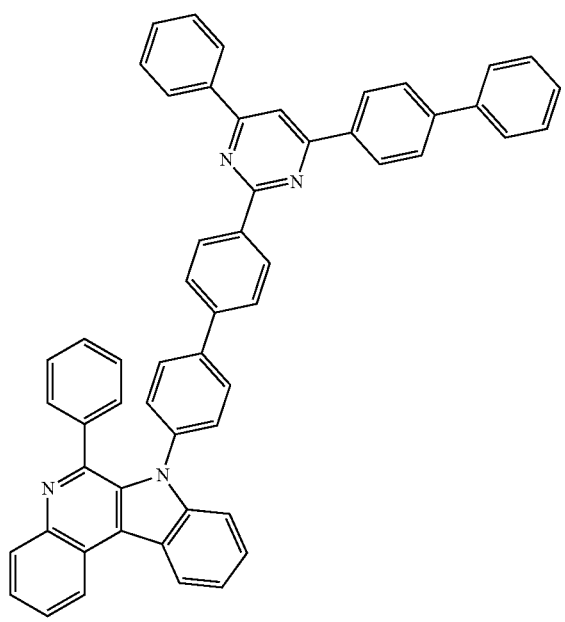
345
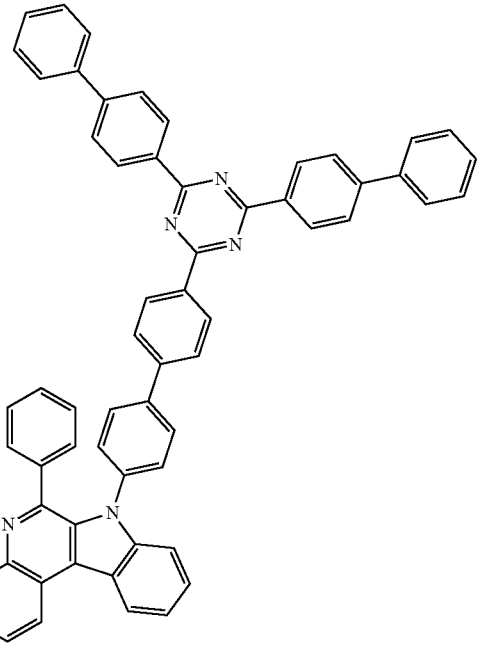
346
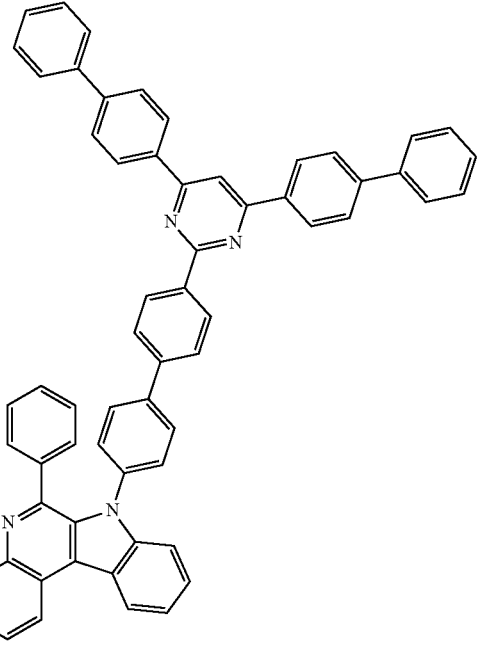

347
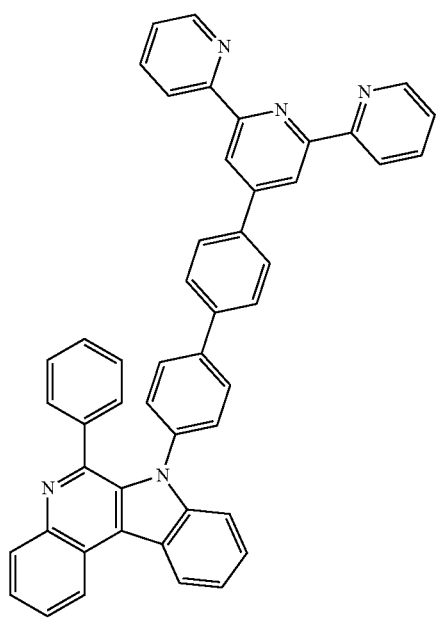
348
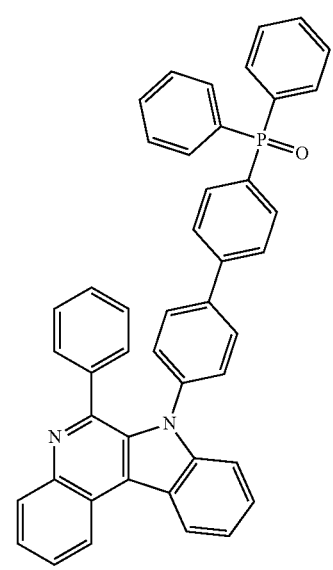
349
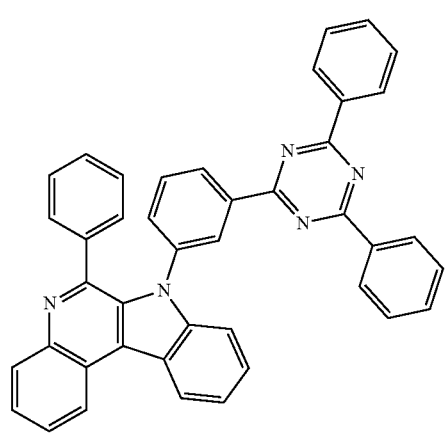
350
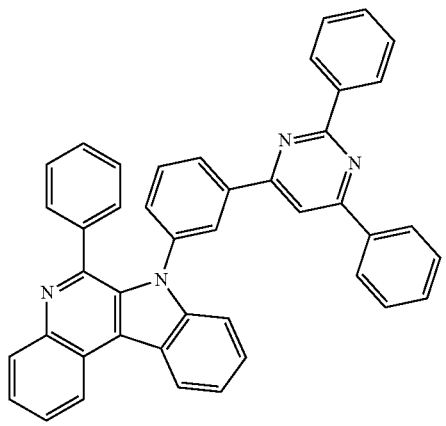
351
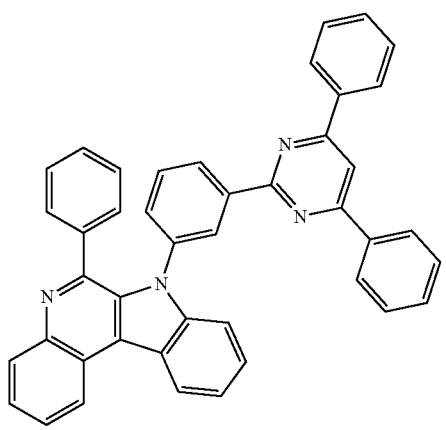
352
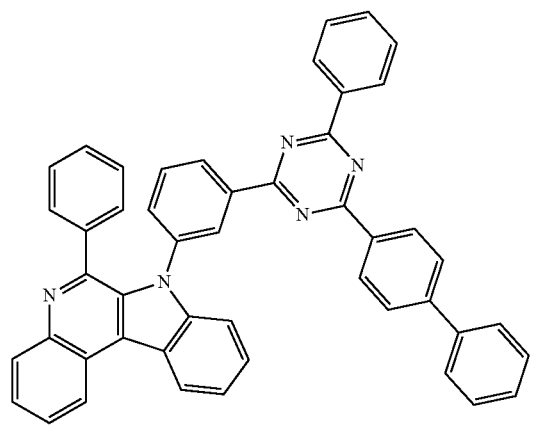

-continued
353
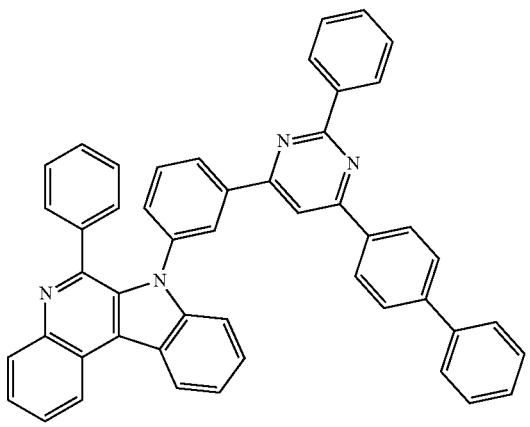
354
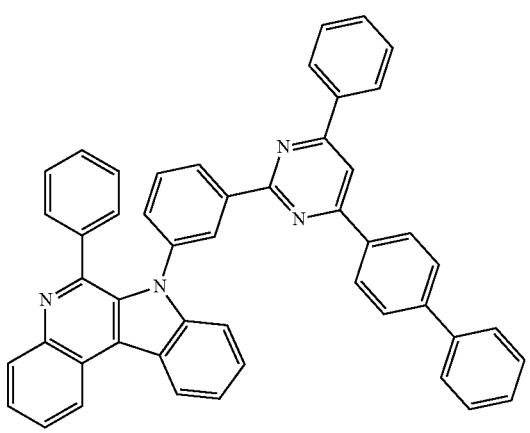
355
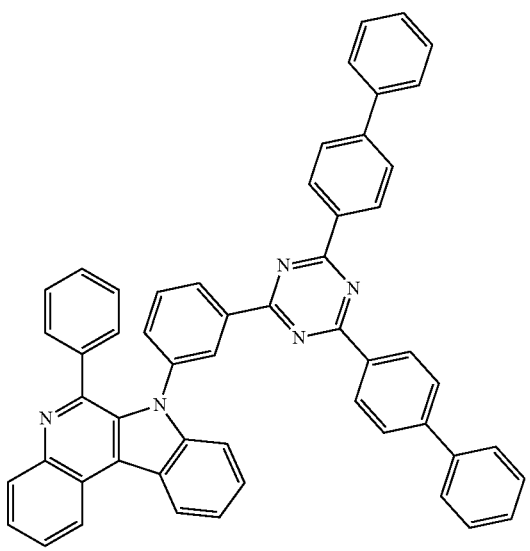
-continued
356
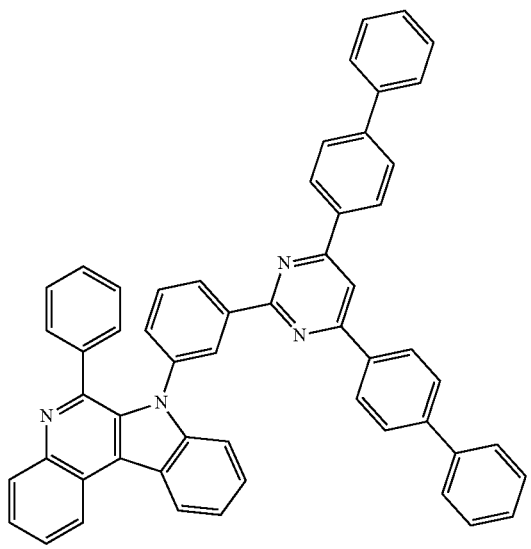
357
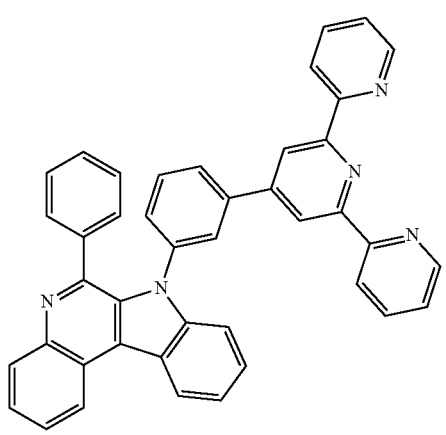
358
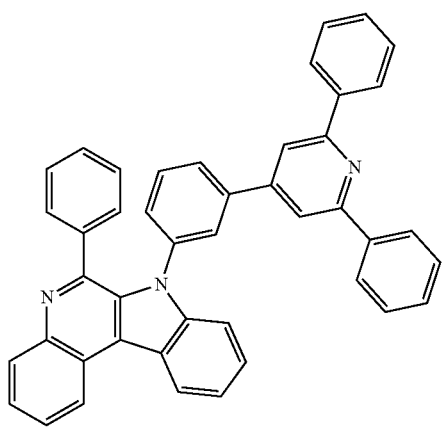

359
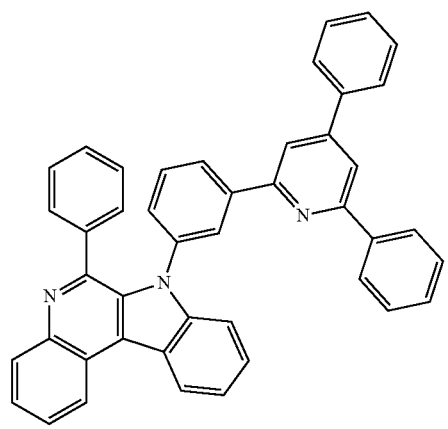
360
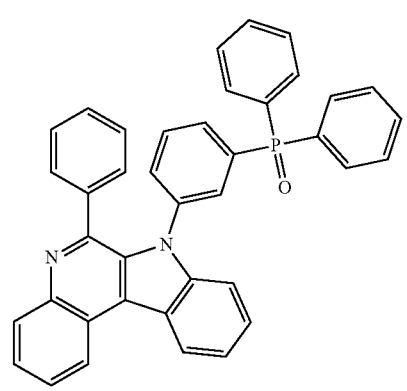
361
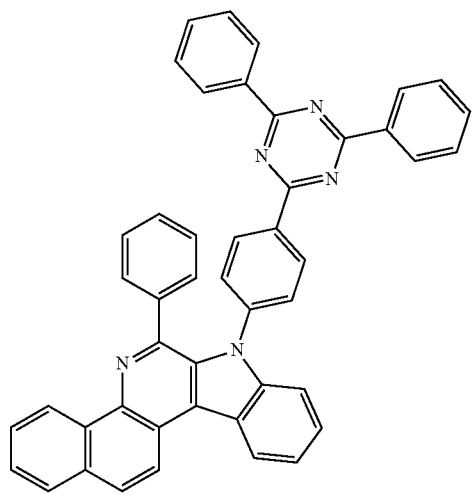
362
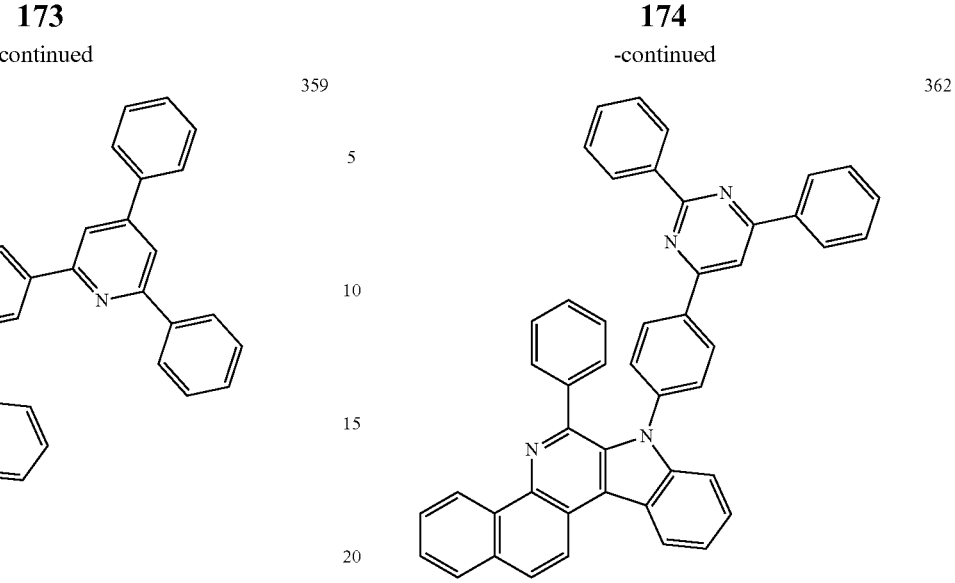
363
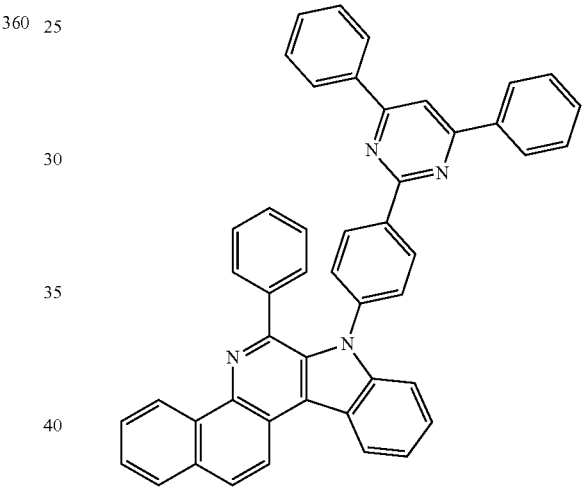
364
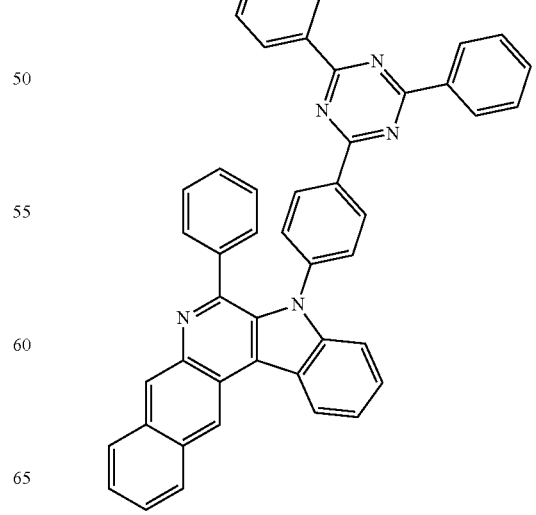

-continued
365
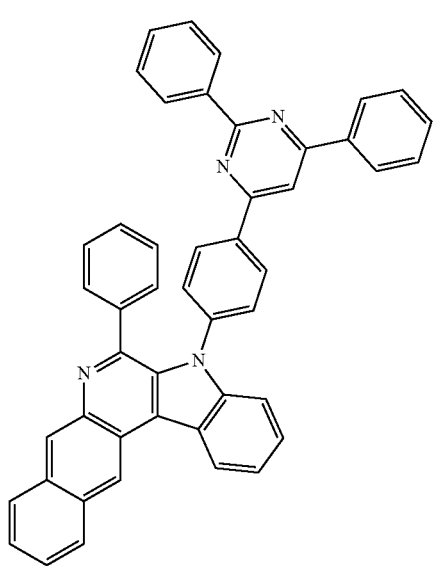
366
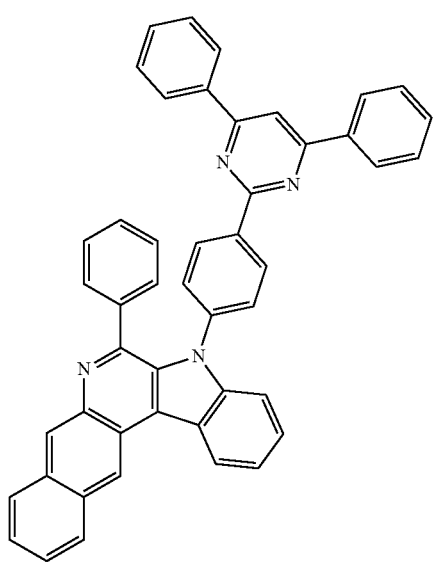
367
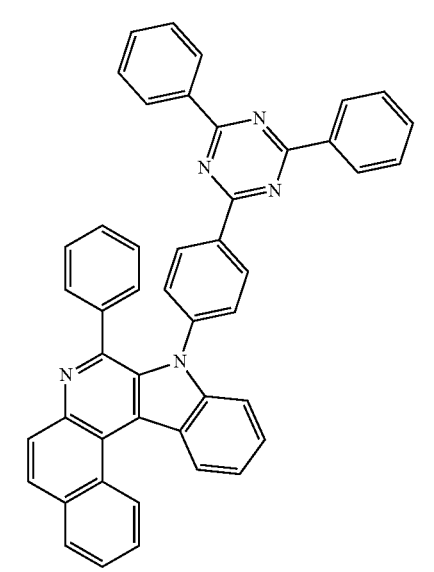
-continued
368
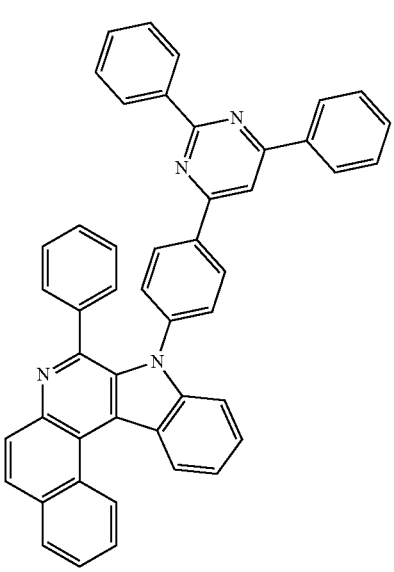
369
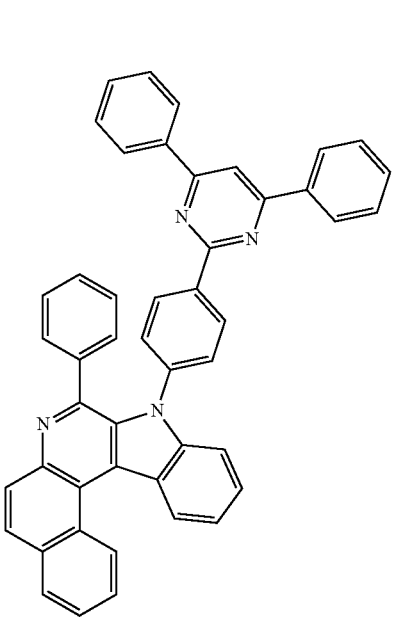
370
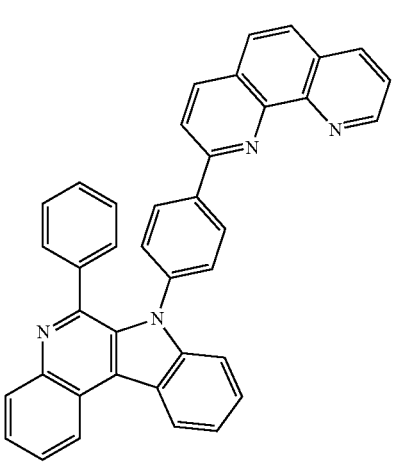

177
-continued
371
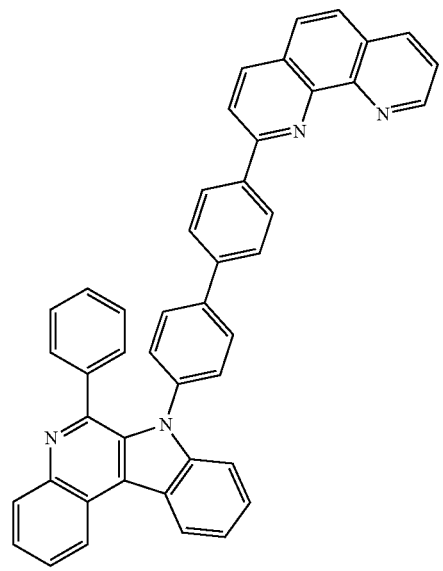
372
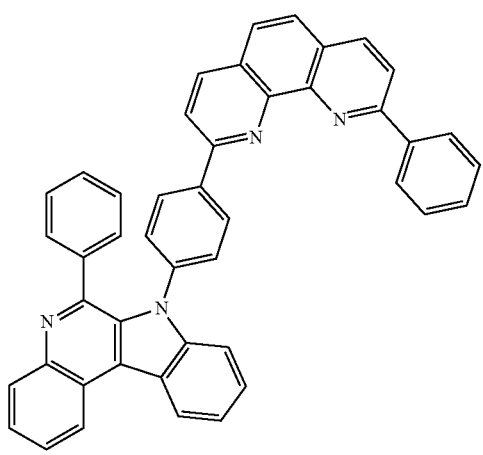
373
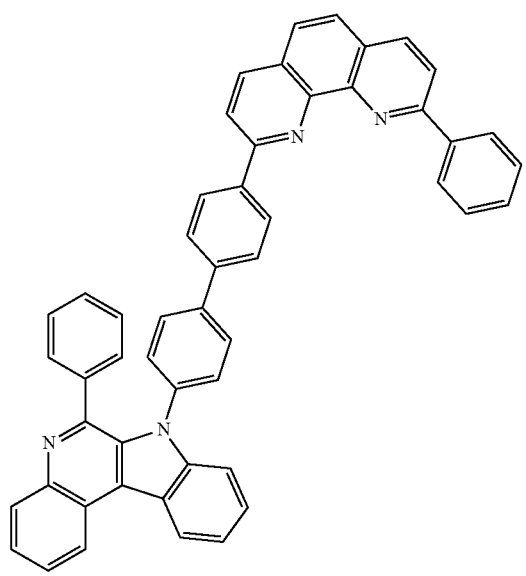
178
-continued
374
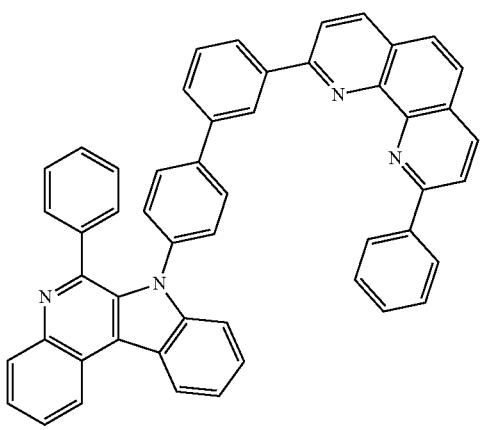
375
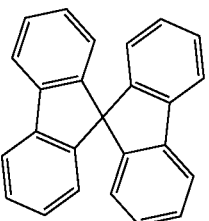
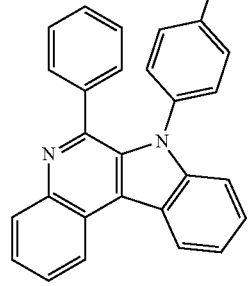
376
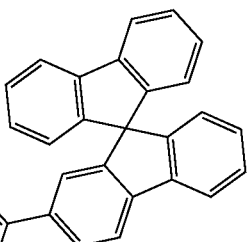
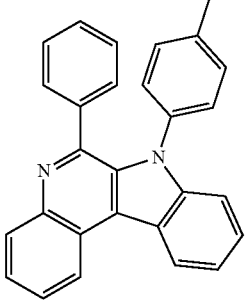

377
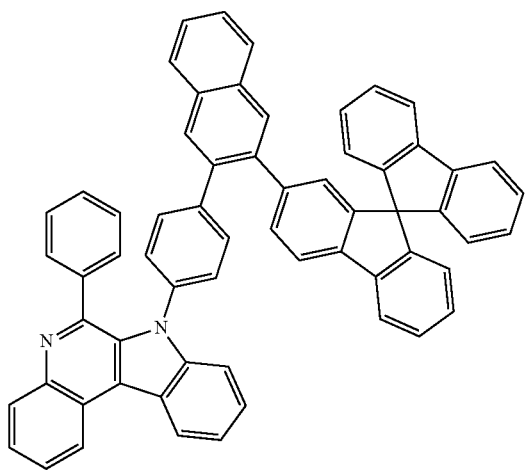
380
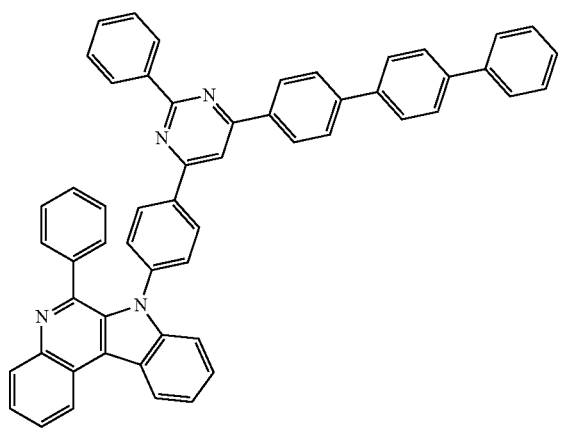
378
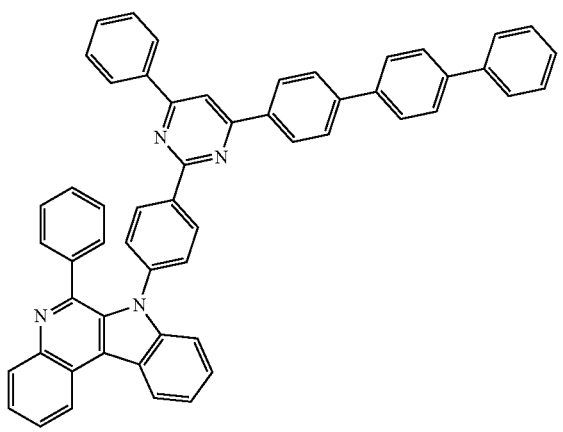
381
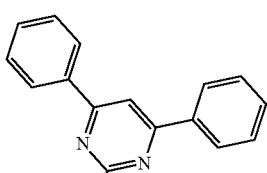
379
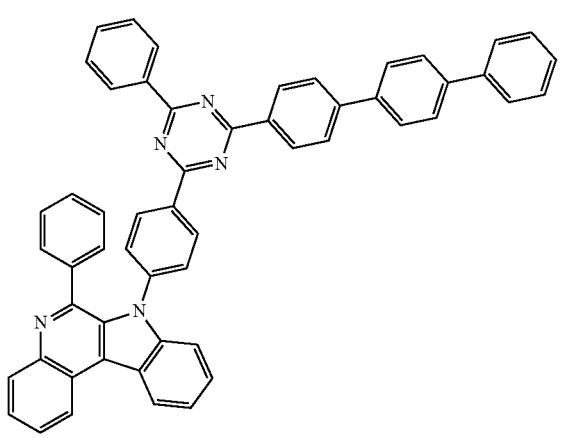
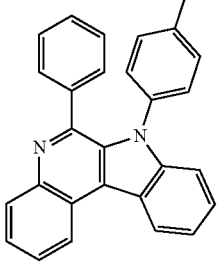

-continued
382
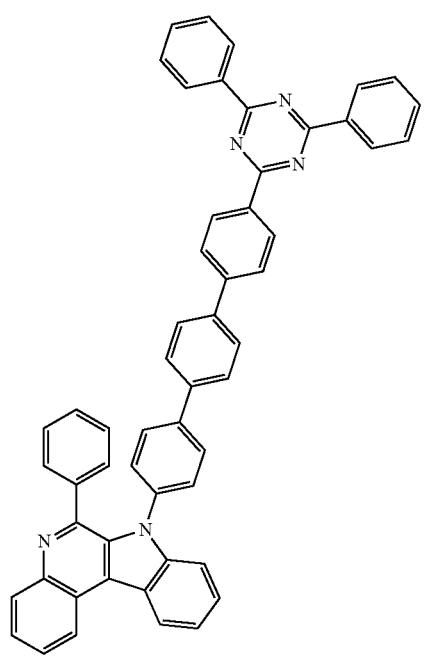
383
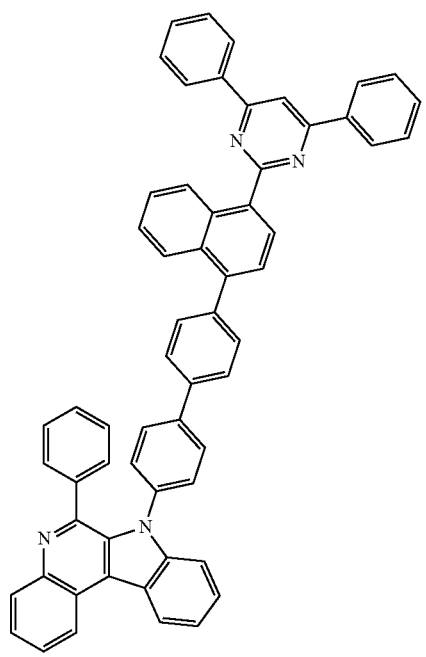
-continued
384
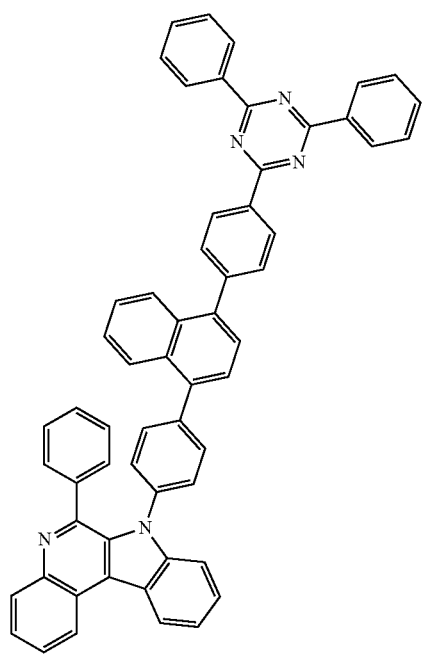
385
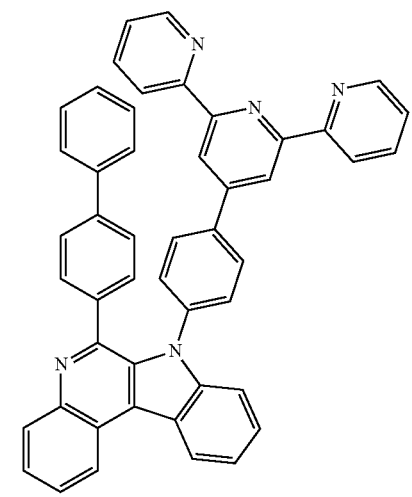
386
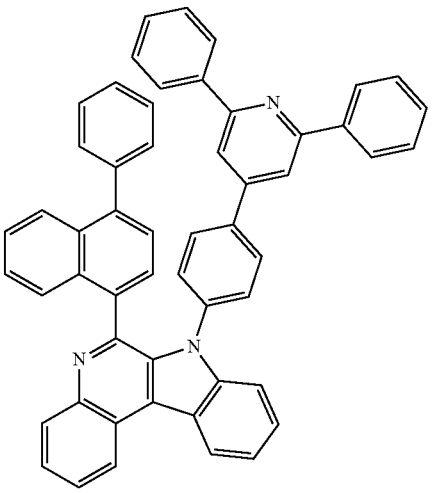

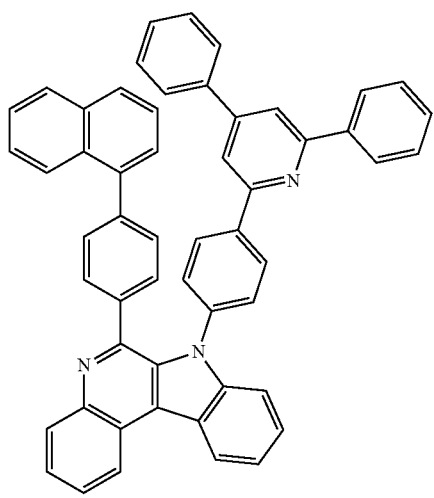
387
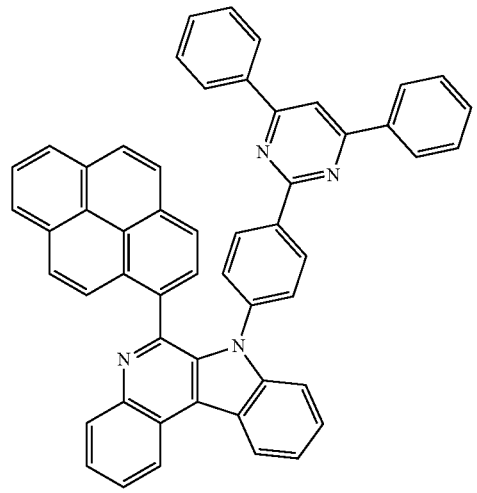
390
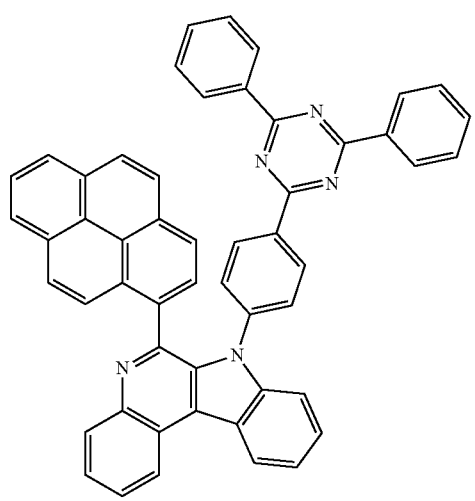
388
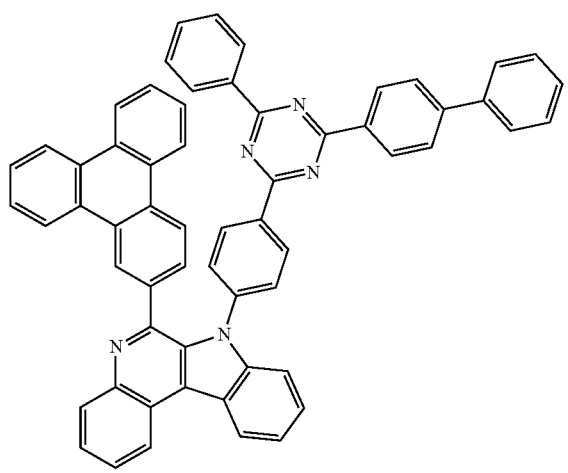
391
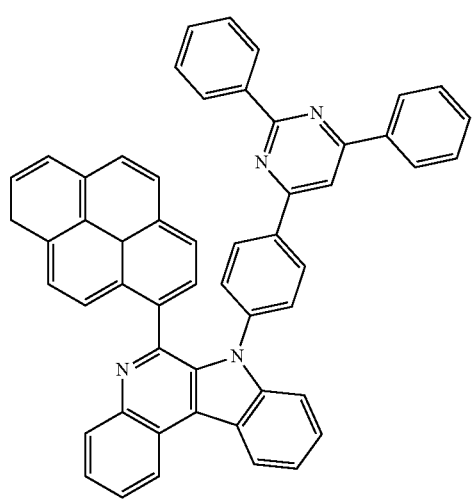
389
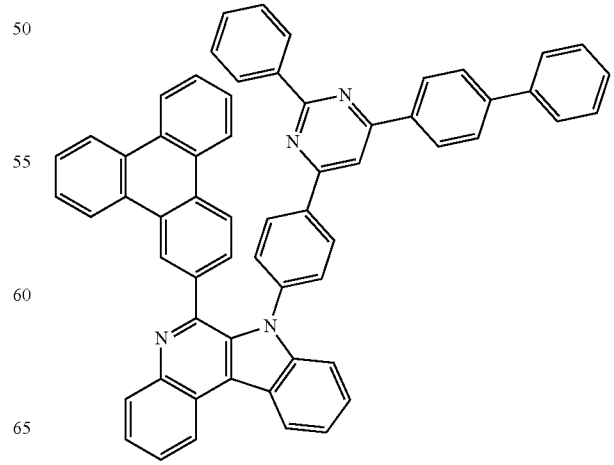
392

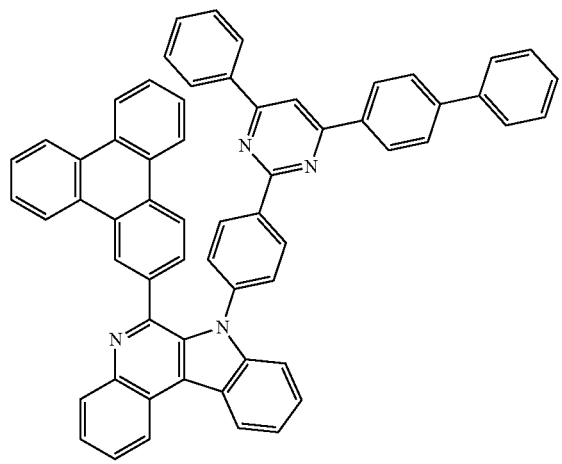
393
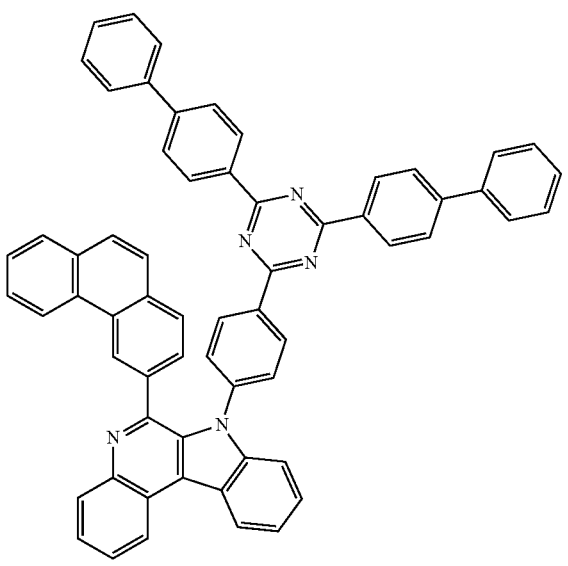
394
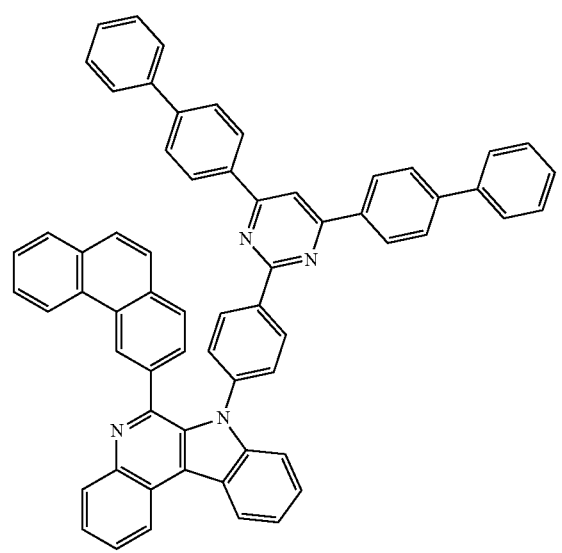
395
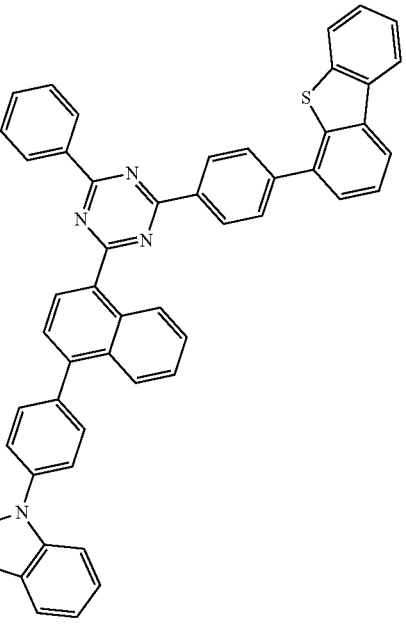
396
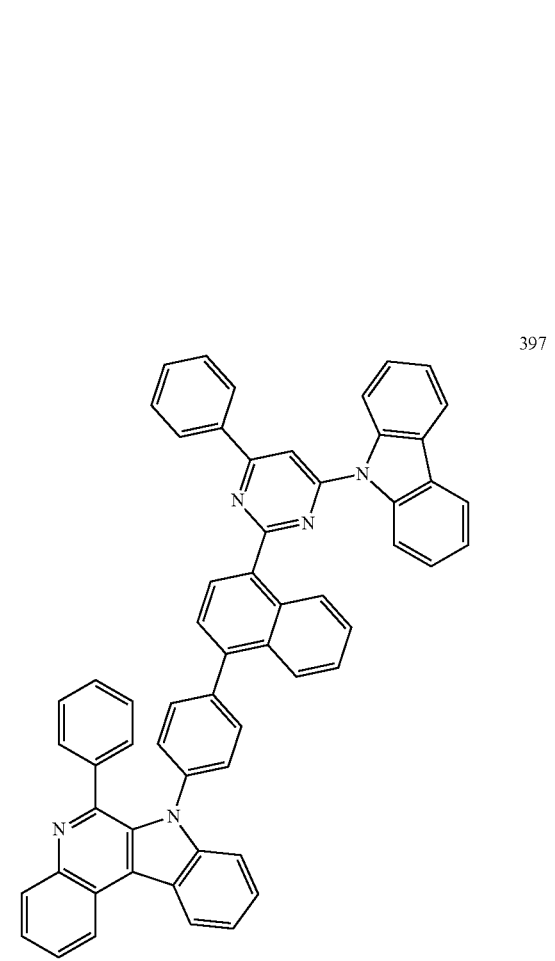
397

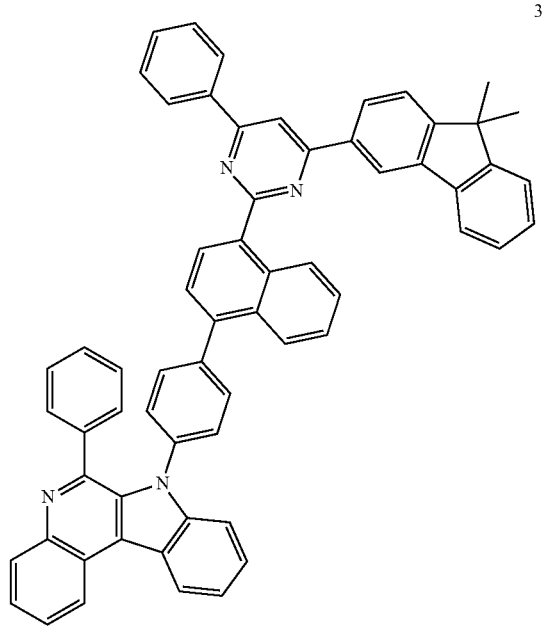
398
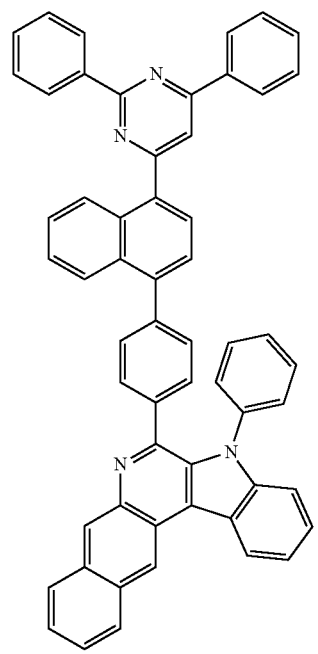
400
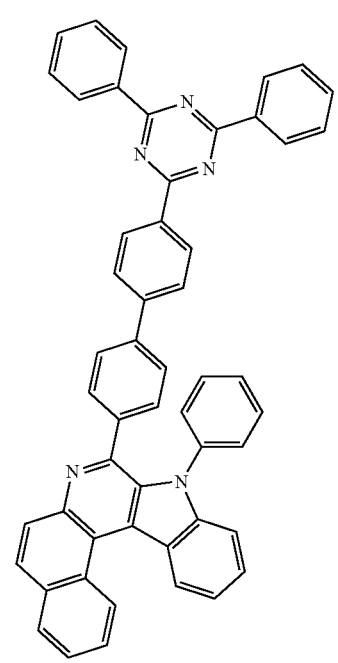
399
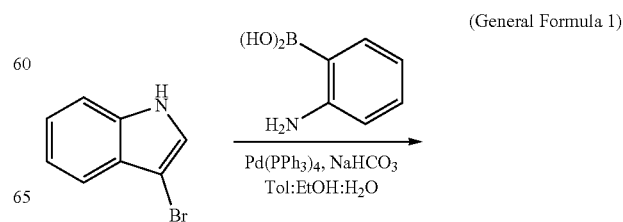
401
The compound according to one embodiment of the present application may be prepared according to the following General Formula 1.
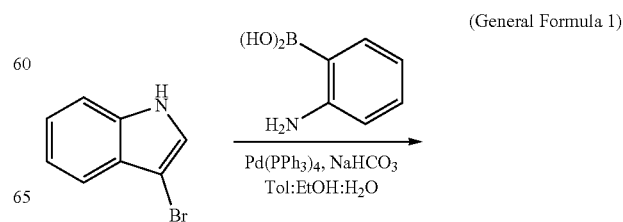

-continued

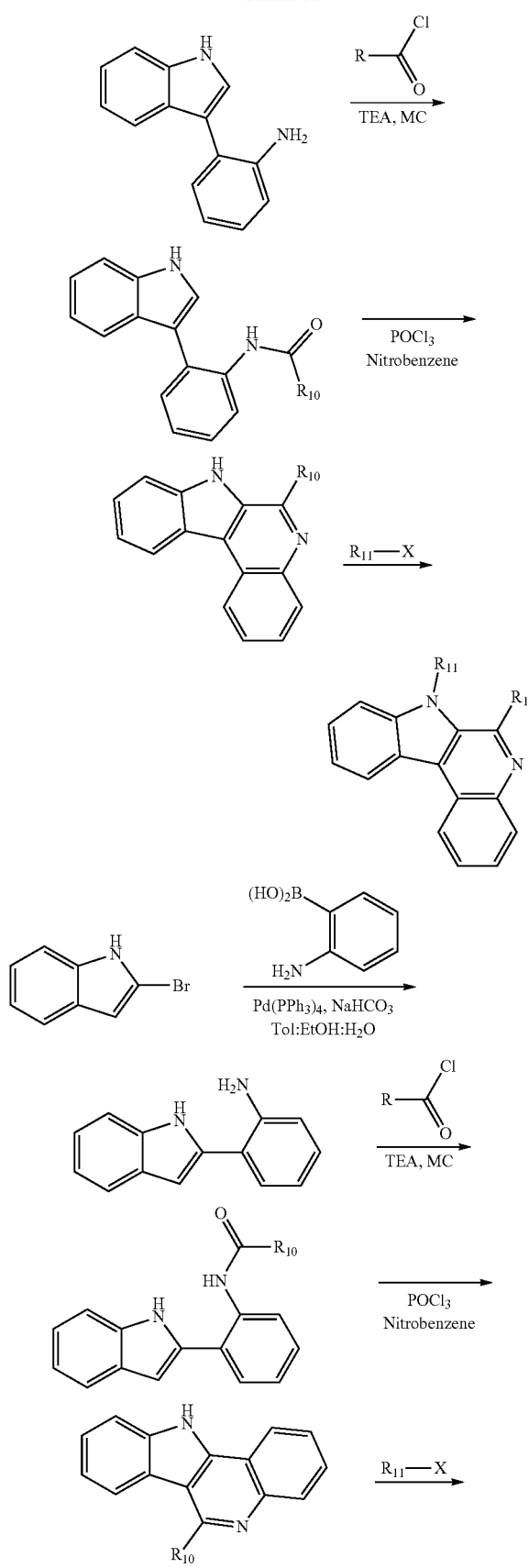

-continued

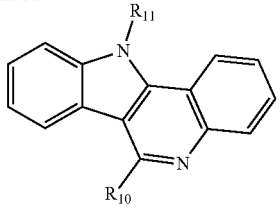

In General Formula 1, $R_{10}$ or $R_{11}$ has the same definition as $Ar_1$ or $Ar_2$ of Chemical Formula 1.

In addition, by introducing various substituents to the structure of Chemical Formulae 1 to 9, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formulae 1 to 9, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

The heterocyclic compound according to one embodiment of the present application may be prepared through a multistep chemical reaction. Some intermediate compounds are prepared first, and the compound of Chemical Formula 1 may be prepared from the intermediate compounds. More specifically, the heterocyclic compound according to one embodiment of the present application may be prepared based on preparation examples to describe later.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

In the organic light emitting device of the present disclosure, the organic material layer comprises an electron injection layer or an electron transfer layer, and the electron injection layer or the electron transfer layer may comprise the heterocyclic compound.

In the organic light emitting device of the present disclosure, the organic material layer comprises an electron transfer layer, and the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises a hole blocking layer, and the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising Chemical Formulae 1 to 9 may further comprise other materials as necessary.

In addition, the organic light emitting device according to one embodiment of the present application comprises an anode, a cathode, and two or more stacks provided between the anode and the cathode, wherein the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application may comprise an anode, a first stack provided on the anode and comprising a first light emitting layer, a charge generation layer provided on the first stack, a second stack provided on the charge generation layer and comprising a second light emitting layer, and a cathode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in FIG. 4.

Herein, the first electron blocking layer, the first hole blocking layer and the second hole blocking layer and the like described in FIG. 4 may not be included in some cases.

In the organic light emitting device according to one embodiment of the present application, materials other than the compounds of Chemical Formulae 1 to 9 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri [phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

<Preparation Example 1> Preparation of Compound 1

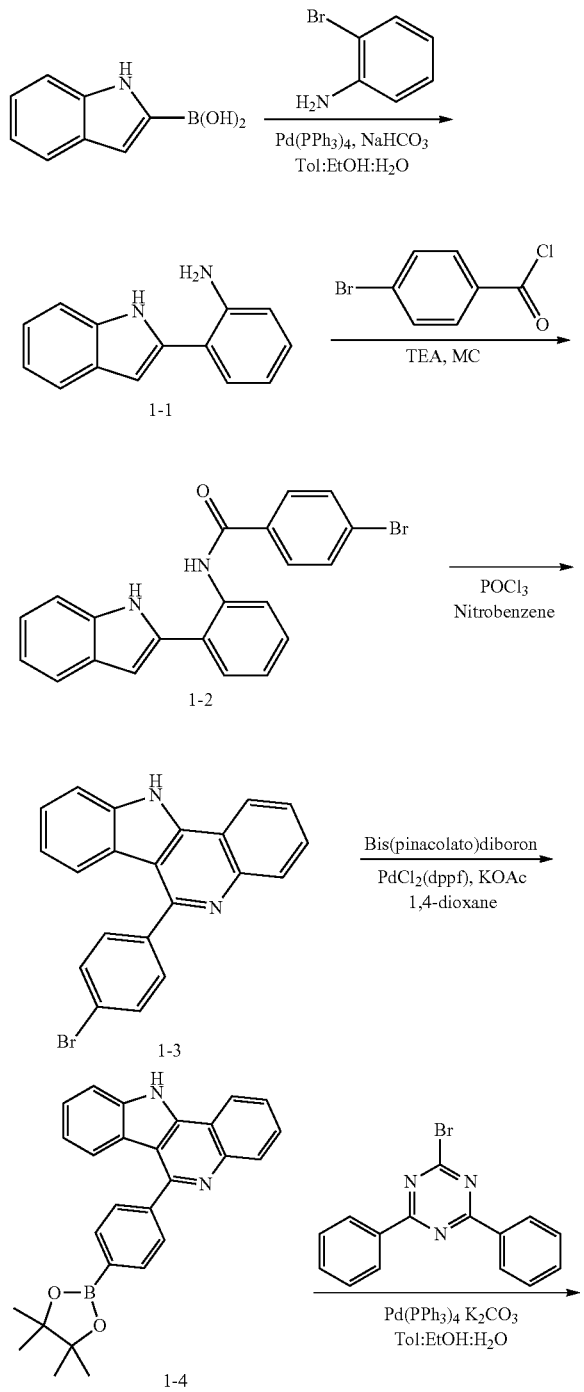

-continued

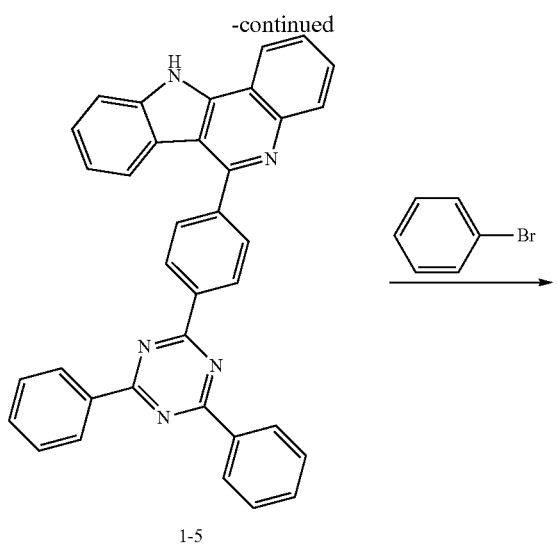

1-5

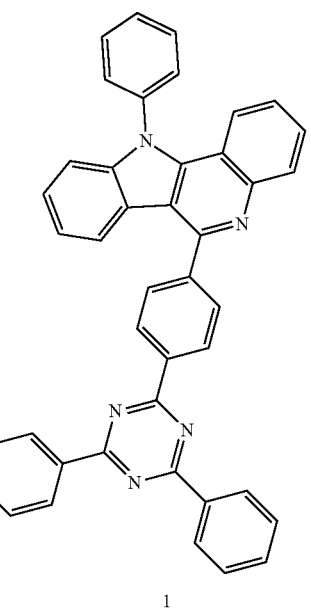

1

1) Preparation of Compound 1-1

After dissolving (1H-indol-2-yl)boronic acid (100 g, 0.621 mol) and 2-bromoaniline (96 g, 0.558 mol) in toluene, EtOH and H$_2$O (1000 mL:200 mL:200 mL), Pd(PPh$_3$)$_4$ (35.8 g, 0.031 mol) and NaHCO$_3$ (156.5 g, 1.863 mol) were introduced thereto, and the result was stirred for 3 hours at 100° C. After the reaction was completed, MC(Methylene Chloride) and distilled water were introduced to the reaction solution for extraction. After that, the result was dried with anhydrous MgSO$_4$, and the solvent was removed using a rotary evaporator to obtain Compound 1-1 (94 g, 72%) in a liquid form.

2) Preparation of Compound 1-2

Compound 1-1 (94 g, 0.451 mol) and triethylamine (42 mL, 0.451 mol) were introduced to MC (1200 mL) and dissolved therein. 4-Bromobenzoyl chloride (108.9 g, 0.496 mol) dissolved in MC (300 mL) was slowly added dropwise to the mixture at 0° C. After the reaction was completed, MC and distilled water were introduced to the reaction solution for extraction. After that, the result was dried with anhydrous MgSO$_4$, and the solvent was removed using a rotary evaporator to obtain Compound 1-2 (150 g, 85%) in a liquid form.

3) Preparation of Compound 1-3

After dissolving Compound 1-2 (150 g, 0.383 mol) in nitrobenzene (1500 mL), POCl$_3$ (35 mL, 0.383 mol) was slowly added dropwise thereto. The result was reacted for 15 hours at 140° C. After the reaction was completed, a solution dissolving NaHCO$_3$ in distilled water was slowly introduced to the reaction solution, and the result was stirred. Produced solids were filtered and collected. The collected solids were recrystallized with MC and MeOH to obtain Compound 1-3 (68 g, 48%) in a solid form.

4) Preparation of Compound 1-4

After dissolving Compound 1-3 (10 g, 0.026 mol), bis (pinacolato)diboron (9.9 g, 0.039 mol), KOAc (7.6 g, 0.078 mol) and PdCl$_2$(dppf) (0.9 g, 0.0013 mol) in 1,4-dioxane (200 mL), the result was reacted for 5 hours at 90° C. After the reaction was completed, MC and distilled water were introduced to the reaction solution for extraction. After that, the result was dried with anhydrous MgSO$_4$, and the solvent was removed using a rotary evaporator to obtain Compound 1-4 (10 g, 91%).

5) Preparation of Compound 1-5

After dissolving Compound 1-4 (10 g, 0.023 mol) and 2-bromo-4,6-diphenyl-1,3,5-triazine (7 g, 0.023 mol) in toluene, EtOH and H$_2$O (100 mL:20 mL:20 mL), Pd(PPh$_3$)$_4$ (1.3 g, 0.0011 mol) and K$_2$CO$_3$ (9.5 g, 0.069 mol) were introduced thereto, and the result was stirred for 5 hours at 100° C. After the reaction was completed, MC and distilled water were introduced to the reaction solution for extraction. After that, the result was dried with anhydrous MgSO$_4$, and the solvent was removed using a rotary evaporator to obtain Compound 1-5 (9 g, 74%).

6) Preparation of Compound 1

After dissolving Compound 1-5 (9 g, 0.017 mol) and bromobenzene (3.2 g, 0.021 mol) in toluene (100 mL), Pd$_2$(dba)$_3$ (1.5 g, 0.0017 mol), tri-tert-butylphosphine (0.6 g, 0.034 mol) and sodium tert-butoxide (4.9 g, 0.051 mol) were introduced thereto, and the result was stirred for 15 hours at 100° C. After the reaction was completed, the result was cooled to room temperature, and produced solids were filtered and dried to obtain Compound 1 (7.5 g, 73%).

A target compound was synthesized in the same manner as in Preparation Example 1 except that Intermediate A of the following Table 1 was used instead of 2-bromo-4,6-diphenyl-1,3,5-triazine.

TABLE 1
| Compound Number | Intermediate A | Target Compound | Yield |
|---|---|---|---|
| 2 | 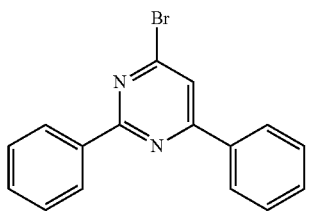 | 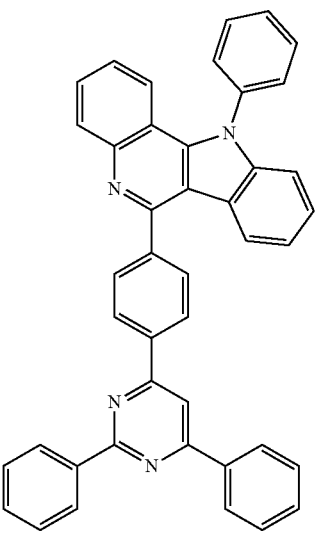 | 61% |
| 4 | 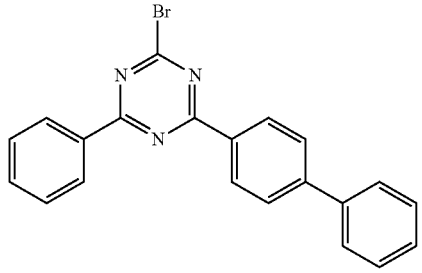 | 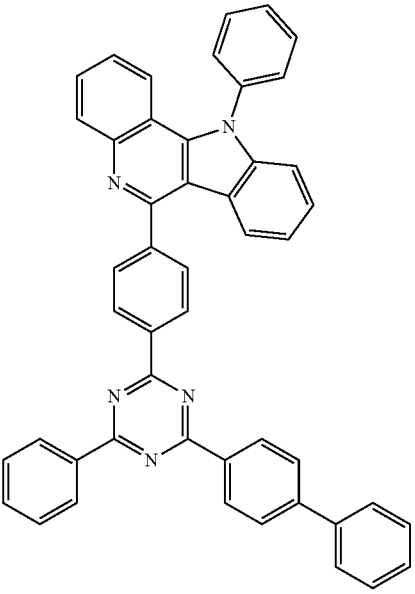 | 65% |

TABLE 1-continued

| Compound Number | Intermediate A | Target Compound | Yield |
|---|---|---|---|
| 6 | | | 66% |
| 7 | | | 64% |

TABLE 1-continued
| Compound Number | Intermediate A | Target Compound | Yield |
|---|---|---|---|
| 8 | 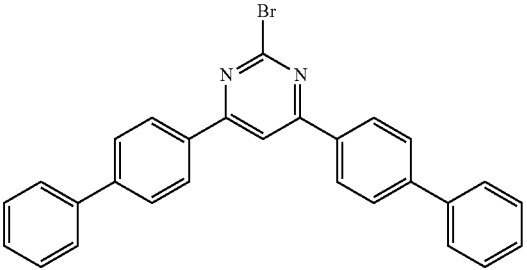 | 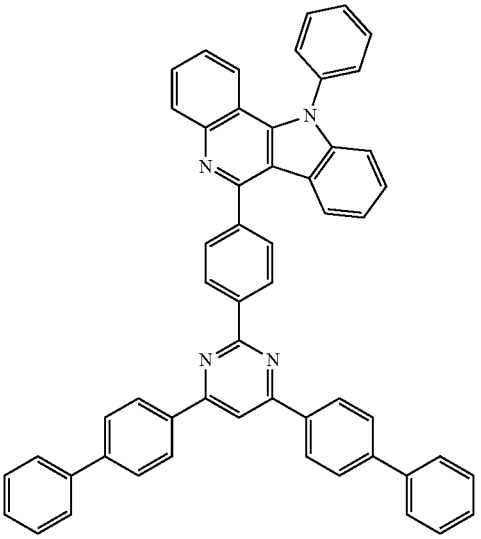 | 69% |
| 26 | 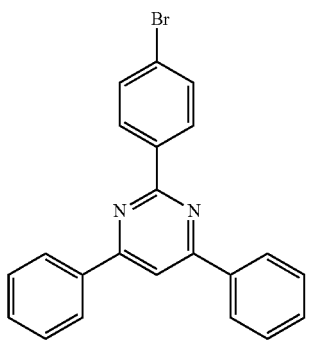 | 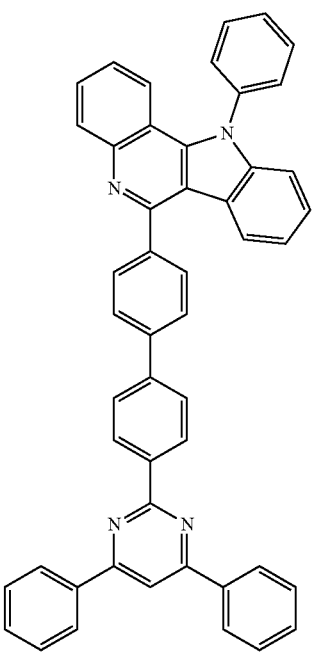 | 71% |

TABLE 1-continued

| Compound Number | Intermediate A | Target Compound | Yield |
|---|---|---|---|
| 28 | (structure) | (structure) | 77% |
| 31 | (structure) | (structure) | 70% |

TABLE 1-continued

| Compound Number | Intermediate A | Target Compound | Yield |
|---|---|---|---|
| 33 | | | 54% |
| 66 | | | 61% |

TABLE 1-continued
| Compound Number | Intermediate A | Target Compound | Yield |
|---|---|---|---|
| 68 | 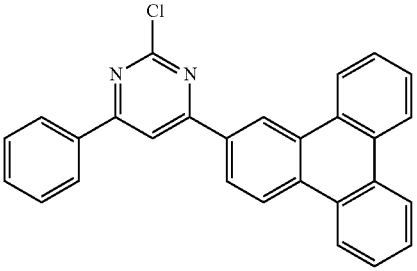 | 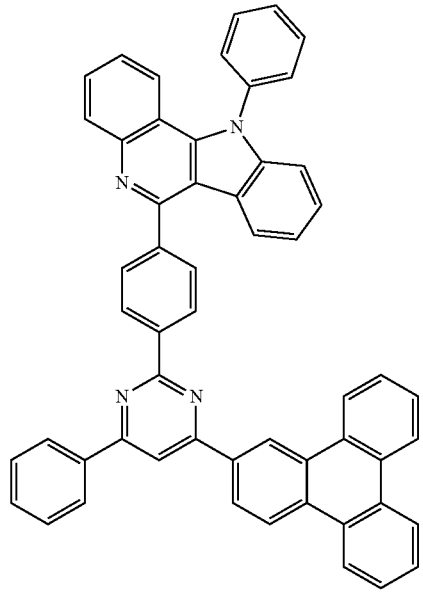 | 66% |
| 70 | 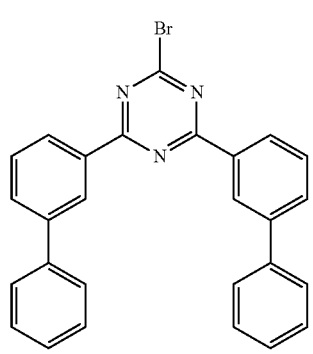 | 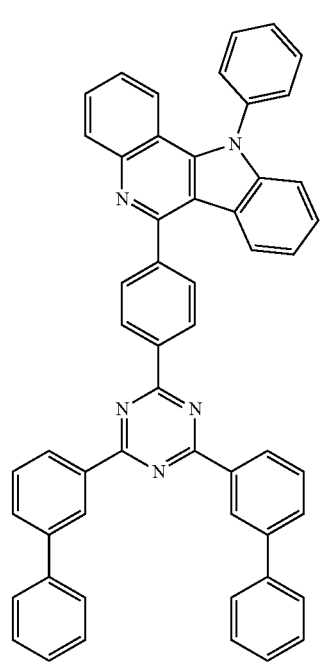 | 64% |

TABLE 1-continued

| Compound Number | Intermediate A | Target Compound | Yield |
|---|---|---|---|
| 73 | (2-bromo-4-phenyl-6-([1,1'-biphenyl]-3-yl)pyrimidine) | (target structure) | 65% |
| 74 | (4-bromo-6-phenyl-2-([1,1'-biphenyl]-3-yl)pyrimidine) | (target structure) | 66% |

TABLE 1-continued

| Compound Number | Intermediate A | Target Compound | Yield |
|---|---|---|---|
| 77 | | | 68% |
| 78 | | | 66% |

TABLE 1-continued

| Compound Number | Intermediate A | Target Compound | Yield |
|---|---|---|---|
| 88 | | | 66% |
| 93 | | | 64% |

TABLE 1-continued
| Compound Number | Intermediate A | Target Compound | Yield |
|---|---|---|---|
| 96 | 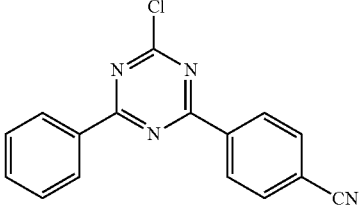 | 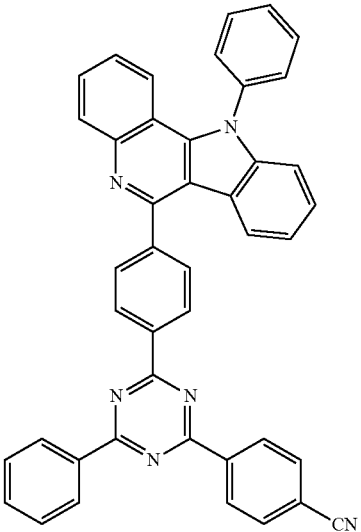 | 60% |
| 100 | 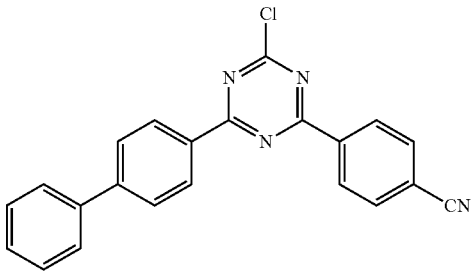 | 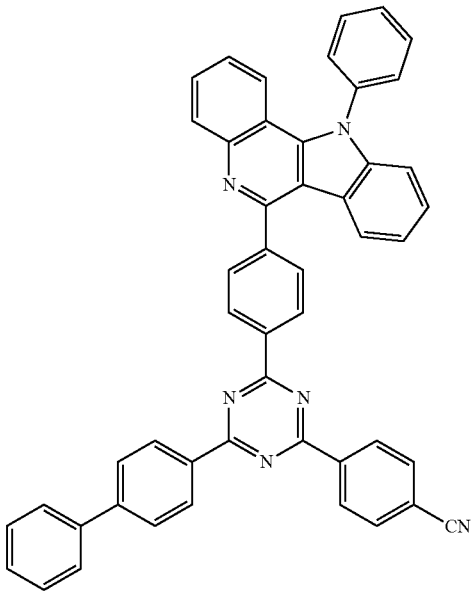 | 61% |

TABLE 1-continued
| Compound Number | Intermediate A | Target Compound | Yield |
|---|---|---|---|
| 101 | 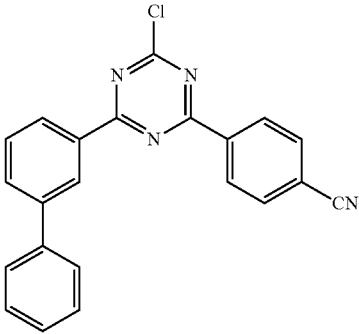 | 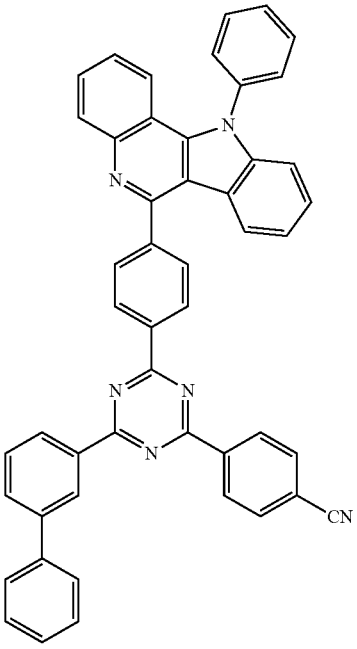 | 60% |
| 104 | 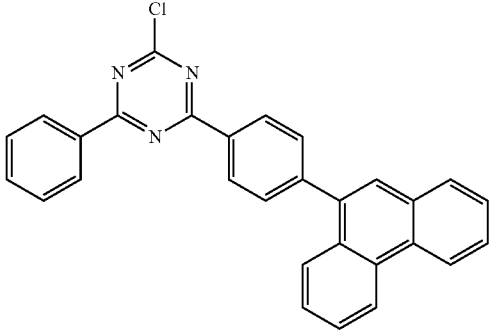 | 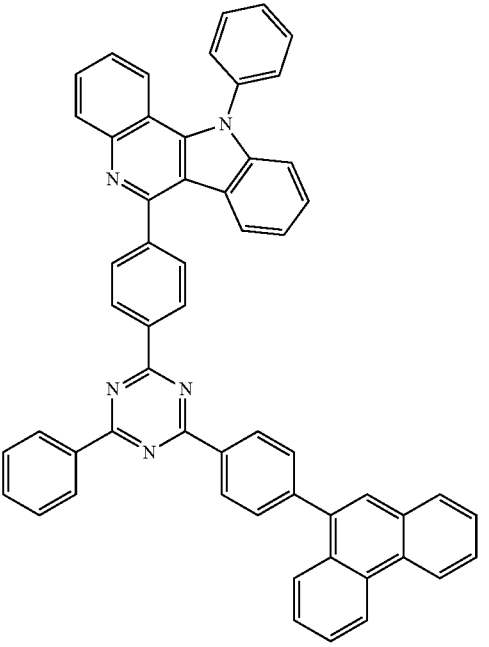 | 64% |

TABLE 1-continued
| Compound Number | Intermediate A | Target Compound | Yield |
|---|---|---|---|
| 105 | 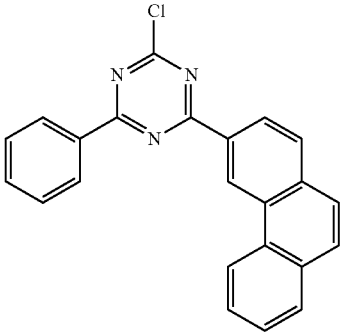 | 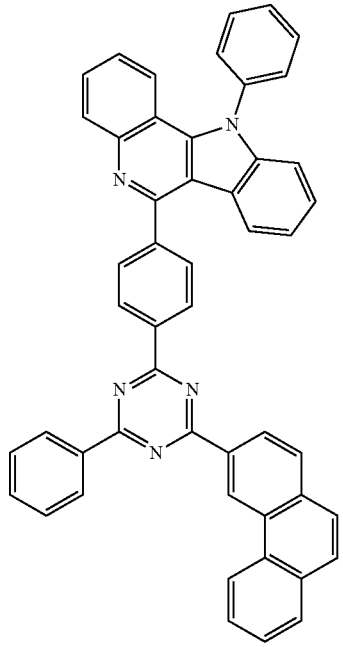 | 61% |
| 108 | 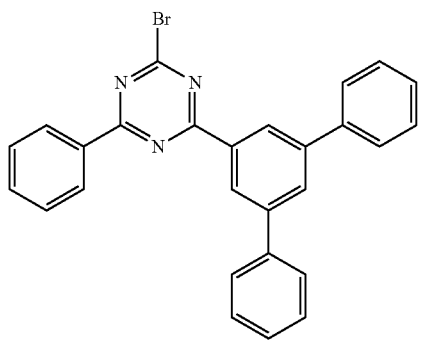 | 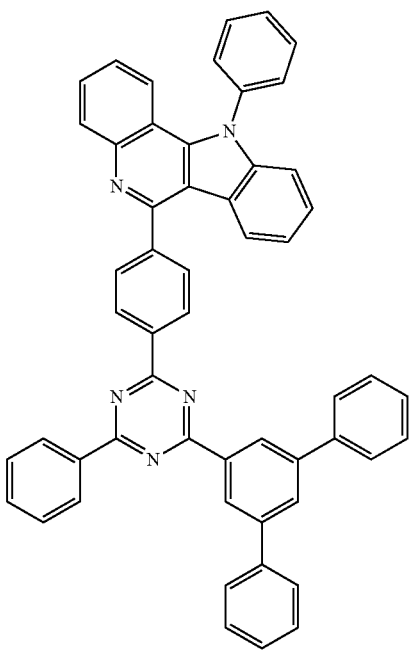 | 59% |

TABLE 1-continued

| Compound Number | Intermediate A | Target Compound | Yield |
|---|---|---|---|
| 117 | | | 58% |
| 131 | | | 65% |

TABLE 1-continued

| Compound Number | Intermediate A | Target Compound | Yield |
|---|---|---|---|
| 132 | (4-bromonaphthalen-1-yl)-2,6-diphenylpyrimidine | | 61% |

A target compound was synthesized in the same manner as in Preparation Example 1 except that Intermediate B of the following Table 2 was used instead of 4-bromobenzoyl chloride, and Intermediate C of the following Table 2 was used instead of 2-bromo-4,6-diphenyl-1,3,5-triazine.

TABLE 2

| Compound Number | Intermediate B | Intermediate C | Compound | Yield |
|---|---|---|---|---|
| 16 | 4-bromo-1-naphthoyl chloride | 2-bromo-4,6-diphenylpyrimidine | | 60% |

TABLE 2-continued

| Compound Number | Intermediate B | Intermediate C | Compound | Yield |
|---|---|---|---|---|
| 21 | | | | 64% |
| 35 | | | | 66% |
| 37 | | | | 61% |

TABLE 2-continued

| Compound Number | Intermediate B | Intermediate C | Compound | Yield |
|---|---|---|---|---|
| 39 | 3-bromobenzoyl chloride | 4-bromo-2-phenyl-6-(biphenyl-4-yl)pyrimidine | (compound structure) | 63% |
| 41 | 3-bromobenzoyl chloride | 2-bromo-4,6-bis(biphenyl-4-yl)-1,3,5-triazine | (compound structure) | 63% |

TABLE 2-continued

| Compound Number | Intermediate B | Intermediate C | Compound | Yield |
|---|---|---|---|---|
| 42 | | | | 64% |
| 115 | | | | 66% |
| 120 | | | | 62% |

A target compound was synthesized in the same manner as in Preparation Example 1 except that Intermediate D of the following Table 3 was used instead of 2-bromoaniline, and Intermediate E of the following Table 3 was used instead of 2-bromo-4,6-diphenyl-1,3,5-triazine.

TABLE 3

| Compound Number | Intermediate D | Intermediate E | Compound | Yield |
|---|---|---|---|---|
| 45 | | | | 51% |
| 59 | | | | 52% |

US 11,678,576 B2
TABLE 3-continued
| Compound Number | Intermediate D | Intermediate E | Compound | Yield |
|---|---|---|---|---|
| 65 | 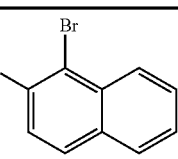 |  |  | 49% |
<Preparation Example 2> Preparation of Compound 135
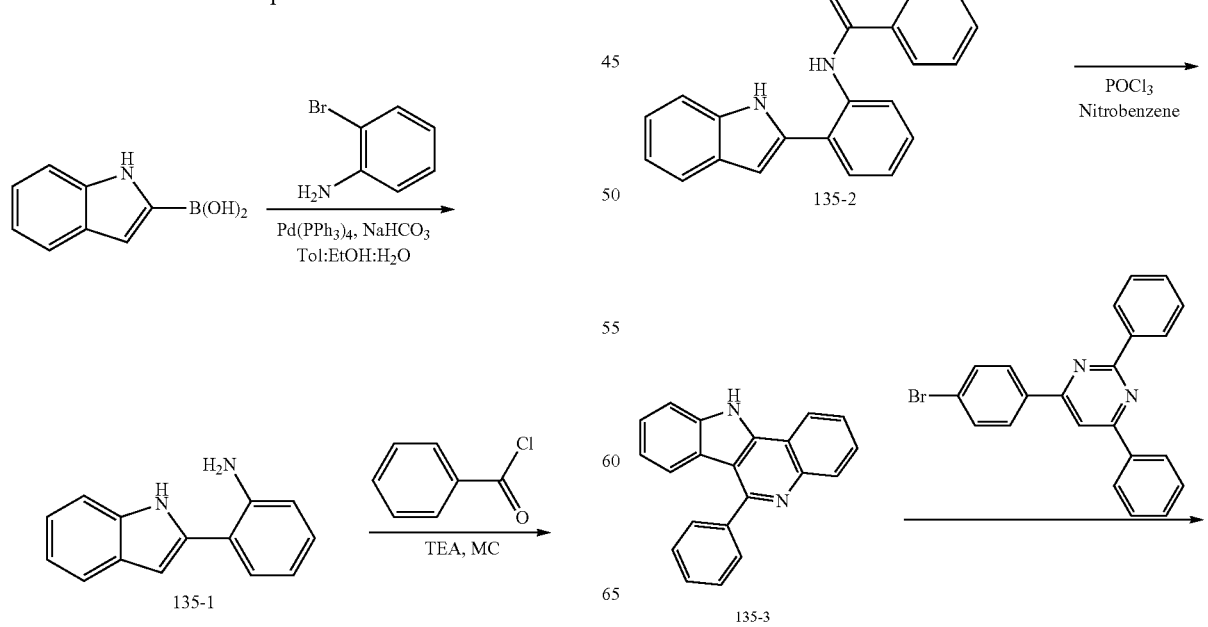

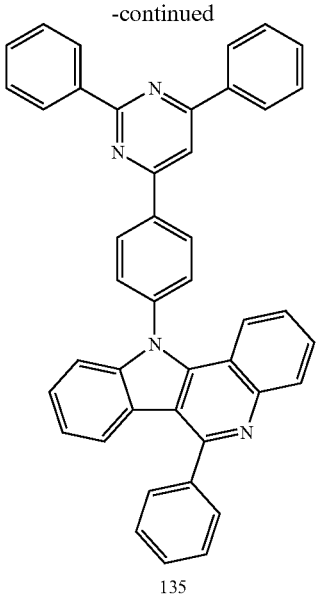

135

1) Preparation of Compound 135-1

After dissolving (1H-indol-2-yl)boronic acid (100 g, 0.621 mol) and 2-bromoaniline (96 g, 0.558 mol) in toluene, EtOH and $H_2O$ (1000 mL:200 mL:200 mL), $Pd(PPh_3)_4$ (35.8 g, 0.031 mol) and $NaHCO_3$ (156.5 g, 1.863 mol) were introduced thereto, and the result was stirred for 3 hours at 100° C. After the reaction was completed, MC and distilled water were introduced to the reaction solution for extraction. After that, the result was dried with anhydrous $MgSO_4$, and the solvent was removed using a rotary evaporator to obtain Compound 135-1 (94 g, 72%) in a liquid form.

2) Preparation of Compound 135-2

Compound 135-1 (94 g, 0.451 mol) and triethylamine (42 mL, 0.451 mol) were introduced to MC (1200 mL) and dissolved therein. Benzoyl chloride (69.7 g, 0.496 mol) dissolved in MC (300 mL) was slowly added dropwise to the mixture at 0° C. After the reaction was completed, MC and distilled water were introduced to the reaction solution for extraction. After that, the result was dried with anhydrous $MgSO_4$, and the solvent was removed using a rotary evaporator to obtain Compound 135-2 (112 g, 80%) in a liquid form.

3) Preparation of Compound 135-3

After dissolving Compound 135-2 (112 g, 0.358 mol) in nitrobenzene (1000 mL), $POCl_3$ (33 mL, 0.358 mol) was slowly added dropwise thereto. The result was reacted for 15 hours at 140° C. After the reaction was completed, a solution dissolving $NaHCO_3$ in distilled water was slowly introduced to the reaction solution, and the result was stirred. Produced solids were filtered and collected. The collected solids were recrystallized with MC and MeOH to obtain Compound 135-3 (54 g, 51%) in a solid form.

4) Preparation of Compound 135

After dissolving Compound 135-3 (9 g, 0.030 mol) and 4-(4-bromophenyl)-2,6-diphenylpyrimidine (11.8 g, 0.030 mol) in toluene (100 mL), $Pd_2(dba)_3$ (2.8 g, 0.003 mol), tri-tert-butylphosphine (1.2 g, 0.006 mol) and sodium tert-butoxide (5.7 g, 0.062 mol) were introduced thereto, and the result was stirred for 15 hours at 100° C. After the reaction was completed, the result was cooled to room temperature, and produced solids were filtered and dried to obtain Compound 135 (9.4 g, 52%).

A target compound was synthesized in the same manner as in Preparation Example 2 except that Intermediate F of the following Table 4 was used instead of 4-(4-bromophenyl)-2,6-diphenylpyrimidine.

TABLE 4

| Compound Number | Intermediate F | Compound | Yield |
|---|---|---|---|
| 134 | (structure) | (structure) | 56% |

TABLE 4-continued

| Compound Number | Intermediate F | Compound | Yield |
|---|---|---|---|
| 137 | | | 55% |
| 139 | | | 59% |

TABLE 4-continued

| Compound Number | Intermediate F | Compound | Yield |
|---|---|---|---|
| 141 | | | 61% |
| 143 | | | 66% |

TABLE 4-continued

| Compound Number | Intermediate F | Compound | Yield |
|---|---|---|---|
| 148 | | | 63% |
| 149 | | | 58% |

TABLE 4-continued
| Compound Number | Intermediate F | Compound | Yield |
|---|---|---|---|
| 152 | 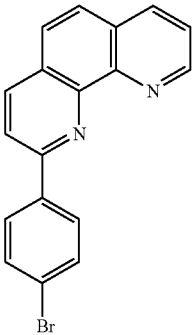 [SMILES: Brc1ccc(-c2ccc3ccc4cccnc4c3n2)cc1] | 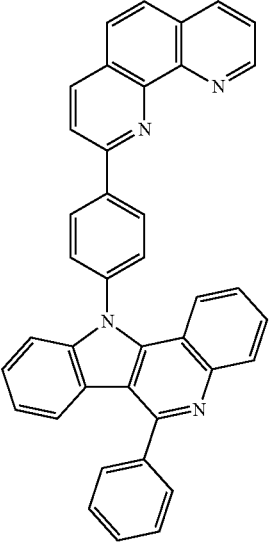 [SMILES: c1ccc(-c2nc3ccccc3c3c2c2ccccc2n3-c2ccc(-c3ccc4ccc5cccnc5c4n3)cc2)cc1] | 59% |
| 155 | 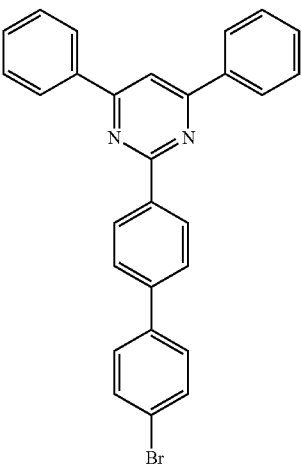 [SMILES: Brc1ccc(-c2ccc(-c3nc(-c4ccccc4)cc(-c4ccccc4)n3)cc2)cc1] | 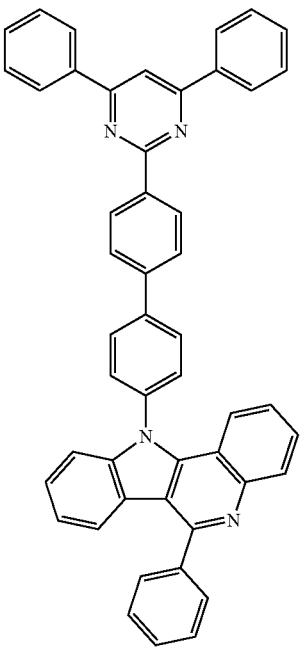 | 65% |

TABLE 4-continued
| Compound Number | Intermediate F | Compound | Yield |
|---|---|---|---|
| 156 | 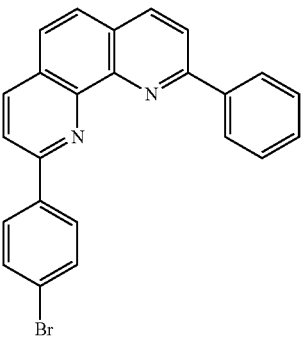 [SMILES: Brc1ccc(-c2ccc3ccc4ccc(-c5ccccc5)nc4c3n2)cc1] | 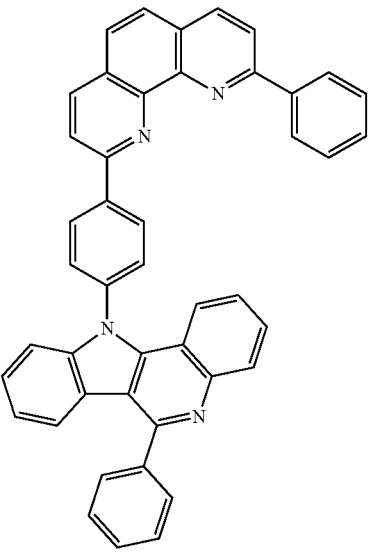 [SMILES: c1ccc(-c2ccc3ccc4ccc(-c5ccc(-n6c7ccccc7c7c(-c8ccccc8)nc8ccccc8c76)cc5)nc4c3n2)cc1] | 63% |
| 157 | 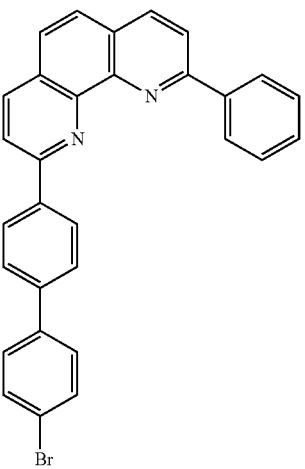 [SMILES: Brc1ccc(-c2ccc(-c3ccc4ccc5ccc(-c6ccccc6)nc5c4n3)cc2)cc1] | 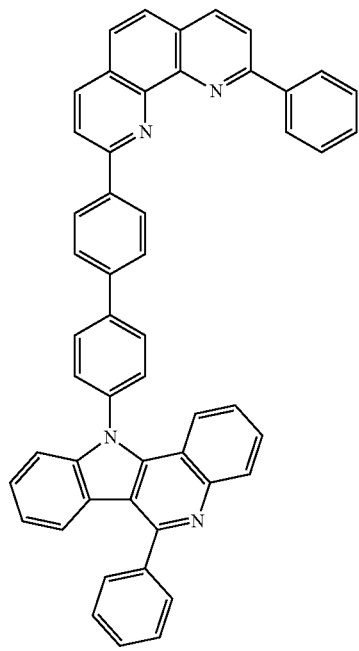 [SMILES: c1ccc(-c2ccc3ccc4ccc(-c5ccc(-c6ccc(-n7c8ccccc8c8c(-c9ccccc9)nc9ccccc9c87)cc6)cc5)nc4c3n2)cc1] | 66% |

TABLE 4-continued
| Compound Number | Intermediate F | Compound | Yield |
|---|---|---|---|
| 158 | 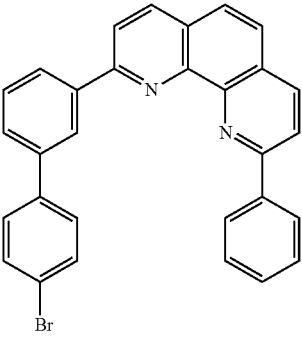 [SMILES: Brc1ccc(-c2cccc(-c3ccc4ccc5ccc(-c6ccccc6)nc5c4n3)c2)cc1] | 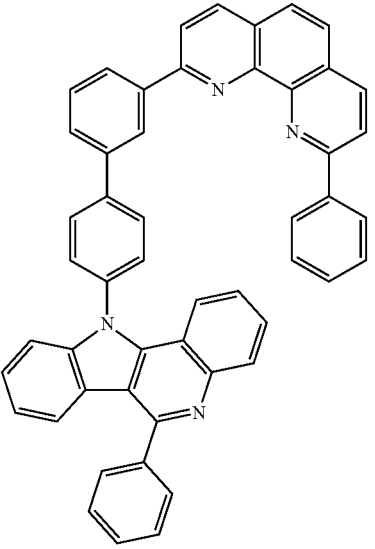 [SMILES: c1ccc(-c2ccc3ccc4ccc(-c5cccc(-c6ccc(-n7c8ccccc8c8c(-c9ccccc9)nc9ccccc9c87)cc6)c5)nc4c3n2)cc1] | 63% |
| 159 | 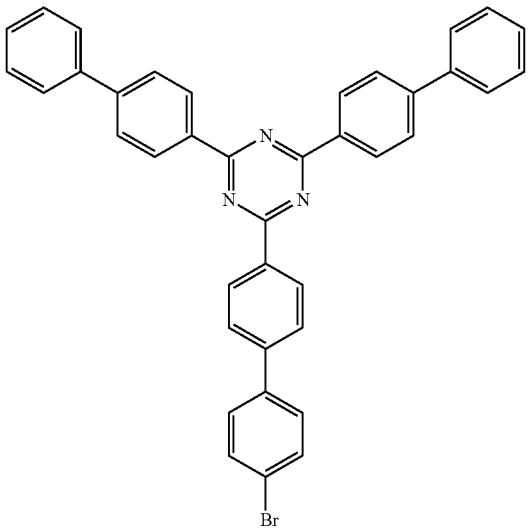 [SMILES: Brc1ccc(-c2ccc(-c3nc(-c4ccc(-c5ccccc5)cc4)nc(-c4ccc(-c5ccccc5)cc4)n3)cc2)cc1] | 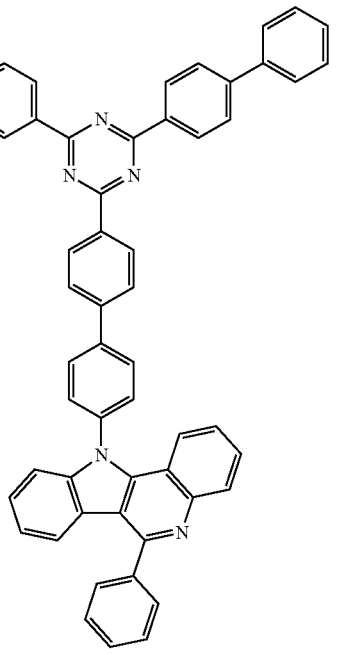 | 63% |

TABLE 4-continued

| Compound Number | Intermediate F | Compound | Yield |
|---|---|---|---|
| 161 | | | 66% |
| 165 | | | 66% |

TABLE 4-continued
| Compound Number | Intermediate F | Compound | Yield |
|---|---|---|---|
| 168 | 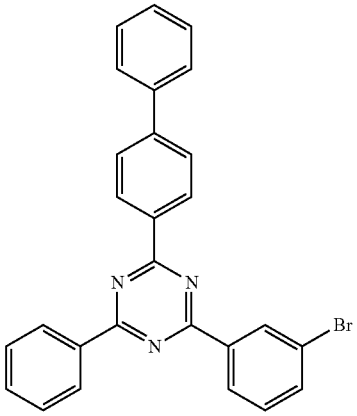 | 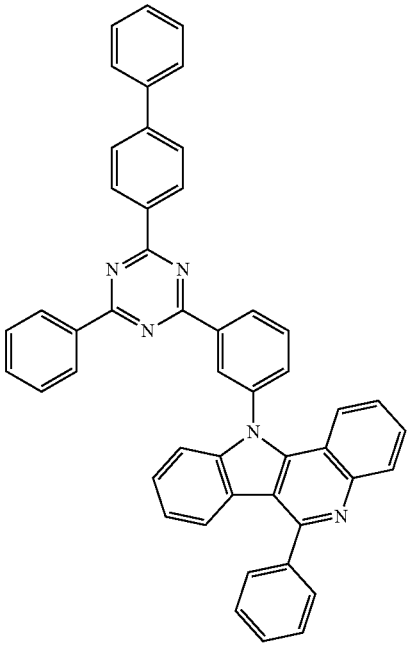 [SMILES: c1ccc(-c2ccc(-c3nc(-c4ccccc4)nc(-c4cccc(-n5c6ccccc6c6c(-c7ccccc7)nc7ccccc7c65)c4)n3)cc2)cc1] | 60% |
| 169 | 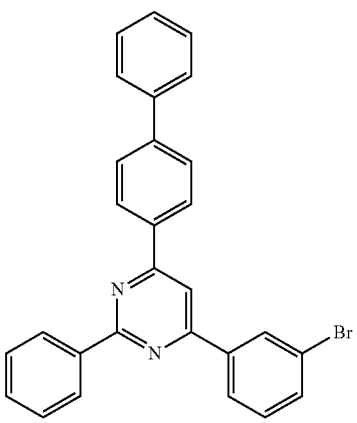 [SMILES: Brc1cccc(-c2cc(-c3ccc(-c4ccccc4)cc3)nc(-c3ccccc3)n2)c1] | 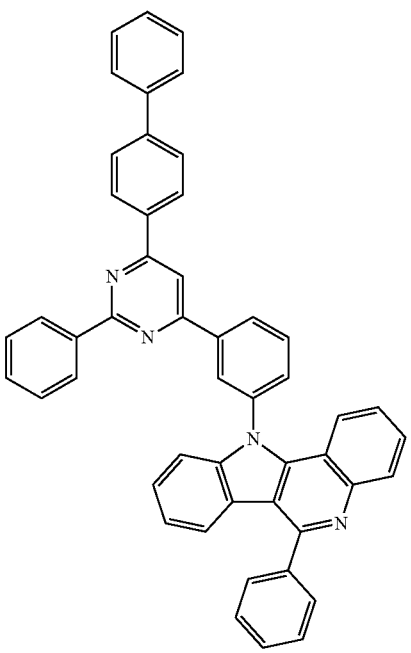 [SMILES: c1ccc(-c2ccc(-c3cc(-c4cccc(-n5c6ccccc6c6c(-c7ccccc7)nc7ccccc7c65)c4)nc(-c4ccccc4)n3)cc2)cc1] | 61% |

TABLE 4-continued
| Compound Number | Intermediate F | Compound | Yield |
|---|---|---|---|
| 203 | 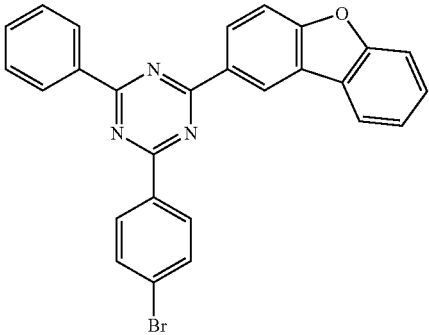 [SMILES: Brc1ccc(-c2nc(-c3ccccc3)nc(-c3ccc4oc5ccccc5c4c3)n2)cc1] | 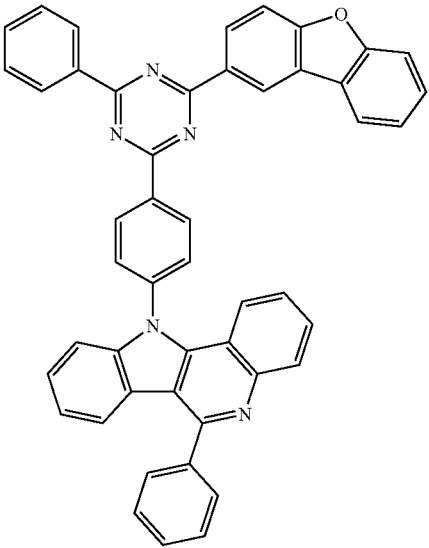 [SMILES: c1ccc(-c2nc(-c3ccc(-n4c5ccccc5c5c(-c6ccccc6)nc6ccccc6c54)cc3)nc(-c3ccc4oc5ccccc5c4c3)n2)cc1] | 65% |
| 205 | 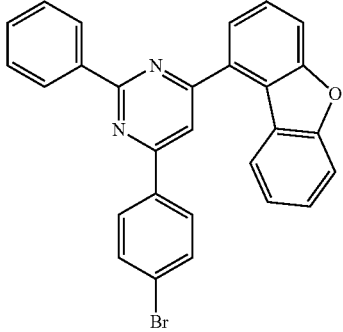 [SMILES: Brc1ccc(-c2cc(-c3cccc4oc5ccccc5c34)nc(-c3ccccc3)n2)cc1] | 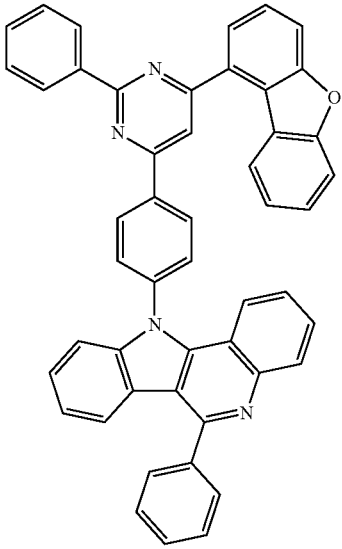 [SMILES: c1ccc(-c2nc(-c3ccc(-n4c5ccccc5c5c(-c6ccccc6)nc6ccccc6c54)cc3)cc(-c3cccc4oc5ccccc5c34)n2)cc1] | 61% |

TABLE 4-continued
| Compound Number | Intermediate F | Compound | Yield |
|---|---|---|---|
| 209 | 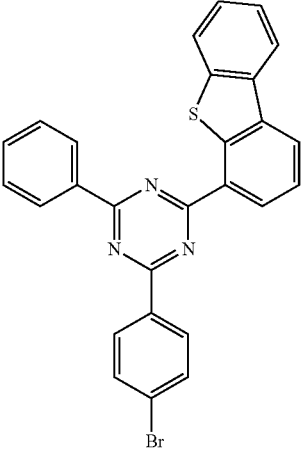 [SMILES: Brc1ccc(-c2nc(-c3ccccc3)nc(-c3cccc4c3sc3ccccc34)n2)cc1] | 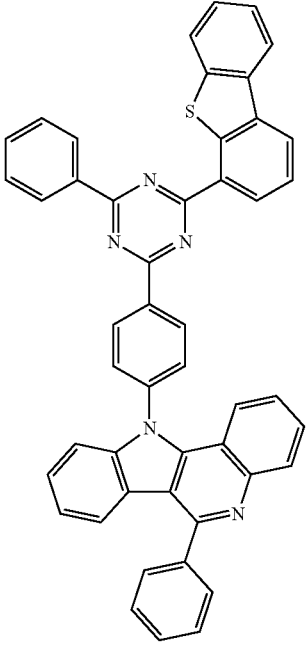 [SMILES: c1ccc(-c2nc(-c3ccc(-n4c5ccccc5c5c(-c6ccccc6)nc6ccccc6c54)cc3)nc(-c3cccc4c3sc3ccccc34)n2)cc1] | 60% |
| 212 | 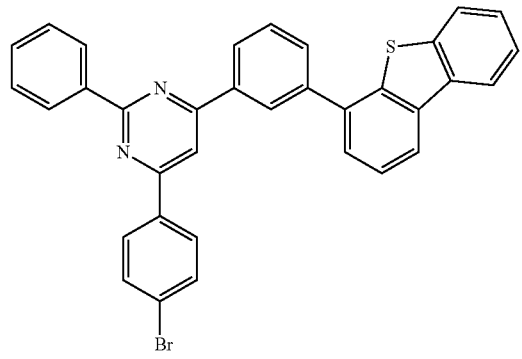 [SMILES: Brc1ccc(-c2cc(-c3cccc(-c4cccc5c4sc4ccccc45)c3)nc(-c3ccccc3)n2)cc1] | 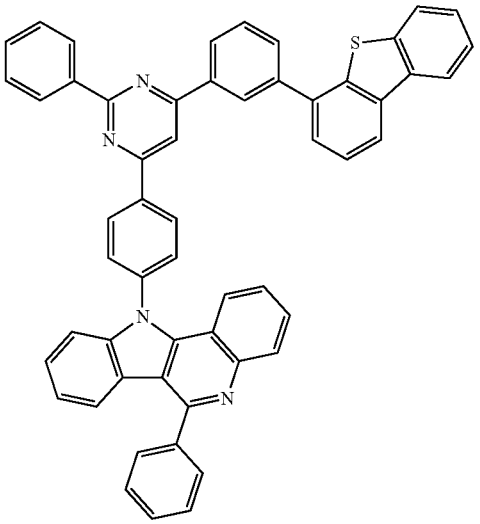 [SMILES: c1ccc(-c2nc(-c3ccc(-n4c5ccccc5c5c(-c6ccccc6)nc6ccccc6c54)cc3)cc(-c3cccc(-c4cccc5c4sc4ccccc45)c3)n2)cc1] | 61% |

TABLE 4-continued
| Compound Number | Intermediate F | Compound | Yield |
|---|---|---|---|
| 234 | 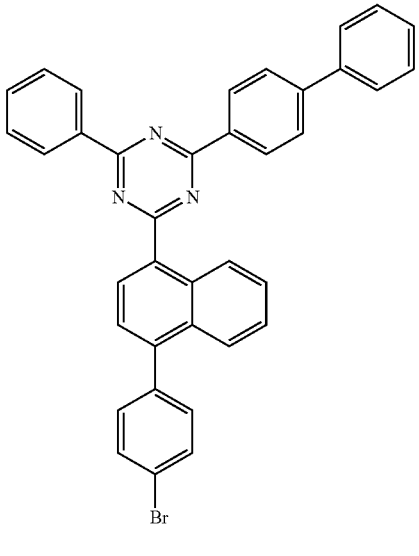 | 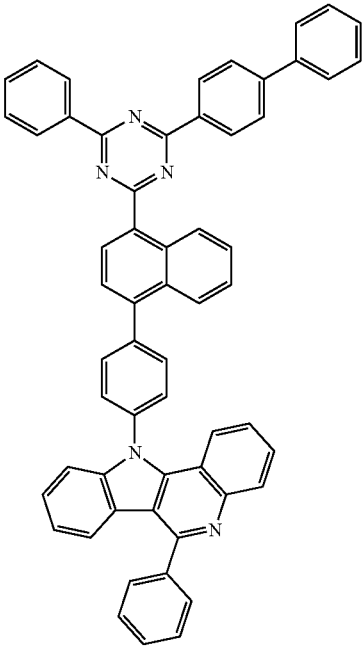 [SMILES: c1ccc(-c2ccc(-c3nc(-c4ccccc4)nc(-c4ccc(-c5ccc(-n6c7ccccc7c7c(-c8ccccc8)nc8ccccc8c76)cc5)c5ccccc45)n3)cc2)cc1] | 61% |
| 236 | 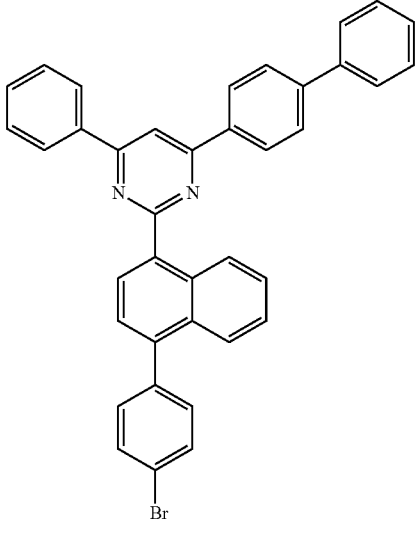 [SMILES: Brc1ccc(-c2ccc(-c3nc(-c4ccccc4)cc(-c4ccc(-c5ccccc5)cc4)n3)c3ccccc23)cc1] | 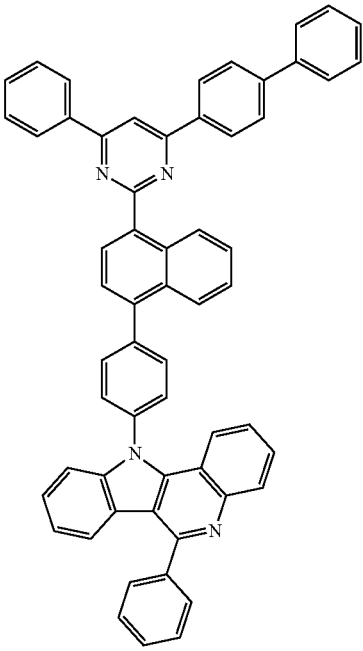 [SMILES: c1ccc(-c2ccc(-c3cc(-c4ccccc4)nc(-c4ccc(-c5ccc(-n6c7ccccc7c7c(-c8ccccc8)nc8ccccc8c76)cc5)c5ccccc45)n3)cc2)cc1] | 58% |

A target compound was synthesized in the same manner as in Preparation Example 2 except that Intermediate G of the following Table 5 was used instead of benzoyl chloride, and Intermediate H of the following Table 5 was used instead of 4-(4-bromophenyl)-2,6-diphenylpyrimidine.

TABLE 5

| Compound Number | Intermediate G | Intermediate H | Compound | Yield |
|---|---|---|---|---|
| 213 | | | | 45% |
| 218 | | | | 51% |

TABLE 5-continued
| Compound Number | Intermediate G | Intermediate H | Compound | Yield |
|---|---|---|---|---|
| 219 | 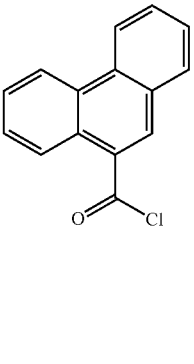 [SMILES: O=C(Cl)c1cc2ccccc2c2ccccc12] | 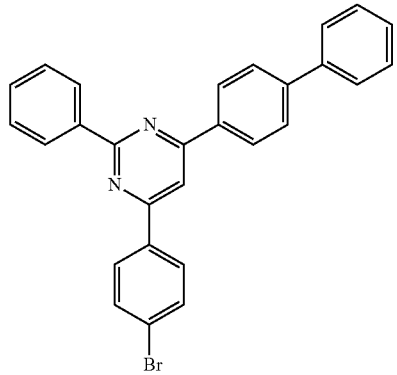 | 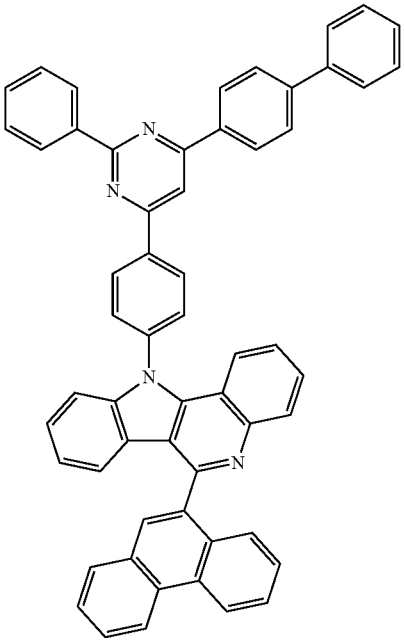 [SMILES: c1ccc(-c2ccc(-c3nc(-c4ccccc4)nc(-c4ccc(-n5c6ccccc6c6c(-c7cc8ccccc8c8ccccc78)nc7ccccc7c65)cc4)n3)cc2)cc1] | 54% |
| 222 | 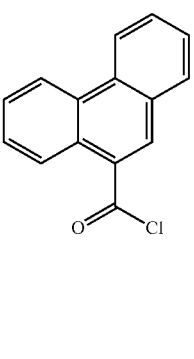 [SMILES: O=C(Cl)c1cc2ccccc2c2ccccc12] | 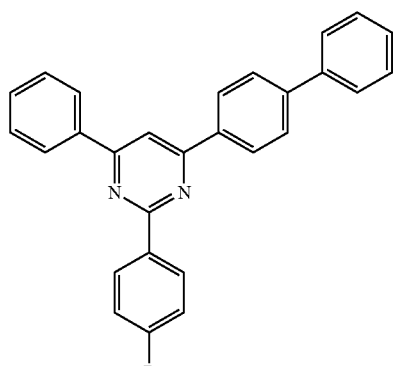 | 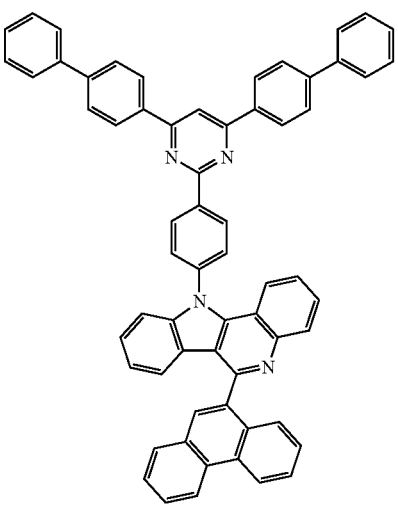 [SMILES: c1ccc(-c2ccc(-c3cc(-c4ccc(-c5ccccc5)cc4)nc(-c4ccc(-n5c6ccccc6c6c(-c7cc8ccccc8c8ccccc78)nc7ccccc7c65)cc4)n3)cc2)cc1] | 51% |

TABLE 5-continued
| Compound Number | Intermediate G | Intermediate H | Compound | Yield |
|---|---|---|---|---|
| 228 | 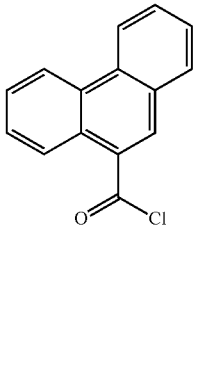 [SMILES: O=C(Cl)c1cc2ccccc2c2ccccc12] | 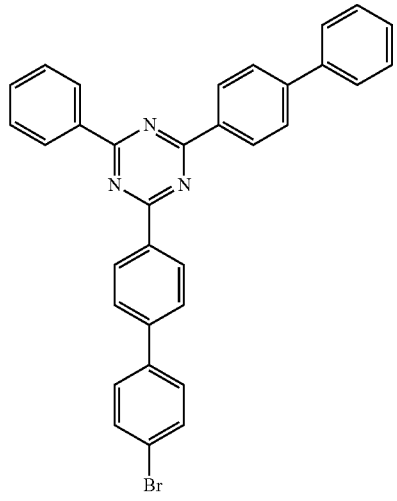 [SMILES: Brc1ccc(-c2ccc(-c3nc(-c4ccccc4)nc(-c4ccc(-c5ccccc5)cc4)n3)cc2)cc1] | 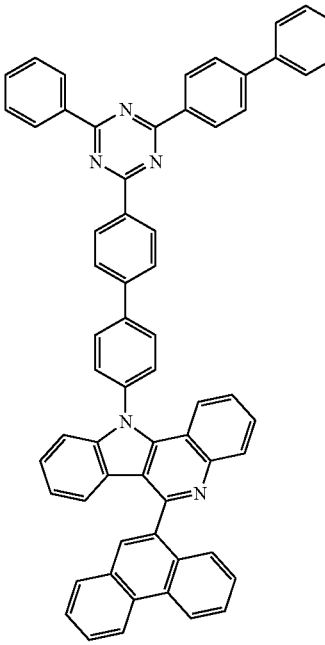 | 53% |
| 229 | 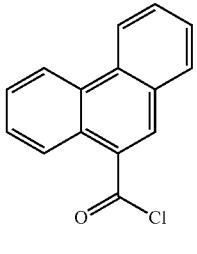 [SMILES: O=C(Cl)c1cc2ccccc2c2ccccc12] | 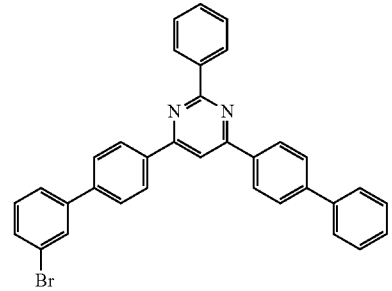 [SMILES: Brc1cccc(-c2ccc(-c3cc(-c4ccc(-c5ccccc5)cc4)nc(-c4ccccc4)n3)cc2)c1] | 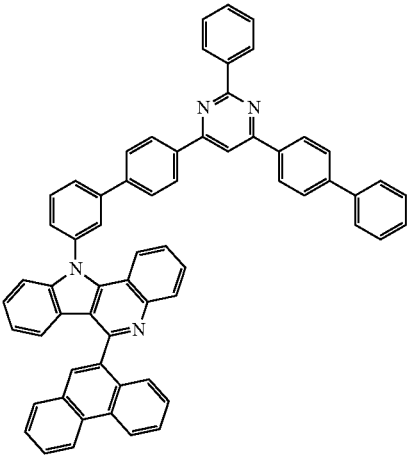 [SMILES: c1ccc(-c2ccc(-c3cc(-c4ccc(-c5cccc(-n6c7ccccc7c7c(-c8cc9ccccc9c9ccccc89)nc8ccccc8c76)c5)cc4)nc(-c4ccccc4)n3)cc2)cc1] | 53% |

A target compound was synthesized in the same manner as in Preparation Example 2 except that Intermediate I of the following Table 6 was used instead of 2-bromoaniline, and Intermediate J of the following Table 6 was used instead of 4-(4-bromophenyl)-2,6-diphenylpyrimidine.
TABLE 6
| Compound Number | Intermediate I | Intermediate J | Compound | Yield |
|---|---|---|---|---|
| 187 | 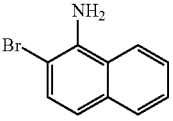 | 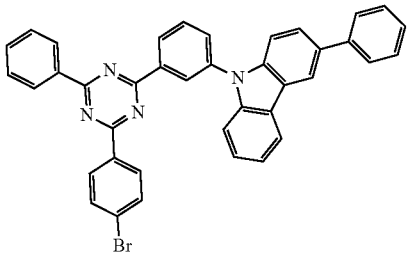 [SMILES: Brc1ccc(-c2nc(-c3ccccc3)nc(-c3cccc(-n4c5ccccc5c5cc(-c6ccccc6)ccc54)c3)n2)cc1] | 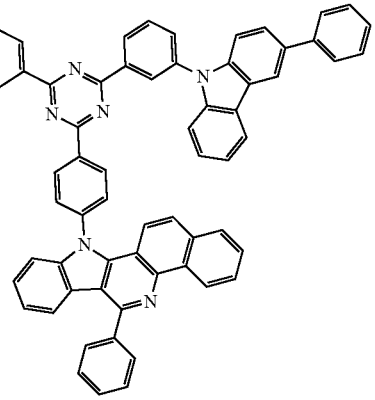 | 49% |
| 192 | 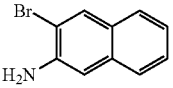 | 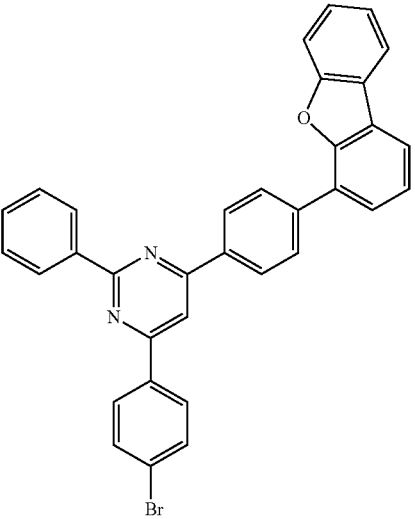 [SMILES: Brc1ccc(-c2cc(-c3ccc(-c4cccc5c4oc4ccccc45)cc3)nc(-c3ccccc3)n2)cc1] | 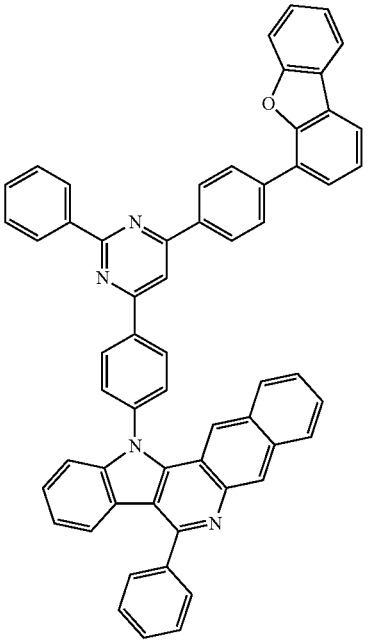 [SMILES: c1ccc(-c2nc(-c3ccc(-c4cccc5c4oc4ccccc45)cc3)cc(-c3ccc(-n4c5ccccc5c5c(-c6ccccc6)nc6cc7ccccc7cc6c54)cc3)n2)cc1] | 50% |

TABLE 6-continued
| Compound Number | Intermediate I | Intermediate J | Compound | Yield |
|---|---|---|---|---|
| 195 | 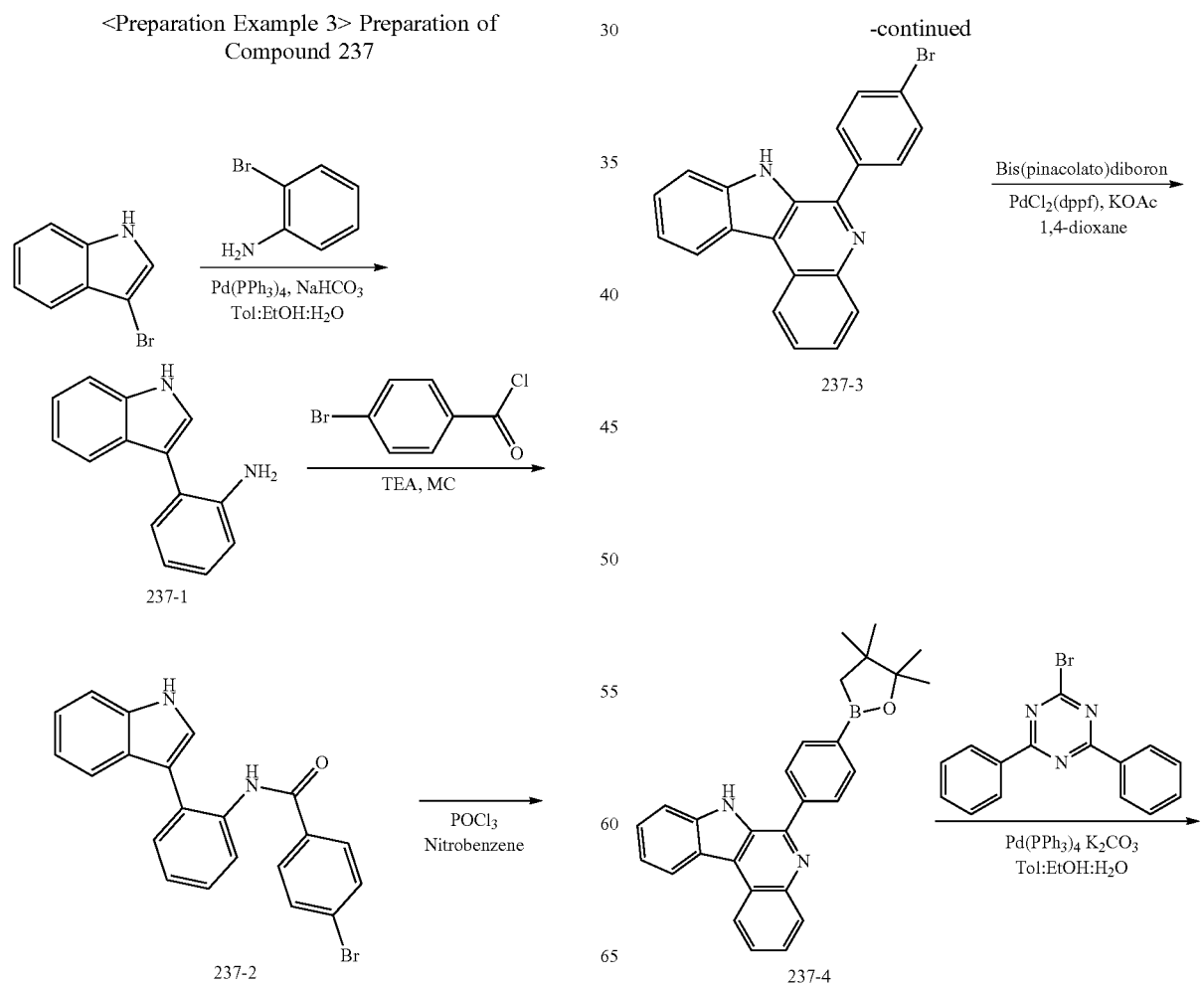 | | | 51% |
<Preparation Example 3> Preparation of Compound 237

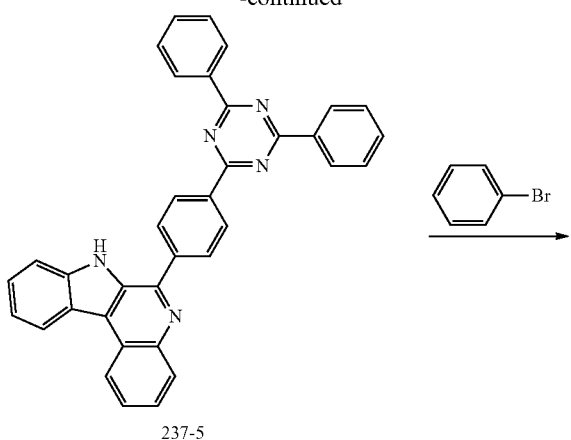

237-5

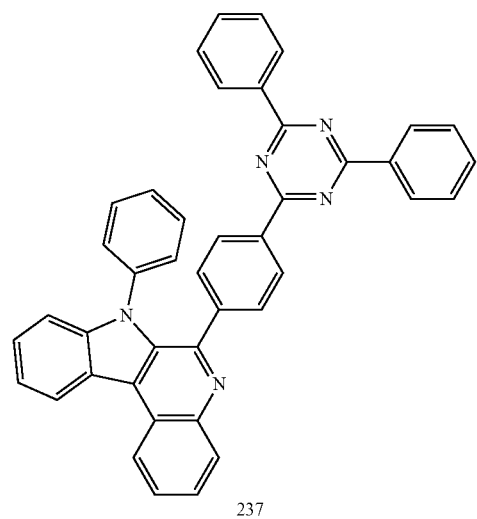

237

1) Preparation of Compound 237-1

After dissolving (1H-indol-3-yl)boronic acid (100 g, 0.621 mol) and 2-bromoaniline (96 g, 0.558 mol) in toluene, EtOH and H₂O (1000 mL:200 mL:200 mL), Pd(PPh₃)₄ (35.8 g, 0.031 mol) and NaHCO₃ (156.5 g, 1.863 mol) were introduced thereto, and the result was stirred for 3 hours at 100° C. After the reaction was completed, MC and distilled water were introduced to the reaction solution for extraction. After that, the result was dried with anhydrous MgSO₄, and the solvent was removed using a rotary evaporator to obtain Compound 237-1 (94 g, 72%) in a liquid form.

2) Preparation of Compound 237-2

Compound 237-1 (94 g, 0.451 mol) and triethylamine (42 mL, 0.451 mol) were introduced to MC (1200 mL) and dissolved therein. 4-Bromobenzoyl chloride (108.9 g, 0.496 mol) dissolved in MC (300 mL) was slowly added dropwise to the mixture at 0° C. After the reaction was completed, MC and distilled water were introduced to the reaction solution for extraction. After that, the result was dried with anhydrous MgSO₄, and the solvent was removed using a rotary evaporator to obtain Compound 237-2 (150 g, 85%) in a liquid form.

3) Preparation of Compound 237-3

After dissolving Compound 237-2 (150 g, 0.383 mol) in nitrobenzene (1500 mL), POCl₃ (35 mL, 0.383 mol) was slowly added dropwise thereto. The result was reacted for 15 hours at 140° C. After the reaction was completed, a solution dissolving NaHCO₃ in distilled water was slowly introduced to the reaction solution, and the result was stirred. Produced solids were filtered and collected. The collected solids were recrystallized with MC and MeOH to obtain Compound 237-3 (68 g, 48%) in a solid form.

4) Preparation of Compound 237-4

After dissolving Compound 237-3 (10 g, 0.026 mol), bis(pinacolato)diboron (9.9 g, 0.039 mol), KOAc (7.6 g, 0.078 mol) and PdCl₂(dppf) (0.9 g, 0.0013 mol) in 1,4-dioxane (200 mL), the result was reacted for 5 hours at 90° C. After the reaction was completed, MC and distilled water were introduced to the reaction solution for extraction. After that, the result was dried with anhydrous MgSO₄, and the solvent was removed using a rotary evaporator to obtain Compound 237-4 (10 g, 91%).

5) Preparation of Compound 237-5

After dissolving Compound 237-4 (8 g, 0.019 mol) and 2-bromo-4,6-diphenyl-1,3,5-triazine (5.9 g, 0.019 mol) in toluene, EtOH and H₂O (80 mL:10 mL:10 mL), Pd(PPh₃)₄ (1.1 g, 0.0009 mol) and K₂CO₃ (7.8 g, 0.057 mol) were introduced thereto, and the result was stirred for 5 hours at 100° C. After the reaction was completed, MC and distilled water were introduced to the reaction solution for extraction. After that, the result was dried with anhydrous MgSO₄, and the solvent was removed using a rotary evaporator to obtain Compound 237-5 (7.4 g, 75%).

6) Preparation of Compound 237

After dissolving Compound 237-5 (7.4 g, 0.014 mol) and bromobenzene (3.2 g, 0.021 mol) in toluene (100 mL), Pd₂(dba)₃ (1.2 g, 0.0014 mol), tri-tert-butylphosphine (0.5 g, 0.0028 mol) and sodium tert-butoxide (2.7 g, 0.028 mol) were introduced thereto, and the result was stirred for 15 hours at 100° C. After the reaction was completed, the result was cooled to room temperature, and produced solids were filtered and dried to obtain Compound 237 (6.5 g, 77%).

A target compound was synthesized in the same manner as in Preparation Example 3 except that Intermediate K of the following Table 7 was used instead of 2-bromo-4,6-diphenyl-1,3,5-triazine.

TABLE 7

| Compound Number | Intermediate K | Compound | Yield |
|---|---|---|---|
| 238 | | | 70% |
| 240 | | | 68% |
| 242 | | | 72% |

TABLE 7-continued
| Compound Number | Intermediate K | Compound | Yield |
|---|---|---|---|
| 259 | 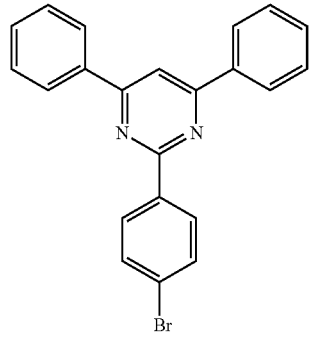 [SMILES: Brc1ccc(-c2nc(-c3ccccc3)cc(-c3ccccc3)n2)cc1] | 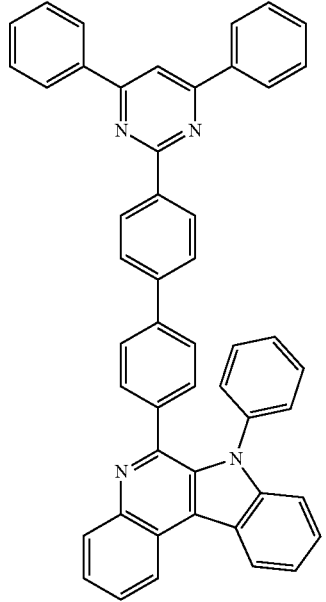 [SMILES: c1ccc(-c2cc(-c3ccccc3)nc(-c3ccc(-c4ccc(-c5nc6ccccc6c6c7ccccc7n(-c7ccccc7)c56)cc4)cc3)n2)cc1] | 73% |
| 263 | 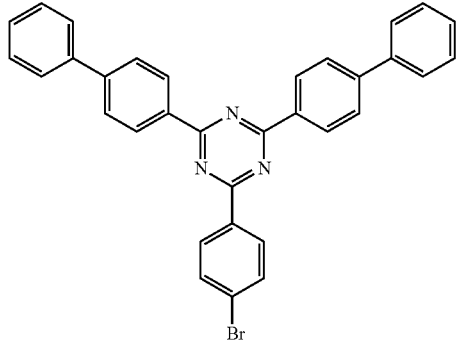 [SMILES: Brc1ccc(-c2nc(-c3ccc(-c4ccccc4)cc3)nc(-c3ccc(-c4ccccc4)cc3)n2)cc1] | 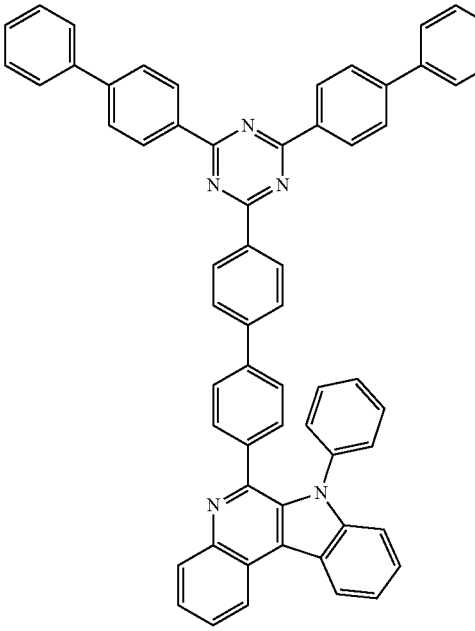 | 75% |

TABLE 7-continued
| Compound Number | Intermediate K | Compound | Yield |
|---|---|---|---|
| 264 | 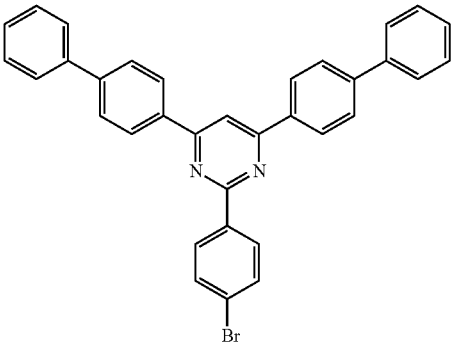 [SMILES: Brc1ccc(-c2nc(-c3ccc(-c4ccccc4)cc3)cc(-c3ccc(-c4ccccc4)cc3)n2)cc1] | 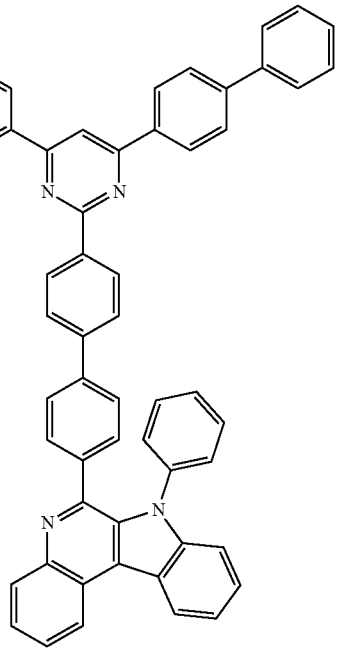 | 69% |
| 277 | 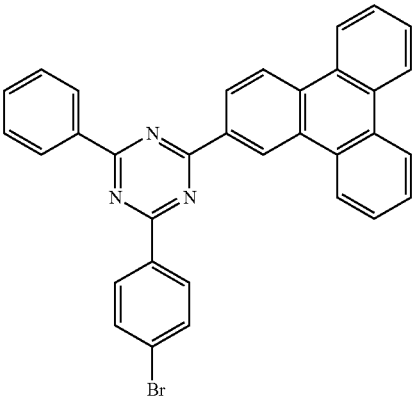 [SMILES: Brc1ccc(-c2nc(-c3ccccc3)nc(-c3ccc4c5ccccc5c5ccccc5c4c3)n2)cc1] | 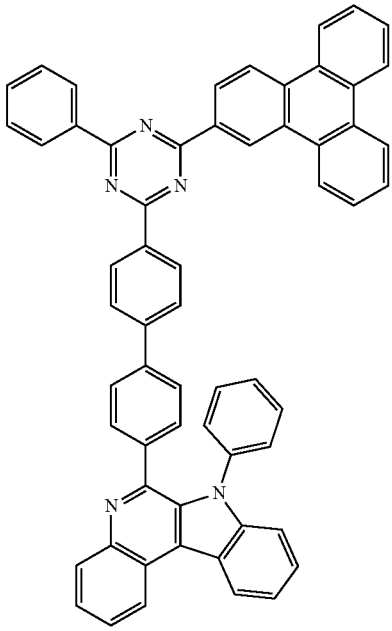 [SMILES: c1ccc(-c2nc(-c3ccc(-c4ccc(-c5nc6ccccc6c6c7ccccc7n(-c7ccccc7)c56)cc4)cc3)nc(-c3ccc4c5ccccc5c5ccccc5c4c3)n2)cc1] | 58% |

TABLE 7-continued

| Compound Number | Intermediate K | Compound | Yield |
|---|---|---|---|
| 278 | | | 55% |
| 282 | | | 59% |

TABLE 7-continued
| Compound Number | Intermediate K | Compound | Yield |
|---|---|---|---|
| 283 | 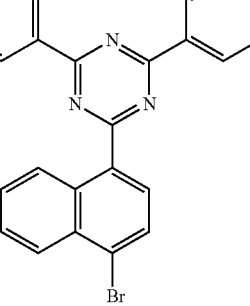 | 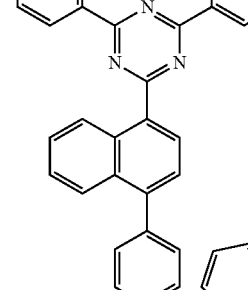 | 64% |
| 284 |  |  | 66% |

TABLE 7-continued

| Compound Number | Intermediate K | Compound | Yield |
|---|---|---|---|
| 288 | | | 68% |
| 290 | | | 65% |

TABLE 7-continued
| Compound Number | Intermediate K | Compound | Yield |
|---|---|---|---|
| 292 | 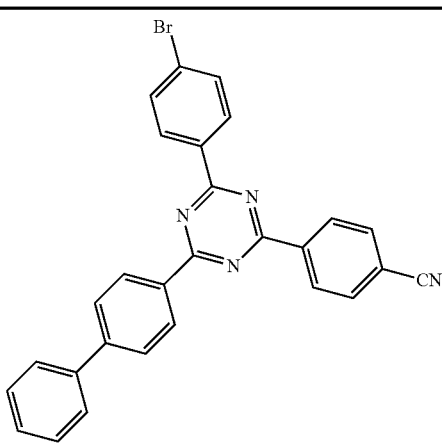 | 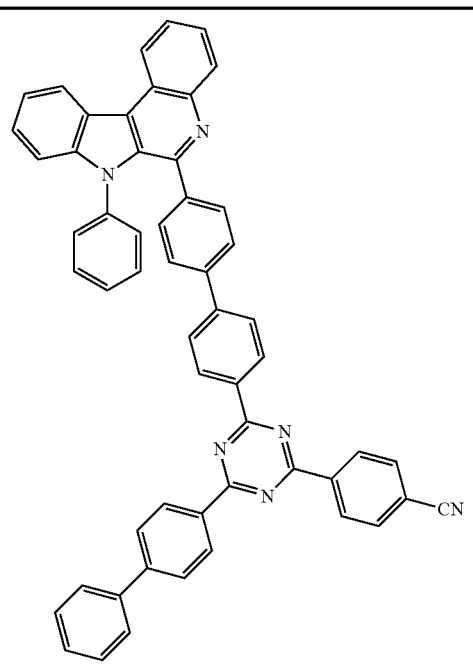 | 67% |
| 293 | 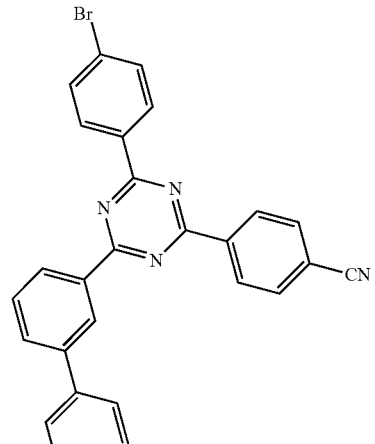 | 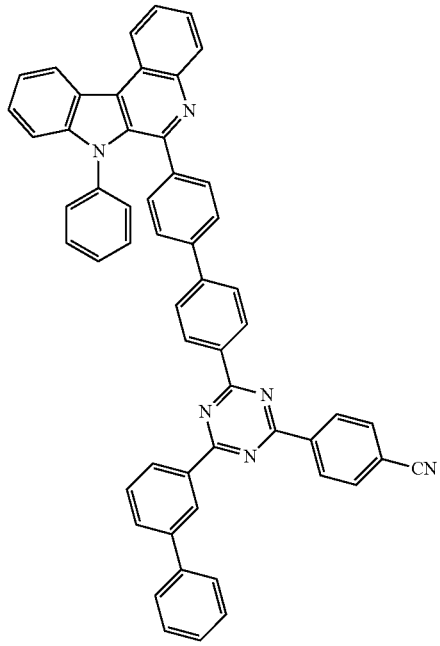 [SMILES: N#Cc1ccc(-c2nc(-c3ccc(-c4ccc(-c5nc6ccccc6c6c7ccccc7n(-c7ccccc7)c56)cc4)cc3)nc(-c3cccc(-c4ccccc4)c3)n2)cc1] | 69% |

TABLE 7-continued

| Compound Number | Intermediate K | Compound | Yield |
|---|---|---|---|
| 296 | | | 67% |
| 299 | | | 64% |

TABLE 7-continued
| Compound Number | Intermediate K | Compound | Yield |
|---|---|---|---|
| 300 | 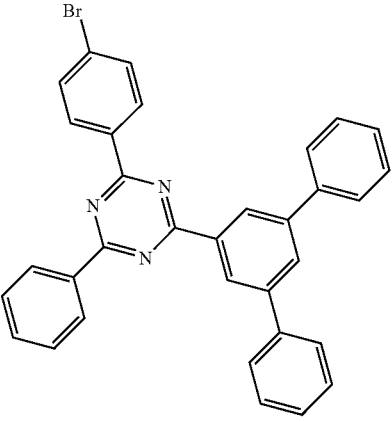 [SMILES: Brc1ccc(-c2nc(-c3ccccc3)nc(-c3cc(-c4ccccc4)cc(-c4ccccc4)c3)n2)cc1] | 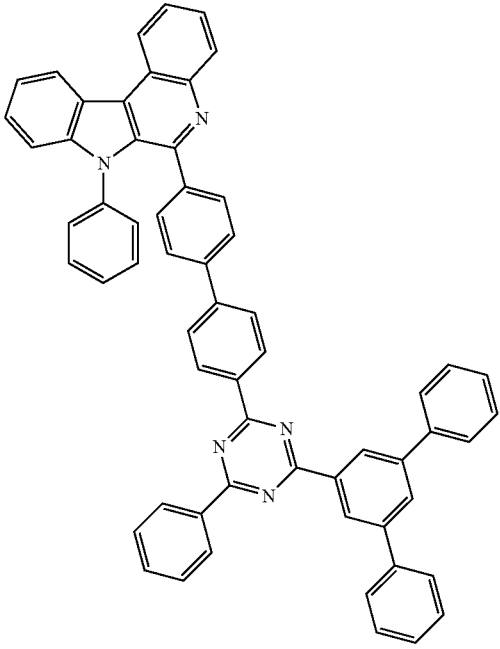 [SMILES: c1ccc(-c2cc(-c3ccccc3)cc(-c3nc(-c4ccccc4)nc(-c4ccc(-c5ccc(-c6nc7ccccc7c7c8ccccc8n(-c8ccccc8)c67)cc5)cc4)n3)c2)cc1] | 61% |
| 303 | 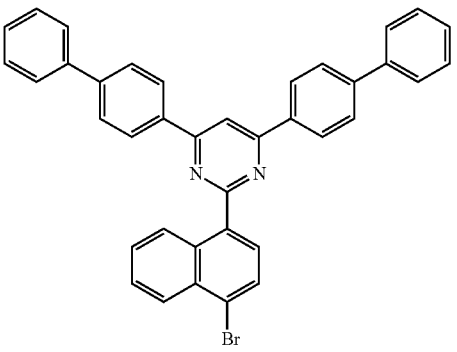 [SMILES: Brc1ccc(-c2nc(-c3ccc(-c4ccccc4)cc3)cc(-c3ccc(-c4ccccc4)cc3)n2)c2ccccc12] | 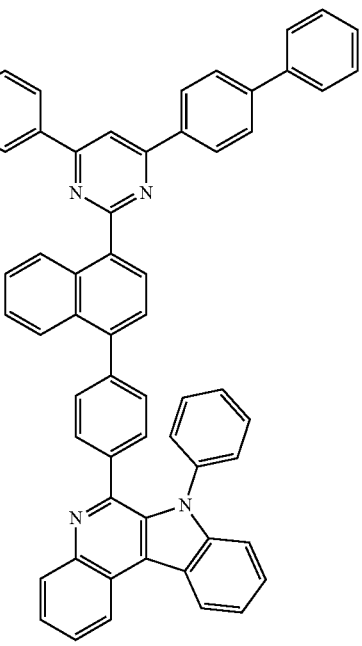 | 66% |

TABLE 7-continued
| Compound Number | Intermediate K | Compound | Yield |
|---|---|---|---|
| 304 | 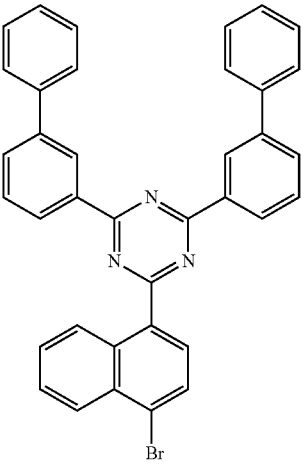 [SMILES: Brc1ccc(-c2nc(-c3cccc(-c4ccccc4)c3)nc(-c3cccc(-c4ccccc4)c3)n2)c2ccccc12] | 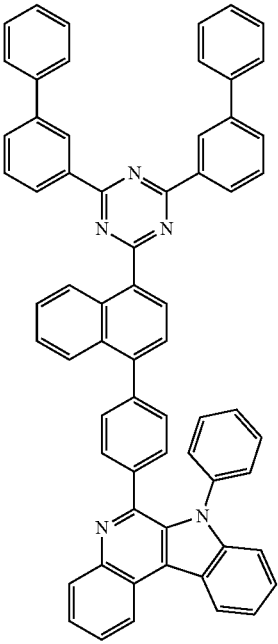 [SMILES: c1ccc(-c2cccc(-c3nc(-c4cccc(-c5ccccc5)c4)nc(-c4ccc(-c5ccc(-c6nc7ccccc7c7c8ccccc8n(-c8ccccc8)c67)cc5)c5ccccc45)n3)c2)cc1] | 64% |
| 306 | 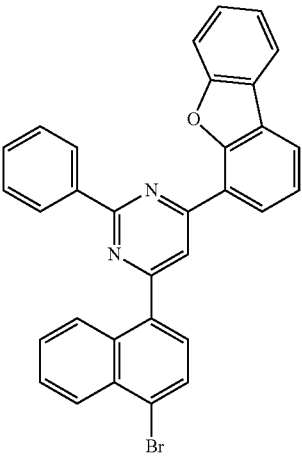 [SMILES: Brc1ccc(-c2cc(-c3cccc4c3oc3ccccc34)nc(-c3ccccc3)n2)c2ccccc12] | 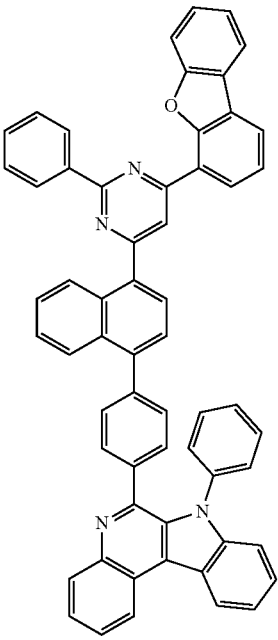 | 62% |

TABLE 7-continued

| Compound Number | Intermediate K | Compound | Yield |
|---|---|---|---|
| 308 | [structure] | [structure] | 61% |

A target compound was synthesized in the same manner as in Preparation Example 3 except that Intermediate L of the following Table 8 was used instead of 4-bromobenzoyl chloride, and Intermediate M of the following Table 8 was used instead of 2-bromo-4,6-diphenyl-1,3,5-triazine.

TABLE 8

| Compound Number | Intermediate L | Intermediate M | Compound | Yield |
|---|---|---|---|---|
| 248 | [structure] | [structure] | [structure] | 70% |

TABLE 8-continued

| Compound Number | Intermediate L | Intermediate M | Compound | Yield |
|---|---|---|---|---|
| 250 | | | | 74% |
| 251 | | | | 73% |
| 253 | | | | 73% |

TABLE 8-continued

| Compound Number | Intermediate L | Intermediate M | Compound | Yield |
|---|---|---|---|---|
| 267 | | | | 69% |
| 270 | | | | 70% |
| 273 | | | | 72% |

TABLE 8-continued

| Compound Number | Intermediate L | Intermediate M | Compound | Yield |
|---|---|---|---|---|
| 305 | | | | 71% |
| 313 | | | | 72% |

A target compound was synthesized in the same manner as in Preparation Example 3 except that Intermediate N of the following Table 9 was used instead of 2-bromoaniline, and Intermediate O of the following Table 9 was used instead of 2-bromo-4,6-diphenyl-1,3,5-triazine.

TABLE 9

| Compound Number | Intermediate N | Intermediate O | Compound | Yield |
|---|---|---|---|---|
| 399 | | | | 50% |
| 400 | | | | 51% |

TABLE 9-continued
| Compound Number | Intermediate N | Intermediate O | Compound | Yield |
|---|---|---|---|---|
| 401 | 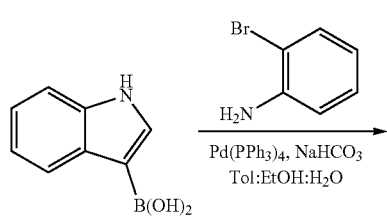 | 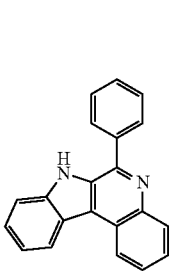 | 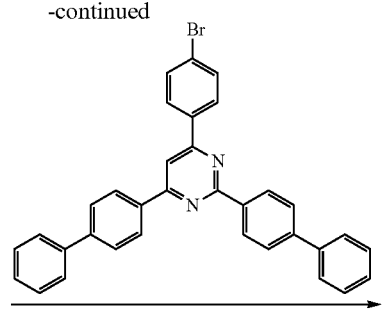 | 59% |
<Preparation Example 4> Preparation of Compound 345
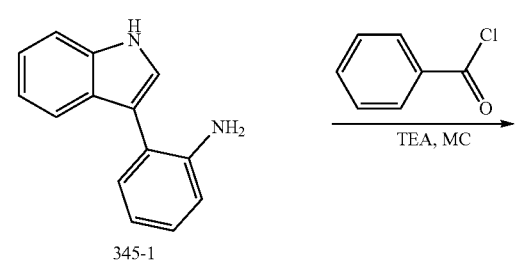
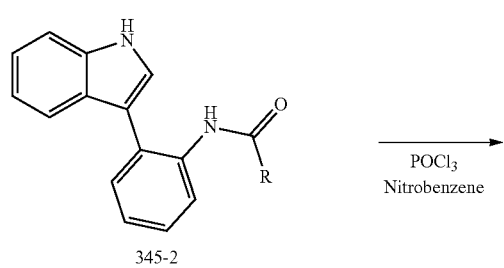
345-1
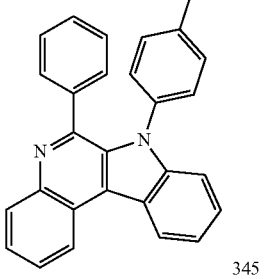
345-2
-continued
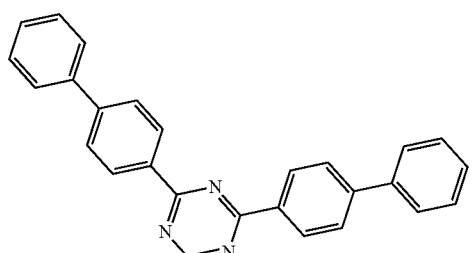
345-3
345

1) Preparation of Compound 345-1

After dissolving (1H-indol-3-yl)boronic acid (100 g, 0.621 mol) and 2-bromoaniline (96 g, 0.558 mol) in toluene, EtOH and $H_2O$ (1000 mL:200 mL:200 mL), $Pd(PPh_3)_4$ (35.8 g, 0.031 mol) and $NaHCO_3$ (156.5 g, 1.863 mol) were introduced thereto, and the result was stirred for 3 hours at 100° C. After the reaction was completed, MC and distilled water were introduced to the reaction solution for extraction. After that, the result was dried with anhydrous $MgSO_4$, and the solvent was removed using a rotary evaporator to obtain Compound 345-1 (94 g, 72%) in a liquid form.

2) Preparation of Compound 345-2

Compound 345-1 (94 g, 0.451 mol) and triethylamine (42 mL, 0.451 mol) were introduced to MC (1200 mL) and dissolved therein. Benzoyl chloride (69.7 g, 0.496 mol) dissolved in MC (300 mL) was slowly added dropwise to the mixture at 0° C. After the reaction was completed, MC and distilled water were introduced to the reaction solution for extraction. After that, the result was dried with anhydrous $MgSO_4$, and the solvent was removed using a rotary evaporator to obtain Compound 345-2 (112 g, 80%) in a liquid form.

3) Preparation of Compound 345-3

After dissolving Compound 345-2 (112 g, 0.358 mol) in nitrobenzene (1000 mL), $POCl_3$ (33 mL, 0.358 mol) was slowly added dropwise thereto. The result was reacted for 15 hours at 140° C. After the reaction was completed, a solution dissolving $NaHCO_3$ in distilled water was slowly introduced to the reaction solution, and the result was stirred. Produced solids were filtered and collected. The collected solids were recrystallized with MC and MeOH to obtain Compound 345-3 (54 g, 51%) in a solid form.

4) Preparation of Compound 345

After dissolving Compound 345-3 (9 g, 0.030 mol), 2,4-di([1,1'-biphenyl]-4-yl)-6-(4-bromophenyl)pyrimidine (4.7 g, 0.030 mol) in toluene (100 mL), $Pd_2(dba)_3$ (2.8 g, 0.003 mol), tri-tert-butylphosphine (1.2 g, 0.006 mol) and sodium tert-butoxide (5.7 g, 0.062 mol) were introduced thereto, and the result was stirred for 15 hours at 100° C. After the reaction was completed, the result was cooled to room temperature, and produced solids were filtered and dried to obtain Compound 345 (15 g, 60%).

A target compound was synthesized in the same manner as in Preparation Example 4 except that Intermediate P of the following Table 10 was used instead of 2,4-di([1,1'-biphenyl]-4-yl)-6-(4-bromophenyl)pyrimidine.

TABLE 10

| Compound Number | Intermediate P | Compound | Yield |
|---|---|---|---|
| 321 | | | 69% |
| 324 | | | 68% |

TABLE 10-continued

| Compound Number | Intermediate P | Compound | Yield |
|---|---|---|---|
| 325 | | | 66% |
| 332 | | | 66% |

TABLE 10-continued

| Compound Number | Intermediate P | Compound | Yield |
|---|---|---|---|
| 336 | | | 66% |
| 339 | | | 68% |

TABLE 10-continued

| Compound Number | Intermediate P | Compound | Yield |
|---|---|---|---|
| 343 | | | 67% |
| 352 | | | 68% |
| 353 | | | 67% |

TABLE 10-continued

| Compound Number | Intermediate P | Compound | Yield |
|---|---|---|---|
| 370 | | | 61% |
| 372 | | | 60% |
| 373 | | | 64% |

TABLE 10-continued

| Compound Number | Intermediate P | Compound | Yield |
|---|---|---|---|
| 374 | | | 63% |
| 376 | | | 61% |
| 379 | | | 66% |

TABLE 10-continued

| Compound Number | Intermediate P | Compound | Yield |
|---|---|---|---|
| 380 | | | 61% |
| 381 | | | 64% |

TABLE 10-continued
| Compound Number | Intermediate P | Compound | Yield |
|---|---|---|---|
| 382 | 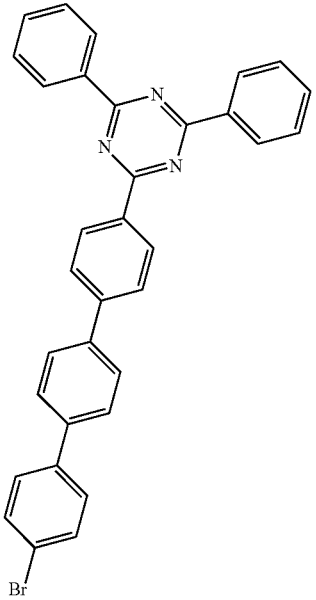 | 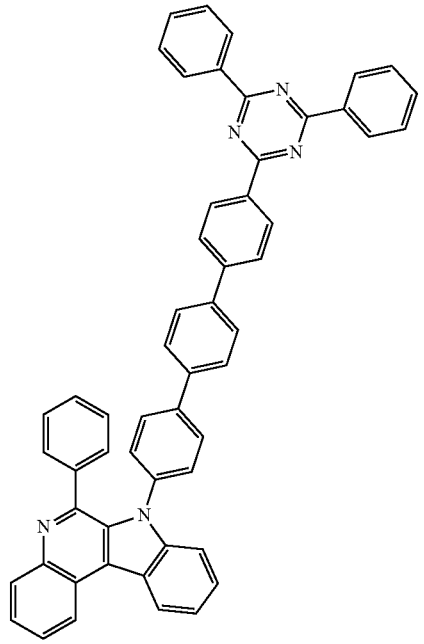 | 61% |
| 384 | 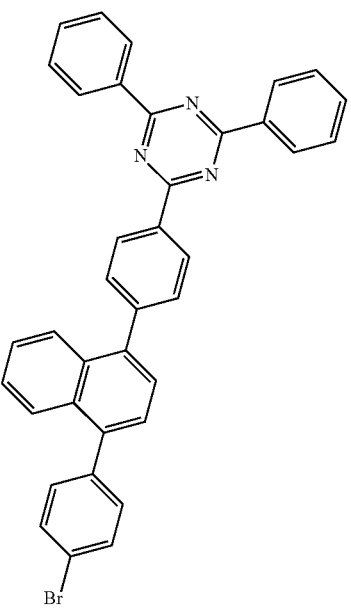 | 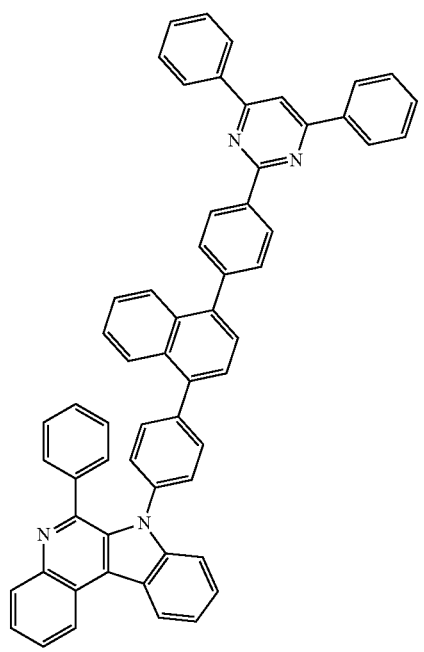 | 59% |

TABLE 10-continued

| Compound Number | Intermediate P | Compound | Yield |
|---|---|---|---|
| 397 | (structure) | (structure) | 59% |
| 396 | (structure) | (structure) | 60% |

TABLE 10-continued

| Compound Number | Intermediate P | Compound | Yield |
|---|---|---|---|
| 398 | | | 61% |

A target compound was synthesized in the same manner as in Preparation Example 4 except that Intermediate Q of the following Table 11 was used instead of benzoyl chloride, and Intermediate R of the following Table 11 was used instead of 2,4-di([1,1'-biphenyl]-4-yl)-6-(4-bromophenyl)pyrimidine.

TABLE 11

| Compound Number | Intermediate Q | Intermediate R | Compound | Yield |
|---|---|---|---|---|
| 388 | | | | 60% |

TABLE 11-continued

| Compound Number | Intermediate Q | Intermediate R | Compound | Yield |
|---|---|---|---|---|
| 391 | | | | 55% |
| 395 | | | | 51% |

A target compound was synthesized in the same manner as in Preparation Example 4 except that Intermediate S of the following Table 12 was used instead of 2-bromoaniline, and Intermediate T of the following Table 12 was used instead of 2,4-di([1,1'-biphenyl]-4-yl)-6-(4-bromophenyl)pyrimidine.

TABLE 12

| Compound Number | Intermediate S | Intermediate T | Compound | Yield |
|---|---|---|---|---|
| 363 | | | | 50% |

TABLE 12-continued

| Compound Number | Intermediate S | Intermediate T | Compound | Yield |
|---|---|---|---|---|
| 365 | 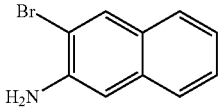 | 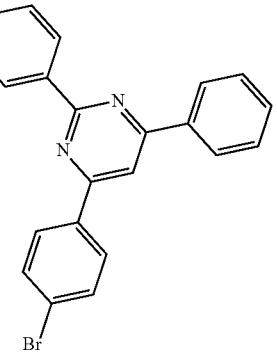 | 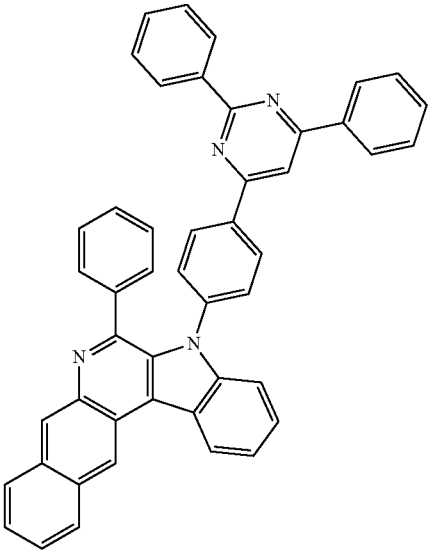 | 51% |
| 367 | 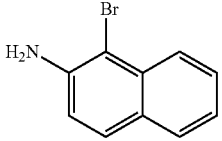 | 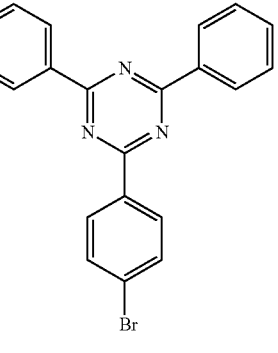 | 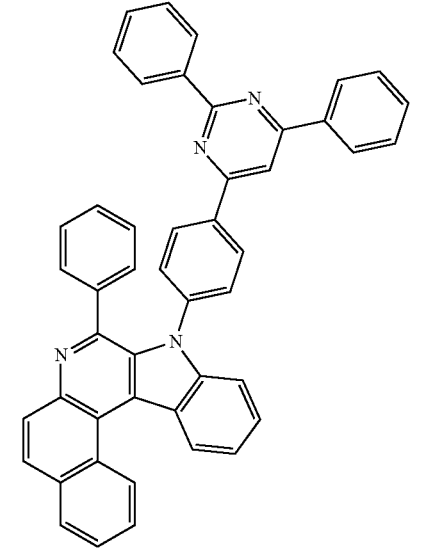 | 52% |

Compounds other than the compounds described in Table 1 to Table 12 were also prepared in the same manner as in the preparation examples described above.

The following Table 13 and Table 14 present 1H NMR data and FD-MS data of the synthesized compounds, and through the following data, syntheses of target compounds may be identified.

TABLE 13

| NO | $^1$H NMR (CDCl$_3$, 300 Mz) |
|---|---|
| 1 | δ = 8.69(2H, d), 8.55(1H, d), 8.42(1H, d), 8.36(4H, d), 7.96~7.85(6H, m), 7.62~7.50(11H, m), 7.35(1H, t), 7.16(1H, t) |
| 2 | δ = 8.69(2H, d), 8.55(1H, d), 8.42~8.30(5H, m), 7.94~7.87(6H, m), 7.62~7.50(11H, m), 7.35(1H, t), 7.16(1H, t) |

TABLE 13-continued

| NO | $^1$H NMR (CDCl$_3$, 300 Mz) |
|---|---|
| 4 | δ = 8.69(2H, d), 8.55(1H, d), 8.42~8.36(3H, m), 7.96~7.85(8H, m), 7.75(2H, d), 7.62~7.35(12H, m), 7.25(2H, d), 7.16(1H, t) |
| 6 | δ = 8.69(2H, d), 8.55(1H, d), 8.42(1H, d), 8.30(2H, d), 8.23(1H, s), 7.94~7.85(10H, m), 7.75(1H, d), 7.62~7.49(12H, m), 7.16(1H, t) |
| 7 | δ = 8.69(2H, d), 8.55(1H, d), 8.42(1H, d), 7.96(10H, m), 7.75(4H, d), 7.62~7.41(12H, m), 7.25(4H, m), 7.16(1H, t) |
| 8 | δ = 8.69(2H, d), 8.55(1H, d), 8.42(d, 1H), 8.30(4H, d), 8.23(1H, s), 7.94~7.75(14H, m), 7.62~7.41(12H, m), 7.16(1H, t) |
| 16 | δ = 8.97(2H, d), 8.68(1H, d), 8.55(1H, d), 8.42(1H, d), 8.29(1H, d), 8.23(1H, s), 7.94~7.85(7H, m), 7.62~7.49(13H, m), 7.35(1H, t), 7.16(1H, t) |

TABLE 13-continued

| NO | ¹H NMR (CDCl₃, 300 Mz) |
|---|---|
| 21 | δ = 8.97(2H, d), 8.68(1H, d), 8.55(1H, d), 8.42(1H, d), 8.30(4H, d), 8.29(1H, d), 8.23(1H, s), 7.94~7.75(12H, m), 7.62~7.41(14H, m), 7.16(1H, t) |
| 26 | δ = 8.69(2H, d), 8.55(1H, d), 8.42(1H, d), 8.23(1H, s), 7.94~7.85(12H, m), 7.62~7.49(11H, m), 7.35(1H, t), 7.25(2H, d), 7.16(1H, t) |
| 28 | δ = 8.69(2H, d), 8.55(1H, d), 8.42(1H, d), 8.35~8.30(6H, m), 7.94~7.85(10H, m), 7.75(2H, d), 7.62~7.35(12H, m), 7.16(1H, t) |
| 31 | δ = 8.69(2H, d), 8.55(1H, d), 8.42(1H, d), 8.30(4H, d), 8.23(1H, s), 7.96~7.85(12H, m), 7.75(4H, d), 7.62~7.41(12H, m), 7.25(2H, d), 7.16(1H, t) |
| 33 | δ = 9.18(2H, d), 8.14(2H, d), 8.69(2H, d), 8.55(2H, d), 8.42(1H, d), 7.94(2H, d), 7.85(4H, d), 7.74(2H, t), 7.62~7.50(5H, m), 7.35(1H, t), 7.25~7.16(7H, m) |
| 35 | δ = 8.55(1H, d), 8.42~8.33(8H, m), 7.94~7.85(4H, m), 7.73(1H, t), 7.62~7.50(11H, m), 7.35(1H, t), 7.16(1H, t) |
| 37 | δ = 8.55(1H, d), 8.42~8.33(4H, m), 8.23(1H, s), 7.94~7.85(8H, m), 7.73(1H, t), 7.62~7.49(11H, m), 7.35(1H, t), 7.16(1H, t) |
| 39 | δ = 8.55(1H, d), 8.42~8.30(7H, m), 8.23(1H, s), 7.94~7.85(7H, m), 7.75(2H, d), 7.73(1H, t), 7.62~7.35(12H, m), 7.16(1H, t) |
| 41 | δ = 8.55(1H, d), 8.42~8.33(4H, m), 7.96~7.85(8H, m), 7.75~7.73(5H, m), 7.62~7.35(12H, m), 7.25(4H, d), 7.16(1H, t) |
| 42 | δ = 8.55(1H, d), 8.42~8.30(8H, m), 8.23(1H, s), 7.94~7.75(13H, m), 7.62~7.35(12H, m), 7.16(1H, t) |
| 45 | δ = 8.69(2H, d), 8.51(2H, d), 8.36(4H, d), 8.20(1H, d), 8.11(1H, d), 7.96(2H, d), 7.94(1H, d), 7.90(1H, d), 7.72~7.50(13H, m), 7.35(1H, t), 7.16(1H, t) |
| 59 | δ = 8.69(2H, d), 8.55(1H, d), 8.28(1H, d), 8.11(1H, d), 8.03(1H, s), 7.96~7.94(7H, m), 7.79~7.41(23H, m), 7.16(1H, t) |
| 65 | δ = 8.69(2H, d), 8.55(1H, d), 8.35(2H, d), 8.30(2H, d), 8.23(1H, s), 8.09~7.85(10H, m), 7.62~7.49(13H, m), 7.35(1H, t), 7.25(2H, d), 7.16(1H, t) |
| 66 | δ = 8.79(1H, d), 8.69(2H, d), 8.55(1H, d), 8.42~8.30(6H, m), 8.15(1H, d), 7.96~7.85(6H, m), 7.70~7.50(13H, m), 7.35(1H, t), 7.16(1H, t) |
| 68 | δ = 8.79(1H, d), 8.69(2H, d), 8.55(1H, d), 8.42(1H, d), 8.33(2H, d), 8.30(1H, d), 8.23(1H, s), 8.15(1H, d), 7.96~7.85(8H, m), 7.70~7.49(13H, m), 7.35(1H, t), 7.16(1H, t) |
| 70 | δ = 8.69(2H, d), 8.55(1H, d), 8.42(1H, d), 8.38(2H, d), 7.94~7.85(8H, m), 7.75~7.73(4H, m), 7.61~7.35(14H, m), 7.16(1H, t) |
| 73 | δ = 8.69(2H, d), 8.55(1H, d), 8.42(1H, d), 8.23(1H, s), 7.96~7.85(10H, m), 7.75(2H, d), 7.73(1H, t), 7.62~7.35(13H, m), 7.16(1H, t) |
| 74 | δ = 8.69(2H, d), 8.55(1H, d), 8.42(1H, d), 8.38(1H, t), 8.30(2H, d), 8.23(1H, s), 7.94~7.87(7H, m), 7.75(2H, d), 7.73(1H, t), 7.62~7.41(13H, m), 7.16(1H, t) |
| 77 | δ = 8.69(2H, d), 8.55(2H, d), 8.42(1H, d), 8.36(2H, d), 8.19(1H, d), 7.96~7.85(7H, m), 7.62~7.50(10H, m), 7.35(2H, t), 7.20(2H, d), 7.16(2H, t) |
| 78 | δ = 8.69(2H, d), 8.55(1H, d), 8.42(1H, d), 8.36(2H, d), 8.19(1H, d), 7.94~7.85(11H, m), 7.62~7.50(10H, m), 7.35(1H, t), 7.20~7.16(3H, t) |
| 88 | δ = 8.69(2H, d), 8.55(1H, d), 8.42(1H, d), 8.36(2H, d), 8.09(1H, d), 7.94~7.78(9H, m), 7.62~7.50(9H, m), 7.38(1H, t), 7.35(1H, t), 7.28(1H, d), 1.69(6H, s) |
| 93 | δ = 8.69(2H, d), 8.55(1H, d), 8.42(1H, d), 8.35(2H, d), 8.30(2H, d), 8.23(1H, s), 8.09(1H, d), 7.94~7.73(10H, m), 7.62~7.50(10H, m), 7.38~7.28(3H, m), 7.16(1H, t), 1.69(6H, s) |
| 96 | δ = 8.69(2H, d), 8.55(1H, d), 8.42(1H, d), 8.36(2H, d), 7.96~7.82(10H, m), 7.62~7.50(8H, m), 7.35(1H, t), 7.16(1H, t) |
| 100 | δ = 8.69(2H, d), 8.55(1H, d), 8.42(1H, d), 7.96~7.75(14H, m), 7.62~7.35(9H, m), 7.25(2H, d), 7.16(1H, t) |
| 101 | δ = 8.69(2H, d), 8.55(1H, d), 8.42(1H, d), 7.94~7.75(14H, m), 7.62~7.35(10H, m), 7.16(1H, t) |
| 104 | δ = 9.08(1H, d), 8.84(1H, d), 8.69(2H, d), 8.55(1H, d), 8.42(1H, d), 8.36(2H, d), 8.27(1H, d), 8.05(1H, s), 7.96~7.85(9H, m), 7.70~7.50(12H, m), 7.35(1H, t), 7.25(2H, d), 7.16(1H, t) |
| 105 | δ = 9.27(1H, d), 8.85(1H, d), 8.69(2H, d), 8.55(1H, d), 8.42(1H, d), 8.36(2H, d), 8.15(1H, d), 7.96~7.85(7H, m), 7.75~7.50(12H, m), 7.35(1H, t), 7.16(1H, t) |
| 108 | δ = 8.69(2H, d), 8.55(1H, d), 8.42(1H, d), 8.36(2H, d), 8.04(3H, s), 7.96~7.85(6H, m), 7.75(4H, d), 7.62~7.35(15H, m), 7.16(1H, t) |
| 115 | δ = 8.95(1H, d), 8.55(1H, d), 8.45~8.42(2H, d), 8.30~8.20(5H, m), 7.94~7.85(10H, m), 7.62~7.35(14H, m), 7.25(2H, d), 7.16(1H, t) |
| 117 | δ = 8.93(1H, d), 8.69(2H, d), 8.55(1H, d), 8.42~8.23(8H, m), 7.94~7.85(6H, m), 7.72(1H, d), 7.62~7.35(14H, m), 7.25(4H, d), 7.16(1H, t) |
| 120 | δ = 8.95(1H, d), 8.55(1H, d), 8.45(1H, d), 8.42(1H, d), 8.25(1H, d), 8.23(1H, s), 8.20(1H, d), 7.94~7.85(10H, m), 7.75(4H, d), 7.73(2H, d), 7.62~7.35(16H, m), 7.25(2H, d), 7.16(1H, t) |
| 131 | δ = 9.02(1H, d), 8.95(1H, d), 8.69(2H, d), 8.55(1H, d), 8.42(1H, d), 8.36(4H, d), 8.06(1H, d), 7.94~7.84(5H, m), 7.62~7.46(13H, m), 7.35(1H, t), 7.25(2H, d), 7.16(1H, t) |
| 132 | δ = 9.02(1H, d), 8.95(1H, d), 8.69(2H, d), 8.55(1H, d), 8.42(1H, d), 8.35(2H, d), 8.23(1H, s), 8.06(1H, d), 7.94~7.84(7H, m), 7.62~7.49(13H, m), 7.35(1H, t), 7.25(2H, d), 7.16(1H, t) |
| 134 | δ = 8.55(1H, d), 8.42~8.36(5H, m), 8.19(2H, d), 7.94~7.85(8H, m), 7.65(2H, d), 7.50~7.49(7H, m), 7.35(1H, t), 7.16(1H, t) |
| 135 | δ = 8.55(1H, d), 8.42~8.36(4H, m), 8.35(1H, d), 8.23(1H, s), 8.19(2H, d), 7.94~7.87(10H, m), 7.65(2H, t), 7.55~7.49(7H, m), 7.35(1H, t), 7.16(1H, t) |
| 137 | δ = 8.55(1H, d), 8.42~8.36(3H, d), 8.19(2H, d), 7.96~7.85(10H, m), 7.75(2H, d), 7.65(2H, t), 7.50~7.35(8H, m), 7.25(2H, d), 7.16(1H, t) |
| 139 | δ = 8.55(1H, d), 8.42(1H, d), 8.30(2H, d), 8.23(1H, s), 8.19(2H, d), 7.94~7.85(12H, m), 7.75(2H, d), 7.65(2H, t), 7.55~7.35(8H, m), 7.16(1H, t) |
| 141 | δ = 8.55(1H, d), 8.42(1H, d), 8.30~8.19(7H, m), 7.94~7.75(16H, m), 7.65(2H, t), 7.49~7.35(8H, m), 7.16(1H, t) |
| 143 | δ = 8.97(1H, d), 8.55(1H, d), 8.42~8.36(5H, m), 8.24~8.12(4H, m), 7.94~7.79(5H, m), 7.65~7.49(11H, m), 7.35(1H, t), 7.16(1H, t) |
| 148 | δ = 8.97(1H, d), 8.55(1H, d), 8.42(1H, d), 8.30~8.12(7H, m), 7.94~7.35(23H, m), 7.16(1H, t) |
| 149 | δ = 8.97(1H, d), 8.55(1H, d), 8.42(1H, d), 8.24~8.19(3H, d), 7.94~7.35(25H, m), 7.25(4H, d), 7.16(1H, t) |
| 152 | δ = 8.80(1H, d), 8.71(1H, d), 8.55(1H, d), 8.45(1H, d), 8.42(1H, d), 8.30(2H, d), 8.20(1H, d), 8.19(2H, d), 7.94~7.85(7H, m), 7.65~7.49(4H, m), 7.35(1H, t), 7.29(1H, d), 7.16(1H, t) |
| 155 | δ = 8.55(1H, d), 8.42(1H, d), 8.23(1H, s), 8.19(2H, d), 7.94~7.85(14H, m), 7.65(2H, t), 7.55~7.49(7H, m), 7.35(1H, t), 7.25(2H, d), 7.16(1H, t) |
| 156 | δ = 8.71(2H, d), 8.55(1H, d), 8.42(1H, d), 8.33(2H, d), 8.30(2H, d), 8.20(1H, d), 8.19(2H, d), 7.94~7.85(7H, m), 7.65~7.49(6H, m), 7.35(1H, t), 7.29(2H, d), 7.16(1H, t) |
| 157 | δ = 8.71(2H, d), 8.69(2H, d), 8.55(1H, d), 8.42(1H, d), 8.33(2H, d), 8.19(2H, d), 7.94~7.85(11H, m), 7.65~7.49(6H, m), 7.35(1H, t), 7.29(2H, d), 7.16(1H, t) |
| 158 | δ = 8.71(2H, d), 8.55(1H, d), 8.42(1H, d), 8.33(4H, d), 8.19(2H, d), 7.94~7.85(9H, m), 7.73~7.49(8H, m), 7.35~7.29(3H, m), 7.16(1H, t) |
| 159 | δ = 8.55(1H, d), 8.42(1H, d), 8.19(2H, d), 7.96~7.85(14H, m), 7.75(4H, d), 7.65(2H, t), 7.49~7.35(8H, m), 7.25~7.16(7H, m), |
| 161 | δ = 9.18(2H, d), 9.14(2H, s), 8.55(3H, d), 8.42(1H, d), 8.19(2H, d), 7.94~7.85(8H, m), 7.74~7.65(4H, d), 7.49(1H, t), 7.35(1H, t), 7.25~7.16(7H, m) |
| 165 | δ = 8.55(1H, d), 8.42~8.36(5H, m), 8.24(2H, d), 8.19(2H, d), 7.94~7.85(4H, m), 7.68~7.60(4H, m), 7.50(7H, t), 7.35(1H, t), 7.16(1H, t) |
| 168 | δ = 8.55(1H, d), 8.42~8.36(3H, m), 8.24~8.19(4H, d), 7.96~7.85(6H, m), 7.75~7.60(6H, m), 7.50~7.35(8H, m), 7.25(2H, d), 7.16(1H, t) |
| 169 | δ = 8.55(1H, d), 8.42~8.30(5H, m), 8.23~8.19(4H, m), 7.94~7.65(13H, m), 7.50~7.35(8H, m), 7.16(1H, t) |
| 187 | δ = 8.55(2H, d), 8.51(1H, d), 8.36(2H, d), 8.24~8.11(6H, m), 7.99~7.90(9H, m), 7.77~7.60(9H, m), 7.50~7.35(9H, m), 7.16(1H, t) |

TABLE 13-continued

| NO | ¹H NMR (CDCl₃, 300 Mz) |
|---|---|
| 192 | δ = 8.55(1H, d), 8.35~7.91(18H, m), 7.75~7.65(5H, m), 7.50~7.25(11H, m), 7.16(1H, t) |
| 195 | δ = 8.55(2H, d), 8.35(2H, d), 8.23(1H, s), 8.19(2H, d), 8.06~7.91(10H, m), 7.65~7.49(11H, m), 7.35(1H, t), 7.16(1H, t) |
| 203 | δ = 8.55(1H, d), 8.42~8.36(3H, d), 8.19(2H, d), 7.98~7.79(12H, m), 7.65(2H, t), 7.54~7.49(5H, m), 7.39(1H, t), 7.35(1H, t), 7.31(1H, t), 7.16(1H, t) |
| 205 | δ = 8.55(1H, d), 8.42(1H, d), 8.35(2H, d), 8.30(2H, d), 8.23(1H, s), 8.19(2H, d), 7.98~7.82(10H, m), 7.69~7.49(9H, m), 7.39~7.25(5H, m), 7.16(1H, t) |
| 209 | δ = 8.55(1H, d), 8.45~8.36(4H, d), 8.19(2H, d), 7.94~7.85(10H, m), 7.70~7.49(9H, m), 7.35(1H, t), 7.16(1H, t) |
| 212 | δ = 8.55(2H, d), 8.45~8.32(5H, m), 8.23(1H, s), 8.19(2H, d), 7.94~7.85(11H, m), 7.73~7.49(11H, m), 7.35(1H, t), 7.16(1H, t) |
| 213 | δ = 8.55(1H, d), 8.42(2H, d), 8.36(4H, d), 8.21(1H, d), 8.10(2H, d), 7.94~7.80(10H, m), 7.69(1H, d), 7.55~7.50(7H, m), 7.35(1H, t), 7.16(1H, t) |
| 218 | δ = 9.08(1H, d), 8.84(1H, d), 8.55(1H, d), 8.44(1H, s), 8.42~8.36(3H, d), 8.17(1H, d), 7.96~7.85(11H, m), 7.75~7.62(6H, m), 7.50~7.35(7H, m), 7.25(2H, d), 7.16(1H, s) |
| 219 | δ = 9.08(1H, d), 8.84(1H, d), 8.55(1H, d), 8.44~8.30(6H, m), 8.23(1H, s), 8.17(1H, d), 7.94~7.85(11H, m), 7.75~7.62(6H, m), 7.50~7.35(7H, m), 7.16(1H, t) |
| 222 | δ = 9.08(1H, d), 8.84(1H, d), 8.55(1H, d), 8.44~8.42(2H, d), 8.30(4H, d), 8.23(1H, s), 8.17(1H, d), 7.94~7.63(21H, m), 7.49~7.35(7H, m), 7.16(1H, t) |
| 228 | δ = 9.08(1H, d), 8.84(1H, d), 8.55(1H, d), 8.44(1H, s), 8.42(1H, d), 8.36(2H, d) 8.17(1H, d), 7.96~7.85(14H, m), 7.75~7.62(6H, m), 7.50~7.35(7H, m), 7.25(4H, d), 7.16(1H, t) |
| 229 | δ = 9.08(1H, d), 8.84(1H, d), 8.55(1H, d), 8.44(1H, s), 8.42~8.17(10H, m), 7.94~7.85(9H, m), 7.75~7.60(8H, m), 7.50~7.35(8H, m), 7.16(1H, t) |
| 234 | δ = 9.02(1H, d), 8.95(1H, d), 8.55(1H, d), 8.42(1H, d), 8.36(2H, d), 8.19(2H, d), 8.06(1H, d), 7.96~7.84(11H, m), 7.75(2H, d), 7.65(2H, t), 7.50~7.35(10H, m), 7.25(2H, d), 7.16(1H, t) |
| 236 | δ = 9.02(1H, d), 8.95(1H, d), 8.55(1H, d), 8.42(1H, d), 8.30(2H, d), 8.19(2H, d), 8.06(1H, d), 7.94~7.85(13H, m), 7.75(2H, d), 7.65~7.35(12H, m), 7.16(1H, t) |
| 237 | δ = 8.69(2H, d), 8.55(1H, d), 8.36(4H, d), 8.20(1H, d), 7.96~7.94(4H, d), 7.85(1H, t), 7.70~7.50(12H, m), 7.35(1H, t), 7.16(1H, t) |
| 238 | δ = 8.69(2H, d), 8.55(1H, d), 8.35(2H, d), 8.30(2H, d), 8.23(1H, s), 8.20(1H, d), 7.94(4H, d), 7.70~7.49(12H, m), 7.35(1H, t), 7.16(1H, t) |
| 240 | δ = 8.69(2H, d), 8.55(1H, d), )8.36(2H, d), 8.20(1H, d), 7.96~7.94(6H, m), 7.85(1H, t), 7.70~7.35(15H, m), 7.25(2H, d), 7.16(1H, t) |
| 242 | δ = 8.69(2H, d), 8.55(1H, d), 8.30(2H, d), 8.23(1H, s), 8.20(1H, d), 7.96~7.85(9H, m), 7.70~7.35(15H, m), 7.16(1H, t) |
| 248 | δ = 8.97(2H, d), 8.68(1H, d), 8.55(1H, d), 8.35~8.20(5H, m), 7.94~7.85(5H, m), 7.62~7.50(14H, m), 7.35(1H, t), 7.16(1H, t) |
| 250 | δ = 8.97(2H, d), 8.89(1H, d), 8.55(1H, d), 8.36~8.29(3H, d), 8.20(1H, d), 7.94(4H, d), 7.85(1H, t), 7.70~7.35(17H, m), 7.25(2H, d), 7.16(1H, t) |
| 251 | δ = 8.97(2H, d), 8.68(1H, d), 8.55(1H, d), 8.35~8.20(7H, m), 7.94(2H, d), 7.85(2H, d), 7.75~7.35(17H, m), 7.16(1H, t) |
| 253 | δ = 8.97(2H, d), 8.68(1H, d), 8.55(1H, d), 8.29(1H, d), 8.20(1H, d), 7.96~7.94(7H, m), 7.70~7.35(19H, m), 7.25(4H, d), 7.16(1H, t) |
| 259 | δ = 8.69(2H, d), 8.55(1H, d), 8.23(1H, s), 8.20(1H, d), 7.94~7.85(11H, m), 7.70~7.49(12H, m), 7.35(1H, t), 7.25(2H, d), 7.16(1H, t) |
| 263 | δ = 8.69(2H, d), 8.55(1H, d), 8.20(1H, d), 7.96~7.85(11H, m), 7.70~7.41(17H, m), 7.25(6H, d), 7.16(1H, t) |
| 264 | δ = 8.69(2H, d), 8.55(1H, d), 8.30(4H, d), 8.23(1H, s), 8.20(1H, d), 7.96~7.41(28H, m), 7.25(2H, d), 7.16(1H, t) |
| 267 | δ = 8.55(1H, d), 8.38(1H, s), 8.36(4H, d), 8.33(2H, s), 8.20(1H, d), 7.94(2H, d), 7.85(1H, t), 7.70~7.50(13H, m), 7.35(1H, d), 7.16(1H, t) |
| 270 | δ = 8.55(1H, d), 8.38(1H, s), 8.36(4H, d), 8.20(1H, d), 7.96(4H, d), 7.70~7.35(16H, m), 7.25(2H, d), 7.16(1H, t) |
| 273 | δ = 8.55(1H, d), 8.38(1H, d), 8.33(3H, d), 8.20(1H, d), 7.96~7.94(7H, m), 7.70~7.35(18H, m), 7.25(4H, d), 7.16(1H, t) |
| 277 | δ = 9.60(1H, d), 9.27(1H, s), 8.69(2H, d), 8.55(1H, d), 8.30(3H, d), 8.20~8.15(2H, d), 7.96~7.85(7H, m), 7.70~7.50(15H, m), 7.35(1H, t), 7.25(2H, d), 7.16(1H, t) |
| 278 | δ = 9.60(1H, d), 9.27(1H, s), 8.69(2H, d), 8.55(1H, d), 8.37~8.30(5H, m), 8.20(1H, d), 7.96~7.85(9H, m), 7.70~7.50(15H, m), 7.35(1H, t), 7.25~7.16(5H, m) |
| 282 | δ = 9.60(1H, d), 9.27(1H, s), 8.69(2H, d), 8.55(1H, d), 8.37~8.30(3H, d), 8.23(1H, s), 8.20(1H, d), 7.96~7.85(11H, m), 7.70~7.49(16H, m), 7.35(1H, t), 7.25(2H, d), 7.16(1H, t) |
| 283 | δ = 9.02(1H, d), 8.95(1H, d), 8.69(2H, d), 8.55(1H, d), 8.36(2H, d), 8.20(1H, d), 8.08(1H, d), 8.06(1H, d), 7.98~7.84(6H, m), 7.70~7.35(18H, m), 7.16(1H, t) |
| 284 | δ = 8.69(2H, d), 8.55(1H, d), 8.36(2H, d), 8.20(1H, d), 8.09(1H, d), 7.94~7.50(20H, m), 7.38~7.25(5H, m), 7.16(1H, t), 1.69(6H, s) |
| 288 | δ = 8.69(2H, d), 8.55(1H, d), 8.36(2H, d), 8.20(1H, d), 7.96~7.82(11H, m), 7.70~7.50(9H, m), 7.35(1H, t), 7.25(2H, d), 7.16(1H, t) |
| 290 | δ = 8.69(2H, d), 8.55(1H, d), 8.23(1H, s), 8.20(1H, d), 8.12(1H, d), 8.02~7.85(11H, m), 7.70~7.49(10H, m), 7.35(1H, t), 7.25(2H, d), 7.16(1H, t) |
| 292 | δ = 8.69(2H, d), 8.55(1H, d), 8.20(1H, d), 7.96~7.35(25H, m), 7.25(4H, d), 7.16(1H, t) |
| 293 | δ = 8.69(2H, d), 8.55(1H, d), 8.38(1H, d), 8.20(1H, d), 7.95~7.35(26H, m), 7.25(2H, d), 7.16(1H, t) |
| 296 | δ = 9.08(1H, d), 8.84(1H, d), 8.69(2H, d), 8.55(1H, d), 8.36(2H, d), 8.27~8.20(2H, d), 8.05(1H, s), 7.96~7.85(10H, m), 7.70~7.50(13H, m), 7.35(1H, t), 7.25(2H, d), 7.16(1H, t) |
| 299 | δ = 9.27(1H, d), 8.85(1H, d), 8.69(2H, d), 8.55~8.52(2H, d), 8.23~8.15(3H, m), 7.96~7.85(10H, m), 7.75~7.49(13H, m), 7.35(1H, t), 7.25(2H, d), 7.16(1H, t) |
| 300 | δ = 8.69(2H, d), 8.55(1H, d), 8.36(2H, d), 8.20(1H, d), 8.04(3H, s), 7.96~7.94(4H, d), 7.85(3H, t), 7.70~7.35(20H, m), 7.25(2H, d), 7.16(1H, t) |
| 303 | δ = 9.02(1H, d), 8.95(1H, d), 8.69(2H, d), 8.55(1H, d), 8.30~8.20(6H, m), 8.06(1H, d), 7.95~7.35(27H, m), 7.25(2H, d), 7.16(1H, t) |
| 304 | δ = 9.02((1H, d), 8.95(1H, d), 8.69(2H, d), 8.55(1H, d), 8.38(1H, d), 8.20(1H, d), 8.06(1H, d), 7.94~7.41(29H, m), 7.25(2H, d), 7.16(1H, t) |
| 305 | δ = 9.60(1H, d), 9.27(1H, s), 8.97(2H, d), 8.68(1H, d), 8.55(1H, d), 8.38~8.30(7H, m), 8.20(1H, d), 7.94(3H, d), 7.85(1H, t), 7.73~7.50(19H, m), 7.35(1H, t), 7.16(1H, t) |
| 306 | δ = 9.02(1H, d), 8.95(1H, d), 8.69(2H, d), 8.55(1H, d), 8.35(2H, d), 8.23(1H, s), 8.20(1H, d), 8.08(1H, d), 8.06(1H, d), 7.98~7.94(3H, m), 8.85~8.84(2H, t), 7.74~7.39(19H, m), 7.16(1H, t) |
| 308 | δ = 8.95(1H, d), 8.69(2H, d), 8.55(1H, d), 8.36(2H, d), 8.20(3H, d), 8.06(1H, d), 7.96~7.94(4H, m), 7.85(1H, d), 7.70~7.50(13H, m), 7.39~7.16(9H, m) |
| 313 | δ = 8.55(1H, d), 8.35~8.30(7H, m), 8.23(1H, s), 8.20(1H, d), 7.94(3H, d), 7.85(3H, d), 7.60~7.35(17H, m), 7.25(2H, d), 7.16(1H, t) |
| 321 | δ = 8.55(1H, d), 8.23(1H, s), 8.20(1H, d), 7.94~7.85(12H, m), 7.70(1H, t), 7.55~7.49(7H, m), 7.35(1H, t), 7.28(2H, t), 7.16(1H, t) |
| 324 | δ = 8.55(1H, d), 8.30(2H, d), 8.23(1H, s), 8.20(1H, d), 7.94~7.85(13H, m), 7.75(2H, d), 7.70(1H, t), 7.55~7.28(10H, m), 7.16(1H, t) |
| 325 | δ = 8.55(1H, d), 8.20(1H, d), 7.96~7.85(13H, m), 7.75(4H, d), 7.70(1H, t), 7.49~7.28(14H, m), 7.16(1H, t) |
| 332 | δ = 8.97(1H, d), 8.55(1H, d), 8.36(2H, d), 8.28~8.20(2H, d), 8.12(1H, d), 7.96~7.70(11H, m), 7.50~7.16(15H, m) |
| 336 | δ = 8.97(1H, d), 8.55(1H, d), 8.30~8.20(7H, m), 8.12(1H, d), 7.94~7.70(15H, m), 7.59~7.28(12H, m), 7.16(1H, t) |
| 339 | δ = 8.55(1H, d), 8.36(4H, d), 8.20(1H, d), 7.96~7.85(11H, m), 7.70(1H, t), 7.50(7H, m), 7.35~7.28(5H, m), 7.16(1H, t) |
| 343 | δ = 8.55(1H, d), 8.35~8.30(6H, d), 8.23(1H, s), 8.20(1H, d), 7.94~7.86(13H, m), 7.75(3H, t), 7.50~7.28(10H, m), 7.16(1H, t) |

TABLE 13-continued

| NO | ¹H NMR (CDCl₃, 300 Mz) |
|---|---|
| 345 | δ = 8.55(1H, d), 8.20(1H, d), 7.96~7.85(15H, m), 7.75(4H, d), 7.70(1H, t), 7.49~7.16(17H, m) |
| 352 | δ = 8.55(1H, d), 8.36(2H, d), 8.24~8.20(3H, m), 7.96~7.85(7H, m), 7.75(5H, d), 7.50~7.28(12H, m), 7.16(1H, t) |
| 353 | δ = 8.55(1H, d), 8.35~8.30(4H, d), 8.23~8.20(3H, m), 7.94~7.75(13H, m), 7.50~7.28(10H, m), 7.16(1H, t) |
| 363 | δ = 8.55(1H, d), 8.51(1H, d), 8.23(1H, s), 8.20(1H, d), 8.11(1H, d), 7.94~7.86(12H, m), 7.72~7.67(2H, t), 7.55~7.49(7H, m), 7.35~7.28(3H, t), 7.16(1H, t) |
| 365 | δ = 8.55(1H, d), 8.35~8.23(4H, m), 8.11(1H, d), 8.03(1H, s), 7.94~7.86(9H, m), 7.75~7.69(3H, m), 7.55~7.49(7H, m), 7.35~7.28(3H, m), 7.16(1H, t) |
| 367 | δ = 8.55(1H, d), 8.44(1H, d), 8.36(4H, d), 8.06~7.86(10H, m), 7.61~7.50(9H, m), 7.35~7.28(3H, m), 7.16(1H, t) |
| 370 | δ = 8.80(1H, d), 8.71(1H, d), 8.55(1H, d), 8.45(1H, d), 8.30(2H, d), 8.20(2H, d), 7.94~7.85(8H, m), 7.70(1, t), 7.56~7.49(2H, t), 7.35~7.28(4H, d), 7.16(1H, t) |
| 372 | δ = 8.71(2H, d), 8.55(1H, d), 8.33~8.30(4H, d), 8.20(2H, d), 7.94~7.85(8H, m), 7.70(1H, t), 7.55~7.49(4H, m), 7.35~7.29(5H, m), 7.16(1H, t) |
| 373 | δ = 8.71~8.69(4H, d), 8.55(1H, d), 8.33(2H, d), 8.20(2H, d), 7.94~7.86(12H, m), 7.70(1H, t), 7.55~7.49(4H, m), 7.35~7.28(5H, m), 7.16(1H, t) |
| 374 | δ = 8.71(2H, d), 8.55(1H, d), 8.33(4H, d), 8.20(2H, d), 7.94~7.85(10H, m), 7.73~7.70(2H, t), 7.61~7.49(5H, m), 7.35~7.28(5H, m), 7.16(1H, t) |
| 376 | δ = 8.55(1H, d), 8.20(1H, d), 8.09(1H, d), 7.94~7.70(17H, m), 7.61~7.28(15H, m), 7.16(1H, t) |
| 379 | δ = 8.55(1H, d), 8.36(2H, d), 8.20(1H, d), 7.96~7.86(11H, m), 7.75~7.70(3H, t), 7.50~7.16(17H, m) |
| 380 | δ = 8.55(1H, d), 8.35~8.30(4H, d), 8.23~8.20(3H, d), 7.94~7.85(11H, m), 7.75~7.70(3H, t), 7.50~7.28(14H, m), 7.16(1H, t) |
| 381 | δ = 8.55(1H, d), 8.23(1H, s), 8.20(1H, d), 7.94~7.85(15H, m), 7.70(1H, t), 7.55~7.49(7H, m), 7.49~7.25(9H, m), 7.16(1H, t) |
| 382 | δ = 8.55(1H, d), 8.36(4H, d), 8.20(1H, d), 7.96~7.85(11H, m), 7.70(1H, t), 7.50(7H, m), 7.25~7.16(10H, m) |
| 384 | δ = 9.00(2H, d), 8.55(1H, d), 8.36(4H, d), 8.20(1H, d), 7.96~7.85(11H, m), 7.70(1H, t), 7.61(2H, d), 7.50~7.49(7H, m), 7.39~7.28(7H, m), 7.16(1H, t) |
| 388 | δ = 8.55~8.52(3H, d), 8.36~8.31(5H, d), 8.20(1H, d), 8.08~8.04(4H, m), 7.94~7.85(8H, m), 7.70(2H, d), 7.50(6H, s), 7.35(1H, t), 7.16(1H, t) |
| 391 | δ = 9.66(1H, s), 8.79(1H, d), 8.54(2H, d), 8.36~8.33(4H, d), 8.20(1H, d), 7.96~7.85(9H, m), 7.75~7.64(7H, m), 7.50~7.35(8H, m), 7.25(2H, d), 7.16(1H, t) |
| 395 | δ = 9.66(1H, s), 8.85(1H, d), 8.55(3H, d), 8.30~8.20(6H, m), 7.94~7.63(21H, m), 7.49~7.35(7H, m), 7.16(1H, t) |
| 396 | δ = 9.02(1H, d), 8.95(1H, d), 8.55(1H, d), 8.45(1H, d), 8.36~8.32(3H, d), 8.20(1H, d), 8.06(1H, d), 7.96~7.85(13H, m), 7.70(2H, t), 7.52~7.46(8H, m), 7.35~7.25(5H, m), 7.16(1H, t) |
| 397 | δ = 9.02(1H, d), 8.95(1H, d), 8.55(1H, d), 8.20(1H, d), 8.06(1H, d), 7.94~7.84(13H, m), 7.70(1H, t), 7.55~7.49(8H, m), 7.35~7.16(8H, m) |
| 398 | δ = 9.02(1H, d), 8.95(1H, d), 8.55(1H, d), 8.23(1H, s), 8.20(1H, d), 8.18(1H, s), 8.06(1H, d), 7.94~7.86(13H, m), 7.74~7.64(3H, m), 7.55~7.28(12H, m), 7.16(1H, t) |
| 399 | δ = 8.69(2H, d), 8.55(2H, d), 8.36(4H, d), 8.06~7.94(6H, m), 7.85(2H, d), 7.63~7.50(13H, m), 7.35(1H, t), 7.25(2H, d), 7.16(1H, t) |
| 400 | δ = 9.02(1H, d), 8.95(1H, d), 8.69(2H, d), 8.55(1H, d), 8.35(2H, d), 8.23(1H, s), 8.28(1H, d), 8.11(1H, d), 8.03(1H, s), 8.06(1H, d), 7.94(1H, d), 7.84(1H, d), 7.75~7.46(16H, m), 7.35(1H, t), 7.25(2H, d), 7.16(1H, t) |
| 401 | δ = 8.69(2H, d), 8.55(1H, d), 8.51(1H, d), 8.23(1H, s), 8.20(1H, d), 8.11(1H, d), 7.96~7.90(8H, m), 7.72~7.49(13H, m), 7.35(1H, t), 7.16(1H, t) |

TABLE 14

| Compound | FD-MS |
|---|---|
| 1 | m/z = 601.71 (C42H27N5 = 601.22) |
| 2 | m/z = 600.72 (C43H28N4 = 600.23) |
| 3 | m/z = 600.72 (C43H28N4 = 600.23) |
| 4 | m/z = 677.81 (C48H31N5 = 677.23) |
| 5 | m/z = 676.81 (C49H32N4 = 676.26) |
| 6 | m/z = 676.82 (C49H32N4 = 676.26) |
| 7 | m/z = 753.90 (C54H35N5 = 753.28) |
| 8 | m/z = 752.92 (C55H36N4 = 752.29) |
| 9 | m/z = 601.71 (C42H27N5 = 601.22) |
| 10 | m/z = 599.73 (C44H29N3 = 599.23) |
| 11 | m/z = 599.73 (C44H29N3 = 599.23) |
| 12 | m/z = 675.83 (C50H33N3 = 675.26) |
| 13 | m/z = 570.63 (C39H27N2OP = 570.18) |
| 14 | m/z = 651.77 (C46H29N5 = 651.24) |
| 15 | m/z = 650.78 (C47H30N4-650.24) |
| 16 | m/z = 650.78 (C47H30N4 = 650.24) |
| 17 | m/z = 727.87 (C52H33N5 = 727.27) |
| 18 | m/z = 726.88 (C53H34N4 = 726.27) |
| 19 | m/z = 726.88 (C53H34N4 = 726.27) |
| 20 | m/z = 803.96 (C58H37N5 = 803.30) |
| 21 | m/z = 802.98 (C59H38N4 = 802.31) |
| 22 | m/z = 651.77 (C46H29N5 = 651.24) |
| 23 | m/z = 620.69 (C43H29N2OP = 620.20) |
| 24 | m/z = 677.81 (C48H31N5 = 677.25) |
| 25 | m/z = 676.82 (C49H32N4 = 676.26) |
| 26 | m/z = 676.82 (C49H32N4 = 676.26) |
| 27 | m/z = 753.90 (C54H35N5 = 753.28) |
| 28 | m/z = 752.91 (C55H36N4 = 752.29) |
| 29 | m/z = 752.92 (C55H36N4 = 752.29) |
| 30 | m/z = 830.00 (C60H39N5 = 829.31) |
| 31 | m/z = 829.01 (C61H40N4 = 828.32) |
| 32 | m/z = 829.01 (C61H40N4 = 828.32) |
| 33 | m/z = 677.81 (C48H31N5 = 677.25) |
| 34 | m/z = 646.73 (C45H31N2OP = 646.21) |
| 35 | m/z = 601.71 (C42H27N5 = 601.22) |
| 36 | m/z = 600.72 (C43H28N4 = 600.23) |
| 37 | m/z = 600.72 (C43H28N4 = 600.23) |
| 38 | m/z = 677.81 (C48H31N5 = 677.25) |
| 39 | m/z = 676.82 (C49H32N4 = 676.26) |

TABLE 14-continued

| Compound | FD-MS |
|---|---|
| 40 | m/z = 676.82 (C49H32N4 = 676.26) |
| 41 | m/z = 753.90 (C54H35N5 = 753.28) |
| 42 | m/z = 752.92 (C55H36N4 = 752.29) |
| 43 | m/z = 601.71 (C42H27N5 = 601.22) |
| 44 | m/z = 570.63 (C39H27N2OP = 570.18) |
| 45 | m/z = 651.77 (C46H29N5 = 651.24) |
| 46 | m/z = 650.78 (C47H30N4 = 650.24) |
| 47 | m/z = 650.78 (C47H30N4 = 650.24) |
| 48 | m/z = 727.87 (C52H33N5 = 727.27) |
| 49 | m/z = 726.88 (C53H34N4 = 726.27) |
| 50 | m/z = 726.88 (C53H34N4 = 726.27) |
| 51 | m/z = 803.96 (C58H37N5 = 803.30) |
| 52 | m/z = 802.98 (C59H38N4 = 802.30) |
| 53 | m/z = 651.77 (c46H29N5 = 651.24) |
| 54 | m/z = 650.78 (C47H30N4 = 650.24) |
| 55 | m/z = 650.78 (C47H30N4 = 650.24) |
| 56 | m/z = 727.87 (C52H33N5 = 727.27) |
| 57 | m/z = 726.88 (C53H34N4 = 726.27) |
| 58 | m/z = 726.88 (C53H34N4 = 726.27) |
| 59 | m/z = 803.96 (C58H37N5 = 803.30) |
| 60 | m/z = 802.91 (C59H38N4 = 802.31) |
| 61 | m/z = 651.77 (C46H29N5 = 651.24) |
| 62 | m/z = 650.78 (C47H30N4 = 650.24) |
| 63 | m/z = 650.78 (C47H30N4 = 650.24) |
| 64 | m/z = 803.96 (C58H37N5 = 803.30) |
| 65 | m/z = 802.98 (C59H38N4 = 802.31) |
| 66 | m/z = 751.89 (C54H33N5 = 751.27) |
| 67 | m/z = 750.90 (C55H34N4 = 750.27) |
| 68 | m/z = 750.90 (C55H34N4 = 750.27) |
| 69 | m/z = 750.90 (C55H34N4 = 750.27) |
| 70 | m/z = 753.90 (C54H35N5 = 753.28) |
| 71 | m/z = 677.81 (C48H31N5 = 677.25) |
| 72 | m/z = 676.82 (C49H32N4 = 676.26) |
| 73 | m/z = 676.82 (C49H32N4 = 676.26) |
| 74 | m/z = 676.82 (C49H32N4 = 676.26) |
| 75 | m/z = 752.92 (C55H36N4 = 752.29) |
| 76 | m/z = 752.92 (C55H36N4 = 752.29) |
| 77 | m/z = 690.81 (C48H30N6 = 690.25) |
| 78 | m/z = 766.90 (C54H34N6 = 766.28) |
| 79 | m/z = 766.90 (C54H32N6 = 766.28) |
| 80 | m/z = 689.82 (C49H31N5 = 689.25) |
| 81 | m/z = 765.92 (C55H35N5 = 765.28) |
| 82 | m/z = 765.92 (C55H35N5 = 765.28) |
| 83 | m/z = 689.82 (C49H31N5 = 689.25) |
| 84 | m/z = 765.92 (C55H35N5 = 765.28) |
| 85 | m/z = 765.92 (C55H35N5 = 765.28) |
| 86 | m/z = 765.92 (C55H35N5 = 765.28) |
| 87 | m/z = 765.92 (C55H35N5 = 765.28) |
| 88 | m/z = 717.87 (C51H35N5 = 717.28) |
| 89 | m/z = 716.88 (C52H36N4 = 716.29) |
| 90 | m/z = 716.88 (C52H36N4 = 716.29) |
| 91 | m/z = 716.88 (C52H36N4 = 716.29) |
| 92 | m/z = 793.97 (C57H39N5 = 793.32) |
| 93 | m/z = 792.98 (C58H40N4 = 792.32) |
| 94 | m/z = 792.98 (C58H40N4 = 792.32) |
| 95 | m/z = 792.98 (C58H40N4 = 792.32) |
| 96 | m/z = 626.72 (C43H26N6 = 626.22) |
| 97 | m/z = 625.73 (C44H27N5 = 625.22) |
| 98 | m/z = 625.73 (C44H27N5 = 625.22) |
| 99 | m/z = 625.73 (C44H27N5 = 625.22) |
| 100 | m/z = 702.82 (C49H30N6 = 702.25) |
| 101 | m/z = 702.82 (C49H30N6 = 702.25) |
| 102 | m/z = 701.83 (C50H31N5 = 701.25) |
| 103 | m/z = 701.83 (C50H31N5 = 701.25) |
| 104 | m/z = 777.93 (C56H35N5 = 777.28) |
| 105 | m/z = 701.83 (C50H31N5 = 701.25) |
| 106 | m/z = 776.94 (C57H36N4 = 776.29) |
| 107 | m/z = 700.84 (C51H32N4 = 700.26) |
| 108 | m/z = 753.90 (C54H35N5 = 753.28) |
| 109 | m/z = 752.92 (C55H36N4 = 752.29) |
| 110 | m/z = 651.77 (C46H29N5 = 651.24) |
| 111 | m/z = 650.78 (C47H30N4 = 650.24) |
| 112 | m/z = 650.78 (C47H30N4 = 650.24) |
| 113 | m/z = 803.96 (C58H37N5 = 803.30) |
| 114 | m/z = 802.98 (C59H38N4 = 802.31) |
| 115 | m/z = 802.98 (C59H38N4 = 802.31) |
| 116 | m/z = 803.96 (C58H37N5 = 803.30) |
| 117 | m/z = 802.98 (C59H38N4 = 802.31) |

TABLE 14-continued

| Compound | FD-MS |
|---|---|
| 118 | m/z = 802.98 (C59H38N4 = 802.31) |
| 119 | m/z = 777.93 (C56H35N5 = 777.28) |
| 120 | m/z = 879.07 (C65H42N4 = 878.34) |
| 121 | m/z = 651.77 (C46H29H5 = 651.24) |
| 122 | m/z = 650.78 (C47H30N4 = 650.24) |
| 123 | m/z = 650.78 (C47H30N4 = 650.24) |
| 124 | m/z = 727.87 (C52H33N5 = 727.27) |
| 125 | m/z = 726.88 (C53H34N4 = 726.27) |
| 126 | m/z = 726.88 (C53H34N4 = 726.27) |
| 127 | m/z = 803.96 (C58H37N5 = 803.30) |
| 128 | m/z = 802.98 (C59H38N4 = 802.31) |
| 129 | m/z = 651.77 (C46H29N5 = 651.24) |
| 130 | m/z = 620.69 (C43H29N2OP = 620.20) |
| 131 | m/z = 727.87 (C52H33N5 = 727.27) |
| 132 | m/z = 726.88 (C53H34N4 = 726.27) |
| 133 | m/z = 726.88 (C53H34N4 = 726.27) |
| 134 | m/z = 601.71 (C42H27N5 = 601.22) |
| 135 | m/z = 600.72 (C43H28N4 = 600.23) |
| 136 | m/z = 600.72 (C43H28N4 = 600.23) |
| 137 | m/z = 677.81 (C48H31N5 = 677.25) |
| 138 | m/z = 676.82 (C49H32N4 = 676.26) |
| 139 | m/z = 676.82 (C49H32N4 = 676.26) |
| 140 | m/z = 753.90 (C54H35N5 = 753.28) |
| 141 | m/z = 752.92 (C55H36N4 = 752.29) |
| 142 | m/z = 601.71 (C42H27N5 = 601.22) |
| 143 | m/z = 651.77 (C46H29N5 = 651.24) |
| 144 | m/z = 650.78 (C47H30N4 = 650.24) |
| 145 | m/z = 650.78 (C47H30N4 = 650.24) |
| 146 | m/z = 727.87 (C52H33N5 = 727.27) |
| 147 | m/z = 726.88 (C53H34N4 = 726.27) |
| 148 | m/z = 726.88 (C53H34N4 = 726.27) |
| 149 | m/z = 803.96 (C58H37N5 = 803.30) |
| 150 | m/z = 802.98 (C59H38N4 = 802.31) |
| 151 | m/z = 651.77 (C46H29N5 = 651.24) |
| 152 | m/z = 548.69 (C39H24N4 = 548.20) |
| 153 | m/z = 677.81 (C48H31N5 = 677.25) |
| 154 | m/z = 676.82 (C49H32N4 = 676.26) |
| 155 | m/z = 676.82 (C49H32N4 = 676.26) |
| 156 | m/z = 624.74 (C45H28N4 = 624.23) |
| 157 | m/z = 700.84 (C51H32N4 = 700.26) |
| 158 | m/z = 700.84 (C51H32N4 = 700.26) |
| 159 | m/z = 830.00 (C60H39N5 = 829.32) |
| 160 | m/z = 829.01 (C61H40N4 = 828.32) |
| 161 | m/z = 677.81 (C48H31N5 = 677.25) |
| 162 | m/z = 675.83 (C50H33N3 = 675.26) |
| 163 | m/z = 751.93 (C56H37N3 = 751.29) |
| 164 | m/z = 646.73 (C45H31N2OP = 646.21) |
| 165 | m/z = 601.71 (C42H27N5 = 601.22) |
| 166 | m/z = 600.72 (C43H28N4 = 600.23) |
| 167 | m/z = 600.72 (C43H28N4 = 600.23) |
| 168 | m/z = 677.81 (C48H31N5 = 677.25) |
| 169 | m/z = 676.82 (C49H32N4 = 676.26) |
| 170 | m/z = 676.82 (C49H32N4 = 676.26) |
| 171 | m/z = 753.90 (C54H35N5 = 753.28) |
| 172 | m/z = 752.92 (C55H36N4 = 752.29) |
| 173 | m/z = 601.71 (C42H27N5 = 601.22) |
| 174 | m/z = 599.73 (C44H29N3 = 599.23) |
| 175 | m/z = 599.73 (C44H29N3 = 599.23) |
| 176 | m/z = 675.83 (C50H33N3 = 675.26) |
| 177 | m/z = 675.83 (C50H33N3 = 675.26) |
| 178 | m/z = 570.63 (C39H27N2OP = 570.18) |
| 179 | m/z = 651.77 (C46H29N5 = 651.24) |
| 180 | m/z = 650.78 (C47H30N4 = 650.24) |
| 181 | m/z = 650.78 (C47H30N4 = 650.24) |
| 182 | m/z = 727.87 (C52H33N5 = 727.27) |
| 183 | m/z = 726.88 (C53H34N4 = 726.27) |
| 184 | m/z = 726.88 (C53H34N4 = 726.27) |
| 185 | m/z = 816.96 (C58H36N6 = 816.30) |
| 186 | m/z = 816.96 (C58H36N6 = 816.30) |
| 187 | m/z = 893.06 (C64H40N6 = 892.33) |
| 188 | m/z = 651.77 (C46H29N5 = 651.24) |
| 189 | m/z = 650.78 (C47H30N4 = 650.24) |
| 190 | m/z = 650.78 (C47H30N4 = 650.24) |
| 191 | m/z = 817.95 (C58H35N5O = 817.28) |
| 192 | m/z = 816.96 (C59H36N4O = 816.28) |
| 193 | m/z = 816.96 (C59H36N4O = 816.28) |
| 194 | m/a = 651.77 (C46H29N5 = 651.24) |
| 195 | m/z = 650.78 (C47H30N4 = 650.24) |

TABLE 14-continued

| Compound | FD-MS |
|---|---|
| 196 | m/z = 650.78 (C47H30N4 = 650.24) |
| 197 | m/z = 727.87 (C52H33N5 = 727.27) |
| 198 | m/z = 726.88 (C53H34N4 = 726.27) |
| 199 | m/z = 726.88 (C53H34N4 = 726.27) |
| 200 | m/z = 834.01 (C58H35N5S = 833.26) |
| 201 | m/z = 833.02 (C59H36N4S = 832.26) |
| 202 | m/a = 756.92 (C53H32N4S = 756.23) |
| 203 | m/z = 691.79 (C48H29N5O = 691.23) |
| 204 | m/z = 691.79 (C48H29N4O = 691.23) |
| 205 | m/z = 766.90 (C55H34N4O = 766.27) |
| 206 | m/z = 766.90 (C55H34N4O = 766.27) |
| 207 | m/z = 701.83 (C50H31N5 = 701.25) |
| 208 | m/z = 700.84 (C51H32N4 = 700.26) |
| 209 | m/z = 707.85 (C48H29N5S = 707.21) |
| 210 | m/z = 706.86 (C49H30N4S = 706.21) |
| 211 | m/z = 782.96 (C55H34N4S = 782.25) |
| 212 | m/z = 782.96 (C55H34N4S = 782.25) |
| 213 | m/z = 725.85 (C52H31N5 = 725.25) |
| 214 | m/z = 724.86 (C53H32N4 = 724.26) |
| 215 | m/z = 701.83 (C50H31N5 = 701.25) |
| 216 | m/z = 700.84 (C51H32N4 = 700.26) |
| 217 | m/z = 700.84 (C51H32N4 = 700.26) |
| 218 | m/z = 777.93 (C56H35N5 = 777.28) |
| 219 | m/z = 776.94 (C57H36N4 = 776.29) |
| 220 | m/z = 776.94 (C57H36N4 = 776.29) |
| 221 | m/z = 854.02 (C62H39N5 = 853.32) |
| 222 | m/z = 853.04 (C63H40N4 = 852.32) |
| 223 | m/z = 701.83 (C50H31N5 = 701.25) |
| 224 | m/z = 670.75 (C47H31N2OP = 670.21) |
| 225 | m/z = 777.93 (C56H35N5 = 777.28) |
| 226 | m/z = 776.94 (C57H36N4 = 776.29) |
| 227 | m/z = 827.00 (C61H38N4 = 826.31) |
| 228 | m/z = 854.02 (C62H39N5 = 853.32) |
| 229 | m/z = 853.04 (C63H40N4 = 852.32) |
| 230 | m/z = 903.10 (C67H42N4 = 902.34) |
| 231 | m/z = 854.02 (C62H39N5 = 853.32) |
| 232 | m/z = 853.04 (C63H40N4 = 852.32) |
| 233 | m/z = 777.93 (C56H35N5 = 777.28) |
| 234 | m/z = 803.96 (C58H37N5 = 803.30) |
| 235 | m/z = 802.98 (C59H38N4 = 802.31) |
| 236 | m/z = 802.98 (C59H38N4 = 802.31) |
| 237 | m/z = 601.71 (C42H27N5 = 601.22) |
| 238 | m/z = 600.72 (C43H28N4 = 600.23) |
| 239 | m/z = 600.72 (C43H28N4 = 600.23) |
| 240 | m/z = 677.81 (C48H31N5 = 677.25) |
| 241 | m/z = 676.82 (C49H32N4 = 676.26) |
| 242 | m/z = 676.82 (C49H32N4 = 676.26) |
| 243 | m/z = 753.90 (C54H35N4 = 753.28) |
| 244 | m/z = 752.92 (C55H36N4 = 752.29) |
| 245 | m/z = 601.71 (C42H27N4 = 601.22) |
| 246 | m/z = 570.63 (C39H27N2OP = 570.18) |
| 247 | m/z = 651.77 (C46H29N5 = 651.24) |
| 248 | m/z = 650.78 (C47H30N4 = 650.24) |
| 249 | m/z = 650.78 (C47H30N4 = 650.24) |
| 250 | m/z = 727.87 (C52H33N5 = 727.27) |
| 251 | m/z = 726.88 (C53H34N4 = 726.27) |
| 252 | m/z = 726.88 (C53H34N4 = 726.27) |
| 253 | m/z = 803.96 (C58H37N5 = 803.30) |
| 254 | m/z = 802.98 (C59H38N4 = 802.31) |
| 255 | m/z = 651.77 (C46H29N5 = 651.24) |
| 256 | m/z = 620.69 (C43H29N2OP = 620.20) |
| 257 | m/z = 677.81 (C48H31N5 = 677.25) |
| 258 | m/z = 676.82 (C49H32N4 = 676.26) |
| 259 | m/z = 676.82 (C49H32N4 = 676.26) |
| 260 | m/z = 753.90 (C54H35N5 = 753.28) |
| 261 | m/z = 752.92 (C55H36N4 = 752.29) |
| 262 | m/z = 752.29 (C55H36N4 = 752.29) |
| 263 | m/z = 830.00 (C60H39N5 = 829.32) |
| 264 | m/z = 829.01 (C61H40N4 = 828.32) |
| 265 | m/z = 677.81 (C48H31N5 = 677.25) |
| 266 | m/z = 646.73 (C45H31N2OP = 646.21) |
| 267 | m/z = 601.71 (C42H27N5 = 601.22) |
| 268 | m/z = 600.72 (C43H28N4 = 600.23) |
| 269 | m/z = 600.72 (C43H28N4 = 600.23) |
| 270 | m/z = 677.81 (C48H31N5 = 677.25) |
| 271 | m/z = 676.82 (C49H32N4 = 676.26) |
| 272 | m/z = 676.82 (C49H32N4 = 676.26) |
| 273 | m/z = 753.90 (C54H35N5 = 753.28) |

TABLE 14-continued

| Compound | FD-MS |
|---|---|
| 274 | m/z = 752.92 (C55H36N4 = 752.29) |
| 275 | m/z = 601.71 (C42H27N5 = 601.22) |
| 276 | m/z = 570.63 (C39H27N2OP = 570.18) |
| 277 | m/z = 827.99 (C60H37N5 = 827.30) |
| 278 | m/z = 904.08 (C66H41N5 = 903.33) |
| 279 | m/z = 904.08 (C66H41N5 = 903.33) |
| 280 | m/z = 827.00 (C61H38N4 = 826.31) |
| 281 | m/z = 903.10 (C67H42N4 = 902.32) |
| 282 | m/z = 903.10 (C67H42N4 = 902.23) |
| 283 | m/z = 817.95 (C58H35N5O = 817.28) |
| 284 | m/z = 793.97 (C57H39N5 = 793.32) |
| 285 | m/z = 792.98 (C58H40N4 = 792.32) |
| 286 | m/z = 792.98 (C58H40N4 = 792.32) |
| 287 | m/z = 792.98 (C58H40N4 = 792.32) |
| 288 | m/z = 702.82 (C49H30N6 = 702.25) |
| 289 | m/z = 701.83 (C50H31N5 = 701.25) |
| 290 | m/z = 701.83 (C50H31N5 = 701.25) |
| 291 | m/z = 701.83 (C50H31N5 = 701.25) |
| 292 | m/z = 778.91 (C55H34N6 = 778.28) |
| 293 | m/z = 778.91 (C55H34N6 = 778.28) |
| 294 | m/z = 777.93 (C56H35N5 = 777.28) |
| 295 | m/z = 777.93 (C56H35N5 = 777.28) |
| 296 | m/z = 854.02 (C62H39N5 = 853.32) |
| 297 | m/z = 777.93 (C56H35N5 = 777.28) |
| 298 | m/z = 853.04 (C63H40N4 = 852.32) |
| 299 | m/z = 776.94 (C57H36N4 = 776.29) |
| 300 | m/z = 830.00 (C60H39N5 = 829.32) |
| 301 | m/z = 829.01 (C61H40N4 = 828.32) |
| 302 | m/z = 880.06 (C64H41N5 = 879.33) |
| 303 | m/z = 879.07 (C65H42N4 = 878.34) |
| 304 | m/z = 880.06 (C64H41N5 = 879.33) |
| 305 | m/z = 878.05 (C64H39N5 = 877.32) |
| 306 | m/z = 816.96 (C59H36N4O = 816.28) |
| 307 | m/z = 893.06 (C65H40N4O = 829.32) |
| 308 | m/z = 894.05 (C64H39N5O = 893.31) |
| 309 | m/z = 601.71 (C42H27N5 = 601.22) |
| 310 | m/z = 600.72 (C43H28N4 = 600.23) |
| 311 | m/z = 600.72 (C43H28N4 = 600.23) |
| 312 | m/z = 677.81 (C48H31N5 = 677.25) |
| 313 | m/z = 752.92 (Cm55H36N4 = 752.29) |
| 314 | m/z = 752.92 (c55H36N4 = 752.29) |
| 315 | m/z = 753.90 C(54H35N5 = 753.28) |
| 316 | m/z = 752.92 (C55H36N4 = 752.29) |
| 317 | m/z = 677.82 (C48H31N5 = 677.25) |
| 318 | m/z = 570.63 (C39H27N2OP = 570.18) |
| 319 | m/z = 601.71 (C42H27N5 = 601.22) |
| 320 | m/z = 600.72 (C43H28N4 = 600.23) |
| 321 | m/z = 600.72 (C43H28N4 = 600.23) |
| 322 | m/z = 677.81 (C48H31N5 = 677.25) |
| 323 | m/z = 676.82 (C49H32N4 = 676.26) |
| 324 | m/z = 676.82 (C49H32N4 = 676.26) |
| 325 | m/z = 753.90 (C54H35N5 = 753.28) |
| 326 | m/z = 752.92 (C55H36N4 = 752.29) |
| 327 | m/z = 601.71 (C42H27N5 = 601.22) |
| 328 | m/z = 570.63 (C39H27N2OP = 570.18) |
| 329 | m/z = 651.77 (C46H29N5 = 651.24) |
| 330 | m/z = 650.78 (C47H30N4 = 650.24) |
| 331 | m/z = 650.78 (C47H30N4 = 650.24). |
| 332 | m/z = 727.87 (C52H33N5 = 727.27) |
| 333 | m/z = 726.88 (C53H34N4 = 726.27) |
| 334 | m/z = 726.88 (C53H34N4 = 726.27) |
| 335 | m/z = 803.96 (C58H37N5 = 803.30) |
| 336 | m/z = 802.98 (C59H38N4 = 802.31) |
| 337 | m/z = 651.77 (C46H29N5 = 651.24) |
| 338 | m/z = 620.69 (C43H29N2OP = 620.20) |
| 339 | m/z = 677.81 (C548H31N5 = 677.25) |
| 340 | m/z = 676.82 (C49H32N4 = 676.26) |
| 341 | m/z = 676.82 (C49H32N4 = 676.26) |
| 342 | m/z = 753.90 (C54H35N5 = 753.28) |
| 343 | m/z = 752.92 (C55H36NN4 = 752.29) |
| 344 | m/z = 752.92 (C55H36N4 = 752.29) |
| 345 | m/z = 830.00 (C60H39N5 = 829.32) |
| 346 | m/z = 829.01 (C61H40N4 = 828.32) |
| 347 | m/z = 677.81 (C48H31N5 = 677.25) |
| 348 | m/z = 646.73 (C45H31N2OP = 646.21) |
| 349 | m/z = 601.71 (C42H27N5 = 601.22) |
| 350 | m/z = 600.72 (C43H28N4 = 600.23) |
| 351 | m/z = 600.72 (C43H28N4 = 600.23) |

TABLE 14-continued

| Compound | FD-MS |
|---|---|
| 352 | m/z = 677.81 (C48H31N5 = 677.25) |
| 353 | m/z = 676.82 (C49H32N4 = 676.26) |
| 354 | m/z = 676.82 (C49H32N4 = 676.26) |
| 355 | m/z = 753.90 (C54H35N5 = 753.28) |
| 356 | m/z = 752.92 (C55H36N4 = 752.29) |
| 357 | m/z = 601.71 (C42H27N5 = 601.22) |
| 358 | m/z = 599.73 (C44H29N3 = 599.23) |
| 359 | m/z = 599.73 (C44H29N3 = 599.23) |
| 360 | m/z = 570.63 (C39H27N2OP = 570.18) |
| 361 | m/z = 651.77 (C46H29N5 = 651.24) |
| 362 | m/z = 650.78 (C47H30N4 = 650.24) |
| 363 | m/z = 650.78 (C47H30N4 = 650.24) |
| 364 | m/z = 651.77 (C46H29N5 = 651.24) |
| 365 | m/z = 650.78 (C47H30N4 = 6050.24) |
| 366 | m/z = 650.78 (C47H30N4 = 650.24) |
| 367 | m/z = 651.77 (C46H29N5 = 651.24) |
| 368 | m/z = 650.78 (C47H30N4 = 650.24) |
| 369 | m/z = 650.78 (C47H30N4 = 650.24) |
| 370 | m/z = 548.64 (C39H24N4 = 548.20) |
| 371 | m/z = 624.74 (C45H28N4 = 624.23) |
| 372 | m/z = 624.74 (C45H28N4 = 624.23) |
| 373 | m/z = 700.84 (C51H32N4 = 700.26) |
| 374 | m/z = 700.84 (C51H32N4 = 700.26) |
| 375 | m/z = 760.94 (C58H36N2 = 760.28) |
| 376 | m/z = 760.94 (C58H36N2 = 760.28) |
| 377 | m/z = 811.00 (C62H38N2 = 810.30) |
| 378 | m/z = 752.92 (C55H36N4 = 752.29) |
| 379 | m/z = 853.90 (C54H35N5 = 753.28) |
| 380 | m/z = 752.92 (C55H36N4 = 752.29) |
| 381 | m/z = 752.92 (C55H36N4 = 752.29) |
| 382 | m/z = 753.90 (C54H35N5 = 753.28) |
| 383 | m/z = 802.98 (C59H38N4 = 802.31) |
| 384 | m/z = 803.96 (C58H37N5 = 803.30) |
| 385 | m/z = 677.81 (C48H31N5 = 677.25) |
| 386 | m/z = 725.89 (C54H35N3 = 725.28) |
| 387 | m/z = 725.89 (C54H35N3 = 725.28) |
| 388 | m/z = 725.85 (C52H31N5 = 725.25) |
| 389 | m/z = 726.88 (C53H34N4 = 726.27) |
| 390 | m/z = 724.86 (C53H32N4 = 724.26) |
| 391 | m/z = 827.99 (C60H37N5 = 827.30) |
| 392 | m/z = 827.00 (C61H38N4 = 826.31) |
| 393 | m/z = 827.00 (C61H38N4 = 826.31) |
| 394 | m/z = 854.02 (C62H39N5 = 853.32) |
| 395 | m/z = 853.04 (C63H40N4 = 852.32) |
| 396 | m/z = 910.11 (C64H39N5S = 909.29) |
| 397 | m/z = 815.98 (C59H37N5 = 815.30) |
| 398 | m/z = 843.04 (C62H42N4 = 842.34) |
| 399 | m/z = 727.87 (C52H33N5 = 727.27) |
| 400 | m/z = 776.94 (C57H36N4 = 776.29) |
| 401 | m/z = 650.78 (C47H30N4 = 650.24) |

<Experimental Example 1> Manufacture of Organic Light Emitting Device

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum depositor, and the following 4,4',4"-tris(N,N-(2-naphthyl)-phenylamino)triphenylamine (2-TNATA) was introduced to a cell in the vacuum depositor.

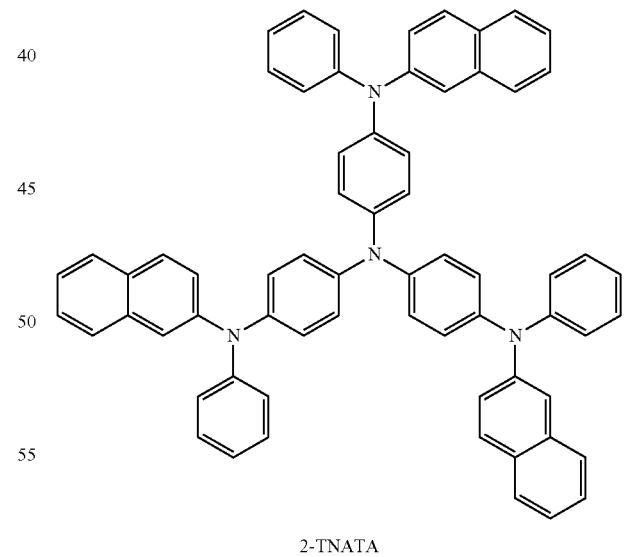

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum depositor, the following N,N'-bis(α-naphthyl)-N,N'-diphenyl-4,4'-diamine (NPB)

was introduced, and evaporated by applying a current to the cell to deposit a hole transfer layer having a thickness of 300 Å on the hole injection layer.

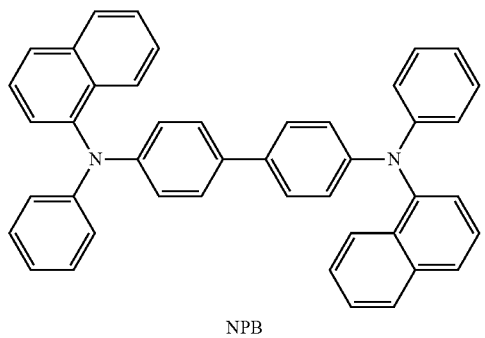

NPB

After forming the hole injection layer and the hole transfer layer as above, a blue light emitting material having a structure as below was deposited thereon as a light emitting layer. Specifically, in one side cell in the vacuum depositor, H1, a blue light emitting host material, was vacuum deposited to a thickness of 200 Å, and D1, a blue light emitting dopant material, was vacuum deposited thereon by 5% with respect to the host material.

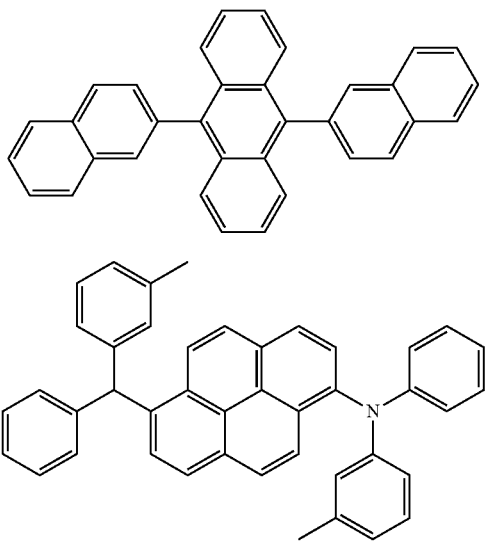

Subsequently, one of compounds described in Table 15 was deposited to a thickness of 300 Å as an electron transfer layer.

As an electron injection layer, lithium fluoride (LiF) was deposited to a thickness of 10 Å, and an Al cathode was employed to have a thickness of 1,000 Å to manufacture an OLED.

Meanwhile, all the organic compounds required to manufacture the OLED were vacuum sublimation purified under $10^{-6}$ torr to $10^{-8}$ torr by each material to be used in the OLED manufacture.

Results of measuring a driving voltage, light emission efficiency, a color coordinate (CIE) and a lifetime of the blue organic light emitting device manufactured according to the present disclosure are as shown in Table 15.

TABLE 15

| | Compound | Driving Voltage (V) | Light Emission Efficiency (cd/A) | CIE (x, y) | Lifetime (T95) |
|---|---|---|---|---|---|
| Comparative Example 1 | E1 | 5.70 | 6.00 | (0.134, 0.102) | 20 |
| Comparative Example 2 | A | 5.33 | 4.21 | (0.134, 0.100) | 12 |
| Comparative Example 3 | B | 5.31 | 4.10 | (0.134, 0.100) | 8 |
| Comparative Example 4 | C | 5.26 | 4.98 | (0.134, 0.100) | 9 |
| Example 1 | 1 | 5.45 | 6.21 | (0.134, 0.101) | 37 |
| Example 2 | 2 | 5.44 | 6.22 | (0.134, 0.102) | 34 |
| Example 3 | 4 | 5.62 | 5.95 | (0.134, 0.103) | 42 |
| Example 4 | 6 | 4.98 | 6.44 | (0.134, 0.100) | 40 |
| Example 5 | 7 | 5.62 | 6.38 | (0.134, 0.100) | 35 |
| Example 6 | 8 | 4.72 | 6.20 | (0.134, 0.102) | 48 |
| Example 7 | 16 | 5.45 | 6.44 | (0.134, 0.103) | 33 |
| Example 8 | 21 | 5.44 | 6.34 | (0.134, 0.102) | 36 |
| Example 9 | 26 | 5.62 | 6.20 | (0.134, 0.101) | 39 |
| Example 10 | 28 | 5.40 | 6.12 | (0.134, 0.103) | 44 |
| Example 11 | 31 | 5.60 | 6.21 | (0.134, 0.102) | 43 |
| Example 12 | 33 | 5.45 | 6.22 | (0.134, 0.101) | 37 |
| Example 13 | 35 | 4.98 | 6.38 | (0.134, 0.101) | 42 |
| Example 14 | 37 | 5.62 | 6.20 | (0.134, 0.100) | 45 |
| Example 15 | 39 | 4.72 | 6.12 | (0.134, 0.100) | 43 |
| Example 16 | 41 | 4.91 | 6.21 | (0.134, 0.101) | 41 |
| Example 17 | 42 | 4.98 | 6.22 | (0.134, 0.100) | 40 |
| Example 18 | 45 | 5.62 | 5.95 | (0.134, 0.100) | 33 |
| Example 19 | 59 | 5.44 | 6.13 | (0.134, 0.102) | 25 |
| Example 20 | 65 | 5.38 | 6.38 | (0.134, 0.101) | 39 |
| Example 21 | 66 | 5.38 | 6.20 | (0.134, 0.103) | 40 |
| Example 22 | 68 | 5.39 | 6.25 | (0.134, 0.102) | 41 |
| Example 23 | 70 | 4.96 | 6.21 | (0.134, 0.101) | 37 |
| Example 24 | 73 | 4.91 | 6.22 | (0.134, 0.102) | 33 |
| Example 25 | 74 | 4.91 | 6.12 | (0.134, 0.101) | 42 |
| Example 26 | 77 | 4.98 | 6.51 | (0.134, 0.101) | 39 |
| Example 27 | 78 | 5.62 | 6.21 | (0.134, 0.100) | 41 |
| Example 28 | 88 | 5.39 | 5.95 | (0.134, 0.101) | 34 |
| Example 29 | 93 | 5.38 | 5.85 | (0.134, 0.101) | 35 |
| Example 30 | 96 | 5.38 | 6.38 | (0.134, 0.101) | 39 |
| Example 31 | 100 | 5.38 | 6.20 | (0.134, 0.103) | 40 |
| Example 32 | 101 | 5.39 | 6.42 | (0.134, 0.102) | 43 |
| Example 33 | 104 | 4.96 | 6.21 | (0.134, 0.101) | 37 |
| Example 34 | 105 | 4.91 | 6.22 | (0.134, 0.102) | 33 |
| Example 35 | 108 | 4.91 | 6.12 | (0.134, 0.101) | 37 |
| Example 36 | 115 | 5.38 | 6.38 | (0.134, 0.101) | 39 |
| Example 37 | 117 | 5.38 | 6.20 | (0.134, 0.103) | 40 |
| Example 38 | 120 | 5.39 | 6.62 | (0.134, 0.102) | 43 |
| Example 39 | 131 | 4.96 | 6.21 | (0.134, 0.101) | 37 |
| Example 40 | 132 | 4.91 | 6.22 | (0.134, 0.102) | 33 |
| Example 41 | 134 | 4.91 | 6.12 | (0.134, 0.101) | 42 |
| Example 42 | 135 | 4.98 | 6.51 | (0.134, 0.101) | 39 |
| Example 43 | 137 | 5.62 | 6.21 | (0.134, 0.100) | 41 |
| Example 44 | 139 | 5.39 | 5.95 | (0.134, 0.101) | 34 |
| Example 45 | 141 | 5.10 | 6.88 | (0.134, 0.100) | 41 |
| Example 46 | 143 | 5.38 | 6.38 | (0.134, 0.101) | 39 |
| Example 47 | 148 | 5.38 | 6.20 | (0.134, 0.103) | 40 |
| Example 48 | 149 | 5.11 | 6.62 | (0.134, 0.102) | 43 |
| Example 49 | 155 | 4.95 | 6.22 | (0.134, 0.100) | 41 |
| Example 50 | 157 | 4.98 | 6.92 | (0.134, 0.100) | 40 |
| Example 51 | 159 | 5.62 | 5.98 | (0.134, 0.100) | 39 |
| Example 52 | 161 | 4.75 | 6.53 | (0.134, 0.102) | 40 |
| Example 53 | 165 | 4.72 | 6.35 | (0.134, 0.102) | 42 |
| Example 54 | 168 | 4.91 | 6.93 | (0.134, 0.100) | 45 |
| Example 55 | 169 | 4.93 | 6.95 | (0.134, 0.100) | 40 |
| Example 56 | 187 | 4.98 | 6.21 | (0.134, 0.100) | 40 |
| Example 57 | 192 | 5.62 | 5.98 | (0.134, 0.100) | 34 |
| Example 58 | 195 | 5.31 | 6.53 | (0.134, 0.102) | 35 |
| Example 59 | 203 | 4.79 | 6.55 | (0.134, 0.102) | 48 |
| Example 60 | 205 | 5.40 | 6.13 | (0.134, 0.101) | 39 |
| Example 61 | 209 | 5.44 | 6.04 | (0.134, 0.100) | 41 |
| Example 62 | 212 | 5.39 | 6.01 | (0.134, 0.101) | 34 |
| Example 63 | 213 | 4.96 | 6.88 | (0.134, 0.100) | 45 |
| Example 64 | 218 | 4.95 | 6.95 | (0.134, 0.100) | 41 |
| Example 65 | 219 | 4.98 | 6.22 | (0.134, 0.100) | 40 |
| Example 66 | 222 | 5.62 | 5.98 | (0.134, 0.100) | 33 |
| Example 67 | 228 | 4.75 | 6.53 | (0.134, 0.102) | 40 |

TABLE 15-continued

| Compound | Driving Voltage (V) | Light Emission Efficiency (cd/A) | CIE (x, y) | Lifetime (T95) |
|---|---|---|---|---|
| Example 68 | 229 | 5.40 | 6.12 | (0.134, 0.101) | 39 |
| Example 69 | 234 | 5.44 | 6.21 | (0.134, 0.100) | 41 |
| Example 70 | 236 | 5.39 | 6.20 | (0.134, 0.101) | 36 |
| Example 71 | 237 | 5.39 | 6.88 | (0.134, 0.100) | 45 |
| Example 72 | 238 | 5.21 | 6.93 | (0.134, 0.100) | 43 |
| Example 73 | 240 | 5.13 | 6.95 | (0.134, 0.100) | 41 |
| Example 74 | 242 | 5.05 | 6.22 | (0.134, 0.100) | 40 |
| Example 75 | 248 | 4.91 | 5.98 | (0.134, 0.100) | 33 |
| Example 76 | 250 | 4.72 | 6.53 | (0.134, 0.102) | 48 |
| Example 77 | 251 | 5.40 | 6.12 | (0.134, 0.101) | 39 |
| Example 78 | 253 | 5.43 | 6.53 | (0.134, 0.102) | 48 |
| Example 79 | 259 | 5.33 | 6.53 | (0.134, 0.102) | 48 |
| Example 80 | 263 | 4.91 | 6.98 | (0.134, 0.100) | 43 |
| Example 81 | 264 | 4.91 | 6.12 | (0.134, 0.100) | 35 |
| Example 82 | 267 | 4.98 | 6.22 | (0.134, 0.100) | 40 |
| Example 83 | 270 | 5.62 | 5.98 | (0.134, 0.100) | 38 |
| Example 84 | 273 | 4.72 | 6.53 | (0.134, 0.102) | 48 |
| Example 85 | 277 | 4.72 | 6.33 | (0.134, 0.102) | 41 |
| Example 86 | 278 | 4.63 | 6.53 | (0.134, 0.102) | 48 |
| Example 87 | 282 | 4.91 | 6.82 | (0.134, 0.100) | 43 |
| Example 88 | 283 | 4.99 | 6.95 | (0.134, 0.100) | 41 |
| Example 89 | 284 | 4.98 | 6.22 | (0.134, 0.100) | 40 |
| Example 90 | 288 | 5.62 | 5.98 | (0.134, 0.100) | 33 |
| Example 91 | 290 | 5.43 | 6.53 | (0.134, 0.102) | 41 |
| Example 92 | 292 | 4.88 | 6.89 | (0.134, 0.102) | 42 |
| Example 93 | 293 | 5.40 | 6.12 | (0.134, 0.101) | 39 |
| Example 94 | 296 | 5.41 | 5.89 | (0.134, 0.100) | 41 |
| Example 95 | 299 | 5.39 | 6.01 | (0.134, 0.101) | 32 |
| Example 96 | 300 | 4.63 | 6.53 | (0.134, 0.102) | 48 |
| Example 97 | 303 | 4.91 | 6.82 | (0.134, 0.100) | 43 |
| Example 98 | 304 | 4.72 | 6.53 | (0.134, 0.102) | 38 |
| Example 99 | 305 | 4.91 | 6.78 | (0.134, 0.100) | 43 |
| Example 100 | 306 | 4.90 | 6.95 | (0.134, 0.100) | 41 |
| Example 101 | 308 | 4.98 | 6.22 | (0.134, 0.100) | 40 |
| Example 102 | 313 | 5.62 | 5.98 | (0.134, 0.100) | 33 |
| Example 103 | 321 | 5.21 | 6.03 | (0.134, 0.101) | 33 |
| Example 104 | 324 | 5.39 | 6.01 | (0.134, 0.101) | 32 |
| Example 105 | 325 | 5.33 | 6.04 | (0.134, 0.101) | 33 |
| Example 106 | 332 | 4.91 | 6.93 | (0.134, 0.100) | 43 |
| Example 107 | 336 | 4.77 | 6.95 | (0.134, 0.100) | 41 |
| Example 108 | 339 | 4.98 | 6.22 | (0.134, 0.100) | 40 |
| Example 109 | 343 | 5.03 | 5.98 | (0.134, 0.100) | 39 |
| Example 110 | 345 | 4.71 | 6.51 | (0.134, 0.102) | 41 |
| Example 111 | 352 | 4.72 | 6.53 | (0.134, 0.102) | 48 |
| Example 112 | 353 | 4.74 | 6.59 | (0.134, 0.102) | 45 |
| Example 113 | 363 | 5.42 | 6.13 | (0.134, 0.101) | 39 |
| Example 114 | 365 | 4.72 | 6.53 | (0.134, 0.102) | 38 |
| Example 115 | 367 | 4.91 | 6.78 | (0.134, 0.100) | 43 |
| Example 116 | 370 | 5.44 | 5.89 | (0.134, 0.100) | 41 |
| Example 117 | 372 | 5.36 | 6.01 | (0.134, 0.101) | 32 |
| Example 118 | 373 | 4.96 | 6.82 | (0.134, 0.100) | 45 |
| Example 119 | 374 | 4.91 | 6.93 | (0.134, 0.100) | 43 |
| Example 120 | 376 | 4.95 | 6.95 | (0.134, 0.100) | 41 |
| Example 121 | 379 | 5.34 | 6.11 | (0.134, 0.101) | 38 |
| Example 122 | 380 | 4.86 | 6.76 | (0.134, 0.100) | 45 |
| Example 123 | 381 | 4.94 | 6.73 | (0.134, 0.102) | 42 |
| Example 124 | 382 | 4.91 | 6.55 | (0.134, 0.100) | 46 |
| Example 125 | 384 | 5.31 | 6.29 | (0.134, 0.100) | 42 |
| Example 126 | 388 | 5.22 | 6.11 | (0.134, 0.100) | 35 |
| Example 127 | 391 | 5.33 | 6.24 | (0.134, 0.102) | 41 |
| Example 128 | 395 | 5.31 | 6.57 | (0.134, 0.102) | 46 |
| Example 129 | 396 | 4.72 | 6.53 | (0.134, 0.102) | 35 |
| Example 130 | 397 | 4.79 | 6.55 | (0.134, 0.102) | 48 |
| Example 131 | 398 | 5.40 | 6.13 | (0.134, 0.101) | 39 |
| Example 132 | 399 | 5.12 | 5.89 | (0.134, 0.100) | 41 |
| Example 133 | 400 | 5.31 | 6.01 | (0.134, 0.101) | 34 |
| Example 134 | 401 | 5.11 | 6.88 | (0.134, 0.100) | 45 |

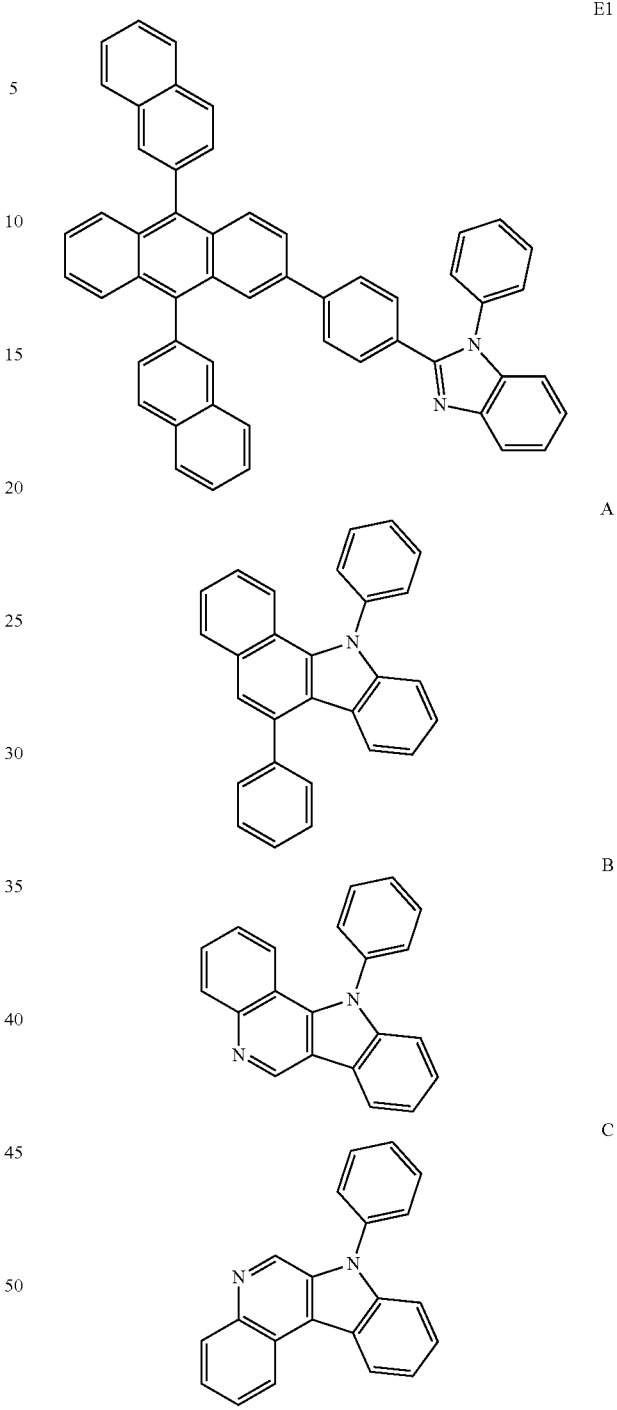

As seen from the results of Table 15, the organic light emitting device using the electron transfer layer material of the blue organic light emitting device of the present disclosure had a lower driving voltage, and significantly improved light emission efficiency and lifetime compared to Comparative Example 1.

In addition, it was identified that light emission efficiency and lifetime were more superior compared to Comparative Example 2 to Comparative Example 4. Particularly, it can be seen that Compounds B and C of Comparative Examples 3 and 4 had the core structure of the present application substituted with one substituent. It was identified that, when substituted with one substituent, thermal stability was reduced compared to the compound substituted with two like the heterocyclic compound of Chemical Formula 1 of the present application, and a lifetime decreased particularly.

<Experimental Example 2> Manufacture of Organic Light Emitting Device

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum depositor, and the following 4,4',4"-tris(N,N-(2-naphthyl)-phenylamino)triphenylamine (2-TNATA) was introduced to a cell in the vacuum depositor.

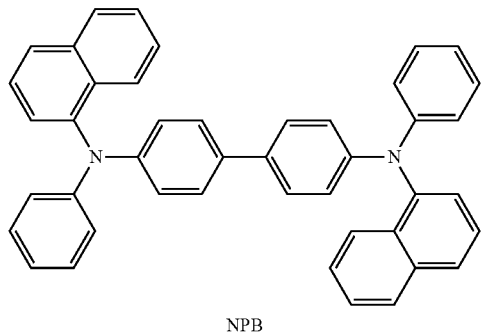

NPB

After forming the hole injection layer and the hole transfer layer as above, a blue light emitting material having a structure as below was deposited thereon as a light emitting layer. Specifically, in one side cell in the vacuum depositor, H1, a blue light emitting host material, was vacuum deposited to a thickness of 200 Å, and D1, a blue light emitting dopant material, was vacuum deposited thereon to 5% with respect to the host material.

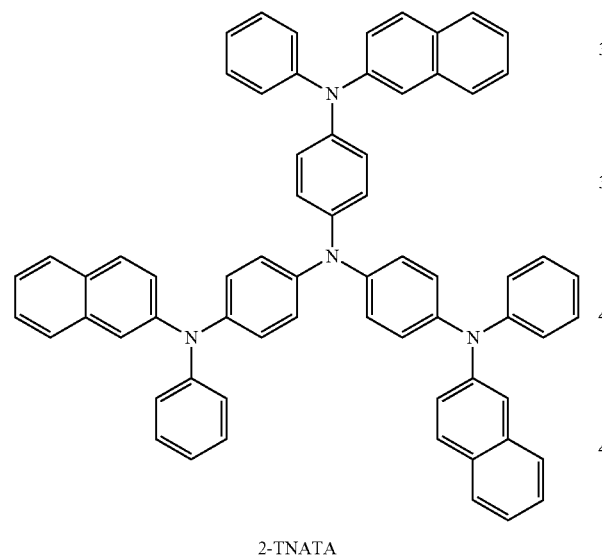

2-TNATA

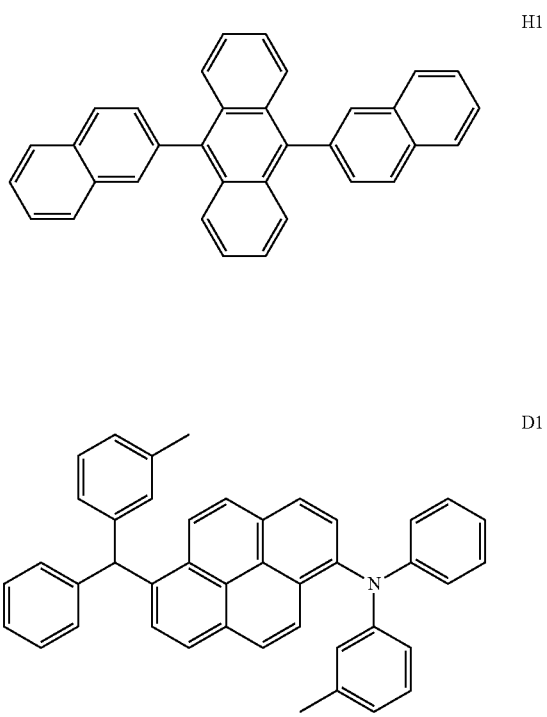

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum depositor, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

Subsequently, a compound of the following structural formula E1 was deposited to a thickness of 300 Å as an electron transfer layer.

E1

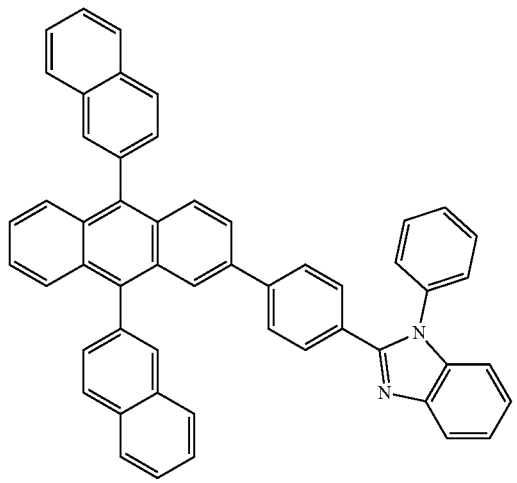

As an electron injection layer, lithium fluoride (LiF) was deposited to a thickness of 10 Å, and an Al cathode was employed to have a thickness of 1,000 Å to manufacture an OLED.

Meanwhile, all the organic compounds required to manufacture the OLED were vacuum sublimation purified under $10^{-6}$ torr to $10^{-8}$ torr by each material to be used in the OLED manufacture.

An electroluminescent device was manufactured in the same manner as in Experimental Example 2 except that, after forming the electron transfer layer E1 to a thickness of 250 Å, a hole blocking layer was formed on the electron transfer layer to a thickness of 50 Å using a compound presented in the following Table 16.

Results of measuring a driving voltage, light emission efficiency, a color coordinate (CIE) and a lifetime of the blue organic light emitting device manufactured according to the present disclosure are as shown in Table 16.

TABLE 16

| | Compound | Driving Voltage (V) | Light Emission Efficiency (cd/A) | CIE (x, y) | Lifetime (T95) |
|---|---|---|---|---|---|
| Comparative Example 5 | — | 5.51 | 5.94 | (0.134, 0.100) | 31 |
| Comparative Example 6 | A | 5.21 | 4.12 | (0.134, 0.101) | 12 |
| Comparative Example 7 | B | 5.33 | 4.01 | (0.134, 0.100) | 11 |
| Comparative Example 8 | C | 5.31 | 4.01 | (0.134, 0.100) | 11 |
| Example 135 | 2 | 5.14 | 6.89 | (0.134, 0.102) | 54 |
| Example 136 | 8 | 5.34 | 6.58 | (0.134, 0.101) | 44 |
| Example 137 | 68 | 5.38 | 6.51 | (0.134, 0.103) | 47 |
| Example 138 | 77 | 5.11 | 6.75 | (0.134, 0.102) | 46 |
| Example 139 | 104 | 5.42 | 6.21 | (0.134, 0.101) | 54 |
| Example 140 | 108 | 5.13 | 6.63 | (0.134, 0.102) | 52 |
| Example 141 | 120 | 5.05 | 6.66 | (0.134, 0.101) | 49 |
| Example 142 | 205 | 5.42 | 6.13 | (0.134, 0.101) | 41 |
| Example 143 | 212 | 5.14 | 6.89 | (0.134, 0.102) | 54 |
| Example 144 | 213 | 5.34 | 6.58 | (0.134, 0.101) | 44 |
| Example 145 | 273 | 5.38 | 6.51 | (0.134, 0.103) | 47 |
| Example 146 | 277 | 5.11 | 6.75 | (0.134, 0.102) | 46 |
| Example 147 | 288 | 5.32 | 6.25 | (0.134, 0.101) | 55 |
| Example 148 | 388 | 5.14 | 6.46 | (0.134, 0.102) | 51 |
| Example 149 | 391 | 5.04 | 6.62 | (0.134, 0.101) | 55 |
| Example 150 | 395 | 5.32 | 6.25 | (0.134, 0.101) | 55 |

As seen from the results of Table 16, the organic light emitting device using the hole blocking layer material of the blue organic light emitting device of the present disclosure had a lower driving voltage, and significantly improved light emission efficiency and lifetime compared to Comparative Example 5. In addition, light emission efficiency and lifetime were significantly improved compared to Comparative Example 6 to Comparative Example 8. Particularly, it can be seen that Compounds B and C of Comparative Examples 7 and 8 had the core structure of the present application substituted with one substituent. It was identified that, when substituted with one substituent, thermal stability was reduced compared to the compound substituted with two like the heterocyclic compound of Chemical Formula 1 of the present application, and a lifetime decreased particularly.

Such a reason is due to the fact that the compound of Chemical Formula 1 of the present application is a bipolar type having both a p-type and an n-type, and is capable of blocking hole leakage and effectively trapping excitons in the light emitting layer.

<Experimental Example 3> Manufacture of Organic Light Emitting Device

1) Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for ITO work function and remaining film removal, and the substrate was transferred to a thermal deposition apparatus for organic deposition.

On the transparent ITO electrode (anode), an organic material was formed in a 2 stack white organic light emitting device (WOLED) structure. As for the first stack, TAPC was thermal vacuum deposited to a thickness of 300 Å first to form a hole transfer layer. After forming the hole transfer layer, a light emitting layer was thermal vacuum deposited thereon as follows. The light emitting layer was deposited to 300 Å by doping FIrpic to TCz1, a host, by 8% as a blue phosphorescent dopant. After forming an electron transfer layer to 400 Å using TmPyPB, a charge generation layer was formed to 100 Å by doping $Cs_2CO_3$ to the compound listed in the following Table 17 by 20%.

As for the second stack, $MoO_3$ was thermal vacuum deposited to a thickness of 50 Å first to form a hole injection layer. A hole transfer layer, a common layer, was formed by doping $MoO_3$ to TAPC by 20% to 100 Å and depositing TAPC to 300 Å. A light emitting layer was deposited thereon to 300 Å by doping $Ir(ppy)_3$, a green phosphorescent dopant, to TCz1, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic light emitting device.

Meanwhile, all the organic compounds required to manufacture the OLED were vacuum sublimation purified under $10^{-6}$ torr to $10^{-8}$ torr by each material to be used in the OLED manufacture.

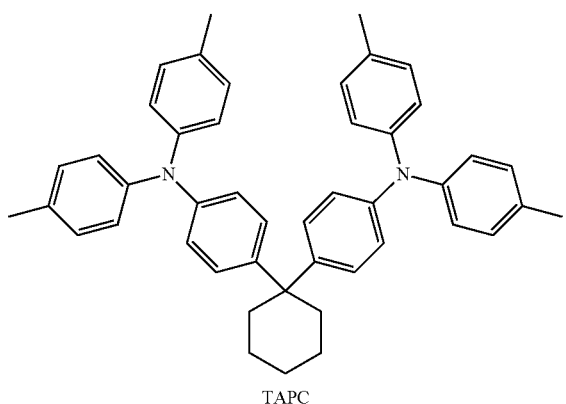
TAPC
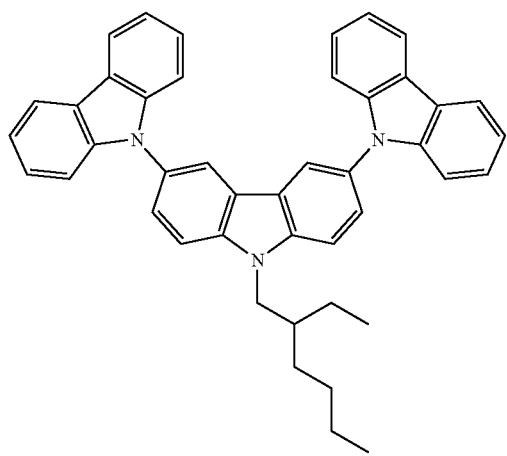
TCz1
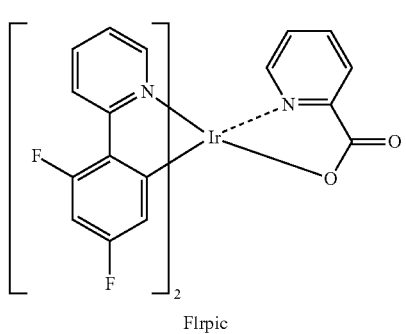
FIrpic
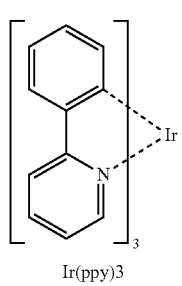
Ir(ppy)3
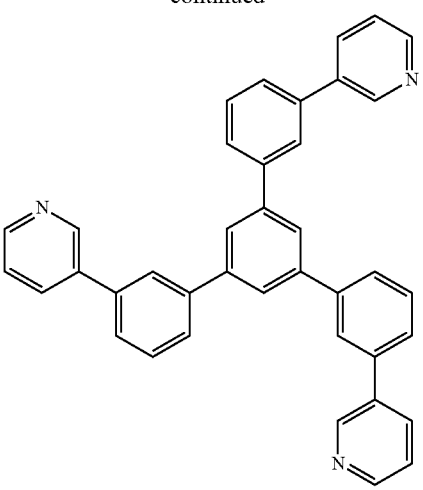
TmPyPB
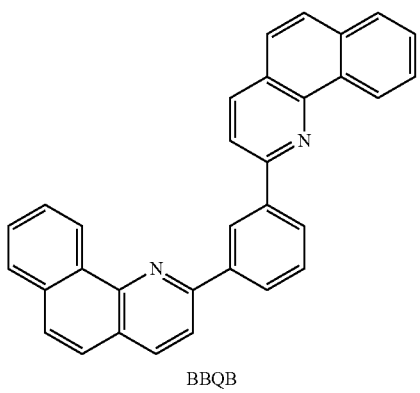
BBQB
TBQB
Results of measuring a driving voltage, light emission efficiency, a color coordinate (CIE) and a lifetime (T95) of the white organic light emitting device manufactured according to the present disclosure are as shown in the following Table 17.

TABLE 17

| | Compound | Driving Voltage (V) | Light Emission Efficiency (cd/A) | CIE (x, y) | Lifetime (T95) |
|---|---|---|---|---|---|
| Comparative Example 9 | TmPyPB | 8.57 | 57.61 | (0.212, 0.433) | 22 |
| Comparative Example 10 | BBQB | 8.43 | 58.11 | (0.220, 0.429) | 22 |
| Comparative Example 11 | TBQB | 8.47 | 58.90 | (0.222, 0.430) | 26 |
| Comparative Example 12 | A | 7.21 | 41.11 | (0.201, 0.398) | 9 |
| Comparative Example 13 | B | 7.28 | 41.12 | (0.189, 0.388) | 6 |
| Comparative Example 14 | C | 7.22 | 41.01 | (0.188, 0.388) | 6 |
| Example 1 | 1 | 7.24 | 61.88 | (0.209, 0.415) | 23 |
| Example 2 | 33 | 6.98 | 60.58 | (0.224, 0.429) | 30 |
| Example 3 | 66 | 6.89 | 72.10 | (0.243, 0.442) | 38 |
| Example 4 | 78 | 6.71 | 69.65 | (0.205, 0.411) | 41 |
| Example 5 | 101 | 6.49 | 71.44 | (0.243, 0.442) | 39 |
| Example 6 | 152 | 7.34 | 58.29 | (0.209, 0.419) | 30 |
| Example 7 | 156 | 7.21 | 59.33 | (0.210, 0.420) | 29 |
| Example 8 | 157 | 7.44 | 69.65 | (0.205, 0.411) | 33 |
| Example 9 | 158 | 7.41 | 71.44 | (0.243, 0.442) | 35 |
| Example 10 | 296 | 6.95 | 58.29 | (0.209, 0.419) | 34 |
| Example 11 | 299 | 7.21 | 59.33 | (0.210, 0.420) | 29 |
| Example 12 | 370 | 6.71 | 69.65 | (0.205, 0.411) | 41 |
| Example 13 | 372 | 6.49 | 71.44 | (0.243, 0.442) | 39 |
| Example 14 | 373 | 6.95 | 58.29 | (0.209, 0.419) | 34 |

As seen from the results of Table 17, the organic light emitting device using the charge generation layer material of the 2-stack white organic light emitting device of the present disclosure had a lower driving voltage and improved light emission efficiency compared to Comparative Example 9 to Comparative Example 11. In addition, compared to Comparative Examples 12 to 14, a driving voltage was similar, however, light emission efficiency and lifetime were significantly improved.

Particularly, it can be seen that Compounds B and C of Comparative Examples 13 and 14 had the core structure of the present application substituted with one substituent. It was identified that, when substituted with one substituent, thermal stability was reduced compared to the compound substituted with two like the heterocyclic compound of Chemical Formula 1 of the present application, and a lifetime decreased particularly.

The invention claimed is:

1. A heterocyclic compound represented by any one of the following Chemical Formulae 2 to 9:

[Chemical Formula 2]

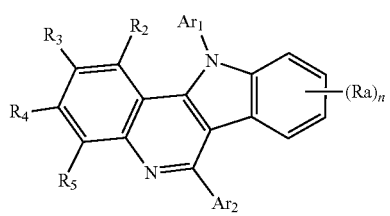

[Chemical Formula 3]

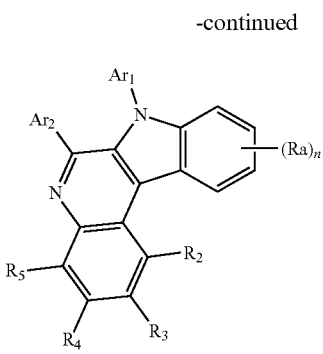

[Chemical Formula 4]

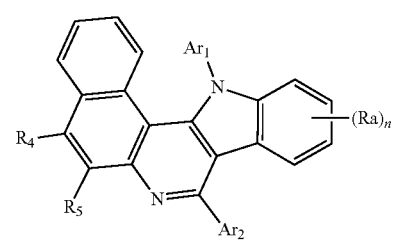

[Chemical Formula 5]

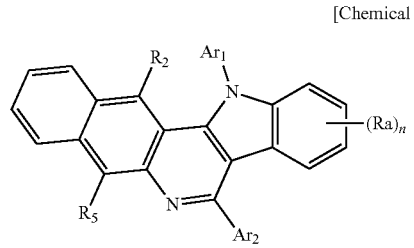

[Chemical Formula 6]

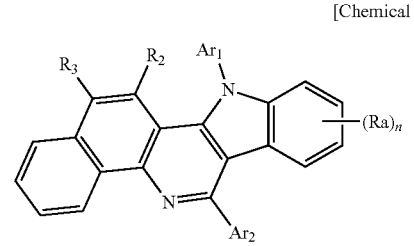

[Chemical Formula 7]

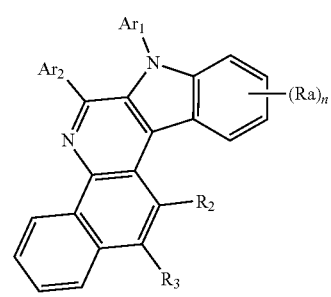

[Chemical Formula 8]

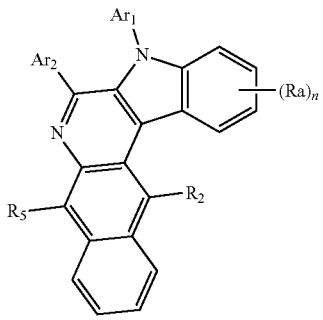

[Chemical Formula 9]

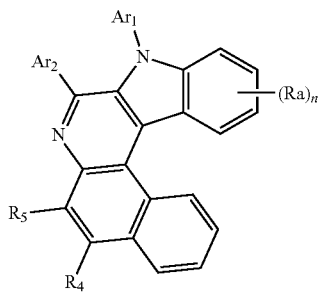

wherein, in Chemical Formulae 2 to 9,
$R_2$ to $R_5$ are the same as or different from each other, and each independently selected from the group consisting of hydrogen; or deuterium;
Ra is hydrogen;
$Ar_1$ is represented by -(L1)p-(Z1)q;
$Ar_2$ is represented by -(L2)r-(Z2)s;
L1 is a phenylene group; a biphenylene group; a naphthalene group; a trivalent pyridine group; a trivalent pyrimidine group; or a trivalent triazine group;
L2 is a phenylene group; a biphenylene group; a naphthalene group; a phenanthrenylene group; a triphenylenylene group; a fluoranthenylene group; a pyrenylene group; a trivalent pyridine group; a trivalent pyrimidine group; or a trivalent triazine group,
Z1 is selected from the group consisting of hydrogen; deuterium; a substituted or unsubstituted phenyl group; a substituted or unsubstituted biphenyl group; a substituted or unsubstituted fluorene group; a substituted or unsubstituted pyridine group; a substituted or unsubstituted pyrimidine group; a substituted or unsubstituted triazine group; a carbazole group; a dibenzofuran group; a dibenzothiophene group; a substituted or unsubstituted phenanthroline group, —P(=O)RR';
Z2 is selected from the group consisting of hydrogen; deuterium; a substituted or unsubstituted phenyl group; a substituted or unsubstituted biphenyl group; a triphenylene group; a substituted or unsubstituted fluorene group; a phenanthrene group; a substituted or unsubstituted pyridine group; a substituted or unsubstituted pyrimidine group; a substituted or unsubstituted triazine group; a carbazole group; a dibenzofuran group; a dibenzothiophene group; a substituted or unsubstituted phenanthroline group or —P(=O)RR',
R and R' are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group;
p and r are an integer of 1 to 4;
q and s are an integer of 1 to 3; and
n is an integer of 0 to 4.

2. The heterocyclic compound of claim 1, wherein the "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted; and
R, R' and R" have the same definitions as in Chemical Formulae 2 to 9.

3. The heterocyclic compound of claim 1, wherein Chemical Formulae 2 to 9 are represented by any one of the following compounds:

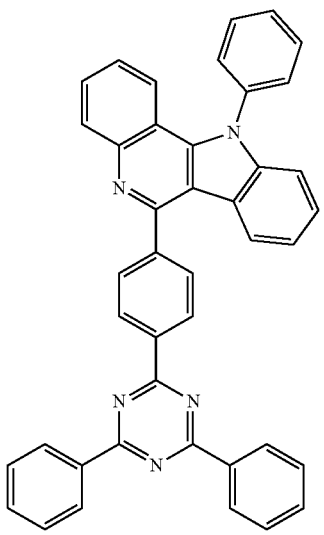

1

357
-continued
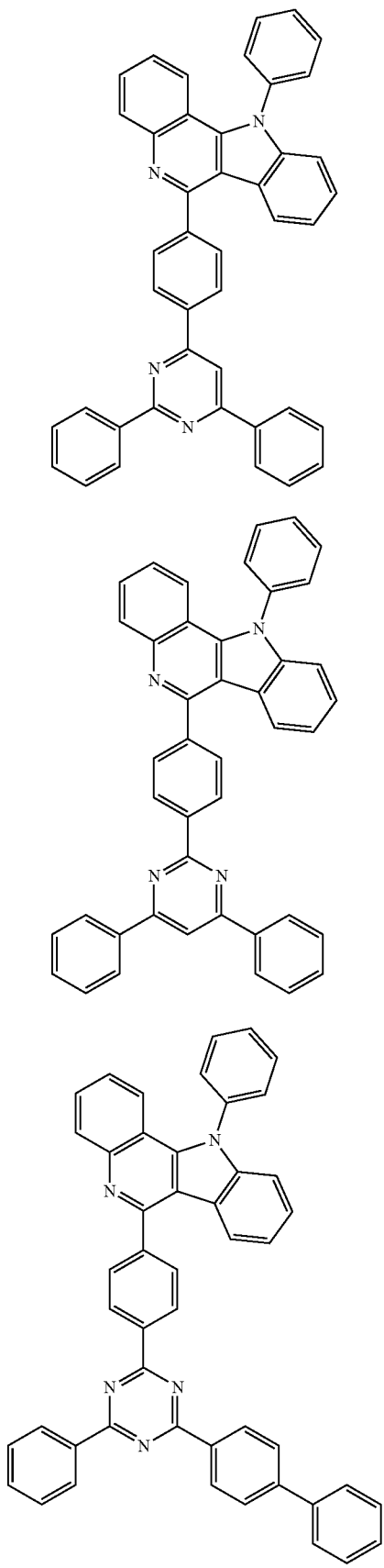
358
-continued
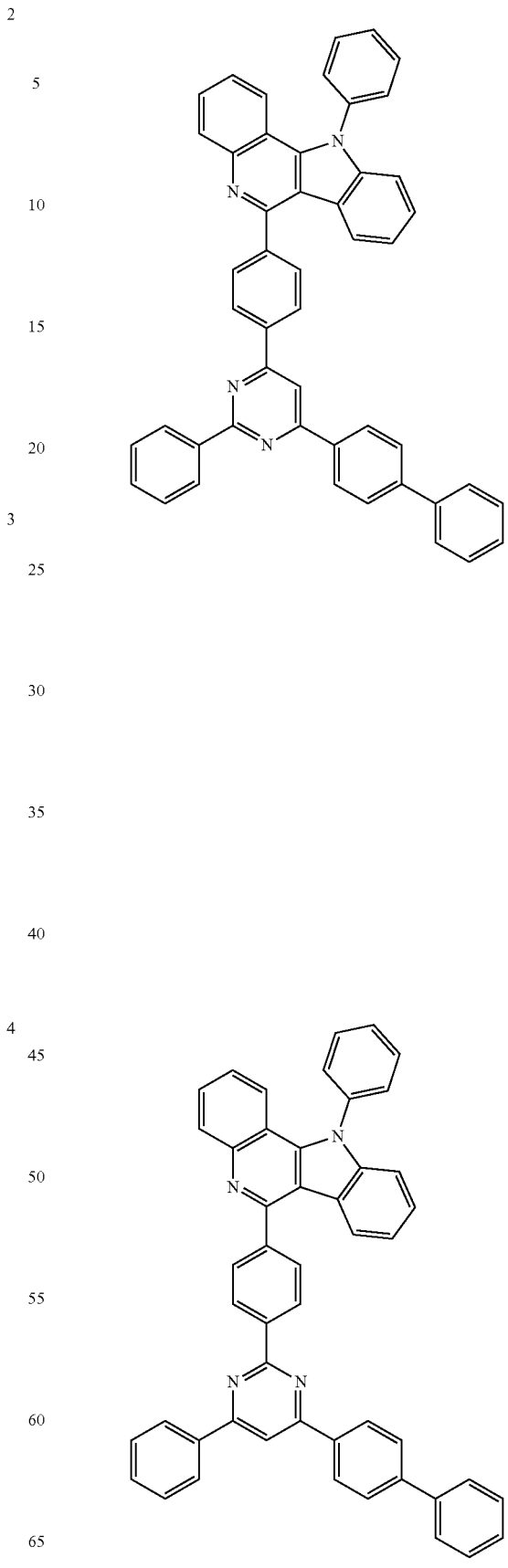

7
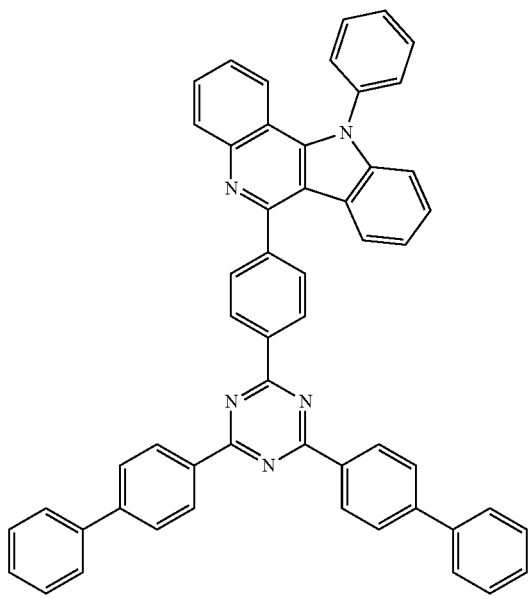
9
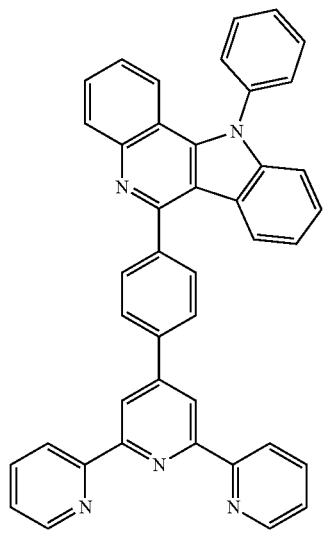
10
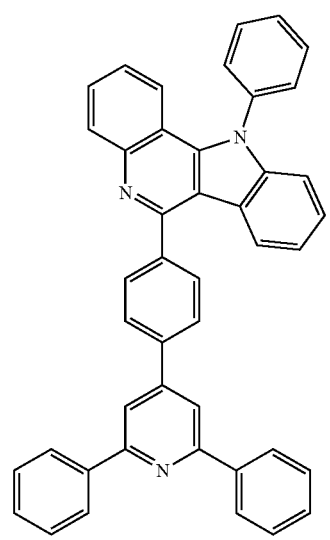
8
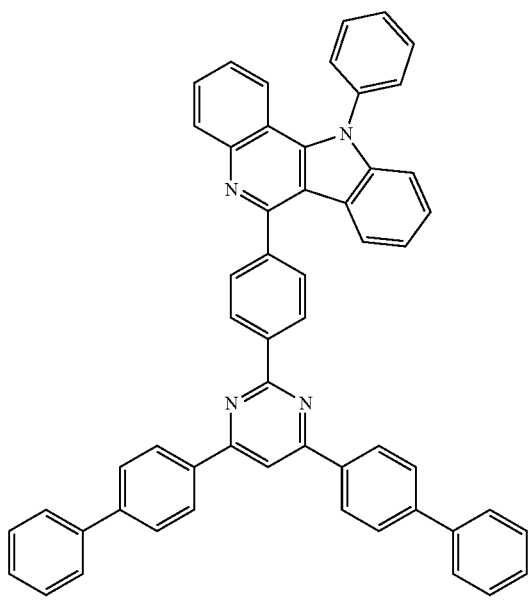
11

361
-continued
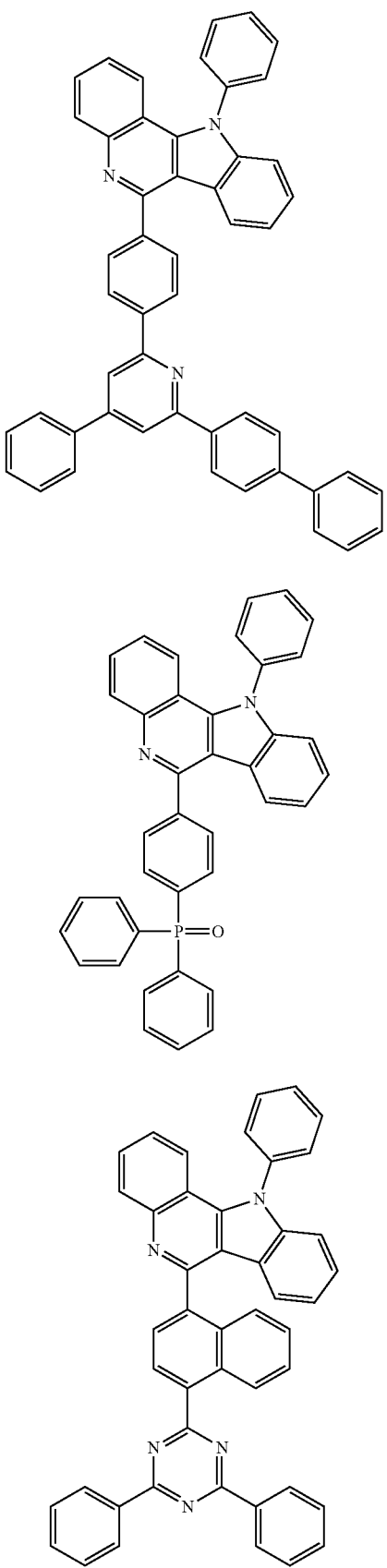
12
13
14
362
-continued
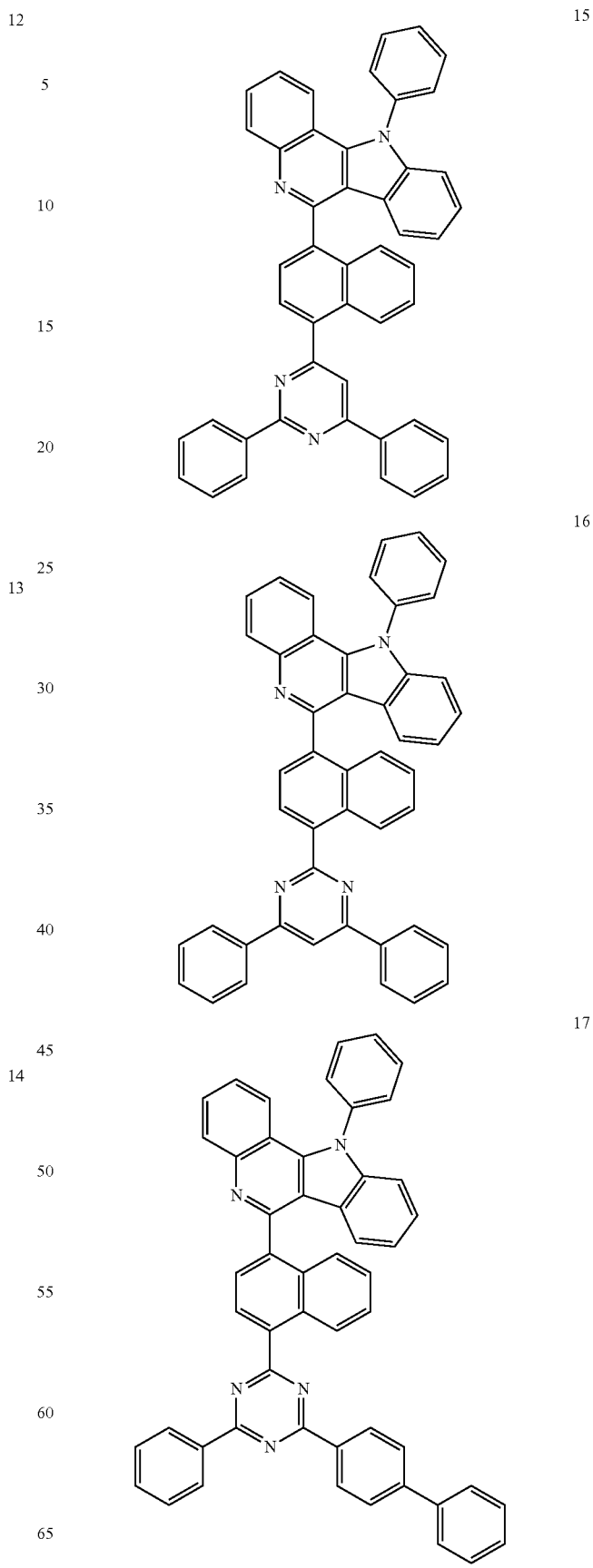
15
16
17

363
-continued
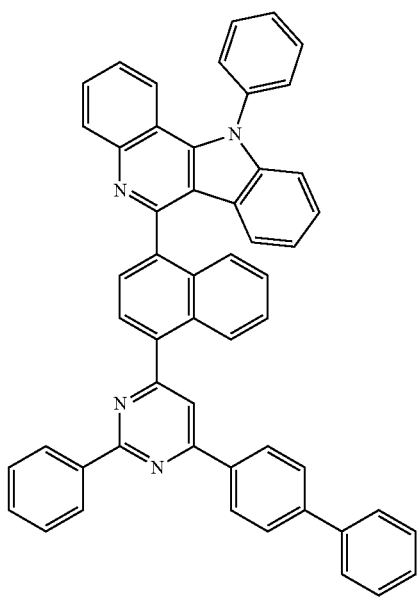
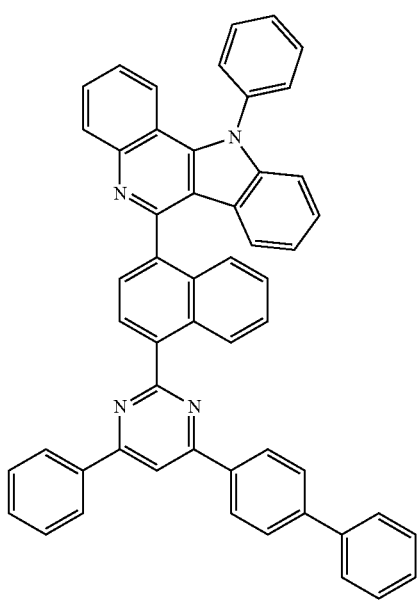
364
-continued
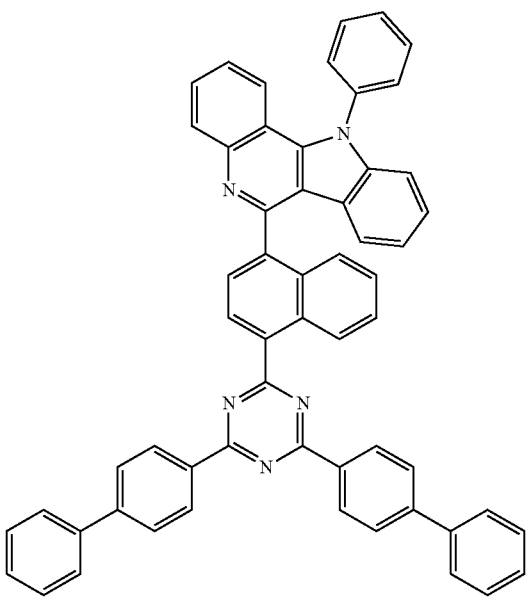
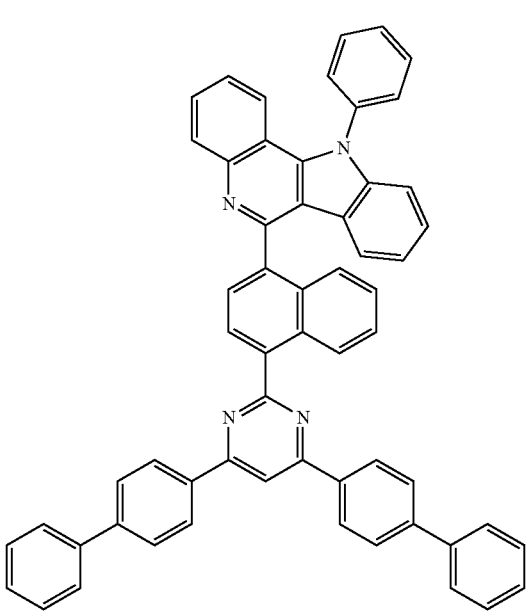

365
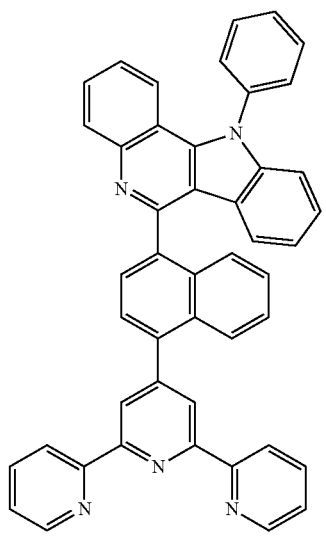
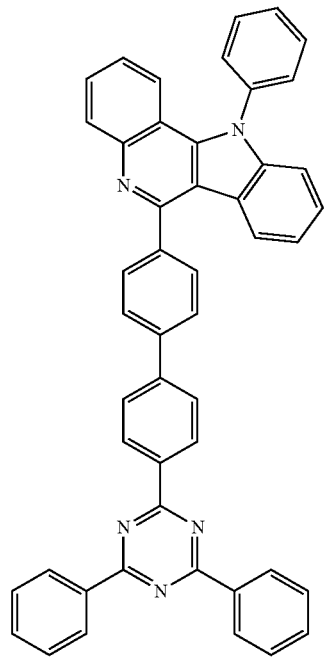
366
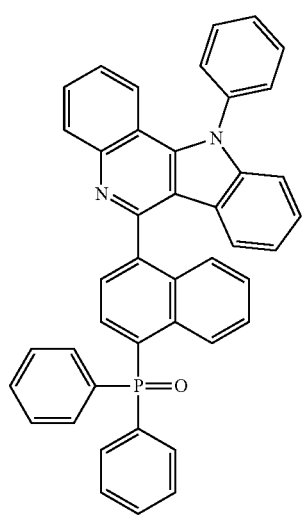
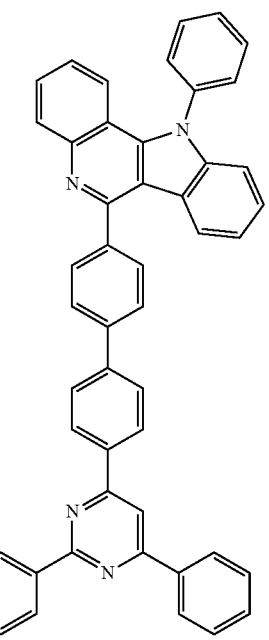

26
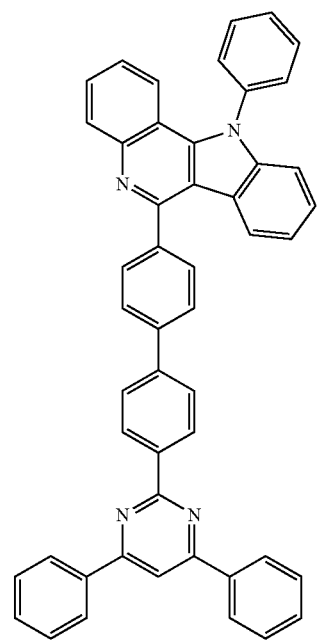
27
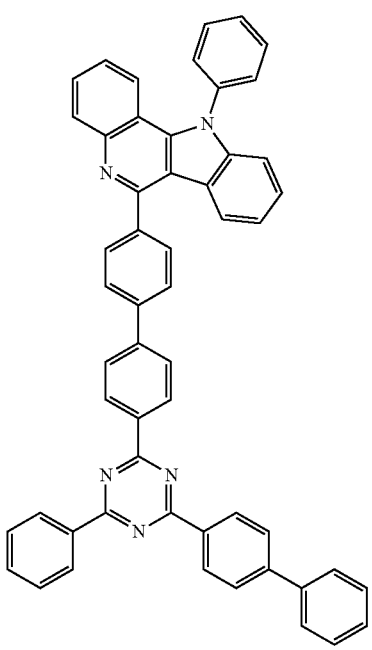
28
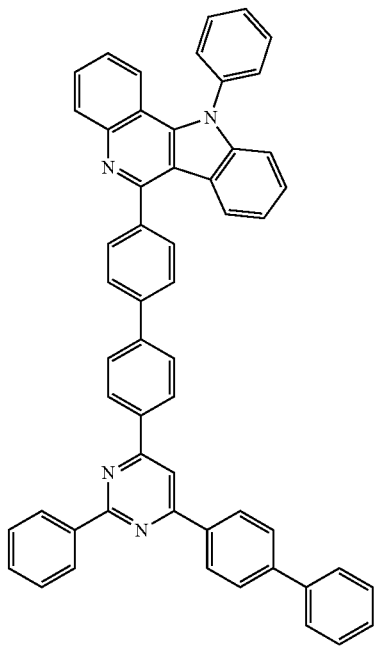
29
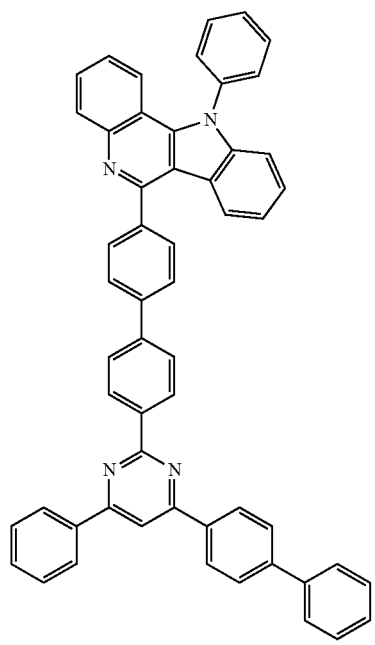

30
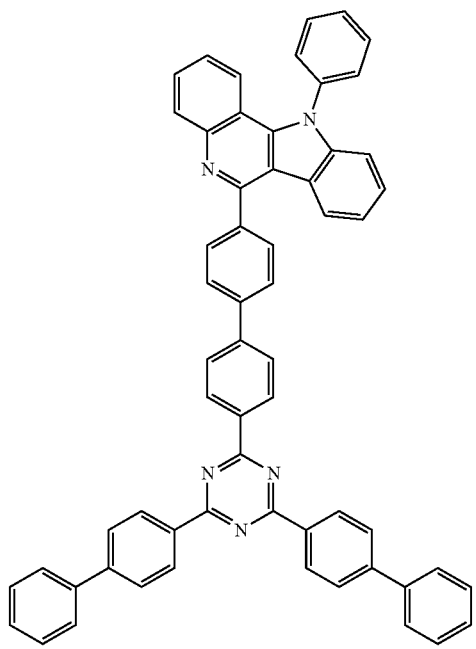
31
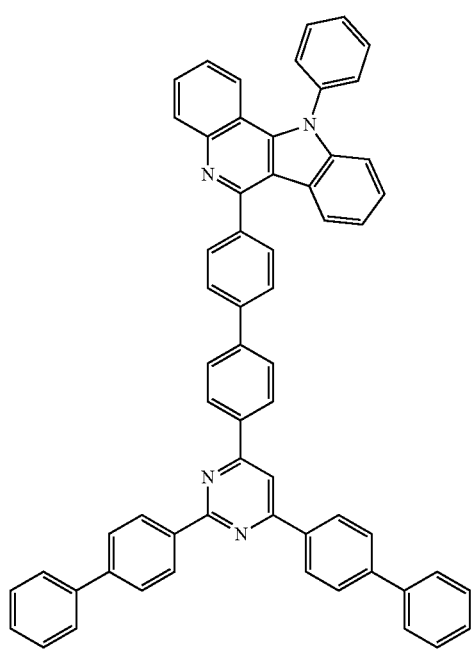
32
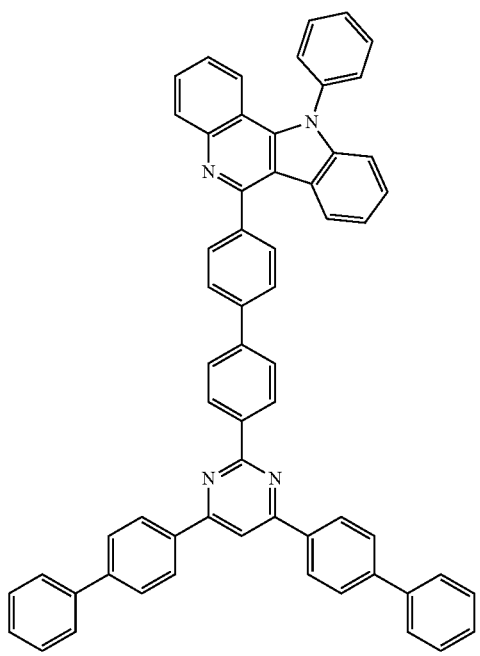
33
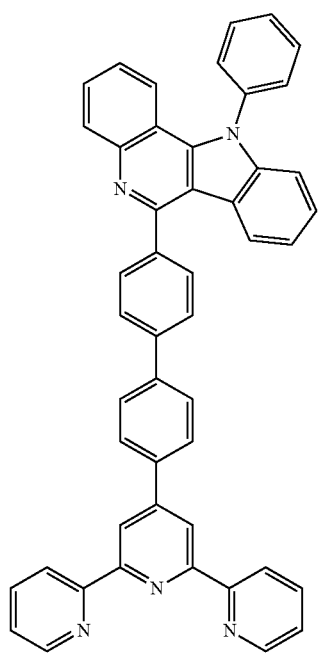

34
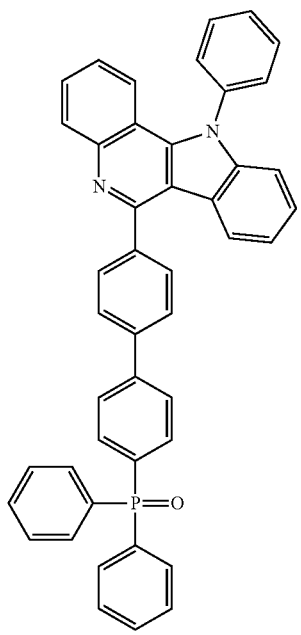
36
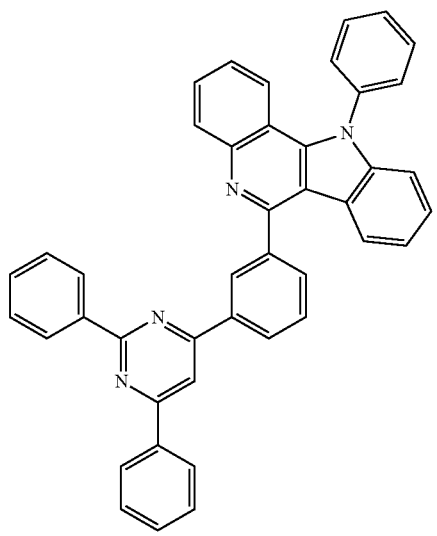
35
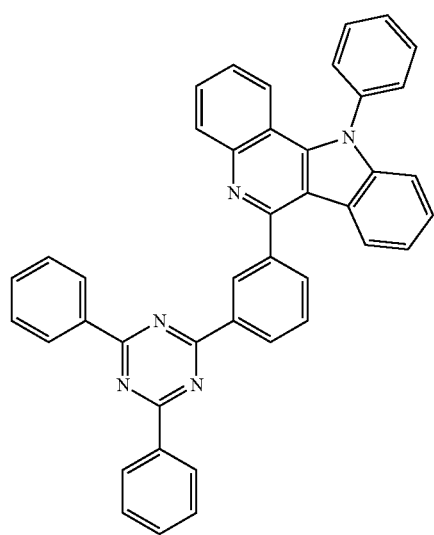
37
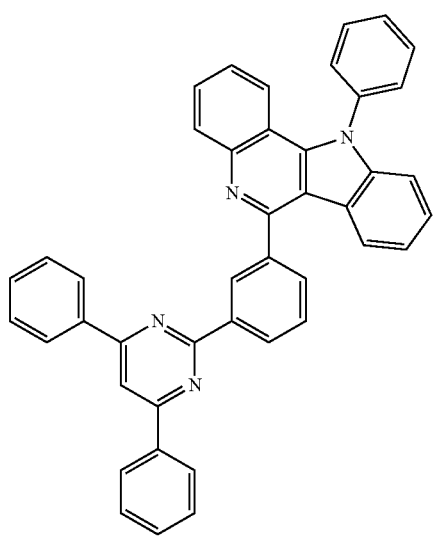

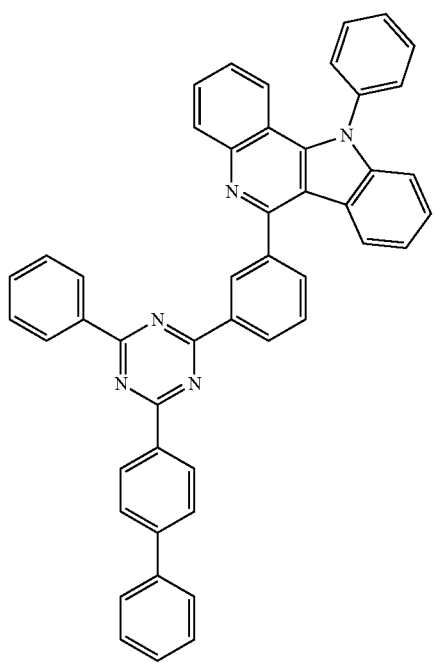
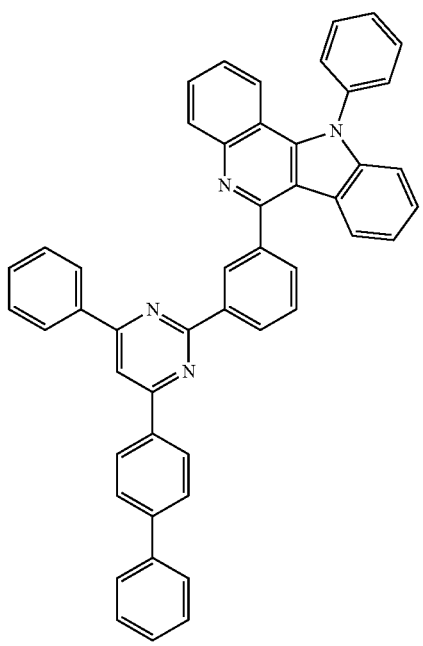
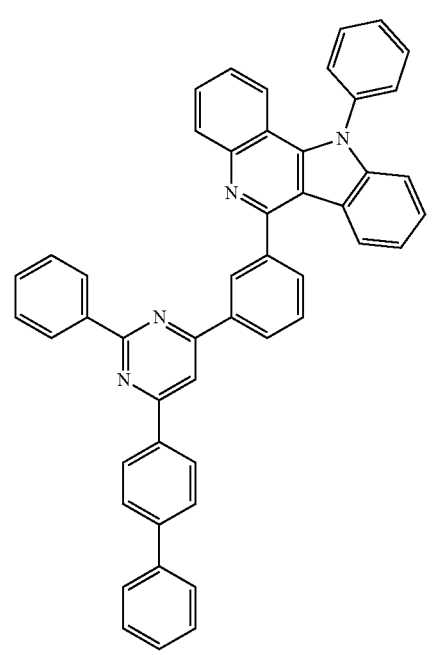
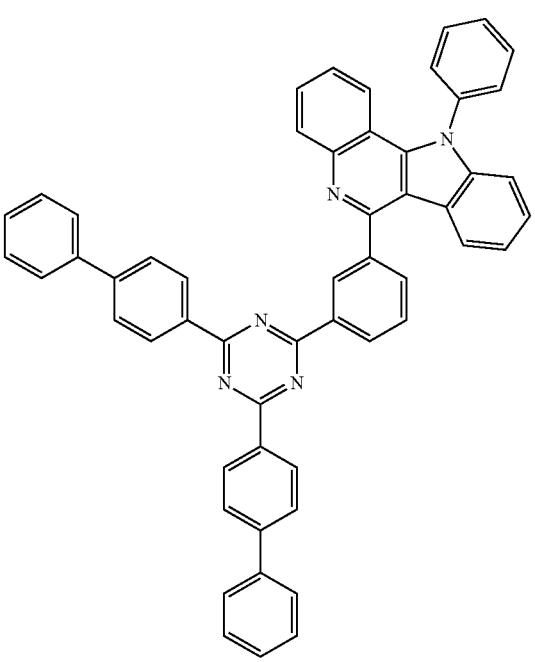

375
-continued
42
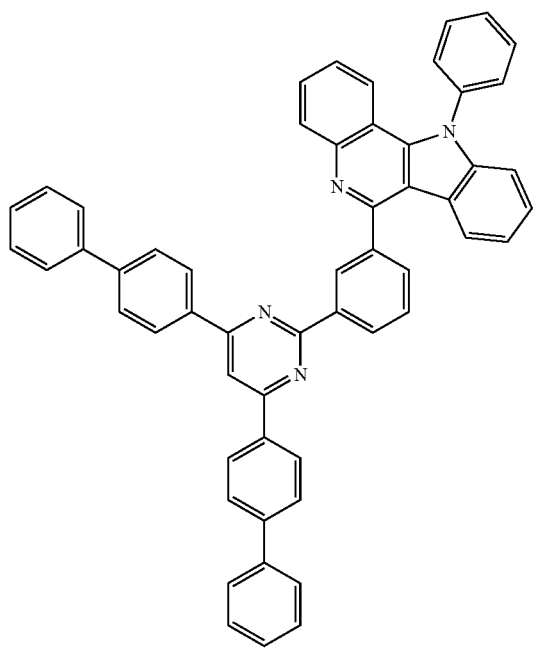
42
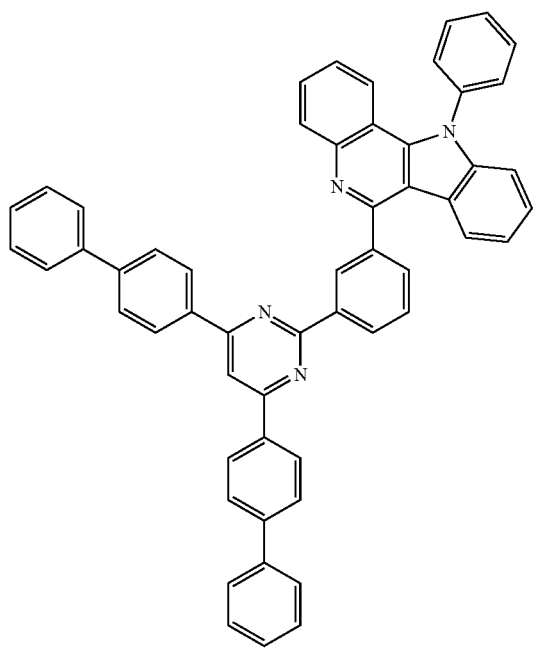
44
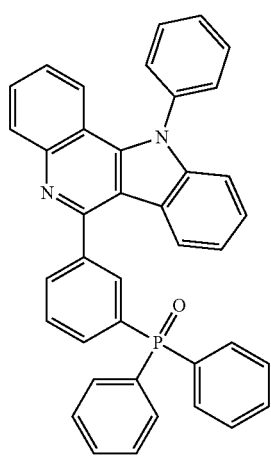
376
-continued
45
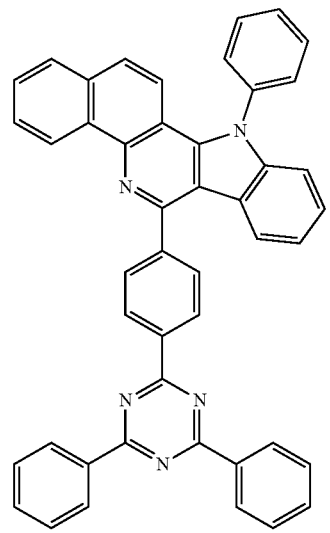
46
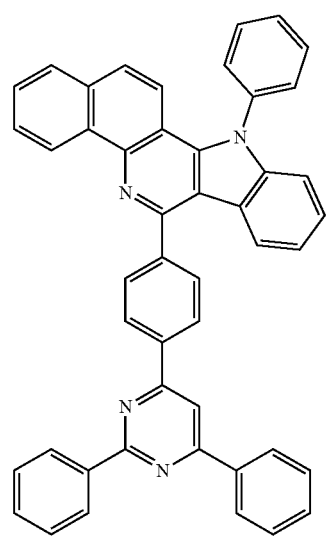
47
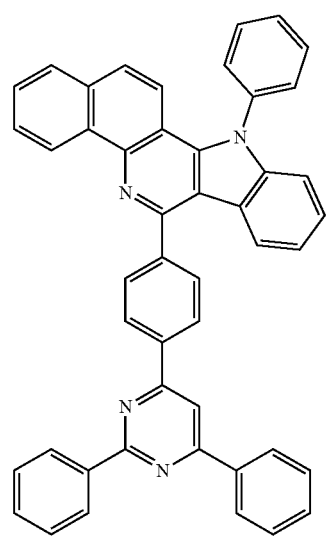

377
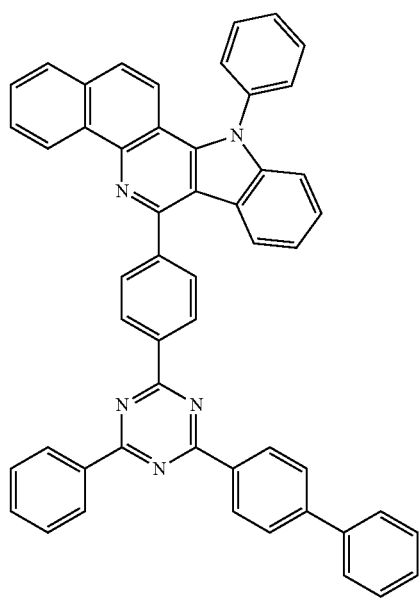
378
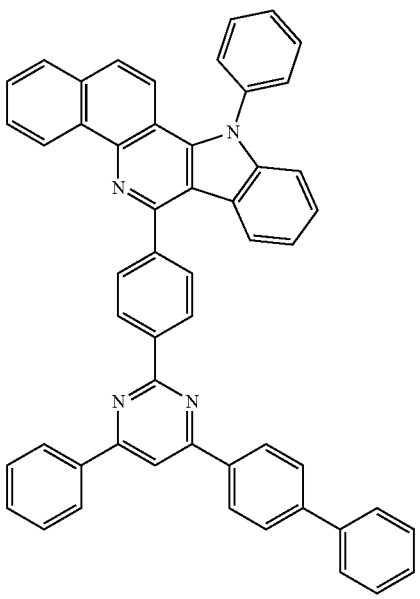
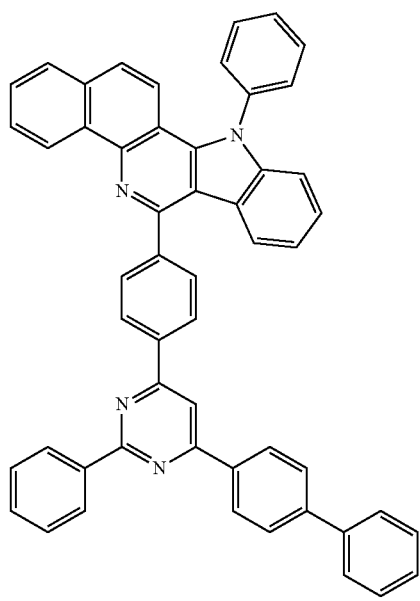
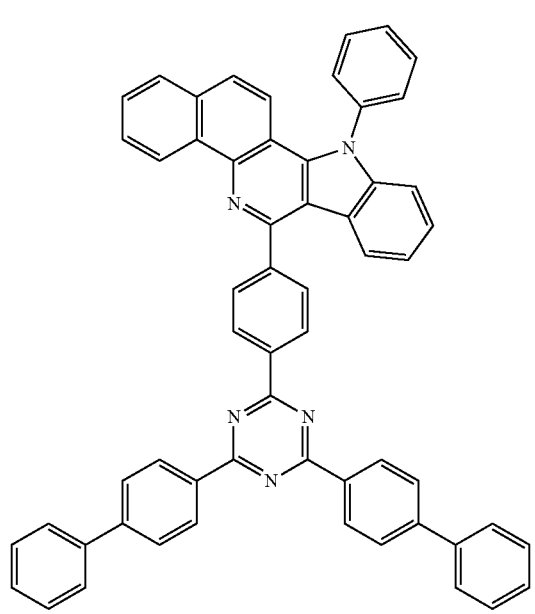

379 -continued
52
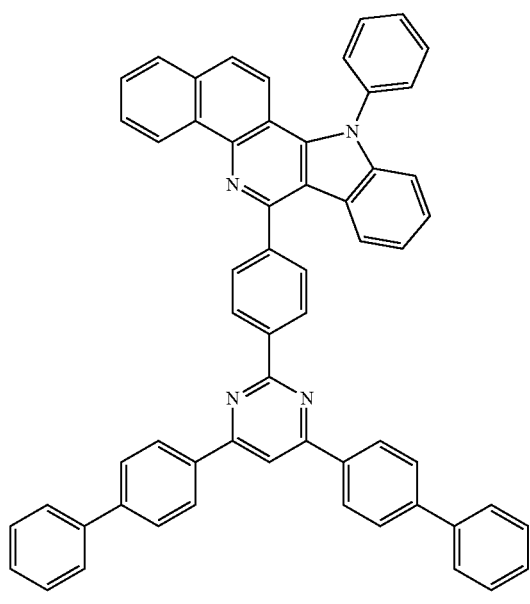
53
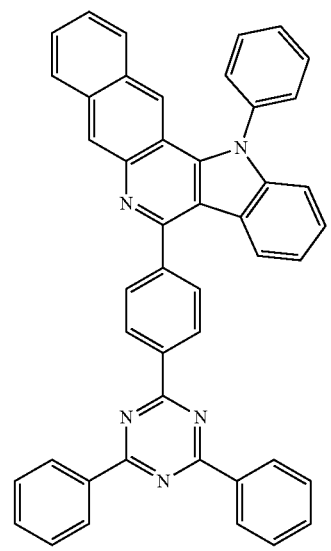
380 -continued
54
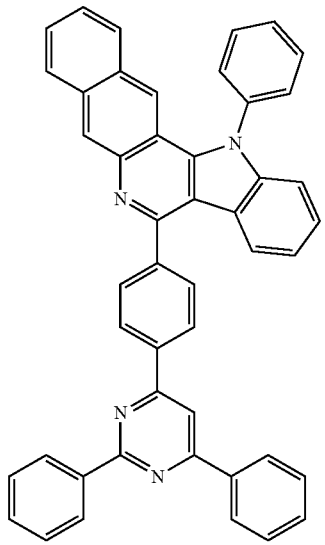
55
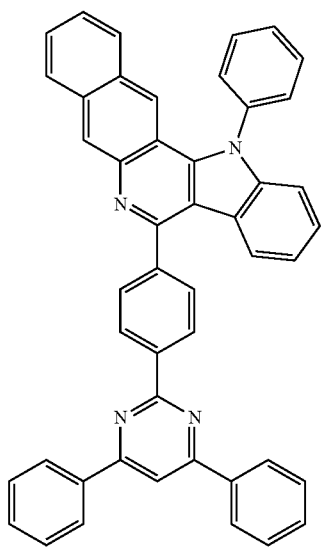

381
-continued
56
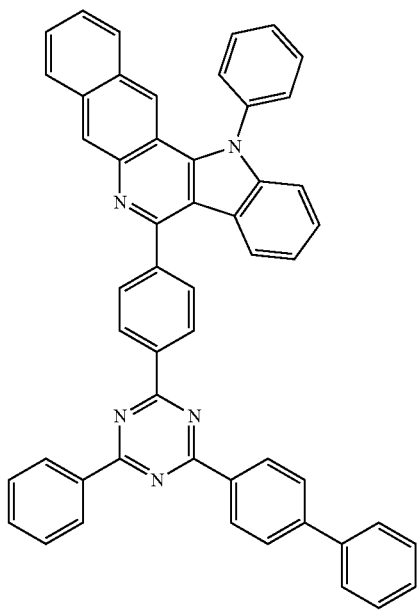
57
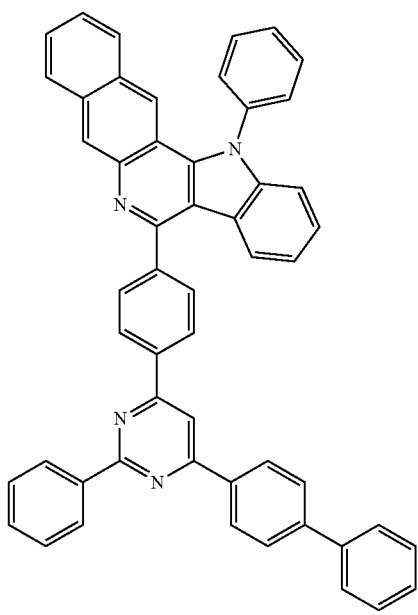
382
-continued
58
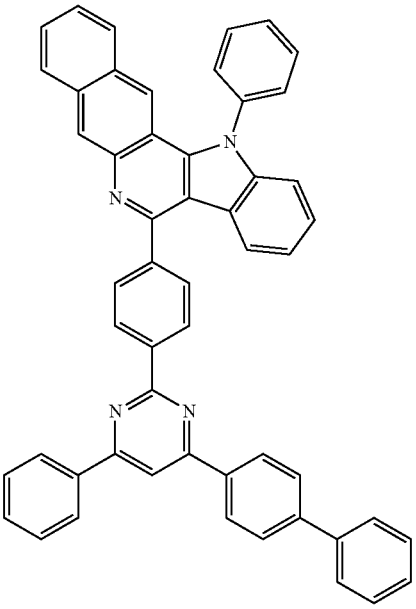
59
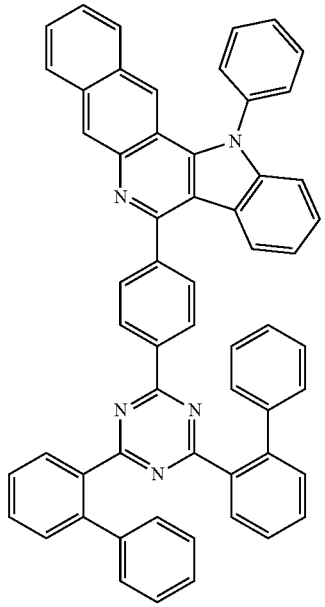

383
-continued
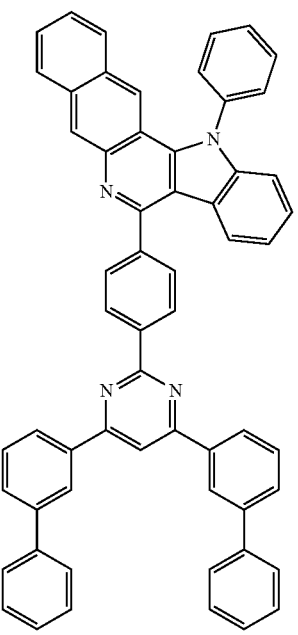
60
384
-continued
61
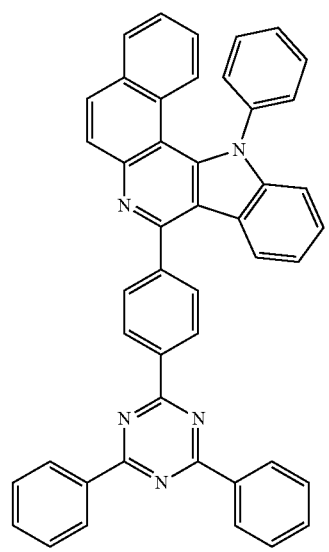
63
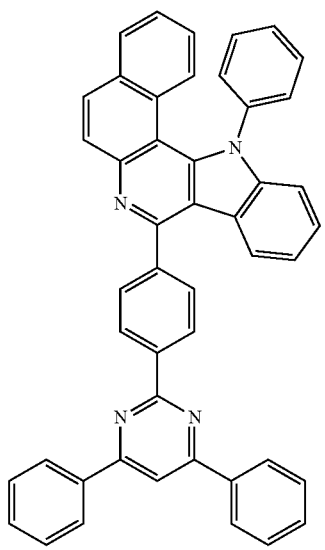

64
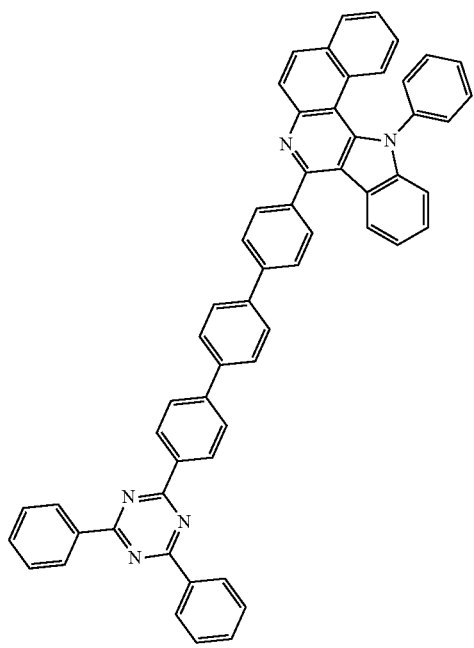
66
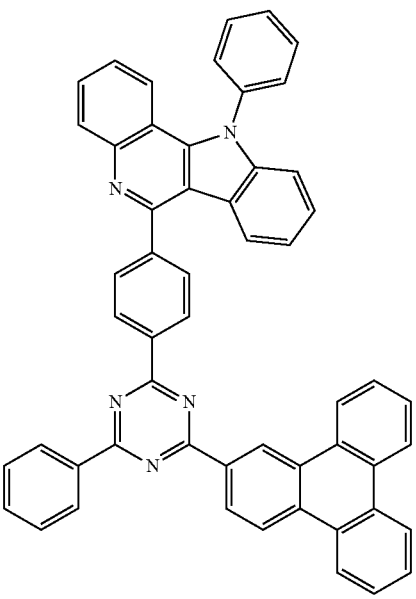
65
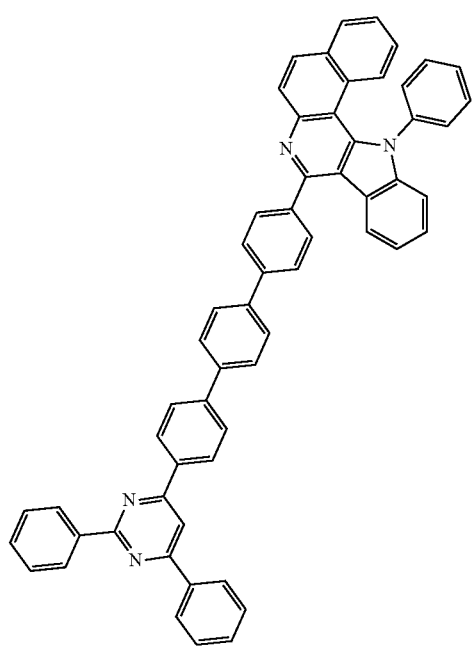
67
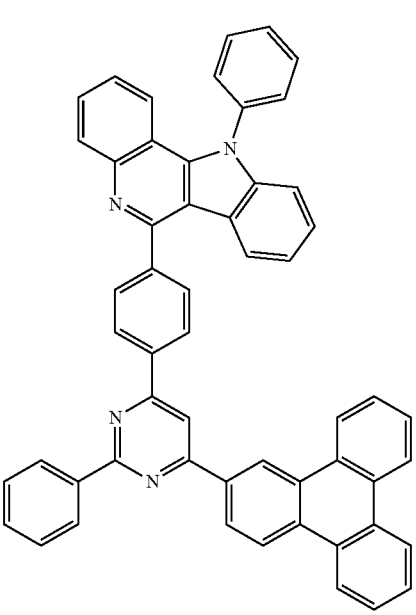

68
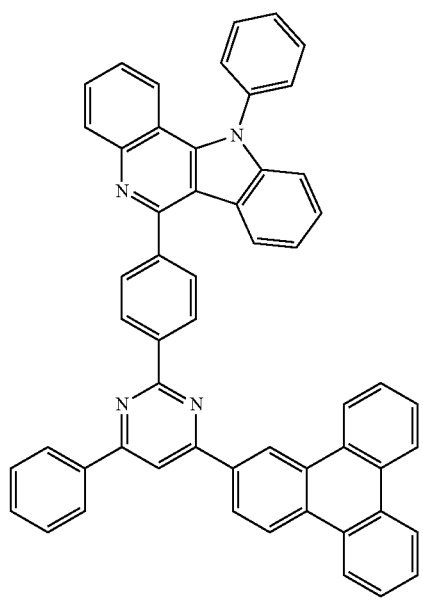
69
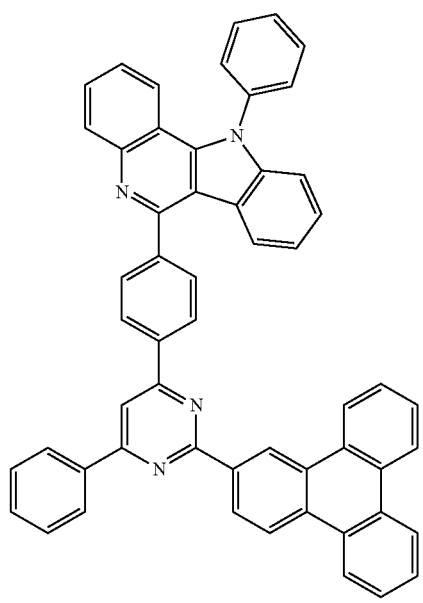
70
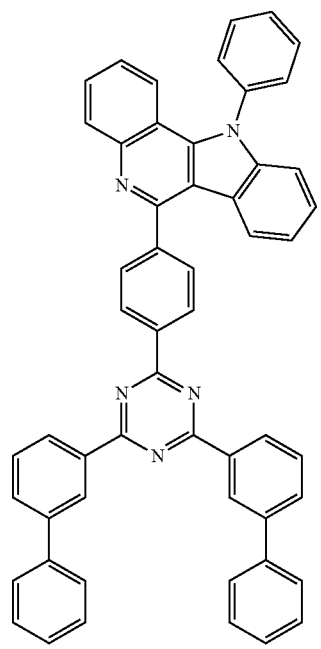
71
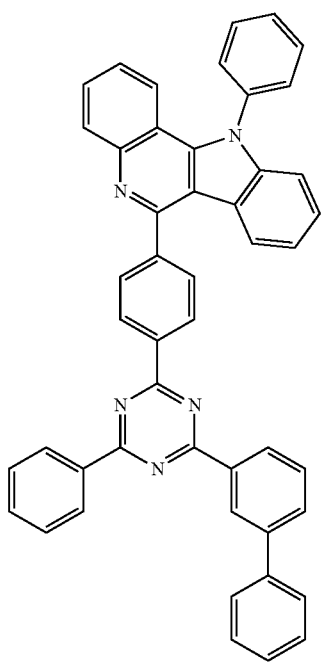

389
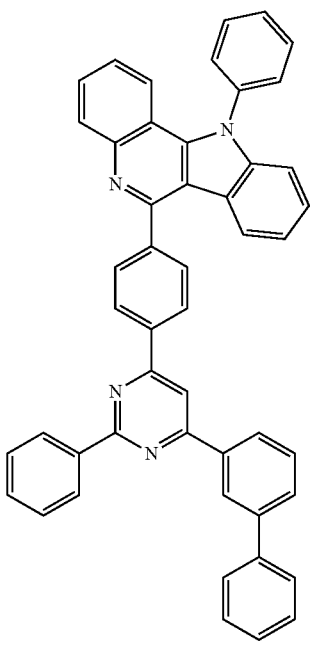
390
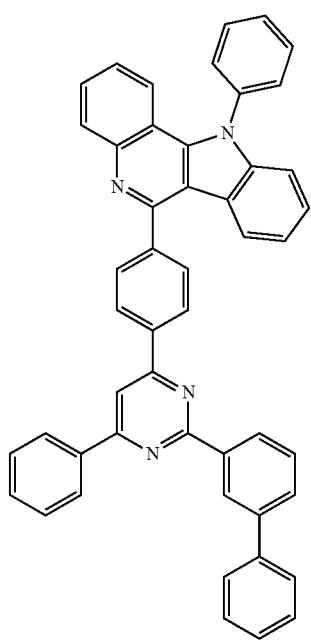
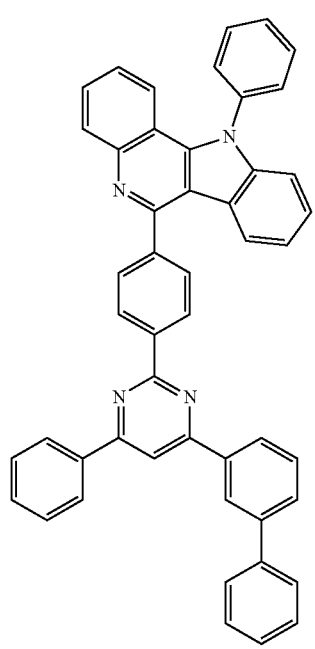
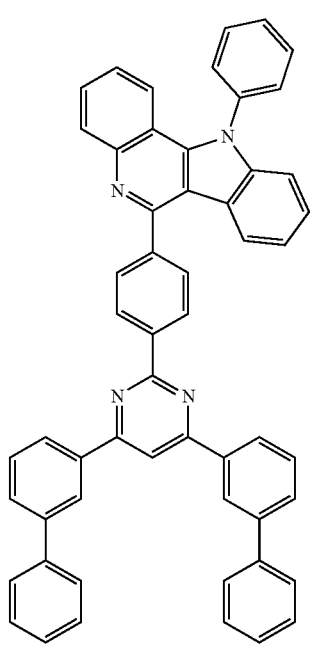

391
-continued
76
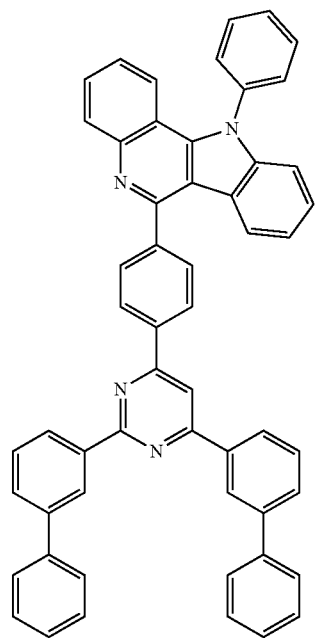
392
-continued
78
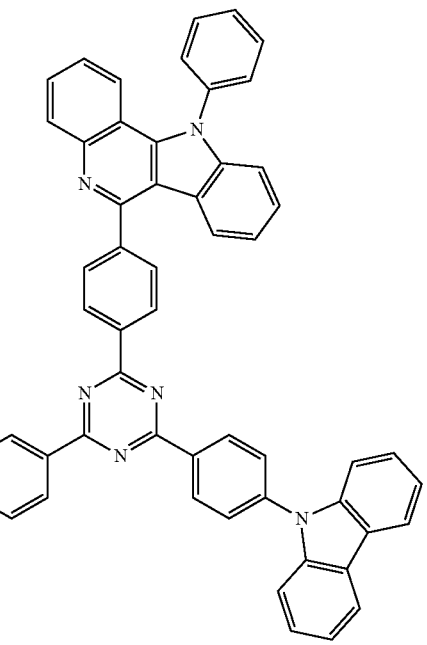
77
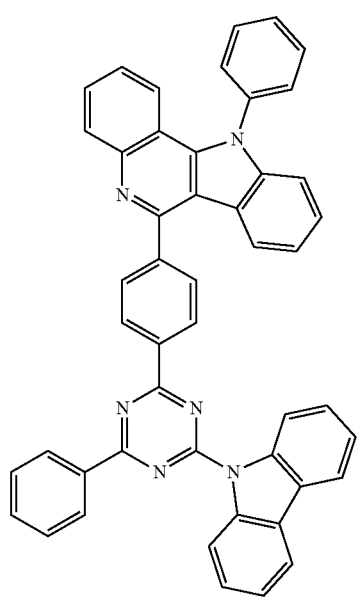
79
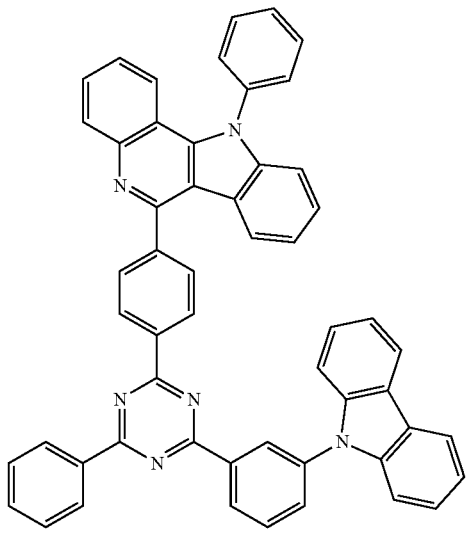

393
-continued
80
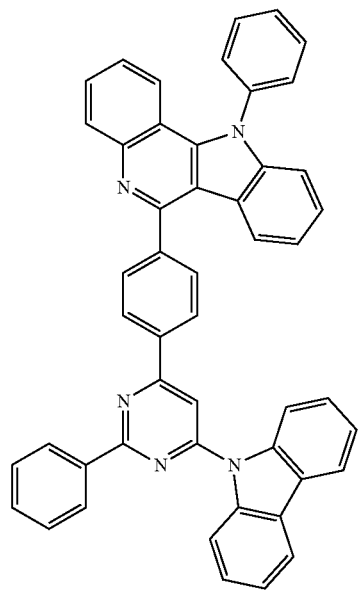
394
-continued
82
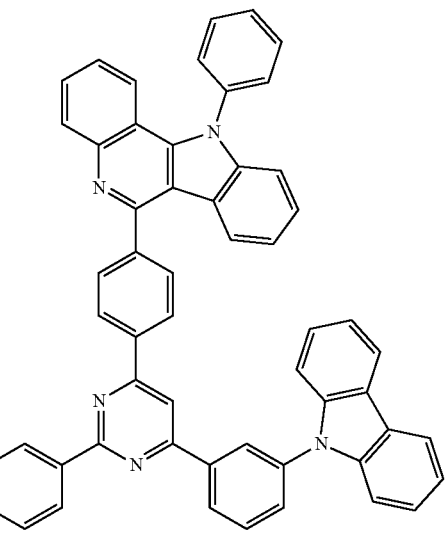
81
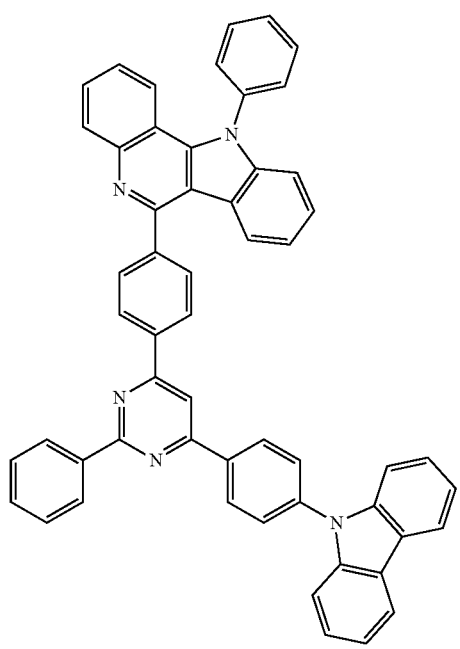
83
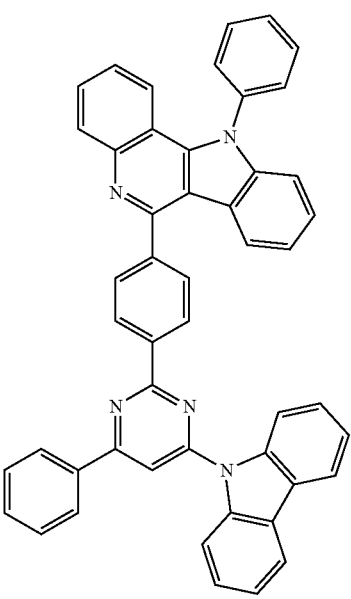

395
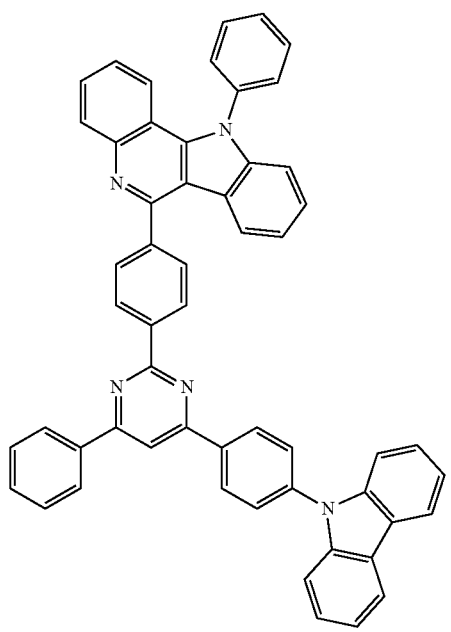
84
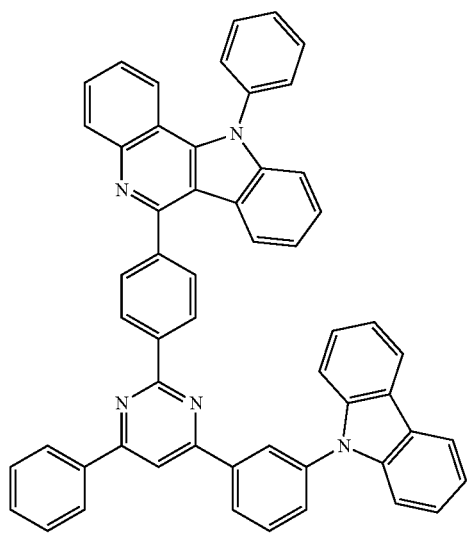
85
396
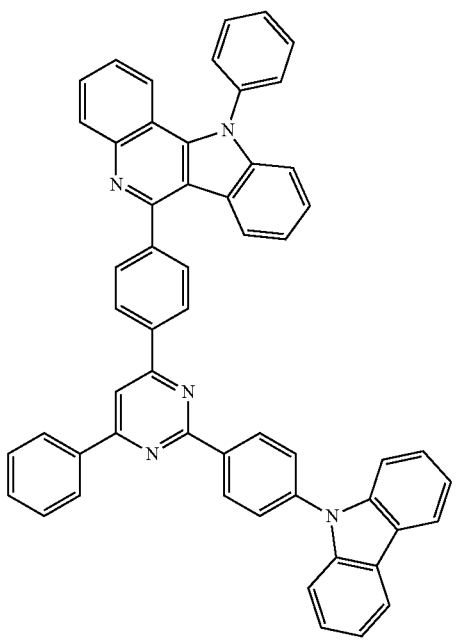
86
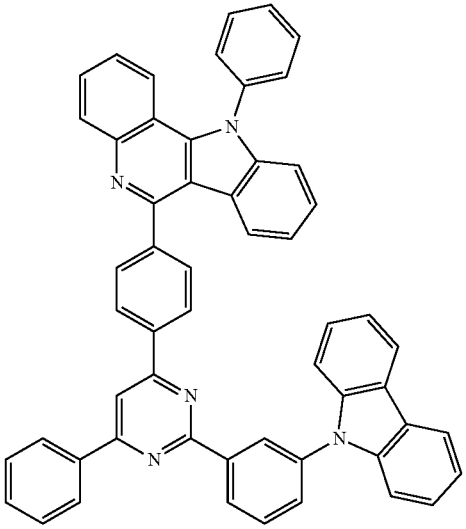
87

397
-continued
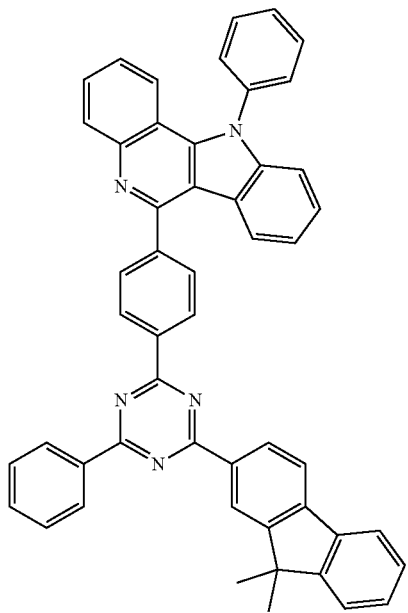
88
89
398
-continued
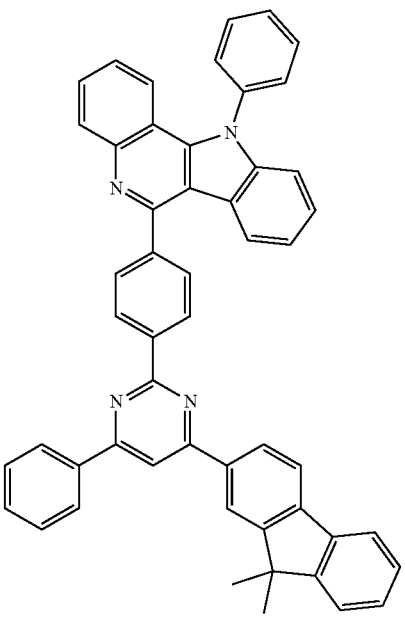
90
91

399
-continued
92
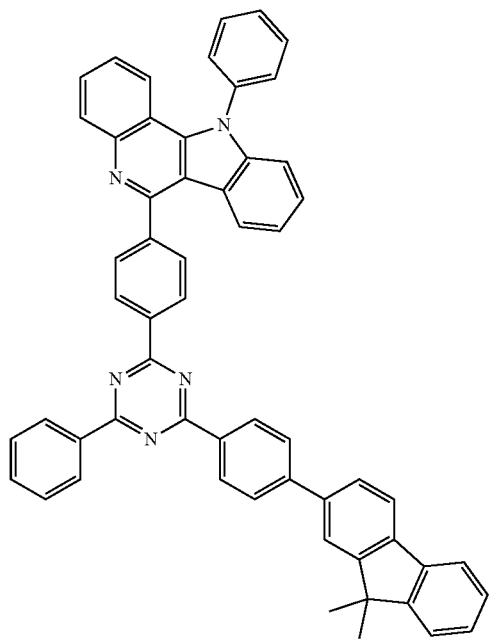
93
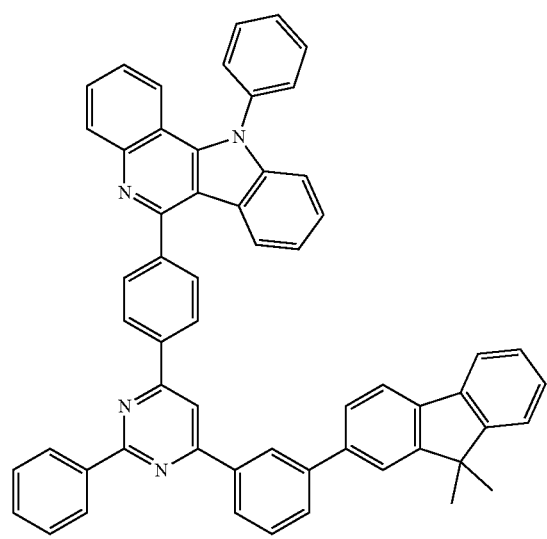
400
-continued
94
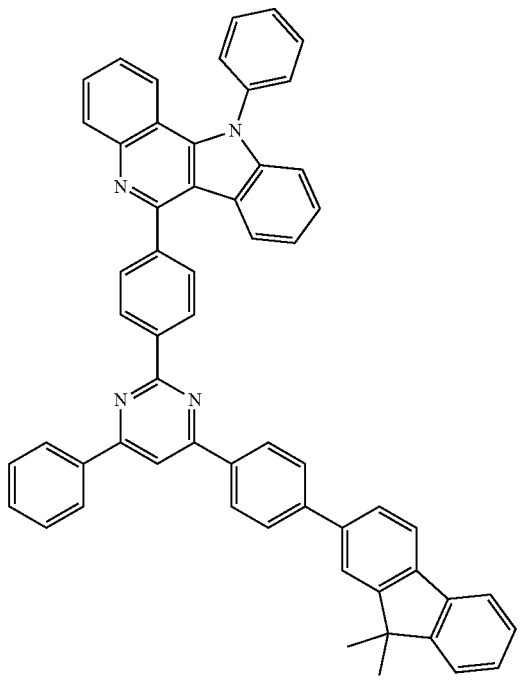
95
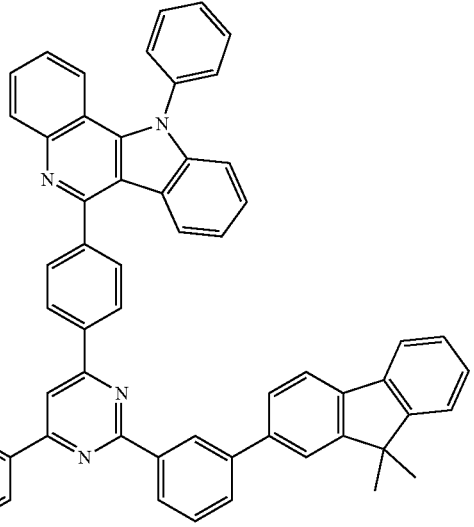

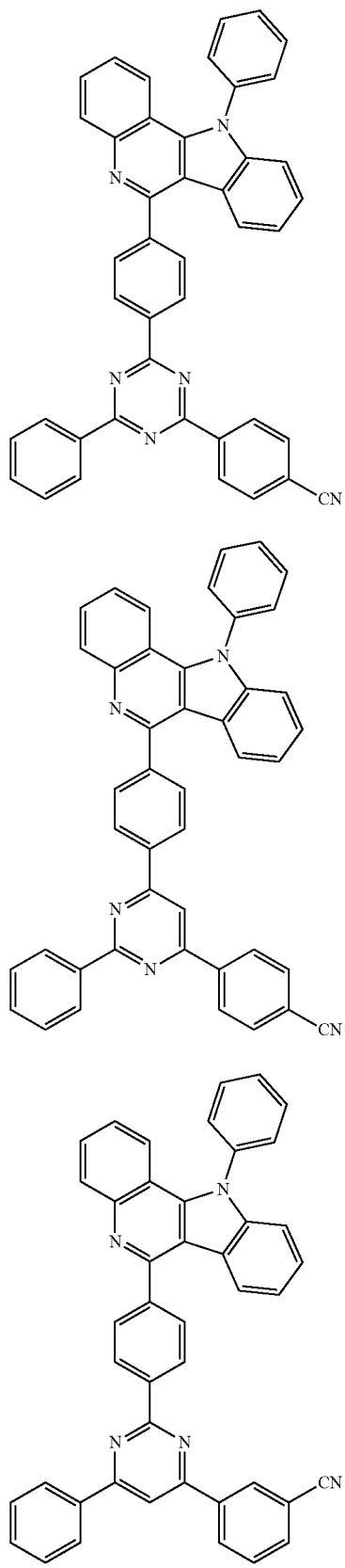

403
-continued
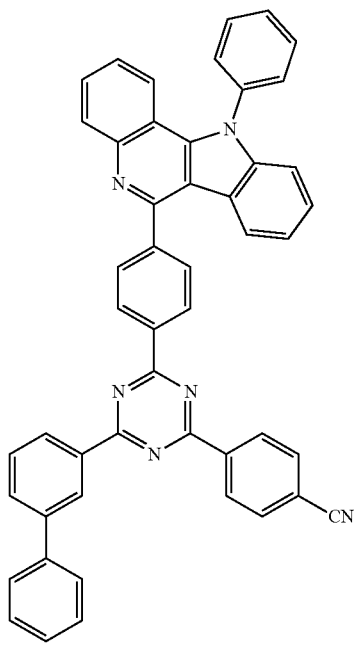
404
-continued
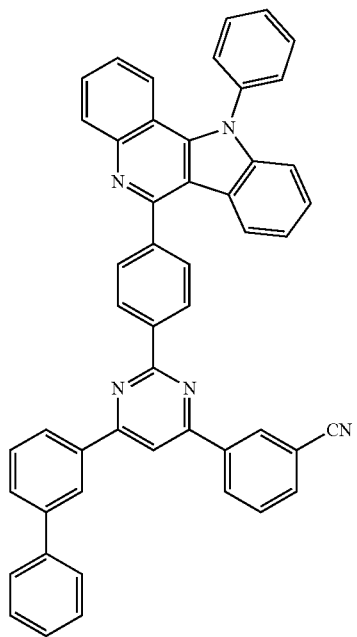
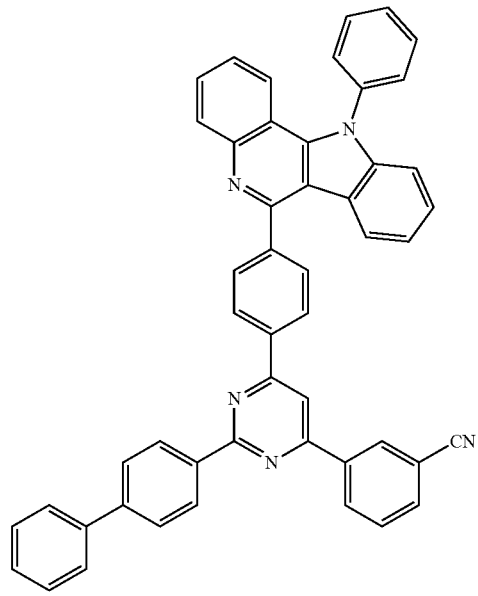

405
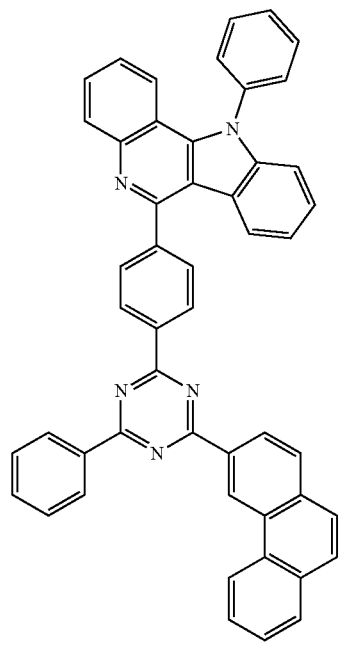
406
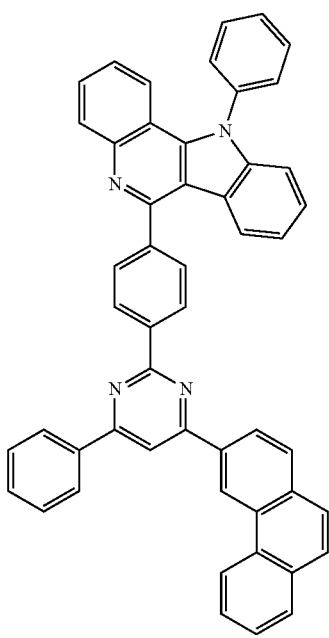
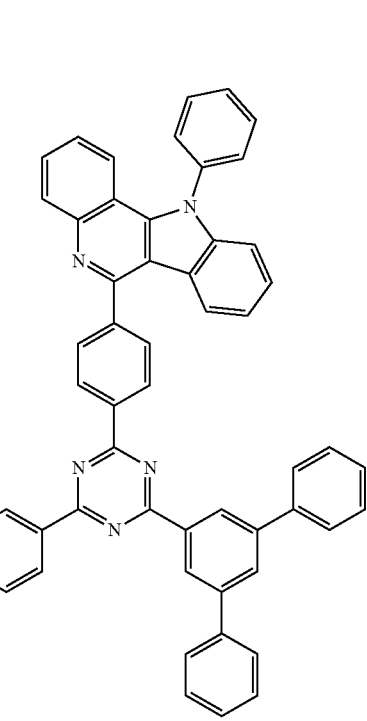

109
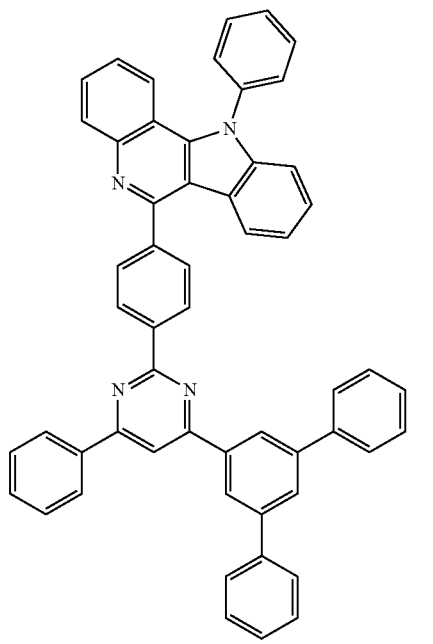
110
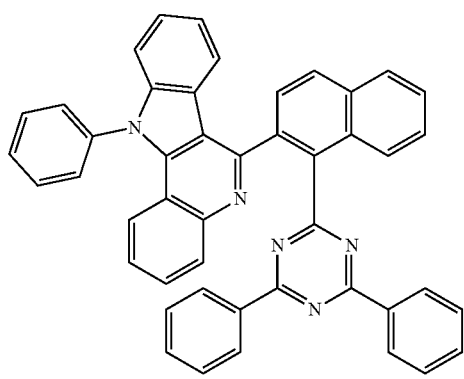
111
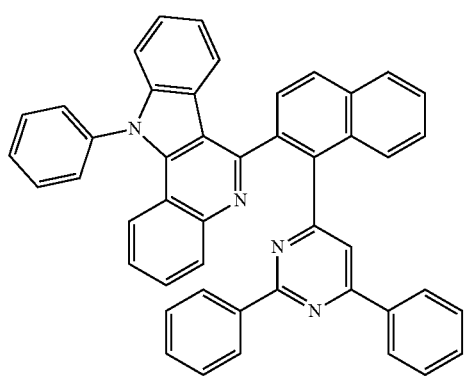
112
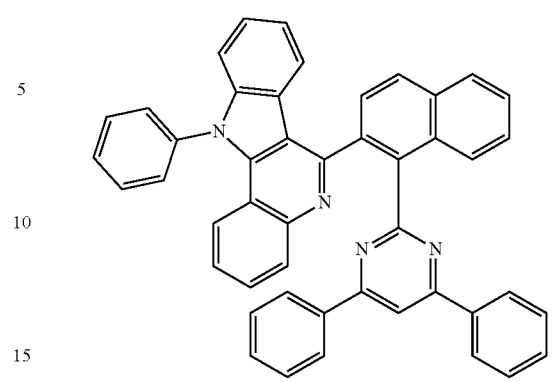
113
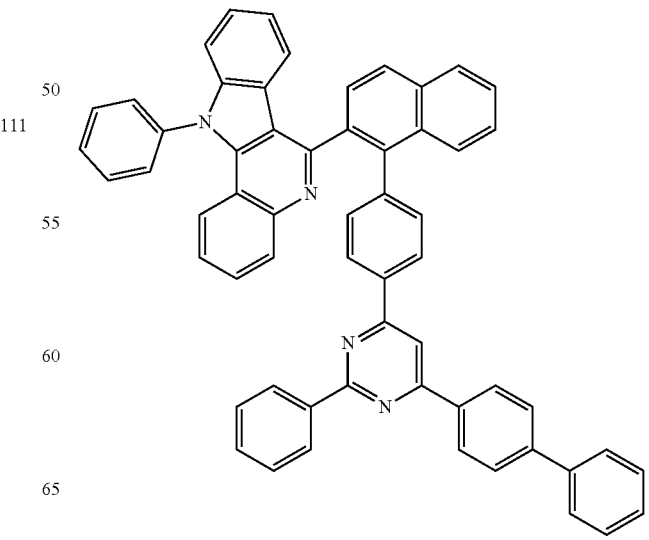
114

409
-continued
115
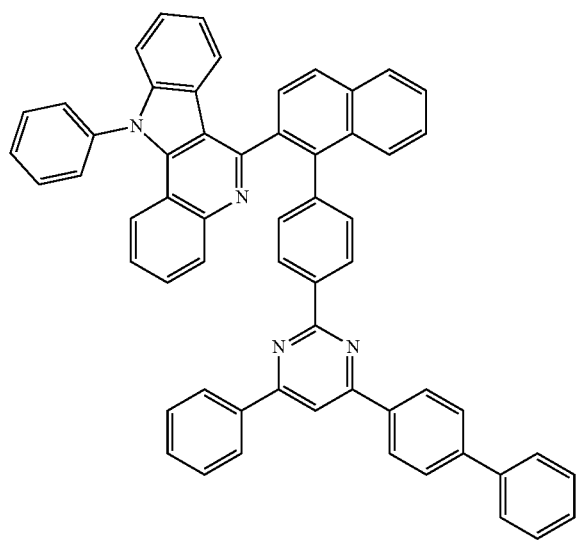
116
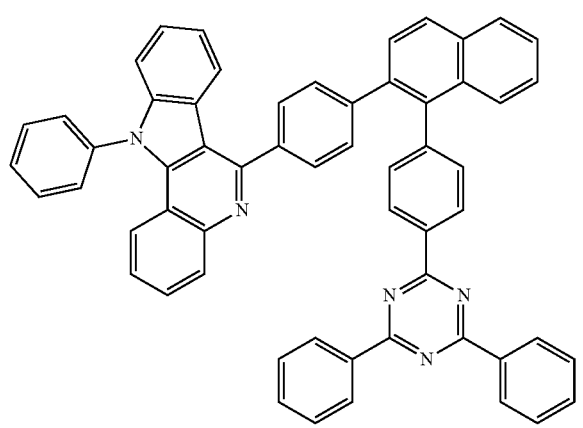
117
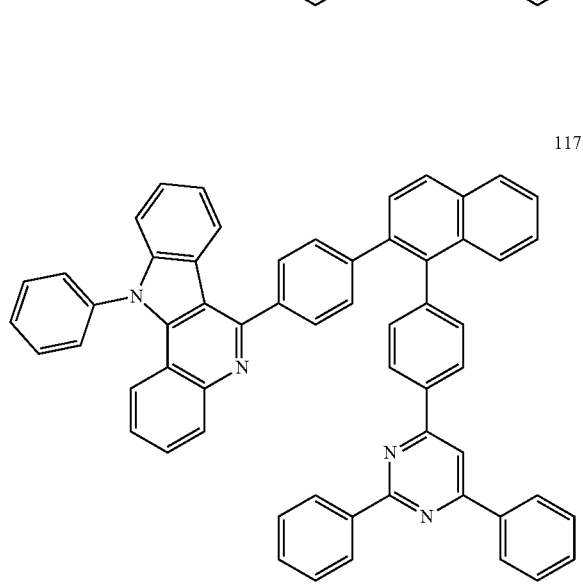
410
-continued
118
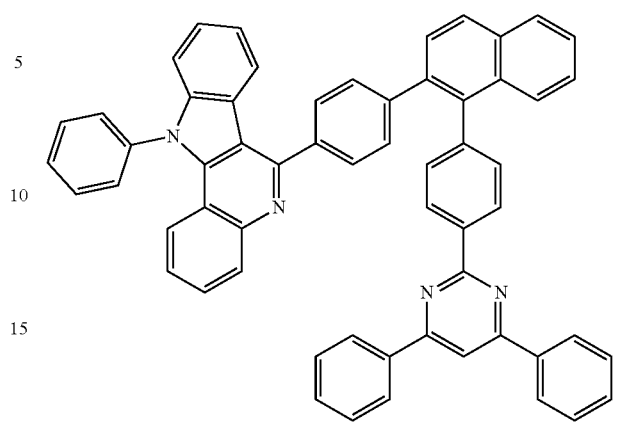
119
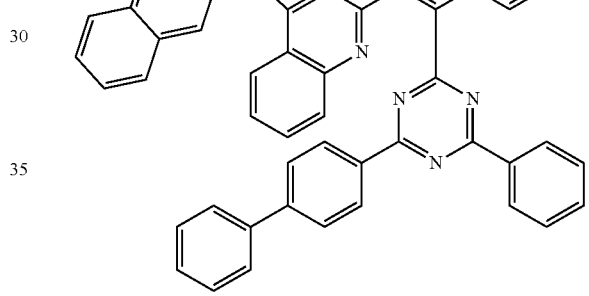
120
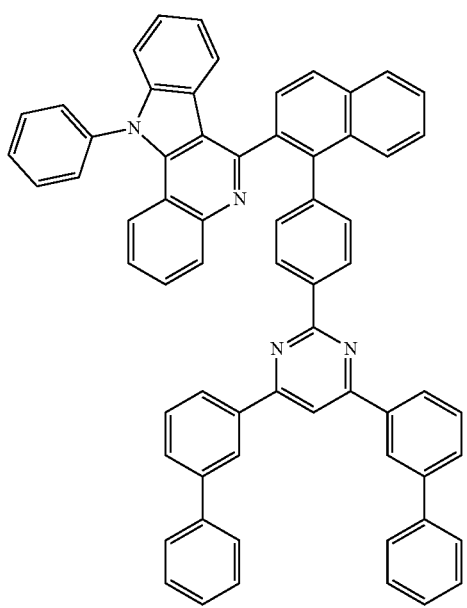

411
-continued
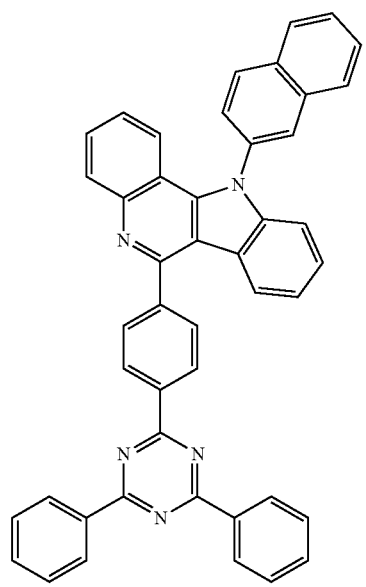
121
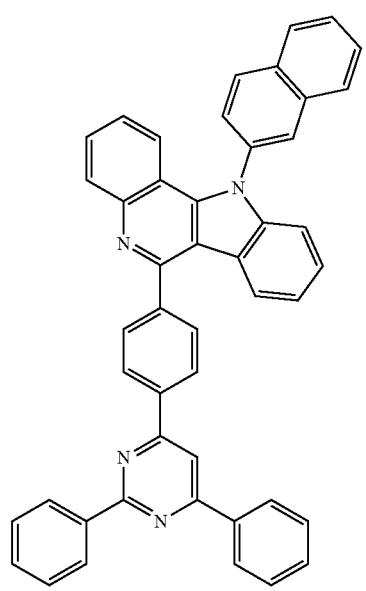
122
412
-continued
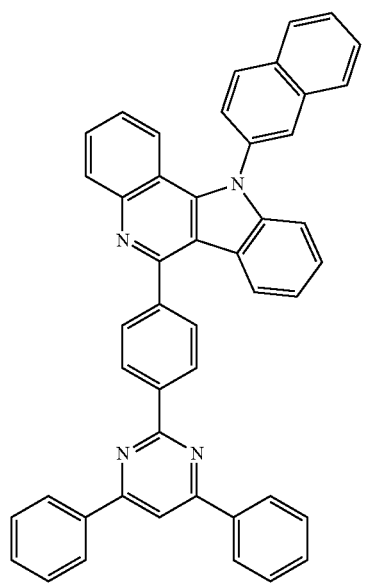
123
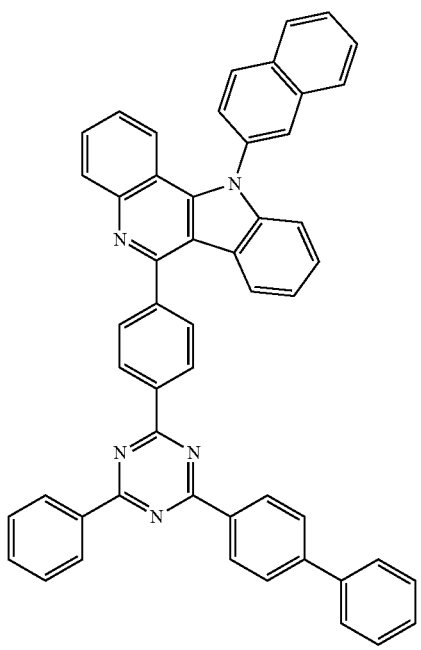
124

-continued
125
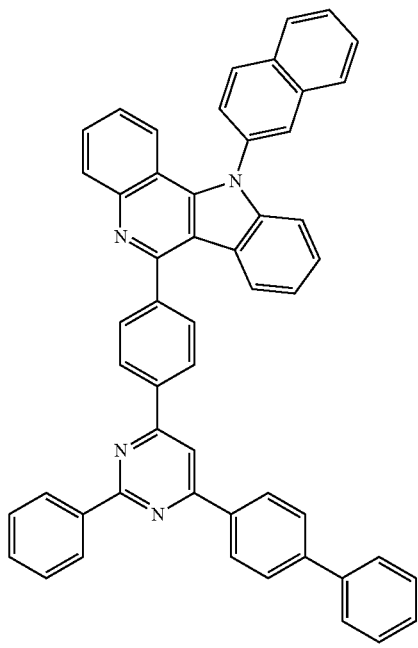
127
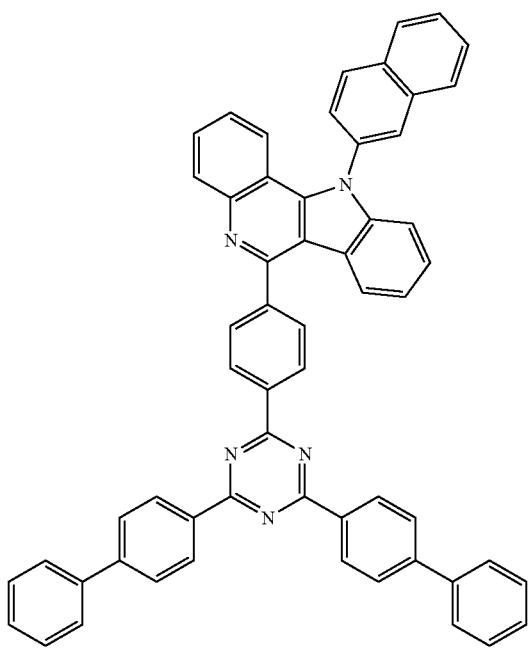
126
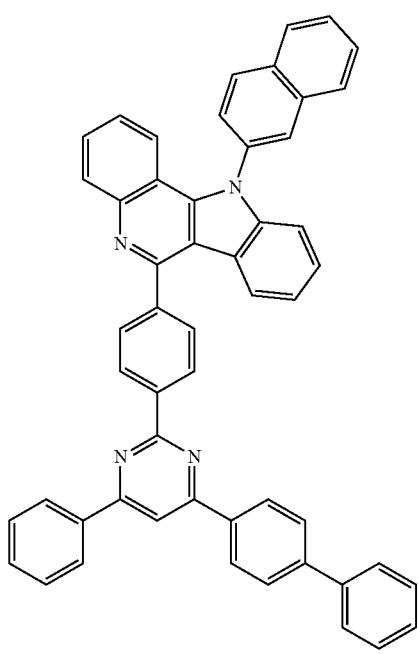
128
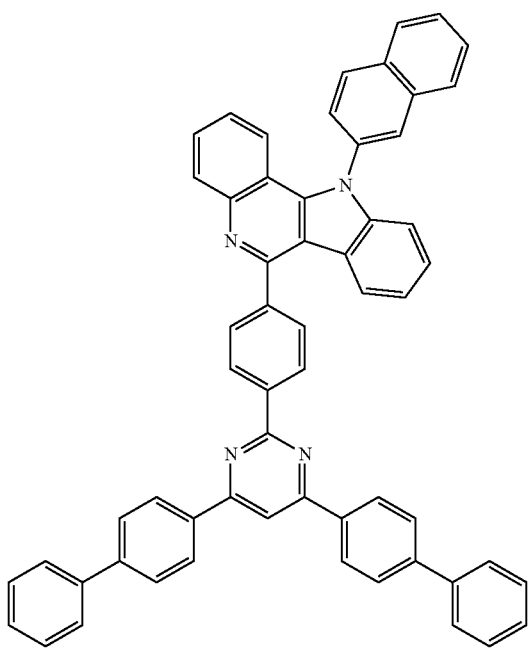

129
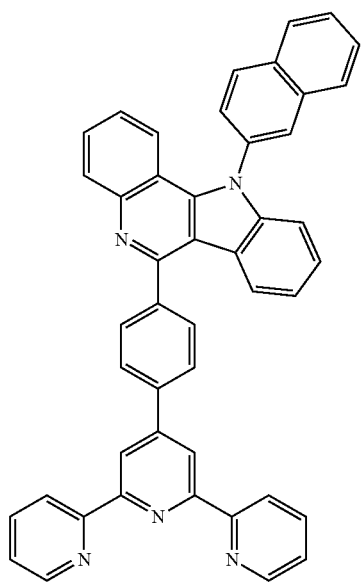
130
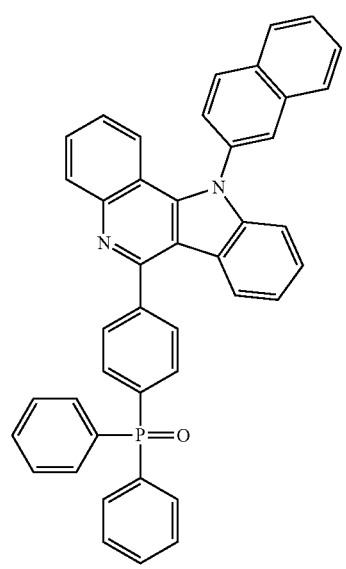
131
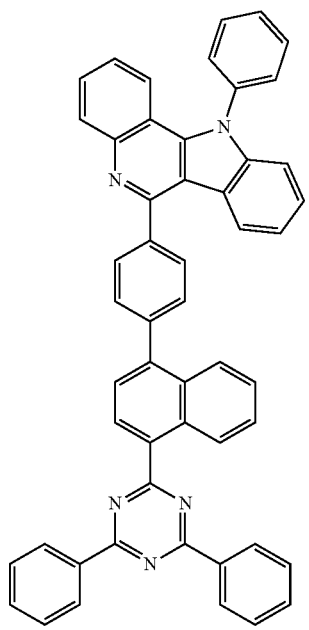
132
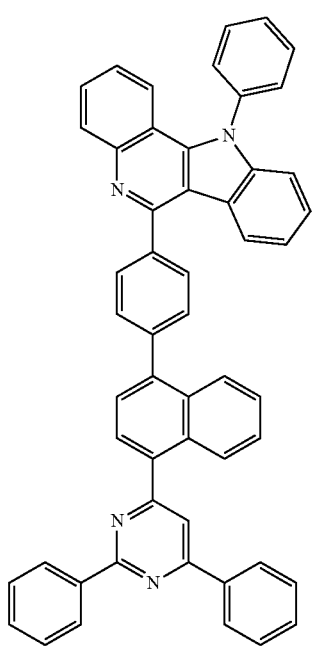

417
-continued
133
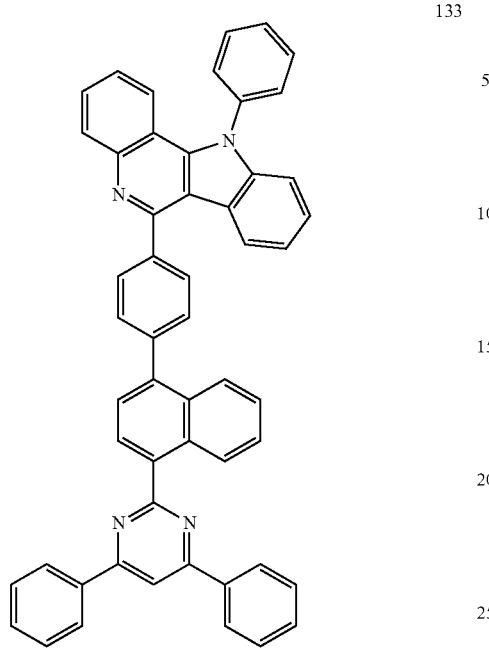
134
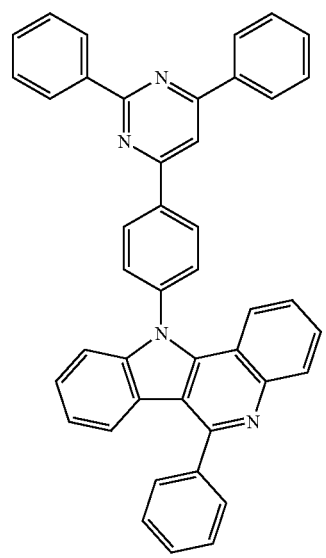
418
-continued
135
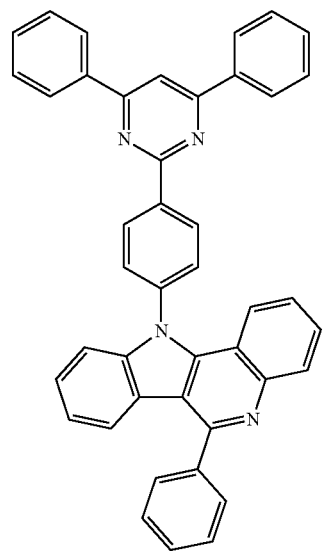
136

419
-continued
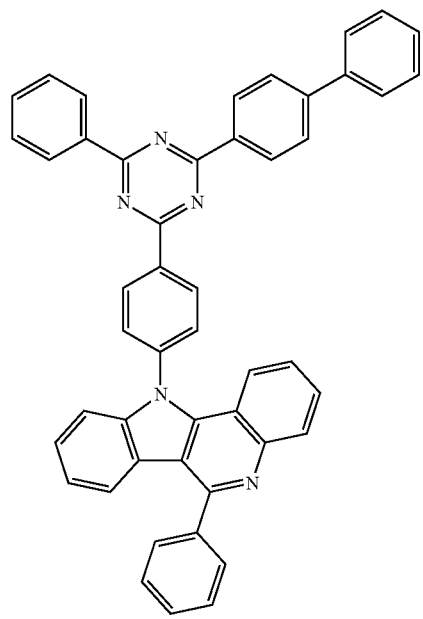
137
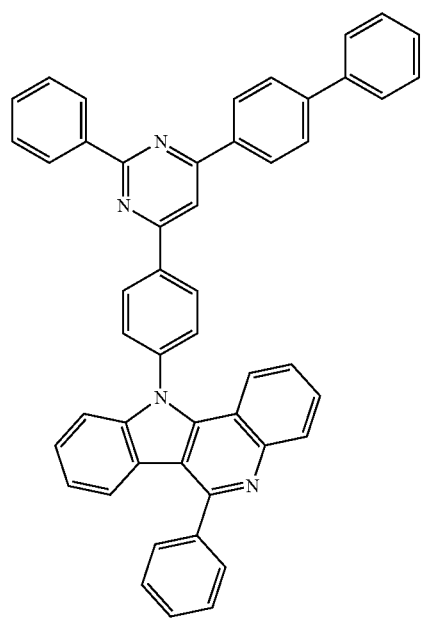
138
420
-continued
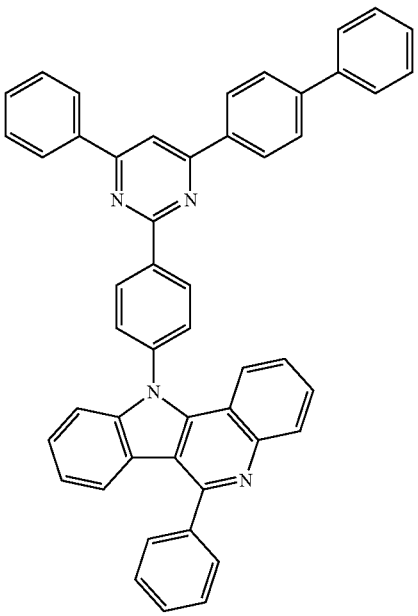
139
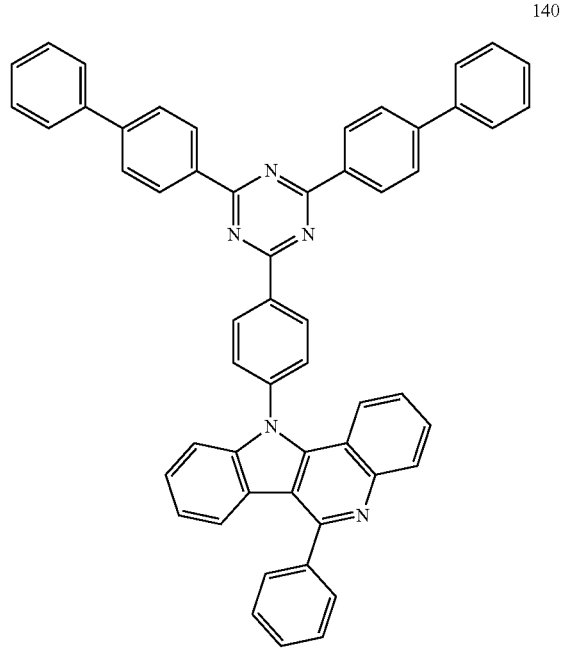
140

421
-continued
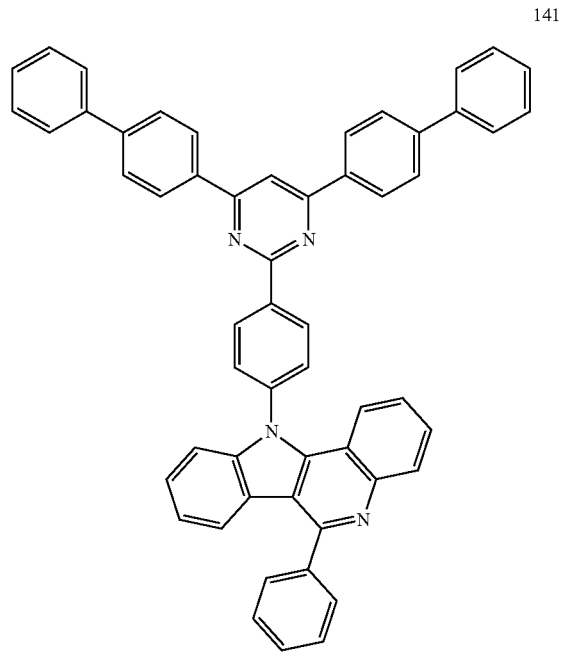
141
422
-continued
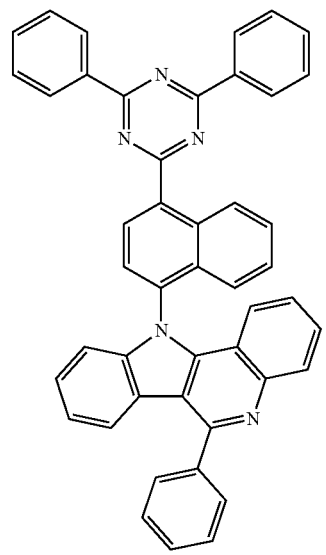
143
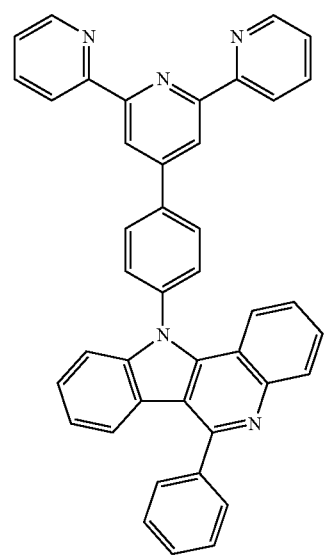
142
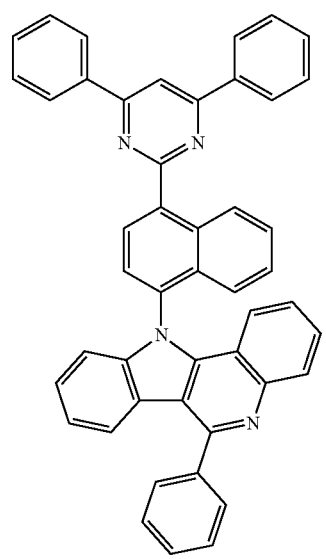
145

423
-continued
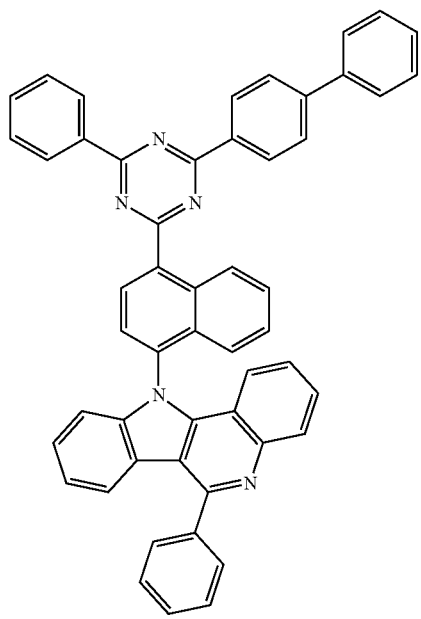
146
424
-continued
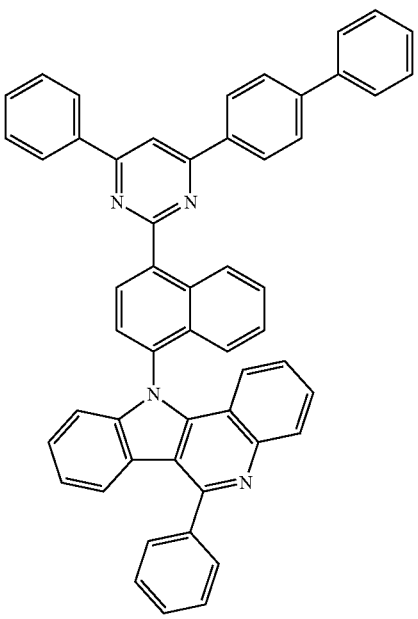
148
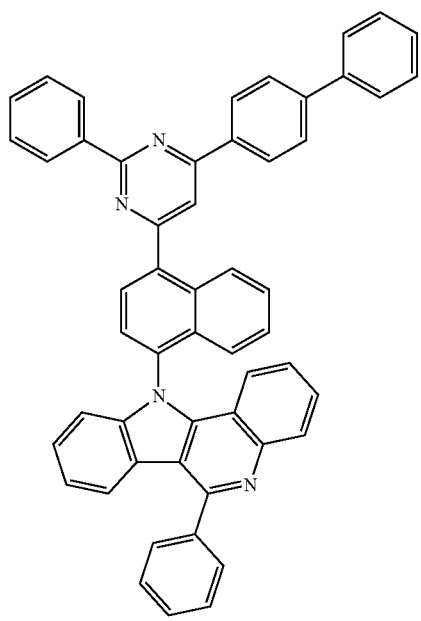
147
149

425
-continued
150
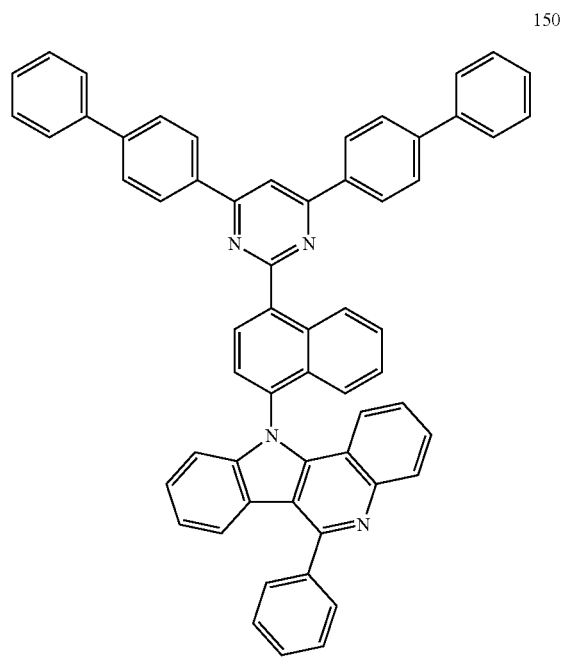
151
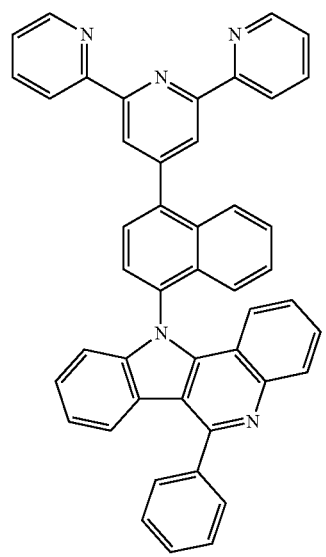
426
-continued
152
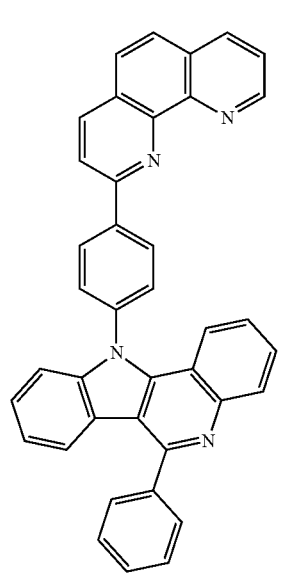
153
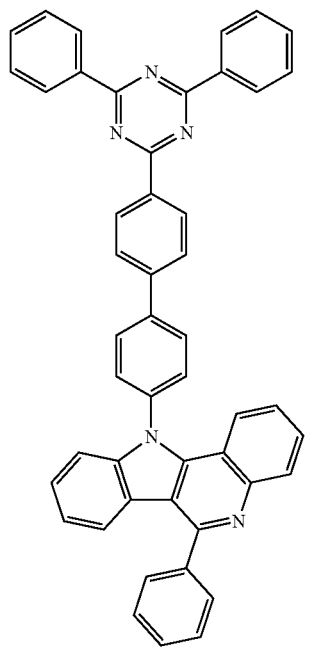

427
-continued
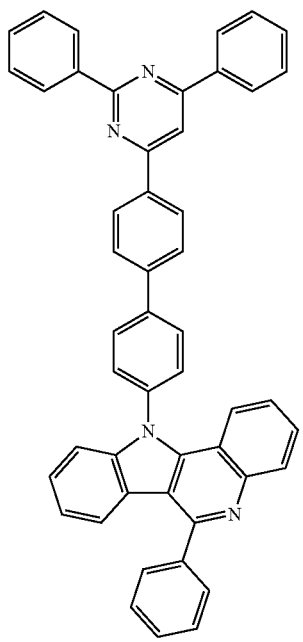
154
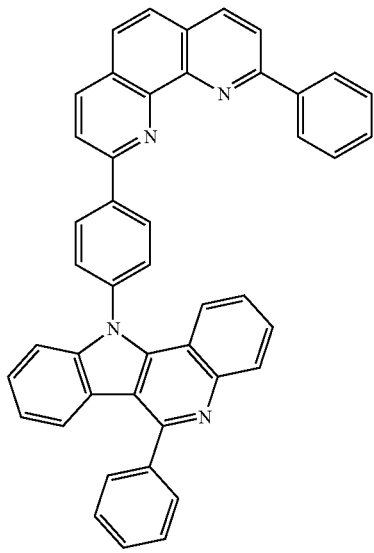
156
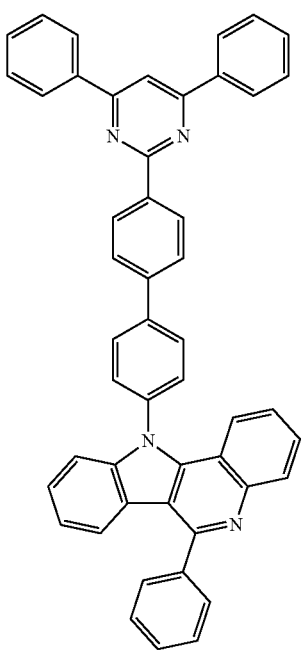
155
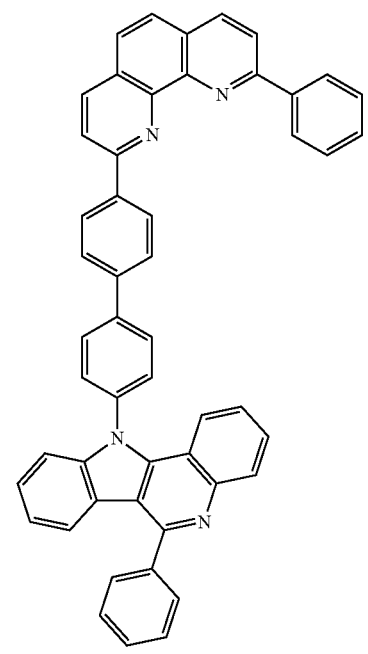
157
428
-continued 429
-continued
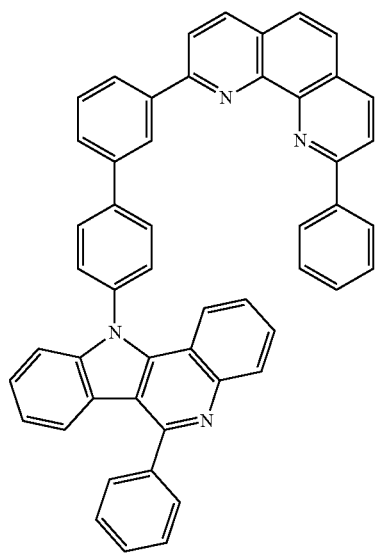
158
430
-continued
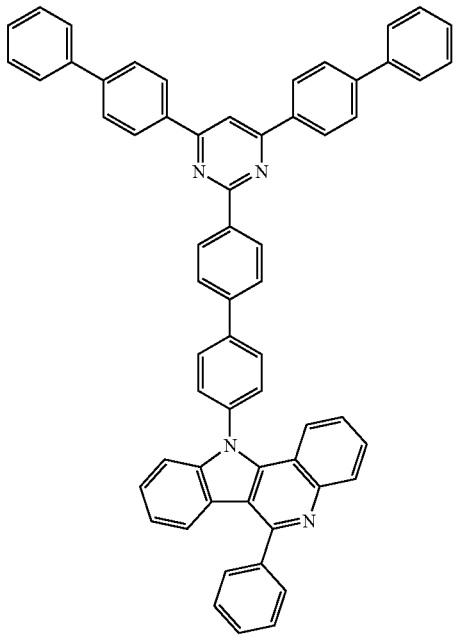
160
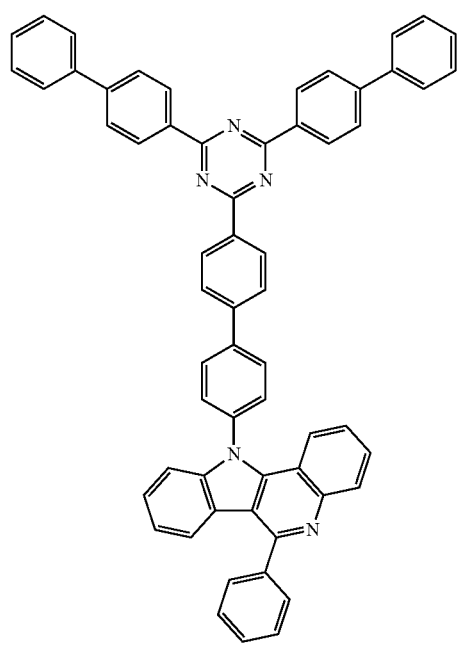
159
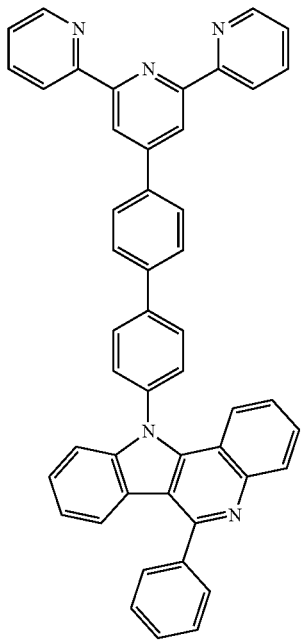
161

431
-continued
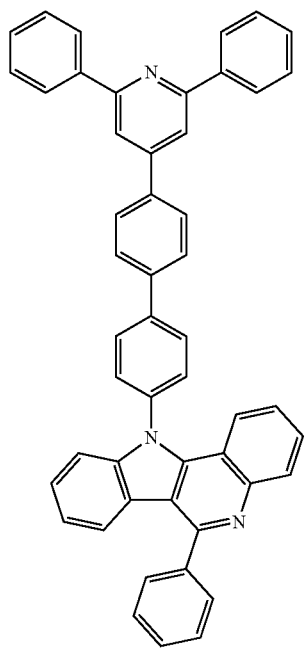
162
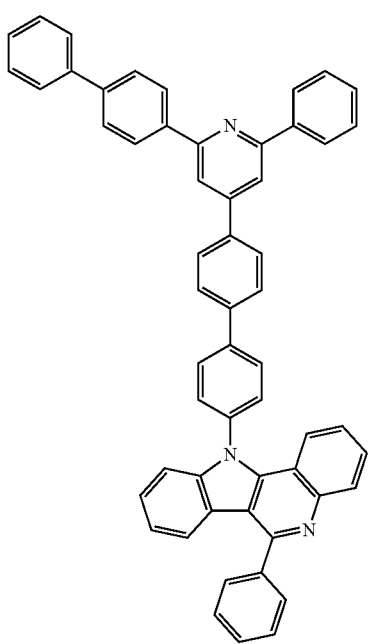
163
432
-continued
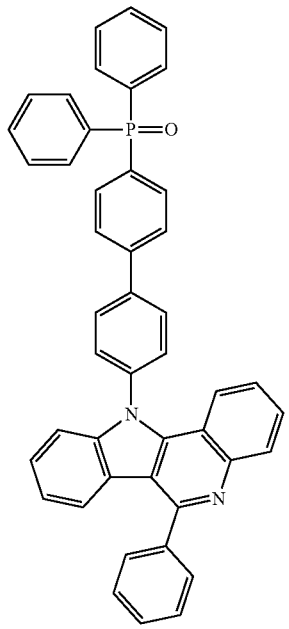
164
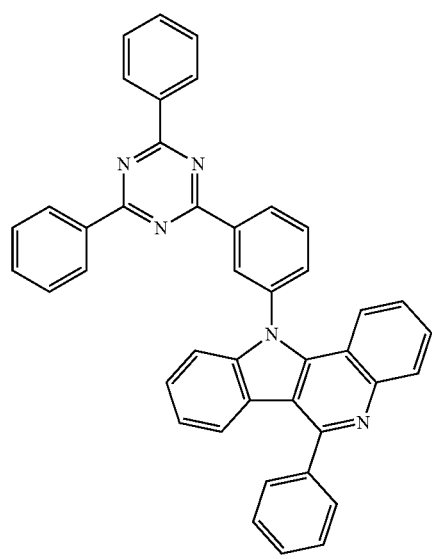
165

433
-continued
166
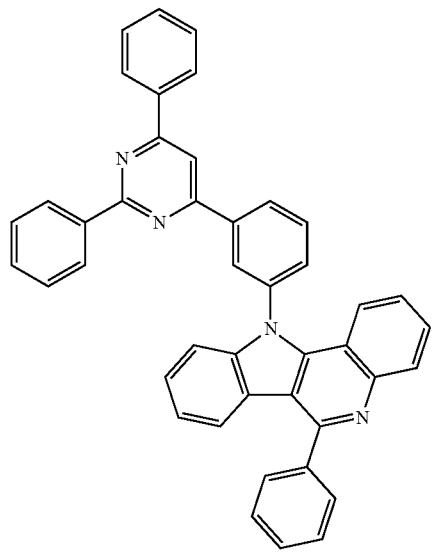
167
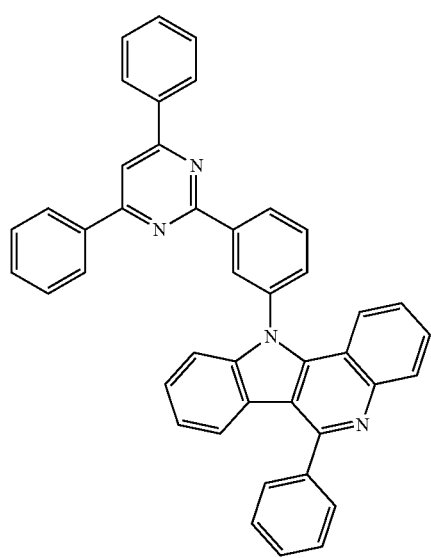
434
-continued
168
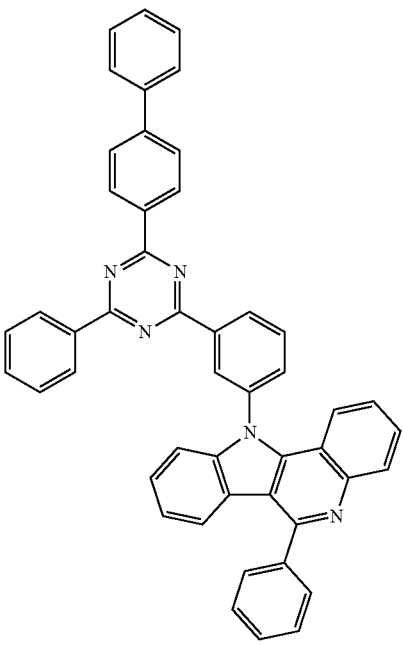
169
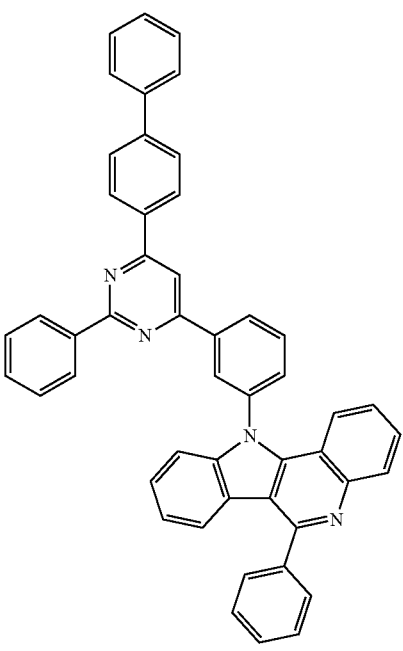

435
-continued
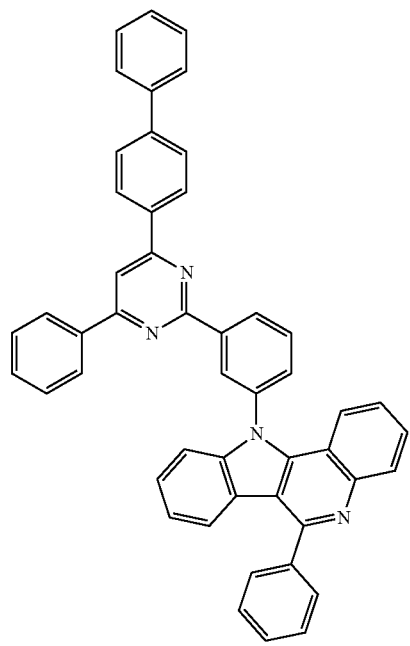
170
436
-continued
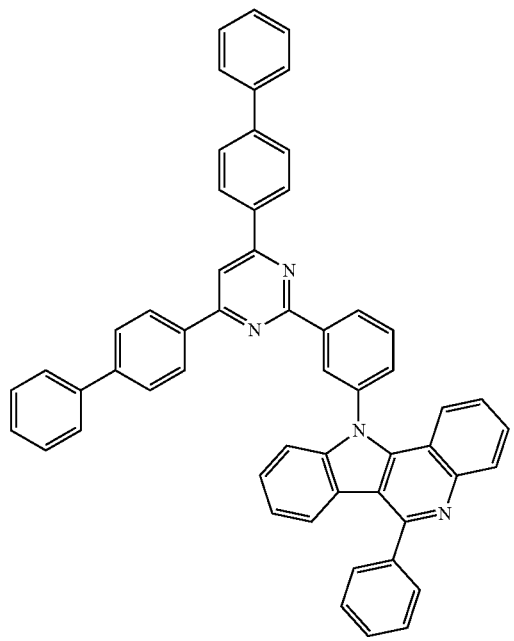
172
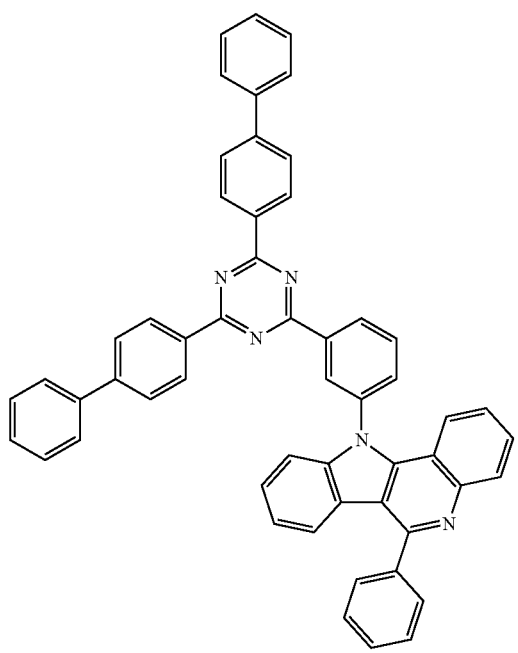
171
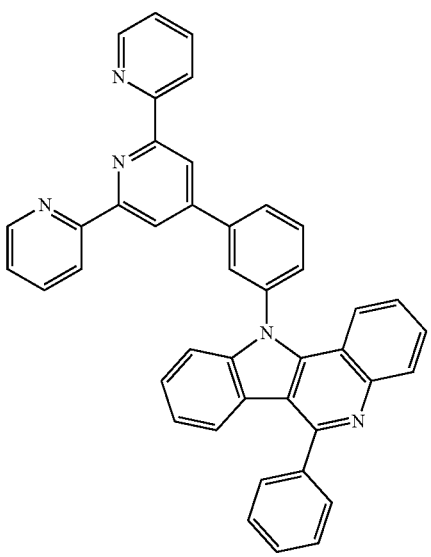
173

-continued
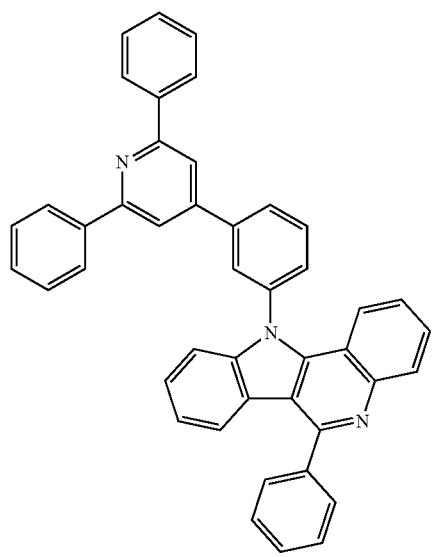
174
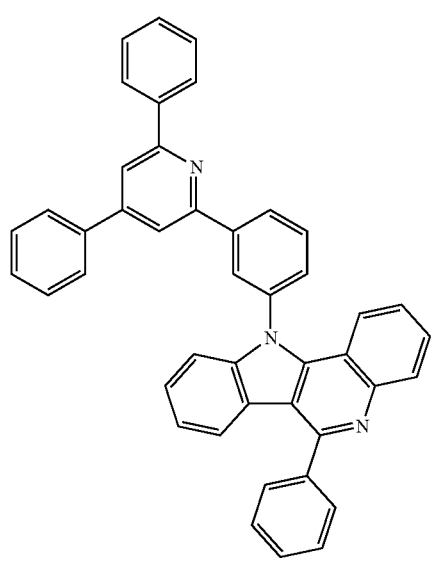
175
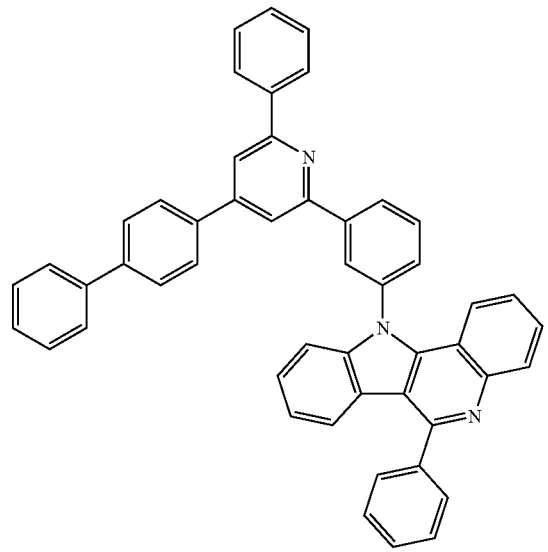
176
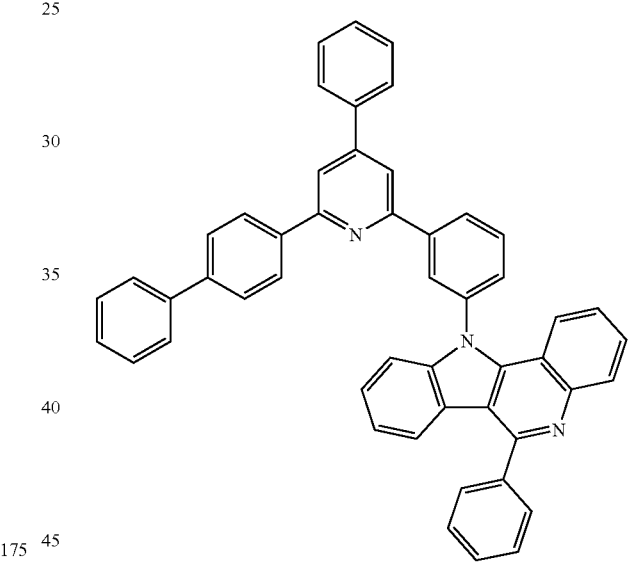
177
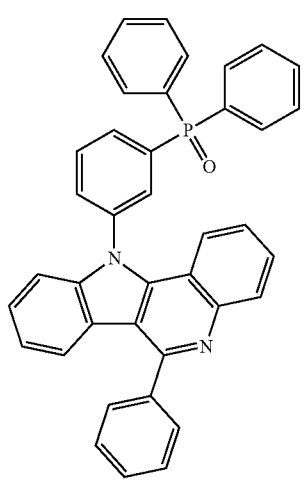
178

439
179
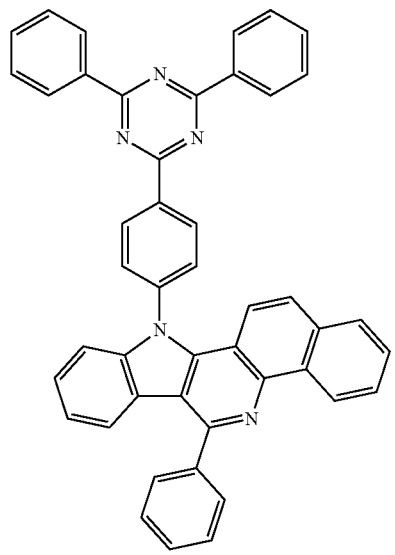
180
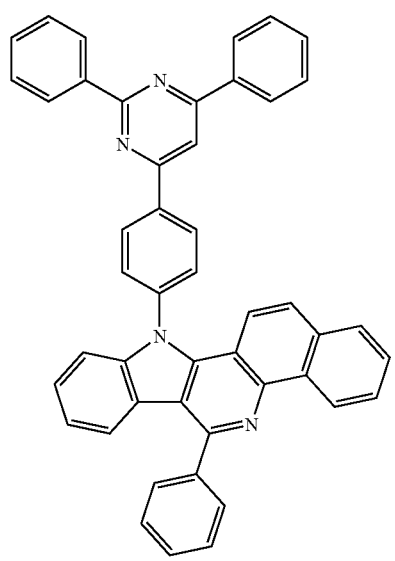
181
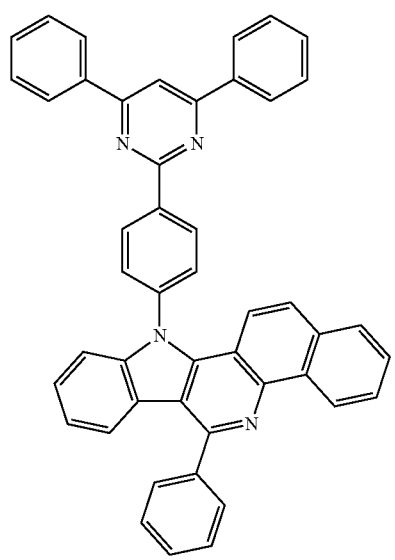
440
182
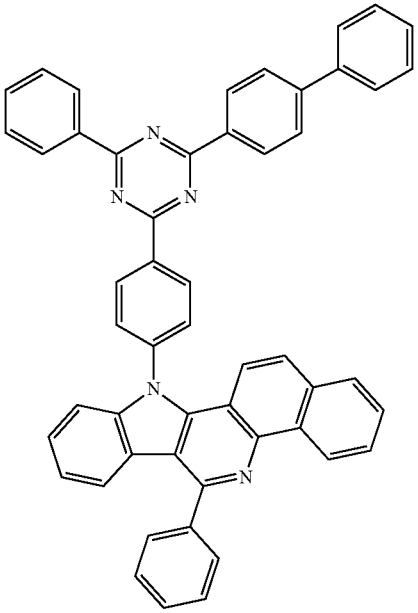
183
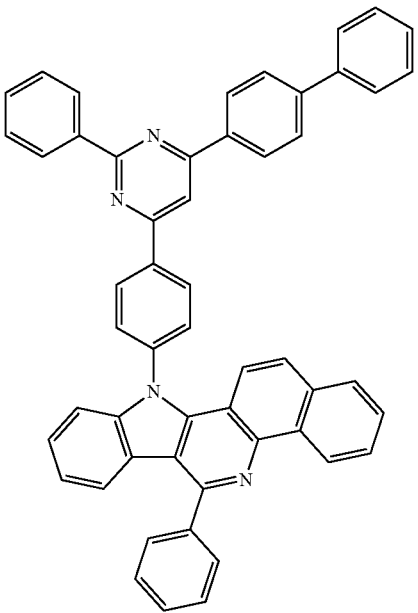

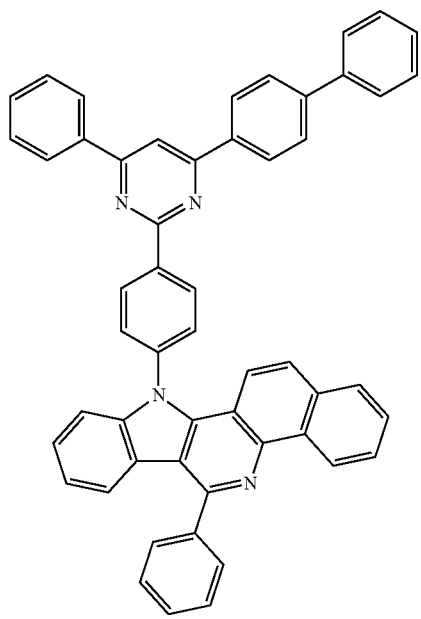
184
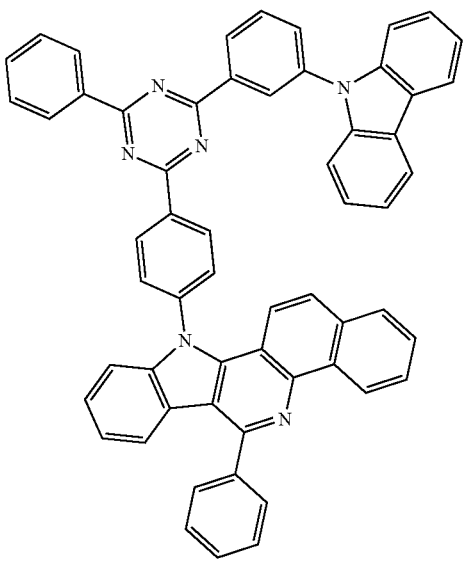
186
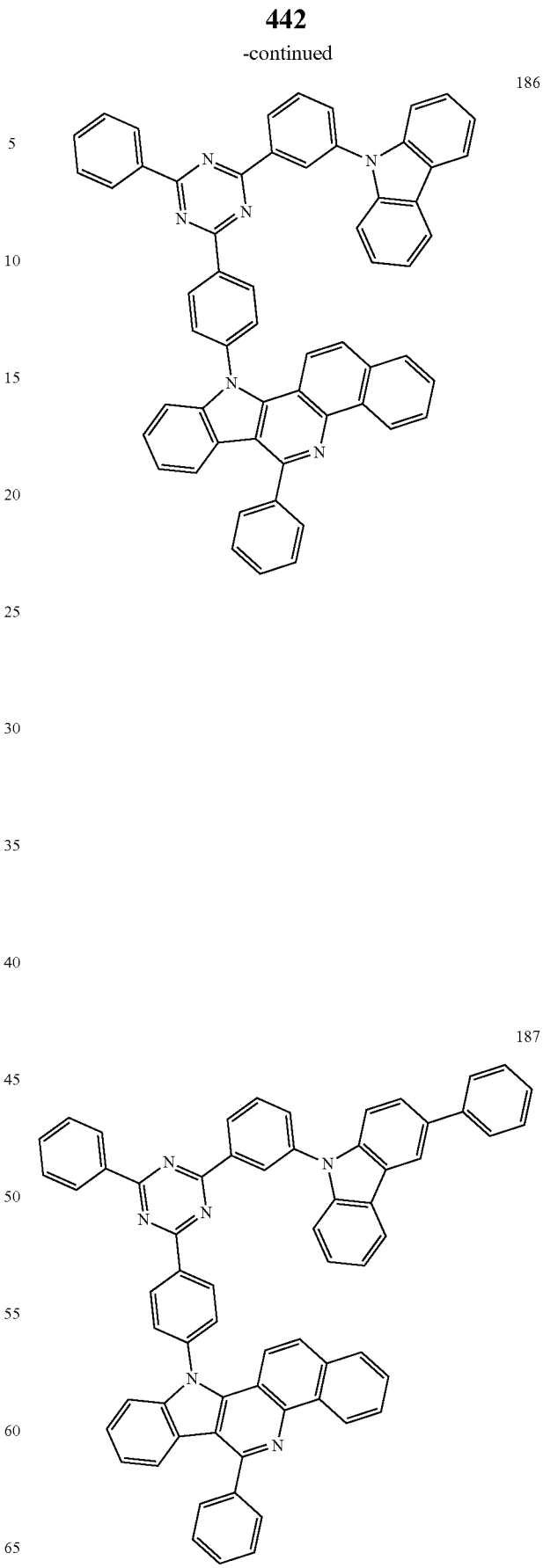
185
187

443
-continued
444
-continued
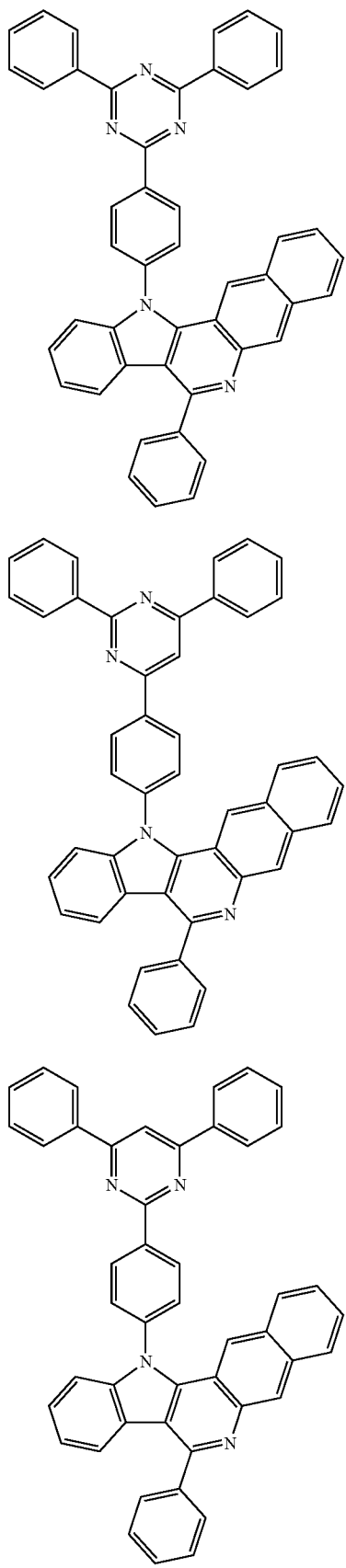
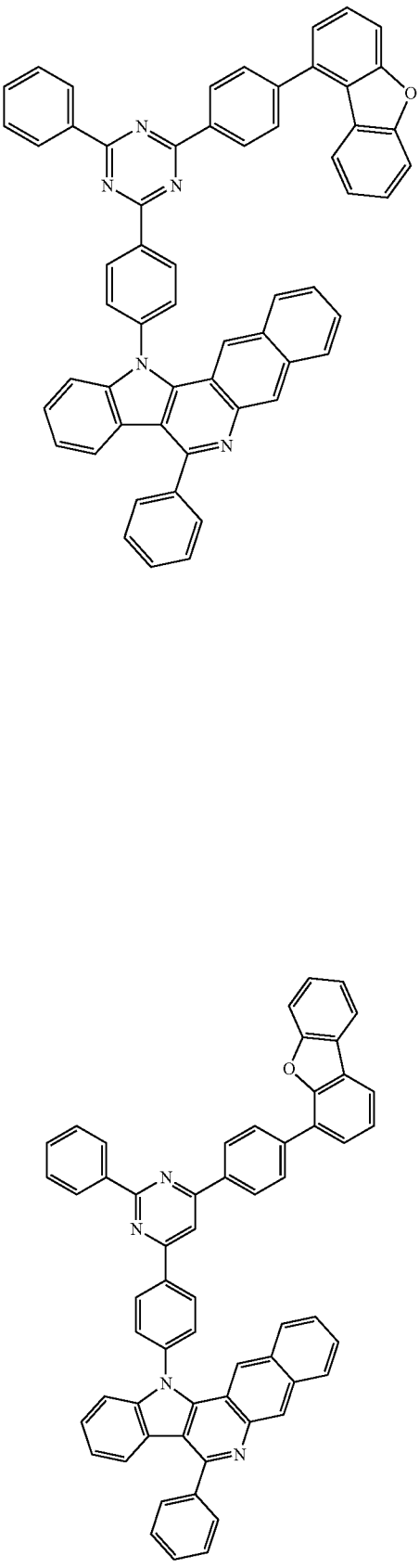

193
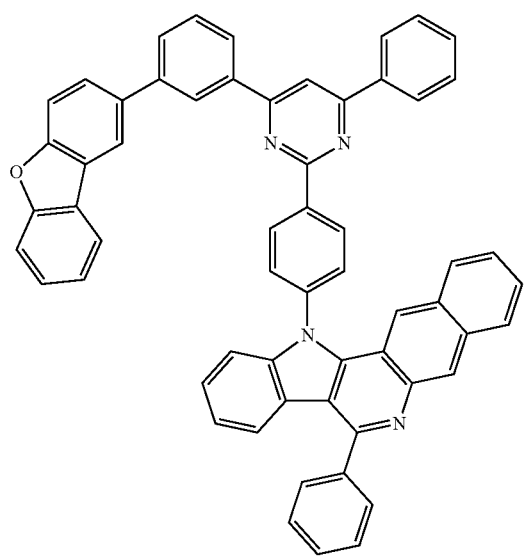
195
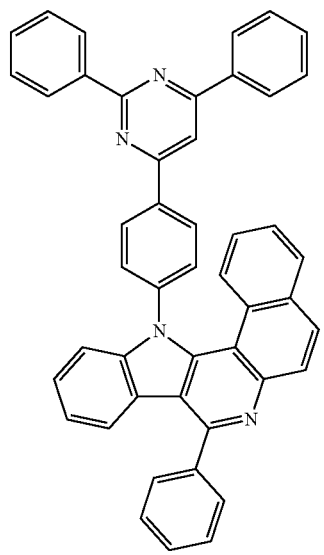
194
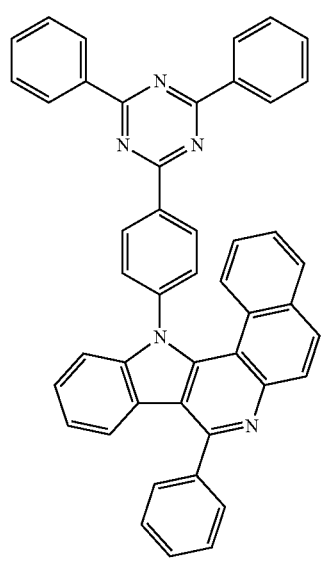
196
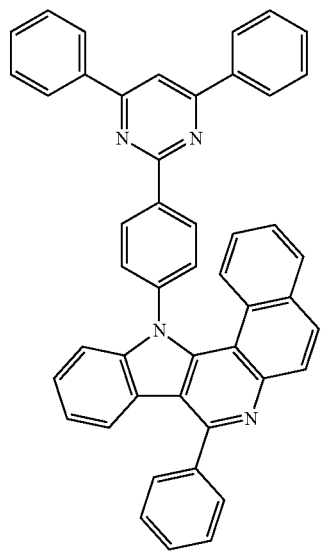

447
-continued
197
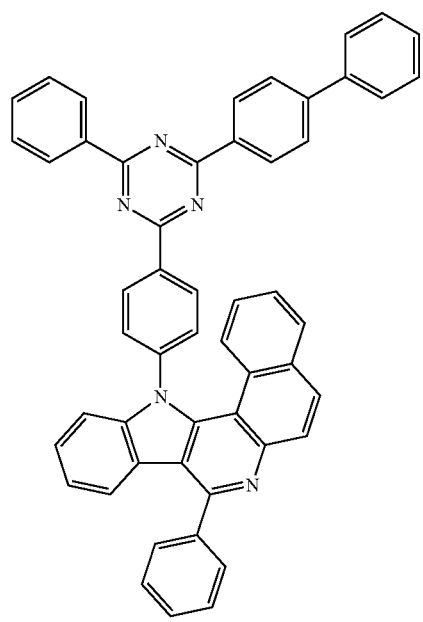
198
448
-continued
199
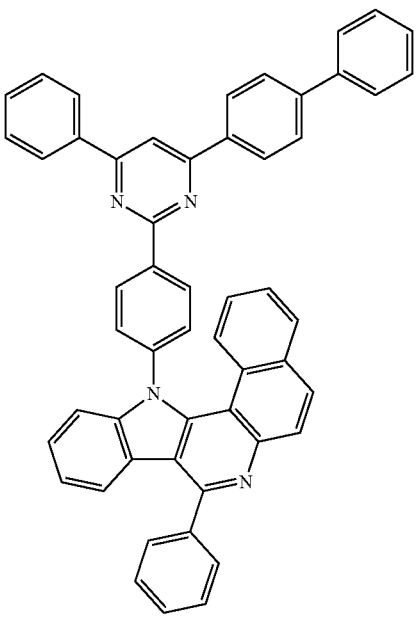
200
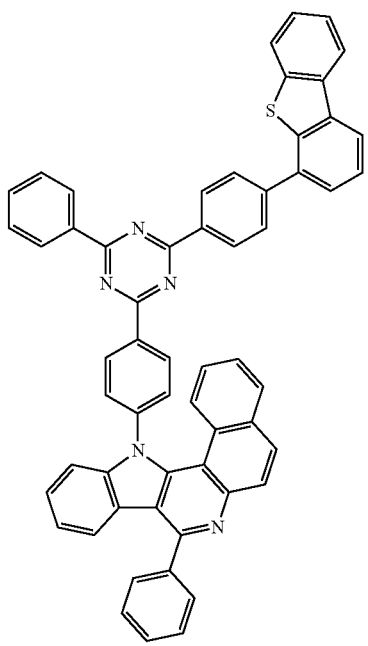

449
-continued
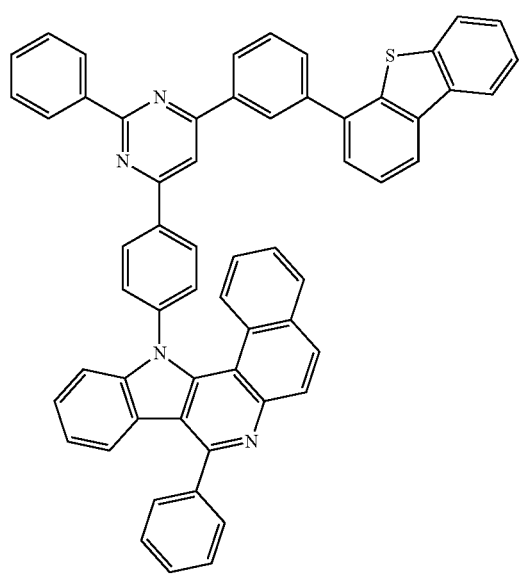
201
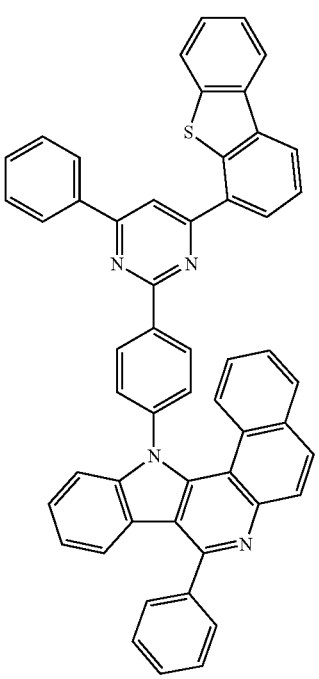
202
450
-continued
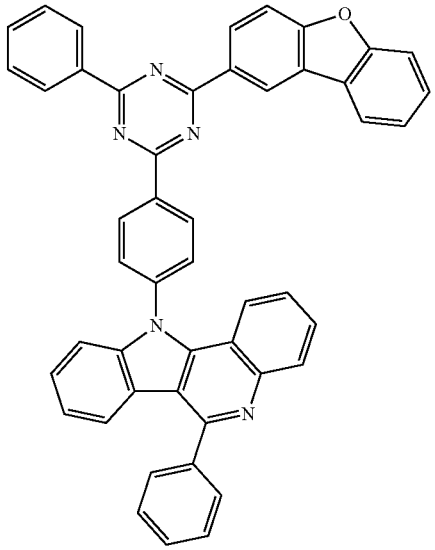
203
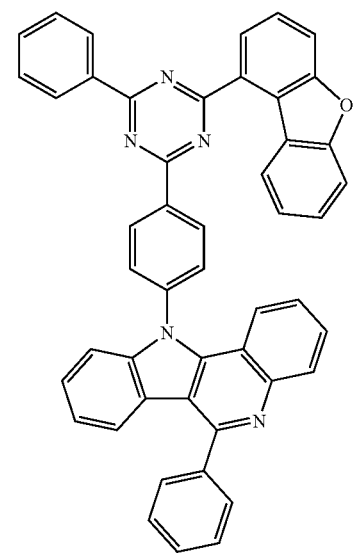
204

-continued
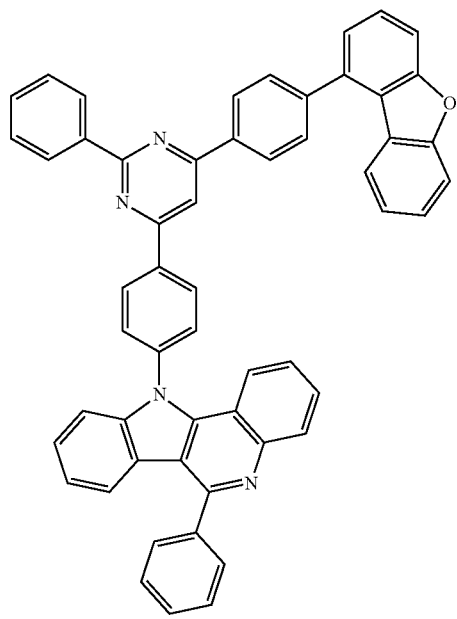
205
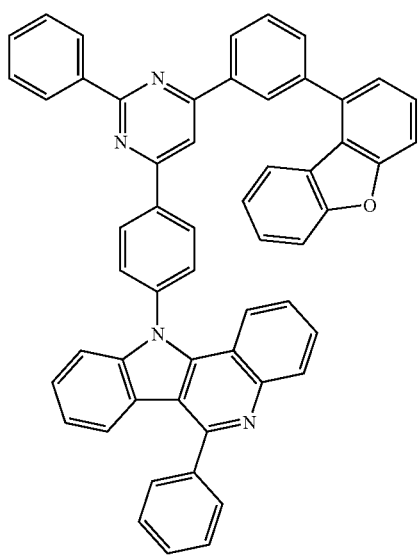
206
-continued
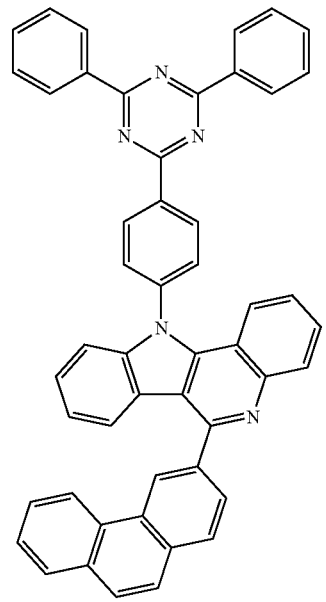
207
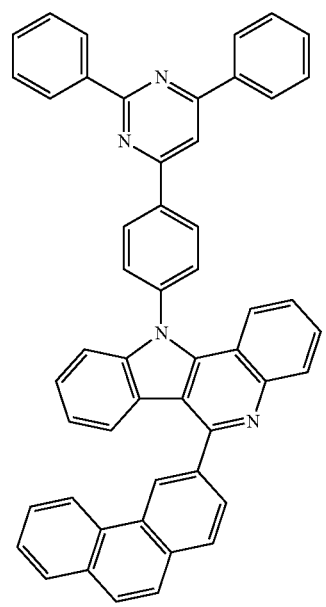
208

453
-continued
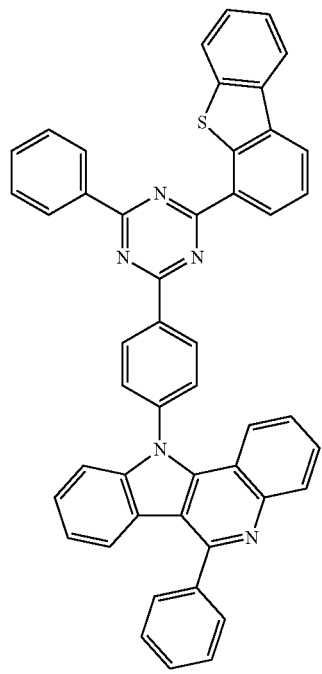
209
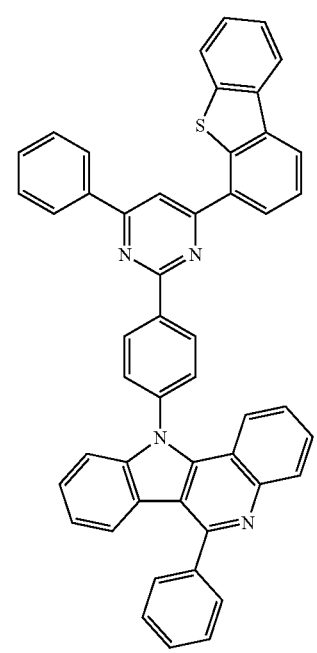
210
454
-continued
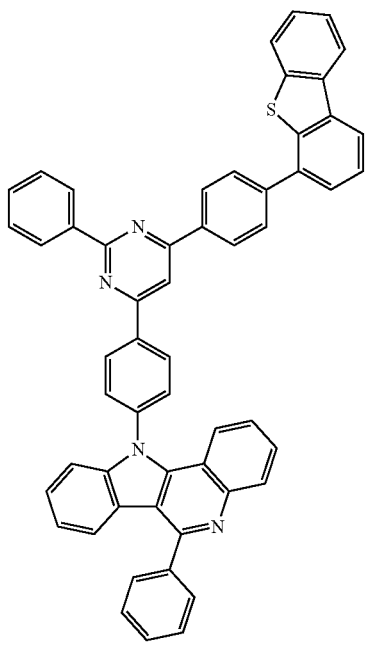
211
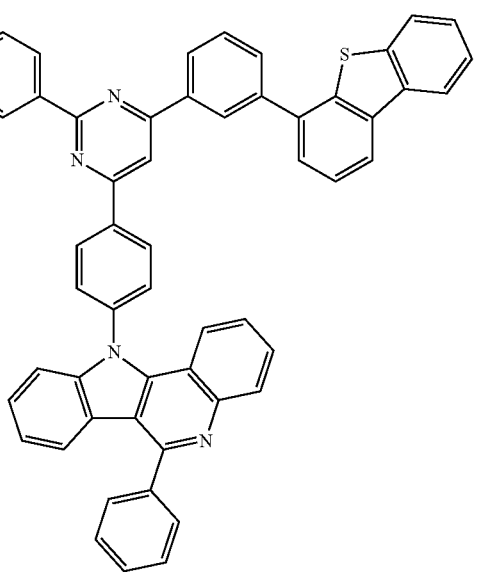
212

455
-continued
213
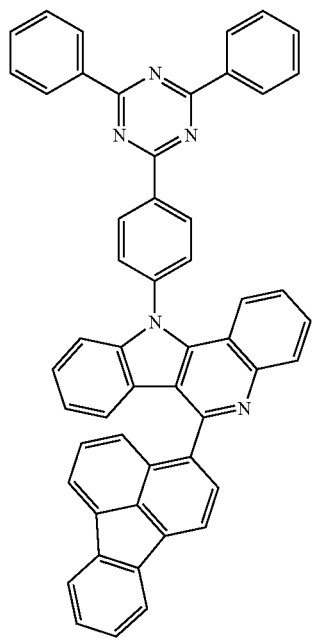
214
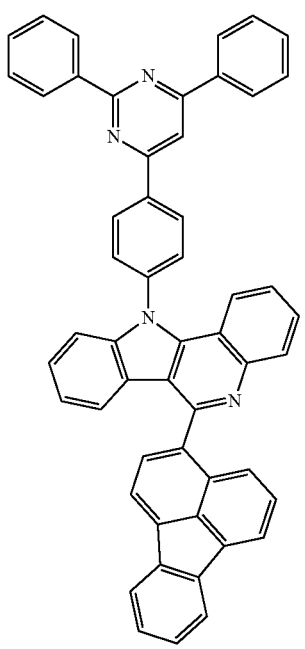
456
-continued
215
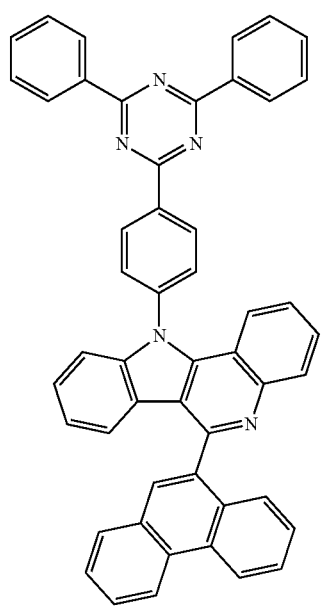
216
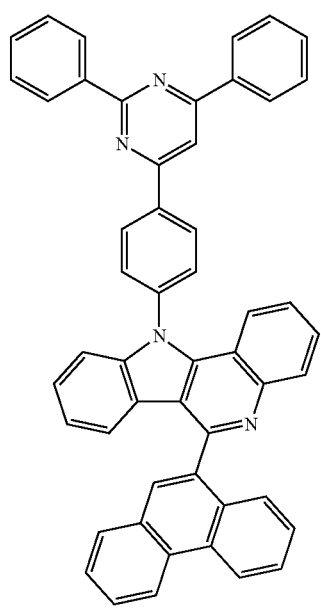

457
-continued
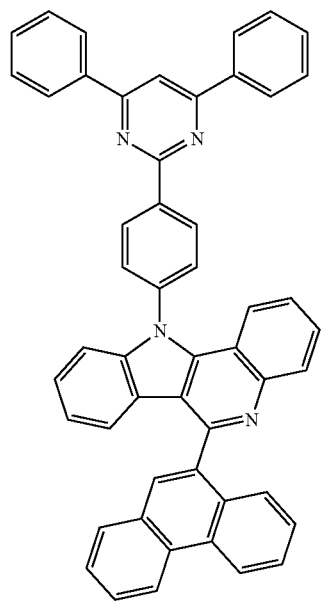
217
458
-continued
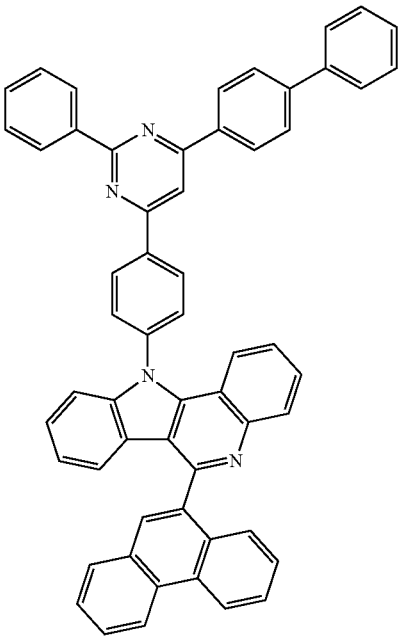
219
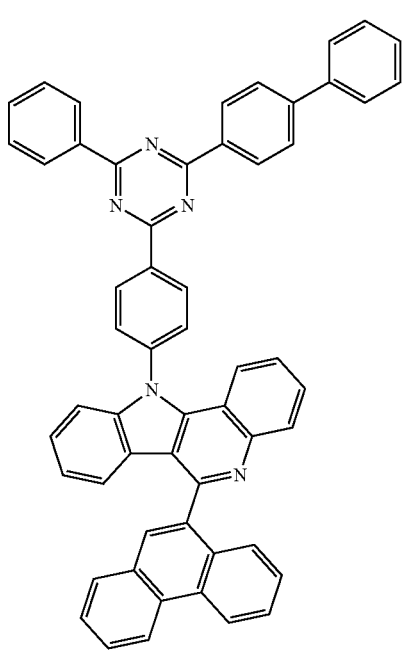
218
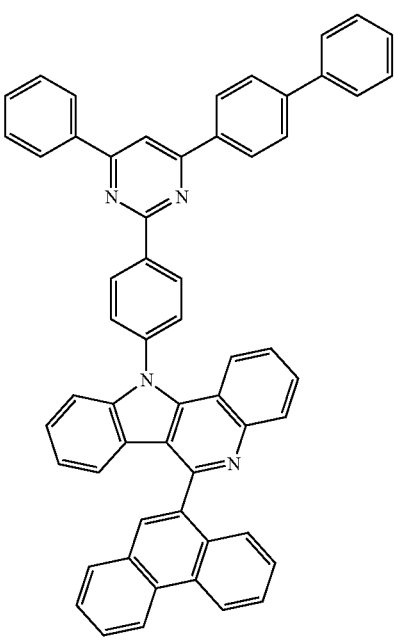
220

459
-continued
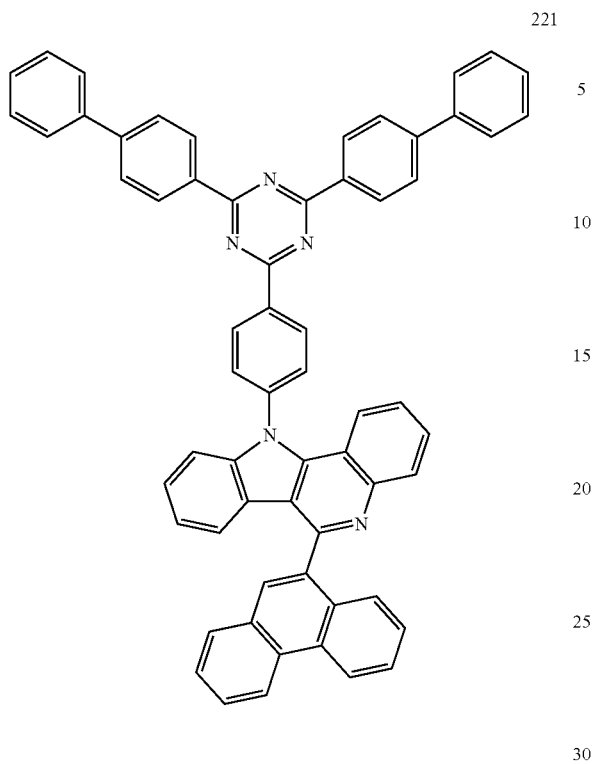
221
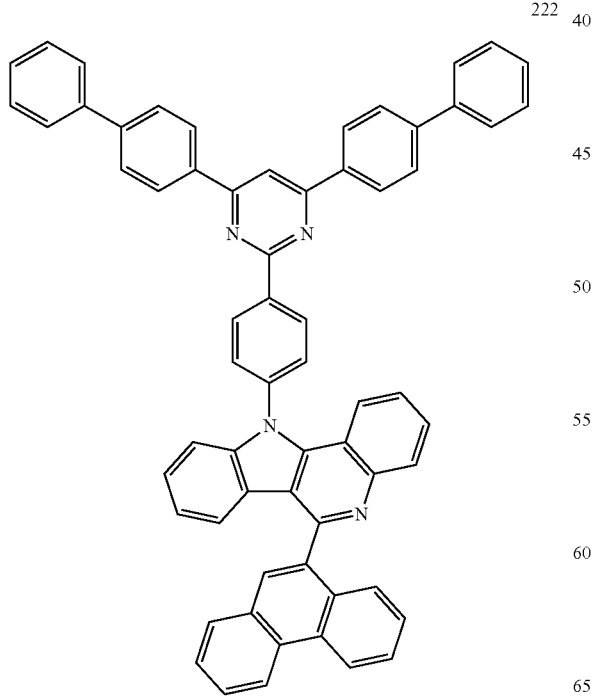
222
460
-continued
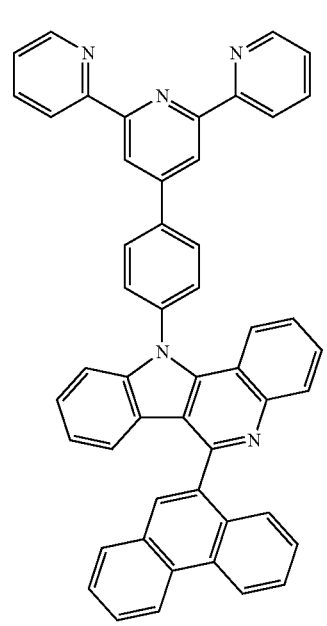
223
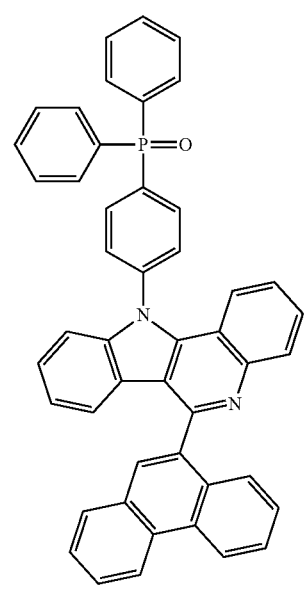
224

461
-continued
225
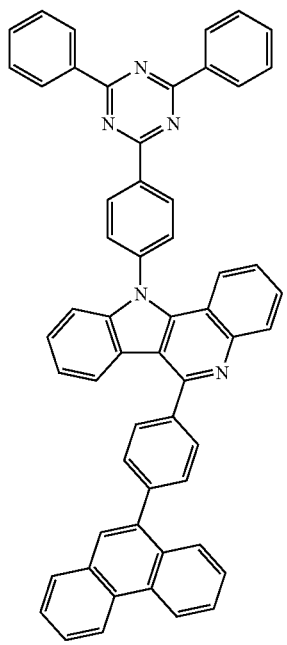
226
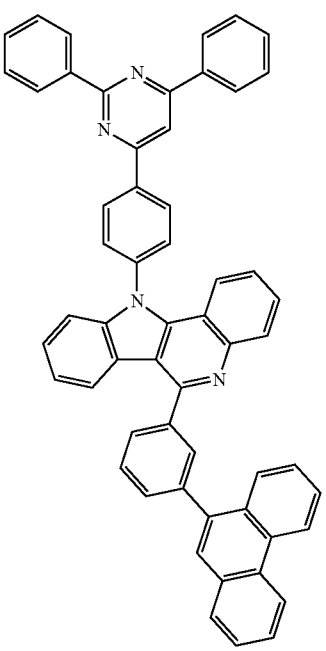
462
-continued
227
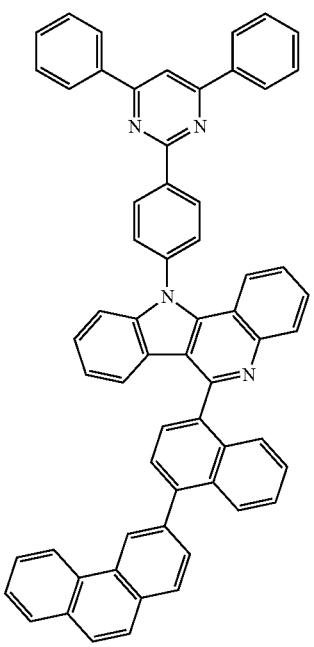
228
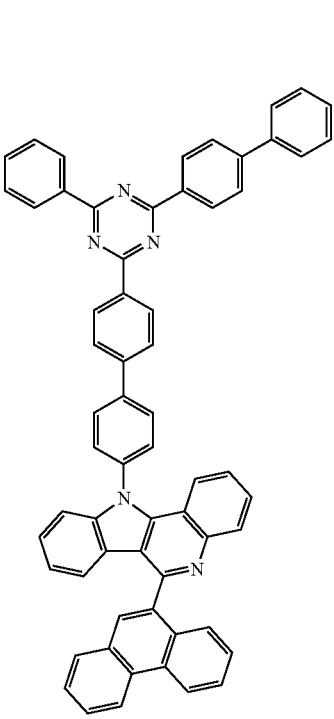

463
-continued
229
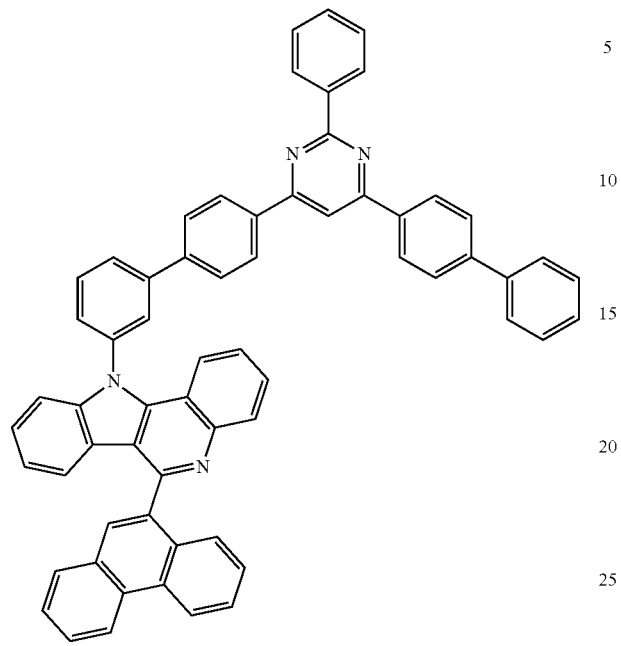
230
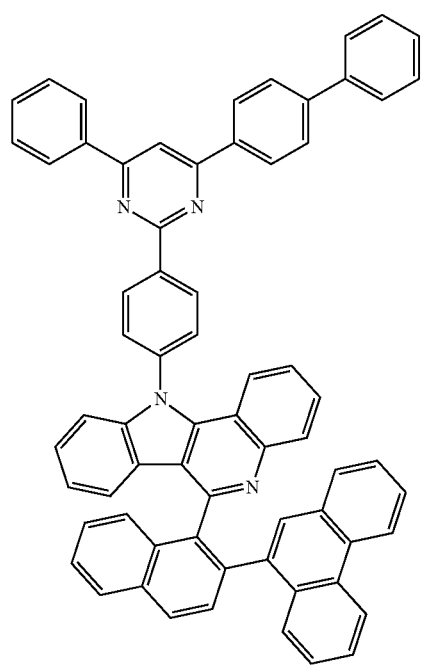
464
-continued
231
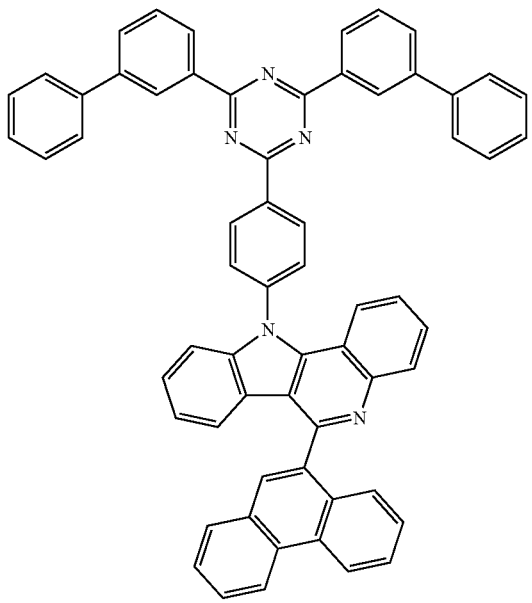
232
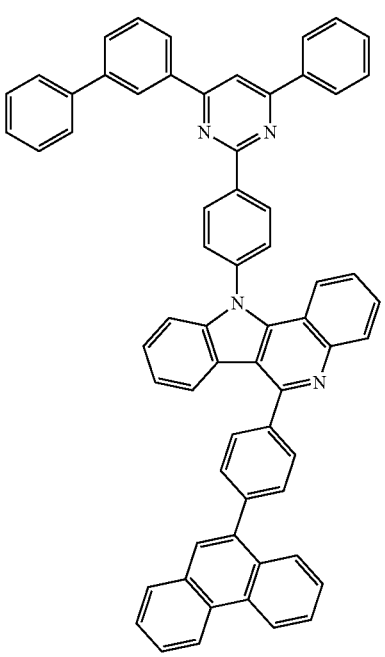

233
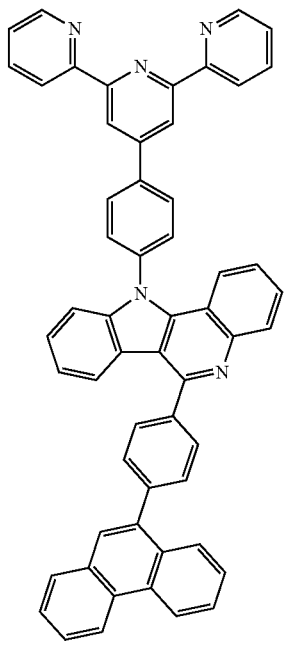
234
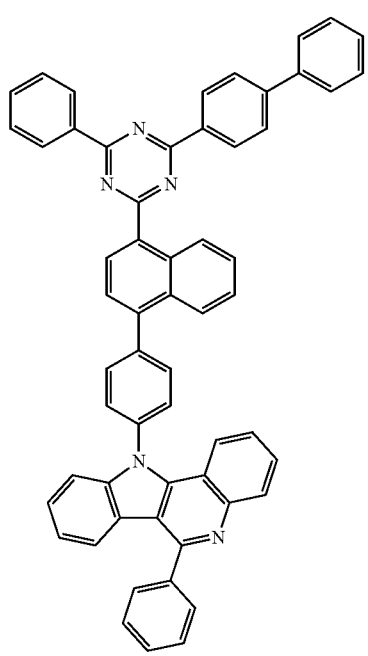
235
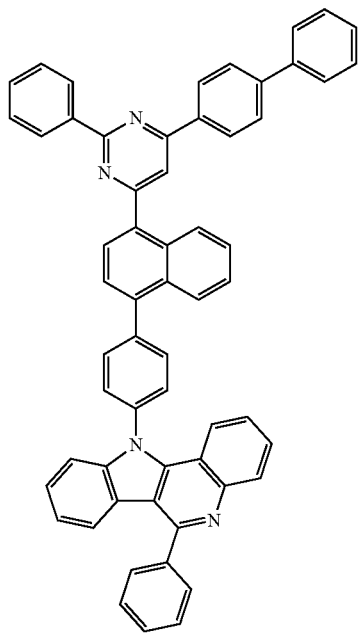
236
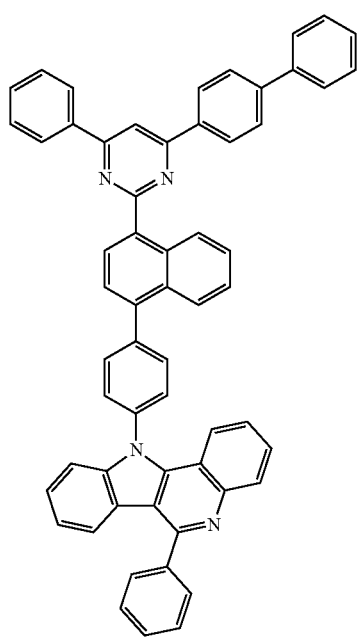

237
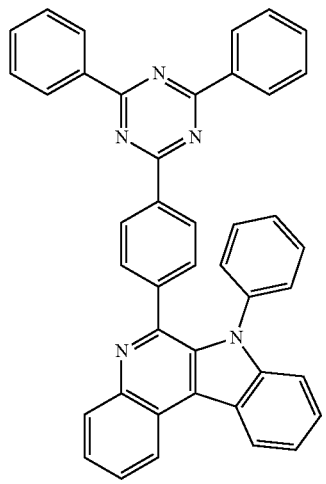
238
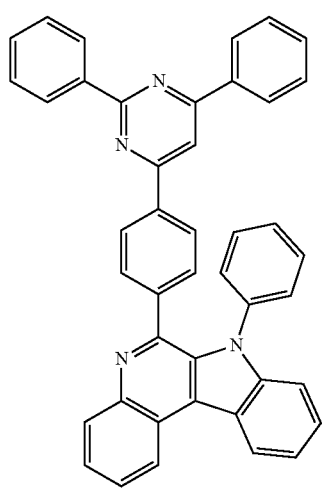
239
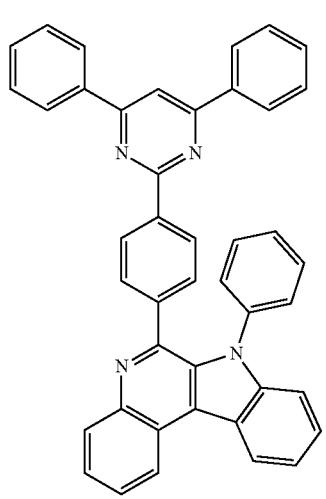
240
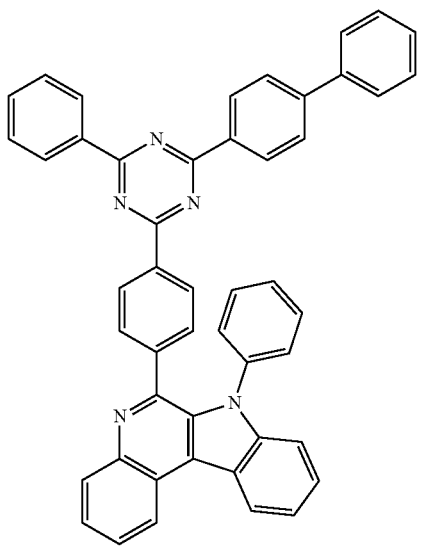
241
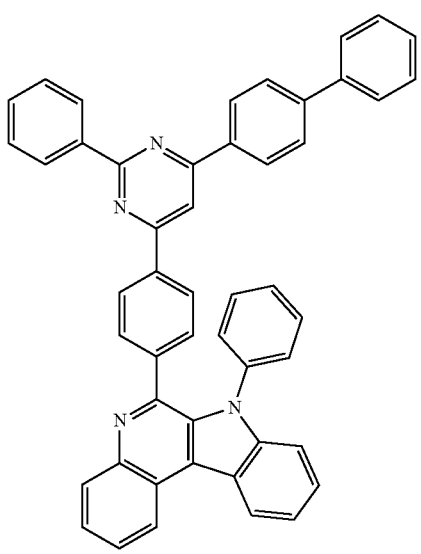
242
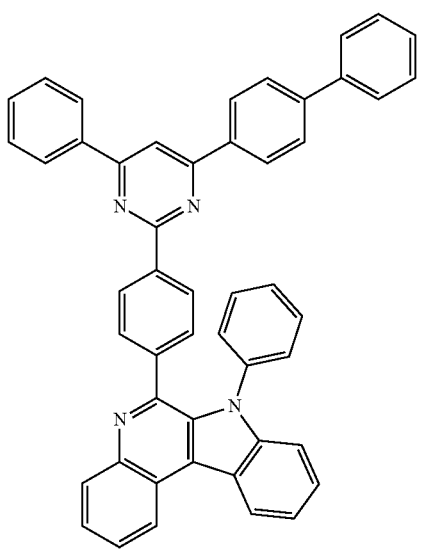

-continued
243
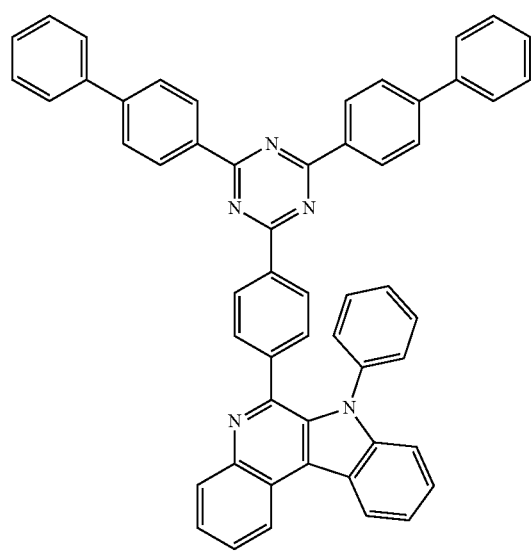
244
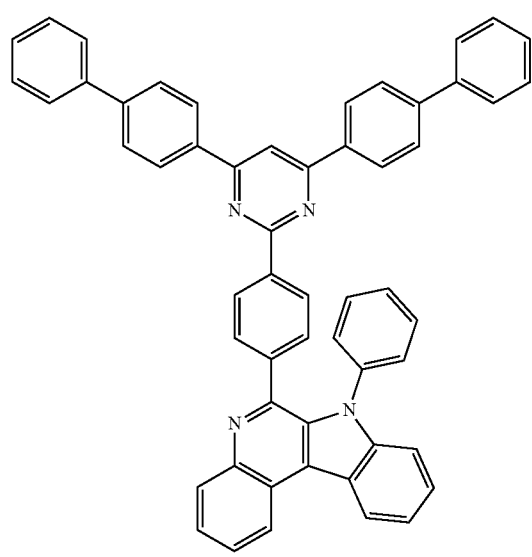
245
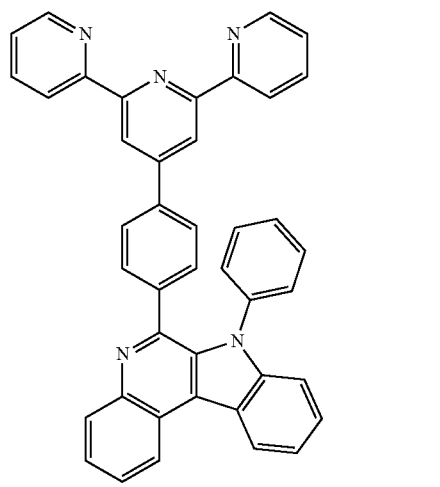
-continued
346
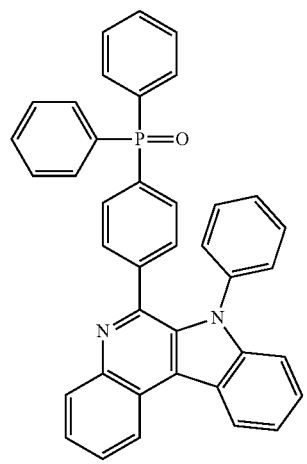
347
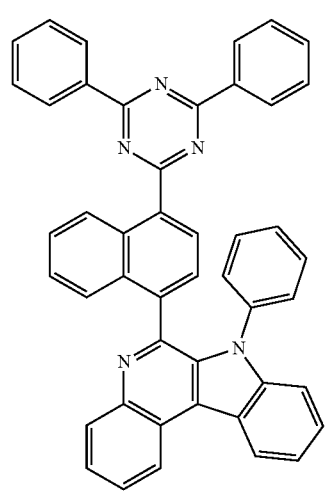
348
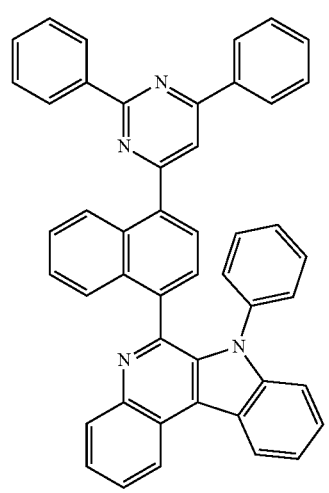

-continued
249
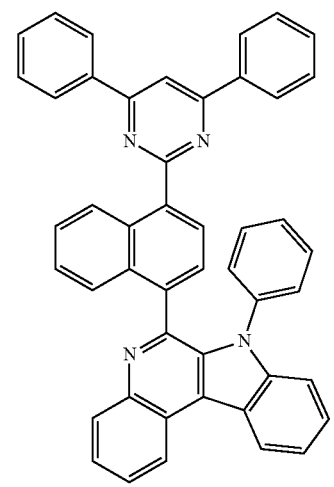 [SMILES: c1ccc(-c2cc(-c3ccc(-c4nc5ccccc5c5c6ccccc6n(-c6ccccc6)c45)c4ccccc34)nc(-c3ccccc3)n2)cc1]
250
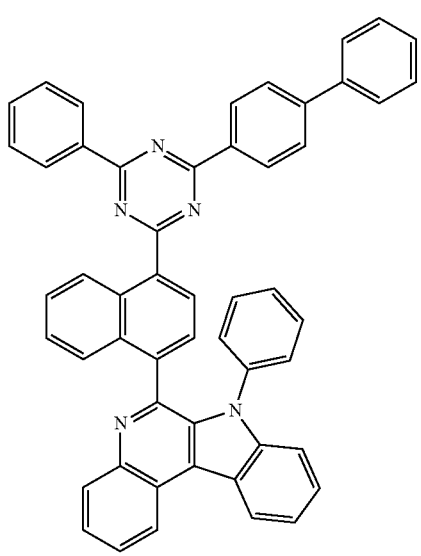 [SMILES: c1ccc(-c2ccc(-c3cc(-c4ccc(-c5nc6ccccc6c6c7ccccc7n(-c7ccccc7)c56)c5ccccc45)nc(-c4ccccc4)n3)cc2)cc1]
251
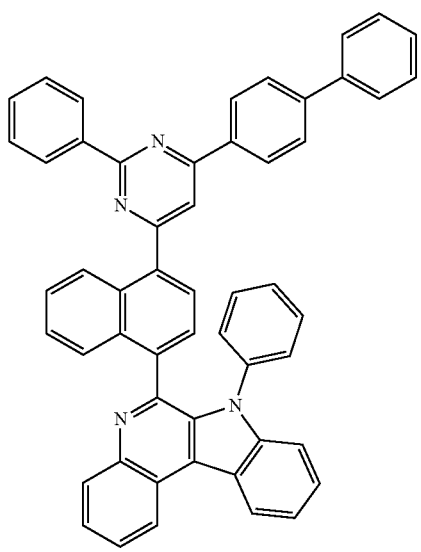 [SMILES: c1ccc(-c2ccc(-c3cc(-c4ccc(-c5nc6ccccc6c6c7ccccc7n(-c7ccccc7)c56)c5ccccc45)nc(-c4ccccc4)n3)cc2)cc1]
-continued
252
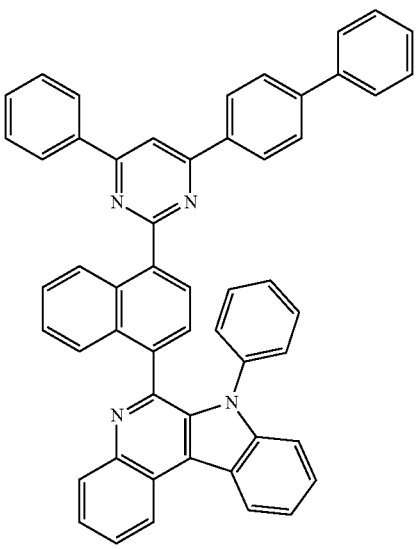
253
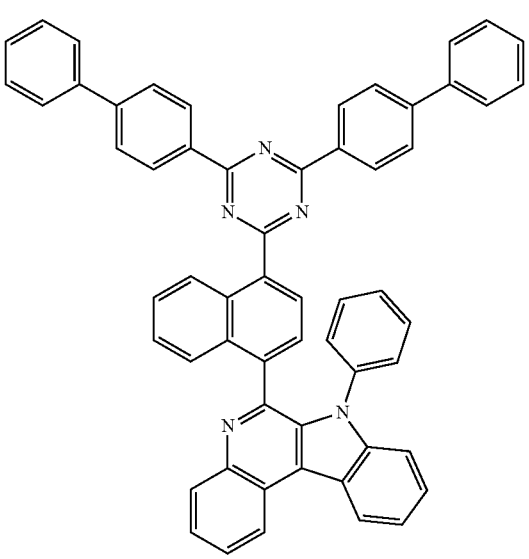 [SMILES: c1ccc(-c2ccc(-c3nc(-c4ccc(-c5ccccc5)cc4)nc(-c4ccc(-c5nc6ccccc6c6c7ccccc7n(-c7ccccc7)c56)c5ccccc45)n3)cc2)cc1]
254
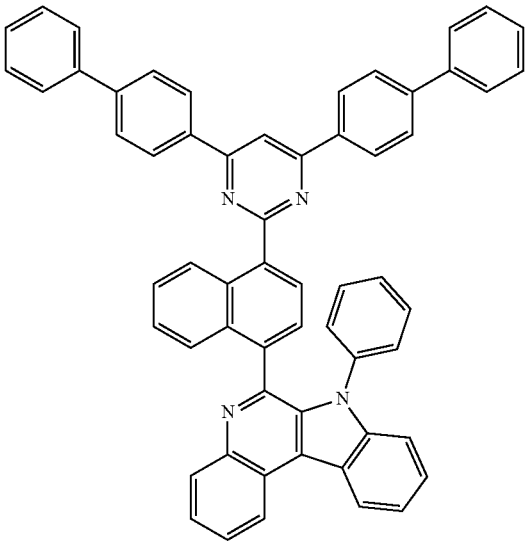

255
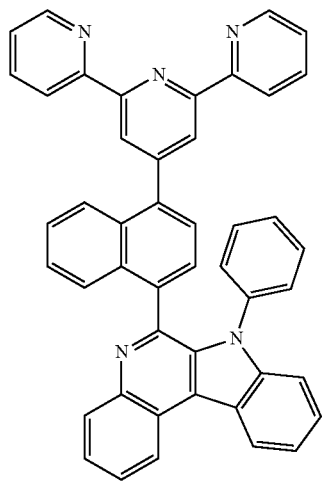
256
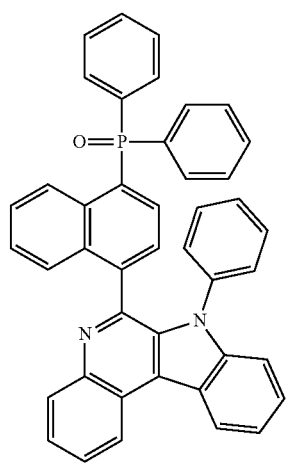
257
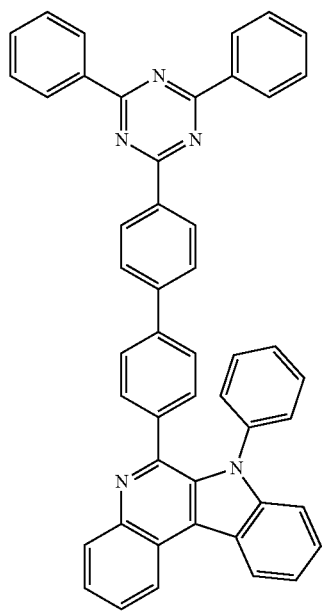
258
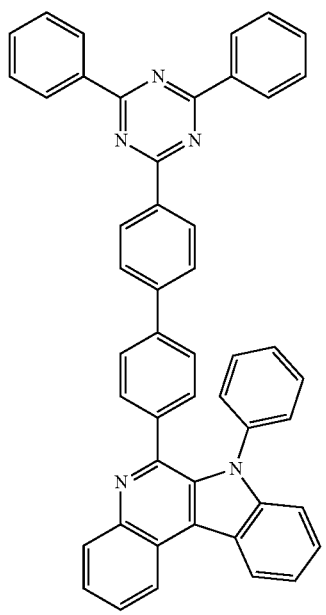
259
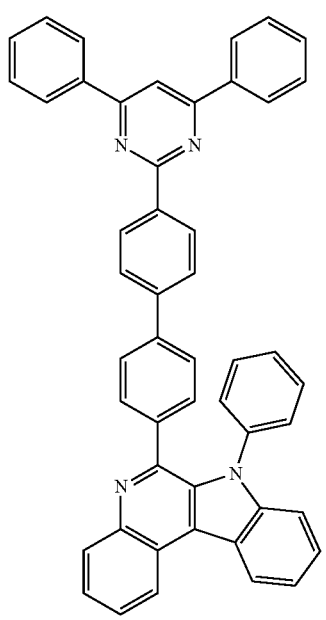

475
-continued
260
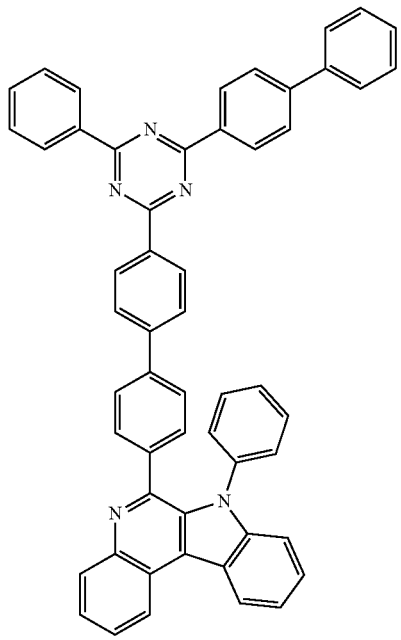
261
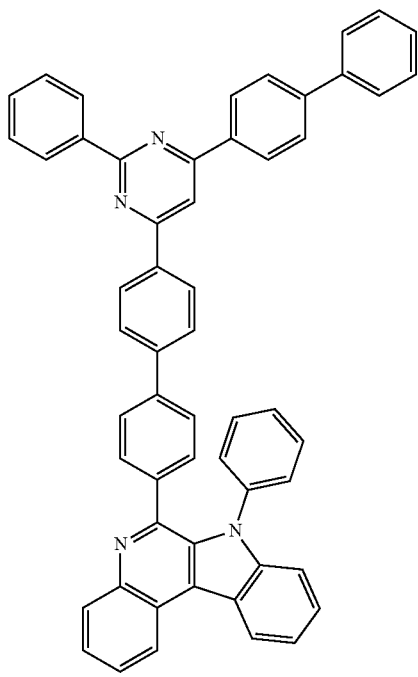
476
-continued
262
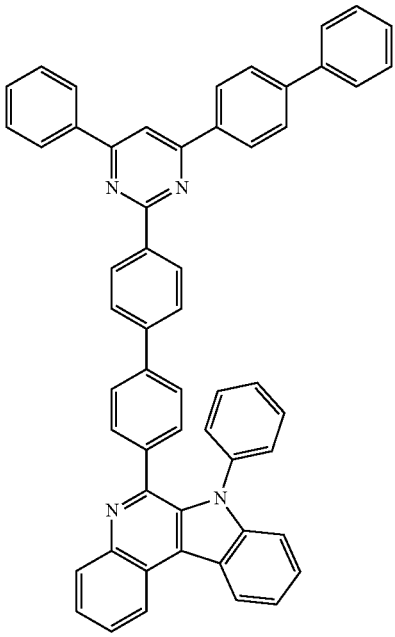
263
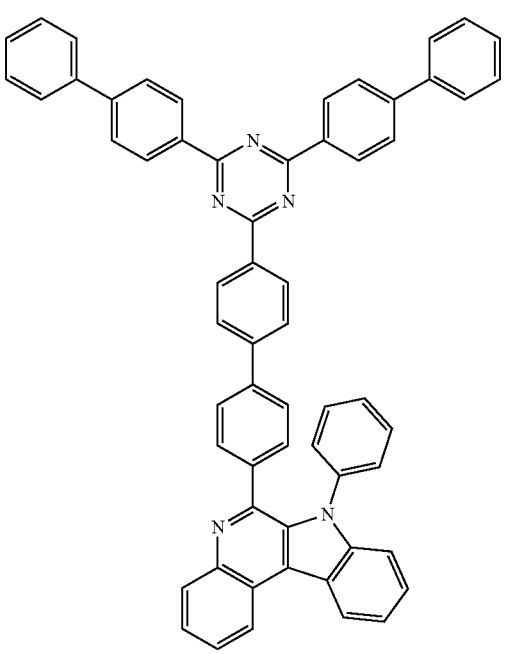

477
-continued
264
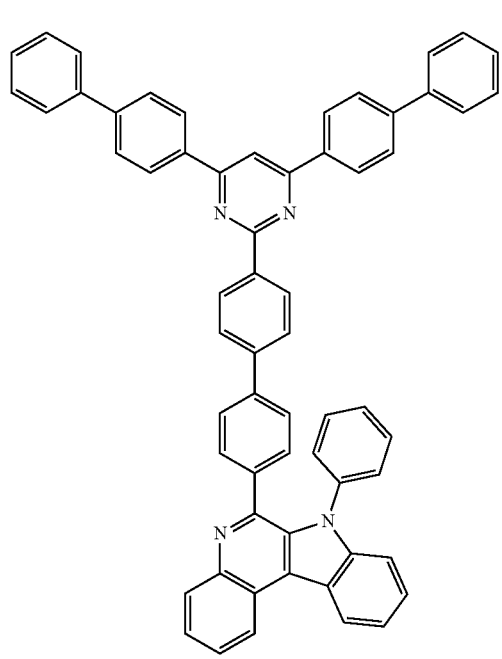
265
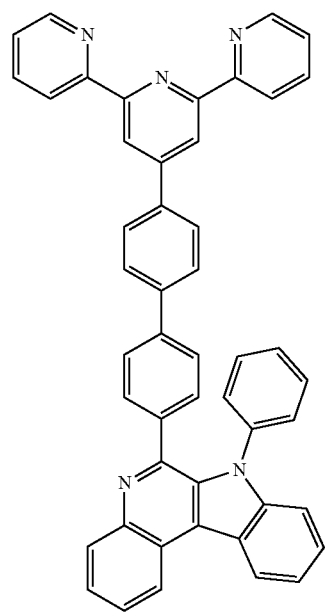
478
-continued
266
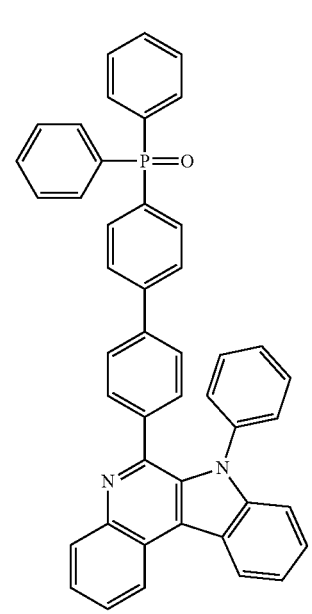
267
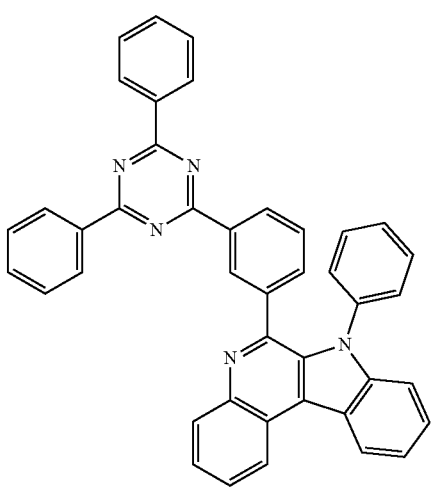 [SMILES: c1ccc(-c2nc(-c3ccccc3)nc(-c3cccc(-c4nc5ccccc5c5c6ccccc6n(-c6ccccc6)c45)c3)n2)cc1]
268
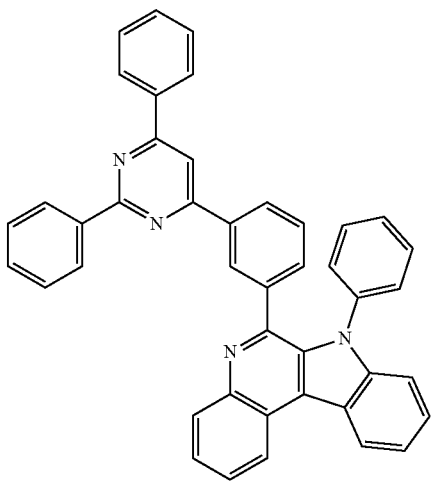

479
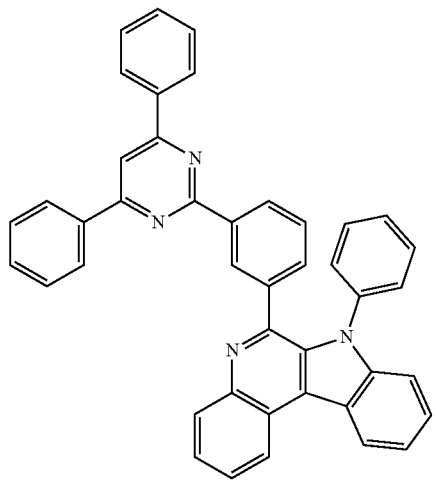
480
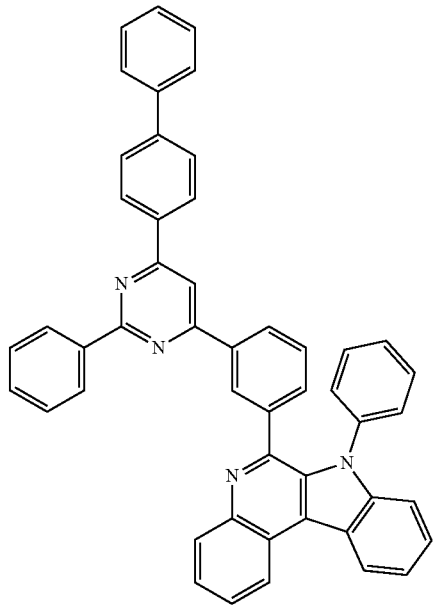
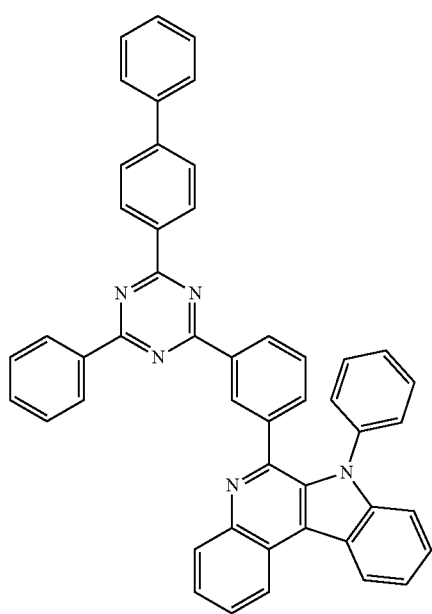 [SMILES: c1ccc(-c2ccc(-c3nc(-c4ccccc4)nc(-c4cccc(-c5nc6ccccc6c6c7ccccc7n(-c7ccccc7)c56)c4)n3)cc2)cc1]
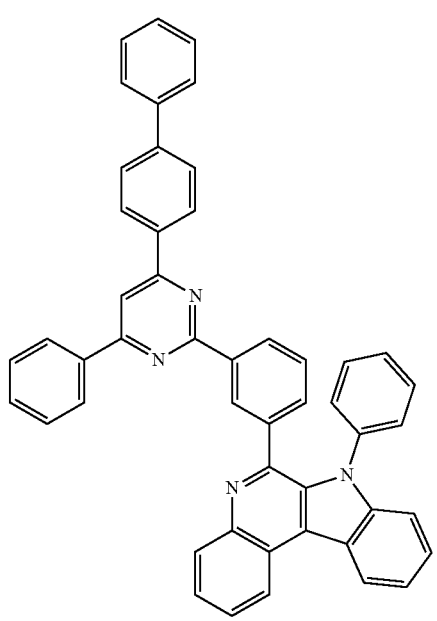

273
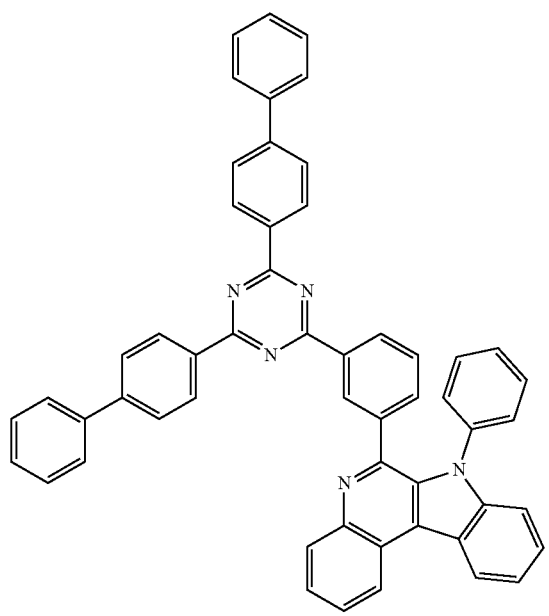 [SMILES: c1ccc(-c2ccc(-c3nc(-c4ccc(-c5ccccc5)cc4)nc(-c4cccc(-c5nc6ccccc6c6c7ccccc7n(-c7ccccc7)c56)c4)n3)cc2)cc1]
274
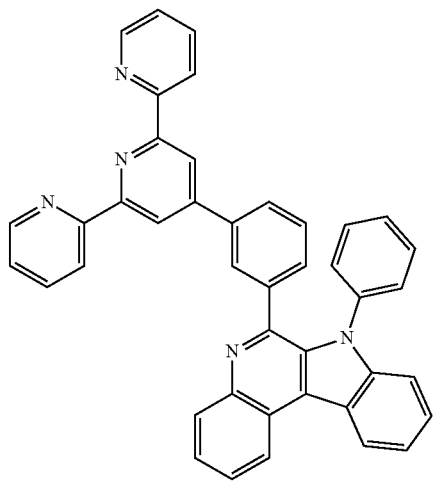
275
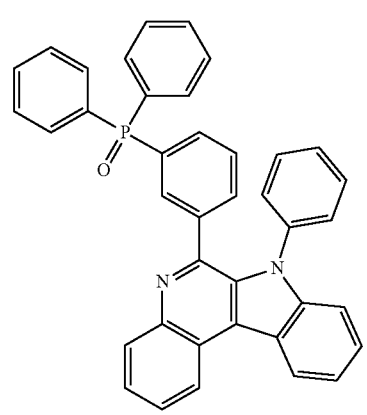
276
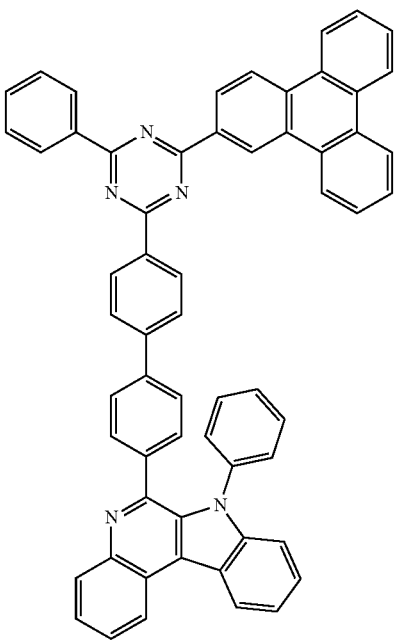
277

483
-continued
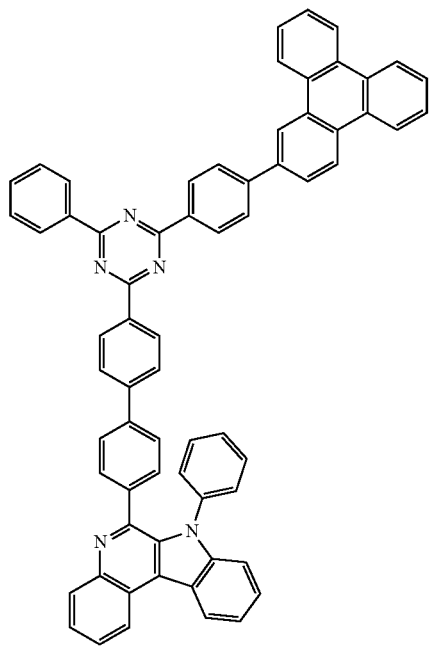
484
-continued
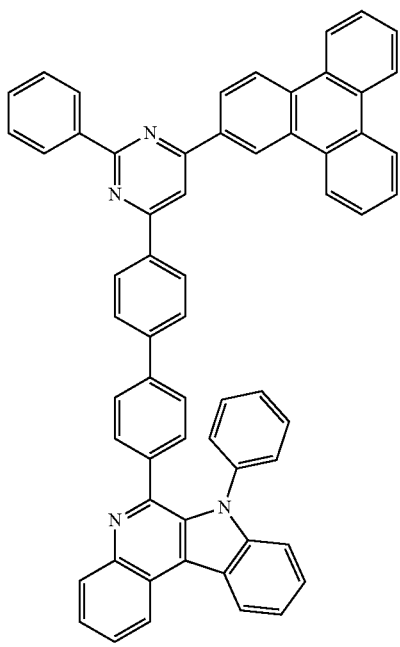
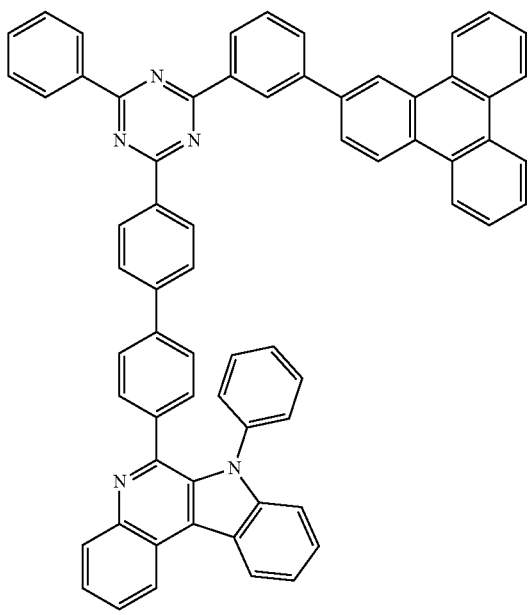
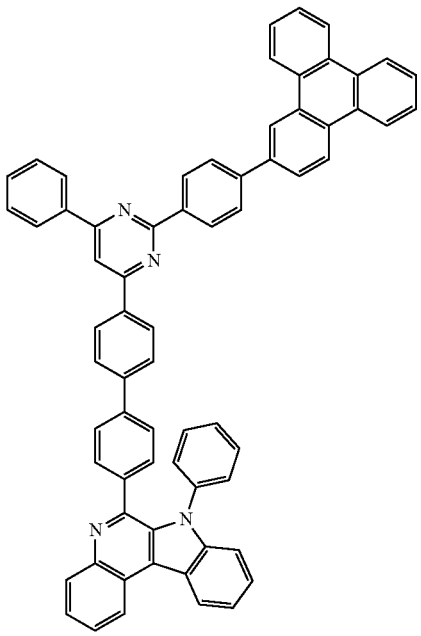

282
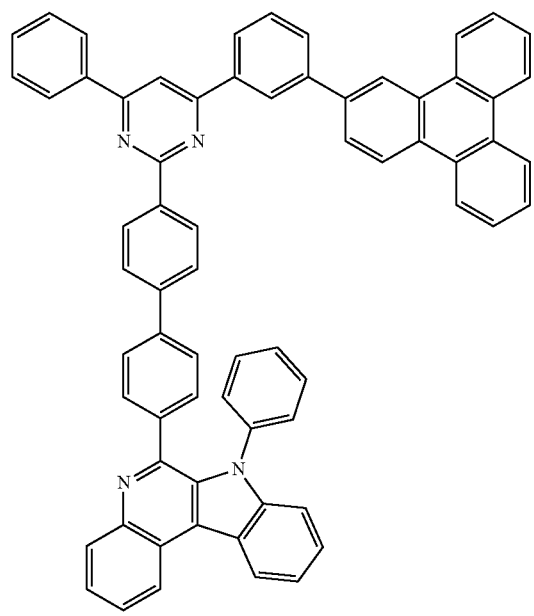
283
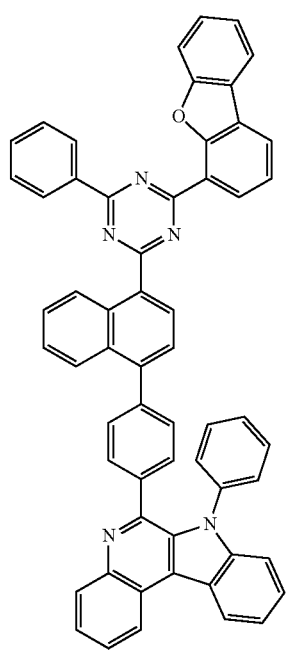
284
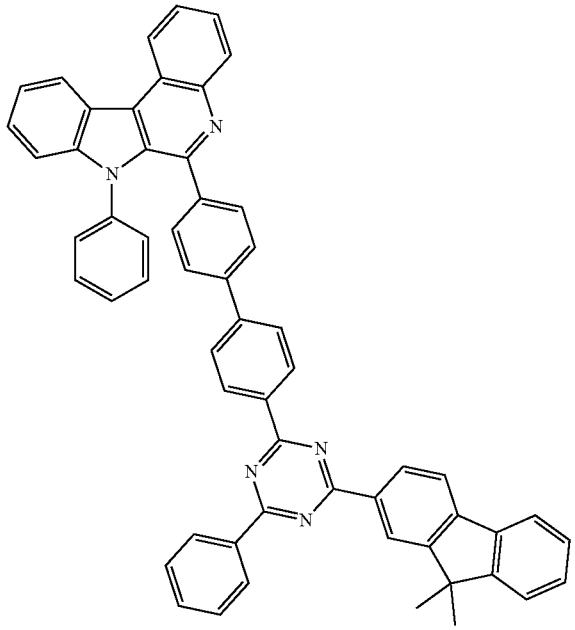
285
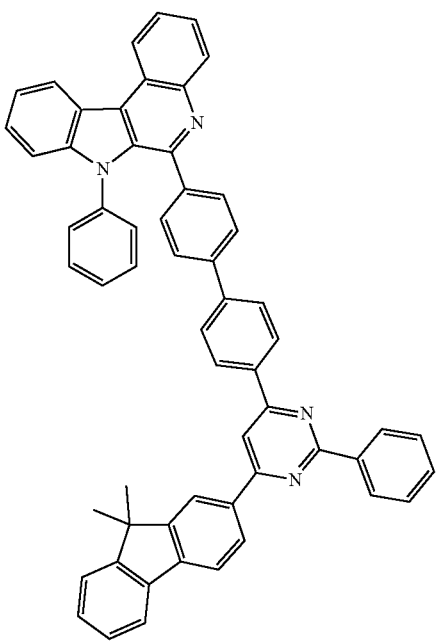

487
-continued
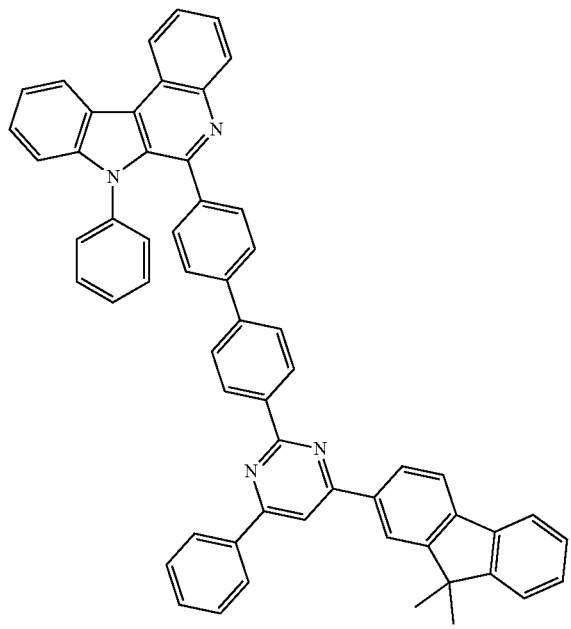
286
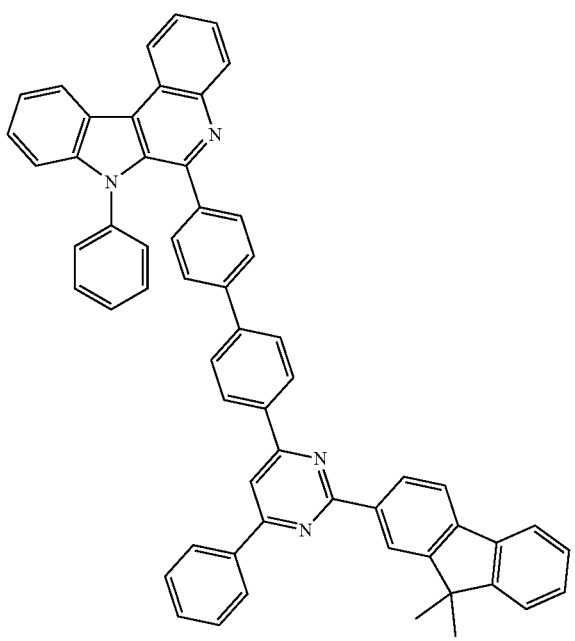
287
488
-continued
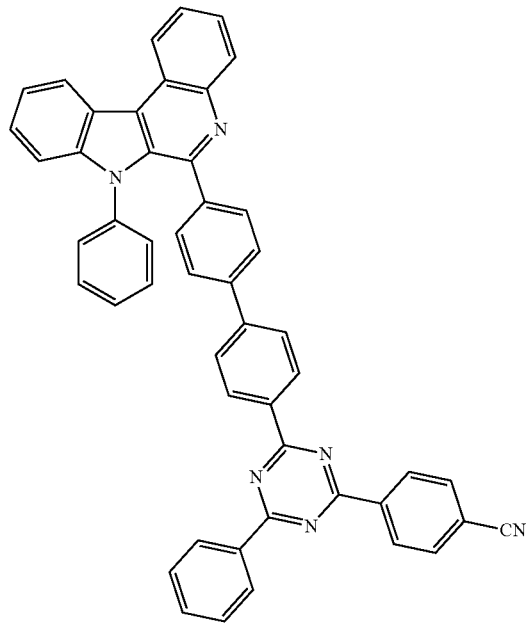
288
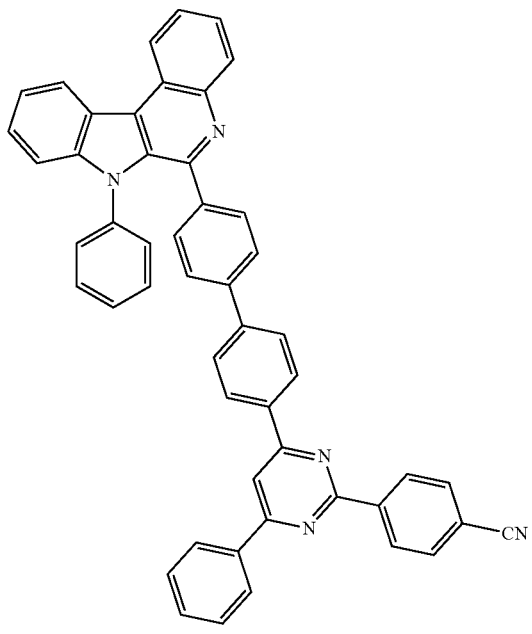
289

489
-continued
290
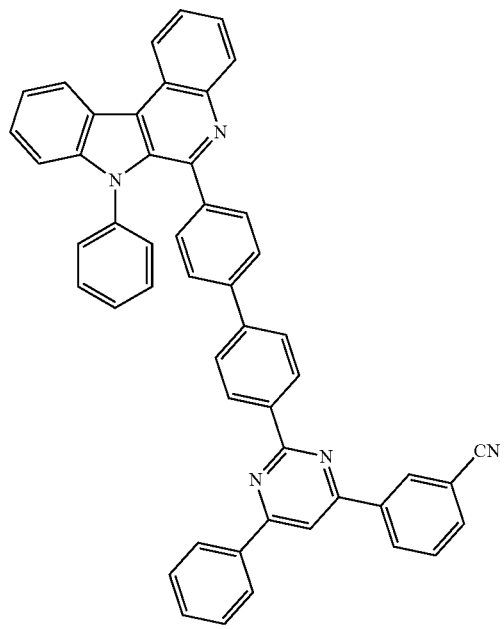
291
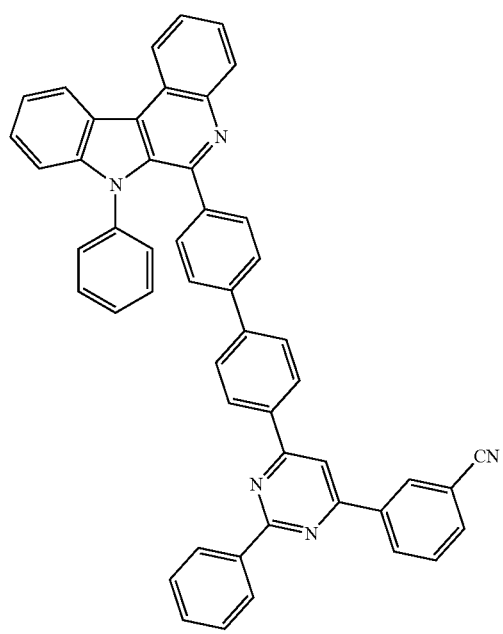
490
-continued
292
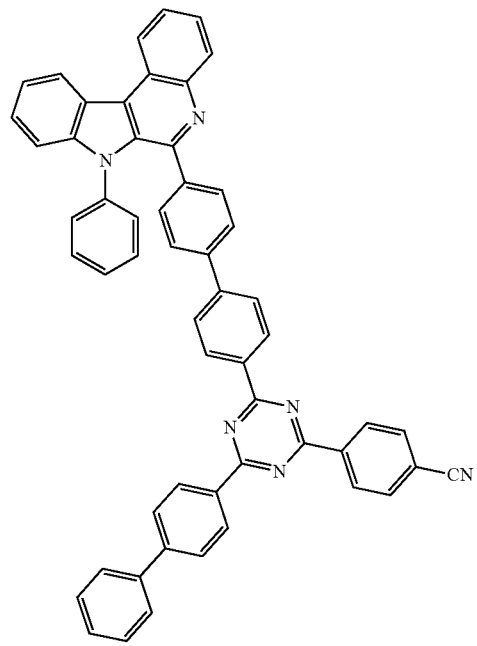
293
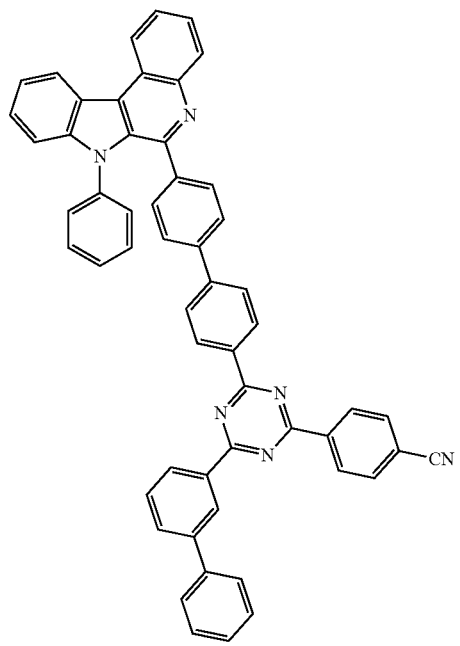

491
-continued
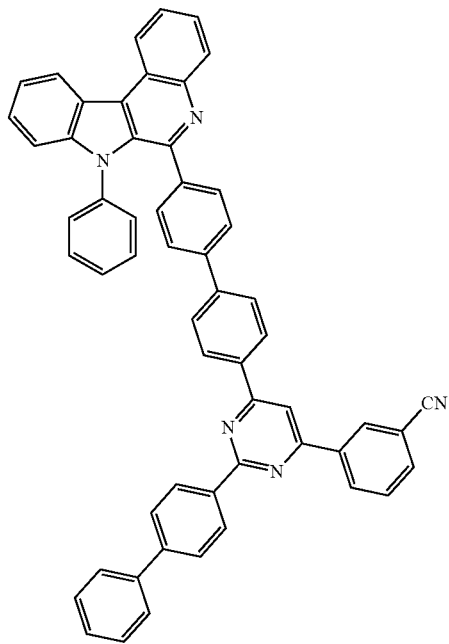
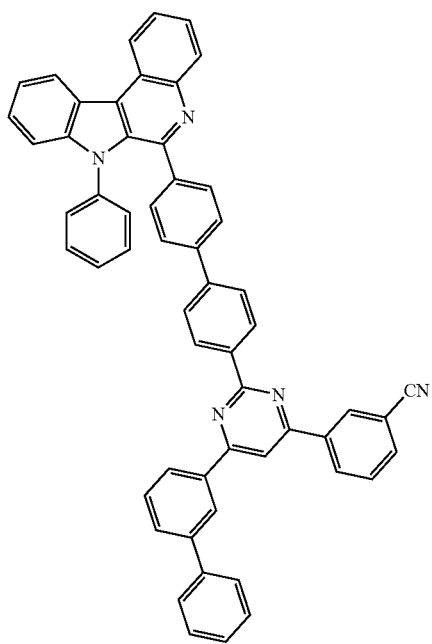
492
-continued
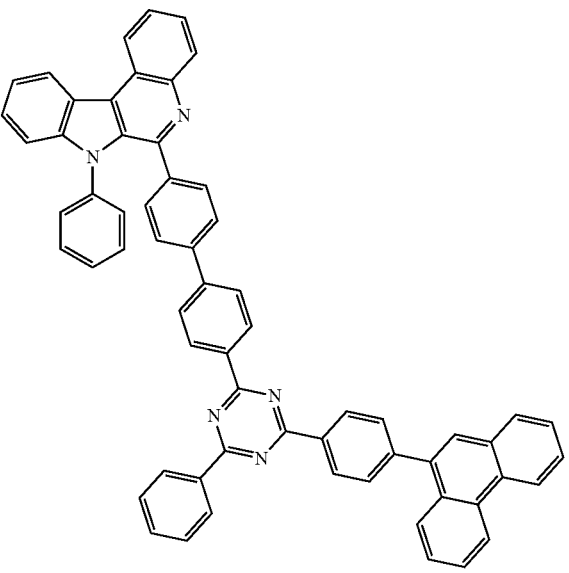
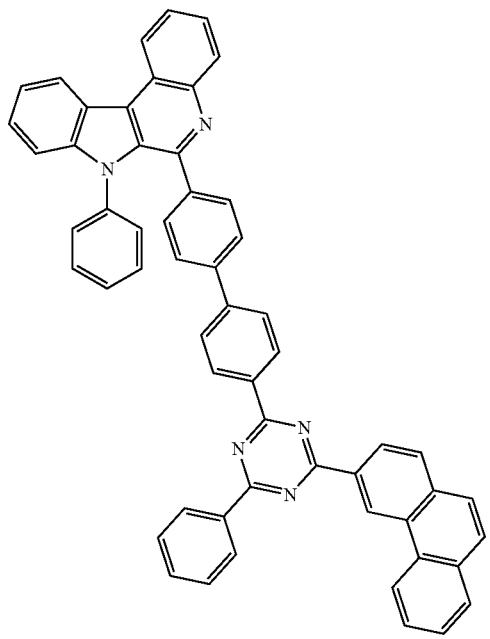

493
-continued
298
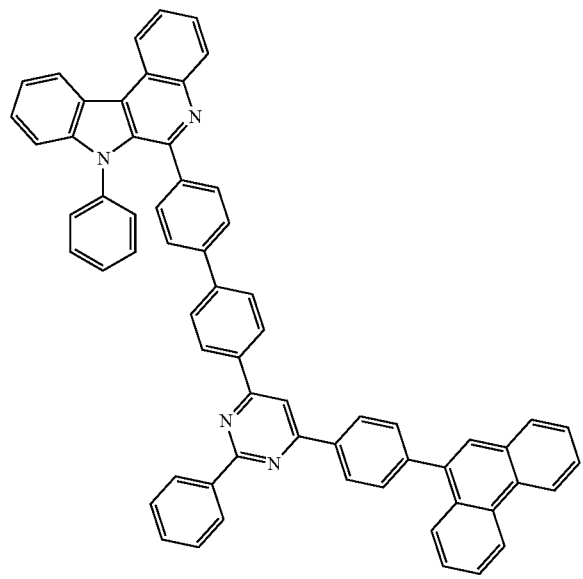
299
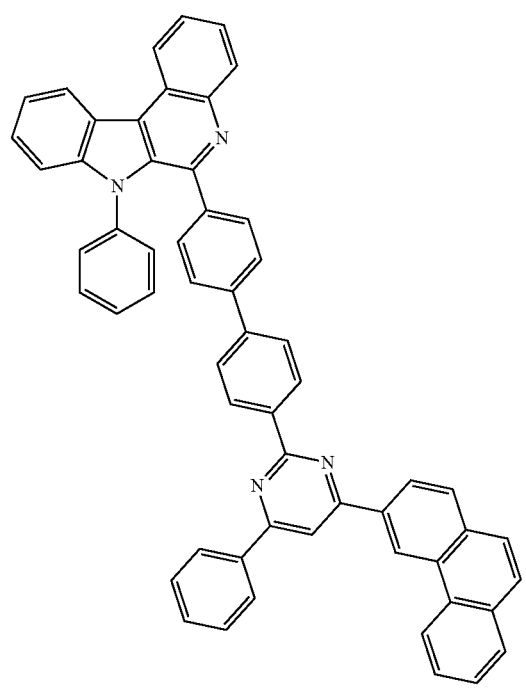
494
-continued
300
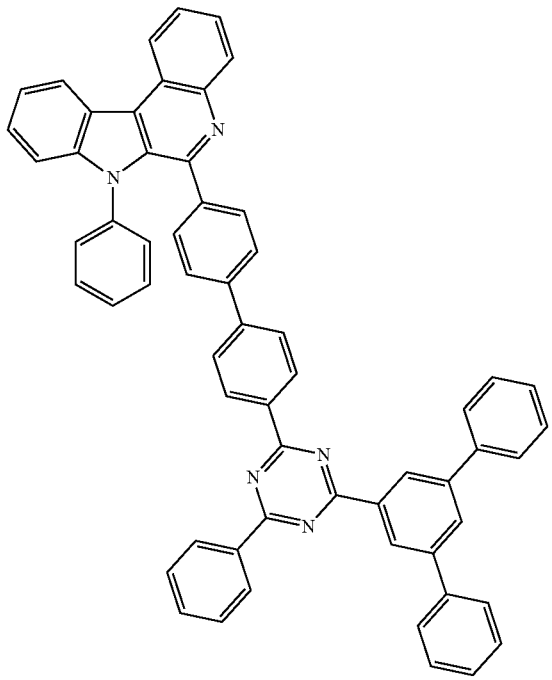
301
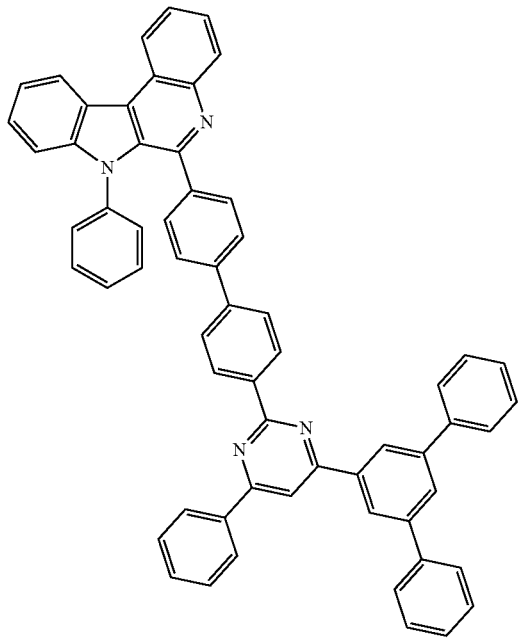

495
-continued
496
-continued
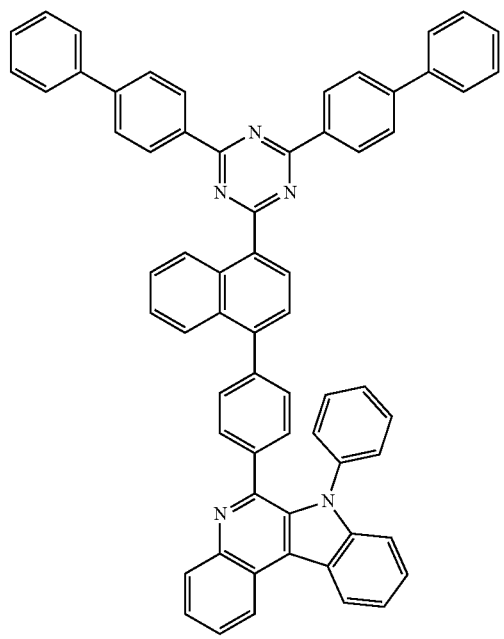
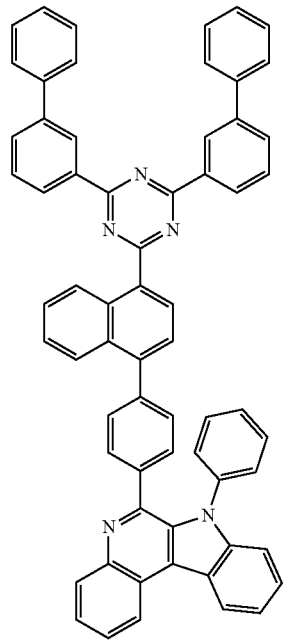
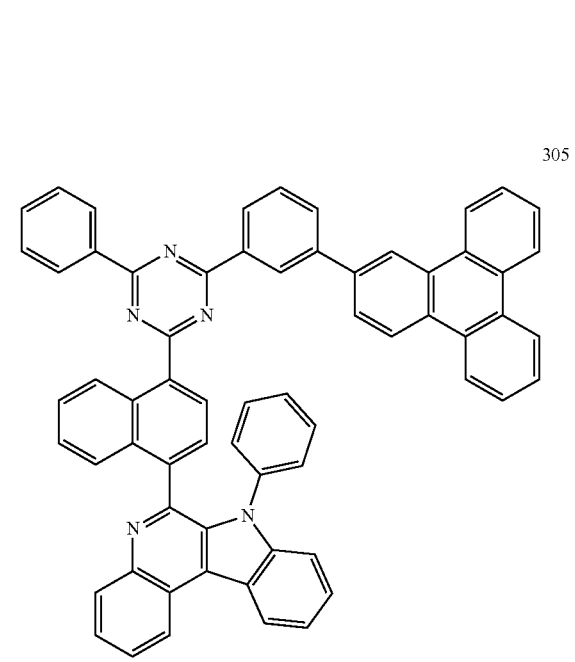

497
-continued
306
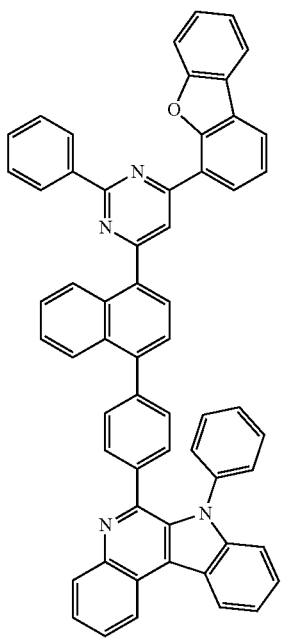
307
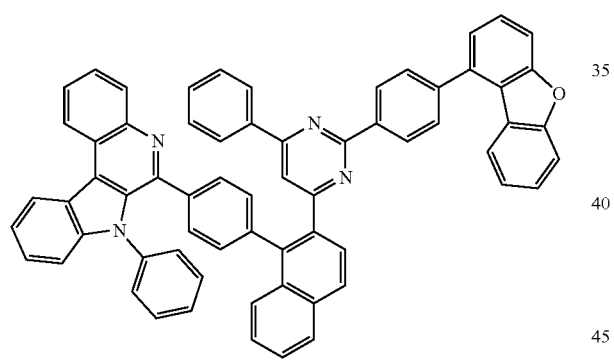
308
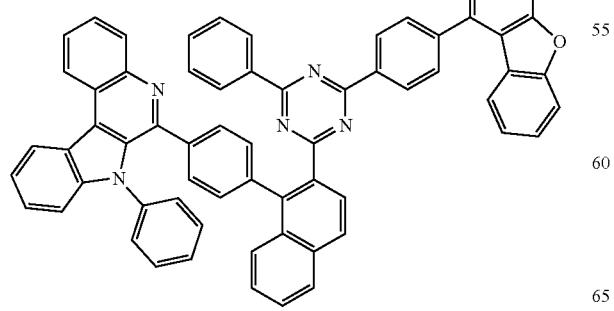
498
-continued
309
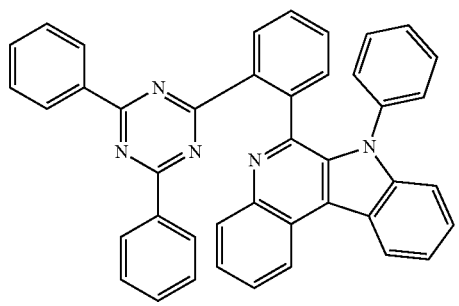
310
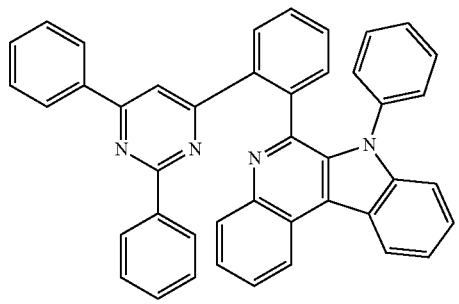
311
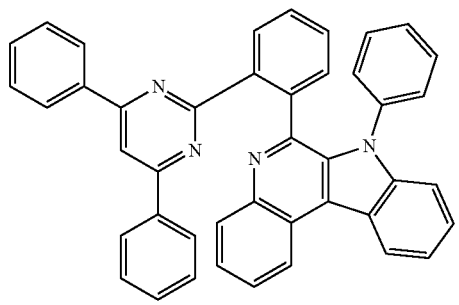
312
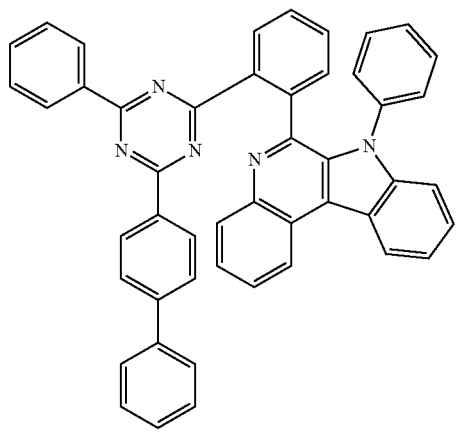

499
-continued
313
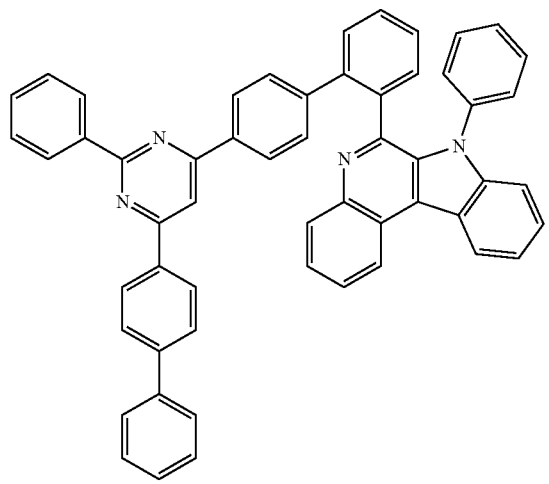 [SMILES: c1ccc(-c2ccc(-c3cc(-c4ccc(-c5ccccc5-c5nc6ccccc6c6c7ccccc7n(-c7ccccc7)c56)cc4)nc(-c4ccccc4)n3)cc2)cc1]
314
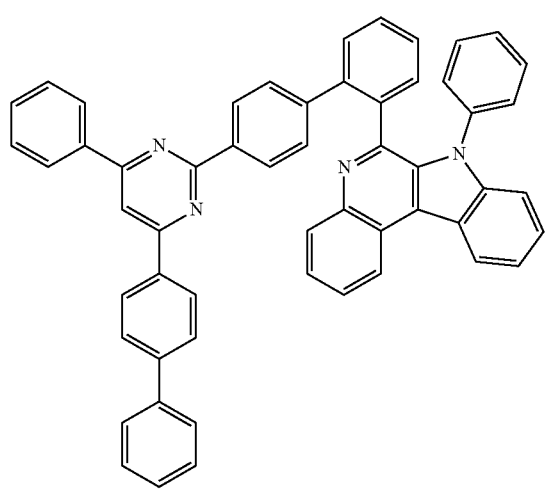
315
500
-continued
316
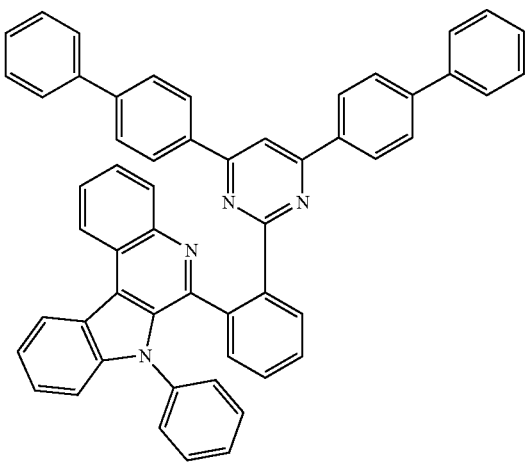
317
318
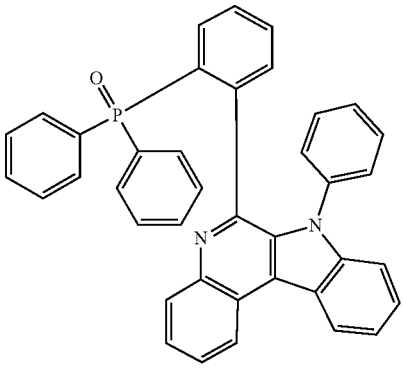

-continued
319
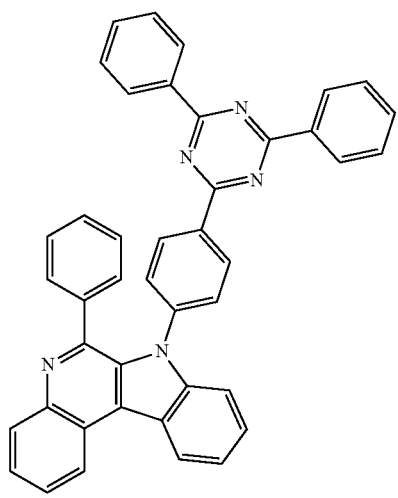
320
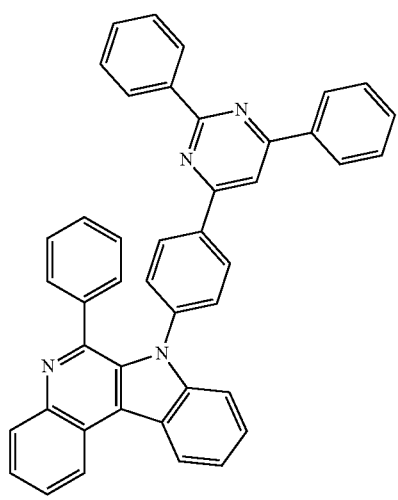
321
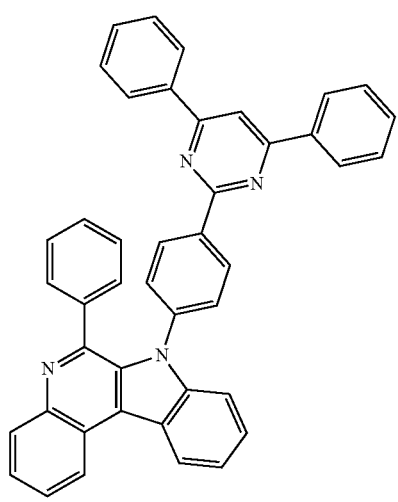 [SMILES: c1ccc(-c2cc(-c3ccccc3)nc(-c3ccc(-n4c5ccccc5c5c6ccccc6nc(-c6ccccc6)c54)cc3)n2)cc1]
-continued
322
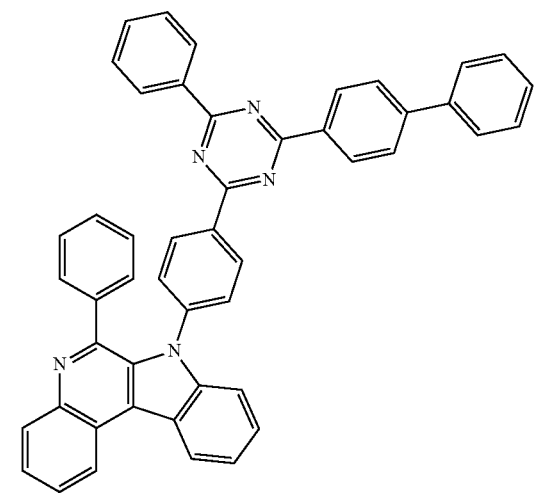
323
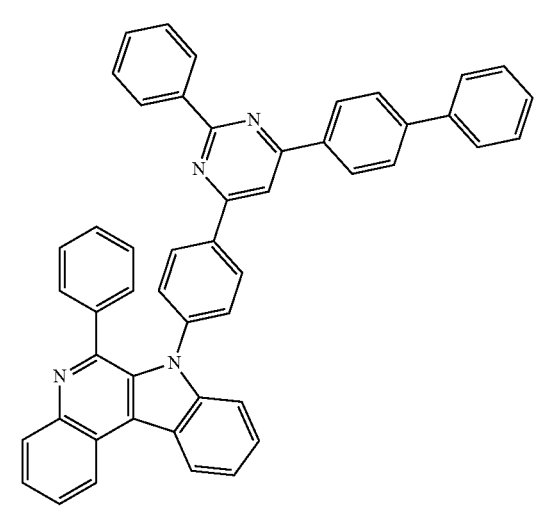
324
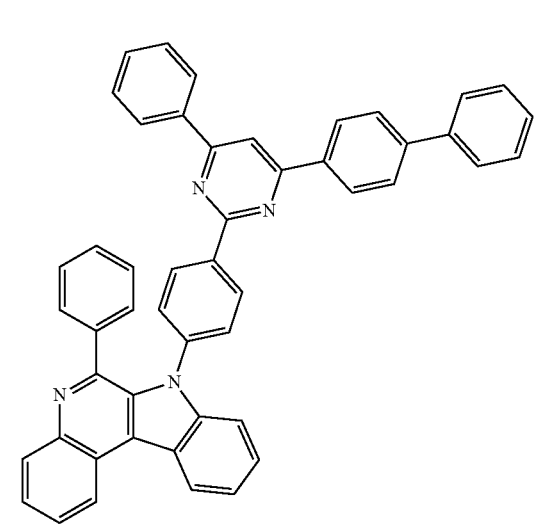 [SMILES: c1ccc(-c2ccc(-c3cc(-c4ccccc4)nc(-c4ccc(-n5c6ccccc6c6c7ccccc7nc(-c7ccccc7)c65)cc4)n3)cc2)cc1]

325
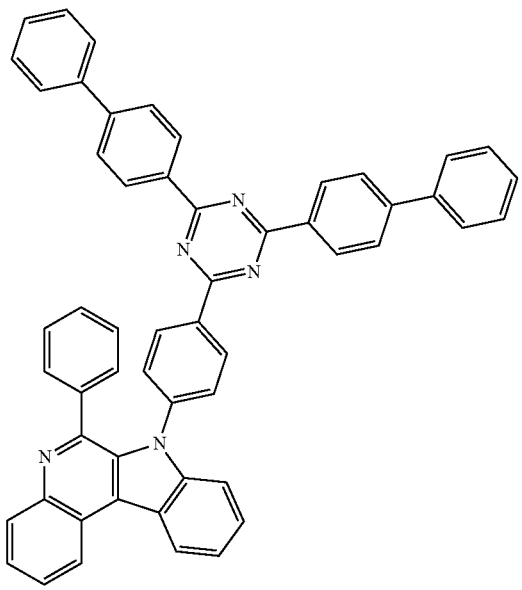
326
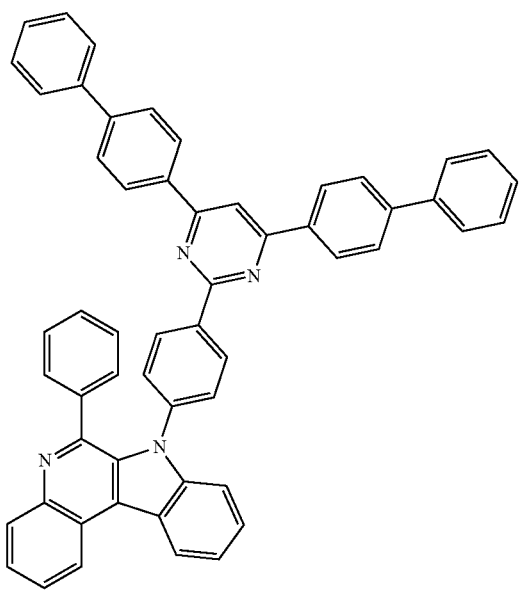 [SMILES: c1ccc(-c2ccc(-c3nc(-c4ccc(-c5ccccc5)cc4)nc(-c4ccc(-n5c6ccccc6c6c7ccccc7nc(-c7ccccc7)c65)cc4)n3)cc2)cc1]
327
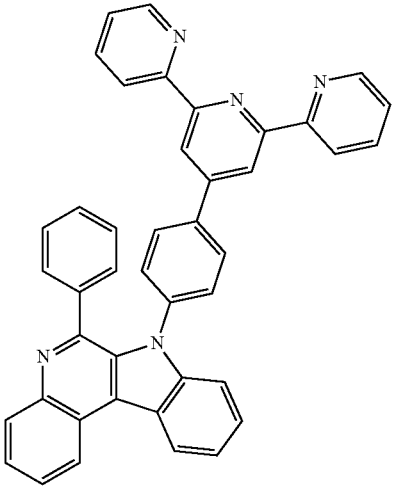
328
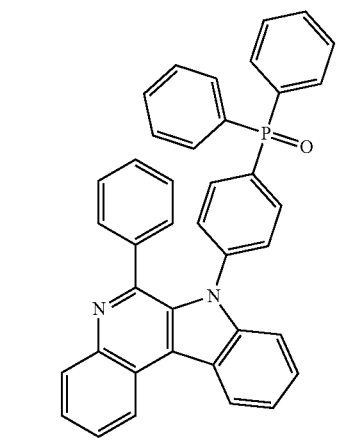
329
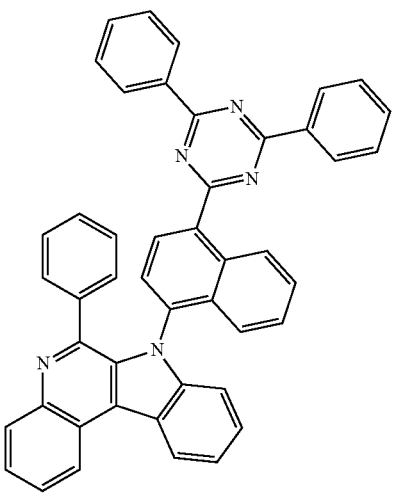

505
-continued
330
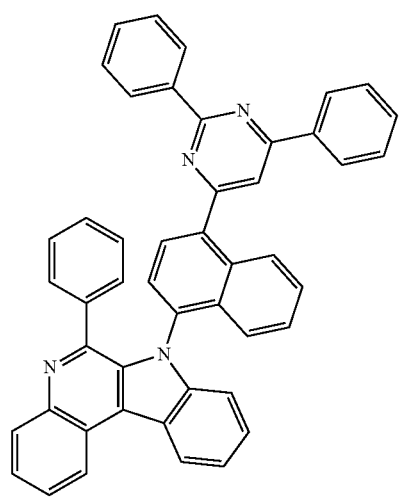
331
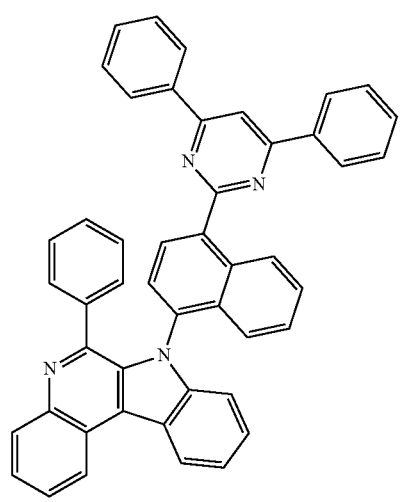
332
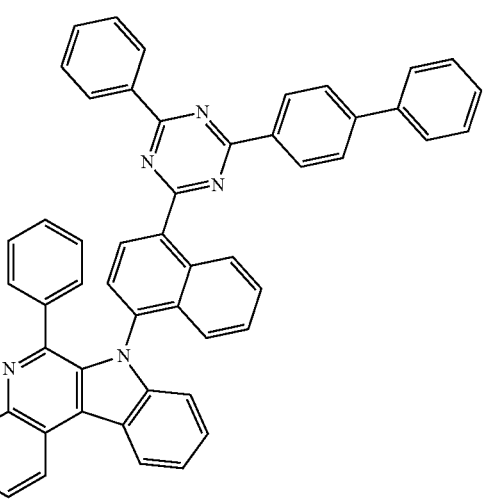
506
-continued
333
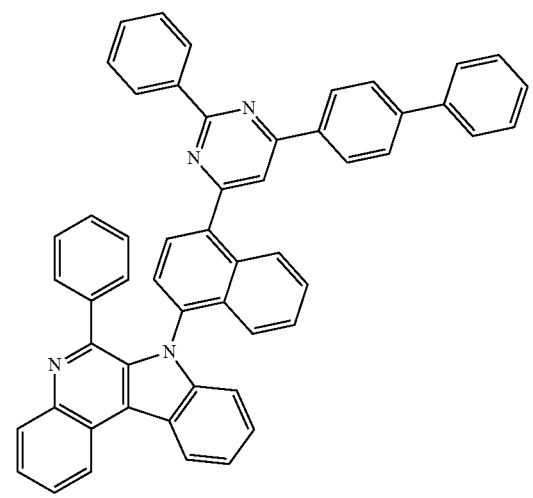 [SMILES: c1ccc(-c2ccc(-c3nc(-c4ccccc4)nc(-c4ccc(-n5c6ccccc6c6c7ccccc7nc(-c7ccccc7)c65)c5ccccc45)n3)cc2)cc1]
334
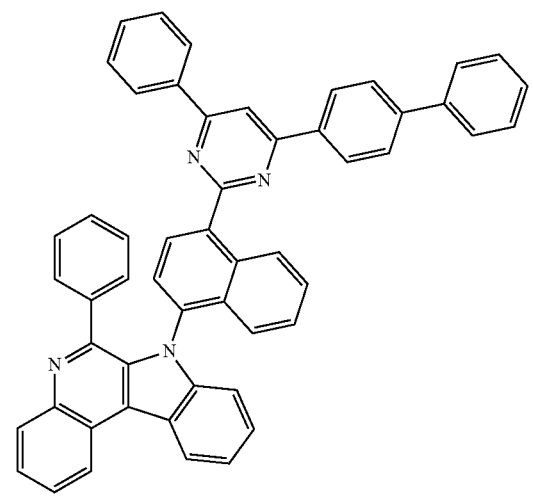
335
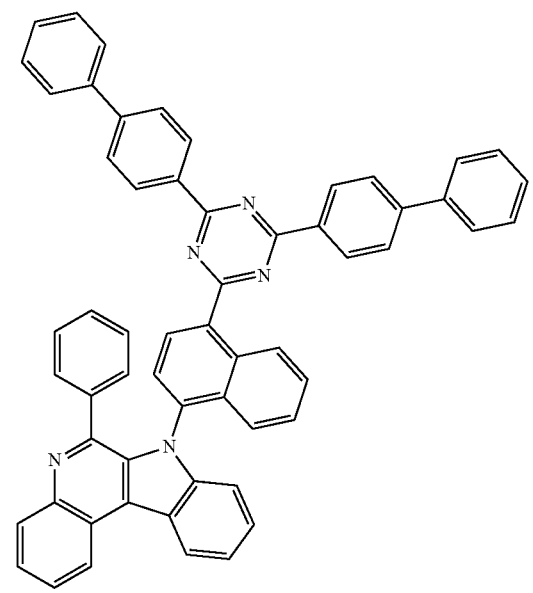

507
-continued
336
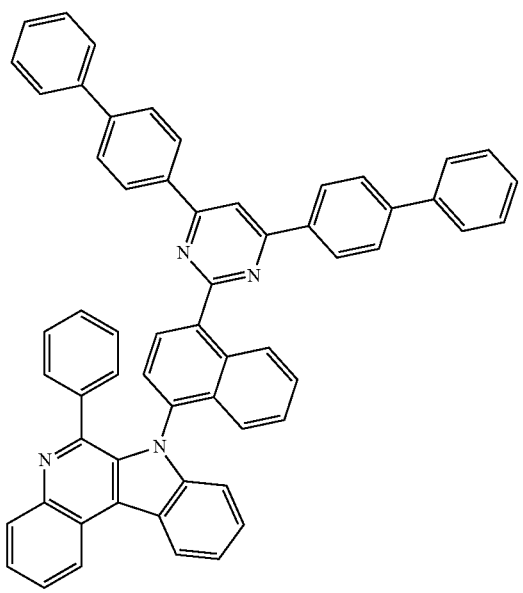 [SMILES: c1ccc(-c2ccc(-c3cc(-c4ccc(-c5ccccc5)cc4)nc(-c4ccc(-n5c6ccccc6c6c7ccccc7nc(-c7ccccc7)c65)c5ccccc45)n3)cc2)cc1]
337
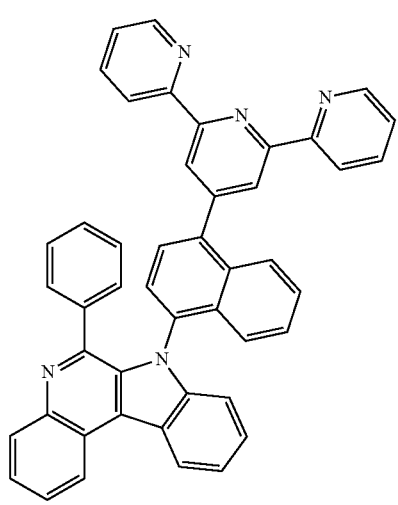
338
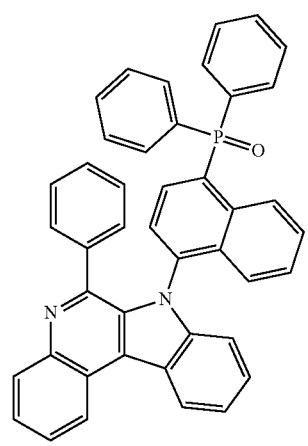
508
-continued
339
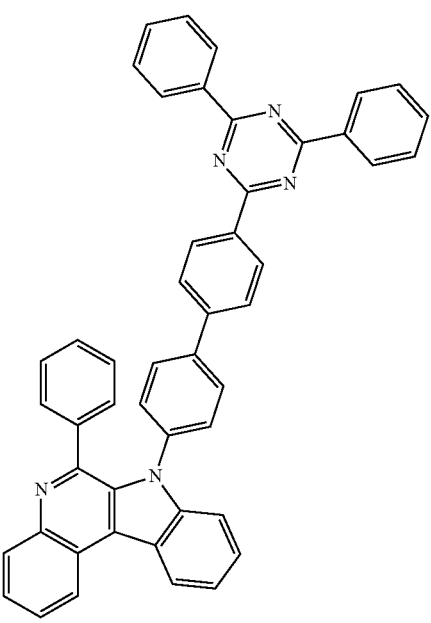 [SMILES: c1ccc(-c2nc(-c3ccccc3)nc(-c3ccc(-c4ccc(-n5c6ccccc6c6c7ccccc7nc(-c7ccccc7)c65)cc4)cc3)n2)cc1]
340
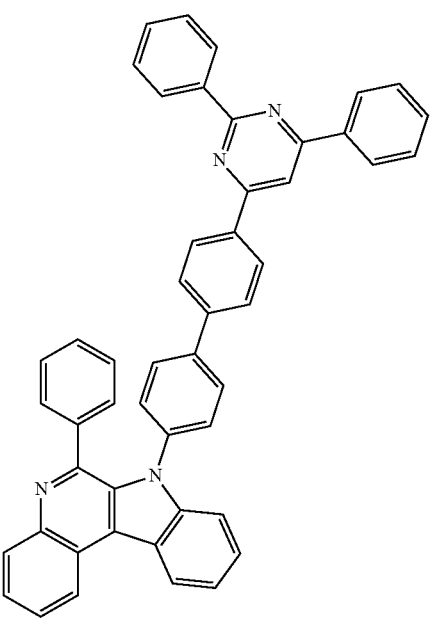

509
-continued
341
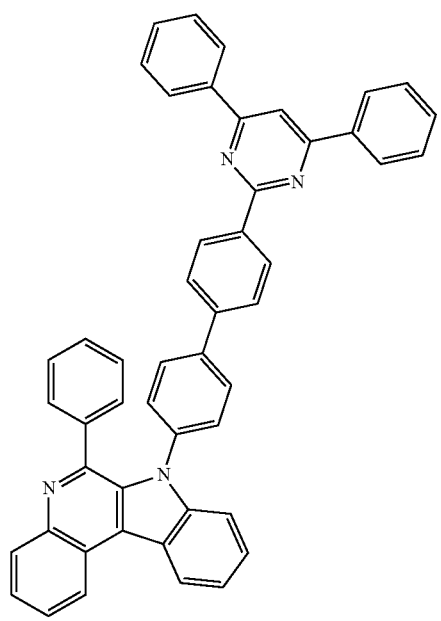
342
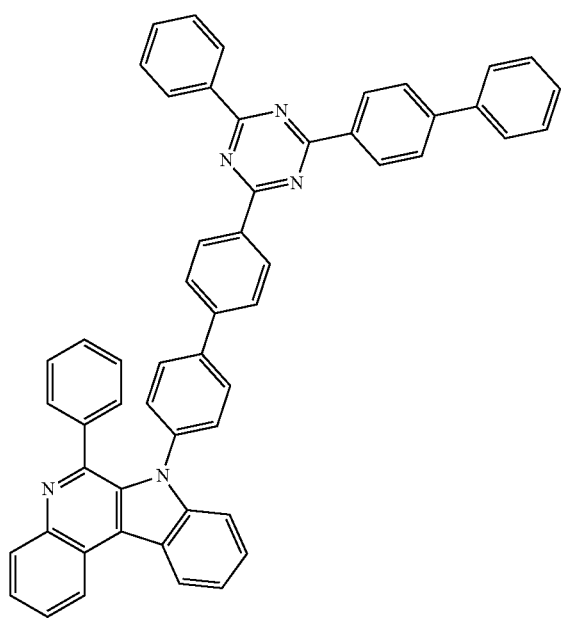 [SMILES: c1ccc(-c2ccc(-c3nc(-c4ccccc4)nc(-c4ccc(-c5ccc(-n6c7ccccc7c7c8ccccc8nc(-c8ccccc8)c76)cc5)cc4)n3)cc2)cc1]
510
-continued
343
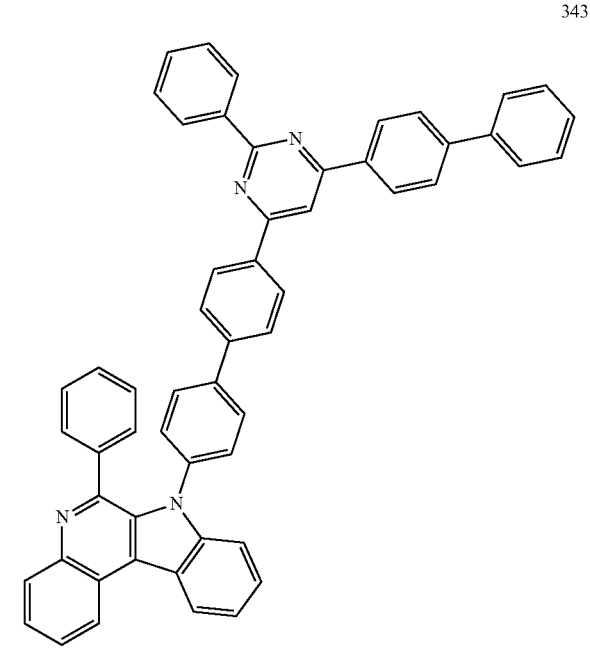
344
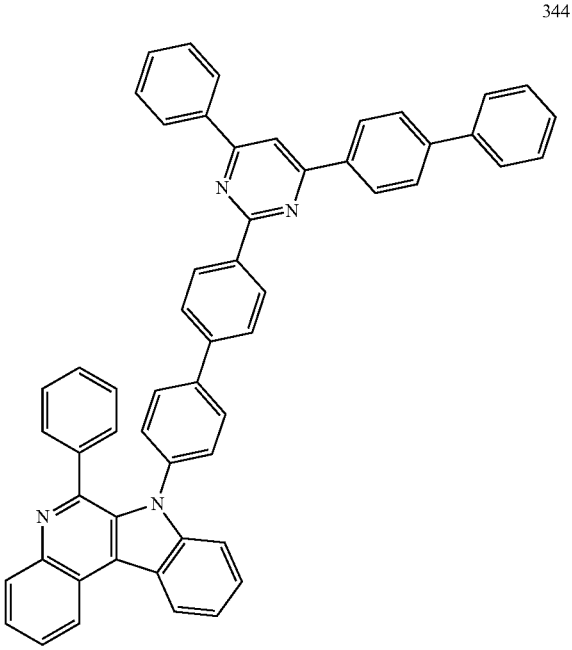

511
-continued
345
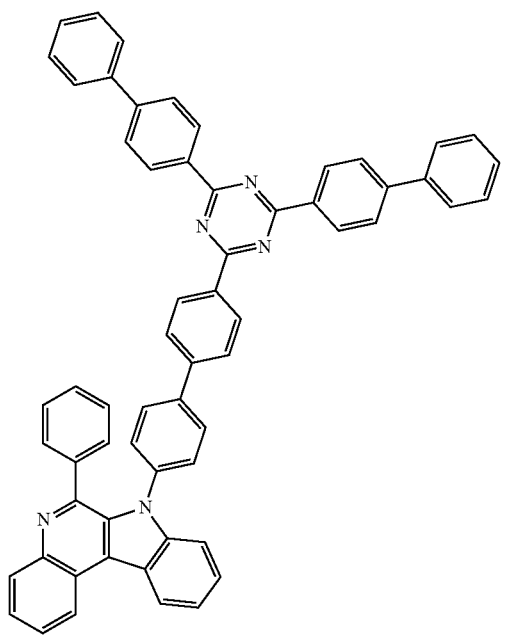
346
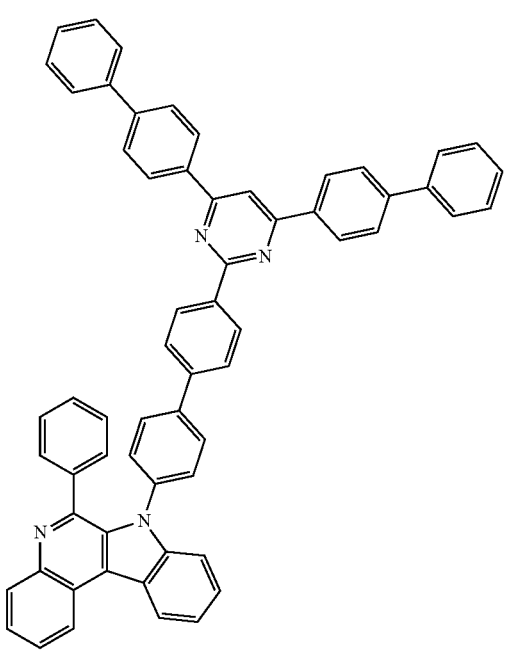
512
-continued
347
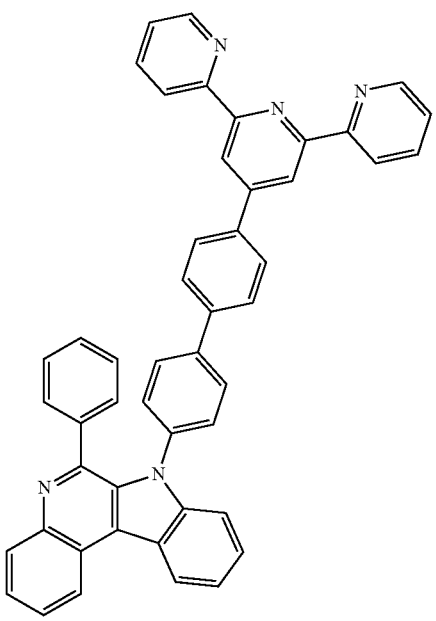
348
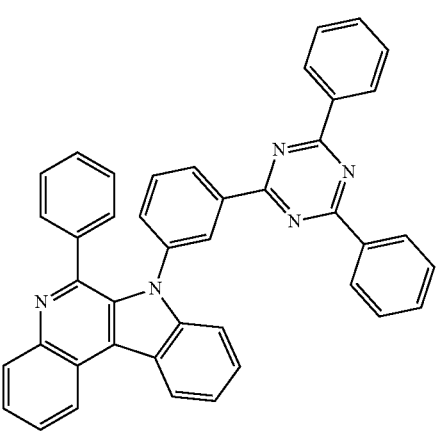
349

513
-continued
350
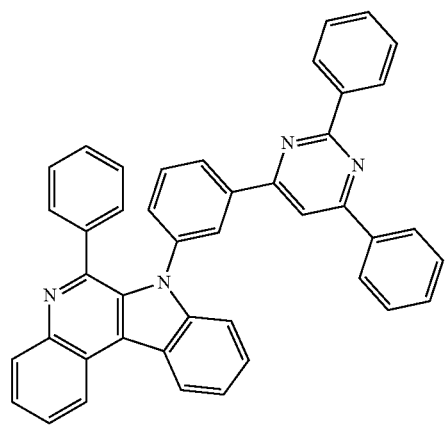
351
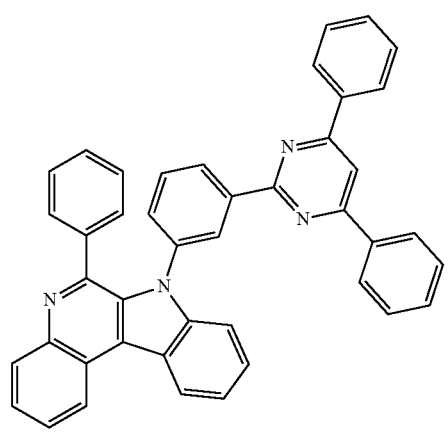
352
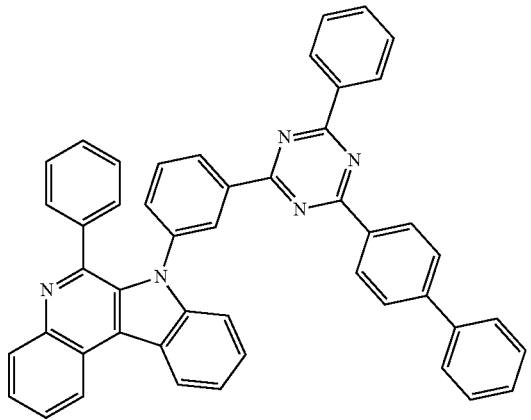 [SMILES: c1ccc(-c2ccc(-c3nc(-c4ccccc4)nc(-c4cccc(-n5c6ccccc6c6c7ccccc7nc(-c7ccccc7)c65)c4)n3)cc2)cc1]
514
-continued
353
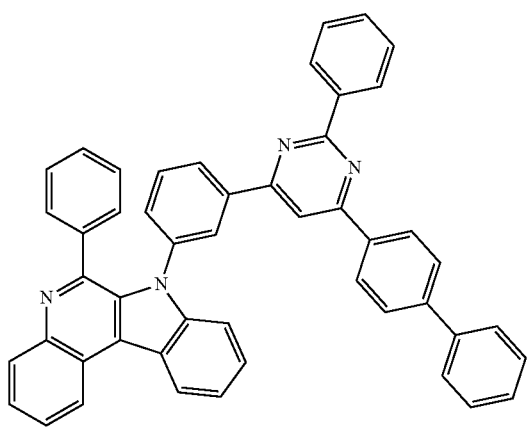 [SMILES: c1ccc(-c2ccc(-c3cc(-c4cccc(-n5c6ccccc6c6c7ccccc7nc(-c7ccccc7)c65)c4)nc(-c4ccccc4)n3)cc2)cc1]
354
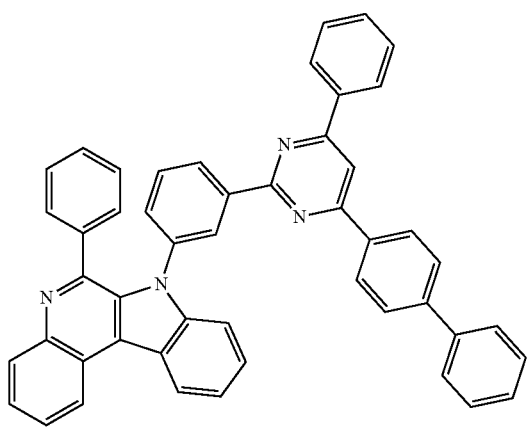
355
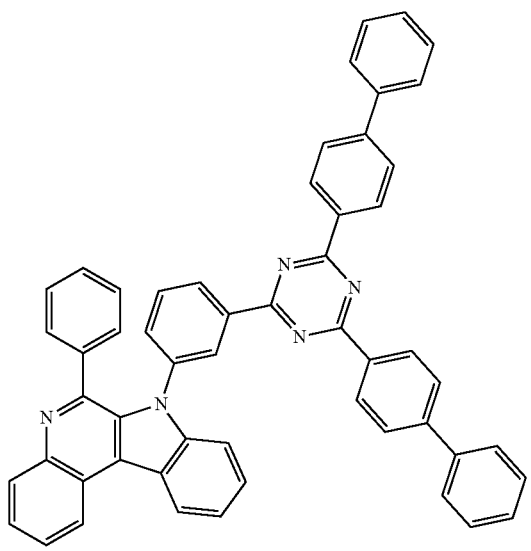

356 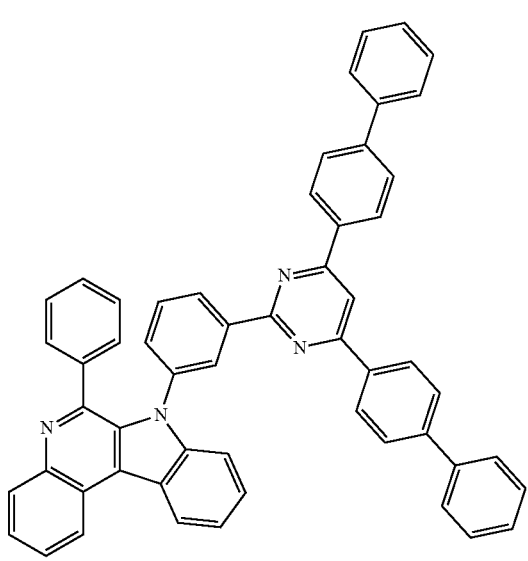
357 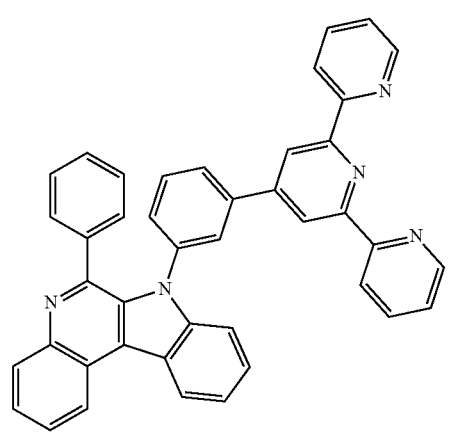
358 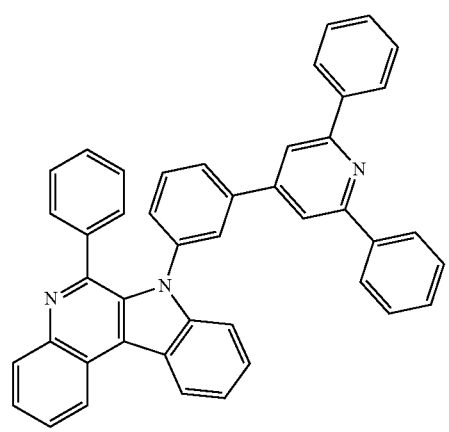
359 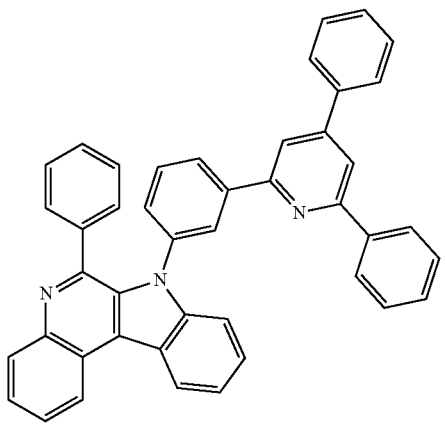
360 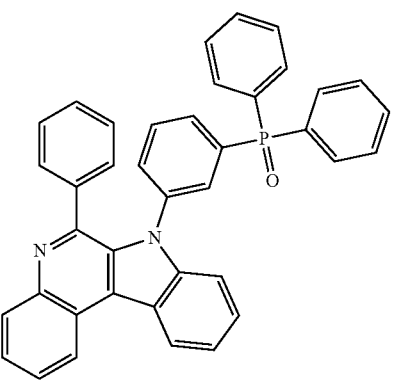
361 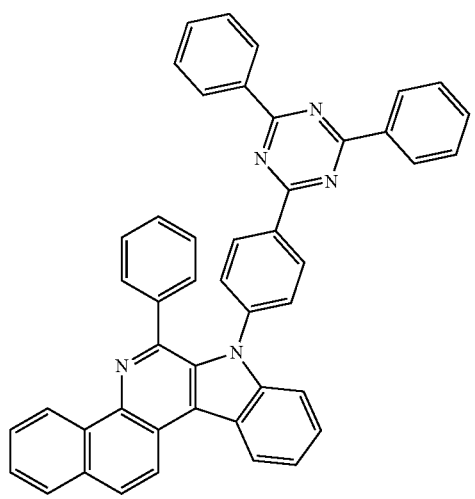

517
-continued
362
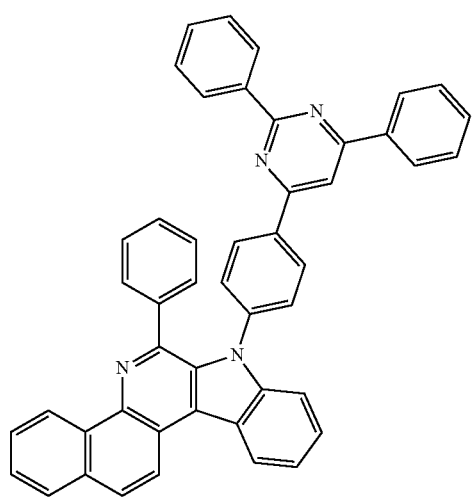
363
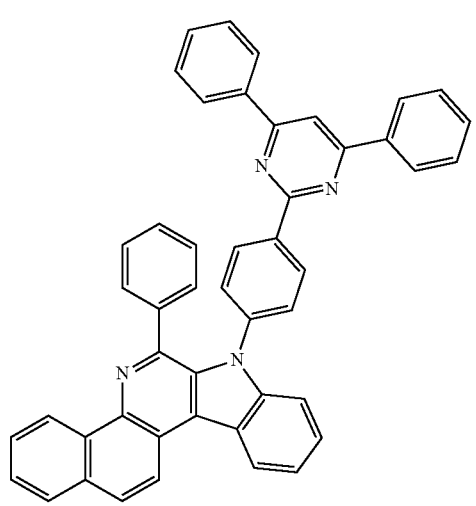
364
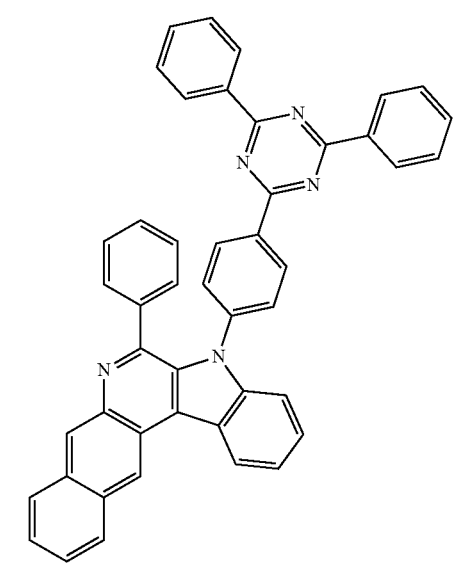
518
-continued
365
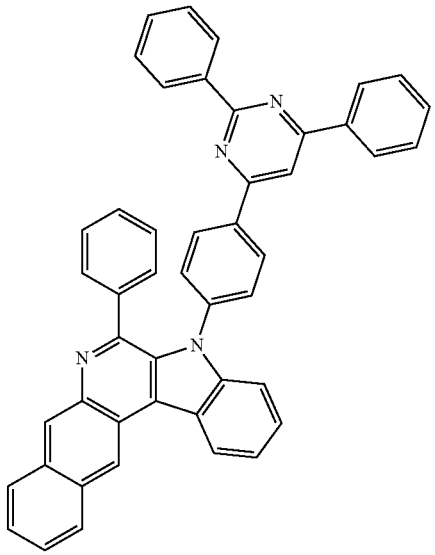
366
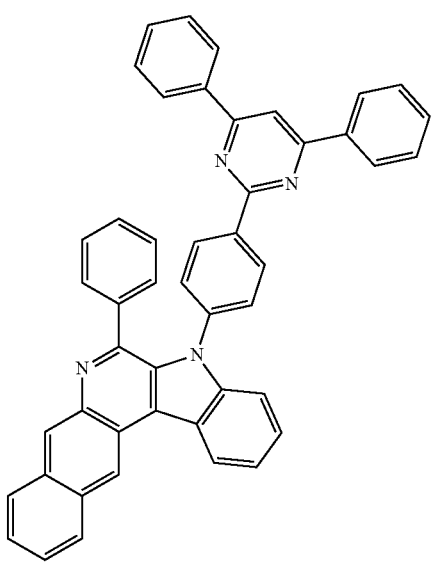
367
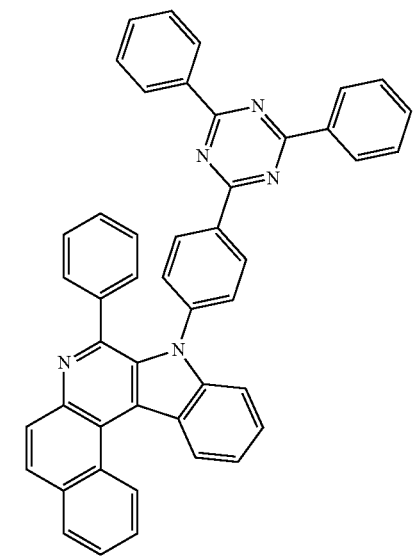

519 -continued
368
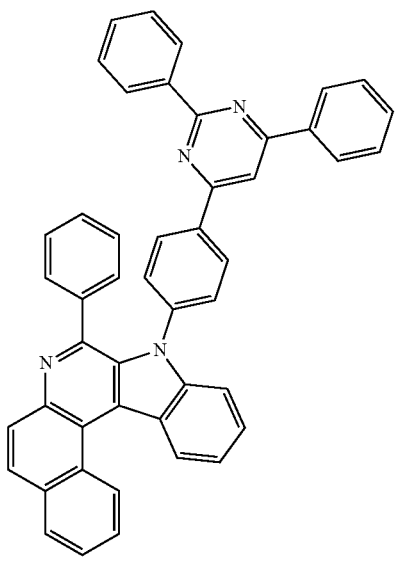
369
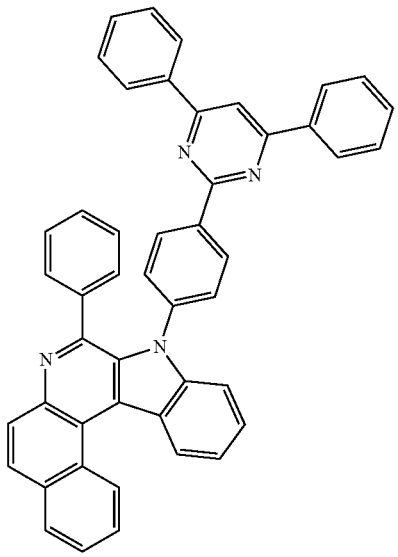
370
520 -continued
371
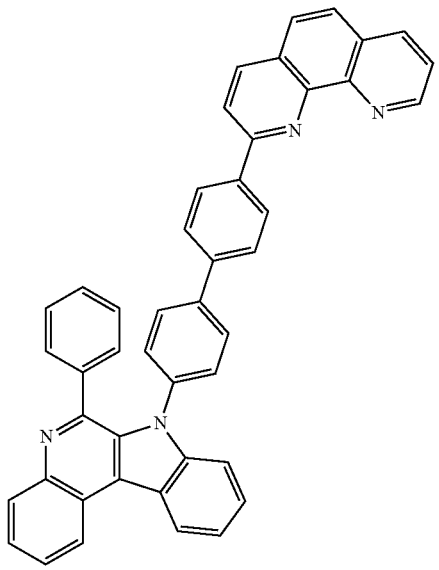
372
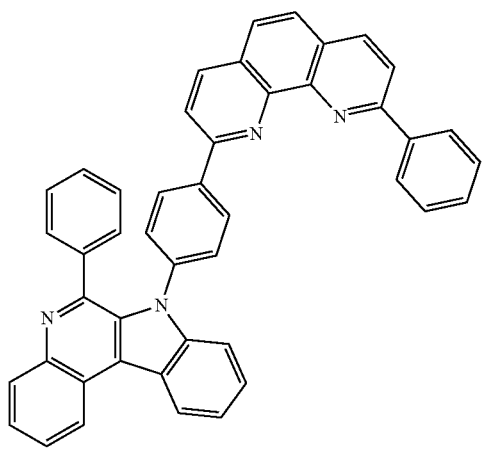 [SMILES: c1ccc(-c2ccc3ccc4ccc(-c5ccc(-n6c7ccccc7c7c8ccccc8nc(-c8ccccc8)c76)cc5)nc4c3n2)cc1]
373
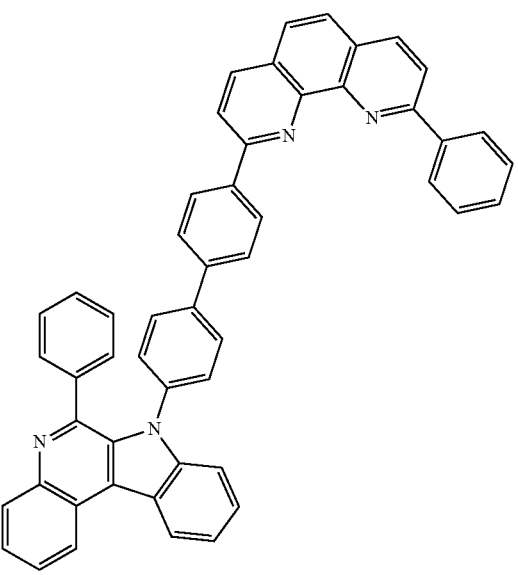 [SMILES: c1ccc(-c2ccc3ccc4ccc(-c5ccc(-c6ccc(-n7c8ccccc8c8c9ccccc9nc(-c9ccccc9)c87)cc6)cc5)nc4c3n2)cc1]

521
-continued
522
-continued
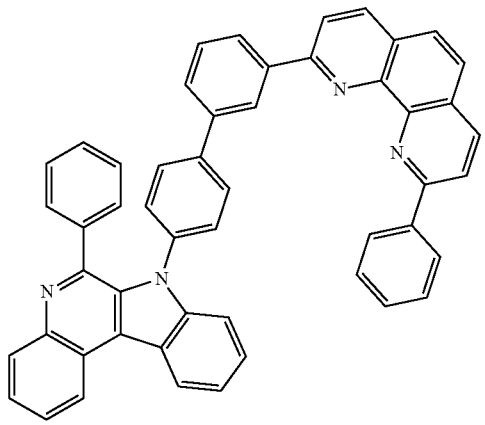 [SMILES: c1ccc(-c2ccc3ccc4ccc(-c5cccc(-c6ccc(-n7c8ccccc8c8c9ccccc9nc(-c9ccccc9)c87)cc6)c5)nc4c3n2)cc1]
374
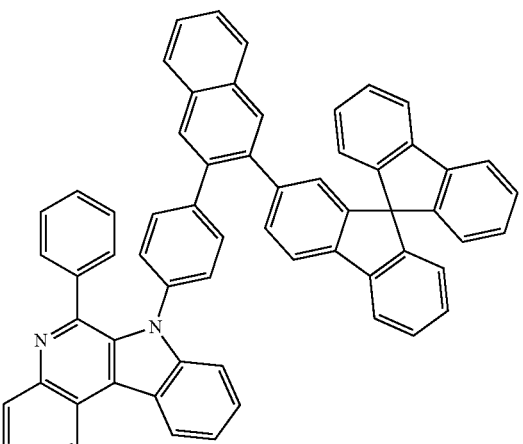
377
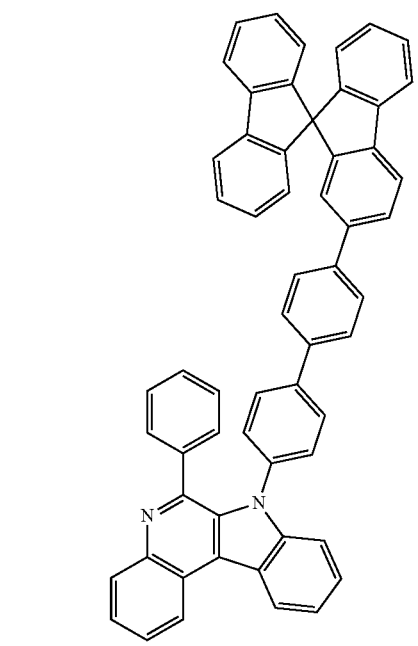
375
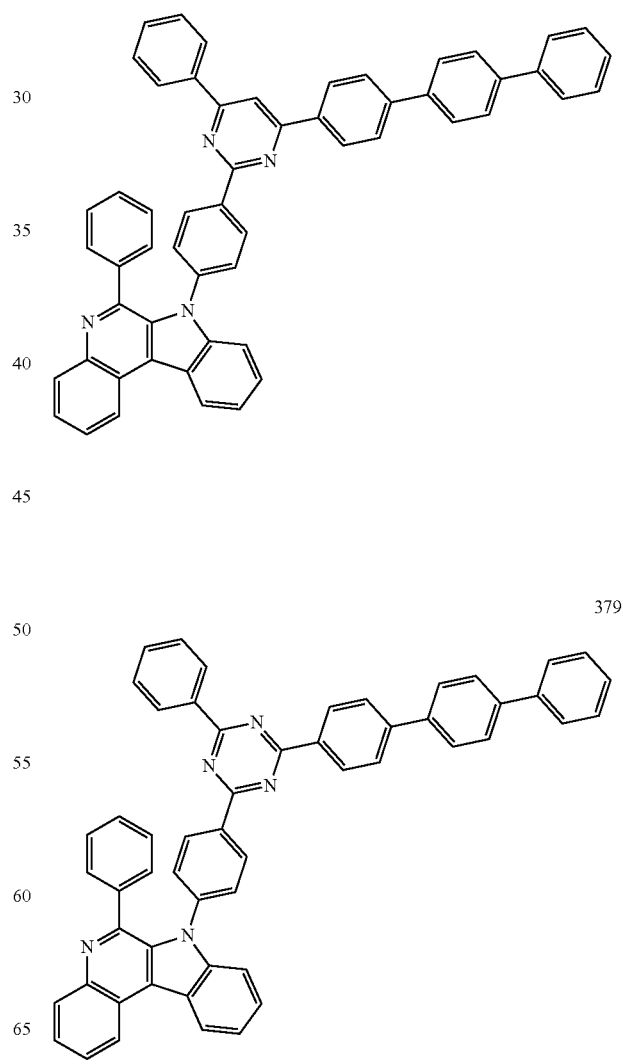
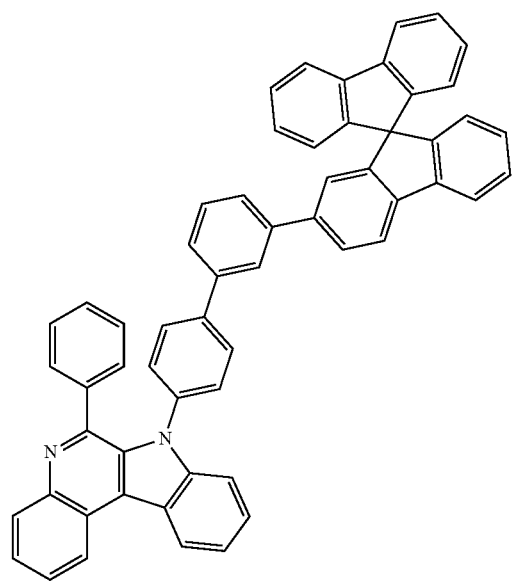 [SMILES: c1ccc(-c2nc3ccccc3c3c4ccccc4n(-c4ccc(-c5cccc(-c6ccc7c(c6)C6(c8ccccc8-c8ccccc86)c6ccccc6-7)c5)cc4)c23)cc1]
376

523
-continued
380
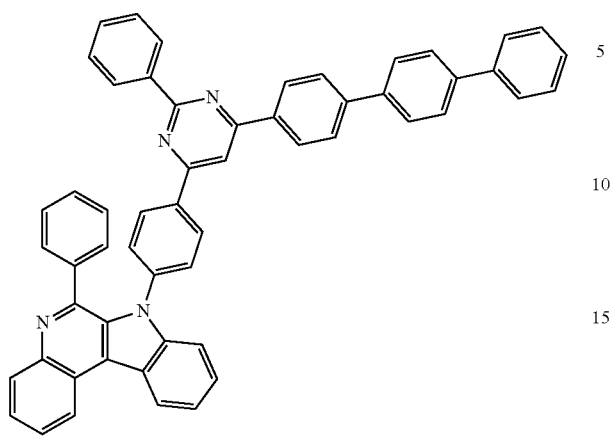
381
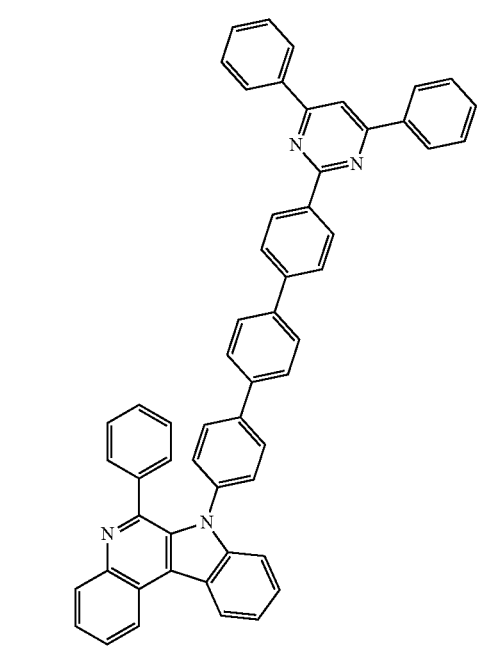
524
-continued
382
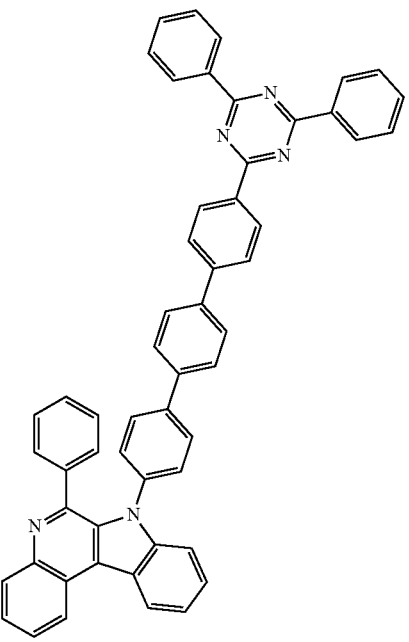 [SMILES: c1ccc(-c2nc(-c3ccccc3)nc(-c3ccc(-c4ccc(-c5ccc(-n6c7ccccc7c7c8ccccc8nc(-c8ccccc8)c76)cc5)cc4)cc3)n2)cc1]
383
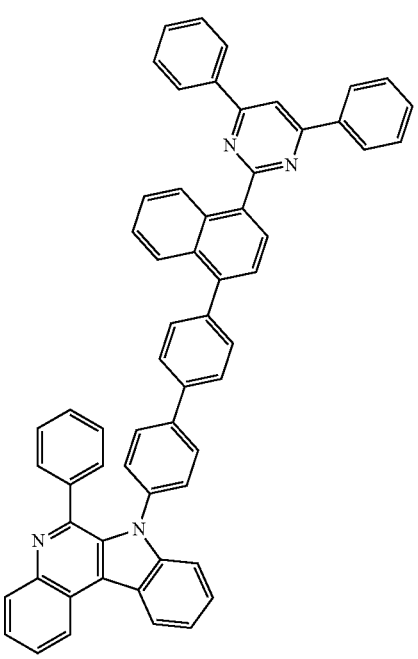

384
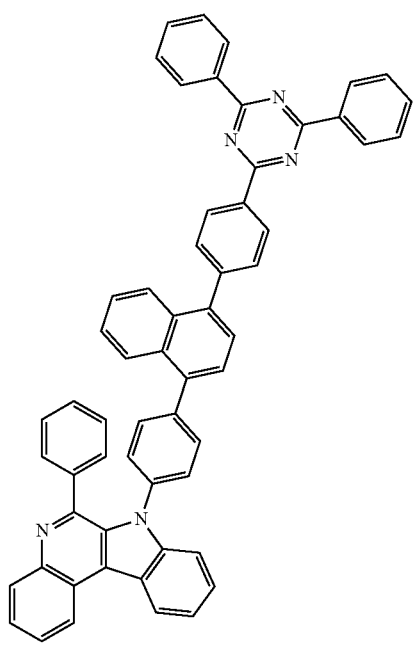 [SMILES: c1ccc(-c2cc(-c3ccccc3)nc(-c3ccc(-c4ccc(-c5ccc(-n6c7ccccc7c7c8ccccc8nc(-c8ccccc8)c76)cc5)c5ccccc45)cc3)n2)cc1]
385
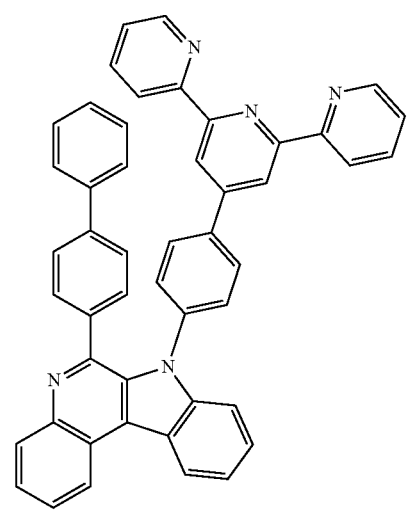
386
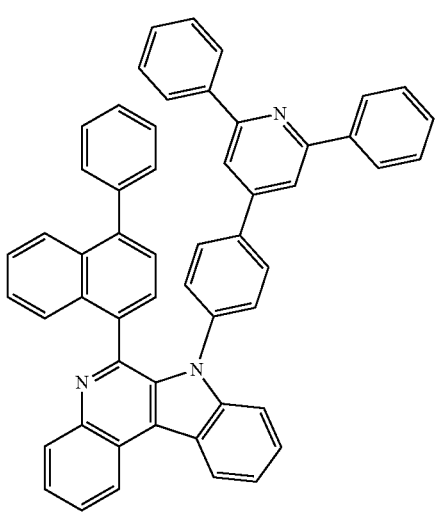
387
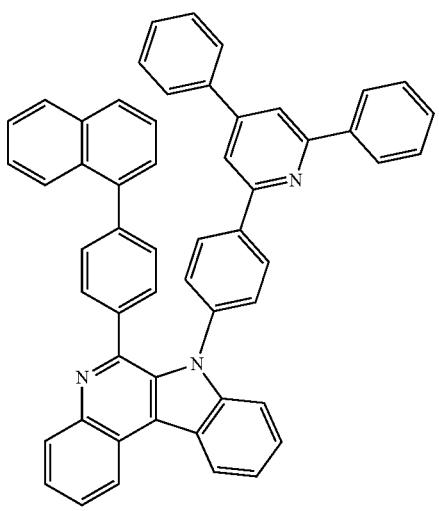
388
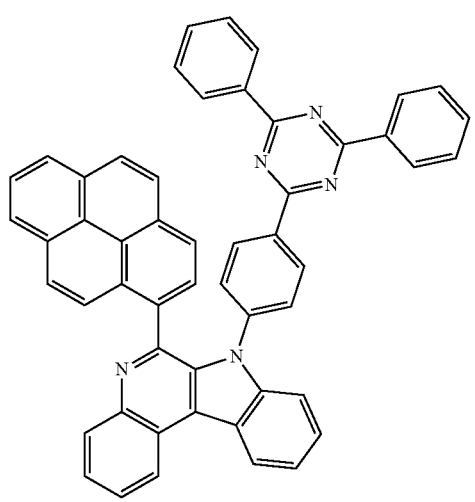
389
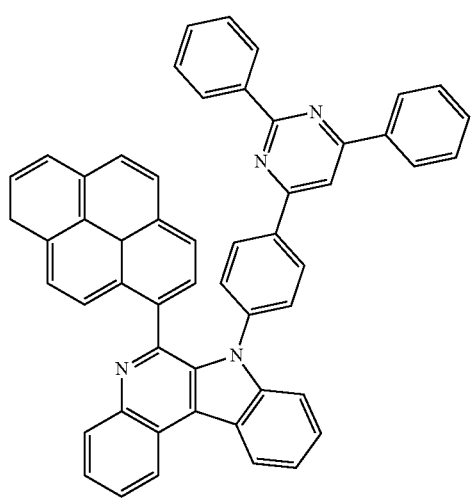

527
-continued
390
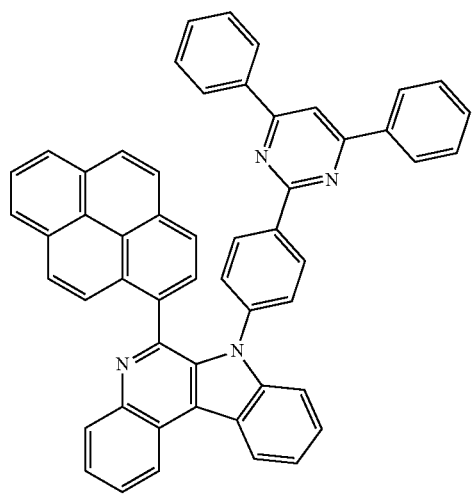 [SMILES: c1ccc(-c2nc(-c3ccccc3)nc(-c3ccc(-n4c5ccccc5c5c6ccccc6nc(-c6ccc7ccc8cccc9ccc6c7c89)c54)cc3)n2)cc1]
391
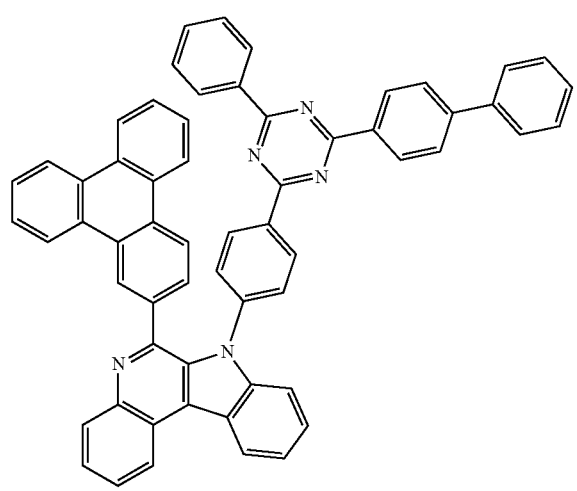
392
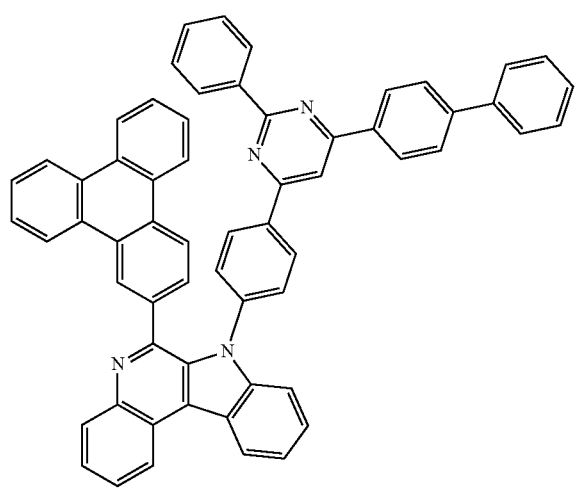
528
-continued
393
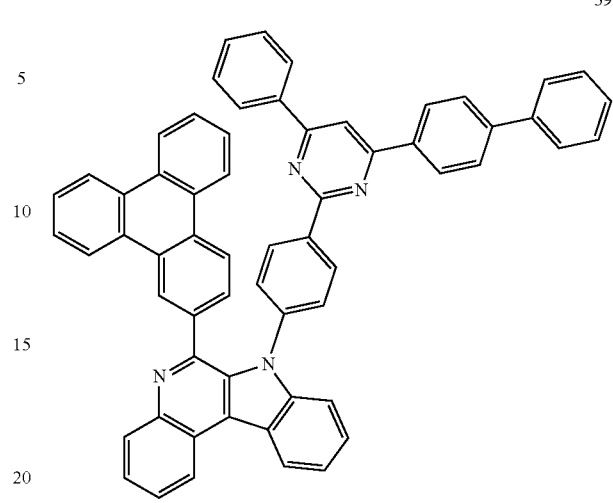
394
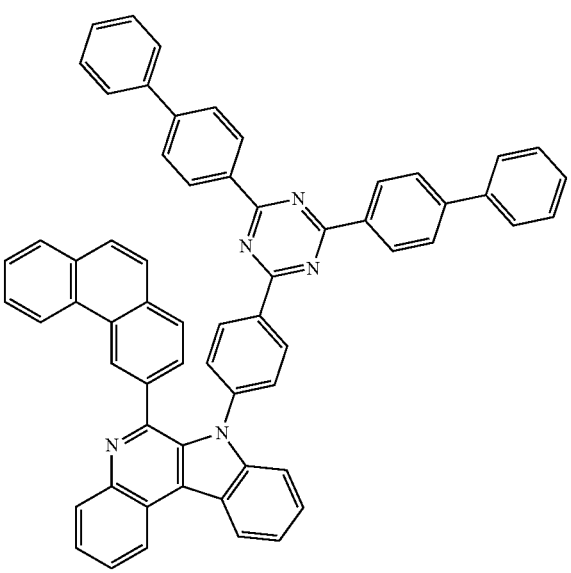 [SMILES: c1ccc(-c2ccc(-c3nc(-c4ccc(-c5ccccc5)cc4)nc(-c4ccc(-n5c6ccccc6c6c7ccccc7nc(-c7ccc8ccc9ccccc9c8c7)c65)cc4)n3)cc2)cc1]
395
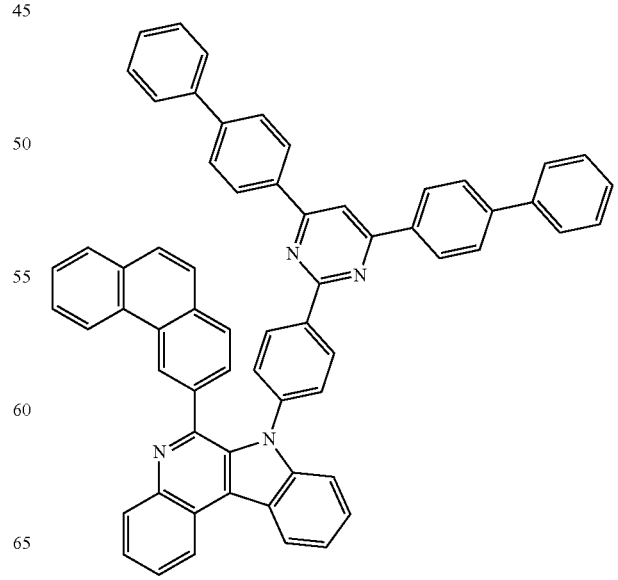

529
-continued
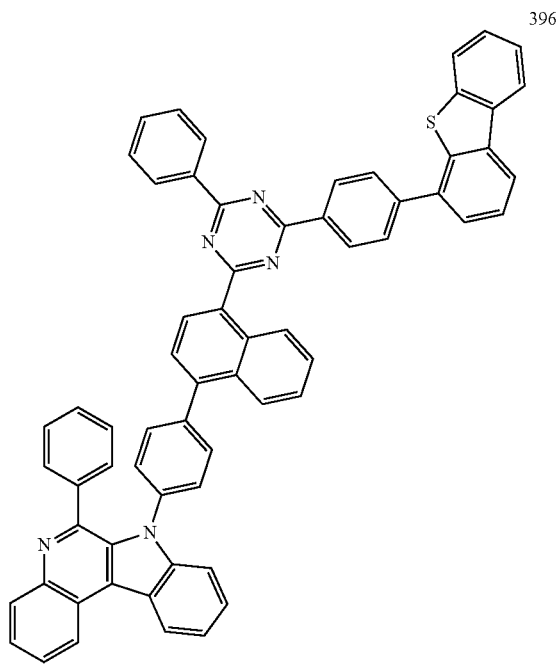
530
-continued
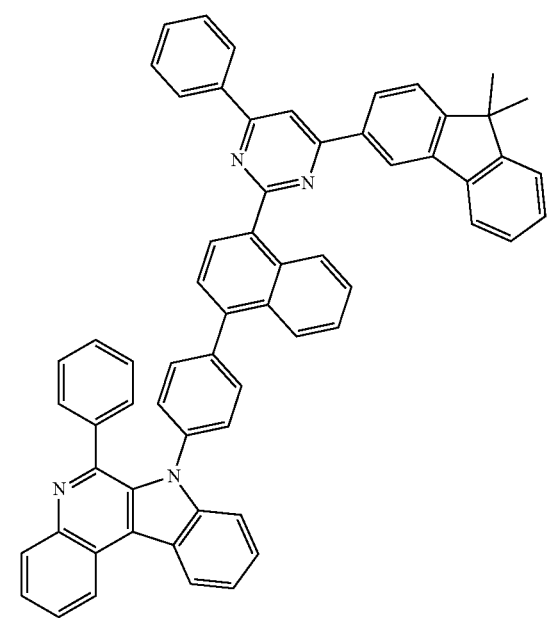

-continued

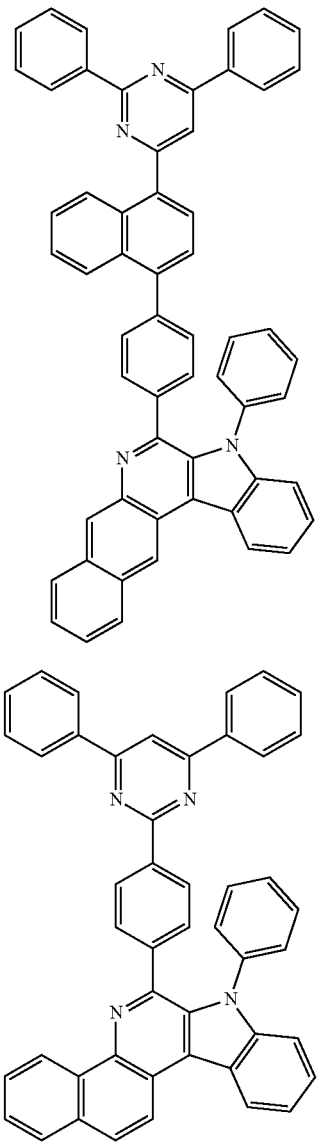

4. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

5. The organic light emitting device of claim 4, wherein the organic material layer comprises a light emitting layer, and the light emitting layer comprises the heterocyclic compound.

6. The organic light emitting device of claim 4, wherein the organic material layer comprises an electron injection layer or an electron transfer layer, and the electron injection layer or the electron transfer layer comprises the heterocyclic compound.

7. The organic light emitting device of claim 4, wherein the organic material layer comprises an electron blocking layer or a hole blocking layer, and the electron blocking layer or the hole blocking layer comprises the heterocyclic compound.

8. The organic light emitting device of claim 4, further comprising one, two or more layers selected form the group consisting of a light emitting layer, a hole injection layer, a hole transfer layer, an electron injection layer, an electron transfer layer, an electron blocking layer and a hole blocking layer.

9. The organic light emitting device of claim 4, comprising:
a first electrode;
a first stack provided on the first electrode and comprising a first light emitting layer;
a charge generation layer provided on the first stack;
a second stack provided on the charge generation layer and comprising a second light emitting layer; and
a second electrode provided on the second stack.

10. The organic light emitting device of claim 9, wherein the charge generation layer comprises the heterocyclic compound.

11. The organic light emitting device of claim 9, wherein the charge generation layer is an N-type charge generation layer, and the charge generation layer comprises the heterocyclic compound.

* * * * *